United States Patent
Chakraborty et al.

(10) Patent No.: US 10,925,935 B2
(45) Date of Patent: *Feb. 23, 2021

(54) TERMINALLY MODIFIED RNA

(71) Applicant: Moderna TX, Inc., Cambridge, MA (US)

(72) Inventors: Tirtha Chakraborty, Medford, MA (US); Stephane Bancel, Cambridge, MA (US); Stephen G. Hoge, Brookline, MA (US); Atanu Roy, Stoneham, MA (US); Antonin De Fougerolles, Waterloo (BE); Noubar B. Afeyan, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/152,945

(22) Filed: Oct. 5, 2018

(65) Prior Publication Data

US 2019/0290742 A1 Sep. 26, 2019

Related U.S. Application Data

(60) Continuation of application No. 15/429,532, filed on Feb. 10, 2017, now Pat. No. 10,155,029, which is a division of application No. 14/043,927, filed on Oct. 2, 2013, now Pat. No. 9,597,380.

(60) Provisional application No. 61/839,903, filed on Jun. 27, 2013, provisional application No. 61/737,224, filed on Dec. 14, 2012, provisional application No. 61/758,921, filed on Jan. 31, 2013, provisional application No. 61/842,709, filed on Jul. 3, 2013, provisional application No. 61/775,509, filed on Mar. 9, 2013, provisional application No. 61/829,372, filed on May 31, 2013, provisional application No. 61/781,139, filed on Mar. 14, 2013, provisional application No. 61/857,436, filed on Jul. 23, 2013, provisional application No. 61/829,359, filed on May 31, 2013, provisional application No. 61/729,933, filed on Nov. 26, 2012.

(51) Int. Cl.
*A61K 39/00* (2006.01)
*C12N 15/67* (2006.01)

(52) U.S. Cl.
CPC .............. *A61K 39/00* (2013.01); *C12N 15/67* (2013.01)

(58) Field of Classification Search
None
See application file for complete search history.

(56) References Cited

U.S. PATENT DOCUMENTS

| 6,377,804 | B1 | 4/2002 | Lintulampi |
| 9,597,380 | B2 | 3/2017 | Chakraborty et al. |
| 9,751,925 | B2 | 9/2017 | Hoge et al. |
| 10,155,029 | B2 | 12/2018 | Chakraborty et al. |
| 2005/0032730 | A1 | 2/2005 | Von Der Mulbe et al. |
| 2009/0286852 | A1 | 11/2009 | Kariko et al. |
| 2011/0244026 | A1 | 10/2011 | Guild et al. |
| 2012/0065252 | A1 | 3/2012 | Schrum et al. |
| 2012/0195936 | A1 † | 8/2012 | Rudolph |
| 2012/0251618 | A1 | 10/2012 | Schrum et al. |
| 2014/0073687 | A1 | 3/2014 | Chien et al. |
| 2014/0147454 | A1 | 5/2014 | Chakraborty et al. |
| 2014/0200261 | A1 | 7/2014 | Hoge et al. |
| 2014/0206852 | A1 | 7/2014 | Hoge et al. |

FOREIGN PATENT DOCUMENTS

| EP | 2700708 | A2 | 2/2014 | |
| JP | 2016-504050 | A | 2/2016 | |
| WO | 2004076622 | A2 | 9/2004 | |
| WO | 2006111512 | A1 | 10/2006 | |
| WO | 2006128245 | A1 † | 12/2006 | |
| WO | 2007/000668 | A2 | 1/2007 | |
| WO | 2007/024708 | A2 | 3/2007 | |
| WO | 2010/055413 | A1 | 5/2010 | |
| WO | WO-2011005786 | A2 * | 1/2011 | ........... C12N 15/111 |
| WO | 2011/012316 | A2 | 2/2011 | |
| WO | 2011130624 | A2 | 10/2011 | |
| WO | 2012009644 | A2 | 1/2012 | |
| WO | 2012/019630 | A1 | 2/2012 | |
| WO | 2012019168 | A2 | 2/2012 | |
| WO | 2012045075 | A1 | 4/2012 | |
| WO | 2012135805 | A2 | 10/2012 | |
| WO | 2012138453 | A1 | 10/2012 | |
| WO | 2013/090648 | A1 | 6/2013 | |
| WO | 2013090648 | A2 † | 6/2013 | |
| WO | 2013103659 | A1 | 7/2013 | |
| WO | 2013/151666 | A2 | 10/2013 | |
| WO | 2013151669 | A1 | 10/2013 | |
| WO | 2013151672 | A2 | 10/2013 | |
| WO | 2014/081507 | A1 | 5/2014 | |
| WO | 2014/113089 | A2 | 7/2014 | |
| WO | 2015/007871 | A2 | 1/2015 | |
| WO | 2015048744 | A2 | 4/2015 | |
| WO | 2016/011306 | A2 | 1/2016 | |
| WO | 2016/170176 | A1 | 10/2016 | |
| WO | 2017112943 | A1 | 6/2017 | |

OTHER PUBLICATIONS

Su, et al. (Apr. 1, 2011) "In vitro and in vivo mRNA delivery using lipid-enveloped pH-responsive polymer nanoparticles", Molecular Phamaceutics, 8: 744-787. (Year: 2011).*

(Continued)

*Primary Examiner* — Robert M Kelly
(74) *Attorney, Agent, or Firm* — Nelson Mullins Riley & Scarborough LLP; Amy E. Mandragouras, Esq.; Ariana D. Harris

(57) ABSTRACT

The invention relates to compositions and methods for the manufacture and optimization of modified mRNA molecules via optimization of their terminal architecture.

37 Claims, 4 Drawing Sheets

Specification includes a Sequence Listing.

(56) References Cited

OTHER PUBLICATIONS

Anadarini, "Adenovirus vector-mediated in vivo gene transfer of OX40 ligand to tumor cells enhances antitumor immunity of tumor-bearing hosts," Cancer Research, vol. 64:3281-3287 (2004).
Anderson, B.R. et al., "Incorporation of pseudouridine into mRNA enhances translation by diminishing PKR activation," Nucleic Acids Research, vol. 38(17):36-38 (2010).
Annoni, A. et al., "In vivo delivery of a microRNA-regulated transgene induces antigen-specific regulatory T cells and promotes immunologic tolerance," Blood, vol. 114: 5152-5161 (2009).
Brown, B.D. et al., "Endogenous mircroRNA can be broadly exploited to regulate transgene expression according to tissue, lineage and differentiation state", Nature Biotechnology, vol. 25:1457-1467 (2007).
Cawood, R. et al., "Use of tissue-specific microRNA to control pathology of wild-type adenovirus without attenuation of its ability to kill cancer cells," PLOS Pathogens, Public Library of Science, vol. 5(5): e1000440: (2009).
Dannull, J. et al., "Enhancing the immunostimulatory function of dendritic cells by transfection with mRNA encoding OX40 ligand," Blood, vol. 105 (8):3206-3213 (2005).
Extended European Search Report, EP Application No. 18179340.7, dated Nov. 9, 2018, 14 pages.
International Preliminary Report on Patentability, PCT/US2013/062943, dated May 26, 2015, 11 pages.
International Search Report and Written Opinion, PCT/US2013/062943, dated Jan. 7, 2014, 17 pages.
International Search Report and Written Opinion, PCT/US2016/068552, dated Mar. 21, 2017, 14 pages.
Kariko K. et al., "Incorporation of pseudouridine into mRNA yields superior nonimmunogenic vector with increased translational capacity and biological stability," Molecular Therapy, Nature Publishing Group, vol. 16 (11):1833-1840 (2008).
Kariko, K. et al., "Generating the optimal mRNA for therapy: HPLC 11-13, purification eliminates immune activation and improves translation of nucleoside-modified, protein-encoding mRNA," Nucleic Acids Research, vol. 39 (21): e142-1 (2011).
Kariko, K. et al., "Suppression of RNA Recognition by Toll-like Receptors: The Impact of Nucleoside Modification and the Evolutionary Origin of RNA," Immunity, vol. 23: 165-175 (2005).
Kormann, M.S. et al., "Expression of therapeutic proteins after delivery of chemically modified mRNA in mice," Nature Biotechnology, vol. 29(2):154-159 (2011).
Kron, M. et al., "mlRNA-mediated silencing in hepatocytes can increase adaptive immune responses to adenovirus vector-delivered transgenic antigens," Molecular Therapy, vol. 19(8):1547-1557 (2011).
Lennox, KA, et al., "Chemical modification and design of anti-miRNA oligonucleotides," Gene Therapy, vol. 18 (12):1111-1120 (2011).
Nemani, M. et al., "Activation of the human homologue of the Drosophila sina gene in apoptosis and tumor suppression," Proc. Natl. Acad. Sci. USA, vol. 93 (17):9039-9042 (1996).
Pichard, V. et al., "Specific Micro RNA-Regulated TetR-KRAB Transcriptional Control of Transgene Expression in Viral Vector-Transduced Cells", PLOS ONE, vol. 7(12):e51952 (2012).
Rotondaro, L. et al., "Efficiency of different viral promoters in directing gene expression in mammalian cells: effect of 3'-untranslated sequences," Gene, vol. 168(2):195-198 (1996).
Sahin, U. et al., "mRNA-based therapeutics - developing a new class of drugs," Nature Reviews Drug Discovery, vol. 13(10)759-780 (2014).
Singh, R. et al., "Nanoengineering artificial lipid envelopes around adenovirus by self-assembly," ACS Nano, vol. 2 (5):1040-1050 (2008).
Smirnov, D.A. et al., "ATM Gene mutations result in both recessive and dominant expression phenotypes of genes and microRNAs", The American Journal of Human Genetics, vol. 83: 243-253 (2008).
Suzuki, T. et al., "miR-122a-Regulated Expression of a Suicide Gene Prevents Hepatotoxicity Without Altering Antitumor Effects in Suicide Gene Therapy," Molecular Therapy, vol. 16(10): 1719-1726 (2008).
Van Der Jeught, K. et al., "Targeting the tumor microenvironment to enhance antitumor immune responses," Oncotarget, vol. 6(3):1359-1381 (2015).
Vinuesa, C. et al "Logic and Extent of miRNA-Mediated Control of Autoimmune Gene Expression," International Reviews of Immunology, vol. 28 (304):112-138 (2009).
Wang Y. et al., "Systemic delivery of modified mRNA encoding herpes simplex virus 1 thymidine kinase for targeted cancer gene therapy", Mol Ther., vol. 21(2):358-367 (2013).
Wolff, L. et al., "Effect of tissue-specific promoters and microRNA recognition elements on stability of transgene expression after hydrodynamic naked plasmid DNA delivery," Human Gene Therapy, vol. 20, pp. 374-388 (2009).
Yang, L. et al., "miR-146a controls the resolution of T cell responses in mice", The Journal of Experimental Medicine, vol. 209 (9):1655-1670, (2012).
U.S. Appl. No. 15/429,532, filed Feb. 10, 2017, Tirtha Chakraborty.
U.S. Appl. No. 14/043,927, filed Oct. 2, 2013, Tirtha Chakraborty.
U.S. Appl. No. 16/036,170, filed Jul. 16, 2018, Stephen G. Hoge.
U.S. Appl. No. 14/135,876, filed Dec. 20, 2013, Stephen G. Hoge.
U.S. Appl. No. 14/041,011, filed Sep. 30, 2013, Stephen G. Hoge.
U.S. Appl. No. 14/043,927, filed Jan. 30, 2017, K. Hiriyanna.
U.S. Appl. No. 14/043,927, filed Sep. 21, 2016, K. Hiriyanna.
U.S. Appl. No. 14/043,927, filed Jun. 10, 2016, K. Hiriyanna.
U.S. Appl. No. 14/043,927, filed Oct. 19, 2015, K. Hiriyanna.
U.S. Appl. No. 14/043,927, filed Sep. 23, 2014, K. Hiriyanna.
U.S. Appl. No. 14/043,927, filed Jun. 5, 2014, K. Hiriyanna.
U.S. Appl. No. 14/041,011, filed Jan. 22, 2018, J. Wu.
U.S. Appl. No. 14/041,011, filed Sep. 16, 2016, J. Wu.
U.S. Appl. No. 14/041,011, filed Feb. 2, 2016, J. Wu.
U.S. Appl. No. 14/041,011, filed Apr. 22, 2015, J. Wu.
U.S. Appl. No. 14/135,876, filed Jul. 31, 2014, J. Wu.
U.S. Appl. No. 14/135,876, filed Mar. 6, 2014, J. Wu.
U.S. Appl. No. 15/429,532, filed Oct. 3, 2018, R. Kelly.
U.S. Appl. No. 15/429,532, filed Jun. 1, 2018, R. Kelly.
Kariko et al., "Incorporation of pseudouridine into mRNA yields superior nonimmunogenic vector with increased translational capacity and biological stability," Mol Ther., 16(11)1 833-1840, 2008.†

\* cited by examiner
† cited by third party

PRIOR ART

TERMINALLY MODIFIED RNA

CROSS REFERENCE TO RELATED APPLICATIONS

This application is a continuation of U.S. patent application Ser. Nos. 15/429,532, filed on Feb. 10, 2017, which is now U.S. Pat. No. 10,155,029, issued on Dec. 18, 2018, which application is a divisional of U.S. patent application Ser. No. 14/043,927, filed on Oct. 2, 2013, which is now U.S. Pat. No. 9,597,380, issued on Mar. 21, 2017, entitled Terminally Modified RNA, which claims priority to U.S. Provisional Patent Application No. 61/729,933, filed Nov. 26, 2012, entitled Terminally Optimized Modified RNAs, U.S. Provisional Patent Application No. 61/737,224, filed Dec. 14, 2012, entitled Terminally Optimized Modified RNAs, U.S. Provisional Patent Application No. 61/758,921, filed Jan. 31, 2013, entitled Differential Targeting Using RNA Constructs, U.S. Provisional Patent Application No. 61/781,139, filed Mar. 14, 2013, entitled Differential Targeting Using RNA Constructs, U.S. Provisional Patent Application No. 61/829,359, filed May 31, 2013, entitled Differential Targeting Using RNA Constructs, U.S. Provisional Patent Application No. 61/839,903, filed Jun. 27, 2013, entitled Differential Targeting Using RNA Constructs, U.S. Provisional Patent Application No. 61/842,709, filed Jul. 3, 2013, entitled Differential Targeting Using RNA Constructs, U.S. Provisional Patent Application No. 61/857,436, filed Jul. 23, 2013, entitled Differential Targeting Using RNA Constructs, U.S. Provisional Patent Application No. 61/775,509, filed Mar. 9, 2013, entitled Heterologous Untranslated Regions for mRNA and U.S. Provisional Patent Application No. 61/829,372, filed May 31, 2013, entitled Heterologous Untranslated Regions for mRNA; the contents of each of which are herein incorporated by reference in their entireties.

REFERENCE TO SEQUENCE LISTING

The instant application contains a Sequence Listing which has been submitted electronicatlly in ASCII format and is hereby incorporated by reference in its entirety. Said ASCII copy, created on Oct. 5, 2018, is named MDN_039BDVCN_SL.txt and is 3263014 bytes in size.

FIELD OF THE INVENTION

The invention relates to compositions and methods for the manufacture and use of modified and/or optimized mRNA and their use in combination with one or more modified or wild type mRNA encoding an RNA binding protein.

BACKGROUND OF THE INVENTION

Naturally occurring RNAs are synthesized from four basic ribonucleotides: ATP, CTP, UTP and GTP, but may contain post-transcriptionally modified nucleotides. Further, approximately one hundred different nucleoside modifications have been identified in RNA (Rozenski, J, Crain, P, and McCloskey, J. (1999). The RNA Modification Database: 1999 update. Nucl Acids Res 27: 196-197, herein incorporated by reference in its entirety).

There are multiple problems with prior methodologies of effecting protein expression. For example, heterologous deoxyribonucleic acid (DNA) introduced into a cell can be inherited by daughter cells (whether or not the heterologous DNA has integrated into the chromosome) or by offspring. Introduced DNA can integrate into host cell genomic DNA at some frequency, resulting in alterations and/or damage to the host cell genomic DNA. In addition, multiple steps must occur before a protein is made. Once inside the cell, DNA must be transported into the nucleus where it is transcribed into RNA. The RNA transcribed from DNA must then enter the cytoplasm where it is translated into protein. This need for multiple processing steps creates lag times before the generation of a protein of interest. Further, it is difficult to obtain DNA expression in cells; frequently DNA enters cells but is not expressed or not expressed at reasonable rates or concentrations. This can be a particular problem when DNA is introduced into cells such as primary cells or modified cell lines. The role of nucleoside modifications on the immunostimulatory potential, stability, and on the translation efficiency of RNA, and the consequent benefits to this for enhancing protein expression and producing therapeutics have been previously explored. Such studies are detailed in published co-pending International Publication No WO2012019168 filed Aug. 5, 201, International Publication No WO2012045082 filed Oct. 3, 2011, International Publication No WO2012045075 filed Oct. 3, 2011, International Publication No WO2013052523 filed Oct. 3, 2012, and International Publication No WO2013090648 filed Dec. 14, 2012 the contents of which are incorporated herein by reference in their entirety.

The use of modified polynucleotides in the fields of antibodies, viruses, veterinary applications and a variety of in vivo settings have been explored and are disclosed in, for example, co-pending and co-owned U.S. Provisional Patent Application No. 61/618,862, filed Apr. 2, 2012, entitled Modified Polynucleotides for the Production of Biologics; U.S. Provisional Patent Application No. 61/681,645, filed Aug. 10, 2012, entitled Modified Polynucleotides for the Production of Biologics; U.S. Provisional Patent Application No. 61/737,130, filed Dec. 14, 2012, entitled Modified Polynucleotides for the Production of Biologics; U.S. Provisional Patent Application No. 61/618,866, filed Apr. 2, 2012, entitled Modified Polynucleotides for the Production of Antibodies; U.S. Provisional Patent Application No. 61/681,647, filed Aug. 10, 2012, entitled Modified Polynucleotides for the Production of Antibodies; U.S. Provisional Patent Application No. 61/737,134, filed Dec. 14, 2012, entitled Modified Polynucleotides for the Production of Antibodies; U.S. Provisional Patent Application No. 61/618,868, filed Apr. 2, 2012, entitled Modified Polynucleotides for the Production of Vaccines; U.S. Provisional Patent Application No. 61/681,648, filed Aug. 10, 2012, entitled Modified Polynucleotides for the Production of Vaccines; U.S. Provisional Patent Application No. 61/737,135, filed Dec. 14, 2012, entitled Modified Polynucleotides for the Production of Vaccines; U.S. Provisional Patent Application No. 61/618,870, filed Apr. 2, 2012, entitled Modified Polynucleotides for the Production of Therapeutic Proteins and Peptides; U.S. Provisional Patent Application No. 61/681,649, filed Aug. 10, 2012, entitled Modified Polynucleotides for the Production of Therapeutic Proteins and Peptides; U.S. Provisional Patent Application No. 61/737,139, filed Dec. 14, 2012, Modified Polynucleotides for the Production of Therapeutic Proteins and Peptides; U.S. Provisional Patent Application No. 61/618,873, filed Apr. 2, 2012, entitled Modified Polynucleotides for the Production of Secreted Proteins; U.S. Provisional Patent Application No. 61/681,650, filed Aug. 10, 2012, entitled Modified Polynucleotides for the Production of Secreted Proteins; U.S. Provisional Patent Application No. 61/737,147, filed Dec. 14, 2012, entitled Modified Polynucleotides for the Production of Secreted Proteins; U.S. Provisional Patent Application No. 61/618,878, filed Apr. 2, 2012, entitled Modified Polynucleotides for the Production of Plasma Membrane Proteins; U.S. Provisional Patent Application No. 61/681,654, filed Aug. 10, 2012, entitled Modified Polynucleotides for the Production of Plasma Membrane Proteins; U.S. Provisional Patent Application No. 61/737,152, filed Dec. 14, 2012, entitled Modified Polynucleotides for the Production of Plasma Membrane Proteins; U.S. Provisional Patent Application No. 61/618,885, filed Apr. 2, 2012, entitled Modified Polynucleotides for the Production of Cytoplasmic and Cytoskeletal Proteins; U.S. Provisional Patent Application No. 61/681,658, filed Aug. 10, 2012, entitled Modified Polynucleotides for the Production of Cytoplasmic and Cytoskeletal Proteins; U.S. Provisional Patent Application No. 61/737,155, filed Dec. 14, 2012, entitled Modified Polynucleotides for the Production of Cytoplasmic and Cytoskeletal Proteins; U.S. Provisional Patent Application No. 61/618,896, filed Apr. 2, 2012, entitled Modified Polynucleotides for the Production of Intracellular Membrane Bound Proteins; U.S. Provisional Patent Application No. 61/668,157, filed Jul. 5, 2012, entitled Modified Polynucleotides for the Production of Intracellular Membrane Bound Proteins; U.S. Provisional Patent Application No. 61/681,661, filed Aug. 10, 2012, entitled Modified Polynucleotides for the Production of Intracellular Membrane Bound Proteins; U.S. Provisional Patent Application No. 61/737,160, filed Dec. 14, 2012, entitled Modified Polynucleotides for the Production of Intracellular Membrane Bound Proteins; U.S. Provisional Patent Application No. 61/618,911, filed Apr. 2, 2012, entitled Modified Polynucleotides for the Production of Nuclear Proteins; U.S. Provisional Patent Application No. 61/681,667, filed Aug. 10, 2012, entitled Modified Polynucleotides for the Production of Nuclear Proteins; U.S. Provisional Patent Application No. 61/737,168, filed Dec. 14, 2012, entitled Modified Polynucleotides for the Production of Nuclear Proteins; U.S. Provisional Patent Application No. 61/618,922, filed Apr. 2, 2012, entitled Modified Polynucleotides for the Production of Proteins; U.S. Provisional Patent Application No. 61/681,675, filed Aug. 10, 2012, entitled Modified Polynucleotides for the Production of Proteins; U.S. Provisional Patent Application No. 61/737,174, filed Dec. 14, 2012, entitled Modified Polynucleotides for the Production of Proteins; U.S. Provisional Patent Application No. 61/618,935, filed Apr. 2, 2012, entitled Modified Polynucleotides for the Production of Proteins Associated with Human Disease; U.S. Provisional Patent Application No. 61/681,687, filed Aug. 10, 2012, entitled Modified Polynucleotides for the Production of Proteins Associated with Human Disease; U.S. Provisional Patent Application No. 61/737,184, filed Dec. 14, 2012, entitled Modified Polynucleotides for the Production of Proteins Associated with Human Disease; U.S. Provisional Patent Application No. 61/618,945, filed Apr. 2, 2012, entitled Modified Polynucleotides for the Production of Proteins Associated with Human Disease; U.S. Provisional Patent Application No. 61/681,696, filed Aug. 10, 2012, entitled Modified Polynucleotides for the Production of Proteins Associated with Human Disease; U.S. Provisional Patent Application No. 61/737,191, filed Dec. 14, 2012, entitled Modified Polynucleotides for the Production of Proteins Associated with Human Disease; U.S. Provisional Patent Application No. 61/618,953, filed Apr. 2, 2012, entitled Modified Polynucleotides for the Production of Proteins Associated with Human Disease; U.S. Provisional Patent Application No. 61/681,704, filed Aug. 10, 2012, entitled Modified Polynucleotides for the Production of Proteins Associated with Human Disease; U.S. Provisional Patent Application No. 61/737,203, filed Dec. 14, 2012, entitled Modified Polynucleotides for the Production of Proteins Associated with Human Disease; U.S. Provisional Patent Application No. 61/681,720, filed Aug. 10, 2012, entitled Modified Polynucleotides for the Production of Cosmetic Proteins and Peptides; U.S. Provisional Patent Application No. 61/737,213, filed Dec. 14, 2012, entitled Modified Polynucleotides for the Production of Cosmetic Proteins and Peptides; U.S. Provisional Patent Application No. 61/681,742, filed Aug. 10, 2012, entitled Modified Polynucleotides for the Production of Oncology-Related Proteins and Peptides; International Application No PCT/US2013/030062, filed Mar. 9, 2013, entitled Modified Polynucleotides for the Production of Biologics and Proteins Associated with Human Disease; U.S. patent application Ser. No. 13/791,922, filed Mar. 9, 2013, entitled Modified Polynucleotides for the Production of Biologics and Proteins Associated with Human Disease; International Application No PCT/US2013/030063, filed Mar. 9, 2013, entitled Modified Polynucleotides; International Application No. PCT/US2013/030064, entitled Modified Polynucleotides for the Production of Secreted Proteins; U.S. patent application Ser. No. 13/791,921, filed Mar. 9, 2013, entitled Modified Polynucleotides for the Production of Secreted Proteins; International Application No PCT/US2013/030059, filed Mar. 9, 2013, entitled Modified Polynucleotides for the Production of Membrane Proteins; International Application No. PCT/US2013/030066, filed Mar. 9, 2013, entitled Modified Polynucleotides for the Production of Cytoplasmic and Cytoskeletal Proteins; International Application No. PCT/US2013/030067, filed Mar. 9, 2013, entitled Modified Polynucleotides for the Production of Nuclear Proteins; International Application No. PCT/US2013/030060, filed Mar. 9, 2013, entitled Modified Polynucleotides for the Production of Proteins; International Application No. PCT/US2013/030061, filed Mar. 9, 2013, entitled Modified Polynucleotides for the Production of Proteins Associated with Human Disease; U.S. patent application Ser. No. 13/791,910, filed Mar. 9, 2013, entitled Modified Polynucleotides for the Production of Proteins Associated with Human Disease; International Application No. PCT/US2013/030068, filed Mar. 9, 2013, entitled Modified Polynucleotides for the Production of Cosmetic Proteins and Peptides; and International Application No. PCT/US2013/030070, filed Mar. 9, 2013, entitled Modified Polynucleotides for the Production of Oncology-Related Proteins and Peptides; International Patent Application No. PCT/US2013/031821, filed Mar. 15, 2013, entitled In Vivo Production of Proteins; the contents of each of which are herein incorporated by reference in their entireties.

Formulations and delivery of modified polynucleotides are described in, for example, co-pending and co-owned International Publication No WO2013090648, filed Dec. 14, 2012, entitled Modified Nucleoside, Nucleotide, Nucleic Acid Compositions and US Publication No US20130156849, filed Dec. 14, 2012, entitled Modified Nucleoside, Nucleotide, Nucleic Acid Compositions; the contents of each of which are herein incorporated by reference in their entireties.

There is a need in the art, therefore, for biological modalities to address the modulation of intracellular translation of nucleic acids. The present invention addresses this need by providing methods and compositions for the manufacture and optimization of modified mRNA molecules via alteration of the terminal architecture of the molecules.

SUMMARY OF THE INVENTION

Disclosed herein are methods of stabilizing or inducing increased protein expression from a modified mRNA. In another method, a cell is contacted with a modified mRNA encoding a polypeptide of interest in combination with a modified mRNA encoding one or more RNA binding proteins.

In one embodiment, provided herein are terminally optimized mRNA comprising first region of linked nucleosides encoding a polypeptide of interest which is located 5' relative to the first region, a second terminal region located 3' relative to the first terminal region and a 3'tailing region. The first terminal region may comprise at least one translation enhancer element (TEE) such as, but not limited to, the TEEs described in Table 28 such as, but not limited to, TEE-001-TEE-705.

The first terminal region may comprise a 5'untranslated region (UTR) which may be the native 5'UTR of the encoded polypeptide of interest or may be heterologous to the encoded polypeptide of interest. In one aspect, the 5'UTR may comprise at least one translation initiation sequence such as a kozak sequence, an internal ribosome entry site (IRES) and/or a fragment thereof. As a non-limiting example, the 5'UTR may comprise at least one fragment of an IRES. As another non-limiting example, the 5'UTR may comprise at least 5 fragments of an IRES. In another aspect, the 5'UTR may comprise a structured UTR.

The second terminal region may comprise at least one microRNA binding site, seed sequence or microRNA binding site without a seed sequence. In one aspect, the microRNA is an immune cell specific microRNA such as, but not limited to, mir-122, miR-142-3p, miR-142-5p, miR-146a and miR-146b.

In one embodiment, the 3'tailing region may comprise a chain terminating nucleoside such as, but not limited to, 3'-deoxyadenosine (cordycepin), 3'-deoxyuridine, 3'-deoxycytosine, 3'-deoxyguanosine, 3'-deoxythymine, 2',3'-dideoxynucleosides, 2',3'-dideoxyadenosine, 2',3'-dideoxyuridine, 2',3'-dideoxycytosine, 2',3'-dideoxyguanosine, 2',3'-dideoxythymine, a 2'-deoxynucleoside, and —O—methylnucleoside. In one aspect, the 3' tailing region is a stem loop sequence or a polyA tail.

In one embodiment, provided herein are terminally optimized mRNA comprising first region of linked nucleosides encoding a polypeptide of interest which is located 5' relative to the first region, a second terminal region located 3' relative to the first terminal region and a 3'tailing region of linked nucleosides and at least one chain terminating nucleoside located 3' relative to the terminally optimized mRNA. In one aspect, the second terminal region may comprise at least one microRNA binding site, seed sequence or microRNA binding site without a seed sequence. In one aspect, the microRNA is an immune cell specific microRNA such as, but not limited to, mir-122, miR-142-3p, miR-142-5p, miR-146a and miR-146b.

The terminally optimized mRNA described herein may comprise at least one modified nucleoside. In one embodiment, the terminally optimized mRNA comprises a pseudouridine analog such as, but not limited to, 1-carboxymethyl-pseudouridine, 1-propynyl-pseudouridine, 1-taurinomethyl-pseudouridine, 1-taurinomethyl-4-thio-pseudouridine, 1-methyl-pseudouridine (m$^1$ψ), 1-methyl-4-thio-pseudouridine (m$^1$s$^4$ψ), 4-thio-1-methyl-pseudouridine, 3-methyl-pseudouridine (m$^3$ψ), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thio-pseudouridine, N1-methyl-pseudouridine, 1-methyl-3-(3-amino-3-carboxypropyl)pseudouridine (acp$^3$ ψ), and 2'-O-methyl-pseudouridine (ψm). In another embodiment, the terminally optimized mRNA comprises the pseudouridine analog 1-methylpseudouridine. In yet another embodiment, the terminally optimized mRNA comprises the pseudouridine analog 1-methylpseudouridine and comprises the modified nucleoside 5-methylcytidine.

The terminally optimized mRNA described herein may comprise at least one 5' cap structure such as, but not limited to, Cap0, Cap1, ARCA, inosine, N1-methyl-guanosine, 2'fluoro-guanosine, 7-deaza-guanosine, 8-oxo-guanosine, 2-amino-guanosine, LNA-guanosine, 2-azido-guanosine, Cap2, Cap4, and CAP-003-CAP-225.

In one aspect, at least one region of the terminally optimized mRNA may be codon optimized. As a non-limiting example, the first region of linked nucleosides may be codon optimized.

Also provided herein are methods of using the terminally optimized mRNA.

In one embodiment, provided is a method of reducing antigen-mediated immune response in an organism by contacting the organism with a terminally optimized mRNA. The terminally optimized mRNA may comprise a first region of linked nucleosides encoding a polypeptide of interest which is located 5' relative to the first region, a second terminal region located 3' relative to the first terminal region and a 3'tailing region. The second terminal region may comprise at least one microRNA binding site, seed sequence or microRNA binding site without a seed sequence. In one aspect, the microRNA is an immune cell specific microRNA such as, but not limited to, mir-122, miR-142-3p, miR-142-5p, miR-146a and miR-146b.

In a another embodiment, terminally optimized mRNA which reduces the antigen-mediated immune response may comprise at least one translation enhancer element (TEE) sequence such as, but not limited to, TEE-001-TEE 705, a chain terminating nucleoside and/or a stem loop sequence.

In yet another embodiment, terminally optimized mRNA which reduces the antigen-mediated immune response may comprise at least one region which is codon optimized. As a non-limiting example, the first region of linked nucleosides may be codon optimized.

The details of various embodiments of the invention are set forth in the description below. Other features, objects, and advantages of the invention will be apparent from the description and the drawings, and from the claims.

DETAILED DESCRIPTION

Figure 1:
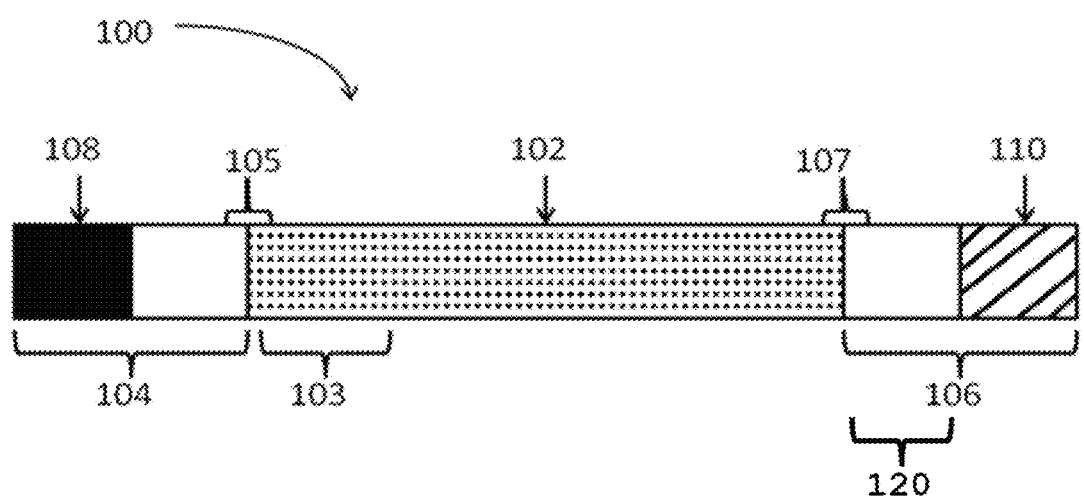
FIG. 1 is a schematic of a primary construct of the present invention.

Described herein are compositions and methods for the manufacture and optimization of modified mRNA molecules via alteration of the terminal architecture of the molecules. Specifically disclosed are methods for increasing protein production by altering the terminal regions of the mRNA. Such terminal regions include at least the 5'untranslated region (UTR), and 3'UTR. Other features which may be modified and found to the 5' or 3' of the coding region include the 5'cap and poly-A tail of the modified mRNAs (modified RNAs).

In general, exogenous nucleic acids, particularly viral nucleic acids, introduced into cells induce an innate immune response, resulting in interferon (IFN) production and cell death. However, it is of great interest for therapeutics, diagnostics, reagents and for biological assays to deliver a nucleic acid, e.g., a ribonucleic acid (RNA) inside a cell, either in vivo or ex vivo, such as to cause intracellular translation of the nucleic acid and production of the encoded protein. Of particular importance is the delivery and function of a non-integrative nucleic acid, as nucleic acids characterized by integration into a target cell are generally imprecise in their expression levels, deleteriously transferable to progeny and neighbor cells, and suffer from the substantial risk of mutation.

The terminal modification described herein may be used in the modified nucleic acids encoding polypeptides of interest, such as, but not limited to, the polypeptides of interest described in, U.S. Provisional Patent Application No. 61/618,862, filed Apr. 2, 2012, entitled Modified Polynucleotides for the Production of Biologics, U.S. Provisional Patent Application No. 61/681,645, filed Aug. 10, 2012, entitled Modified Polynucleotides for the Production of Biologics, U.S. Provisional Patent Application No. 61/737,130, filed Dec. 14, 2012, entitled Modified Polynucleotides for the Production of Biologics, U.S. Provisional Patent Application No. 61/618,866, filed Apr. 2, 2012, entitled Modified Polynucleotides for the Production of Antibodies, U.S. Provisional Patent Application No. 61/681,647, filed Aug. 10, 2012, entitled Modified Polynucleotides for the Production of Antibodies, U.S. Provisional Patent Application No. 61/737,134, filed Dec. 14, 2012, entitled Modified Polynucleotides for the Production of Antibodies, U.S. Provisional Patent Application No. 61/618,868, filed Apr. 2, 2012, entitled Modified Polynucleotides for the Production of Vaccines, U.S. Provisional Patent Application No. 61/681,648, filed Aug. 10, 2012, entitled Modified Polynucleotides for the Production of Vaccines, U.S. Provisional Patent Application No. 61/737,135, filed Dec. 14, 2012, entitled Modified Polynucleotides for the Production of Vaccines, U.S. Provisional Patent Application No. 61/618,870, filed Apr. 2, 2012, entitled Modified Polynucleotides for the Production of Therapeutic Proteins and Peptides, U.S. Provisional Patent Application No. 61/681,649, filed Aug. 10, 2012, entitled Modified Polynucleotides for the Production of Therapeutic Proteins and Peptides, U.S. Provisional Patent Application No. 61/737,139, filed Dec. 14, 2012, Modified Polynucleotides for the Production of Therapeutic Proteins and Peptides, U.S. Provisional Patent Application No. 61/618,873, filed Apr. 2, 2012, entitled Modified Polynucleotides for the Production of Secreted Proteins, U.S. Provisional Patent Application No. 61/681,650, filed Aug. 10, 2012, entitled Modified Polynucleotides for the Production of Secreted Proteins, U.S. Provisional Patent Application No. 61/737,147, filed Dec. 14, 2012, entitled Modified Polynucleotides for the Production of Secreted Proteins, U.S. Provisional Patent Application No. 61/618,878, filed Apr. 2, 2012, entitled Modified Polynucleotides for the Production of Plasma Membrane Proteins, U.S. Provisional Patent Application No. 61/681,654, filed Aug. 10, 2012, entitled Modified Polynucleotides for the Production of Plasma Membrane Proteins, U.S. Provisional Patent Application No. 61/737,152, filed Dec. 14, 2012, entitled Modified Polynucleotides for the Production of Plasma Membrane Proteins, U.S. Provisional Patent Application No. 61/618,885, filed Apr. 2, 2012, entitled Modified Polynucleotides for the Production of Cytoplasmic and Cytoskeletal Proteins, U.S. Provisional Patent Application No. 61/681,658, filed Aug. 10, 2012, entitled Modified Polynucleotides for the Production of Cytoplasmic and Cytoskeletal Proteins, U.S. Provisional Patent Application No. 61/737,155, filed Dec. 14, 2012, entitled Modified Polynucleotides for the Production of Cytoplasmic and Cytoskeletal Proteins, U.S. Provisional Patent Application No. 61/618,896, filed Apr. 2, 2012, entitled Modified Polynucleotides for the Production of Intracellular Membrane Bound Proteins, U.S. Provisional Patent Application No. 61/668,157, filed Jul. 5, 2012, entitled Modified Polynucleotides for the Production of Intracellular Membrane Bound Proteins, U.S. Provisional Patent Application No. 61/681,661, filed Aug. 10, 2012, entitled Modified Polynucleotides for the Production of Intracellular Membrane Bound Proteins, U.S. Provisional Patent Application No. 61/737,160, filed Dec. 14, 2012, entitled Modified Polynucleotides for the Production of Intracellular Membrane Bound Proteins, U.S. Provisional Patent Application No. 61/618,911, filed Apr. 2, 2012, entitled Modified Polynucleotides for the Production of Nuclear Proteins, U.S. Provisional Patent Application No. 61/681,667, filed Aug. 10, 2012, entitled Modified Polynucleotides for the Production of Nuclear Proteins, U.S. Provisional Patent Application No. 61/737,168, filed Dec. 14, 2012, entitled Modified Polynucleotides for the Production of Nuclear Proteins, U.S. Provisional Patent Application No. 61/618,922, filed Apr. 2, 2012, entitled Modified Polynucleotides for the Production of Proteins, U.S. Provisional Patent Application No. 61/681,675, filed Aug. 10, 2012, entitled Modified Polynucleotides for the Production of Proteins, U.S. Provisional Patent Application No. 61/737,174, filed Dec. 14, 2012, entitled Modified Polynucleotides for the Production of Proteins, U.S. Provisional Patent Application No. 61/618,935, filed Apr. 2, 2012, entitled Modified Polynucleotides for the Production of Proteins Associated with Human Disease, U.S. Provisional Patent Application No. 61/681,687, filed Aug. 10, 2012, entitled Modified Polynucleotides for the Production of Proteins Associated with Human Disease, U.S. Provisional Patent Application No. 61/737,184, filed Dec. 14, 2012, entitled Modified Polynucleotides for the Production of Proteins Associated with Human Disease, U.S. Provisional Patent Application No. 61/618,945, filed Apr. 2, 2012, entitled Modified Polynucleotides for the Production of Proteins Associated with Human Disease, U.S. Provisional Patent Application No. 61/681,696, filed Aug. 10, 2012, entitled Modified Polynucleotides for the Production of Proteins Associated with Human Disease, U.S. Provisional Patent Application No. 61/737,191, filed Dec. 14, 2012, entitled Modified Polynucleotides for the Production of Proteins Associated with Human Disease, U.S. Patent Application No. 61/618,953, filed Apr. 2, 2012, entitled Modified Polynucleotides for the Production of Proteins Associated with Human Disease, U.S. Patent Application No. 61/681,704, filed Aug. 10, 2012, entitled Modified Polynucleotides for the Production of Proteins Associated with Human Disease, U.S. Patent Application No. 61/737,203, filed Dec. 14, 2012, entitled Modified Polynucleotides for the Production of Proteins Associated with Human Disease, International Application No PCT/US2013/030062, filed Mar. 9, 2013, entitled Modified Polynucleotides for the Production of Biologics and Proteins Associated with Human Disease; International Application No PCT/US2013/030063, filed Mar. 9, 2013, entitled Modified Polynucloetides; International Application No. PCT/US2013/030064, entitled Modified Polynucleotides for the Production of Secreted Proteins; International Application No PCT/US2013/030059, filed Mar. 9, 2013, entitled Modified Polynucleotides for the Production of Membrane Proteins; International Application No. PCT/US2013/030066, filed Mar. 9, 2013, entitled Modified Polynucleotides for the Production of Cytoplasmic and Cytoskeletal Proteins; International Application No. PCT/US2013/030067, filed Mar. 9, 2013, entitled Modified Polynucleotides for the Production of Nuclear Proteins; International Application No. PCT/US2013/030060, filed Mar. 9, 2013, entitled Modified Polynucleotides for the Production of Proteins; International Application No. PCT/US2013/030061, filed Mar. 9, 2013, entitled Modified Polynucleotides for the Production of Proteins Associated with Human Disease; International Application No. PCT/US2013/030068, filed Mar. 9, 2013, entitled Modified Polynucleotides for the Production of Cosmetic Proteins and Peptides; International Application No. PCT/US2013/030070, filed Mar. 9, 2013, entitled Modified Polynucleotides for the Production of Oncology-Related Proteins and Peptides; and International Application No. PCT/US2013/031821, filed Mar. 15, 2013, entitled In Vivo Production of Proteins, U.S. Provisional Patent Application No. 61/753,661, filed Jan. 17, 2013, entitled Signal-Sensor Polynucleotide for the Alteration of Cellular Phenotypes and Microenvironments, U.S. Provisional Patent Application No. 61/754,159, filed Jan. 18, 2013, entitled Signal-Sensor Polynucleotide for the Alteration of Cellular Phenotypes and Microenvironments, U.S. Provisional Patent Application No. 61/781,097, filed Mar. 14, 2013, entitled Signal-Sensor Polynucleotide for the Alteration of Cellular Phenotypes and Microenvironments, U.S. Provisional Patent Application No. 61/829,334, filed May 31, 2013, entitled Signal-Sensor Polynucleotide for the Alteration of Cellular Phenotypes and Microenvironments, U.S. Provisional Patent Application No. 61/729,933, filed Nov. 26, 2012, entitled Terminally Optimized Modified RNAs, U.S. Provisional Patent Application No. 61/737,224, filed Dec. 14, 2012, entitled Terminally Optimized Modified RNAs, U.S. Provisional Patent Application No. 61/758,921, filed Jan. 31, 2013, entitled Differential Targeting Using RNA Constructs, U.S. Provisional Patent Application No. 61/781,139, filed Mar. 14, 2013, entitled Differential Targeting Using RNA Constructs, U.S. Provisional Application No. 61/829,359, filed May 31, 2013, entitled Differential Targeting Using RNA Constructs, the contents of each of which are herein incorporated by reference in their entireties.

Provided herein in part are nucleic acid molecules encoding polypeptides capable of modulating a cell's status, function and/or activity, and methods of making and using these nucleic acids and polypeptides. As described herein and in co-pending and co-owned International Publication No WO2012019168 filed Aug. 5, 2011, International Publication No WO2012045082 filed Oct. 3, 2011, International Publication No WO2012045075 filed Oct. 3, 2011, International Publication No WO2013052523 filed Oct. 3, 2012, and International Publication No WO2013090648 filed Dec. 14, 2012, the contents of each of which are incorporated by reference herein in their entirety, these modified nucleic acid molecules are capable of reducing the innate immune activity of a population of cells into which they are introduced, thus increasing the efficiency of protein production in that cell population.

In addition to utilization of non-natural nucleosides and nucleotides, such as those described in US Patent Publication No US20130115272, filed Oct. 3, 2012 (the contents of which are herein incorporated by reference in its entirety), in the modified RNAs of the present invention, it has now been discovered that concomitant use of altered terminal architecture may also serve to increase protein production from a cell population.

I. Compositions of the Invention

This invention provides nucleic acid molecules, including RNAs such as mRNAs, which may be synthetic, that contain one or more modified nucleosides (termed "modified nucleic acids" or "modified nucleic acid molecules") and polynucleotides, primary constructs and modified mRNA (mmRNA), which have useful properties including the lack of a substantial induction of the innate immune response of a cell into which the mRNA is introduced. Because these modified nucleic acids enhance the efficiency of protein production, intracellular retention of nucleic acids, and viability of contacted cells, as well as possess reduced immunogenicity, these nucleic acids having these properties are termed "enhanced" nucleic acids or modified RNAs herein.

In one embodiment, the polynucleotides are nucleic acid transcripts which encode one or more polypeptides of interest that, when translated, deliver a signal to the cell which results in the therapeutic benefit to the organism. The signal polynucleotides may optionally further comprise a sequence (translatable or not) which sense the microenvironement of the polynucleotide and alters (a) the function or phenotype outcome associated with the peptide or protein which is translated, (b) the expression level of the signal polynucleotide, and/or both.

The term "nucleic acid," in its broadest sense, includes any compound and/or substance that comprise a polymer of nucleotides. These polymers are often referred to as polynucleotides.

Exemplary nucleic acids include ribonucleic acids (RNAs), deoxyribonucleic acids (DNAs), threose nucleic acids (TNAs), glycol nucleic acids (GNAs), peptide nucleic acids (PNAs), locked nucleic acids (LNAs) or hybrids thereof. They may also include RNAi-inducing agents, RNAi agents, siRNAs, shRNAs, miRNAs, antisense RNAs, ribozymes, catalytic DNA, tRNA, RNAs that induce triple helix formation, aptamers, vectors, etc. In preferred embodiments, the modified nucleic acid molecule is one or more messenger RNAs (mRNAs).

In preferred embodiments, the polynucleotide or nucleic acid molecule is a messenger RNA (mRNA). As used herein, the term "messenger RNA" (mRNA) refers to any polynucleotide which encodes a polypeptide of interest and which is capable of being translated to produce the encoded polypeptide of interest in vitro, in vivo, in situ or ex vivo. Polynucleotides of the invention may be mRNA or any nucleic acid molecule and may or may not be chemically modified.

Traditionally, the basic components of an mRNA molecule include at least a coding region, a 5'UTR, a 3'UTR, a 5' cap and a poly-A tail. Building on this wild type modular structure, the present invention expands the scope of functionality of traditional mRNA molecules by providing polynucleotides or primary RNA constructs which maintain a modular organization, but which comprise one or more structural and/or chemical modifications or alterations which impart useful properties to the polynucleotide including, in some embodiments, the lack of a substantial induction of the innate immune response of a cell into which the polynucleotide is introduced. As such, modified mRNA molecules of the present invention, which may be synthetic, are termed "mmRNA." As used herein, a "structural" feature or modification is one in which two or more linked nucleotides are inserted, deleted, duplicated, inverted or randomized in a polynucleotide polynucleotide, primary construct or mmRNA without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" may be chemically modified to "AT-5meC-G". The same polynucleotide may be structurally modified from "ATCG" to "ATCCCG". Here, the dinucleotide "CC" has been inserted, resulting in a structural modification to the polynucleotide.

Provided are modified nucleic acids containing a translatable region and one, two, or more than two different nucleoside modifications. In some embodiments, the modified nucleic acid exhibits reduced degradation in a cell into which the nucleic acid is introduced, relative to a corresponding unmodified nucleic acid.

In some embodiments, the chemical modifications can be located on the sugar moiety of the nucleotide In some embodiments, the chemical modifications can be located on the phosphate backbone of the nucleotide In certain embodiments it is desirable to intracellularly degrade a modified nucleic acid introduced into the cell, for example if precise timing of protein production is desired. Thus, the invention provides a modified nucleic acid containing a degradation domain, which is capable of being acted on in a directed manner within a cell.

Polynucleotide, Primary Construct or mmRNA Architecture

The polynucleotides of the present invention are distinguished from wild type mRNA in their functional and/or structural design features which serve to, as evidenced herein, overcome existing problems of effective polypeptide production using nucleic acid-based therapeutics.

FIG. 1 shows a representative primary construct 100 of the present invention. As used herein, the term "primary construct" or "primary mRNA construct" refers to polynucleotide transcript which encodes one or more polypeptides of interest and which retains sufficient structural and/or chemical features to allow the polypeptide of interest encoded therein to be translated. Primary constructs may be polynucleotides of the invention. When structurally or chemically modified, the primary construct may be referred to as a mmRNA.

Returning to FIG. 1, the primary construct 100 here contains a first region of linked nucleotides 102 that is flanked by a first flanking region 104 and a second flaking region 106. As used herein, the "first region" may be referred to as a "coding region" or "region encoding" or simply the "first region." This first region may include, but is not limited to, the encoded polypeptide of interest. The polypeptide of interest may comprise at its 5' terminus one or more signal peptide sequences encoded by a signal peptide sequence region 103. The flanking region 104 may comprise a region of linked nucleotides comprising one or more complete or incomplete 5' UTRs sequences. The flanking region 104 may also comprise a 5' terminal cap 108. The second flanking region 106 may comprise a region of linked nucleotides comprising one or more complete or incomplete 3' UTRs. The flanking region 106 may also comprise a 3' tailing sequence 110 and a 3'UTR 120.

Bridging the 5' terminus of the first region 102 and the first flanking region 104 is a first operational region 105. Traditionally this operational region comprises a start codon. The operational region may alternatively comprise any translation initiation sequence or signal including a start codon.

Bridging the 3' terminus of the first region 102 and the second flanking region 106 is a second operational region 107. Traditionally this operational region comprises a stop codon. The operational region may alternatively comprise any translation initiation sequence or signal including a stop codon. According to the present invention, multiple serial stop codons may also be used. In one embodiment, the operation region of the present invention may comprise two stop codons. The first stop codon may be "TGA" and the second stop codon may be selected from the group consisting of "TAA," "TGA" and "TAG." The operation region may further comprise three stop codons. The third stop codon may be selected from the group consisting of "TAA," "TGA" and "TAG."

Figure 2:
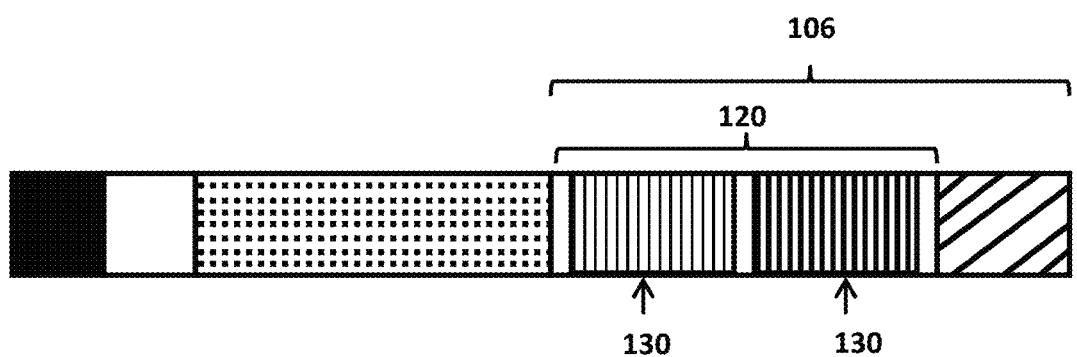
FIG. 2 is an expanded schematic of the second flanking region of a primary construct of the present invention illustrating the sensor elements of the polynucleotide.

Turning to FIG. 2, the 3'UTR 120 of the second flanking region 106 may comprise one or more sensor sequences 130. These sensor sequences as discussed herein operate as pseudo-receptors (or binding sites) for ligands of the local microenvironment of the primary construct or polynucleotide. For example, microRNA bindng sites or miRNA seeds may be used as sensors such that they function as pseudoreceptors for any microRNAs present in the environment of the polynucleotide.

Generally, the shortest length of the first region of the primary construct of the present invention can be the length of a nucleic acid sequence that is sufficient to encode for a dipeptide, a tripeptide, a tetrapeptide, a pentapeptide, a hexapeptide, a heptapeptide, an octapeptide, a nonapeptide, or a decapeptide. In another embodiment, the length may be sufficient to encode a peptide of 2-30 amino acids, e.g. 5-30, 10-30, 2-25, 5-25, 10-25, or 10-20 amino acids. The length may be sufficient to encode for a peptide of at least 11, 12, 13, 14, 15, 17, 20, 25 or 30 amino acids, or a peptide that is no longer than 40 amino acids, e.g. no longer than 35, 30, 25, 20, 17, 15, 14, 13, 12, 11 or 10 amino acids. Examples of dipeptides that the polynucleotide sequences can encode or include, but are not limited to, carnosine and anserine.

Generally, the length of the first region encoding the polypeptide of interest of the present invention is greater than about 30 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000, 4,000, 5,000, 6,000, 7,000, 8,000, 9,000, 10,000, 20,000, 30,000, 40,000, 50,000, 60,000, 70,000, 80,000, 90,000 or up to and including 100,000 nucleotides). As used herein, the "first region" may be referred to as a "coding region" or "region encoding" or simply the "first region."

In some embodiments, the polynucleotide polynucleotide, primary construct, or mmRNA includes from about 30 to about 100,000 nucleotides (e.g., from 30 to 50, from 30 to 100, from 30 to 250, from 30 to 500, from 30 to 1,000, from 30 to 1,500, from 30 to 3,000, from 30 to 5,000, from 30 to 7,000, from 30 to 10,000, from 30 to 25,000, from 30 to 50,000, from 30 to 70,000, from 100 to 250, from 100 to 500, from 100 to 1,000, from 100 to 1,500, from 100 to 3,000, from 100 to 5,000, from 100 to 7,000, from 100 to 10,000, from 100 to 25,000, from 100 to 50,000, from 100 to 70,000, from 100 to 100,000, from 500 to 1,000, from 500 to 1,500, from 500 to 2,000, from 500 to 3,000, from 500 to 5,000, from 500 to 7,000, from 500 to 10,000, from 500 to 25,000, from 500 to 50,000, from 500 to 70,000, from 500 to 100,000, from 1,000 to 1,500, from 1,000 to 2,000, from 1,000 to 3,000, from 1,000 to 5,000, from 1,000 to 7,000, from 1,000 to 10,000, from 1,000 to 25,000, from 1,000 to 50,000, from 1,000 to 70,000, from 1,000 to 100,000, from 1,500 to 3,000, from 1,500 to 5,000, from 1,500 to 7,000, from 1,500 to 10,000, from 1,500 to 25,000, from 1,500 to 50,000, from 1,500 to 70,000, from 1,500 to 100,000, from 2,000 to 3,000, from 2,000 to 5,000, from 2,000 to 7,000, from 2,000 to 10,000, from 2,000 to 25,000, from 2,000 to 50,000, from 2,000 to 70,000, and from 2,000 to 100,000).

According to the present invention, the first and second flanking regions may range independently from 15-1,000 nucleotides in length (e.g., greater than 30, 40, 45, 50, 55, 60, 70, 80, 90, 100, 120, 140, 160, 180, 200, 250, 300, 350, 400, 450, 500, 600, 700, 800, and 900 nucleotides or at least 30, 40, 45, 50, 55, 60, 70, 80, 90, 100, 120, 140, 160, 180, 200, 250, 300, 350, 400, 450, 500, 600, 700, 800, 900, and 1,000 nucleotides).

According to the present invention, the tailing sequence may range from absent to 500 nucleotides in length (e.g., at least 60, 70, 80, 90, 120, 140, 160, 180, 200, 250, 300, 350, 400, 450, or 500 nucleotides). Where the tailing region is a polyA tail, the length may be determined in units of or as a function of polyA binding protein binding. In this embodiment, the polyA tail is long enough to bind at least 4 monomers of polyA binding protein. PolyA binding protein monomers bind to stretches of approximately 38 nucleotides. As such, it has been observed that polyA tails of about 80 nucleotides and 160 nucleotides are functional.

According to the present invention, the capping region may comprise a single cap or a series of nucleotides forming the cap. In this embodiment the capping region may be from 1 to 10, e.g. 2-9, 3-8, 4-7, 1-5, 5-10, or at least 2, or 10 or fewer nucleotides in length. In some embodiments, the cap is absent.

According to the present invention, the first and second operational regions may range from 3 to 40, e.g., 5-30, 10-20, 15, or at least 4, or 30 or fewer nucleotides in length and may comprise, in addition to a start and/or stop codon, one or more signal and/or restriction sequences.

Cyclic Polynucleotides

According to the present invention, a nucleic acid, modified RNA or primary construct may be cyclized, or concatemerized, to generate a translation competent molecule to assist interactions between poly-A binding proteins and 5'-end binding proteins. The mechanism of cyclization or concatemerization may occur through at least 3 different routes: 1) chemical, 2) enzymatic, and 3) ribozyme catalyzed. The newly formed 5'-/3'-linkage may be intramolecular or intermolecular.

In the first route, the 5'-end and the 3'-end of the nucleic acid contain chemically reactive groups that, when close together, form a new covalent linkage between the 5'-end and the 3'-end of the molecule. The 5'-end may contain an NHS-ester reactive group and the 3'-end may contain a 3'-amino-terminated nucleotide such that in an organic solvent the 3'-amino-terminated nucleotide on the 3'-end of a synthetic mRNA molecule will undergo a nucleophilic attack on the 5'-NHS-ester moiety forming a new 5'-/3'-amide bond.

In the second route, T4 RNA ligase may be used to enzymatically link a 5'-phosphorylated nucleic acid molecule to the 3'-hydroxyl group of a nucleic acid forming a new phosphorodiester linkage. In an example reaction, 1 µg of a nucleic acid molecule is incubated at 37° C. for 1 hour with 1-10 units of T4 RNA ligase (New England Biolabs, Ipswich, Mass.) according to the manufacturer's protocol. The ligation reaction may occur in the presence of a split oligonucleotide capable of base-pairing with both the 5'- and 3'-region in juxtaposition to assist the enzymatic ligation reaction.

In the third route, either the 5'- or 3'-end of the cDNA template encodes a ligase ribozyme sequence such that during in vitro transcription, the resultant nucleic acid molecule can contain an active ribozyme sequence capable of ligating the 5'-end of a nucleic acid molecule to the 3'-end of a nucleic acid molecule. The ligase ribozyme may be derived from the Group I Intron, Group I Intron, Hepatitis Delta Virus, Hairpin ribozyme or may be selected by SELEX (systematic evolution of ligands by exponential enrichment). The ribozyme ligase reaction may take 1 to 24 hours at temperatures between 0 and 37° C.

Polynucleotide Multimers

According to the present invention, multiple distinct nucleic acids, modified RNA or primary constructs may be linked together through the 3'-end using nucleotides which are modified at the 3'-terminus. Chemical conjugation may be used to control the stoichiometry of delivery into cells. For example, the glyoxylate cycle enzymes, isocitrate lyase and malate synthase, may be supplied into HepG2 cells at a 1:1 ratio to alter cellular fatty acid metabolism. This ratio may be controlled by chemically linking nucleic acids or modified RNA using a 3'-azido terminated nucleotide on one nucleic acids or modified RNA species and a C5-ethynyl or alkynyl-containing nucleotide on the opposite nucleic acids or modified RNA species. The modified nucleotide is added post-transcriptionally using terminal transferase (New England Biolabs, Ipswich, Mass.) according to the manufacturer's protocol. After the addition of the 3'-modified nucleotide, the two nucleic acids or modified RNA species may be combined in an aqueous solution, in the presence or absence of copper, to form a new covalent linkage via a click chemistry mechanism as described in the literature.

In another example, more than two polynucleotides may be linked together using a functionalized linker molecule. For example, a functionalized saccharide molecule may be chemically modified to contain multiple chemical reactive groups (SH—, $NH_2$—, $N_3$, etc. ... ) to react with the cognate moiety on a 3'-functionalized mRNA molecule (i.e., a 3'-maleimide ester, 3'-NHS-ester, alkynyl). The number of reactive groups on the modified saccharide can be controlled in a stoichiometric fashion to directly control the stoichiometric ratio of conjugated nucleic acid or mRNA.

Modified RNA Conjugates and Combinations

In order to further enhance protein production, nucleic acids, modified RNA, polynucleotides or primary constructs of the present invention can be designed to be conjugated to other polynucleotides, dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases, proteins, e.g., glycoproteins, or peptides, e.g., molecules having a specific affinity for a co-ligand, or antibodies e.g., an antibody, that binds to a specified cell type such as a cancer cell, endothelial cell, or bone cell, hormones and hormone receptors, non-peptidic species, such as lipids, lectins, carbohydrates, vitamins, cofactors, or a drug.

Conjugation may result in increased stability and/or half life and may be particularly useful in targeting the nucleic acids, modified RNA, polynucleotides or primary constructs to specific sites in the cell, tissue or organism.

According to the present invention, the nucleic acids, modified RNA or primary construct may be administered with, or further encode one or more of RNAi agents, siRNAs, shRNAs, miRNAs, miRNA binding sites, antisense RNAs, ribozymes, catalytic DNA, tRNA, RNAs that induce triple helix formation, aptamers or vectors, and the like.

Bifunctional Polynucleotides

In one embodiment of the invention are bifunctional polynucleotides (e.g., bifunctional nucleic acids, bifunctional modified RNA or bifunctional primary constructs). As the name implies, bifunctional polynucleotides are those having or capable of at least two functions. These molecules may also by convention be referred to as multi-functional.

The multiple functionalities of bifunctional polynucleotides may be encoded by the RNA (the function may not manifest until the encoded product is translated) or may be a property of the polynucleotide itself. It may be structural or chemical. Bifunctional modified polynucleotides may comprise a function that is covalently or electrostatically associated with the polynucleotides. Further, the two functions may be provided in the context of a complex of a modified RNA and another molecule.

Bifunctional polynucleotides may encode peptides which are anti-proliferative. These peptides may be linear, cyclic, constrained or random coil. They may function as aptamers, signaling molecules, ligands or mimics or mimetics thereof. Anti-proliferative peptides may, as translated, be from 3 to 50 amino acids in length. They may be 5-40, 10-30, or approximately 15 amino acids long. They may be single chain, multichain or branched and may form complexes, aggregates or any multi-unit structure once translated.

Noncoding Polynucleotides

As described herein, provided are nucleic acids, modified RNA, polynucleotides and primary constructs having sequences that are partially or substantially not translatable, e.g., having a noncoding region. Such molecules are generally not translated, but can exert an effect on protein production by one or more of binding to and sequestering one or more translational machinery components such as a ribosomal protein or a transfer RNA (tRNA), thereby effectively reducing protein expression in the cell or modulating one or more pathways or cascades in a cell which in turn alters protein levels. The nucleic acids, polynucleotides, primary constructs or mRNA may contain or encode one or more long noncoding RNA (lncRNA, or lincRNA) or portion thereof, a small nucleolar RNA (sno-RNA), micro RNA (miRNA), small interfering RNA (siRNA) or Piwi-interacting RNA (piRNA).

Polypeptides of Interest

According to the present invention, the primary construct is designed to encode one or more polypeptides of interest or fragments thereof. A polypeptide of interest may include, but is not limited to, whole polypeptides, a plurality of polypeptides or fragments of polypeptides, which independently may be encoded by one or more nucleic acids, a plurality of nucleic acids, fragments of nucleic acids or variants of any of the aforementioned. As used herein, the term "polypeptides of interest" refers to any polypeptide which is selected to be encoded in the primary construct of the present invention. As used herein, "polypeptide" means a polymer of amino acid residues (natural or unnatural) linked together most often by peptide bonds. The term, as used herein, refers to proteins, polypeptides, and peptides of any size, structure, or function. In some instances the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. They may also comprise single chain or multichain polypeptides such as antibodies or insulin and may be associated or linked. Most commonly disulfide linkages are found in multichain polypeptides. The term polypeptide may also apply to amino acid polymers in which one or more amino acid residues are an artificial chemical analogue of a corresponding naturally occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence.

In some embodiments "variant mimics" are provided. As used herein, the term "variant mimic" is one which contains one or more amino acids which would mimic an activated sequence. For example, glutamate may serve as a mimic for phosphoro-threonine and/or phosphoro-serine. Alternatively, variant mimics may result in deactivation or in an inactivated product containing the mimic, e.g., phenylalanine may act as an inactivating substitution for tyrosine; or alanine may act as an inactivating substitution for serine.

"Homology" as it applies to amino acid sequences is defined as the percentage of residues in the candidate amino acid sequence that are identical with the residues in the amino acid sequence of a second sequence after aligning the sequences and introducing gaps, if necessary, to achieve the maximum percent homology. Methods and computer programs for the alignment are well known in the art. It is understood that homology depends on a calculation of percent identity but may differ in value due to gaps and penalties introduced in the calculation.

By "homologs" as it applies to polypeptide sequences means the corresponding sequence of other species having substantial identity to a second sequence of a second species.

"Analogs" is meant to include polypeptide variants which differ by one or more amino acid alterations, e.g., substitutions, additions or deletions of amino acid residues that still maintain one or more of the properties of the parent or starting polypeptide.

The present invention contemplates several types of compositions which are polypeptide based including variants and derivatives. These include substitutional, insertional, deletion and covalent variants and derivatives. The term "derivative" is used synonymously with the term "variant" but generally refers to a molecule that has been modified and/or changed in any way relative to a reference molecule or starting molecule.

As such, polynucleotides encoding polypeptides of interest containing substitutions, insertions and/or additions, deletions and covalent modifications with respect to reference sequences are included within the scope of this invention. For example, sequence tags or amino acids, such as one or more lysines, can be added to the peptide sequences of the invention (e.g., at the N-terminal or C-terminal ends). Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to polypeptides are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid.

"Deletional variants" when referring to polypeptides are those with one or more amino acids in the native or starting amino acid sequence removed. Ordinarily, deletional variants will have one or more amino acids deleted in a particular region of the molecule.

"Covalent derivatives" when referring to polypeptides include modifications of a native or starting protein with an organic proteinaceous or non-proteinaceous derivatizing agent, and/or post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the polypeptides produced in accordance with the present invention.

Other post-translational modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)).

"Features" when referring to polypeptides are defined as distinct amino acid sequence-based components of a molecule. Features of the polypeptides encoded by the mmRNA of the present invention include surface manifestations, local conformational shape, folds, loops, half-loops, domains, half-domains, sites, termini or any combination thereof.

As used herein when referring to polypeptides the term "surface manifestation" refers to a polypeptide based component of a protein appearing on an outermost surface.

As used herein when referring to polypeptides the term "local conformational shape" means a polypeptide based structural manifestation of a protein which is located within a definable space of the protein.

As used herein when referring to polypeptides the term "fold" refers to the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of energetic forces. Regions formed in this way include hydrophobic and hydrophilic pockets, and the like.

As used herein the term "turn" as it relates to protein conformation means a bend which alters the direction of the backbone of a peptide or polypeptide and may involve one, two, three or more amino acid residues.

As used herein when referring to polypeptides the term "loop" refers to a structural feature of a polypeptide which may serve to reverse the direction of the backbone of a peptide or polypeptide. Where the loop is found in a polypeptide and only alters the direction of the backbone, it may comprise four or more amino acid residues. Oliva et al. have identified at least 5 classes of protein loops (J. Mol Biol 266 (4): 814-830; 1997). Loops may be open or closed. Closed loops or "cyclic" loops may comprise 2, 3, 4, 5, 6, 7, 8, 9, 10 or more amino acids between the bridging moieties. Such bridging moieties may comprise a cysteine-cysteine bridge (Cys-Cys) typical in polypeptides having disulfide bridges or alternatively bridging moieties may be non-protein based such as the dibromozylyl agents used herein.

As used herein when referring to polypeptides the term "half-loop" refers to a portion of an identified loop having at least half the number of amino acid resides as the loop from which it is derived. It is understood that loops may not always contain an even number of amino acid residues. Therefore, in those cases where a loop contains or is identified to comprise an odd number of amino acids, a half-loop of the odd-numbered loop will comprise the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+/−0.5 being 3 or 4).

As used herein when referring to polypeptides the term "domain" refers to a motif of a polypeptide having one or more identifiable structural or functional characteristics or properties (e.g., binding capacity, serving as a site for protein-protein interactions).

As used herein when referring to polypeptides the term "half-domain" means a portion of an identified domain having at least half the number of amino acid resides as the domain from which it is derived. It is understood that domains may not always contain an even number of amino acid residues. Therefore, in those cases where a domain contains or is identified to comprise an odd number of amino acids, a half-domain of the odd-numbered domain will comprise the whole number portion or next whole number portion of the domain (number of amino acids of the domain/2+/−0.5 amino acids). For example, a domain identified as a 7 amino acid domain could produce half-domains of 3 amino acids or 4 amino acids (7/2=3.5+/−0.5 being 3 or 4). It is also understood that sub-domains may be identified within domains or half-domains, these subdomains possessing less than all of the structural or functional properties identified in the domains or half domains from which they were derived. It is also understood that the amino acids that comprise any of the domain types herein need not be contiguous along the backbone of the polypeptide (i.e., nonadjacent amino acids may fold structurally to produce a domain, half-domain or subdomain).

As used herein when referring to polypeptides the terms "site" as it pertains to amino acid based embodiments is used synonymously with "amino acid residue" and "amino acid side chain." A site represents a position within a peptide or polypeptide that may be modified, manipulated, altered, derivatized or varied within the polypeptide based molecules of the present invention.

As used herein the terms "termini" or "terminus" when referring to polypeptides refers to an extremity of a peptide or polypeptide. Such extremity is not limited only to the first or final site of the peptide or polypeptide but may include additional amino acids in the terminal regions. The polypeptide based molecules of the present invention may be characterized as having both an N-terminus (terminated by an amino acid with a free amino group (NH2)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

Once any of the features have been identified or defined as a desired component of a polypeptide to be encoded by the primary construct or mmRNA of the invention, any of several manipulations and/or modifications of these features may be performed by moving, swapping, inverting, deleting, randomizing or duplicating. Furthermore, it is understood that manipulation of features may result in the same outcome as a modification to the molecules of the invention. For example, a manipulation which involved deleting a domain would result in the alteration of the length of a molecule just as modification of a nucleic acid to encode less than a full length molecule would.

Modifications and manipulations can be accomplished by methods known in the art such as, but not limited to, site directed mutagenesis. The resulting modified molecules may then be tested for activity using in vitro or in vivo assays such as those described herein or any other suitable screening assay known in the art.

According to the present invention, the polypeptides may comprise a consensus sequence which is discovered through rounds of experimentation. As used herein a "consensus" sequence is a single sequence which represents a collective population of sequences allowing for variability at one or more sites.

As recognized by those skilled in the art, protein fragments, functional protein domains, and homologous proteins are also considered to be within the scope of polypeptides of interest of this invention. For example, provided herein is any protein fragment (meaning an polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of about 20, about 30, about 40, about 50, or about 100 amino acids which are about 40%, about 50%, about 60%, about 70%, about 80%, about 90%, about 95%, or about 100% identical to any of the sequences described herein can be utilized in accordance with the invention. In certain embodiments, a polypeptide to be utilized in accordance with the invention includes 2, 3, 4, 5, 6, 7, 8, 9, 10, or more mutations as shown in any of the sequences provided or referenced herein.

Encoded Polypeptides of Interest

The primary constructs, modified nucleic acids or mmRNA of the present invention may be designed to encode polypeptides of interest such as peptides and proteins.

In one embodiment, primary constructs, modified nucleic acids or mmRNA of the present invention may encode variant polypeptides which have a certain identity with a reference polypeptide sequence. As used herein, a "reference polypeptide sequence" refers to a starting polypeptide sequence. Reference sequences may be wild type sequences or any sequence to which reference is made in the design of another sequence. A "reference polypeptide sequence" may, e.g., be any one of the protein sequence listed in U.S. Provisional Patent Application No. 61/618,862, filed Apr. 2, 2012, entitled Modified Polynucleotides for the Production of Biologics, U.S. Provisional Patent Application No. 61/681,645, filed Aug. 10, 2012, entitled Modified Polynucleotides for the Production of Biologics, U.S. Provisional Patent Application No. 61/737,130, filed Dec. 14, 2012, entitled Modified Polynucleotides for the Production of Biologics, U.S. Provisional Patent Application No. 61/618,866, filed Apr. 2, 2012, entitled Modified Polynucleotides for the Production of Antibodies, U.S. Provisional Patent Application No. 61/681,647, filed Aug. 10, 2012, entitled Modified Polynucleotides for the Production of Antibodies, U.S. Provisional Patent Application No. 61/737,134, filed Dec. 14, 2012, entitled Modified Polynucleotides for the Production of Antibodies, U.S. Provisional Patent Application No. 61/618,868, filed Apr. 2, 2012, entitled Modified Polynucleotides for the Production of Vaccines, U.S. Provisional Patent Application No. 61/681,648, filed Aug. 10, 2012, entitled Modified Polynucleotides for the Production of Vaccines, U.S. Provisional Patent Application No. 61/737,135, filed Dec. 14, 2012, entitled Modified Polynucleotides for the Production of Vaccines, U.S. Provisional Patent Application No. 61/618,870, filed Apr. 2, 2012, entitled Modified Polynucleotides for the Production of Therapeutic Proteins and Peptides, U.S. Provisional Patent Application No. 61/681,649, filed Aug. 10, 2012, entitled Modified Polynucleotides for the Production of Therapeutic Proteins and Peptides, U.S. Provisional Patent Application No. 61/737,139, filed Dec. 14, 2012, Modified Polynucleotides for the Production of Therapeutic Proteins and Peptides, U.S. Provisional Patent Application No. 61/618,873, filed Apr. 2, 2012, entitled Modified Polynucleotides for the Production of Secreted Proteins, U.S. Provisional Patent Application No. 61/681,650, filed Aug. 10, 2012, entitled Modified Polynucleotides for the Production of Secreted Proteins, U.S. Provisional Patent Application No. 61/737,147, filed Dec. 14, 2012, entitled Modified Polynucleotides for the Production of Secreted Proteins, U.S. Provisional Patent Application No. 61/618,878, filed Apr. 2, 2012, entitled Modified Polynucleotides for the Production of Plasma Membrane Proteins, U.S. Provisional Patent Application No. 61/681,654, filed Aug. 10, 2012, entitled Modified Polynucleotides for the Production of Plasma Membrane Proteins, U.S. Provisional Patent Application No. 61/737,152, filed Dec. 14, 2012, entitled Modified Polynucleotides for the Production of Plasma Membrane Proteins, U.S. Provisional Patent Application No. 61/618,885, filed Apr. 2, 2012, entitled Modified Polynucleotides for the Production of Cytoplasmic and Cytoskeletal Proteins, U.S. Provisional Patent Application No. 61/681,658, filed Aug. 10, 2012, entitled Modified Polynucleotides for the Production of Cytoplasmic and Cytoskeletal Proteins, U.S. Provisional Patent Application No. 61/737,155, filed Dec. 14, 2012, entitled Modified Polynucleotides for the Production of Cytoplasmic and Cytoskeletal Proteins, U.S. Provisional Patent Application No. 61/618,896, filed Apr. 2, 2012, entitled Modified Polynucleotides for the Production of Intracellular Membrane Bound Proteins, U.S. Provisional Patent Application No. 61/668,157, filed Jul. 5, 2012, entitled Modified Polynucleotides for the Production of Intracellular Membrane Bound Proteins, U.S. Provisional Patent Application No. 61/681,661, filed Aug. 10, 2012, entitled Modified Polynucleotides for the Production of Intracellular Membrane Bound Proteins, U.S. Provisional Patent Application No. 61/737,160, filed Dec. 14, 2012, entitled Modified Polynucleotides for the Production of Intracellular Membrane Bound Proteins, U.S. Provisional Patent Application No. 61/618,911, filed Apr. 2, 2012, entitled Modified Polynucleotides for the Production of Nuclear Proteins, U.S. Provisional Patent Application No. 61/681,667, filed Aug. 10, 2012, entitled Modified Polynucleotides for the Production of Nuclear Proteins, U.S. Provisional Patent Application No. 61/737,168, filed Dec. 14, 2012, entitled Modified Polynucleotides for the Production of Nuclear Proteins, U.S. Provisional Patent Application No. 61/618,922, filed Apr. 2, 2012, entitled Modified Polynucleotides for the Production of Proteins, U.S. Provisional Patent Application No. 61/681,675, filed Aug. 10, 2012, entitled Modified Polynucleotides for the Production of Proteins, U.S. Provisional Patent Application No. 61/737,174, filed Dec. 14, 2012, entitled Modified Polynucleotides for the Production of Proteins, U.S. Provisional Patent Application No. 61/618,935, filed Apr. 2, 2012, entitled Modified Polynucleotides for the Production of Proteins Associated with Human Disease, U.S. Provisional Patent Application No. 61/681,687, filed Aug. 10, 2012, entitled Modified Polynucleotides for the Production of Proteins Associated with Human Disease, U.S. Provisional Patent Application No. 61/737,184, filed Dec. 14, 2012, entitled Modified Polynucleotides for the Production of Proteins Associated with Human Disease, U.S. Provisional Patent Application No. 61/618,945, filed Apr. 2, 2012, entitled Modified Polynucleotides for the Production of Proteins Associated with Human Disease, U.S. Provisional Patent Application No. 61/681,696, filed Aug. 10, 2012, entitled Modified Polynucleotides for the Production of Proteins Associated with Human Disease, U.S. Provisional Patent Application No. 61/737,191, filed Dec. 14, 2012, entitled Modified Polynucleotides for the Production of Proteins Associated with Human Disease, U.S. Patent Application No. 61/618,953, filed Apr. 2, 2012, entitled Modified Polynucleotides for the Production of Proteins Associated with Human Disease, U.S. Patent Application No. 61/681,704, filed Aug. 10, 2012, entitled Modified Polynucleotides for the Production of Proteins Associated with Human Disease, U.S. Patent Application No. 61/737,203, filed Dec. 14, 2012, entitled Modified Polynucleotides for the Production of Proteins Associated with Human Disease, International Application No PCT/US2013/030062, filed Mar. 9, 2013, entitled Modified Polynucleotides for the Production of Biologics and Proteins Associated with Human Disease; International Application No PCT/US2013/030063, filed Mar. 9, 2013, entitled Modified Polynucloetides; International Application No. PCT/US2013/030064, entitled Modified Polynucleotides for the Production of Secreted Proteins; International Application No PCT/US2013/030059, filed Mar. 9, 2013, entitled Modified Polynucleotides for the Production of Membrane Proteins; International Application No. PCT/US2013/030066, filed Mar. 9, 2013, entitled Modified Polynucleotides for the Production of Cytoplasmic and Cytoskeletal Proteins; International Application No. PCT/US2013/030067, filed Mar. 9, 2013, entitled Modified Polynucleotides for the Production of Nuclear Proteins; International Application No. PCT/US2013/030060, filed Mar. 9, 2013, entitled Modified Polynucleotides for the Production of Proteins; International Application No. PCT/US2013/030061, filed Mar. 9, 2013, entitled Modified Polynucleotides for the Production of Proteins Associated with Human Disease; International Application No. PCT/US2013/030068, filed Mar. 9, 2013, entitled Modified Polynucleotides for the Production of Cosmetic Proteins and Peptides; International Application No. PCT/US2013/030070, filed Mar. 9, 2013, entitled Modified Polynucleotides for the Production of Oncology-Related Proteins and Peptides; and International Application No. PCT/US2013/031821, filed Mar. 15, 2013, entitled In Vivo Production of Proteins, the contents of each of which are herein incorporated by reference in their entireties.

The term "identity" as known in the art, refers to a relationship between the sequences of two or more peptides, as determined by comparing the sequences. In the art, identity also means the degree of sequence relatedness between peptides, as determined by the number of matches between strings of two or more amino acid residues. Identity measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

In some embodiments, the polypeptide variant may have the same or a similar activity as the reference polypeptide. Alternatively, the variant may have an altered activity (e.g., increased or decreased) relative to a reference polypeptide. Generally, variants of a particular polynucleotide or polypeptide of the invention will have at least about 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.) Other tools are described herein, specifically in the definition of "identity."

Default parameters in the BLAST algorithm include, for example, an expect threshold of 10, Word size of 28, Match/Mismatch Scores 1, −2, Gap costs Linear. Any filter can be applied as well as a selection for species specific repeats, e.g., *Homo sapiens*.

In one embodiment, the polynucleotides, primary constructs, modified nucleic acids and/or mmRNA may be used to treat a disease, disorder and/or condition in a subject.

In one embodiment, the polynucleotides, primary constructs, modified nucleic acids and/or mmRNA may be used to reduce, eliminate or prevent tumor growth in a subject.

In one embodiment, the polynucleotides, primary constructs and/or mmRNA may be used to reduce and/or ameliorate at least one symptom of cancer in a subject. A symptom of cancer may include, but is not limited to, weakness, aches and pains, fever, fatigue, weight loss, blood clots, increased blood calcium levels, low white blood cell count, short of breath, dizziness, headaches, hyperpigmentation, jaundice, erthema, pruritis, excessive hair growth, change in bowel habits, change in bladder function, long-lasting sores, white patches inside the mouth, white spots on the tongue, unusual bleeding or discharge, thickening or lump on parts of the body, indigestion, trouble swallowing, changes in warts or moles, change in new skin and nagging cough or hoarseness. Further, the polynucleotides, primary constructs, modified nucleic acid and/or mmRNA may reduce a side-effect associated with cancer such as, but not limited to, chemo brain, peripheral neuropathy, fatigue, depression, nausea, vomiting, pain, anemia, lymphedema, infections, sexual side effects, reduced fertility or infertility, ostomics, insomnia and hair loss.

Terminal Architecture Modifications: Untranslated Regions (UTRs)

Untranslated regions (UTRs) of a gene are transcribed but not translated. The 5'UTR starts at the transcription start site and continues to the start codon but does not include the start codon; whereas, the 3'UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the nucleic acids or modified RNA of the present invention to enhance the stability of the molecule. The specific features can also be incorporated to ensure controlled down-regulation of the transcript in case they are misdirected to undesired organs sites. The untranslated regions may be incorporated into a vector system which can produce mRNA and/or be delivered to a cell, tissue and/or organism to produce a polypeptide of interest.

5' UTR and Translation Initiation

Natural 5'UTRs bear features which play roles in for translation initiation. They harbor signatures like Kozak sequences which are commonly known to be involved in the process by which the ribosome initiates translation of many genes. Kozak sequences have the consensus CCR(A/G) CCAUGG, where R is a purine (adenine or guanine) three bases upstream of the start codon (AUG), which is followed by another 'G'. 5'UTR also have been known to form secondary structures which are involved in elongation factor binding.

5'UTR secondary structures involved in elongation factor binding can interact with other RNA binding molecules in the 5'UTR or 3'UTR to regulate gene expression. For example, the elongation factor EIF4A2 binding to a secondarily structured element in the 5'UTR is necessary for microRNA mediated repression (Meijer H A et al., Science, 2013, 340, 82-85, herein incorporated by reference in its entirety). The different secondary structures in the 5'UTR can be incorporated into the flanking region to either stabilize or selectively destalized mRNAs in specific tissues or cells.

By engineering the features typically found in abundantly expressed genes of specific target organs, one can enhance the stability and protein production of the nucleic acids or mRNA of the invention. For example, introduction of 5' UTR of liver-expressed mRNA, such as albumin, serum amyloid A, Apolipoprotein A/B/E, transferrin, alpha fetoprotein, erythropoietin, or Factor VIII, could be used to enhance expression of a nucleic acid molecule, such as a mmRNA, in hepatic cell lines or liver. Likewise, use of 5' UTR from other tissue-specific mRNA to improve expression in that tissue is possible—for muscle (MyoD, Myosin, Myoglobin, Myogenin, Herculin), for endothelial cells (Tie-1, CD36), for myeloid cells (C/EBP, AML1, G-CSF, GM-CSF, CD11b, MSR, Fr-1, i-NOS), for leukocytes (CD45, CD18), for adipose tissue (CD36, GLUT4, ACRP30, adiponectin) and for lung epithelial cells (SP-A/B/C/D).

Other non-UTR sequences may be incorporated into the 5' (or 3' UTR) UTRs. For example, introns or portions of introns sequences may be incorporated into the flanking regions of the nucleic acids or mRNA of the invention. Incorporation of intronic sequences may increase protein production as well as mRNA levels.

In one embodiment, at least one fragment of IRES sequences from a GTX gene may be included in the 5'UTR. As a non-limiting example, the fragment may be an 18 nucleotide sequence from the IRES of the GTX gene. As another non-limiting example, an 18 nucleotide sequence fragment from the IRES sequence of a GTX gene may be tandemly repeated in the 5'UTR of a polynucleotide described herein. The 18 nucleotide sequence may be repeated in the 5'UTR at least one, at least twice, at least three times, at least four times, at least five times, at least six times, at least seven times, at least eight times, at least nine times or more than ten times In one embodiment, a 5'UTR may include at least five 18 nucleotide fragments of IRES sequences from a GTX gene may be included in the 5'UTR (see e.g., the 18 nucleotide fragment described in Table 62).

Nucleotides may be mutated, replaced and/or removed from the 5' (or 3') UTRs. For example, one or more nucleotides upstream of the start codon may be replaced with another nucleotide. The nucleotide or nucleotides to be replaced may be 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more than 60 nucleotides upstream of the start codon. As another example, one or more nucleotides upstream of the start codon may be removed from the UTR.

In one embodiment, at least one purine upstream of the start codon may be replaced with a pyrimidine. The purine to be replaced may be 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more than 60 nucleotides upstream of the start codon. As a non-limiting example, an adenine which is three nucleotides upstream of the start codon may be replaced with a thymine. As another non-limiting example, an adenine which is nine nucleotides upstream of the start codon may be replaced with a thymine.

In one embodiment, at least one nucleotide upstream of the start codon may be removed from the UTR. In one aspect, 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more than 60 nucleotides upstream of the start codon may be removed from the UTR of the polynucleotides described herein. As a non-limiting example, the nine nucleotides upstream of the start codon may be removed from the UTR (See e.g., the G-CSF 9de15' construct described in Table 60).
5'UTR, 3'UTR and Translation Enhancer Elements (TEEs)

In one embodiment, the 5'UTR of the polynucleotides, primary constructs, modified nucleic acids and/or mmRNA may include at least one translational enhancer polynucleotide, translation enhancer element, translational enhancer elements (collectively referred to as "TEE"s). As a non-limiting example, the TEE may be located between the transcription promoter and the start codon. The polynucleotides, primary constructs, modified nucleic acids and/or mmRNA with at least one TEE in the 5'UTR may include a cap at the 5'UTR. Further, at least one TEE may be located in the 5'UTR of polynucleotides, primary constructs, modified nucleic acids and/or mmRNA undergoing cap-dependent or cap-independent translation.

The term "translational enhancer element" or "translation enhancer element" (herein collectively referred to as "TEE") refers to sequences that increase the amount of polypeptide or protein produced from an mRNA.

In one aspect, TEEs are conserved elements in the UTR which can promote translational activity of a nucleic acid such as, but not limited to, cap-dependent or cap-independent translation. The conservation of these sequences has been previously shown by Panek et al (Nucleic Acids Research, 2013, 1-10; herein incorporated by reference in its entirety) across 14 species including humans.

In one embodiment, the TEE may be any of the TEEs listed in Table 32 in Example 45, including portion and/or fragments thereof. The TEE sequence may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in Table 32 and/or the TEE sequence may include a 5-30 nucleotide fragment, a 5-25 nucleotide fragment, a 5-20 nucleotide fragment, a 5-15 nucleotide fragment, a 5-10 nucleotide fragment of the TEE sequences disclosed in Table 32.

In one non-limiting example, the TEEs known may be in the 5'-leader of the Gtx homeodomain protein (Chappell et al., Proc. Natl. Acad. Sci. USA 101:9590-9594, 2004, herein incorporated by reference in their entirety).

In another non-limiting example, TEEs are disclosed as SEQ ID NOs: 1-35 in US Patent Publication No. US20090226470, SEQ ID NOs: 1-35 in US Patent Publication US20130177581, SEQ ID NOs: 1-35 in International Patent Publication No. WO2009075886, SEQ ID NOs: 1-5, and 7-645 in International Patent Publication No. WO2012009644, SEQ ID NO: 1 in International Patent Publication No. WO1999024595, SEQ ID NO: 1 in U.S. Pat. No. 6,310,197, and SEQ ID NO: 1 in U.S. Pat. No. 6,849,405, each of which is herein incorporated by reference in its entirety.

In yet another non-limiting example, the TEE may be an internal ribosome entry site (IRES), HCV-IRES or an IRES element such as, but not limited to, those described in U.S. Pat. No. 7,468,275, US Patent Publication Nos. US20070048776 and US20110124100 and International Patent Publication Nos. WO2007025008 and WO2001055369, each of which is herein incorporated by reference in its entirety. The IRES elements may include, but are not limited to, the Gtx sequences (e.g., Gtx9-nt, Gtx8-nt, Gtx7-nt) described by Chappell et al. (Proc. Natl. Acad. Sci. USA 101:9590-9594, 2004) and Zhou et al. (PNAS 102: 6273-6278, 2005) and in US Patent Publication Nos. US20070048776 and US20110124100 and International Patent Publication No. WO2007025008, each of which is herein incorporated by reference in its entirety.

"Translational enhancer polynucleotides" or "translation enhancer polynucleotide sequences" are polynucleotides which include one or more of the specific TEE exemplified herein and/or disclosed in the art (see e.g., U.S. Pat. Nos. 6,310,197, 6,849,405, 7,456,273, 7,183,395, US20090226470, US20070048776, US20110124100, US20090093049, US20130177581, WO2009075886, WO2007025008, WO2012009644, WO2001055371 WO1999024595, and EP2610341A1 and EP2610340A1; each of which is herein incorporated by reference in its entirety) or their variants, homologs or functional derivatives. One or multiple copies of a specific TEE can be present in the polynucleotides, primary constructs, modified nucleic acids and/or mmRNA. The TEEs in the translational enhancer polynucleotides can be organized in one or more sequence segments. A sequence segment can harbor one or more of the specific TEEs exemplified herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the specific TEEs exemplified herein, identical or different number of copies of each of the specific TEEs, and/or identical or different organization of the TEEs within each sequence segment.

In one embodiment, the polynucleotides, primary constructs, modified nucleic acids and/or mmRNA may include at least one TEE that is described in International Patent Publication No. WO1999024595, WO2012009644, WO2009075886, WO2007025008, WO1999024595, European Patent Publication No. EP2610341A1 and EP2610340A1, U.S. Pat. Nos. 6,310,197, 6,849,405, 7,456, 273, 7,183,395, US Patent Publication No. US20090226470, US20110124100, US20070048776, US20090093049, and US20130177581 each of which is herein incorporated by reference in its entirety. The TEE may be located in the 5'UTR of the polynucleotides, primary constructs, modified nucleic acids and/or mmRNA.

In another embodiment, the polynucleotides, primary constructs, modified nucleic acids and/or mmRNA may include at least one TEE that has at least 50%, at least 55%, at least 60%, at least 65%, at least 70%, at least 75%, at least 80%, at least 85%, at least 90%, at least 95% or at least 99% identity with the TEEs described in US Patent Publication Nos. US20090226470, US20070048776, US20130177581 and US20110124100, International Patent Publication No. WO1999024595, WO2012009644, WO2009075886 and WO2007025008, European Patent Publication No. EP2610341A1 and EP2610340A1, U.S. Pat. Nos. 6,310,197, 6,849,405, 7,456,273, 7,183,395, each of which is herein incorporated by reference in its entirety.

In one embodiment, the 5'UTR of the polynucleotides, primary constructs, modified nucleic acids and/or mmRNA may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 5'UTR of the polynucleotides, primary constructs, modified nucleic acids and/or mmRNA of the present invention may be the same or different TEE sequences. The TEE sequences may be in a pattern such as ABABAB or AABBAABBAABB or ABCABCABC or variants thereof repeated once, twice, or more than three times. In these patterns, each letter, A, B, or C represent a different TEE sequence at the nucleotide level.

In one embodiment, the 5'UTR may include a spacer to separate two TEE sequences. As a non-limiting example, the spacer may be a 15 nucleotide spacer and/or other spacers known in the art. As another non-limiting example, the 5'UTR may include a TEE sequence-spacer module repeated at least once, at least twice, at least 3 times, at least 4 times, at least 5 times, at least 6 times, at least 7 times, at least 8 times and at least 9 times or more than 9 times in the 5'UTR.

In another embodiment, the spacer separating two TEE sequences may include other sequences known in the art which may regulate the translation of the polynucleotides, primary constructs, modified nucleic acids and/or mmRNA of the present invention such as, but not limited to, miR sequences described herein (e.g., miR binding sites and miR seeds). As a non-limiting example, each spacer used to separate two TEE sequences may include a different miR sequence or component of a miR sequence (e.g., miR seed sequence).

In one embodiment, the TEE in the 5'UTR of the polynucleotides, primary constructs, modified nucleic acids and/or mmRNA of the present invention may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in US Patent Publication Nos. US20090226470, US20070048776, US20130177581 and US20110124100, International Patent Publication No. WO1999024595, WO2012009644, WO2009075886 and WO2007025008, European Patent Publication No. EP2610341A1 and EP2610340A1, U.S. Pat. Nos. 6,310,197, 6,849,405, 7,456, 273, 7,183,395. In another embodiment, the TEE in the 5'UTR of the polynucleotides, primary constructs, modified nucleic acids and/or mmRNA of the present invention may include a 5-30 nucleotide fragment, a 5-25 nucleotide fragment, a 5-20 nucleotide fragment, a 5-15 nucleotide fragment, a 5-10 nucleotide fragment of the TEE sequences disclosed in US Patent Publication Nos. US20090226470, US20070048776, US20130177581 and US20110124100, International Patent Publication No. WO1999024595, WO2012009644, WO2009075886 and WO2007025008, European Patent Publication No. EP2610341A1 and EP2610340A1, U.S. Pat. Nos. 6,310,197, 6,849,405, 7,456, 273, 7,183,395; each of which are herein incorporated by reference in their entirety.

In one embodiment, the TEE in the 5'UTR of the polynucleotides, primary constructs, modified nucleic acids and/or mmRNA of the present invention may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in Chappell et al. (Proc. Natl. Acad. Sci. USA 101:9590-9594, 2004) and Zhou et al. (PNAS 102:6273-6278, 2005), in Supplemental Table 1 and in Supplemental Table 2 disclosed by Wellensiek et al (Genome-wide profiling of human cap-independent translation-enhancing elements, Nature Methods, 2013; DOI: 10.1038/NMETH.2522); each of which is herein incorporated by reference in its entirety. In another embodiment, the TEE in the 5'UTR of the polynucleotides, primary constructs, modified nucleic acids and/or mmRNA of the present invention may include a 5-30 nucleotide fragment, a 5-25 nucleotide fragment, a 5-20 nucleotide fragment, a 5-15 nucleotide fragment, a 5-10 nucleotide fragment of the TEE sequences disclosed in Chappell et al. (Proc. Natl. Acad. Sci. USA 101:9590-9594, 2004) and Zhou et al. (PNAS 102:6273-6278, 2005), in Supplemental Table 1 and in Supplemental Table 2 disclosed by Wellensiek et al (Genome-wide profiling of human cap-independent translation-enhancing elements, Nature Methods, 2013; DOI:10.1038/NMETH.2522); each of which is herein incorporated by reference in its entirety.

In one embodiment, the TEE used in the 5'UTR of the polynucleotides, primary constructs, modified nucleic acids and/or mmRNA of the present invention is an IRES sequence such as, but not limited to, those described in U.S. Pat. No. 7,468,275 and International Patent Publication No. WO2001055369, each of which is herein incorporated by reference in its entirety.

In one embodiment, the TEEs used in the 5'UTR of the polynucleotides, primary constructs, modified nucleic acids and/or mmRNA of the present invention may be identified by the methods described in US Patent Publication No. US20070048776 and US20110124100 and International Patent Publication Nos. WO2007025008 and WO2012009644, each of which is herein incorporated by reference in its entirety.

In another embodiment, the TEEs used in the 5'UTR of the polynucleotides, primary constructs, modified nucleic acids and/or mmRNA of the present invention may be a transcription regulatory element described in U.S. Pat. Nos. 7,456,273 and 7,183,395, US Patent Publication No. US20090093049, and International Publication No. WO2001055371, each of which is herein incorporated by reference in their entirety. The transcription regulatory elements may be identified by methods known in the art, such as, but not limited to, the methods described in U.S. Pat. Nos. 7,456,273 and 7,183,395, US Patent Publication No. US20090093049, and International Publication No. WO2001055371, each of which is herein incorporated by reference in their entirety.

In yet another embodiment, the TEE used in the 5'UTR of the polynucleotides, primary constructs, modified nucleic acids and/or mmRNA of the present invention is an oligonucleotide or portion thereof as described in U.S. Pat. Nos. 7,456,273 and 7,183,395, US Patent Publication No. US20090093049, and International Publication No. WO2001055371, each of which is herein incorporated by reference in their entirety.

The 5' UTR comprising at least one TEE described herein may be incorporated in a monocistronic sequence such as, but not limited to, a vector system or a nucleic acid vector. As a non-limiting example, the vector systems and nucleic acid vectors may include those described in U.S. Pat. Nos. 7,456,273 and 7,183,395, US Patent Publication No. US20070048776, US20090093049 and US20110124100 and International Patent Publication Nos. WO2007025008 and WO2001055371, each of which is herein incorporated by reference in its entirety.

In one embodiment, the TEEs described herein may be located in the 5'UTR and/or the 3'UTR of the polynucleotides, primary constructs, modified nucleic acids and/or mmRNA. The TEEs located in the 3'UTR may be the same and/or different than the TEEs located in and/or described for incorporation in the 5'UTR.

In one embodiment, the 3'UTR of the polynucleotides, primary constructs, modified nucleic acids and/or mmRNA may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 3'UTR of the polynucleotides, primary constructs, modified nucleic acids and/or mmRNA of the present invention may be the same or different TEE sequences. The TEE sequences may be in a pattern such as ABABAB or AABBAABBAABB or ABCABCABC or variants thereof repeated once, twice, or more than three times. In these patterns, each letter, A, B, or C represent a different TEE sequence at the nucleotide level.

In one embodiment, the 3'UTR may include a spacer to separate two TEE sequences. As a non-limiting example, the spacer may be a 15 nucleotide spacer and/or other spacers known in the art. As another non-limiting example, the 3'UTR may include a TEE sequence-spacer module repeated at least once, at least twice, at least 3 times, at least 4 times, at least 5 times, at least 6 times, at least 7 times, at least 8 times and at least 9 times or more than 9 times in the 3'UTR.

In another embodiment, the spacer separating two TEE sequences may include other sequences known in the art which may regulate the translation of the polynucleotides, primary constructs, modified nucleic acids and/or mmRNA of the present invention such as, but not limited to, miR sequences described herein (e.g., miR binding sites and miR seeds). As a non-limiting example, each spacer used to separate two TEE sequences may include a different miR sequence or component of a miR sequence (e.g., miR seed sequence).

In one embodiment, the incorporation of a miR sequence and/or a TEE sequence changes the shape of the stem loop region which may increase and/or decrease translation. (see e.g, Kedde et al. A Pumilio-induced RNA structure switch in p27-3'UTR controls miR-221 and miR-22 accessibility. Nature Cell Biology. 2010, herein incorporated by reference in its entirety).

Heterologous 5'UTRs

A 5' UTR may be provided as a flanking region to the modified nucleic acids (mRNA), enhanced modified RNA or ribonucleic acids of the invention. 5'UTR may be homologous or heterologous to the coding region found in the modified nucleic acids (mRNA), enhanced modified RNA or ribonucleic acids of the invention. Multiple 5' UTRs may be included in the flanking region and may be the same or of different sequences. Any portion of the flanking regions, including none, may be codon optimized and any may independently contain one or more different structural or chemical modifications, before and/or after codon optimization.

Shown in Lengthy Table 21 in U.S. Provisional Application No. 61/775,509, filed Mar. 9, 2013, entitled Heterologous Untranslated Regions for mRNA and in Lengthy Table 21 and in Table 22 in U.S. Provisional Application No. 61/829,372, filed May 31, 2013, entitled Heterologous Untranslated Regions for mRNA, the contents of each of which is herein incorporated by reference in its entirety, is a listing of the start and stop site of the modified nucleic acids (mRNA), enhanced modified RNA or ribonucleic acids of the invention. In Table 21 each 5'UTR (5'UTR-005 to 5'UTR 68511) is identified by its start and stop site relative to its native or wild type (homologous) transcript (ENST; the identifier used in the ENSEMBL database).

Additional 5'UTR which may be used with the modified nucleic acids, enhanced modified RNA or ribonucleic acids of the invention are shown in the present disclosure in Table 6, Table 38 and Table 41.

To alter one or more properties of the polynucleotides, primary constructs or mmRNA of the invention, 5'UTRs which are heterologous to the coding region of the modified nucleic acids (mRNA), enhanced modified RNA or ribonucleic acids of the invention are engineered into compounds of the invention. The modified nucleic acids (mRNA), enhanced modified RNA or ribonucleic acids are then administered to cells, tissue or organisms and outcomes such as protein level, localization and/or half life are measured to evaluate the beneficial effects the heterologous 5'UTR may have on the modified nucleic acids (mRNA), enhanced modified RNA or ribonucleic acids of the invention. Variants of the 5' UTRs may be utilized wherein one or more nucleotides are added or removed to the termini, including A, T, C or G. 5'UTRs may also be codon-optimized or modified in any manner described herein.

Incorporating microRNA Binding Sites

In one embodiment modified nucleic acids (mRNA), enhanced modified RNA or ribonucleic acids of the invention would not only encode a polypeptide but also a sensor sequence. Sensor sequences include, for example, microRNA binding sites, transcription factor binding sites, structured mRNA sequences and/or motifs, artificial binding sites engineered to act as pseudo-receptors for endogenous nucleic acid binding molecules. Non-limiting examples, of polynucleotides comprising at least one sensor sequence are described in co-pending and co-owned U.S. Provisional Patent Application No. 61/753,661, filed Jan. 17, 2013, entitled Signal-Sensor Polynucleotide for the Alteration of Cellular Phenotypes and Microenvironments, U.S. Provisional Patent Application No. 61/754,159, filed Jan. 18, 2013, entitled Signal-Sensor Polynucleotide for the Alteration of Cellular Phenotypes and Microenvironments, U.S. Provisional Patent Application No. 61/781,097, filed Mar. 14, 2013, entitled Signal-Sensor Polynucleotide for the Alteration of Cellular Phenotypes and Microenvironments, U.S. Provisional Patent Application No. 61/829,334, filed May 31, 2013, entitled Signal-Sensor Polynucleotide for the Alteration of Cellular Phenotypes and Microenvironments, U.S. Provisional Patent Application No. 61/839,893, filed Jun. 27, 2013, entitled Signal-Sensor Polynucleotide for the Alteration of Cellular Phenotypes and Microenvironments, U.S. Provisional Patent Application No. 61/842,733, filed Jul. 3, 2013, entitled Signal-Sensor Polynucleotide for the Alteration of Cellular Phenotypes and Microenvironment, and U.S. Provisional Patent Application No. 61/857,304, filed Jul. 23, 2013, entitled Signla-Sensor Polynucleotide for the Alteration of Cellular Phenotypes and Microenvironment, the contents of each of which are herein incorporated by reference in its entirety.

In one embodiment, microRNA (miRNA) profiling of the target cells or tissues is conducted to determine the presence or absence of miRNA in the cells or tissues.

microRNAs (or miRNA) are 19-25 nucleotide long non-coding RNAs that bind to the 3'UTR of nucleic acid molecules and down-regulate gene expression either by reducing nucleic acid molecule stability or by inhibiting translation. The modified nucleic acids (mRNA), enhanced modified RNA or ribonucleic acids of the invention may comprise one or more microRNA target sequences, microRNA sequences, or microRNA seeds. Such sequences may correspond to any known microRNA such as those taught in US Publication US2005/0261218 and US Publication US2005/0059005, the contents of which are incorporated herein by reference in their entirety. As a non-limiting embodiment, known microRNAs, their sequences and seed sequences in human genome are listed below in Table 11.

A microRNA sequence comprises a "seed" region, i.e., a sequence in the region of positions 2-8 of the mature microRNA, which sequence has perfect Watson-Crick complementarity to the miRNA target sequence. A microRNA seed may comprise positions 2-8 or 2-7 of the mature microRNA. In some embodiments, a microRNA seed may comprise 7 nucleotides (e.g., nucleotides 2-8 of the mature microRNA), wherein the seed-complementary site in the corresponding miRNA target is flanked by an adenine (A) opposed to microRNA position 1. In some embodiments, a microRNA seed may comprise 6 nucleotides (e.g., nucleotides 2-7 of the mature microRNA), wherein the seed-complementary site in the corresponding miRNA target is flanked by an adenine (A) opposed to microRNA position 1. See for example, Grimson A, Farh K K, Johnston W K, Garrett-Engele P, Lim L P, Bartel D P; Mol Cell. 2007 Jul. 6; 27(1):91-105. The bases of the microRNA seed have complete complementarity with the target sequence. By engineering microRNA target sequences into the 3'UTR of nucleic acids or mRNA of the invention one can target the molecule for degradation or reduced translation, provided the microRNA in question is available. This process will reduce the hazard of off target effects upon nucleic acid molecule delivery. Identification of microRNA, microRNA target regions, and their expression patterns and role in biology have been reported (Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein; each of which is herein incorporated by reference in its entirety).

For example, if the mRNA is not intended to be delivered to the liver but ends up there, then miR-122, a microRNA abundant in liver, can inhibit the expression of the gene of interest if one or multiple target sites of miR-122 are engineered into the 3'UTR of the modified nucleic acids, enhanced modified RNA or ribonucleic acids. Introduction of one or multiple binding sites for different microRNA can be engineered to further decrease the longevity, stability, and protein translation of a modified nucleic acids, enhanced modified RNA or ribonucleic acids. As used herein, the term "microRNA site" refers to a microRNA target site or a microRNA recognition site, or any nucleotide sequence to which a microRNA binds or associates. It should be understood that "binding" may follow traditional Watson-Crick hybridization rules or may reflect any stable association of the microRNA with the target sequence at or adjacent to the microRNA site.

Conversely, for the purposes of the modified nucleic acids, enhanced modified RNA or ribonucleic acids of the present invention, microRNA binding sites can be engineered out of (i.e. removed from) sequences in which they naturally occur in order to increase protein expression in specific tissues. For example, miR-122 binding sites may be removed to improve protein expression in the liver.

In one embodiment, the modified nucleic acids, enhanced modified RNA or ribonucleic acids of the present invention may include at least one miRNA-binding site in the 3'UTR in order to direct cytotoxic or cytoprotective mRNA therapeutics to specific cells such as, but not limited to, normal and/or cancerous cells (e.g., HEP3B or SNU449).

In another embodiment, the modified nucleic acids, enhanced modified RNA or ribonucleic acids of the present invention may include three miRNA-binding sites in the 3'UTR in order to direct cytotoxic or cytoprotective mRNA therapeutics to specific cells such as, but not limited to, normal and/or cancerous cells (e.g., HEP3B or SNU449).

Regulation of expression in multiple tissues can be accomplished through introduction or removal or one or several microRNA binding sites. Shown below in Table 12, microRNAs which are differentially expressed in different tissues and cells, and often associated with different types of diseases (e.g. cancer cells). The decision of removal or insertion of microRNA binding sites, or any combination, is dependent on microRNA expression patterns and their profilings in diseases.

Examples of tissues where microRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126).

Specifically, microRNAs are known to be differentially expressed in immune cells (also called hematopoietic cells), such as antigen presenting cells (APCs) (e.g. dendritic cells and macrophages), macrophages, monocytes, B lymphocytes, T lymphocytes, granuocytes, natural killer cells, etc. Immune cell specific microRNAs are involved in immunogenicity, autoimmunity, the immune-response to infection, inflammation, as well as unwanted immune response after gene therapy and tissue/organ transplantation. Immune cells specific microRNAs also regulate many aspects of development, proliferation, differentiation and apoptosis of hematopoietic cells (immune cells). For example, miR-142 and miR-146 are exclusively expressed in the immune cells, particularly abundant in myeloid dendritic cells. It was demonstrated in the art that the immune response to exogenous nucleic acid molecules was shut-off by adding miR- 142 binding sites to the 3'UTR of the delivered gene construct, enabling more stable gene transfer in tissues and cells. miR-142 efficiently degrades the exogenous mRNA in antigen presenting cells and suppresses cytotoxic elimination of transuced cells (Annoni A et al., blood, 2009, 114, 5152-5161; Brown B D, et al., Nat med. 2006, 12(5), 585-591; Brown B D, et al., blood, 2007, 110(13): 4144-4152, each of which is herein incorporated by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing the miR-142 binding site into the 3'-UTR of a polypeptide of the present invention can selectively repress the gene expression in the antigen presenting cells through miR-142 mediated mRNA degradation, limiting antigen presentation in APCs (e.g. dendritic cells) and thereby preventing antigen-mediated immune response after the delivery of the polynucleotides. The polynucleotides are therefore stably expressed in target tissues or cells without triggering cytotoxic elimination.

In one embodiment, microRNAs binding sites that are known to be expressed in immune cells, in particular, the antigen presenting cells, can be engineered into the polynucleotide to suppress the expression of the sensor-signal polynucleotide in APCs through microRNA mediated RNA degradation, subduing the antigen-mediated immune response, while the expression of the polynucleotide is maintained in non-immune cells where the immune cell specific microRNAs are not expressed. For example, to prevent the immunogenic reaction caused by a liver specific protein expression, the miR-122 binding site can be removed and the miR-142 (and/or mirR-146) binding sites can be engineered into the 3-UTR of the polynucleotide.

To further drive the selective degradation and suppression of mRNA in APCs and macrophage, the polynucleotide may include another negative regulatory element in the 3-UTR, either alone or in combination with mir-142 and/or mir-146 binding sites. As a non-limiting example, one regulatory element is the Constitutive Decay Elements (CDEs).

Immune cells specific microRNAs include, but are not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-5p, hsa-let-7i-3p, hsa-let-7i-5p, miR-10a-3p, miR-10a-5p, miR-1184, hsa-let-7f-1-3p, hsa-let-7f-2-5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR-150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-197-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-5p, miR-29c-3p, miR-29c-5p, miR-30e-3p, miR-30e-5p, miR-331-5p, miR-339-3p, miR-339-5p, miR-345-3p, miR-345-5p, miR-346, miR-34a-3p, miR-34a-5p, miR-363-3p, miR-363-5p, miR-372, miR-377-3p, miR-377-5p, miR-493-3p, miR-493-5p, miR-542, miR-548b-5p, miR548c-5p, miR-548i, miR-548j, miR-548n, miR-574-3p, miR-598, miR-718, miR-935, miR-99a-3p, miR-99a-5p, miR-99b-3p and miR-99b-5p. microRNAs that are enriched in specific types of immune cells are listed in Table 13. Furthermore, novel miroRNAs are discovered in the immune cells in the art through micro-array hybridization and microtome analysis (Jima D D et al, Blood, 2010, 116:e118-e127; Vaz C et al., BMC Genomics, 2010, 11,288, the content of each of which is incorporated herein by reference in its entirety.)

MicroRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR-199b-3p, miR-199b-5p, miR-296-5p, miR-557, miR-581, miR-939-3p, miR-939-5p. MicroRNA binding sites from any liver specific microRNA can be introduced to or removed from the polynucleotides to regulate the expression of the polynucleotides in the liver. Liver specific microRNAs binding sites can be engineered alone or further in combination with immune cells (e.g. APCs) microRNA binding sites in order to prevent immune reaction against protein expression in the liver.

MicroRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, miR-381-5p. MicroRNA binding sites from any lung specific microRNA can be introduced to or removed from the polynucleotide to regulate the expression of the polynucleotide in the lung. Lung specific microRNAs binding sites can be engineered alone or further in combination with immune cells (e.g. APCs) microRNA binding sites in order to prevent an immune reaction against protein expression in the lung.

MicroRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451b, miR-499a-3p, miR-499a-5p, miR-499b-3p, miR-499b-5p, miR-744-3p, miR-744-5p, miR-92b-3p and miR-92b-5p. MicroRNA binding sites from any heart specific microRNA can be introduced to or removed from the polynucleotides to regulate the expression of the polynucleotides in the heart. Heart specific microRNAs binding sites can be engineered alone or further in combination with immune cells (e.g. APCs) microRNA binding sites to prevent an immune reaction against protein expression in the heart.

MicroRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-30c-5p, miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510, miR-516a-3p, miR-548b-5p, miR-548c-5p, miR-571, miR-7-1-3p, miR-7-2-3p, miR-7-5p, miR-802, miR-922, miR-9-3p and miR-9-5p. MicroRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, miR-657. MicroRNA binding sites from any CNS specific microRNA can be introduced to or removed from the polynucleotides to regulate the expression of the polynucleotide in the nervous system. Nervous system specific microRNAs binding sites can be engineered alone or further in combination with immune cells (e.g. APCs) microRNA binding sites in order to prevent immune reaction against protein expression in the nervous system.

MicroRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p and miR-944. MicroRNA binding sites from any pancreas specific microRNA can be introduced to or removed from the polynucleotide to regulate the expression of the polynucleotide in the pancreas. Pancreas specific microRNAs binding sites can be engineered alone or further in combination with immune cells (e.g. APCs) microRNA binding sites in order to prevent an immune reaction against protein expression in the pancreas.

MicroRNAs that are known to be expressed in the kidney further include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-30c-1-3p, miR-30c-2-3p, miR30c-5p, miR-324-3p, miR-335-3p, miR-335-5p, miR-363-3p, miR-363-5p and miR-562. MicroRNA binding sites from any kidney specific microRNA can be introduced to or removed from the polynucleotide to regulate the expression of the polynucleotide in the kidney. Kidney specific microRNAs binding sites can be engineered alone or further in combination with immune cells (e.g. APCs) microRNA binding sites to prevent an immune reaction against protein expression in the kidney.

MicroRNAs that are known to be expressed in the muscle further include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p and miR-25-5p. MicroRNA binding sites from any muscle specific microRNA can be introduced to or removed from the polynucleotide to regulate the expression of the polynucleotide in the muscle. Muscle specific microRNAs binding sites can be engineered alone or further in combination with immune cells (e.g. APCs) microRNA binding sites to prevent an immune reaction against protein expression in the muscle.

MicroRNAs are differentially expressed in different types of cells, such as endothelial cells, epithelial cells and adipocytes. For example, microRNAs that are expressed in endothelial cells include, but are not limited to, let-7b-3p, let-7b-5p, miR-100-3p, miR-100-5p, miR-101-3p, miR-101-5p, miR-126-3p, miR-126-5p, miR-1236-3p, miR-1236-5p, miR-130a-3p, miR-130a-5p, miR-17-5p, miR-17-3p, miR-18a-3p, miR-18a-5p, miR-19a-3p, miR-19a-5p, miR-19b-1-5p, miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p and miR-92b-5p. Many novel microRNAs are discovered in endothelial cells from deep-sequencing analysis (Voellenkle C et al., RNA, 2012, 18, 472-484, herein incorporated by reference in its entirety) microRNA binding sites from any endothelial cell specific microRNA can be introduced to or removed from the polynucleotide to modulate the expression of the polynucleotide in the endothelial cells in various conditions.

For further example, microRNAs that are expressed in epithelial cells include, but are not limited to, let-7b-3p, let-7b-5p, miR-1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR-34a, miR-34b-5p, miR-34c-5p, miR-449a, miR-449b-3p, miR-449b-5p specific in respiratory ciliated epithelial cells; let-7 family, miR-133a, miR-133b, miR-126 specific in lung epithelial cells; miR-382-3p, miR-382-5p specific in renal epithelial cells and miR-762 specific in corneal epithelial cells. MicroRNA binding sites from any epithelial cell specific MicroRNA can be introduced to or removed from the polynucleotide to modulate the expression of the polynucleotide in the epithelial cells in various conditions.

In addition, a large group of microRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (Kuppusamy K T et al., Curr. Mol Med, 2013, 13(5), 757-764; Vidigal J A and Ventura A, Semin Cancer Biol. 2012, 22(5-6), 428-436; Goff L A et al., PLoS One, 2009, 4:e7192; Morin R D et al., Genome Res, 2008, 18, 610-621; Yoo J K et al., Stem Cells Dev. 2012, 21(11), 2049-2057, each of which is herein incorporated by reference in its entirety). MicroRNAs abundant in embryonic stem cells include, but are not limited to, let-7a-2-3p, let-a-3p, let-7a-5p, let7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR-200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-548l, miR-548m, miR-548n, miR-548o-3p, miR-548o-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel microRNAs are discovered by deep sequencing in human embryonic stem cells (Morin R D et al., Genome Res, 2008, 18, 610-621; Goff L A et al., PLoS One, 2009, 4:e7192; Bar M et al., Stem cells, 2008, 26, 2496-2505, the content of each of which is incorporated herein by references in its entirety).

In one embodiment, the binding sites of embryonic stem cell specific microRNAs can be included in or removed from the 3-UTR of the polynucleotide to modulate the development and/or differentiation of embryonic stem cells, to inhibit the senescence of stem cells in a degenerative condition (e.g. degenerative diseases), or to stimulate the senescence and apoptosis of stem cells in a disease condition (e.g. cancer stem cells).

Many microRNA expression studies are conducted in the art to profile the differential expression of microRNAs in various cancer cells/tissues and other diseases. Some microRNAs are abnormally over-expressed in certain cancer cells and others are under-expressed. For example, microRNAs are differentially expressed in cancer cells (WO2008/154098, US2013/0059015, US2013/0042333, WO2011/157294); cancer stem cells (US2012/0053224); pancreatic cancers and diseases (US2009/0131348, US2011/0171646, US2010/0286232, U.S. Pat. No. 8,389,210); asthma and inflammation (U.S. Pat. No. 8,415,096); prostate cancer (US2013/0053264); hepatocellular carcinoma (WO2012/151212, US2012/0329672, WO2008/054828, U.S. Pat. No. 8,252,538); lung cancer cells (WO2011/076143, WO2013/033640, WO2009/070653, US2010/0323357); cutaneous T cell lymphoma (WO2013/011378); colorectal cancer cells (WO2011/0281756, WO2011/076142); cancer positive lympho nodes (WO2009/100430, US2009/0263803); nasopharyngeal carcinoma (EP2112235); chronic obstructive pulmonary disease (US2012/0264626, US2013/0053263); thyroid cancer (WO2013/066678); ovarian cancer cells (US2012/0309645, WO2011/095623); breast cancer cells (WO2008/154098, WO2007/081740, US2012/0214699), leukemia and lymphoma (WO2008/073915, US2009/0092974, US2012/0316081, US2012/0283310, WO2010/018563, the content of each of which is incorporated herein by reference in their entirety.)

As a non-limiting example, microRNA sites that are over-expressed in certain cancer and/or tumor cells can be removed from the 3-UTR of the polynucleotide encoding the polypeptide of interest, restoring the expression suppressed by the over-expressed microRNAs in cancer cells, thus ameliorating the corresponsive biological function, for instance, transcription stimulation and/or repression, cell cycle arrest, apoptosis and cell death. Normal cells and tissues, wherein microRNAs expression is not up-regulated, will remain unaffected.

MicroRNA can also regulate complex biological processes such as angiogenesis (miR-132) (Anand and Cheresh Curr Opin Hematol 2011 18:171-176). In the modified nucleic acids, enhanced modified RNA or ribonucleic acids of the invention, binding sites for microRNAs that are involved in such processes may be removed or introduced, in order to tailor the expression of the modified nucleic acids, enhanced modified RNA or ribonucleic acids expression to biologically relevant cell types or to the context of relevant biological processes. In this context, the mRNA are defined as auxotrophic mRNA.

MicroRNA gene regulation may be influenced by the sequence surrounding the microRNA such as, but not limited to, the species of the surrounding sequence, the type of sequence (e.g., heterologous, homologous and artificial), regulatory elements in the surrounding sequence and/or structural elements in the surrounding sequence. The microRNA may be influenced by the 5'UTR and/or the 3'UTR. As a non-limiting example, a non-human 3'UTR may increase the regulatory effect of the microRNA sequence on the expression of a polypeptide of interest compared to a human 3'UTR of the same sequence type.

In one embodiment, other regulatory elements and/or structural elements of the 5'-UTR can influence microRNA mediated gene regulation. One example of a regulatory element and/or structural element is a structured IRES (Internal Ribosome Entry Site) in the 5'UTR, which is necessary for the binding of translational elongation factors to initiate protein translation. EIF4A2 binding to this secondarily structured element in the 5'UTR is necessary for microRNA mediated gene expression (Meijer H A et al., Science, 2013, 340, 82-85, herein incorporated by reference in its entirety). The modified nucleic acids, enhanced modified RNA or ribonucleic acids of the invention can further be modified to include this structured 5'-UTR in order to enhance microRNA mediated gene regulation.

At least one microRNA site can be engineered into the 3' UTR of the modified nucleic acids, enhanced modified RNA or ribonucleic acids of the present invention. In this context, at least two, at least three, at least four, at least five, at least six, at least seven, at least eight, at least nine, at least ten or more microRNA sites may be engineered into the 3' UTR of the ribonucleic acids of the present invention. In one embodiment, the microRNA sites incorporated into the modified nucleic acids, enhanced modified RNA or ribonucleic acids may be the same or may be different microRNA sites. In another embodiment, the microRNA sites incorporated into the modified nucleic acids, enhanced modified RNA or ribonucleic acids may target the same or different tissues in the body. As a non-limiting example, through the introduction of tissue-, cell-type-, or disease-specific microRNA binding sites in the 3' UTR of a modified nucleic acid mRNA, the degree of expression in specific cell types (e.g. hepatocytes, myeloid cells, endothelial cells, cancer cells, etc.) can be reduced.

In one embodiment, a microRNA site can be engineered near the 5' terminus of the 3'UTR, about halfway between the 5' terminus and 3'terminus of the 3'UTR and/or near the 3'terminus of the 3'UTR. As a non-limiting example, a microRNA site may be engineered near the 5' terminus of the 3'UTR and about halfway between the 5' terminus and 3'terminus of the 3'UTR. As another non-limiting example, a microRNA site may be engineered near the 3'terminus of the 3'UTR and about halfway between the 5' terminus and 3'terminus of the 3'UTR. As yet another non-limiting example, a microRNA site may be engineered near the 5' terminus of the 3'UTR and near the 3' terminus of the 3'UTR.

In another embodiment, a 3'UTR can comprise 4 microRNA sites. The microRNA sites may be complete microRNA binding sites, microRNA seed sequences and/or microRNA binding site sequences without the seed sequence.

In one embodiment, a nucleic acid of the invention may be engineered to include at least one microRNA in order to dampen the antigen presentation by antigen presenting cells. The microRNA may be the complete microRNA sequence, the microRNA seed sequence, the microRNA sequence without the seed or a combination thereof. As a non-limiting example, the microRNA incorporated into the nucleic acid may be specific to the hematopoietic system. As another non-limiting example, the microRNA incorporated into the nucleic acid of the invention to dampen antigen presentation is miR-142-3p.

In one embodiment, a nucleic acid may be engineered to include microRNA sites which are expressed in different tissues of a subject. As a non-limiting example, a modified nucleic acid, enhanced modified RNA or ribonucleic acid of the present invention may be engineered to include miR-192 and miR-122 to regulate expression of the modified nucleic acid, enhanced modified RNA or ribonucleic acid in the liver and kidneys of a subject. In another embodiment, a modified nucleic acid, enhanced modified RNA or ribonucleic acid may be engineered to include more than one microRNA sites for the same tissue. For example, a modified nucleic acid, enhanced modified RNA or ribonucleic acid of the present invention may be engineered to include miR-17-92 and miR-126 to regulate expression of the modified nucleic acid, enhanced modified RNA or ribonucleic acid in endothelial cells of a subject.

In one embodiment, the therapeutic window and or differential expression associated with the target polypeptide encoded by the modified nucleic acid, enhanced modified RNA or ribonucleic acid encoding a signal (also referred to herein as a polynucleotide) of the invention may be altered. For example, polynucleotides may be designed whereby a death signal is more highly expressed in cancer cells (or a survival signal in a normal cell) by virtue of the miRNA signature of those cells. Where a cancer cell expresses a lower level of a particular miRNA, the polynucleotide encoding the binding site for that miRNA (or miRNAs) would be more highly expressed. Hence, the target polypeptide encoded by the polynucleotide is selected as a protein which triggers or induces cell death. Neighboring noncancer cells, harboring a higher expression of the same miRNA would be less affected by the encoded death signal as the polynucleotide would be expressed at a lower level due to the affects of the miRNA binding to the binding site or "sensor" encoded in the 3'UTR. Conversely, cell survival or cytoprotective signals may be delivered to tissues containing cancer and non cancerous cells where a miRNA has a higher expression in the cancer cells—the result being a lower survival signal to the cancer cell and a larger survival signature to the normal cell. Multiple polynucleotides may be designed and administered having different signals according to the previous paradigm.

In one embodiment, the expression of a nucleic acid may be controlled by incorporating at least one sensor sequence in the nucleic acid and formulating the nucleic acid. As a non-limiting example, a nucleic acid may be targeted to an orthotopic tumor by having a nucleic acid incorporating a miR-122 binding site and formulated in a lipid nanoparticle comprising the cationic lipid DLin-KC2-DMA (see e.g., the experiments described in Example 49A and 49B).

According to the present invention, the polynucleotides may be modified as to avoid the deficiencies of other polypeptide-encoding molecules of the art. Hence, in this embodiment the polynucleotides are referred to as modified polynucleotides.

Through an understanding of the expression patterns of microRNA in different cell types, modified nucleic acids, enhanced modified RNA or ribonucleic acids such as polynucleotides can be engineered for more targeted expression in specific cell types or only under specific biological conditions. Through introduction of tissue-specific microRNA binding sites, modified nucleic acids, enhanced modified RNA or ribonucleic acids, could be designed that would be optimal for protein expression in a tissue or in the context of a biological condition.

Transfection experiments can be conducted in relevant cell lines, using engineered modified nucleic acids, enhanced modified RNA or ribonucleic acids and protein production can be assayed at various time points post-transfection. For example, cells can be transfected with different microRNA binding site-engineering nucleic acids or mRNA and by using an ELISA kit to the relevant protein and assaying protein produced at 6 hr, 12 hr, 24 hr, 48 hr, 72 hr and 7 days post-transfection. In vivo experiments can also be conducted using microRNA-binding site-engineered molecules to examine changes in tissue-specific expression of formulated modified nucleic acids, enhanced modified RNA or ribonucleic acids.

Non-limiting examples of cell lines which may be useful in these investigations include those from ATCC (Manassas, Va.) including MRC-5, A549, T84, NCI-H2126 [H2126], NCI-H1688 [H1688], WI-38, WI-38 VA-13 subline 2RA, WI-26 VA4, C3A [HepG2/C3A, derivative of Hep G2 (ATCC HB-8065)], THLE-3, H69AR, NCI-H292 [H292], CFPAC-1, NTERA-2 cl.D1 [NT2/D1], DMS 79, DMS 53, DMS 153, DMS 114, MSTO-211H, SW 1573 [SW-1573, SW1573], SW 1271 [SW-1271, SW1271], SHP-77, SNU-398, SNU-449, SNU-182, SNU-475, SNU-387, SNU-423, NL20, NL20-TA [NL20T-A], THLE-2, HBE135-E6E7, HCC827, HCC4006, NCI-H23 [H23], NCI-H1299, NCI-H187 [H187], NCI-H358 [H-358, H358], NCI-H378 [H378], NCI-H522 [H522], NCI-H526 [H526], NCI-H727 [H727], NCI-H810 [H810], NCI-H889 [H889], NCI-H1155 [H1155], NCI-H1404 [H1404], NCI-N87 [N87], NCI-H196 [H196], NCI-H211 [H211], NCI-H220 [H220], NCI-H250 [H250], NCI-H524 [H524], NCI-H647 [H647], NCI-H650 [H650], NCI-H711 [H711], NCI-H719 [H719], NCI-H740 [H740], NCI-H748 [H748], NCI-H774 [H774], NCI-H838 [H838], NCI-H841 [H841], NCI-H847 [H847], NCI-H865 [H865], NCI-H920 [H920], NCI-H1048 [H1048], NCI-H1092 [H1092], NCI-H1105 [H1105], NCI-H1184 [H1184], NCI-H1238 [H1238], NCI-H1341 [H1341], NCI-H1385 [H1385], NCI-H1417 [H1417], NCI-H1435 [H1435], NCI-H1436 [H1436], NCI-H1437 [H1437], NCI-H1522 [H1522], NCI-H1563 [H1563], NCI-H1568 [H1568], NCI-H1573 [H1573], NCI-H1581 [H1581], NCI-H1618 [H1618], NCI-H1623 [H1623], NCI-H1650 [H-1650, H1650], NCI-H1651 [H1651], NCI-H1666 [H-1666, H1666], NCI-H1672 [H1672], NCI-H1693 [H1693], NCI-H1694 [H1694], NCI-H1703 [H1703], NCI-H1734 [H-1734, H1734], NCI-H1755 [H1755], NCI-H1755 [H1755], NCI-H1770 [H1770], NCI-H1793 [H1793], NCI-H1836 [H1836], NCI-H1838 [H1838], NCI-H1869 [H1869], NCI-H1876 [H1876], NCI-H1882 [H1882], NCI-H1915 [H1915], NCI-H1930 [H1930], NCI-H1944 [H1944], NCI-H1975 [H-1975, H1975], NCI-H1993 [H1993], NCI-H2023 [H2023], NCI-H2029 [H2029], NCI-H2030 [H2030], NCI-H2066 [H2066], NCI-H2073 [H2073], NCI-H2081 [H2081], NCI-H2085 [H2085], NCI-H2087 [H2087], NCI-H2106 [H2106], NCI-H2110 [H2110], NCI-H2135 [H2135], NCI-H2141 [H2141], NCI-H2171 [H2171], NCI-H2172 [H2172], NCI-H2195 [H2195], NCI-H2196 [H2196], NCI-H2198 [H2198], NCI-H2227 [H2227], NCI-H2228 [H2228], NCI-H2286 [H2286], NCI-H2291 [H2291], NCI-H2330 [H2330], NCI-H2342 [H2342], NCI-H2347 [H2347], NCI-H2405 [H2405], NCI-H2444 [H2444], UMC-11, NCI-H64 [H64], NCI-H735 [H735], NCI-H735 [H735], NCI-H1963 [H1963], NCI-H2107 [H2107], NCI-H2108 [H2108], NCI-H2122 [H2122], Hs 573.T, Hs 573.Lu, PLC/PRF/5, BEAS-2B, Hep G2, Tera-1, Tera-2, NCI-H69 [H69], NCI-H128 [H128], ChaGo-K-1, NCI-H446 [H446], NCI-H209 [H209], NCI-H146 [H146], NCI-H441 [H441], NCI-H82 [H82], NCI-H460 [H460], NCI-H596 [H596], NCI-H676B [H676B], NCI-H345 [H345], NCI-H820 [H820], NCI-H520 [H520], NCI-H661 [H661], NCI-H510A [H510A, NCI- H510], SK-HEP-1, A-427, Calu-1, Calu-3, Calu-6, SK-LU-1, SK-MES-1, SW 900 [SW-900, SW900], Malme-3M, and Capan-1.

In some embodiments, modified messenger RNA can be designed to incorporate microRNA binding region sites that either have 100% identity to known seed sequences or have less than 100% identity to seed sequences. The seed sequence can be partially mutated to decrease microRNA binding affinity and as such result in reduced downmodulation of that mRNA transcript. In essence, the degree of match or mis-match between the target mRNA and the microRNA seed can act as a rheostat to more finely tune the ability of the microRNA to modulate protein expression. In addition, mutation in the non-seed region of a microRNA binding site may also impact the ability of a microRNA to modulate protein expression.

In one embodiment, a miR sequence may be incorporated into the loop of a stem loop.

In another embodiment, a miR seed sequence may be incorporated in the loop of a stem loop and a miR binding site may be incorporated into the 5' or 3' stem of the stem loop.

In one embodiment, a TEE may be incorporated on the 5'end of the stem of a stem loop and a miR seed may be incorporated into the stem of the stem loop. In another embodiment, a TEE may be incorporated on the 5'end of the stem of a stem loop, a miR seed may be incorporated into the stem of the stem loop and a miR binding site may be incorporated into the 3'end of the stem or the sequence after the stem loop. The miR seed and the miR binding site may be for the same and/or different miR sequences.

In one embodiment, the incorporation of a miR sequence and/or a TEE sequence changes the shape of the stem loop region which may increase and/or decrease translation. (see e.g, Kedde et al. A Pumilio-induced RNA structure switch in p27-3'UTR controls miR-221 and miR-22 accessibility. Nature Cell Biology. 2010, herein incorporated by reference in its entirety).

In one embodiment, the incorporation of a miR sequence and/or a TEE sequence changes the shape of the stem loop region which may increase and/or decrease translation. (see e.g, Kedde et al. A Pumilio-induced RNA structure switch in p27-3'UTR controls miR-221 and miR-22 accessibility. Nature Cell Biology. 2010, herein incorporated by reference in its entirety).

In one embodiment, the 5'UTR may comprise at least one microRNA sequence. The microRNA sequence may be, but is not limited to, a 19 or 22 nucleotide sequence and/or a microRNA sequence without the seed.

In one embodiment the microRNA sequence in the 5'UTR may be used to stabilize the nucleic acid and/or mRNA described herein.

In another embodiment, a microRNA sequence in the 5'UTR may be used to decrease the accessibility of the site of translation initiation such as, but not limited to a start codon. Matsuda et al (PLoS One. 2010 11(5):e15057; herein incorporated by reference in its entirety) used antisense locked nucleic acid (LNA) oligonucleotides and exon-junctino complexes (EJCs) around a start codon (−4 to +37 where the A of the AUG codons is +1) in order to decrease the accessibility to the first start codon (AUG). Matsuda showed that altering the sequence around the start codon with an LNA or EJC the efficiency, length and structural stability of the nucleic acid or mRNA is affected. The nucleic acids or mRNA of the present invention may comprise a microRNA sequence, instead of the LNA or EJC sequence described by Matsuda et al, near the site of translation initiation in order to decrease the accessibility to the site of translation initiation. The site of translation initiation may be prior to, after or within the microRNA sequence. As a non-limiting example, the site of translation initiation may be located within a microRNA sequence such as a seed sequence or binding site. As another non-limiting example, the site of translation initiation may be located within a miR-122 sequence such as the seed sequence or the mir-122 binding site.

In one embodiment, the nucleic acids or mRNA of the present invention may include at least one microRNA in order to dampen the antigen presentation by antigen presenting cells. The microRNA may be the complete microRNA sequence, the microRNA seed sequence, the microRNA sequence without the seed or a combination thereof. As a non-limiting example, the microRNA incorporated into the nucleic acids or mRNA of the present invention may be specific to the hematopoietic system. As another non-limiting example, the microRNA incorporated into the nucleic acids or mRNA of the present invention to dampen antigen presentation is miR-142-3p.

In one embodiment, the nucleic acids or mRNA of the present invention may include at least one microRNA in order to dampen expression of the encoded polypeptide in a cell of interest. As a non-limiting example, the nucleic acids or mRNA of the present invention may include at least one miR-122 binding site in order to dampen expression of an encoded polypeptide of interest in the liver. As another non-limiting example, the nucleic acids or mRNA of the present invention may include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence (see e.g., the experiment outlined in Example 24, 25, 26, 26, 36 and 48).

In one embodiment, the nucleic acids or mRNA of the present invention may comprise at least one microRNA binding site in the 3'UTR in order to selectively degrade mRNA therapeutics in the immune cells to subdue unwanted immunogenic reactions caused by therapeutic delivery. As a non-limiting example, the microRNA binding site may be the modified nucleic acids more unstable in antigen presenting cells. Non-limiting examples of these microRNA include mir-142-5p, mir-142-3p, mir-146a-5p and mir-146-3p.

In one embodiment, the nucleic acids or mRNA of the present invention comprises at least one microRNA sequence in a region of the nucleic acid or mRNA which may interact with a RNA binding protein.

RNA Motifs for RNA Binding Proteins (RBPs)

RNA binding proteins (RBPs) can regulate numerous aspects of co- and post-transcription gene expression such as, but not limited to, RNA splicing, localization, translation, turnover, polyadenylation, capping, modification, export and localization. RNA-binding domains (RBDs), such as, but not limited to, RNA recognition motif (RR) and hnRNP K-homology (KH) domains, typically regulate the sequence association between RBPs and their RNA targets (Ray et al. Nature 2013. 499:172-177; herein incorporated by reference in its entirety). In one embodiment, the canonical RBDs can bind short RNA sequences. In another embodiment, the canonical RBDs can recognize structure RNAs.

Non limiting examples of RNA binding proteins and related nucleic acid and protein sequences are shown in Table 26 in Example 23.

In one embodiment, to increase the stability of the mRNA of interest, an mRNA encoding HuR can be co-transfected or co-injected along with the mRNA of interest into the cells or into the tissue. These proteins can also be tethered to the mRNA of interest in vitro and then administered to the cells together. Poly A tail binding protein, PABP interacts with eukaryotic translation initiation factor eIF4G to stimulate translational initiation. Co-administration of mRNAs encoding these RBPs along with the mRNA drug and/or tethering these proteins to the mRNA drug in vitro and administering the protein-bound mRNA into the cells can increase the translational efficiency of the mRNA. The same concept can be extended to co-administration of mRNA along with mRNAs encoding various translation factors and facilitators as well as with the proteins themselves to influence RNA stability and/or translational efficiency.

In one embodiment, the nucleic acids and/or mRNA may comprise at least one RNA-binding motif such as, but not limited to a RNA-binding domain (RBD).

In one embodiment, the RBD may be any of the RBDs, fragments or variants thereof descried by Ray et al. (Nature 2013. 499:172-177; herein incorporated by reference in its entirety).

In one embodiment, the nucleic acids or mRNA of the present invention may comprise a sequence for at least one RNA-binding domain (RBDs). When the nucleic acids or mRNA of the present invention comprise more than one RBD, the RBDs do not need to be from the same species or even the same structural class.

In one embodiment, at least one flanking region (e.g., the 5'UTR and/or the 3'UTR) may comprise at least one RBD. In another embodiment, the first flanking region and the second flanking region may both comprise at least one RBD. The RBD may be the same or each of the RBDs may have at least 60% sequence identity to the other RBD. As a non-limiting example, at least on RBD may be located before, after and/or within the 3'UTR of the nucleic acid or mRNA of the present invention. As another non-limiting example, at least one RBD may be located before or within the first 300 nucleosides of the 3'UTR.

In another embodiment, the nucleic acids and/or mRNA of the present invention may comprise at least one RBD in the first region of linked nucleosides. The RBD may be located before, after or within a coding region (e.g., the ORF).

In yet another embodiment, the first region of linked nucleosides and/or at least one flanking region may comprise at least on RBD. As a non-limiting example, the first region of linked nucleosides may comprise a RBD related to splicing factors and at least one flanking region may comprise a RBD for stability and/or translation factors.

In one embodiment, the nucleic acids and/or mRNA of the present invention may comprise at least one RBD located in a coding and/or non-coding region of the nucleic acids and/or mRNA.

In one embodiment, at least one RBD may be incorporated into at least one flanking region to increase the stability of the nucleic acid and/or mRNA of the present invention.

In one embodiment, a microRNA sequence in a RNA binding protein motif may be used to decrease the accessibility of the site of translation initiation such as, but not limited to a start codon. The nucleic acids or mRNA of the present invention may comprise a microRNA sequence, instead of the LNA or EJC sequence described by Matsuda et al, near the site of translation initiation in order to decrease the accessibility to the site of translation initiation. The site of translation initiation may be prior to, after or within the microRNA sequence. As a non-limiting example, the site of translation initiation may be located within a microRNA sequence such as a seed sequence or binding site. As another non-limiting example, the site of translation initiation may be located within a miR-122 sequence such as the seed sequence or the mir-122 binding site.

In another embodiment, an antisense locked nucleic acid (LNA) oligonucleotides and exon-junctino complexes (EJCs) may be used in the RNA binding protein motif. The LNA and EJCs may be used around a start codon (−4 to +37 where the A of the AUG codons is +1) in order to decrease the accessibility to the first start codon (AUG).

Other Regulatory Elements in 3'UTR

In addition to microRNA binding sites, other regulatory sequences in the 3'-UTR of natural mRNA, which regulate mRNA stability and translation in different tissues and cells, can be removed or introduced into modified messenger RNA. Such cis-regulatory elements may include, but are not limited to, Cis-RNP (Ribonucleoprotein)/RBP (RNA binding protein) regulatory elements, AU-rich element (AUE), structured stem-loop, constitutive decay elements (CDEs), GC-richness and other structured mRNA motifs (Parker B J et al., Genome Research, 2011, 21, 1929-1943, which is herein incorporated by reference in its entirety). For example, CDEs are a class of regulatory motifs that mediate mRNA degradation through their interaction with Roquin proteins. In particular, CDEs are found in many mRNAs that encode regulators of development and inflammation to limit cytokine production in macrophage (Leppek K et al., 2013, Cell, 153, 869-881, which is herein incorporated by reference in its entirety).

In one embodiment, a particular CDE can be introduced to the nucleic acids or mRNA when the degradation of polypeptides in a cell or tissue is desired. A particular CDE can also be removed from the nucleic acids or mRNA to maintain a more stable mRNA in a cell or tissue for sustaining protein expression.

Auxotrophic mRNA

In one embodiment, the nucleic acids or mRNA of the present invention may be auxotrophic. As used herein, the term "auxotrophic" refers to mRNA that comprises at least one feature that triggers, facilitates or induces the degradation or inactivation of the mRNA in response to spatial or temporal cues such that protein expression is substantially prevented or reduced. Such spatial or temporal cues include the location of the mRNA to be translated such as a particular tissue or organ or cellular environment. Also contemplated are cues involving temperature, pH, ionic strength, moisture content and the like.

In one embodiment, the feature is located in a terminal region of the nucleic acids or mRNA of the present invention. As a non-limiting example, the auxotrophic mRNA may contain a miR binding site in the terminal region which binds to a miR expressed in a selected tissue so that the expression of the auxotrophic mRNA is substantially prevented or reduced in the selected tissue. To this end and for example, an auxotrophic mRNA containing a miR-122 binding site will not produce protein if localized to the liver since miR-122 is expressed in the liver and binding of the miR would effectuate destruction of the auxotrophic mRNA. As a non-limiting example, HEK293 cells do not express miR-122 so there would be little to no downregulation of a nucleic acid or mRNA of the present invention having a miR-122 sequence in HEK293 but for hepatocytes which do express miR-122 there would be a downregulation of a nucleic acid or mRNA of the present invention having a miR-122 sequence in hepatocytes (see e.g., the study outlined Example 14). As another non-limiting example, the miR-122 level can be measured in HeLa cells, primary human hepatocytes and primary rat hepatocytes prior to administration with a nucleic acid or mRNA of the present invention encoding at least one miR-122 binding site, miR-122 binding site without the seed sequence or a miR-122 binding site After administration the expression of the modified nucleic acid with a microRNA sequence can be measured to determine the dampening effect of the miR-122 in the modified nucleic acid (see e.g., the studies outlined in Examples 28, 29, 30, 35, 45, 46 and 47). As yet another non-limiting example, the effectiveness of the miR-122 binding site, miR-122 seed or the miR-122 binding site without the seed in different 3'UTRs may be evaluated in order to determine the proper UTR for the desired outcome such as, but not limited to, the highest dampening effect (see e.g., the study outlined in Example 35 and 46).

In one embodiment, the degradation or inactivation of auxotrophic mRNA may comprise a feature responsive to a change in pH. As a non-limiting example, the auxotrophic mRNA may be triggered in an environment having a pH of between pH 4.5 to 8.0 such as at a pH of 5.0 to 6.0 or a pH of 6.0 to 6.5. The change in pH may be a change of 0.1 unit, 0.2 units, 0.3 units, 0.4 units, 0.5 units, 0.6 units, 0.7 units, 0.8 units, 0.9 units, 1.0 units, 1.1 units, 1.2 units, 1.3 units, 1.4 units, 1.5 units, 1.6 units, 1.7 units, 1.8 units, 1.9 units, 2.0 units, 2.1 units, 2.2 units, 2.3 units, 2.4 units, 2.5 units, 2.6 units, 2.7 units, 2.8 units, 2.9 units, 3.0 units, 3.1 units, 3.2 units, 3.3 units, 3.4 units, 3.5 units, 3.6 units, 3.7 units, 3.8 units, 3.9 units, 4.0 units or more.

In another embodiment, the degradation or inactivation of auxotrophic mRNA may be triggered or induced by changes in temperature. As a non-limiting example, a change of temperature from room temperature to body temperature. The change of temperature may be less than 1° C., less than 5° C., less than 10° C., less than 15° C., less than 20° C., less than 25° C. or more than 25° C.

In yet another embodiment, the degradation or inactivation of auxotrophic mRNA may be triggered or induced by a change in the levels of ions in the subject. The ions may be cations or anions such as, but not limited to, sodium ions, potassium ions, chloride ions, calcium ions, magnesium ions and/or phosphate ions.

3' UTR and the AU Rich Elements

3'UTRs are known to have stretches of Adenosines and Uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) nonamers. Molecules containing this type of AREs include GM-CSF and TNF-a. Class III ARES are less well defined. These U rich regions do not contain an AUUUA motif. c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of nucleic acids or mRNA of the invention. When engineering specific nucleic acids or mRNA, one or more copies of an ARE can be introduced to make nucleic acids or mRNA of the invention less stable and thereby curtail translation and decrease production of the resultant protein. Likewise, AREs can be identified and removed or mutated to increase the intracellular stability and thus increase translation and production of the resultant protein. Transfection experiments can be conducted in relevant cell lines, using nucleic acids or mRNA of the invention and protein production can be assayed at various time points post-transfection. For example, cells can be transfected with different ARE-engineering molecules and by using an ELISA kit to the relevant protein and assaying protein produced at 6 hr, 12 hr, 24 hr, 48 hr, and 7 days post-transfection.

3' UTR and Triple Helices

In one embodiment, nucleic acids of the present invention may include a triple helix on the 3' end of the modified nucleic acid, enhanced modified RNA or ribonucleic acid. The 3' end of the nucleic acids of the present invention may include a triple helix alone or in combination with a Poly-A tail.

In one embodiment, the nucleic acid of the present invention may comprise at least a first and a second U-rich region, a conserved stem loop region between the first and second region and an A-rich region. The first and second U-rich region and the A-rich region may associate to form a triple helix on the 3' end of the nucleic acid. This triple helix may stabilize the nucleic acid, enhance the translational efficiency of the nucleic acid and/or protect the 3' end from degradation. Exemplary triple helices include, but are not limited to, the triple helix sequence of metastasis-associated lung adenocarcinoma transcript 1 (MALAT1), MEN-β and polyadenylated nuclear (PAN) RNA (See Wilusz et al., Genes & Development 2012 26:2392-2407; herein incorporated by reference in its entirety). In one embodiment, the 3' end of the modified nucleic acids, enhanced modified RNA or ribonucleic acids of the present invention comprises a first U-rich region comprising TTTTTCTTTT (SEQ ID NO: 1), a second U-rich region comprising TTTTGCTTTTT (SEQ ID NO: 2) or TTTTGCTTTT (SEQ ID NO: 3), an A-rich region comprising AAAAAGCAAAA (SEQ ID NO: 4). In another embodiment, the 3' end of the nucleic acids of the present invention comprises a triple helix formation structure comprising a first U-rich region, a conserved region, a second U-rich region and an A-rich region.

In one embodiment, the triple helix may be formed from the cleavage of a MALAT1 sequence prior to the cloverleaf structure. While not meaning to be bound by theory, MALAT1 is a long non-coding RNA which, when cleaved, forms a triple helix and a tRNA-like cloverleaf structure. The MALAT1 transcript then localizes to nuclear speckles and the tRNA-like cloverleaf localizes to the cytoplasm (Wilusz et al. Cell 2008 135(5): 919-932; herein incorporated by reference in its entirety).

As a non-limiting example, the terminal end of the nucleic acid of the present invention comprising the MALAT1 sequence can then form a triple helix structure, after RNaseP cleavage from the cloverleaf structure, which stabilizes the nucleic acid (Peart et al. *Non-mRNA 3' end formation: how the other half lives*; WIREs RNA 2013; herein incorporated by reference in its entirety).

In one embodiment, the nucleic acids or mRNA described herein comprise a MALAT1 sequence. In another embodiment, the nucleic acids or mRNA may be polyadenylated. In yet another embodiment, the nucleic acids or mRNA is not polyadenylated but has an increased resistance to degradation compared to unmodified nucleic acids or mRNA.

In one embodiment, the nucleic acids of the present invention may comprise a MALAT1 sequence in the second flanking region (e.g., the 3'UTR). As a non-limiting example, the MALAT1 sequence may be human or mouse (see e.g., the polynucleotides described in Table 37 in Example 38).

In another embodiment, the cloverleaf structure of the MALAT1 sequence may also undergo processing by RNaseZ and CCA adding enzyme to form a tRNA-like structure called mascRNA (MALAT1-associated small cytoplasmic RNA). As a non-limiting example, the mascRNA may encode a protein or a fragment thereof and/or may comprise a microRNA sequence. The mascRNA may comprise at least one chemical modification described herein.

Stem Loop

In one embodiment, the nucleic acids of the present invention may include a stem loop such as, but not limited to, a histone stem loop. The stem loop may be a nucleotide sequence that is about 25 or about 26 nucleotides in length such as, but not limited to, SEQ ID NOs: 7-17 as described in International Patent Publication No. WO2013103659, herein incorporated by reference in its entirety. The histone stem loop may be located 3' relative to the coding region (e.g., at the 3' terminus of the coding region). As a non-limiting example, the stem loop may be located at the 3' end of a nucleic acid described herein.

In one embodiment, the stem loop may be located in the second terminal region. As a non-limiting example, the stem loop may be located within an untranslated region (e.g., 3'UTR) in the second terminal region.

In one embodiment, the nucleic acid such as, but not limited to mRNA, which comprises the histone stem loop may be stabilized by the addition of at least one chain terminating nucleoside. Not wishing to be bound by theory, the addition of at least one chain terminating nucleoside may slow the degradation of a nucleic acid and thus can increase the half-life of the nucleic acid.

In one embodiment, the chain terminating nucleoside may be, but is not limited to, those described in International Patent Publication No. WO2013103659, herein incorporated by reference in its entirety. In another embodiment, the chain terminating nucleosides which may be used with the present invention includes, but is not limited to, 3'-deoxyadenosine (cordycepin), 3'-deoxyuridine, 3'-deoxycytosine, 3'-deoxyguanosine, 3'-deoxythymine, 2',3'-dideoxynucleosides, such as 2',3'-dideoxyadenosine, 2',3'-dideoxyuridine, 2',3'-dideoxycytosine, 2',3'-dideoxyguanosine, 2',3'-dideoxythymine, a 2'-deoxynucleoside, or a —O— methylnucleoside.

In another embodiment, the nucleic acid such as, but not limited to mRNA, which comprises the histone stem loop may be stabilized by a modification to the 3'region of the nucleic acid that can prevent and/or inhibit the addition of oligio(U) (see e.g., International Patent Publication No. WO2013103659, herein incorporated by reference in its entirety).

In yet another embodiment, the nucleic acid such as, but not limited to mRNA, which comprises the histone stem loop may be stabilized by the addition of an oligonucleotide that terminates in a 3'-deoxynucleoside, 2',3'-dideoxynucleoside 3'-0-methylnucleosides, 3'-0-ethylnucleosides, 3'-arabinosides, and other modified nucleosides known in the art and/or described herein.

In one embodiment, the nucleic acids of the present invention may include a histone stem loop, a polyA tail sequence and/or a 5'cap structure. The histone stem loop may be before and/or after the polyA tail sequence. The nucleic acids comprising the histone stem loop and a polyA tail sequence may include a chain terminating nucleoside described herein.

In another embodiment, the nucleic acids of the present invention may include a histone stem loop and a 5'cap structure. The 5'cap structure may include, but is not limited to, those described herein and/or known in the art.

In one embodiment, the conserved stem loop region may comprise a miR sequence described herein. As a non-limiting example, the stem loop region may comprise the seed sequence of a miR sequence described herein. In another non-limiting example, the stem loop region may comprise a miR-122 seed sequence.

In another embodiment, the conserved stem loop region may comprise a miR sequence described herein and may also include a TEE sequence.

In one embodiment, the incorporation of a miR sequence and/or a TEE sequence changes the shape of the stem loop region which may increase and/or decrease translation. (see e.g, Kedde et al. A Pumilio-induced RNA structure switch in p27-3'UTR controls miR-221 and miR-22 accessibility. Nature Cell Biology. 2010, herein incorporated by reference in its entirety).

In one embodiment, the modified nucleic acids described herein may comprise at least one histone stem-loop and a polyA sequence or polyadenylation signal. Non-limiting examples of nucleic acid sequences encoding for at least one histone stem-loop and a polyA sequence or a polyadenylation signal are described in International Patent Publication No. WO2013120497, WO2013120629, WO2013120500, WO2013120627, WO2013120498, WO2013120626, WO2013120499 and WO2013120628, the contents of each of which is herein incorporated by reference in their entirety. In one embodiment, the nucleic acid encoding for a histone stem loop and a polyA sequence or a polyadenylation signal may code for a pathogen antigen or fragment thereof such as the nucleic acid sequences described in International Patent Publication No WO2013120499 and WO2013120628, the contents of which is herein incorporated by reference in its entirety. In another embodiment, the nucleic acid encoding for a histone stem loop and a polyA sequence or a polyadenylation signal may code for a therapeutic protein such as the nucleic acid sequences described in International Patent Publication No WO2013120497 and WO2013120629, the contents of which is herein incorporated by reference in its entirety. In one embodiment, the nucleic acid encoding for a histone stem loop and a polyA sequence or a polyadenylation signal may code for a tumor antigen or fragment thereof such as the nucleic acid sequences described in International Patent Publication No WO2013120500 and WO2013120627, the contents of which is herein incorporated by reference in its entirety. In another embodiment, the nucleic acid encoding for a histone stem loop and a polyA sequence or a polyadenylation signal may code for a allergenic antigen or an autoimmune self-antigen such as the nucleic acid sequences described in International Patent Publication No WO2013120498 and WO2013120626, the contents of which is herein incorporated by reference in its entirety.

5' Capping

The 5' cap structure of an mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns removal during mRNA splicing.

Endogenous mRNA molecules may be 5'-end capped generating a 5'-ppp-5'-triphosphate linkage between a terminal guanosine cap residue and the 5'-terminal transcribed sense nucleotide of the mRNA. This 5'-guanylate cap may then be methylated to generate an N7-methyl-guanylate residue. The ribose sugars of the terminal and/or anteterminal transcribed nucleotides of the 5' end of the mRNA may optionally also be 2'-O-methylated. 5'-decapping through hydrolysis and cleavage of the guanylate cap structure may target a nucleic acid molecule, such as an mRNA molecule, for degradation.

Modifications to the nucleic acids of the present invention may generate a non-hydrolyzable cap structure preventing decapping and thus increasing mRNA half-life. Because cap structure hydrolysis requires cleavage of 5'-ppp-5' phosphorodiester linkages, modified nucleotides may be used during the capping reaction. For example, a Vaccinia Capping Enzyme from New England Biolabs (Ipswich, Mass.) may be used with α-thio-guanosine nucleotides according to the manufacturer's instructions to create a phosphorothioate linkage in the 5'-ppp-5' cap. Additional modified guanosine nucleotides may be used such as α-methyl-phosphonate and seleno-phosphate nucleotides.

Additional modifications include, but are not limited to, 2'-O-methylation of the ribose sugars of 5'-terminal and/or 5'-anteterminal nucleotides of the mRNA (as mentioned above) on the 2'-hydroxyl group of the sugar ring. Multiple distinct 5'-cap structures can be used to generate the 5'-cap of a nucleic acid molecule, such as an mRNA molecule.

Cap analogs, which herein are also referred to as synthetic cap analogs, chemical caps, chemical cap analogs, or structural or functional cap analogs, differ from natural (i.e. endogenous, wild-type or physiological) 5'-caps in their chemical structure, while retaining cap function. Cap analogs may be chemically (i.e. non-enzymatically) or enzymatically synthesized and/linked to a nucleic acid molecule.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine (m$^7$G-3'mppp-G; which may equivalently be designated 3' O-Me-m7G(5')ppp(5')G). The 3'-O atom of the other, unmodified, guanine becomes linked to the 5'-terminal nucleotide of the capped nucleic acid molecule (e.g. an mRNA or mmRNA). The N7- and 3'-O-methylated guanine provides the terminal moiety of the capped nucleic acid molecule (e.g. mRNA or mmRNA).

Another exemplary cap is mCAP, which is similar to ARCA but has a 2'-O-methyl group on guanosine (i.e., N7,2'-O-dimethyl-guanosine-5'-triphosphate-5'-guanosine, m$^7$Gm-ppp-G).

In one embodiment, the cap is a dinucleotide cap analog. As a non-limiting example, the dinucleotide cap analog may be modified at different phosphate positions with a boranophosphate group or a phophoroselenoate group such as the dinucleotide cap analogs described in U.S. Pat. No. 8,519,110, the contents of which are herein incorporated by reference in its entirety.

In another embodiment, the cap is a cap analog is a N7-(4-chlorophenoxyethyl) substituted dicuceotide form of a cap analog known in the art and/or described herein. Non-limiting examples of a N7-(4-chlorophenoxyethyl) substituted dicuceotide form of a cap analog include a N7-(4-chlorophenoxyethyl)-G(5')ppp(5')G and a N7-(4-chlorophenoxyethyl)-m$^{3'-O}$G(5')ppp(5')G cap analog (See e.g., the various cap analogs and the methods of synthesizing cap analogs described in Kore et al. Bioorganic & Medicinal Chemistry 2013 21:4570-4574; the contents of which are herein incorporated by reference in its entirety). In another embodiment, a cap analog of the present invention is a 4-chloro/bromophenoxyethyl analog.

While cap analogs allow for the concomitant capping of a nucleic acid molecule in an in vitro transcription reaction, up to 20% of transcripts remain uncapped. This, as well as the structural differences of a cap analog from an endogenous 5'-cap structures of nucleic acids produced by the endogenous, cellular transcription machinery, may lead to reduced translational competency and reduced cellular stability.

Modified nucleic acids of the invention may also be capped post-transcriptionally, using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'cap structures of the present invention are those which, among other things, have enhanced binding of cap binding proteins, increased half life, reduced susceptibility to 5' endonucleases and/or reduced 5'decapping, as compared to synthetic 5'cap structures known in the art (or to a wild-type, natural or physiological 5'cap structure). For example, recombinant Vaccinia Virus Capping Enzyme and recombinant 2'-O-methyltransferase enzyme can create a canonical 5'-5'-triphosphate linkage between the 5'-terminal nucleotide of an mRNA and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include 7mG(5')ppp(5')N,pN2p (cap 0), 7mG(5')ppp(5')NlmpNp (cap 1), 7mG(5')-ppp(5') NlmpN2mp (cap 2) and m(7)Gpppm(3)(6,6,2')Apm(2')Apm (2')Cpm(2)(3,2')Up (cap 4).

Because the modified nucleic acids may be capped post-transcriptionally, and because this process is more efficient, nearly 100% of the modified nucleic acids may be capped. This is in contrast to ~80% when a cap analog is linked to an mRNA in the course of an in vitro transcription reaction.

According to the present invention, 5' terminal caps may include endogenous caps or cap analogs. According to the present invention, a 5' terminal cap may comprise a guanine analog. Useful guanine analogs include inosine, N1-methyl-guanosine, 2'fluoro-guanosine, 7-deaza-guanosine, 8-oxo-guanosine, 2-amino-guanosine, LNA-guanosine, and 2-azido-guanosine.

In one embodiment, the nucleic acids described herein may contain a modified 5'cap. A modification on the 5'cap may increase the stability of mRNA, increase the half-life of the mRNA, and could increase the mRNA translational efficiency. The modified 5'cap may include, but is not limited to, one or more of the following modifications: modification at the 2' and/or 3' position of a capped guanosine triphosphate (GTP), a replacement of the sugar ring oxygen (that produced the carbocyclic ring) with a methylene moiety (CH$_2$), a modification at the triphosphate bridge moiety of the cap structure, or a modification at the nucleobase (G) moiety.

The 5'cap structure that may be modified includes, but is not limited to, the caps described herein such as Cap0 having the substrate structure for cap dependent translation of:

(CAP-001)

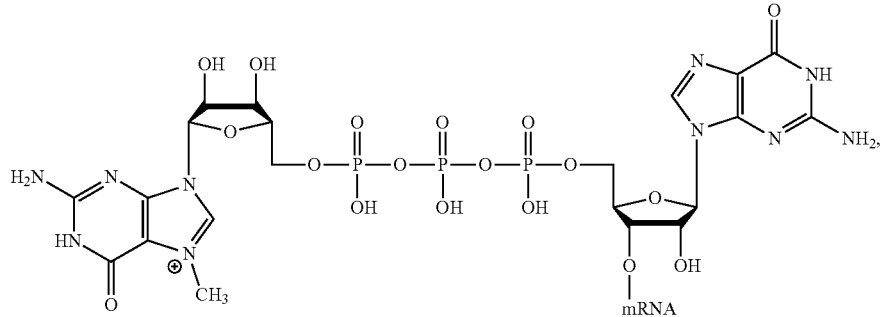

or Cap1 having the substrate structure for cap dependent translation of:

(CAP-002)

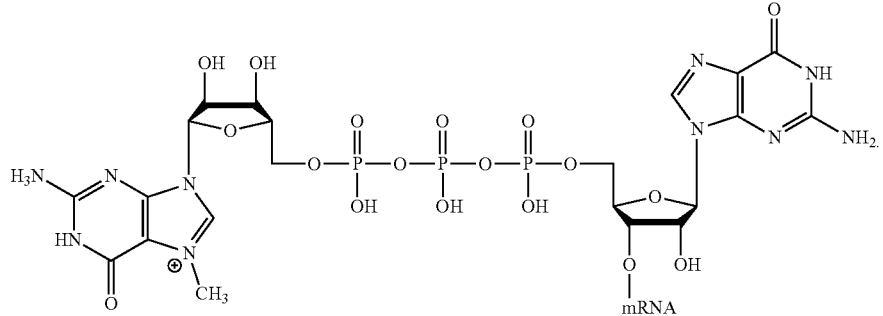

As a non-limiting example, the modified 5'cap may have the substrate structure for cap dependent translation of:

(CAP-003)

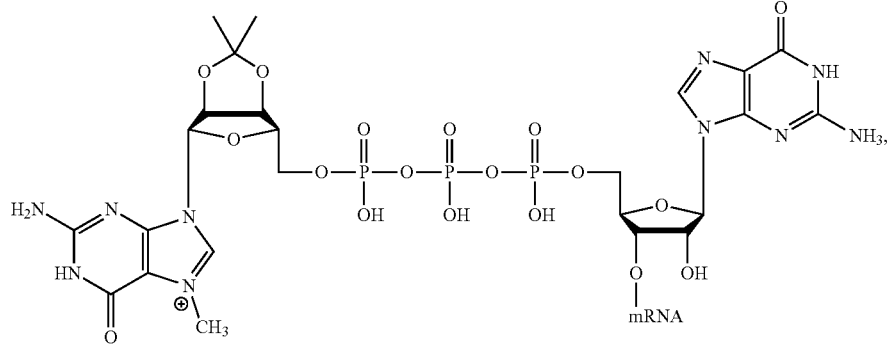

(CAP-004)

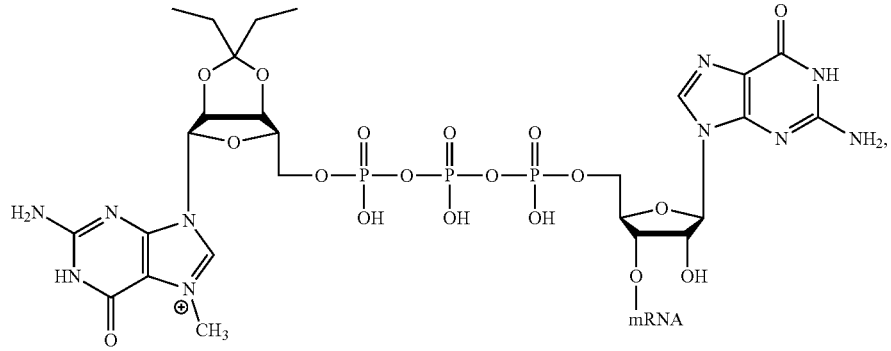

-continued
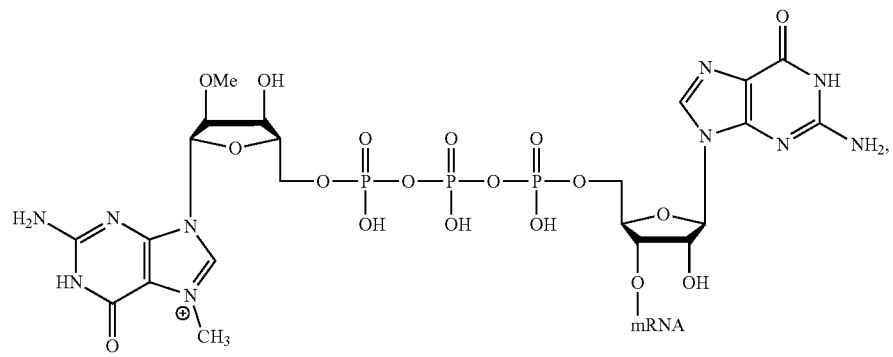
(CAP-005)
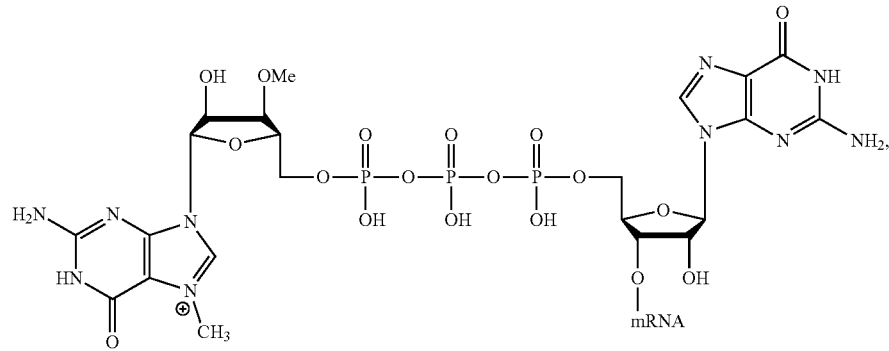
(CAP-006)
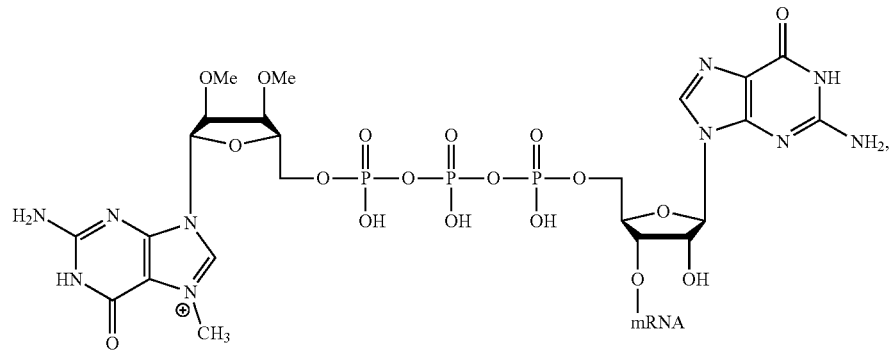
(CAP-007)
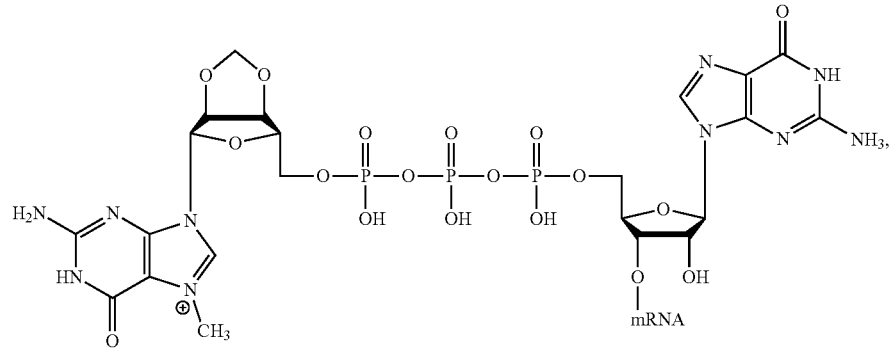
(CAP-008)

(CAP-009)
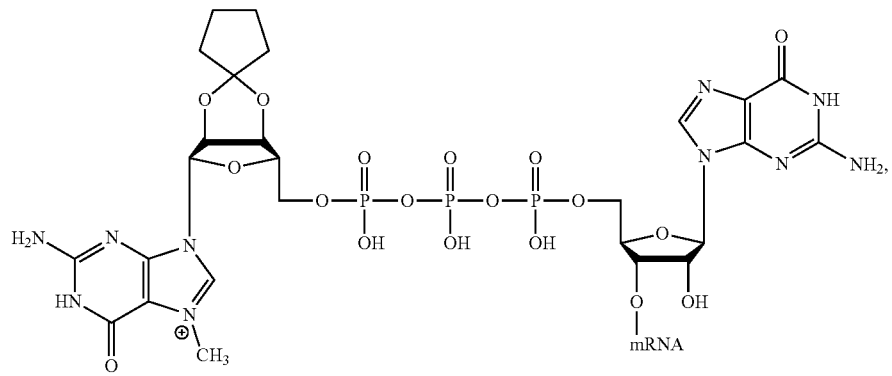
(CAP-010)
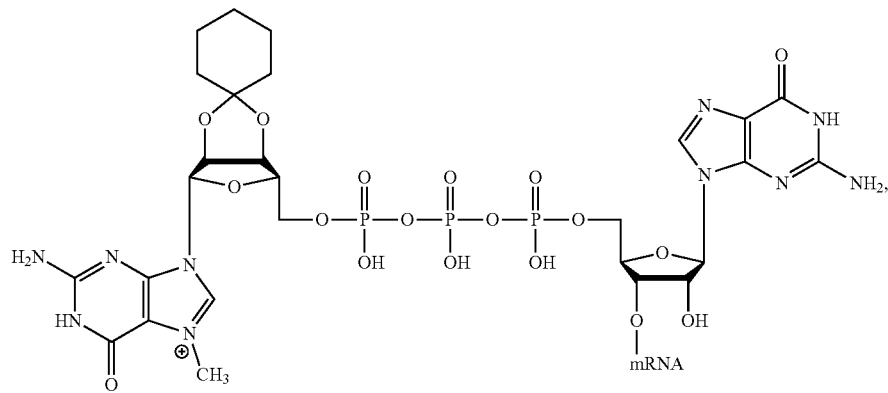
(CAP-011)
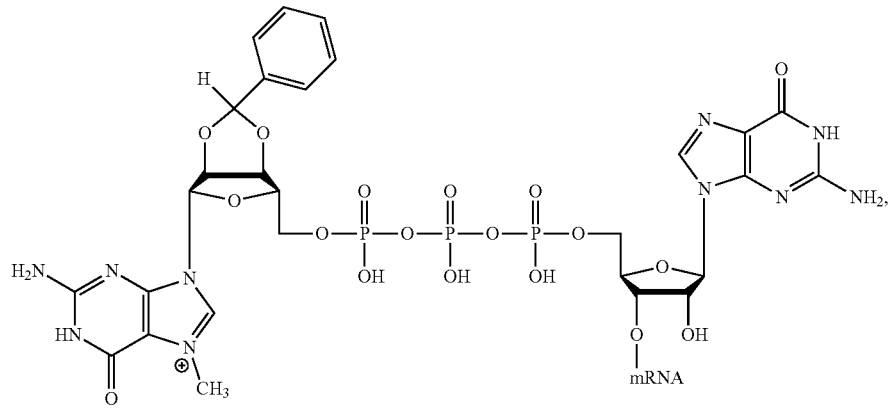
(CAP-012)
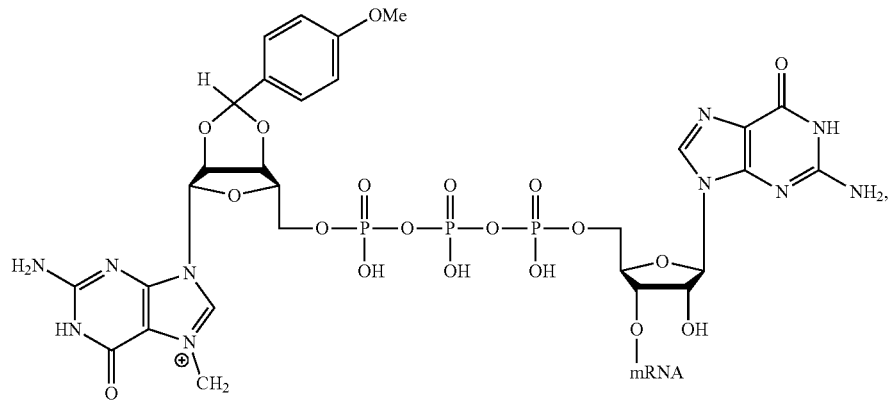

(CAP-013)
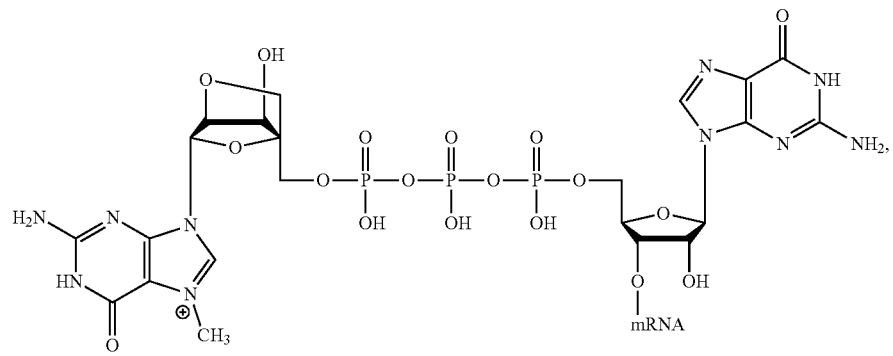
(CAP-014)
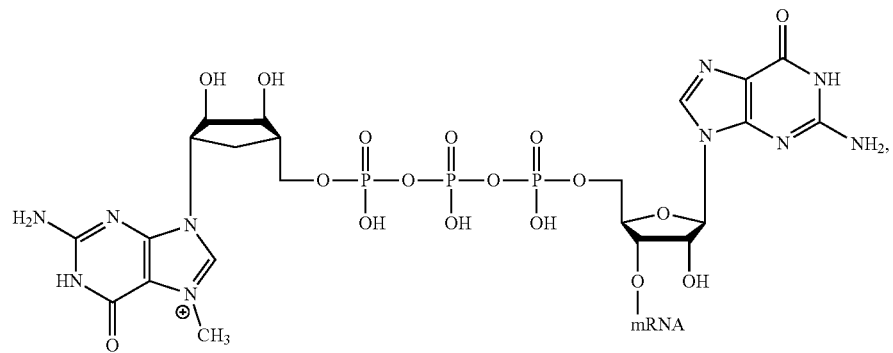
(CAP-015)
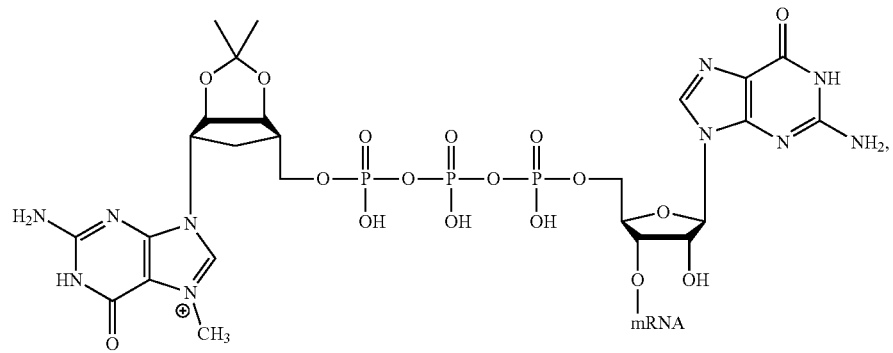
(CAP-016)
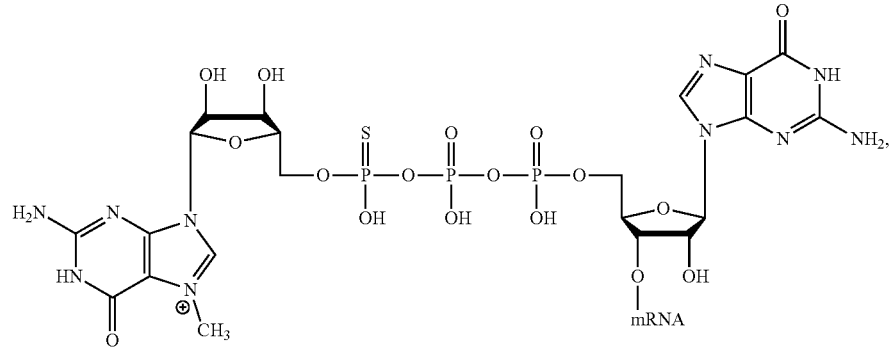

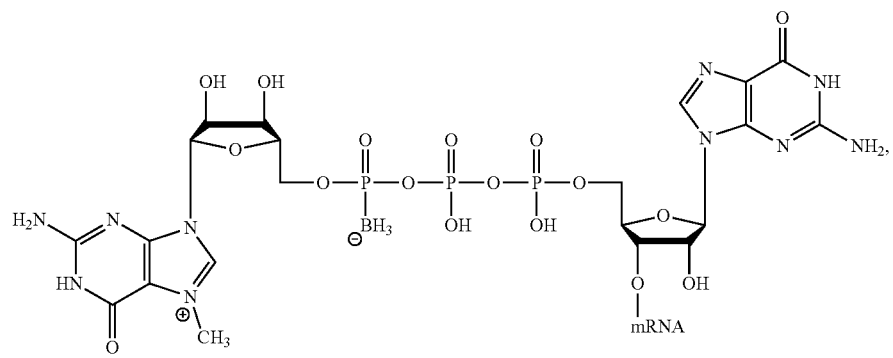
(CAP-017)
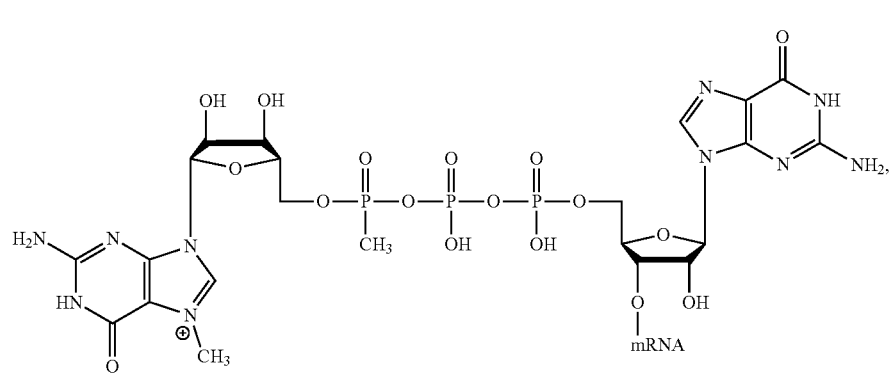
(CAP-018)
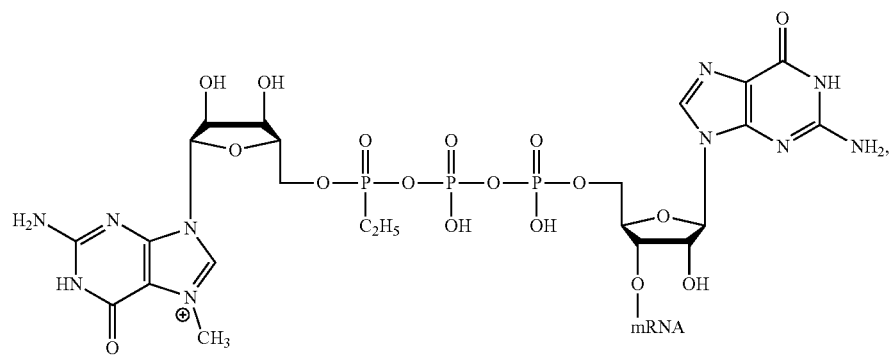
(CAP-019)
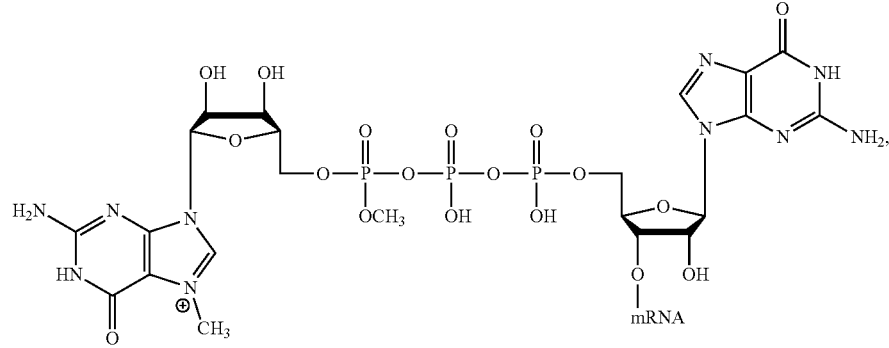
(CAP-020)

-continued

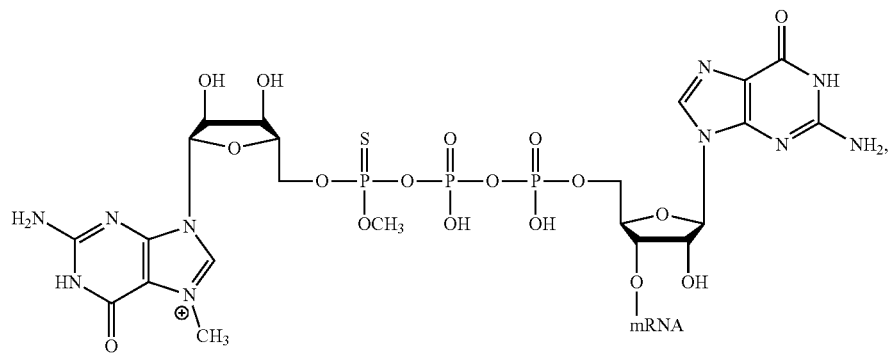

(CAP-021)

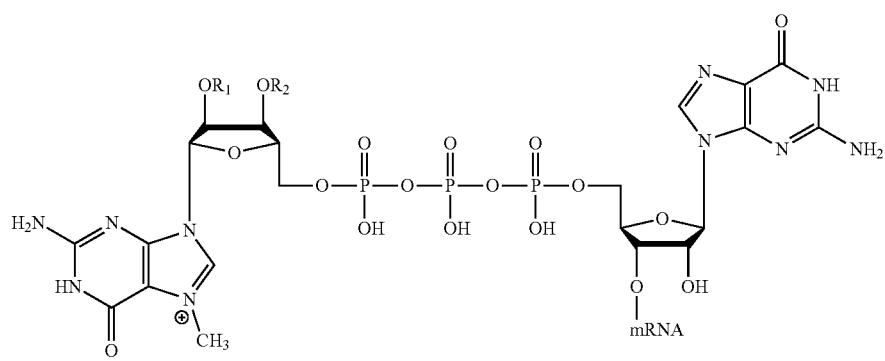

where $R_1$ and $R_2$ are defined in Table 1:

TABLE 1

| Cap Structure Number | $R_1$ | $R_2$ |
|---|---|---|
| CAP-022 | $C_2H_5$ (Ethyl) | H |
| CAP-023 | H | $C_2H_5$ (Ethyl) |
| CAP-024 | $C_2H_5$ (Ethyl) | $C_2H_5$ (Ethyl) |
| CAP-025 | $C_3H_7$ (Propyl) | H |
| CAP-026 | H | $C_3H_7$ (Propyl) |
| CAP-027 | $C_3H_7$ (Propyl) | $C_3H_7$ (Propyl) |
| CAP-028 | $C_4H_9$ (Butyl) | H |
| CAP-029 | H | $C_4H_9$ (Butyl) |
| CAP-030 | $C_4H_9$ (Butyl) | $C_4H_9$ (Butyl) |
| CAP-031 | $C_5H_{11}$ (Pentyl) | H |
| CAP-032 | H | $C_5H_{11}$ (Pentyl) |
| CAP-033 | $C_5H_{11}$ (Pentyl) | $C_5H_{11}$ (Pentyl) |
| CAP-034 | $H_2C-C\equiv CH$ (Propargyl) | H |
| CAP-035 | H | $H_2C-C\equiv CH$ (Propargyl) |
| CAP-036 | $H_2C-C\equiv CH$ (Propargyl) | $H_2C-C\equiv CH$ (Propargyl) |
| CAP-037 | $CH_2CH=CH_2$ (Allyl) | H |
| CAP-038 | H | $CH_2CH=CH_2$ (Allyl) |
| CAP-039 | $CH_2CH=CH_2$ (Allyl) | $CH_2CH=CH_2$ (Allyl) |
| CAP-040 | $CH_2OCH_3$ (MOM) | H |
| CAP-041 | H | $CH_2OCH_3$ (MOM) |
| CAP-042 | $CH_2OCH_3$ (MOM) | $CH_2OCH_3$ (MOM) |
| CAP-043 | $CH_2OCH_2CH_2OCH_3$ (MEM) | H |
| CAP-044 | H | $CH_2OCH_2CH_2OCH_3$ (MEM) |
| CAP-045 | $CH_2OCH_2CH_2OCH_3$ (MEM) | $CH_2OCH_2CH_2OCH_3$ (MEM) |
| CAP-046 | $CH_2SCH_3$ (MTM) | H |
| CAP-047 | H | $CH_2SCH_3$ (MTM) |
| CAP-048 | $CH_2SCH_3$ (MTM) | $CH_2SCH_3$ (MTM) |
| CAP-049 | $CH_2C_6H_5$ (Benzyl) | H |
| CAP-050 | H | $CH_2C_6H_5$ (Benzyl) |
| CAP-051 | $CH_2C_6H_5$ (Benzyl) | $CH_2C_6H_5$ (Benzyl) |
| CAP-052 | $CH_2OCH_2C_6H_5$ (BOM) | H |
| CAP-053 | H | $CH_2OCH_2C_6H_5$ (BOM) |
| CAP-054 | $CH_2OCH_2C_6H_5$ (BOM) | $CH_2OCH_2C_6H_5$ (BOM) |
| CAP-055 | $CH_2C_6H_4$—OMe (p-Methoxybenzyl) | H |
| CAP-056 | H | $CH_2C_6H_4$—OMe (p-Methoxybenzyl) |
| CAP-057 | $CH_2C_6H_4$—OMe (p-Methoxybenzyl) | $CH_2C_6H_4$—OMe (p-Methoxybenzyl) |
| CAP-058 | $CH_2C_6H_4$—$NO_2$ (p-Nitrobenzyl) | H |
| CAP-059 | H | $CH_2C_6H_4$—$NO_2$ (p-Nitrobenzyl) |
| CAP-060 | $CH_2C_6H_4$—$NO_2$ (p-Nitrobenzyl) | $CH_2C_6H_4$—$NO_2$ (p-Nitrobenzyl) |
| CAP-061 | $CH_2C_6H_4$—X (p-Halobenzyl) where X = F, Cl, Br or I | H |
| CAP-062 | H | $CH_2C_6H_4$—X (p-Halobenzyl) where X = F, Cl, Br or I |
| CAP-063 | $CH_2C_6H_4$—X (p-Halobenzyl) where X = F, Cl, Br or I | $CH_2C_6H_4$—X (p-Halobenzyl) where X = F, Cl, Br or I |
| CAP-064 | $CH_2C_6H_4$—$N_3$ (p-Azidobenzyl) | H |
| CAP-065 | H | $CH_2C_6H_4$—$N_3$ (p-Azidobenzyl) |

TABLE 1-continued

| Cap Structure Number | R₁ | R₂ |
|---|---|---|
| CAP-066 | CH₂C₆H₄—N₃ (p-Azidobenzyl) | CH₂C₆H₄—N₃ (p-Azidobenzyl) |
| CAP-067 | CH₂C₆H₄—CF₃ (p-Trifluoromethylbenzyl) | H |
| CAP-068 | H | CH₂C₆H₄—CF₃ (p-Trifluoromethylbenzyl) |
| CAP-069 | CH₂C₆H₄—CF₃ (p-Trifluoromethylbenzyl) | CH₂C₆H₄—CF₃ (p-Trifluoromethylbenzyl) |
| CAP-070 | CH₂C₆H₄—OCF₃ (p-Trifluoromethoxylbenzyl) | H |
| CAP-071 | H | CH₂C₆H₄—OCF₃ (p-Trifluoromethoxylbenzyl) |
| CAP-072 | CH₂C₆H₄—OCF₃ (p-Trifluoromethoxylbenzyl) | CH₂C₆H₄—OCF₃ (p-Trifluoromethoxylbenzyl) |
| CAP-073 | CH₂C₆H₃—(CF₃)₂ [2,4-bis(Trifluoromethyl)benzyl] | H |
| CAP-074 | H | CH₂C₆H₃—(CF₃)₂ [2,4-bis(Trifluoromethyl)benzyl] |
| CAP-075 | CH₂C₆H₃—(CF₃)₂ [2,4-bis(Trifluoromethyl)benzyl] | CH₂C₆H₃—(CF₃)₂ [2,4-bis(Trifluoromethyl)benzyl] |
| CAP-076 | Si(C₆H₅)₂C₄H₉ (t-Butyldiphenylsilyl) | H |
| CAP-077 | H | Si(C₆H₅)₂C₄H₉ (t-Butyldiphenylsilyl) |
| CAP-078 | Si(C₆H₅)₂C₄H₉ (t-Butyldiphenylsilyl) | Si(C₆H₅)₂C₄H₉ (t-Butyldiphenylsilyl) |
| CAP-079 | CH₂CH₂CH=CH₂ (Homoallyl) | H |
| CAP-080 | H | CH₂CH₂CH=CH₂ (Homoallyl) |
| CAP-081 | CH₂CH₂CH=CH₂ (Homoallyl) | CH₂CH₂CH=CH₂ (Homoallyl) |
| CAP-082 | P(O)(OH)₂ (MP) | H |
| CAP-083 | H | P(O)(OH)₂ (MP) |
| CAP-084 | P(O)(OH)₂ (MP) | P(O)(OH)₂ (MP) |
| CAP-085 | P(S)(OH)₂ (Thio-MP) | H |
| CAP-086 | H | P(S)(OH)₂ (Thio-MP) |
| CAP-087 | P(S)(OH)₂ (Thio-MP) | P(S)(OH)₂ (Thio-MP) |
| CAP-088 | P(O)(CH₃)(OH) (Methylphophonate) | H |
| CAP-089 | H | P(O)(CH₃)(OH) (Methylphophonate) |
| CAP-090 | P(O)(CH₃)(OH) (Methylphophonate) | P(O)(CH₃)(OH) (Methylphophonate) |
| CAP-091 | PN(iPr)₂(OCH₂CH₂CN) (Phosporamidite) | H |
| CAP-092 | H | PN(iPr)₂(OCH₂CH₂CN) (Phosporamidite) |
| CAP-093 | PN(iPr)₂(OCH₂CH₂CN) (Phosporamidite) | PN(iPr)₂(OCH₂CH₂CN) (Phosporamidite) |
| CAP-094 | SO₂CH₃ (Methanesulfonic acid) | H |
| CAP-095 | H | SO₂CH₃ (Methanesulfonic acid) |
| CAP-096 | SO₂CH₃ (Methanesulfonic acid) | SO₂CH₃ (Methanesulfonic acid) | where R₁ and R₂ are defined in Table 2:

TABLE 2

| Cap Structure Number | R1 | R2 |
|---|---|---|
| CAP-097 | NH₂ (amino) | H |
| CAP-098 | H | NH₂ (amino) |
| CAP-099 | NH₂ (amino) | NH₂ (amino) |
| CAP-100 | N₃ (Azido) | H |
| CAP-101 | H | N₃ (Azido) |
| CAP-102 | N₃ (Azido) | N₃ (Azido) |
| CAP-103 | X (Halo: F, Cl, Br, I) | H |
| CAP-104 | H | X (Halo: F, Cl, Br, I) |
| CAP-105 | X (Halo: F, Cl, Br, I) | X (Halo: F, Cl, Br, I) |
| CAP-106 | SH (Thiol) | H |
| CAP-107 | H | SH (Thiol) |
| CAP-108 | SH (Thiol) | SH (Thiol) |
| CAP-109 | SCH₃ (Thiomethyl) | H |
| CAP-110 | H | SCH₃ (Thiomethyl) |
| CAP-111 | SCH₃ (Thiomethyl) | SCH₃ (Thiomethyl) |

In Table 1, "MOM" stands for methoxymethyl, "MEM" stands for methoxyethoxymethyl, "MTM" stands for methylthiomethyl, "BOM" stands for benzyloxymethyl and "MP" stands for monophosphonate. In Table 1 and 2, "F" stands for fluorine, "Cl" stands for chlorine, "Br" stands for bromine and "I" stands for iodine.

In a non-limiting example, the modified 5'cap may have the substrate structure for vaccinia mRNA capping enzyme of:

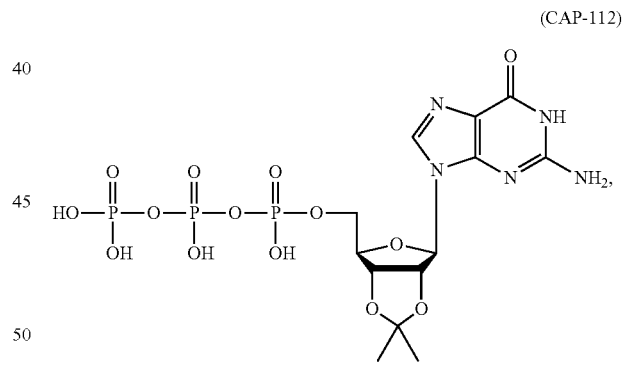

(CAP-112)

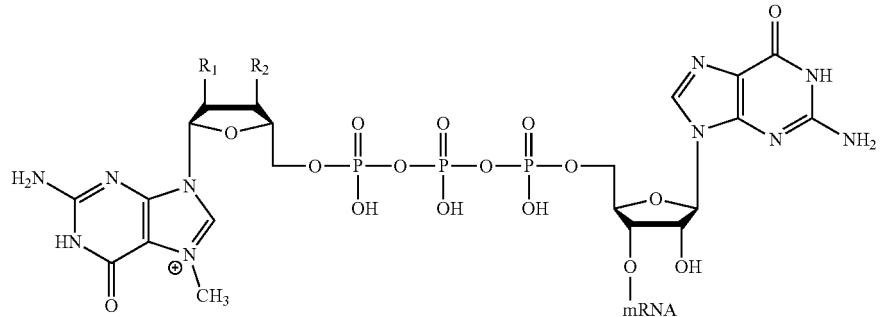

(CAP-113)
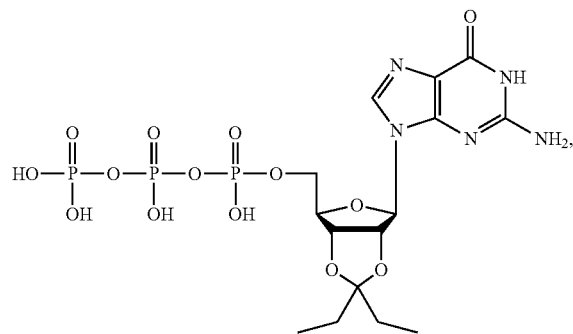
(CAP-114)
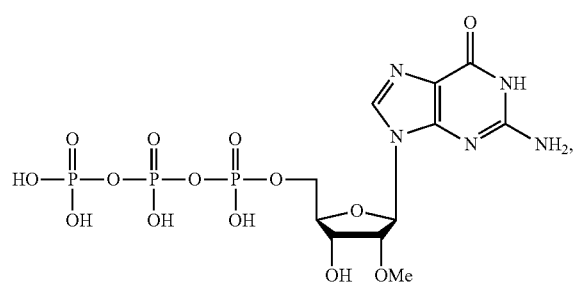
(CAP-118)
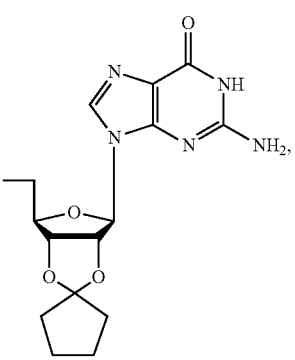
(CAP-115)
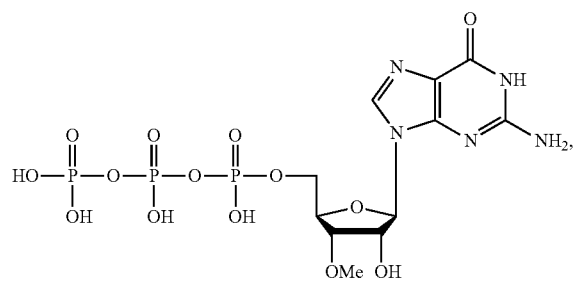
(CAP-119)
(CAP-116)
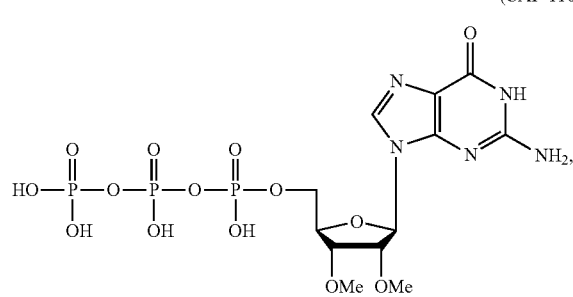
(CAP-120)
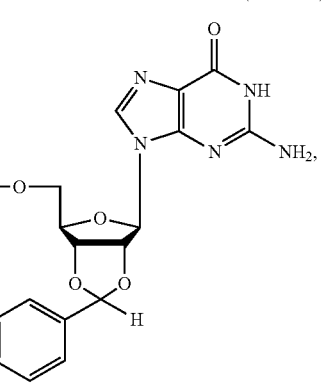
(CAP-117)
(CAP-121)
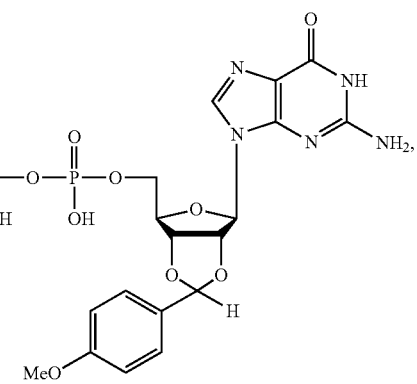

(CAP-122)
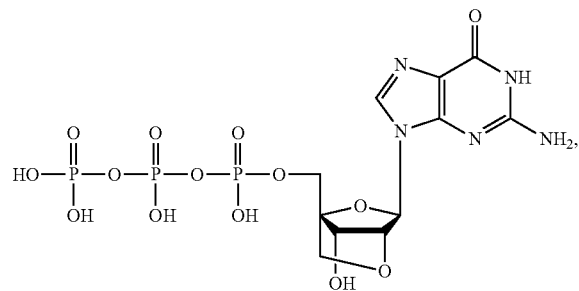
(CAP-123)
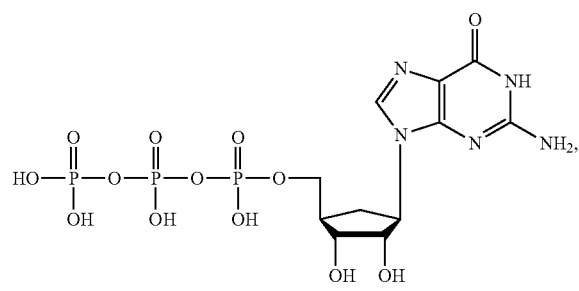
(CAP-124)
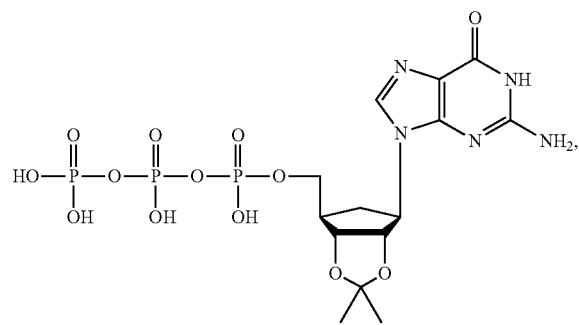
(CAP-125)
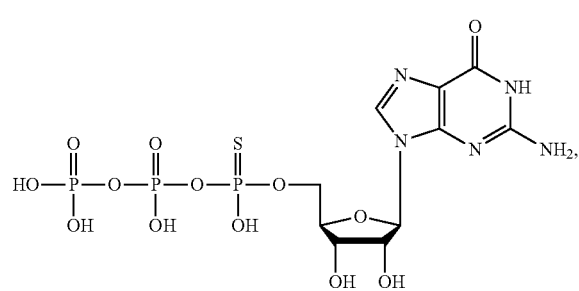
(CAP-126)
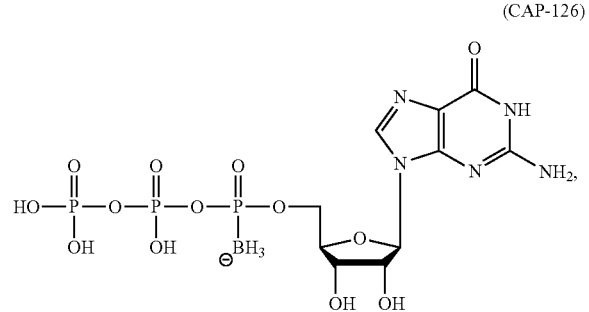
(CAP-127)
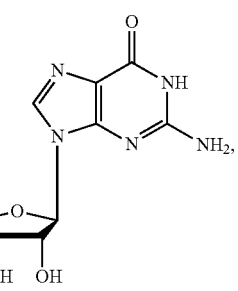
(CAP-128)
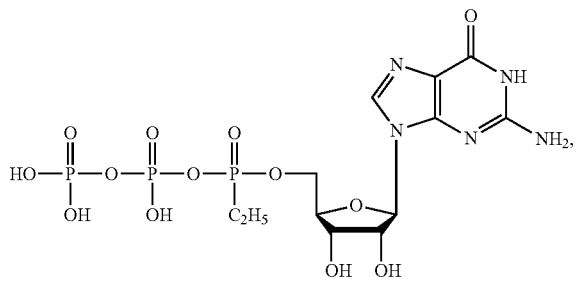
(CAP-129)
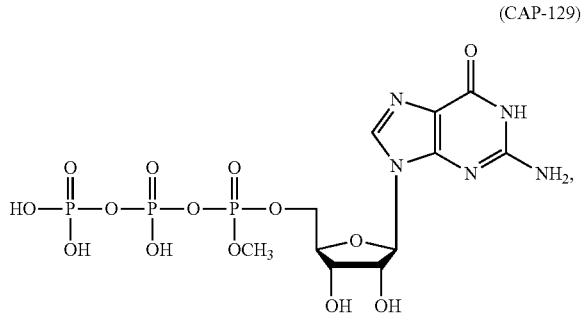
(CAP-130)
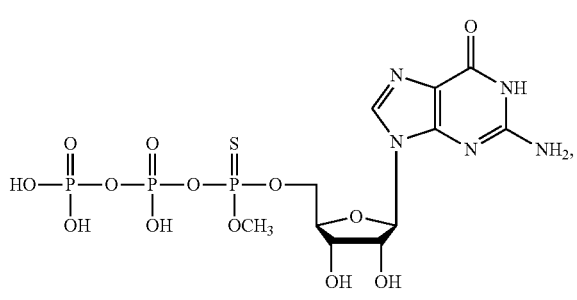
(CAP-131)
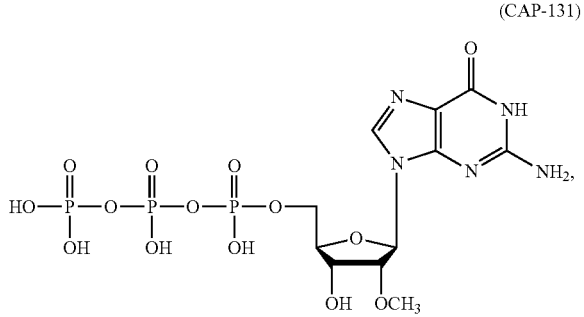

-continued

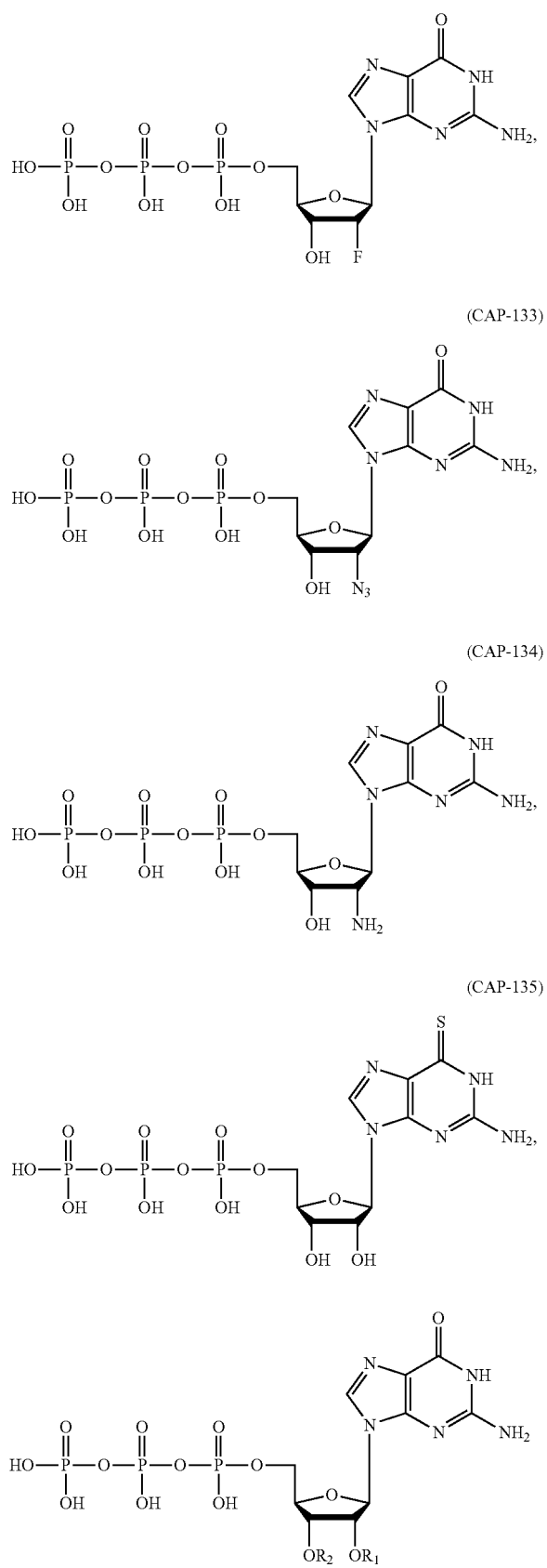

(CAP-132), (CAP-133), (CAP-134), (CAP-135)

where $R_1$ and $R_2$ are defined in Table 3:

TABLE 3

| Cap Structure Number | $R_1$ | $R_2$ |
|---|---|---|
| CAP-136 | $C_2H_5$ (Ethyl) | H |
| CAP-137 | H | $C_2H_5$ (Ethyl) |
| CAP-138 | $C_2H_5$ (Ethyl) | $C_2H_5$ (Ethyl) |
| CAP-139 | $C_3H_7$ (Propyl) | H |
| CAP-140 | H | $C_3H_7$ (Propyl) |
| CAP-141 | $C_3H_7$ (Propyl) | $C_3H_7$ (Propyl) |
| CAP-142 | $C_4H_9$ (Butyl) | H |
| CAP-143 | H | $C_4H_9$ (Butyl) |
| CAP-144 | $C_4H_9$ (Butyl) | $C_4H_9$ (Butyl) |
| CAP-145 | $C_5H_{11}$ (Pentyl) | H |
| CAP-146 | H | $C_5H_{11}$ (Pentyl) |
| CAP-147 | $C_5H_{11}$ (Pentyl) | $C_5H_{11}$ (Pentyl) |
| CAP-148 | $H_2C{-}C{\equiv}CH$ (Propargyl) | H |
| CAP-149 | H | $H_2C{-}C{\equiv}CH$ (Propargyl) |
| CAP-150 | $H_2C{-}C{\equiv}CH$ (Propargyl) | $H_2C{-}C{\equiv}CH$ (Propargyl) |
| CAP-151 | $CH_2CH{=}CH_2$ (Allyl) | H |
| CAP-152 | H | $CH_2CH{=}CH_2$ (Allyl) |
| CAP-153 | $CH_2CH{=}CH_2$ (Allyl) | $CH_2CH{=}CH_2$ (Allyl) |
| CAP-154 | $CH_2OCH_3$ (MOM) | H |
| CAP-155 | H | $CH_2OCH_3$ (MOM) |
| CAP-156 | $CH_2OCH_3$ (MOM) | $CH_2OCH_3$ (MOM) |
| CAP-157 | $CH_2OCH_2CH_2OCH_3$ (MEM) | H |
| CAP-158 | H | $CH_2OCH_2CH_2OCH_3$ (MEM) |
| CAP-159 | $CH_2OCH_2CH_2OCH_3$ (MEM) | $CH_2OCH_2CH_2OCH_3$ (MEM) |
| CAP-160 | $CH_2SCH_3$ (MTM) | H |
| CAP-161 | H | $CH_2SCH_3$ (MTM) |
| CAP-162 | $CH_2SCH_3$ (MTM) | $CH_2SCH_3$ (MTM) |
| CAP-163 | $CH_2C_6H_5$ (Benzyl) | H |
| CAP-164 | H | $CH_2C_6H_5$ (Benzyl) |
| CAP-165 | $CH_2C_6H_5$ (Benzyl) | $CH_2C_6H_5$ (Benzyl) |
| CAP-166 | $CH_2OCH_2C_6H_5$ (BOM) | H |
| CAP-167 | H | $CH_2OCH_2C_6H_5$ (BOM) |
| CAP-168 | $CH_2OCH_2C_6H_5$ (BOM) | $CH_2OCH_2C_6H_5$ (BOM) |
| CAP-169 | $CH_2C_6H_4{-}OMe$ (p-Methoxybenzyl) | H |
| CAP-170 | H | $CH_2C_6H_4{-}OMe$ (p-Methoxybenzyl) |
| CAP-171 | $CH_2C_6H_4{-}OMe$ (p-Methoxybenzyl) | $CH_2C_6H_4{-}OMe$ (p-Methoxybenzyl) |
| CAP-172 | $CH_2C_6H_4{-}NO_2$ (p-Nitrobenzyl) | H |
| CAP-173 | H | $CH_2C_6H_4{-}NO_2$ (p-Nitrobenzyl) |
| CAP-174 | $CH_2C_6H_4{-}NO_2$ (p-Nitrobenzyl) | $CH_2C_6H_4{-}NO_2$ (p-Nitrobenzyl) |
| CAP-175 | $CH_2C_6H_4{-}X$ (p-Halobenzyl) where X = F, Cl, Br or I | H |
| CAP-176 | H | $CH_2C_6H_4{-}X$ (p-Halobenzyl) where X = F, Cl, Br or I |
| CAP-177 | $CH_2C_6H_4{-}X$ (p-Halobenzyl) where X = F, Cl, Br or I | $CH_2C_6H_4{-}X$ (p-Halobenzyl) where X = F, Cl, Br or I |
| CAP-178 | $CH_2C_6H_4{-}N_3$ (p-Azidobenzyl) | H |
| CAP-179 | H | $CH_2C_6H_4{-}N_3$ (p-Azidobenzyl) |
| CAP-180 | $CH_2C_6H_4{-}N_3$ (p-Azidobenzyl) | $CH_2C_6H_4{-}N_3$ (p-Azidobenzyl) |
| CAP-181 | $CH_2C_6H_4{-}CF_3$ (p-Trifluoromethylbenzyl) | H |
| CAP-182 | H | $CH_2C_6H_4{-}CF_3$ (p-Trifluoromethylbenzyl) |
| CAP-183 | $CH_2C_6H_4{-}CF_3$ (p-Trifluoromethylbenzyl) | $CH_2C_6H_4{-}CF_3$ (p-Trifluoromethylbenzyl) |
| CAP-184 | $CH_2C_6H_4{-}OCF_3$ (p-Trifluoromethoxylbenzyl) | H |
| CAP-185 | H | $CH_2C_6H_4{-}OCF_3$ (p-Trifluoromethoxylbenzyl) |
| CAP-186 | $CH_2C_6H_4{-}OCF_3$ (p-Trifluoromethoxylbenzyl) | $CH_2C_6H_4{-}OCF_3$ (p-Trifluoromethoxylbenzyl) |
| CAP-187 | $CH_2C_6H_3{-}(CF_3)_2$ [2,4-bis(Trifluoromethyl)benzyl] | H |
| CAP-188 | H | $CH_2C_6H_3{-}(CF_3)_2$ [2,4-bis(Trifluoromethyl)benzyl] |

TABLE 3-continued

| Cap Structure Number | R₁ | R₂ |
|---|---|---|
| CAP-189 | CH₂C₆H₃—(CF₃)₂ [2,4-bis(Trifluoromethyl)benzyl] | CH₂C₆H₃—(CF₃)₂ [2,4-bis(Trifluoromethyl)benzyl] |
| CAP-190 | Si(C₆H₅)₂C₄H₉ (t-Butyldiphenylsilyl) | H |
| CAP-191 | H | Si(C₆H₅)₂C₄H₉ (t-Butyldiphenylsilyl) |
| CAP-192 | Si(C₆H₅)₂C₄H₉ (t-Butyldiphenylsilyl) | Si(C₆H₅)₂C₄H₉ (t-Butyldiphenylsilyl) |
| CAP-193 | CH₂CH₂CH=CH₂ (Homoallyl) | H |
| CAP-194 | H | CH₂CH₂CH=CH₂ (Homoallyl) |
| CAP-195 | CH₂CH₂CH=CH₂ (Homoallyl) | CH₂CH₂CH=CH₂ (Homoallyl) |
| CAP-196 | P(O)(OH)₂ (MP) | H |
| CAP-197 | H | P(O)(OH)₂ (MP) |
| CAP-198 | P(O)(OH)₂ (MP) | P(O)(OH)₂ (MP) |
| CAP-199 | P(S)(OH)₂ (Thio-MP) | H |
| CAP-200 | H | P(S)(OH)₂ (Thio-MP) |
| CAP-201 | P(S)(OH)₂ (Thio-MP) | P(S)(OH)₂ (Thio-MP) |
| CAP-202 | P(O)(CH₃)(OH) (Methylphophonate) | H |
| CAP-203 | H | P(O)(CH₃)(OH) (Methylphophonate) |
| CAP-204 | P(O)(CH₃)(OH) (Methylphophonate) | P(O)(CH₃)(OH) (Methylphophonate) |
| CAP-205 | PN($^i$Pr)₂(OCH₂CH₂CN) (Phosporamidite) | H |
| CAP-206 | H | PN($^i$Pr)₂(OCH₂CH₂CN) (Phosporamidite) |
| CAP-207 | PN($^i$Pr)₂(OCH₂CH₂CN) (Phosporamidite) | PN($^i$Pr)₂(OCH₂CH₂CN) (Phosporamidite) |
| CAP-208 | SO₂CH₃ (Methanesulfonic acid) | H |
| CAP-209 | H | SO₂CH₃ (Methanesulfonic acid) |
| CAP-210 | SO₂CH₃ (Methanesulfonic acid) | SO₂CH₃ (Methanesulfonic acid) |

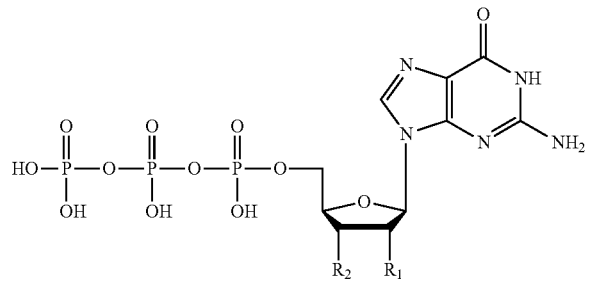

where R₁ and R₂ are defined in Table 4:

TABLE 4

| Cap Structure Number | R1 | R2 |
|---|---|---|
| CAP-211 | NH₂ (amino) | H |
| CAP-212 | H | NH₂ (amino) |
| CAP-213 | NH₂ (amino) | NH₂ (amino) |
| CAP-214 | N₃ (Azido) | H |
| CAP-215 | H | N₃ (Azido) |
| CAP-216 | N₃ (Azido) | N₃ (Azido) |
| CAP-217 | X (Halo: F, Cl, Br, I) | H |
| CAP-218 | H | X (Halo: F, Cl, Br, I) |
| CAP-219 | X (Halo: F, Cl, Br, I) | X (Halo: F, Cl, Br, I) |
| CAP-220 | SH (Thiol) | H |
| CAP-221 | H | SH (Thiol) |
| CAP-222 | SH (Thiol) | SH (Thiol) |
| CAP-223 | SCH₃ (Thiomethyl) | H |
| CAP-224 | H | SCH₃ (Thiomethyl) |
| CAP-225 | SCH₃ (Thiomethyl) | SCH₃ (Thiomethyl) |

In Table 3, "MOM" stands for methoxymethyl, "MEM" stands for methoxyethoxymethyl, "MTM" stands for methylthiomethyl, "BOM" stands for benzyloxymethyl and "MP" stands for monophosphonate. In Table 3 and 4, "F" stands for fluorine, "Cl" stands for chlorine, "Br" stands for bromine and "I" stands for iodine.

In another non-limiting example, of the modified capping structure substrates CAP-112-CAP-225 could be added in the presence of vaccinia capping enzyme with a component to create enzymatic activity such as, but not limited to, S-adenosylmethionine (AdoMet), to form a modified cap for mRNA.

In one embodiment, the replacement of the sugar ring oxygen (that produced the carbocyclic ring) with a methylene moiety (CH₂) could create greater stability to the C—N bond against phosphorylases as the C—N bond is resistant to acid or enzymatic hydrolysis. The methylene moiety may also increase the stability of the triphosphate bridge moiety and thus increasing the stability of the mRNA. As a non-limiting example, the cap substrate structure for cap dependent translation may have the structure such as, but not limited to, CAP-014 and CAP-015 and/or the cap substrate structure for vaccinia mRNA capping enzyme such as, but not limited to, CAP-123 and CAP-124. In another example, CAP-112-CAP-122 and/or CAP-125-CAP-225, can be modified by replacing the sugar ring oxygen (that produced the carbocyclic ring) with a methylene moiety (CH₂).

In another embodiment, the triphophosphate bridge may be modified by the replacement of at least one oxygen with sulfur (thio), a borane (BH₃) moiety, a methyl group, an ethyl group, a methoxy group and/or combinations thereof. This modification could increase the stability of the mRNA towards decapping enzymes. As a non-limiting example, the cap substrate structure for cap dependent translation may have the structure such as, but not limited to, CAP-016-CAP-021 and/or the cap substrate structure for vaccinia mRNA capping enzyme such as, but not limited to, CAP-125-CAP-130. In another example, CAP-003-CAP-015, CAP-022-CAP-124 and/or CAP-131-CAP-225, can be modified on the triphosphate bridge by replacing at least one of the triphosphate bridge oxygens with sulfur (thio), a borane (BH₃) moiety, a methyl group, an ethyl group, a methoxy group and/or combinations thereof.

In one embodiment, CAP-001-134 and/or CAP-136-CAP-225 may be modified to be a thioguanosine analog similar to CAP-135. The thioguanosine analog may comprise additional modifications such as, but not limited to, a modification at the triphosphate moiety (e.g., thio, BH₃, CH₃, C₂H₅, OCH₃, S and S with OCH₃), a modification at the 2' and/or 3' positions of 6-thio guanosine as described herein and/or a replacement of the sugar ring oxygen (that produced the carbocyclic ring) as described herein.

In one embodiment, CAP-001-121 and/or CAP-123-CAP-225 may be modified to be a modified 5'cap similar to CAP-122. The modified 5'cap may comprise additional modifications such as, but not limited to, a modification at the triphosphate moiety (e.g., thio, $BH_3$, $CH_3$, $C_2H_5$, $OCH_3$, S and S with $OCH_3$), a modification at the 2' and/or 3' positions of 6-thio guanosine as described herein and/or a replacement of the sugar ring oxygen (that produced the carbocyclic ring) as described herein.

In one embodiment, the 5'cap modification may be the attachment of biotin or conjufation at the 2' or 3' position of a GTP.

In another embodiment, the 5' cap modification may include a $CF_2$ modified triphosphate moiety.

3' UTR and Viral Sequences

Additional viral sequences such as, but not limited to, the translation enhancer sequence of the barley yellow dwarf virus (BYDV-PAV) can be engineered and inserted in the 3' UTR of the nucleic acids or mRNA of the invention and can stimulate the translation of the construct in vitro and in vivo. Transfection experiments can be conducted in relevant cell lines at and protein production can be assayed by ELISA at 12 hr, 24 hr, 48 hr, 72 hr and day 7 post-transfection.

IRES Sequences

Further, provided are nucleic acids containing an internal ribosome entry site (IRES). First identified as a feature Picorna virus RNA, IRES plays an important role in initiating protein synthesis in absence of the 5' cap structure. An IRES may act as the sole ribosome binding site, or may serve as one of multiple ribosome binding sites of an mRNA. Nucleic acids or mRNA containing more than one functional ribosome binding site may encode several peptides or polypeptides that are translated independently by the ribosomes ("multicistronic nucleic acid molecules"). When nucleic acids or mRNA are provided with an IRES, further optionally provided is a second translatable region. Examples of IRES sequences that can be used according to the invention include without limitation, those from picornaviruses (e.g. FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

Terminal Architecture Modifications: Poly-A Tails

During RNA processing, a long chain of adenine nucleotides (poly-A tail) is normally added to a messenger RNA (mRNA) molecules to increase the stability of the molecule. Immediately after transcription, the 3' end of the transcript is cleaved to free a 3' hydroxyl. Then poly-A polymerase adds a chain of adenine nucleotides to the RNA. The process, called polyadenylation, adds a poly-A tail that is between 100 and 250 residues long.

It has been discovered that unique poly-A tail lengths provide certain advantages to the modified RNAs of the present invention.

Generally, the length of a poly-A tail of the present invention is greater than 30 nucleotides in length. In another embodiment, the poly-A tail is greater than 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 60 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1700 nucleotides. In another embodiment, the length is at least 1800 nucleotides. In another embodiment, the length is at least 1900 nucleotides. In another embodiment, the length is at least 2000 nucleotides. In another embodiment, the length is at least 2500 nucleotides. In another embodiment, the length is at least 3000 nucleotides.

In some embodiments, the nucleic acid or mRNA includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In one embodiment, the poly-A tail may be 80 nucleotides, 120 nucleotides, 160 nucleotides in length on a modified RNA molecule described herein such as, but not limited to, the polyA tail length on the modified RNA described in Example 13.

In another embodiment, the poly-A tail may be 20, 40, 80, 100, 120, 140 or 160 nucleotides in length on a modified RNA molecule described herein such as, but not limited to, the polyA tail length on the modified RNA described in Example 44.

In one embodiment, the poly-A tail is designed relative to the length of the overall modified RNA molecule. This design may be based on the length of the coding region of the modified RNA, the length of a particular feature or region of the modified RNA (such as the mRNA), or based on the length of the ultimate product expressed from the modified RNA. When relative to any additional feature of the modified RNA (e.g., other than the mRNA portion which includes the poly-A tail) the poly-A tail may be 10, 20, 30, 40, 50, 60, 70, 80, 90 or 100% greater in length than the additional feature. The poly-A tail may also be designed as a fraction of the modified RNA to which it belongs. In this context, the poly-A tail may be 10, 20, 30, 40, 50, 60, 70, 80, or 90% or more of the total length of the construct or the total length of the construct minus the poly-A tail.

In one embodiment, engineered binding sites and/or the conjugation of nucleic acids or mRNA for Poly-A binding protein may be used to enhance expression. The engineered binding sites may be sensor sequences which can operate as binding sites for ligands of the local microenvironment of the nucleic acids and/or mRNA. As a non-limiting example, the nucleic acids and/or mRNA may comprise at least one engineered binding site to alter the binding affinity of Poly-A binding protein (PABP) and analogs thereof. The incorporation of at least one engineered binding site may increase the binding affinity of the PABP and analogs thereof.

Additionally, multiple distinct nucleic acids or mRNA may be linked together to the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection. As a non-limiting example, the transfection experiments may be used to evaluate the effect on PABP or analogs thereof binding affinity as a result of the addition of at least one engineered binding site.

In one embodiment, a polyA tail may be used to modulate translation initiation. While not wishing to be bound by theory, the polyA til recruits PABP which in turn can interact with translation initiation complex and thus may be essential for protein synthesis.

In another embodiment, a polyA tail may also be used in the present invention to protect against 3'-5' exonuclease digestion.

In one embodiment, the nucleic acids or mRNA of the present invention are designed to include a polyA-G Quartet. The G-quartet is a cyclic hydrogen bonded array of four guanine nucleotides that can be formed by G-rich sequences in both DNA and RNA. In this embodiment, the G-quartet is incorporated at the end of the poly-A tail. The resultant nucleic acid or mRNA may be assayed for stability, protein production and other parameters including half-life at various time points. It has been discovered that the polyA-G quartet results in protein production equivalent to at least 75% of that seen using a poly-A tail of 120 nucleotides alone.

In one embodiment, the nucleic acids or mRNA of the present invention may comprise a polyA tail and may be stabilized by the addition of a chain terminating nucleoside. The nucleic acids and/or mRNA with a polyA tail may further comprise a 5'cap structure.

In another embodiment, the nucleic acids or mRNA of the present invention may comprise a polyA-G Quartet. The nucleic acids and/or mRNA with a polyA-G Quartet may further comprise a 5'cap structure.

In one embodiment, the chain terminating nucleoside which may be used to stabilize the nucleic acid or mRNA comprising a polyA tail or polyA-G Quartet may be, but is not limited to, those described in International Patent Publication No. WO2013103659, herein incorporated by reference in its entirety. In another embodiment, the chain terminating nucleosides which may be used with the present invention includes, but is not limited to, 3'-deoxyadenosine (cordycepin), 3'-deoxyuridine, 3'-deoxycytosine, 3'-deoxyguanosine, 3'-deoxythymine, 2',3'-dideoxynucleosides, such as 2',3'-dideoxyadenosine, 2',3'-dideoxyuridine, 2',3'-dideoxycytosine, 2',3'-dideoxyguanosine, 2',3'-dideoxythymine, a 2'-deoxynucleoside, or a —O— methylnucleoside.

In another embodiment, the nucleic acid such as, but not limited to mRNA, which comprise a polyA tail or a polyA-G Quartet may be stabilized by a modification to the 3'region of the nucleic acid that can prevent and/or inhibit the addition of oligio(U) (see e.g., International Patent Publication No. WO2013103659, herein incorporated by reference in its entirety).

In yet another embodiment, the nucleic acid such as, but not limited to mRNA, which comprise a polyA tail or a polyA-G Quartet may be stabilized by the addition of an oligonucleotide that terminates in a 3'-deoxynucleoside, 2',3'-dideoxynucleoside 3'-0-methylnucleosides, 3'-0-ethyl- nucleosides, 3'-arabinosides, and other modified nucleosides known in the art and/or described herein.

Quantification

In one embodiment, the polynucleotides, primary constructs, modified nucleic acids or mmRNA of the present invention may be quantified in exosomes derived from one or more bodily fluid. As used herein "bodily fluids" include peripheral blood, serum, plasma, ascites, urine, cerebrospinal fluid (CSF), sputum, saliva, bone marrow, synovial fluid, aqueous humor, amniotic fluid, cerumen, breast milk, bronchoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

In the quantification method, a sample of not more than 2 mL is obtained from the subject and the exosomes isolated by size exclusion chromatography, density gradient centrifugation, differential centrifugation, nanomembrane ultrafiltration, immunoabsorbent capture, affinity purification, microfluidic separation, or combinations thereof. In the analysis, the level or concentration of the polynucleotides, primary construct, modified nucleic acid or mmRNA may be an expression level, presence, absence, truncation or alteration of the administered construct. It is advantageous to correlate the level with one or more clinical phenotypes or with an assay for a human disease biomarker. The assay may be performed using construct specific probes, cytometry, qRT-PCR, real-time PCR, PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of the polynucleotides, primary constructs, modified nucleic acid or mmRNA remaining or delivered. This is possible because the polynucleotides, primary constructs, modified nucleic acid or mmRNA of the present invention differ from the endogenous forms due to the structural and/or chemical modifications.

II. Design and Synthesis of Polynucleotides

Polynucleotides, primary constructs modified nucleic acids or mmRNA for use in accordance with the invention may be prepared according to any available technique including, but not limited to chemical synthesis, enzymatic synthesis, which is generally termed in vitro transcription (IVT) or enzymatic or chemical cleavage of a longer precursor, etc. Methods of synthesizing RNAs are known in the art (see, e.g., Gait, M. J. (ed.) *Oligonucleotide synthesis: a practical approach*, Oxford [Oxfordshire], Washington, D.C.: IRL Press, 1984; and Herdewijn, P. (ed.) *Oligonucleotide synthesis: methods and applications*, Methods in Molecular Biology, v. 288 (Clifton, N.J.) Totowa, N.J.: Humana Press, 2005; both of which are incorporated herein by reference).

The process of design and synthesis of the primary constructs of the invention generally includes the steps of gene construction, mRNA production (either with or without modifications) and purification. In the enzymatic synthesis method, a target polynucleotide sequence encoding the polypeptide of interest is first selected for incorporation into a vector which will be amplified to produce a cDNA template. Optionally, the target polynucleotide sequence and/or any flanking sequences may be codon optimized. The cDNA template is then used to produce mRNA through in vitro transcription (IVT). After production, the mRNA may undergo purification and clean-up processes. The steps of which are provided in more detail below.

Gene Construction

The step of gene construction may include, but is not limited to gene synthesis, vector amplification, plasmid purification, plasmid linearization and clean-up, and cDNA template synthesis and clean-up.

Gene Synthesis

Once a polypeptide of interest, or target, is selected for production, a primary construct is designed. Within the primary construct, a first region of linked nucleosides encoding the polypeptide of interest may be constructed using an open reading frame (ORF) of a selected nucleic acid (DNA or RNA) transcript. The ORF may comprise the wild type ORF, an isoform, variant or a fragment thereof. As used herein, an "open reading frame" or "ORF" is meant to refer to a nucleic acid sequence (DNA or RNA) which is capable of encoding a polypeptide of interest. ORFs often begin with the start codon, ATG and end with a nonsense or termination codon or signal.

Further, the nucleotide sequence of the first region may be codon optimized. Codon optimization methods are known in the art and may be useful in efforts to achieve one or more of several goals. These goals include to match codon frequencies in target and host organisms to ensure proper folding, bias GC content to increase mRNA stability or reduce secondary structures, minimize tandem repeat codons or base runs that may impair gene construction or expression, customize transcriptional and translational control regions, insert or remove protein trafficking sequences, remove/add post translation modification sites in encoded protein (e.g. glycosylation sites), add, remove or shuffle protein domains, insert or delete restriction sites, modify ribosome binding sites and mRNA degradation sites, to adjust translational rates to allow the various domains of the protein to fold properly, or to reduce or eliminate problem secondary structures within the mRNA. Codon optimization tools, algorithms and services are known in the art, non-limiting examples include services from GeneArt (Life Technologies) and/or DNA2.0 (Menlo Park Calif.). In one embodiment, the ORF sequence is optimized using optimization algorithms. Codon options for each amino acid are given in Table 5.

TABLE 5

Codon Options

| Amino Acid | Single Letter Code | Codon Options |
|---|---|---|
| Isoleucine | I | ATT, ATC, ATA |
| Leucine | L | CTT, CTC, CTA, CTG, TTA, TTG |
| Valine | V | GTT, GTC, GTA, GTG |
| Phenylalanine | F | TTT, TTC |
| Methionine | M | ATG |
| Cysteine | C | TGT, TGC |
| Alanine | A | GCT, GCC, GCA, GCG |

TABLE 5-continued

Codon Options

| Amino Acid | Single Letter Code | Codon Options |
|---|---|---|
| Glycine | G | GGT, GGC, GGA, GGG |
| Proline | P | CCT, CCC, CCA, CCG |
| Threonine | T | ACT, ACC, ACA, ACG |
| Serine | S | TCT, TCC, TCA, TCG, AGT, AGC |
| Tyrosine | Y | TAT, TAC |
| Tryptophan | W | TGG |
| Glutamine | Q | CAA, CAG |
| Asparagine | N | AAT, AAC |
| Histidine | H | CAT, CAC |
| Glutamic acid | E | GAA, GAG |
| Aspartic acid | D | GAT, GAC |
| Lysine | K | AAA, AAG |
| Arginine | R | CGT, CGC, CGA, CGG, AGA, AGG |
| Selenocysteine | Sec | UGA in mRNA in presence of Selenocystein insertion element (SECIS) |
| Stop codons | Stop | TAA, TAG, TGA |

In one embodiment, after a nucleotide sequence has been codon optimized it may be further evaluated for regions containing restriction sites. At least one nucleotide within the restriction site regions may be replaced with another nucleotide in order to remove the restriction site from the sequence but the replacement of nucleotides does alter the amino acid sequence which is encoded by the codon optimized nucleotide sequence.

Features, which may be considered beneficial in some embodiments of the present invention, may be encoded by the primary construct and may flank the ORF as a first or second flanking region. The flanking regions may be incorporated into the primary construct before and/or after optimization of the ORF. It is not required that a primary construct contain both a 5' and 3' flanking region. Examples of such features include, but are not limited to, untranslated regions (UTRs), Kozak sequences, an oligo(dT) sequence, and detectable tags and may include multiple cloning sites which may have XbaI recognition.

In some embodiments, a 5' UTR and/or a 3' UTR may be provided as flanking regions. Multiple 5' or 3' UTRs may be included in the flanking regions and may be the same or of different sequences. Any portion of the flanking regions, including none, may be codon optimized and any may independently contain one or more different structural or chemical modifications, before and/or after codon optimization. Combinations of features may be included in the first and second flanking regions and may be contained within other features. For example, the ORF may be flanked by a 5' UTR which may contain a strong Kozak translational initiation signal and/or a 3' UTR which may include an oligo(dT) sequence for templated addition of a poly-A tail.

Tables 2 and 3 provide a listing of exemplary UTRs which may be utilized in the primary construct of the present invention as flanking regions. Shown in Table 6 is a representative listing of a 5'-untranslated region of the invention. Variants of 5' UTRs may be utilized wherein one or more nucleotides are added or removed to the termini, including A, T, C or G.

TABLE 6

5'-Untranslated Regions

| 5' UTR Identifier | Name/ Description | Sequence | SEQ ID NO. |
|---|---|---|---|
| Native | Wild type UTR | See wild type sequence | — |
| 5UTR-001 | Synthetic UTR | GGGAAATAAGAGAGAAAAGAAGAGTAAG AAGAAATATAAGAGCCACC | 5 |
| 5UTR-002 | Upstream UTR | GGGAGATCAGAGAGAAAAGAAGAGTAAGA AGAAATATAAGAGCCACC | 6 |
| 5UTR-003 | Upstream UTR | GGAATAAAAGTCTCAACACAACATATACA AAACAAACGAATCTCAAGCAATCAAGCAT TCTACTTCTATTGCAGCAATTTAAATCATTT CTTTTAAAGCAAAAGCAATTTTCTGAAAAT TTTCACCATTTACGAACGATAGCAAC | 7 |
| 5UTR-004 | Upstream UTR | GGGAGACAAGCUUGGCAUUCCGGUACUGU UGGUAAAGCCACC | 8 |

In another embodiment, the 5' UTR may comprise a first polynucleotide fragment and a second polynucleotide fragment where the first and second fragments may be from the same or different gene. (See e.g., US20100293625 and US20110247090, each of which is herein incorporated by reference in its entirety). As a non-limiting example, the first polynucleotide may be a fragment of the canine, human or mouse SERCA2 gene and/or the second polynucleotide fragment is a fragment of the bovine, mouse, rat or sheep beta-casein gene.

In one embodiment, the first polynucleotide fragment may be located on the 5' end of the second polynucleotide fragment. (See e.g., US20100293625 and US20110247090, each of which is herein incorporated by reference in its entirety).

In another embodiment, the first polynucleotide fragment may comprise the second intron of a sarcoplasmic/endoplasmic reticulum calcium ATPase gene and/or the second polynucleotide fragment comprises at least a portion of the 5' UTR of a eukaryotic casein gene. (See e.g., US20100293625 and US20110247090, each of which is herein incorporated by reference in its entirety). The first polynucleotide fragment may also comprise at least a portion of exon 2 and/or exon 3 of the sarcoplasmic/endoplasmic reticulum calcium ATPase gene. (See e.g., US20100293625 and US20110247090, each of which is herein incorporated by reference in its entirety).

Shown in Table 7 is a representative listing of 3'-untranslated regions of the invention. Variants of 3' UTRs may be utilized wherein one or more nucleotides are added or removed to the termini, including A, T, C or G.

TABLE 7

3'-Untranslated Regions

| 3' UTR Identifier | Name/ Description | Sequence | SEQ ID NO. |
|---|---|---|---|
| 3UTR-001 | Creatine Kinase | GCGCCTGCCCACCTGCCACCGACTGCTGGAAC CCAGCCAGTGGGAGGGCCTGGCCCACCAGAGT CCTGCTCCCTCACTCCTCGCCCCGCCCCCTGTC CCAGAGTCCCACCTGGGGGCTCTCTCCACCCTT CTCAGAGTTCCAGTTTCAACCAGAGTTCCAACC | 9 |

TABLE 7-continued

3'-Untranslated Regions

| 3' UTR Identifier | Name/ Description | Sequence | SEQ ID NO. |
|---|---|---|---|
| | | AATGGGCTCCATCCTCTGGATTCTGGCCAATGA AATATCTCCCTGGCAGGGTCCTCTTCTTTTCCC AGAGCTCCACCCCAACCAGGAGCTCTAGTTAA TGGAGAGCTCCCAGCACACTCGGAGCTTGTGC TTTGTCTCCACGCAAAGCGATAAATAAAAGCA TTGGTGGCCTTTGGTCTTTGAATAAAGCCTGAG TAGGAAGTCTAGA | |
| 3UTR-002 | Myoglobin | GCCCCTGCCGCTCCCACCCCCACCCATCTGGGC CCCGGGTTCAAGAGAGAGCGGGGTCTGATCTC GTGTAGCCATATAGAGTTTGCTTCTGAGTGTCT GCTTTGTTTAGTAGAGGTGGGCAGGAGGAGCT GAGGGGCTGGGGCTGGGGTGTTGAAGTTGGCT TTGCATGCCCAGCGATGCGCCTCCCTGTGGGAT GTCATCACCCTGGGAACCGGGAGTGGCCCTTG GCTCACTGTGTTCTGCATGGTTTGGATCTGAAT TAATTGTCCTTTCTTCTAAATCCCAACCGAACT TCTTCCAACCTCCAAACTGGCTGTAACCCCAAA TCCAAGCCATTAACTACACCTGACAGTAGCAA TTGTCTGATTAATCACTGGCCCCTTGAAGACAG CAGAATGTCCCTTTGCAATGAGGAGGAGATCT GGGCTGGGCGGGCCAGCTGGGGAAGCATTTGA CTATCTGGAACTTGTGTGTGCCTCCTCAGGTAT GGCAGTGACTCACCTGGTTTTAATAAAACAAC CTGCAACATCTCATGGTCTTTGAATAAAGCCTG AGTAGGAAGTCTAGA | 10 |
| 3UTR-003 | α-actin | ACACACTCCACCTCCAGCACGCGACTTCTCAG GACGACGAATCTTCTCAATGGGGGGCGGCTG AGCTCCAGCCACCCCGCAGTCACTTTCTTTGTA ACAACTTCCGTTGCTGCCATCGTAAACTGACAC AGTGTTTATAACGTGTACATACATTAACTTATT ACCTCATTTTGTTATTTTTCGAAACAAAGCCCT GTGGAAGAAAATGGAAAACTTGAAGAAGCATT AAAGTCATTCTGTTAAGCTGCGTAAATGGTCTT TGAATAAAGCCTGAGTAGGAAGTCTAGA | 11 |
| 3UTR-004 | Albumin | CATCACATTTAAAAGCATCTCAGCCTACCATG AGAATAAGAGAAAGAAAATGAAGATCAAAAG CTTATTCATCTGTTTTTCTTTTTCGTTGGTGTAA AGCCAACACCCTGTCTAAAAAACATAAATTTC TTTAATCATTTTGCCTCTTTTCTCTGTGCTTCAA TTAATAAAAAATGGAAAGAATCTAATAGAGTG GTACAGCACTGTTATTTTTCAAAGATGTGTTGC TATCCTGAAAATTCTGTAGGTTCTGTGGAAGTT CCAGTGTTCTCTCTTATTCCACTTCGGTAGAGG ATTTCTAGTTTCTTGTGGGCTAATTAAATAAAT CATTAATACTCTTCTAATGGTCTTTGAATAAAG CCTGAGTAGGAAGTCTAGA | 12 |
| 3UTR-005 | α-globin | GCTGCCTTCTGCGGGGCTTGCCTTCTGGCCATG CCCTTCTTCTCTCCCTTGCACCTGTACCTCTTGG TCTTTGAATAAAGCCTGAGTAGGAAGGCGGCC GCTCGAGCATGCATCTAGA | 13 |
| 3UTR-006 | G-CSF | GCCAAGCCCTCCCCATCCCATGTATTTATCTCT ATTTAATATTTATGTCTATTTAAGCCTCATATTT AAAGACAGGGAAGAGCAGAACGGAGCCCCAG GCCTCTGTGTCCTTCCCTGCATTTCTGAGTTTC ATTCTCCTGCCTGTAGCAGTGAGAAAAAGCTC CTGTCCTCCCATCCCCTGGACTGGGAGGTAGAT AGGTAAATACCAAGTATTTATTACTATGACTGC TCCCCAGCCCTGGCTCTGCAATGGGCACTGGG ATGAGCCGCTGTGAGCCCCTGGTCCTGAGGGT CCCCACCTGGGACCCTTGAGAGTATCAGGTCT CCCACGTGGGAGACAAGAAATCCCTGTTTAAT ATTTAAACAGCAGTGTTCCCCATCTGGGTCCTT GCACCCCTCACTCTGGCCTCAGCCGACTGCAC AGCGGCCCCTGCATCCCCTTGGCTGTGAGGCC CCTGGACAAGCAGAGGTGGCCAGAGCTGGGA GGCATGGCCCTGGGGTCCCACGAATTTGCTGG GGAATCTCGTTTTTCTTCTTAAGACTTTTGGGA CATGGTTTGACTCCCGAACATCACCGACGCGT CTCCTGTTTTTCTGGGTGGCCTCGGGACACCTG | 14 |

TABLE 7-continued

3'-Untranslated Regions

| 3' UTR Identifier | Name/ Description | Sequence | SEQ ID NO. |
|---|---|---|---|
| | | CCCTGCCCCCACGAGGGTCAGGACTGTGACTC TTTTTAGGGCCAGGCAGGTGCCTGGACATTTGC CTTGCTGGACGGGGACTGGGGATGTGGGAGGG AGCAGACAGGAGGAATCATGTCAGGCCTGTGT GTGAAAGGAAGCTCCACTGTCACCCTCCACCT CTTCACCCCCACTCACCAGTGTCCCCTCCACT GTCACATTGTAACTGAACTTCAGGATAATAAA GTGTTTGCCTCCATGGTCTTTGAATAAAGCCTG AGTAGGAAGGCGGCCGCTCGAGCATGCATCTA GA | |
| 3UTR-007 | Col1a2; collagen, type I, alpha 2 | ACTCAATCTAAATTAAAAAAGAAAGAAATTTG AAAAAACTTTCTCTTTGCCATTTCTTCTTCTTCT TTTTTAACTGAAAGCTGAATCCTTCCATTTCTT CTGCACATCTACTTGCTTAAATTGTGGGCAAAA GAGAAAAGAAGGATTGATCAGAGCATTGTGC AATACAGTTTCATTAACTCCTTCCCCCGCTCCC CCAAAAATTTGAATTTTTTTTTCAACACTCTTA CACCTGTTATGGAAAATGTCAACCTTTGTAAG AAAACCAAAATAAAAATTGAAAAATAAAAAC CATAAACATTTGCACCACTTGTGGCTTTTGAAT ATCTTCCACAGAGGGAAGTTTAAAACCCAAAC TTCCAAAGGTTTAAACTACCTCAAAACACTTTC CCATGAGTGTGATCCACATTGTTAGGTGCTGAC CTAGACAGAGATGAACTGAGGTCCTTGTTTTGT TTTGTTCATAATACAAAGGTGCTAATTAATAGT ATTTCAGATACTTGAAGAATGTTGATGGTGCTA GAAGAATTTGAGAAGAAATACTCCTGTATTGA GTTGTATCGTGTGGTGTATTTTTTAAAAAATTT GATTTAGCATTCATATTTTCCATCTTATTCCCA ATTAAAAGTATGCAGATTATTTGCCCAAATCTT CTTCAGATTCAGCATTTGTTCTTTGCCAGTCTC ATTTTCATCTTCTTCCATGGTTCCACAGAAGCT TTGTTTCTTGGGCAAGCAGAAAAATTAAATTGT ACCTATTTTGTATATGTGAGATGTTTAAATAAA TTGTGAAAAAAATGAAATAAAGCATGTTTGGT TTTCCAAAAGAACATAT | 15 |
| 3UTR-008 | Col6a2; collagen, type VI, alpha 2 | CGCCGCCGCCCGGGCCCCGCAGTCGAGGGTCG TGAGCCCACCCCGTCCATGGTGCTAAGCGGGC CCGGGTCCCACACGGCCAGCACCGCTGCTCAC TCGGACGACGCCCTGGGCCTGCACCTCTCCAG CTCCTCCCACGGGGTCCCCGTAGCCCCGGCCC CCGCCCAGCCCCAGGTCTCCCCAGGCCCTCCG CAGGCTGCCCGGCCTCCCTCCCCCTGCAGCCAT CCCAAGGCTCCTGACCTACCTGGCCCCTGAGCT CTGGAGCAAGCCCTGACCCAATAAAGGCTTTG AACCCAT | 16 |
| 3UTR-009 | RPN1; ribophorin I | GGGGCTAGAGCCCTCTCCGCACAGCGTGGAGA CGGGGCAAGGAGGGGGGTTATTAGGATTGGTG GTTTTGTTTTGCTTTGTTTAAAGCCGTGGGAAA ATGGCACAACTTTACCTCTGTGGGAGATGCAA CACTGAGAGCCAAGGGGTGGGAGTTGGGATAA TTTTTATATAAAAGAAGTTTTTCCACTTTGAAT TGCTAAAAGTGGCATTTTTCCTATGTGCAGTCA CTCCTCTCATTTCTAAAATAGGGACGTGGCCAG GCACGGTGGCTCATGCCTGTAATCCCAGCACTT TGGGAGGCCGAGGCAGGCGGCTCACGAGGTCA GGAGATCGAGACTATCCTGGCTAACACGGTAA AACCCTGTCTCTACTAAAAGTACAAAAAATTA GCTGGGCGTGGTGGTGGGCACCTGTAGTCCCA GCTACTCGGGAGGCTGAGGCAGGAGAAAGGC ATGAATCCAAGAGGCAGAGCTTGCAGTGAGCT GAGATCACGCCATTGCACTCCAGCCTGGGCAA CAGTGTTAAGACTCTGTCTCAAATATAAATAA ATAAATAAATAAATAAATAAATAAAAAT AAAGCGAGATGTTGCCCTCAAA | 17 |

TABLE 7-continued

3'-Untranslated Regions

| 3' UTR Identifier | Name/ Description | Sequence | SEQ ID NO. |
|---|---|---|---|
| 3UTR-010 | LRP1; low density lipoprotein receptor-related protein 1 | GGCCCTGCCCCGTCGGACTGCCCCCAGAAAGC CTCCTGCCCCCTGCCAGTGAAGTCCTTCAGTGA GCCCCTCCCCAGCCAGCCCTTCCCTGGCCCCGC CGGATGTATAAATGTAAAAATGAAGGAATTAC ATTTTATATGTGAGCGAGCAAGCCGGCAAGCG AGCACAGTATTATTTCTCCATCCCCTCCCTGCC TGCTCCTTGGCACCCCCATGCTGCCTTCAGGGA GACAGGCAGGGAGGGCTTGGGGCTGCACCTCC TACCCTCCCACCAGAACGCACCCCACTGGGAG AGCTGGTGGTGCAGCCTTCCCCTCCCTGTATAA GACACTTTGCCAAGGCTCTCCCCTCTCGCCCCA TCCCTGCTTGCCCGCTCCCACAGCTTCCTGAGG GCTAATTCTGGGAAGGGAGAGTTCTTTGCTGC CCCTGTCTGGAAGACGTGGCTCTGGGTGAGGT AGGCGGGAAAGGATGGAGTGTTTTAGTTCTTG GGGGAGGCCACCCCAAACCCCAGCCCCAACTC CAGGGGCACCTATGAGATGGCCATGCTCAACC CCCCTCCCAGACAGGCCCTCCCTGTCTCCAGG GCCCCCACCGAGGTTCCCAGGGCTGGAGACTT CCTCTGGTAAACATTCCTCCAGCCTCCCCTCCC CTGGGGACGCCAAGGAGGTGGGCCACACCCAG GAAGGGAAAGCGGGCAGCCCCGTTTTGGGGAC GTGAACGTTTTAATAATTTTTGCTGAATTCCTT TACAACTAAATAACACAGATATTGTTATAAAT AAAATTGT | 18 |
| 3UTR-011 | Nnt1; cardiotrophin-like cytokine factor 1 | ATATTAAGGATCAAGCTGTTAGCTAATAATGC CACCTCTGCAGTTTTGGGAACAGGCAAATAAA GTATCAGTATACATGGTGATGTACATCTGTAGC AAAGCTCTTGGAGAAAATGAAGACTGAAGAA AGCAAAGCAAAAACTGTATAGAGAGATTTTTC AAAAGCAGTAATCCCTCAATTTTAAAAAAGGA TTGAAAATTCTAAATGTCTTTCTGTGCATATTT TTTGTGTTAGGAATCAAAAGTATTTTATAAAAG GAGAAAGAACAGCCTCATTTTAGATGTAGTCC TGTTGGATTTTTTATGCCTCCTCAGTAACCAGA AATGTTTTAAAAAACTAAGTGTTTAGGATTTCA AGACAACATTATACATGGCTCTGAAATATCTG ACACAATGTAAACATTGCAGGCACCTGCATTT TATGTTTTTTTTTTCAACAAATGTGACTAATTT GAAACTTTTATGAACTTCTGAGCTGTCCCCTTG CAATTCAACCGCAGTTTGAATTAATCATATCAA ATCAGTTTTAATTTTTTAAATTGTACTTCAGAG TCTATATTTCAAGGGCACATTTTCTCACTACTA TTTTAATACATTAAAGGACTAAATAATCTTTCA GAGATGCTGGAAACAAATCATTTGCTTTATAT GTTTCATTAGAATACCAATGAAACATACAACT TGAAAATTAGTAATAGTATTTTTGAAGATCCCA TTTCTAATTGGAGATCTCTTTAATTTCGATCAA CTTATAATGTGTAGTACTATATTAAGTGCACTT GAGTGGAATTCAACATTTGACTAATAAAATGA GTTCATCATGTTGGCAAGTGATGTGGCAATTAT CTCTGGTGACAAAAGAGTAAAATCAAATATTT CTGCCTGTTACAAATATCAAGGAAGACCTGCT ACTATGAAATAGATGACATTAATCTGTCTTCAC TGTTTATAATACGGATGGATTTTTTTTCAAATC AGTGTGTGTTTGAGGTCTTATGTAATTGATGA CATTTGAGAGAAATGGTGGCTTTTTTTAGCTAC CTCTTTGTTCATTTAAGCACCAGTAAAGATCAT GTCTTTTTATAGAAGTGTAGATTTTCTTTGTGA CTTTGCTATCGTGCCTAAAGCTCTAAATATAGG TGAATGTGTGATGAATACTCAGATTATTGTCT CTCTATATAATTAGTTTGGTACTAAGTTTCTCA AAAAATTATTAACACATGAAAGACAATCTCTA AACCAGAAAAAGAAGTAGTACAAATTTTGTTA CTGTAATGCTCGCGTTTAGTGAGTTTAAAACAC ACAGTATCTTTTGGTTTTATAATCAGTTTCTATT TTGCTGTGCCTGAGATTAAGATCTGTGTATGTG TGTGTGTGTGTGTGCGTTTGTGTGTTAAAGC AGAAAAGACTTTTTTAAAAGTTTTAAGTGATA AATGCAATTTGTTAATTGATCTTAGATCACTAG TAAACTCAGGGCTGAATTATACCATGTATATTC TATTAGAAGAAAGTAAACACCATCTTTATTCCT GCCCTTTTTCTTCTCTCAAAGTAGTTGTAGTTA | 19 |

TABLE 7-continued

3'-Untranslated Regions

| 3' UTR Identifier | Name/ Description | Sequence | SEQ ID NO. |
|---|---|---|---|
| | | TATCTAGAAAGAAGCAATTTTGATTTCTTGAAA<br>AGGTAGTTCCTGCACTCAGTTTAAACTAAAAA<br>TAATCATACTTGGATTTTATTTATTTTTGTCATA<br>GTAAAAATTTTAATTTATATATATTTTTATTTA<br>GTATTATCTTATTCTTTGCTATTTGCCAATCCTT<br>TGTCATCAATTGTGTTAAATGAATTGAAAATTC<br>ATGCCCTGTTCATTTTATTTTACTTTATTGGTTA<br>GGATATTTAAAGGATTTTTGTATATATAATTTC<br>TTAAATTAATATTCCAAAAGGTTAGTGGACTTA<br>GATTATAAATTATGGCAAAAATCTAAAAACAA<br>CAAAAATGATTTTTATACATTCTATTTCATTAT<br>TCCTCTTTTTCCAATAAGTCATACAATTGGTAG<br>ATATGACTTATTTTATTTTTGTATTATTCACTAT<br>ATCTTTATGATATTTAAGTATAAATAATTAAAA<br>AAATTTATTGTACCTTATAGTCTGTCACCAAAA<br>AAAAAAAATTATCTGTAGGTAGTGAAATGCTA<br>ATGTTGATTTGTCTTTAAGGGCTTGTTAACTAT<br>CCTTTATTTTCTCATTTGTCTTAAATTAGGAGTT<br>TGTGTTTAAATTACTCATCTAAGCAAAAAATGT<br>ATATAAATCCCATTACTGGGTATATACCCAAA<br>GGATTATAAATCATGCTGCTATAAAGACACAT<br>GCACACGTATGTTATTGCAGCACTATTCACAA<br>TAGCAAAGACTTGGAACCAACCCAAATGTCCA<br>TCAATGATAGACTTGATTAAGAAAATGTGCAC<br>ATATACACCATGGAATACTATGCAGCCATAAA<br>AAAGGATGAGTTCATGTCCTTTGTAGGGACAT<br>GGATAAAGCTGGAAACCATCATTCTGAGCAAA<br>CTATTGCAAGGACAGAAAACCAAACACTGCAT<br>GTTCTCACTCATAGGTGGGAATTGAACAATGA<br>GAACACTTGGACACAAGGTGGGGAACACCACA<br>CACCAGGGCCTGTCATGGGGTGGGGGGAGTGG<br>GGAGGGATAGCATTAGGAGATATACCTAATGT<br>AAATGATGAGTTAATGGGTGCAGCACACCAAC<br>ATGGCACATGTATACATATGTAGCAAACCTGC<br>ACGTTGTGCACATGTACCCTAGAACTTAAAGT<br>ATAATTAAAAAAAAAAGAAAACAGAAGCTA<br>TTTATAAAGAAGTTATTTGCTGAAATAAATGTG<br>ATCTTTCCCATTAAAAAAATAAAGAAATTTTG<br>GGGTAAAAAAACACAATATATTGTATTCTTGA<br>AAAATTCTAAGAGAGTGGATGTGAAGTGTTCT<br>CACCACAAAAGTGATAACTAATTGAGGTAATG<br>CACATATTAATTAGAAAGATTTTGTCATTCCAC<br>AATGTATATATACTTAAAAATATGTTATACACA<br>ATAAATACATACATTAAAAAATAAGTAAATGTA | |
| 3UTR-012 | Col6a1;<br>collagen,<br>type VI,<br>alpha 1 | CCCACCCTGCACGCCGGCACCAAACCCTGTCC<br>TCCCACCCCTCCCCACTCATCACTAAACAGAGT<br>AAAATGTGATGCGAATTTTCCCGACCAACCTG<br>ATTCGCTAGATTTTTTTAAGGAAAAGCTTGGA<br>AAGCCAGGACACAACGCTGCTGCCTGCTTTGT<br>GCAGGGTCCTCCGGGGCTCAGCCCTGAGTTGG<br>CATCACCTGCGCAGGGCCCTCTGGGGCTCAGC<br>CCTGAGCTAGTGTCACCTGCACAGGGCCCTCT<br>GAGGCTCAGCCCTGAGCTGGCGTCACCTGTGC<br>AGGGCCCTCTGGGGCTCAGCCCTGAGCTGGCC<br>TCACCTGGGTTCCCCACCCCGGGCTCTCCTGCC<br>CTGCCCTCCTGCCCGCCCTCCCTCCTGCCTGCG<br>CAGCTCCTTCCCTAGGCACCTCTGTGCTGCATC<br>CCACCAGCCTGAGCAAGACGCCCTCTCGGGGC<br>CTGTGCCGCACTAGCCTCCCTCTCCTCTGTCCC<br>CATAGCTGGTTTTTCCCACCAATCCTCACCTAA<br>CAGTTACTTTACAATTAAACTCAAAGCAAGCT<br>CTTCTCCTCAGCTTGGGGCAGCCATTGGCCTCT<br>GTCTCGTTTTGGGAAACCAAGGTCAGGAGGCC<br>GTTGCAGACATAAATCTCGGCGACTCGGCCCC<br>GTCTCCTGAGGGTCCTGCTGGTGACCGGCCTG<br>GACCTTGGCCCTACAGCCCTGGAGGCCGCTGC<br>TGACCAGCACTGACCCCGACCTCAGAGAGTAC<br>TCGCAGGGGCGCTGGCTGCACTCAAGACCCTC<br>GAGATTAACGGTGCTAACCCCGTCTGCTCCTCC<br>CTCCCGCAGAGACTGGGGCCTGGACTGGACAT<br>GAGAGCCCCTTGGTGCCACAGAGGGCTGTGTC<br>TTACTAGAAACAACGCAAACCTCTCCTTCCTCA<br>GAATAGTGATGTGTTCGACGTTTTATCAAAGG | 20 |

TABLE 7-continued

3'-Untranslated Regions

| 3' UTR Identifier | Name/ Description | Sequence | SEQ ID NO. |
|---|---|---|---|
| | | CCCCCTTTCTATGTTCATGTTAGTTTTGCTCCTT CTGTGTTTTTTCTGAACCATATCCATGTTGCT GACTTTTCCAAATAAAGGTTTTCACTCCTCTC | |
| 3UTR-013 | Calr; calreticulin | AGAGGCCTGCCTCCAGGGCTGGACTGAGGCCT GAGCGCTCCTGCCGCAGAGCTGGCCGCGCCAA ATAATGTCTCTGTGAGACTCGAGAACTTTCATT TTTTTCCAGGCTGGTTCGGATTTGGGGTGGATT TTGGTTTTGTTCCCCTCCTCCACTCTCCCCCACC CCCTCCCCGCCCTTTTTTTTTTTTTTTTAAAC TGGTATTTTATCTTTGATTCTCCTTCAGCCCTCA CCCCTGGTTCTCATCTTTCTTGATCAACATCTTT TCTTGCCTCTGTCCCCTTCTCTCATCTCTTAGCT CCCCTCCAACCTGGGGGGCAGTGGTGTGGAGA AGCCACAGGCCTGAGATTTCATCTGCTCTCCTT CCTGGAGCCCAGAGGAGGGCAGCAGAAGGGG GTGGTGTCTCCAACCCCCCAGCACTGAGGAAG AACGGGGCTCTTCTCATTTCACCCCTCCCTTTC TCCCCTGCCCCCAGGACTGGGCCACTTCTGGGT GGGGCAGTGGGTCCCAGATTGGCTCACACTGA GAATGTAAGAACTACAAACAAAATTTCTATTA AATTAAATTTTGTGTCTCC | 21 |
| 3UTR-014 | Col1a1; collagen, type I, alpha 1 | CTCCCTCCATCCCAACCTGGCTCCCTCCCACCC AACCAACTTTCCCCCCAACCCGGAAACAGACA AGCAACCCAAACTGAACCCCCTCAAAAGCCAA AAAATGGGAGACAATTTCACATGGACTTTGGA AAATATTTTTTTCCTTTGCATTCATCTCTCAAAC TTAGTTTTTATCTTTGACCAACCGAACATGACC AAAAACCAAAAGTGCATTCAACCTTACCAAAA AAAAAAAAAAAAAAAGAATAAATAAATAACT TTTTAAAAAAGGAAGCTTGGTCCACTTGCTTGA AGACCCATGCGGGGGTAAGTCCCTTTCTGCCC GTTGGGCTTATGAAACCCCAATGCTGCCCTTTC TGCTCCTTTCTCCACACCCCCCTTGGGGCCTCC CCTCCACTCCTTCCCAAATCTGTCTCCCCAGAA GACACAGGAAACAATGTATTGTCTGCCCAGCA ATCAAAGGCAATGCTCAAACACCCAAGTGGCC CCCACCCTCAGCCCGCTCCTGCCCGCCCAGCA CCCCCAGGCCCTGGGGGACCTGGGGTTCTCAG ACTGCCAAAGAAGCCTTGCCATCTGGCGCTCC CATGGCTCTTGCAACATCTCCCCTTCGTTTTTG AGGGGGTCATGCCGGGGGAGCCACCAGCCCCT CACTGGGTTCGGAGGAGAGTCAGGAAGGGCCA CGACAAAGCAGAAACATCGGATTTGGGGAACG CGTGTCAATCCCTTGTGCCGCAGGGCTGGGCG GGAGAGACTGTTCTGTTCCTTGTGTAACTGTGT TGCTGAAAGACTACCTCGTTCTTGTCTTGATGT GTCACCGGGGCAACTGCCTGGGGGCGGGGATG GGGGCAGGGTGGAAGCGGCTCCCCATTTTATA CCAAAGGTGCTACATCTATGTGATGGGTGGGG TGGGGAGGGAATCACTGGTGCTATAGAAATTG AGATGCCCCCCCAGGCCAGCAAATGTTCCTTTT TGTTCAAAGTCTATTTTTATTCCTTGATATTTTT CTTTTTTTTTTTTTTTTTGTGGATGGGGACTT GTGAATTTTTCTAAAGGTGCTATTTAACATGGG AGGAGAGCGTGTGCGGCTCCAGCCCAGCCCGC TGCTCACTTTCCACCCTCTCTCCACCTGCCTCT GGCTTCTCAGGCCTCTGCTCTCCGACCTCTCTC CTCTGAAACCCTCCTCCACAGCTGCAGCCCATC CTCCCGGCTCCCTCCTAGTCTGTCCTGCGTCCT CTGTCCCGGGTTTCAGAGACAACTTCCCAAA GCACAAAGCAGTTTTTCCCCCTAGGGGTGGGA GGAAGCAAAAGACTCTGTACCTATTTTGTATGT GTATAATAATTTGAGATGTTTTAATTATTTTG ATTGCTGAATAAAGCATGTGGAAATGACCCA AACATAATCCGCAGTGGCCTCCTAATTTCCTTC TTTGGAGTTGGGGGAGGGGTAGACATGGGAA GGGGCTTTGGGGTGATGGGCTTGCCTTCCATTC CTGCCCTTTCCCTCCCCACTATTCTCTTCTAGAT CCCTCCATAACCCCACTCCCCTTTCTCTCACCC TTCTTATACCGCAAACCTTTCTACTTCCTCTTTC ATTTTCTATTCTTGCAATTTCCTTGCACCTTTTC CAAATCCTCTTCTCCCCTGCAATACCATACAGG | 22 |

TABLE 7-continued

3'-Untranslated Regions

| 3' UTR Identifier | Name/ Description | Sequence | SEQ ID NO. |
|---|---|---|---|
| | | CAATCCACGTGCACAACACACACACACACTCT TCACATCTGGGGTTGTCCAAACCTCATACCCAC TCCCCTTCAAGCCCATCCACTCTCCACCCCCTG GATGCCCTGCACTTGGTGGCGGTGGGATGCTC ATGGATACTGGGAGGGTGAGGGGAGTGGAAC CCGTGAGGAGGACCTGGGGGCCTCTCCTTGAA CTGACATGAAGGGTCATCTGGCCTCTGCTCCCT TCTCACCCACGCTGACCTCCTGCCGAAGGAGC AACGCAACAGGAGAGGGGTCTGCTGAGCCTGG CGAGGGTCTGGGAGGGACCAGGAGGAAGGCG TGCTCCCTGCTCGCTGTCCTGGCCCTGGGGGAG TGAGGGAGACAGACACCTGGGAGAGCTGTGG GGAAGGCACTCGCACCGTGCTCTTGGGAAGGA AGGAGACCTGGCCCTGCTCACCACGGACTGGG TGCCTCGACCTCCTGAATCCCAGAACACAAC CCCCCTGGGCTGGGGTGGTCTGGGGAACCATC GTGCCCCCGCCTCCCGCCTACTCCTTTTTAAGC TT | |
| 3UTR-015 | Plod1; procollagen-lysine, 2-oxoglutarate 5-dioxygenase 1 | TTGGCCAGGCCTGACCCTCTTGGACCTTTCTTC TTTGCCGACAACCACTGCCCAGCAGCCTCTGG GACCTCGGGGTCCCAGGGAACCCAGTCCAGCC TCCTGGCTGTTGACTTCCCATTGCTCTTGGAGC CACCAATCAAAGAGATTCAAAGAGATTCCTGC AGGCCAGAGGCGGAACACACCTTTATGGCTGG GGCTCTCCGTGGTGTTCTGGACCCAGCCCCTGG AGACACCATTCACTTTTACTGCTTTGTAGTGAC TCGTGCTCTCCAACCTGTCTTCCTGAAAAACCA AGGCCCCCTTCCCCCACCTCTTCCATGGGGTGA GACTTGAGCAGAACAGGGGCTTCCCCAAGTTG CCCAGAAAGACTGTCTGGGTGAGAAGCCATGG CCAGAGCTTCTCCCAGGCACAGGTGTTGCACC AGGGACTTCTGCTTCAAGTTTTGGGGTAAAGA CACCTGGATCAGACTCCAAGGGCTGCCCTGAG TCTGGGACTTCTGCCTCCATGGCTGGTCATGAG AGCAAACCGTAGTCCCCTGGAGACAGCGACTC CAGAGAACCTCTTGGGAGACAGAAGAGGCATC TGTGCACAGCTCGATCTTCTACTTGCCTGTGGG GAGGGGAGTGACAGGTCCACACACCACACTGG GTCACCCTGTCCTGGATGCCTCTGAAGAGAGG GACAGACCGTCAGAAACTGGAGAGTTTCTATT AAAGGTCATTTAAACCA | 23 |
| 3UTR-016 | Nucb1; nucleobindin 1 | TCCTCCGGGACCCCAGCCCTCAGGATTCCTGAT GCTCCAAGGCGACTGATGGGCGCTGGATGAAG TGGCACAGTCAGCTTCCCTGGGGGCTGGTGTC ATGTTGGGCTCCTGGGGCGGGGCACGGCCTG GCATTTCACGCATTGCTGCCACCCCAGGTCCAC CTGTCTCCACTTTCACAGCCTCCAAGTCTGTGG CTCTTCCCTTCTGTCCTCCGAGGGGCTTGCCTT CTCTCGTGTCCAGTGAGGTGCTCAGTGATCGGC TTAACTTAGAGAAGCCCGCCCCCTCCCCTTCTC CGTCTGTCCCAAGAGGGTCTGCTCTGAGCCTGC GTTCCTAGGTGGCTCGGCCTCAGCTGCCTGGGT TGTGGCCGCCCTAGCATCCTGTATGCCCACAGC TACTGGAATCCCCGCTGCTGCTCCGGGCCAAG CTTCTGGTTGATTAATGAGGGCATGGGTGGT CCCTCAAGACCTTCCCCTACCTTTTGTGGAACC AGTGATGCCTCAAAGACAGTGTCCCCTCCACA GCTGGGTGCCAGGGGCAGGGGATCCTCAGTAT AGCCGGTGAACCCTGATACCAGGAGCCTGGGC CTCCCTGAACCCCTGGCTTCCAGCCATCTCATC GCCAGCCTCCTCCTGGACCTCTTGGCCCCCAGC CCCTTCCCCACACAGCCCCAGAAGGGTCCCAG AGCTGACCCCACTCCAGGACCTAGGCCCAGCC CCTCAGCCTCATCTGGAGCCCCTGAAGACCAG TCCCACCCACCTTTCTGGCCTCATCTGACACTG CTCCGCATCCTGCTGTGTGTCCTGTTCCATGTT CCGGTTCCATCCAAATACACTTTCTGGAACAAA | 24 |

TABLE 7-continued

3'-Untranslated Regions

| 3' UTR Identifier | Name/ Description | Sequence | SEQ ID NO. |
|---|---|---|---|
| 3UTR-017 | α-globin | GCTGGAGCCTCGGTGGCCATGCTTCTTGCCCCT TGGGCCTCCCCCAGCCCCTCCTCCCCTTCCTG CACCCGTACCCCCGTGGTCTTTGAATAAAGTCT GAGTGGGCGGC | 25 |

It should be understood that those listed in the previous tables are examples and that any UTR from any gene may be incorporated into the respective first or second flanking region of the primary construct. Furthermore, multiple wild-type UTRs of any known gene may be utilized. It is also within the scope of the present invention to provide artificial UTRs which are not variants of wild type genes. These UTRs or portions thereof may be placed in the same orientation as in the transcript from which they were selected or may be altered in orientation or location. Hence a 5' or 3' UTR may be inverted, shortened, lengthened, made chimeric with one or more other 5' UTRs or 3' UTRs. As used herein, the term "altered" as it relates to a UTR sequence, means that the UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides. Any of these changes producing an "altered" UTR (whether 3' or 5') comprise a variant UTR.

In one embodiment, a double, triple or quadruple UTR such as a 5' or 3' UTR may be used. As used herein, a "double" UTR is one in which two copies of the same UTR are encoded either in series or substantially in series. For example, a double beta-globin 3' UTR may be used as described in US Patent publication 20100129877, the contents of which are incorporated herein by reference in its entirety.

It is also within the scope of the present invention to have patterned UTRs. As used herein "patterned UTRs" are those UTRs which reflect a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level.

In one embodiment, flanking regions are selected from a family of transcripts whose proteins share a common function, structure, feature of property. For example, polypeptides of interest may belong to a family of proteins which are expressed in a particular cell, tissue or at some time during development. The UTRs from any of these genes may be swapped for any other UTR of the same or different family of proteins to create a new chimeric primary transcript. As used herein, a "family of proteins" is used in the broadest sense to refer to a group of two or more polypeptides of interest which share at least one function, structure, feature, localization, origin, or expression pattern.

After optimization (if desired), the primary construct components are reconstituted and transformed into a vector such as, but not limited to, plasmids, viruses, cosmids, and artificial chromosomes. For example, the optimized construct may be reconstituted and transformed into chemically competent E. coli, yeast, neurospora, maize, drosophila, etc. where high copy plasmid-like or chromosome structures occur by methods described herein. Stop Codons In one embodiment, the primary constructs of the present invention may include at least two stop codons before the 3' untranslated region (UTR). The stop codon may be selected from TGA, TAA and TAG. In one embodiment, the primary constructs of the present invention include the stop codon TGA and one additional stop codon. In a further embodiment the addition stop codon may be TAA.

Vector Amplification

The vector containing the primary construct is then amplified and the plasmid isolated and purified using methods known in the art such as, but not limited to, a maxi prep using the Invitrogen PURELINK™ HiPure Maxiprep Kit (Carlsbad, Calif.).

Plasmid Linearization

The plasmid may then be linearized using methods known in the art such as, but not limited to, the use of restriction enzymes and buffers. The linearization reaction may be purified using methods including, for example Invitrogen's PURELINK™ PCR Micro Kit (Carlsbad, Calif.), and HPLC based purification methods such as, but not limited to, strong anion exchange HPLC, weak anion exchange HPLC, reverse phase HPLC (RP-HPLC), and hydrophobic interaction HPLC (HIC-HPLC) and Invitrogen's standard PURELINK™ PCR Kit (Carlsbad, Calif.). The purification method may be modified depending on the size of the linearization reaction which was conducted. The linearized plasmid is then used to generate cDNA for in vitro transcription (IVT) reactions.

cDNA Template Synthesis

A cDNA template may be synthesized by having a linearized plasmid undergo polymerase chain reaction (PCR). Table 8 is a listing of primers and probes that may be useful in the PCR reactions of the present invention. It should be understood that the listing is not exhaustive and that primer-probe design for any amplification is within the skill of those in the art. Probes may also contain chemically modified bases to increase base-pairing fidelity to the target molecule and base-pairing strength. Such modifications may include 5-methyl-Cytidine, 2, 6-di-amino-purine, 2'-fluoro, phosphoro-thioate, or locked nucleic acids.

TABLE 8

Primers and Probes

| Primer/Probe Identifier | Sequence (5'-3') | Hybridization target | SEQ ID NO. |
|---|---|---|---|
| UFP | TTGGACCCTCGTACAGAAGCTAATACG | cDNA Template | 26 |
| URP | T$_{x160}$CTTCCTACTCAGGCTTTATTCAAAGACCA | cDNA Template | 27 |
| GBA1 | CCTTGACCTTCTGGAACTTC | Acid glucocerebrosidase | 28 |
| GBA2 | CCAAGCACTGAAACGGATAT | Acid glucocerebrosidase | 29 |
| LUC1 | GATGAAAAGTGCTCCAAGGA | Luciferase | 30 |
| LUC2 | AACCGTGATGAAAAGGTACC | Luciferase | 31 |
| LUC3 | TCATGCAGATTGGAAAGGTC | Luciferase | 32 |
| GCSF1 | CTTCTTGGACTGTCCAGAGG | G-CSF | 33 |
| GCSF2 | GCAGTCCCTGATACAAGAAC | G-CSF | 34 |
| GCSF3 | GATTGAAGGTGGCTCGCTAC | G-CSF | 35 |

*UFP is universal forward primer; URP is universal reverse primer.

In one embodiment, the cDNA may be submitted for sequencing analysis before undergoing transcription.

Polynucleotide Production

The process of polynucleotide production may include, but is not limited to, in vitro transcription, cDNA template removal and RNA clean-up, and capping and/or tailing reactions.

In Vitro Transcription

The cDNA produced in the previous step may be transcribed using an in vitro transcription (IVT) system. The system typically comprises a transcription buffer, nucleotide triphosphates (NTPs), an RNase inhibitor and a polymerase. The NTPs may be manufactured in house, may be selected from a supplier, or may be synthesized as described herein. The NTPs may be selected from, but are not limited to, those described herein including natural and unnatural (modified) NTPs. The polymerase may be selected from, but is not limited to, T7 RNA polymerase, T3 RNA polymerase and mutant polymerases such as, but not limited to, polymerases able to be incorporated into modified nucleic acids.

RNA Polymerases

Any number of RNA polymerases or variants may be used in the design of the primary constructs of the present invention.

RNA polymerases may be modified by inserting or deleting amino acids of the RNA polymerase sequence. As a non-limiting example, the RNA polymerase may be modified to exhibit an increased ability to incorporate a 2'-modified nucleotide triphosphate compared to an unmodified RNA polymerase (see International Publication WO2008078180 and U.S. Pat. No. 8,101,385; herein incorporated by reference in their entireties).

Variants may be obtained by evolving an RNA polymerase, optimizing the RNA polymerase amino acid and/or nucleic acid sequence and/or by using other methods known in the art. As a non-limiting example, T7 RNA polymerase variants may be evolved using the continuous directed evolution system set out by Esvelt et al. (Nature (2011) 472(7344):499-503; herein incorporated by reference in its entirety) where clones of T7 RNA polymerase may encode at least one mutation such as, but not limited to, lysine at position 93 substituted for threonine (K93T), I4M, A7T, E63V, V64D, A65E, D66Y, T76N, C125R, S128R, A136T, N165S, G175R, H176L, Y178H, F182L, L196F, G198V, D208Y, E222K, S228A, Q239R, T243N, G259D, M267I, G280C, H300R, D351A, A354S, E356D, L360P, A383V, Y385C, D388Y, S397R, M401T, N410S, K450R, P451T, G452V, E484A, H523L, H524N, G542V, E565K, K577E, K577M, N601S, S684Y, L699I, K713E, N748D, Q754R, E775K, A827V, D851N or L864F. As another non-limiting example, T7 RNA polymerase variants may encode at least mutation as described in U.S. Pub. Nos. 20100120024 and 20070117112; herein incorporated by reference in their entireties. Variants of RNA polymerase may also include, but are not limited to, substitutional variants, conservative amino acid substitution, insertional variants, deletional variants and/or covalent derivatives.

In one embodiment, the primary construct may be designed to be recognized by the wild type or variant RNA polymerases. In doing so, primary construct may be modified to contain sites or regions of sequence changes from the wild type or parent primary construct.

In one embodiment, the primary construct may be designed to include at least one substitution and/or insertion upstream of an RNA polymerase binding or recognition site, downstream of the RNA polymerase binding or recognition site, upstream of the TATA box sequence, downstream of the TATA box sequence of the primary construct but upstream of the coding region of the primary construct, within the 5'UTR, before the 5'UTR and/or after the 5'UTR.

In one embodiment, the 5'UTR of the primary construct may be replaced by the insertion of at least one region and/or string of nucleotides of the same base. The region and/or string of nucleotides may include, but is not limited to, at least 3, at least 4, at least 5, at least 6, at least 7 or at least 8 nucleotides and the nucleotides may be natural and/or unnatural. As a non-limiting example, the group of nucleotides may include 5-8 adenine, cytosine, thymine, a string of any of the other nucleotides disclosed herein and/or combinations thereof.

In one embodiment, the 5'UTR of the primary construct may be replaced by the insertion of at least two regions and/or strings of nucleotides of two different bases such as, but not limited to, adenine, cytosine, thymine, any of the other nucleotides disclosed herein and/or combinations thereof. For example, the 5'UTR may be replaced by inserting 5-8 adenine bases followed by the insertion of 5-8 cytosine bases. In another example, the 5'UTR may be replaced by inserting 5-8 cytosine bases followed by the insertion of 5-8 adenine bases.

In one embodiment, the primary construct may include at least one substitution and/or insertion downstream of the transcription start site which may be recognized by an RNA polymerase. As a non-limiting example, at least one substitution and/or insertion may occur downstream the transcription start site by substituting at least one nucleic acid in the region just downstream of the transcription start site (such as, but not limited to, +1 to +6). Changes to region of nucleotides just downstream of the transcription start site may affect initiation rates, increase apparent nucleotide triphosphate (NTP) reaction constant values, and increase the dissociation of short transcripts from the transcription complex curing initial transcription (Brieba et al, Biochemistry (2002) 41: 5144-5149; herein incorporated by reference in its entirety). The modification, substitution and/or insertion of at least one nucleic acid may cause a silent mutation of the nucleic acid sequence or may cause a mutation in the amino acid sequence.

In one embodiment, the primary construct may include the substitution of at least 1, at least 2, at least 3, at least 4, at least 5, at least 6, at least 7, at least 8, at least 9, at least 10, at least 11, at least 12 or at least 13 guanine bases downstream of the transcription start site.

In one embodiment, the primary construct may include the substitution of at least 1, at least 2, at least 3, at least 4, at least 5 or at least 6 guanine bases in the region just downstream of the transcription start site. As a non-limiting example, if the nucleotides in the region are GGGAGA the guanine bases may be substituted by at least 1, at least 2, at least 3 or at least 4 adenine nucleotides. In another non-limiting example, if the nucleotides in the region are GGGAGA the guanine bases may be substituted by at least 1, at least 2, at least 3 or at least 4 cytosine bases. In another non-limiting example, if the nucleotides in the region are GGGAGA the guanine bases may be substituted by at least 1, at least 2, at least 3 or at least 4 thymine, and/or any of the nucleotides described herein.

In one embodiment, the primary construct may include at least one substitution and/or insertion upstream of the start codon. For the purpose of clarity, one of skill in the art would appreciate that the start codon is the first codon of the protein coding region whereas the transcription start site is the site where transcription begins. The primary construct may include, but is not limited to, at least 1, at least 2, at least 3, at least 4, at least 5, at least 6, at least 7 or at least 8 substitutions and/or insertions of nucleotide bases. The nucleotide bases may be inserted or substituted at 1, at least 1, at least 2, at least 3, at least 4 or at least 5 locations upstream of the start codon. The nucleotides inserted and/or substituted may be the same base (e.g., all A or all C or all T or all G), two different bases (e.g., A and C, A and T, or C and T), three different bases (e.g., A, C and T or A, C and T) or at least four different bases. As a non-limiting example, the guanine base upstream of the coding region in the primary construct may be substituted with adenine, cytosine, thymine, or any of the nucleotides described herein. In another non-limiting example the substitution of guanine bases in the primary construct may be designed so as to leave one guanine base in the region downstream of the transcription start site and before the start codon (see Esvelt et al. Nature (2011) 472(7344):499-503; herein incorporated by reference in its entirety). As a non-limiting example, at least 5 nucleotides may be inserted at 1 location downstream of the transcription start site but upstream of the start codon and the at least 5 nucleotides may be the same base type.

cDNA Template Removal and Clean-Up

The cDNA template may be removed using methods known in the art such as, but not limited to, treatment with Deoxyribonuclease I (DNase I). RNA clean-up may also include a purification method such as, but not limited to, AGENCOURT® CLEANSEQ® system from Beckman Coulter (Danvers, Mass.), HPLC based purification methods such as, but not limited to, strong anion exchange HPLC, weak anion exchange HPLC, reverse phase HPLC (RP-HPLC), and hydrophobic interaction HPLC (HIC-HPLC).

Capping and/or Tailing Reactions

The primary construct or mmRNA may also undergo capping and/or tailing reactions. A capping reaction may be performed by methods known in the art to add a 5' cap to the 5' end of the primary construct. Methods for capping include, but are not limited to, using a Vaccinia Capping enzyme (New England Biolabs, Ipswich, Mass.).

A poly-A tailing reaction may be performed by methods known in the art, such as, but not limited to, 2' O-methyltransferase and by methods as described herein. If the primary construct generated from cDNA does not include a poly-T, it may be beneficial to perform the poly-A-tailing reaction before the primary construct is cleaned.

Purification

The primary construct or mmRNA purification may include, but is not limited to, mRNA or mmRNA clean-up, quality assurance and quality control. mRNA or mmRNA clean-up may be performed by methods known in the arts such as, but not limited to, AGENCOURT® beads (Beckman Coulter Genomics, Danvers, Mass.), poly-T beads, LNA™ oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a polynucleotide such as a "purified mRNA or mmRNA" refers to one that is separated from at least one contaminant. As used herein, a "contaminant" is any substance which makes another unfit, impure or inferior. Thus, a purified polynucleotide (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In another embodiment, the mRNA or mmRNA may be sequenced by methods including, but not limited to reverse-transcriptase-PCR.

In one embodiment, the mRNA or mmRNA may be quantified using methods such as, but not limited to, ultraviolet visible spectroscopy (UV/Vis). A non-limiting example of a UV/Vis spectrometer is a NANODROP® spectrometer (ThermoFisher, Waltham, Mass.). The quantified mRNA or mmRNA may be analyzed in order to determine if the mRNA or mmRNA may be of proper size, check that no degradation of the mRNA or mmRNA has occurred. Degradation of the mRNA and/or mmRNA may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Signal Peptides or Proteins

The primary constructs or mmRNA may also encode additional features which facilitate trafficking of the polypeptides to therapeutically relevant sites. One such feature which aids in protein trafficking is the signal peptide sequence. As used herein, a "signal sequence" or "signal peptide" is a polynucleotide or polypeptide, respectively, which is from about 9 to 200 nucleotides (3-60 amino acids) in length which is incorporated at the 5' (or N-terminus) of the coding region or polypeptide encoded, respectively. Addition of these sequences result in trafficking of the encoded polypeptide to the endoplasmic reticulum through one or more secretory pathways. Some signal peptides are cleaved from the protein by signal peptidase after the proteins are transported.

Table 9 is a representative listing of signal proteins or peptides which may be incorporated for encoding by the polynucleotides, primary constructs or mmRNA of the invention.

TABLE 9

Signal Peptides

| ID | Description | NUCLEOTIDE SEQUENCE (5'-3') | SEQ ID NO. | ENCODED PEPTIDE | SEQ ID NO. |
|---|---|---|---|---|---|
| SS-001 | α-1-antitrypsin | ATGATGCCATCCTCAGTCTCA TGGGGTATTTTGCTCTTGGCG GGTCTGTGCTGTCTCGTGCCG GTGTCGCTCGCA | 36 | MMPSSVSW GILLAGLCC LVPVSLA | 98 |
| SS-002 | G-CSF | ATGGCCGGACCGGCGACTCAG TCGCCCATGAAACTCATGGCC CTGCAGTTGTTGCTTTGGCAC TCAGCCCTCTGGACCGTCCAA GAGGCG | 37 | MAGPATQS PMKLMALQ LLLWHSAL WTVQEA | 99 |
| SS-003 | Factor IX | ATGCAGAGAGTGAACATGATT ATGGCCGAGTCCCCATCGCTC ATCACAATCTGCCTGCTTGGT ACCTGCTTTCCGCCGAATGCA CTGTCTTTCTGGATCACGAGA ATGCAATAAGATCTTGAACC GACCCAAACGG | 38 | MQRVNMIM AESPSLITIC LLGYLLSAE CTVFLDHEN ANKILNRPKR | 100 |
| SS-004 | Prolactin | ATGAAAGGATCATTGCTGTTG CTCCTCGTGTCGAACCTTCTG CTTTGCCAGTCCGTAGCCCCC | 39 | MKGSLLLLL VSNLLLCQS VAP | 101 |
| SS-005 | Albumin | ATGAAATGGGTGACGTTCATC TCACTGTTGTTTTTGTTCTCGT CCGCCTACTCCAGGGGAGTAT TCCGCCGA | 40 | MKWVTFISL LFLFSSAYS RGVFRR | 102 |
| SS-006 | HMMSP38 | ATGTGGTGGCGGCTCTGGTGG CTGCTCCTGTTGCTCCTCTTGC TGTGGCCCATGGTGTGGGCA | 41 | MWWRLWW LLLLLLLLP MWA | 103 |
| MLS-001 | ornithine carbamoyltransferase | TGCTCTTTAACCTCCGCATCCT GTTGAATAACGCTGCGTTCCG AAATGGGCATAACTTCATGGT ACGCAACTTCAGATGCGGCCA GCCACTCCAG | 42 | MLFNLRILL NNAAFRNG HNFMVRNF RCGQPLQ | 104 |
| MLS-002 | Cytochrome C Oxidase subunit 8A | ATGTCCGTCTTGACACCCCTG CTCTTGAGAGGGCTGACGGGG TCCGCTAGACGCCTGCCGGTA CCGCGAGCGAAGATCCACTCC CTG | 43 | MSVLTPLLL RGLTGSARR LPVPRAKIH SL | 105 |
| MLS-003 | Cytochrome C Oxidase subunit 8A | ATGAGCGTGCTCACTCCGTTG CTTCTTCGAGGGCTTACGGGA TCGGCTCGGAGGTTGCCCGTC CCGAGAGCGAAGATCCATTCG TTG | 44 | MSVLTPLLL RGLTGSARR LPVPRAKIH SL | 106 |
| SS-007 | Type III, bacterial | TGACAAAAATAACTTTATCTC CCCAGAATTTTAGAATCCAAA AACAGGAAACCACACTACTA AAAGAAAAATCAACCGAGAA | 45 | MVTKITLSP QNFRIQKQE TTLLKEKST EKNSLAKSI | 107 |

TABLE 9-continued

Signal Peptides

| ID | Description | NUCLEOTIDE SEQUENCE (5'-3') | SEQ ID NO. | ENCODED PEPTIDE | SEQ ID NO. |
|---|---|---|---|---|---|
| | | AAATTCTTTAGCAAAAGTAT TCTCGCAGTAAAAATCACTTC ATCGAATTAAGGTCAAAATTA TCGGAACGTTTTATTTCGCAT AAGAACACT | | LAVKNHFIE LRSKLSERFI SHKNT | |
| SS-008 | Viral | ATGCTGAGCTTTGTGGATACC CGCACCCTGCTGCTGCTGGCG GTGACCAGCTGCCTGGCGACC TGCCAG | 46 | MLSFVDTRT LLLLAVTSC LATCQ | 108 |
| SS-009 | viral | ATGGGCAGCAGCCAGGCGCC GCGCATGGGCAGCGTGGGCG GCCATGGCCTGATGGCGCTGC TGATGGCGGGCCTGATTCTGC CGGGCATTCTGGCG | 47 | MGSSQAPR MGSVGGHG LMALLMAG LILPGILA | 109 |
| SS-010 | Viral | ATGGCGGGCATTTTTTATTTTC TGTTTAGCTTTCTGTTTGGCAT TTGCGAT | 48 | MAGIFYPLF SFLFGICD | 110 |
| SS-011 | Viral | ATGGAAAACCGCCTGCTGCGC GTGTTTCTGGTGTGGGCGGCG CTGACCATGGATGGCGCGAGC GCG | 49 | MENRLLRV FLVWAALT MDGASA | 111 |
| SS-012 | Viral | ATGGCGCGCCAGGGCTGCTTT GGCAGCTATCAGGTGATTAGC CTGTTTACCTTTGCGATTGGC GTGAACCTGTGCCTGGGC | 50 | MARQGCFG SYQVISLFTF AIGVNLCLG | 112 |
| SS-013 | Bacillus | ATGAGCCGCCTGCCGGTGCTG CTGCTGCTGCAGCTGCTGGTG CGCCCGGGCCTGCAG | 51 | MSRLPVLLL LQLLVRPGLQ | 113 |
| SS-014 | Bacillus | ATGAAACAGCAGAAACGCCT GTATGCGCGCCTGCTGACCCT GCTGTTTGCGCTGATTTTTCTG CTGCCGCATAGCAGCGCGAGC GCG | 52 | MKQQKRLY ARLLTLLFA LIFLLPHSSA SA | 114 |
| SS-015 | Secretion signal | ATGGCGACGCCGCTGCCTCCG CCCTCCCCGCGGCACCTGCGG CTGCTGCGGCTGCTGCTCTCC GCCCTCGTCCTCGGC | 53 | MATPLPPPS PRHLRLLRL LLSG | 115 |
| SS-016 | Secretion signal | ATGAAGGCTCCGGGTCGGCTC GTGCTCATCATCCTGTGCTCC GTGGTCTTCTCT | 54 | MKAPGRLV LIILCSVVFS | 116 |
| SS-017 | Secretion signal | ATGCTTCAGCTTTGGAAACTT GTTCTCCTGTGCGGCGTGCTC ACT | 55 | MLQLWKLL CGVLT | 117 |
| SS-018 | Secretion signal | ATGCTTTATCTCCAGGGTTGG AGCATGCCTGCTGTGGCA | 56 | MLYLQGWS MPAVA | 118 |
| SS-019 | Secretion signal | ATGGATAACGTGCAGCCGAA AATAAAACATCGCCCCTTCTG CTTCAGTGTGAAAGGCCACGT GAAGATGCTGCGGCTGGATAT TATCAACTCACTGGTAACAAC AGTATTCATGCTCATCGTATC TGTGTTGGCACTGATACCA | 57 | MDNVQPKI KHRPFCFSV KGHVKMLR LDIINSLVTT VFMLIVSVL ALIP | 119 |
| SS-020 | Secretion signal | ATGCCCTGCCTAGACCAACAG CTCACTGTTCATGCCCTACCCT GCCCTGCCCAGCCCTCCTCTC TGGCCTTCTGCCAAGTGGGGT TCTTAACAGCA | 58 | MPCLDQQL TVHALPCPA QPSSLAFCQ VGFLTA | 120 |
| SS-021 | Secretion signal | ATGAAAACCTTGTTCAATCCA GCCCCTGCCATTGCTGACCTG GATCCCCAGTTCTACACCCTC | 59 | MKTLFNPAP AIADLDPQF YTLSDVFCC | 121 |

TABLE 9-continued

Signal Peptides

| ID | Description | NUCLEOTIDE SEQUENCE (5'-3') | SEQ ID NO. | ENCODED PEPTIDE | SEQ ID NO. |
|---|---|---|---|---|---|
| | | TCAGATGTGTTCTGCTGCAAT GAAAGTGAGGCTGAGATTTTA ACTGGCCTCACGGTGGGCAGC GCTGCAGATGCT | | NESEAEILT GLTVGSAA DA | |
| SS-022 | Secretion signal | ATGAAGCCTCTCCTTGTTGTG TTTGTCTTTCTTTTCCTTTGGG ATCCAGTGCTGGCA | 60 | MKPLLVVF VFLFLWDPV LA | 122 |
| SS-023 | Secretion signal | ATGTCCTGTTCCCTAAAGTTT ACTTTGATTGTAATTTTTTTT ACTGTTGGCTTTCATCCAGC | 61 | MSCSLKFTL IVIFFTCTLS SS | 123 |
| SS-024 | Secretion signal | ATGGTTCTTACTAAACCTCTTC AAAGAAATGGCAGCATGATG AGCTTTGAAAATGTGAAAGAA AAGAGCAGAGAAGGAGGGCC CCATGCACACACACCCGAAGA AGAATTGTGTTTCGTGGTAAC ACACTACCCTCAGGTTCAGAC CACACTCAACCTGTTTTTCCAT ATATTCAAGGTTCTTACTCAA CCACTTTCCCTTCTGTGGGGT | 62 | MVLTKPLQ RNGSMMSF ENVKEKSRE GGPHAHTPE EELCFVVTH TPQVQTTLN LFFHIFKVLT QPLSLLWG | 124 |
| SS-025 | Secretion signal | ATGGCCACCCCGCCATTCCGG CTGATAAGGAAGATGTTTTCC TTCAAGGTGAGCAGATGGATG GGGCTTGCCTGCTTCCGGTCC CTGGCGGCATCC | 63 | MATPPFRLI RKMFSFKVS RWMGLACF RSLAAS | 125 |
| SS-026 | Secretion signal | ATGAGCTTTTTCCAACTCCTG ATGAAAAGGAAGGAACTCAT TCCCTTGGTGGTGTTCATGAC TGTGGCGGCGGGTGGAGCCTC ATCT | 64 | MSFFQLLM KRKELIPLV VFMTVAAG GASS | 126 |
| SS-027 | Secretion signal | ATGGTCTCAGCTCTGCGGGA GCACCCCTGATCAGGGTGCAC TCAAGCCCTGTTTCTTCTCCTT CTGTGAGTGGACCACGGAGGC TGGTGAGCTGCCTGTCATCCC AAAGCTCAGCTCTGAGC | 65 | MVSALRGA PLIRVHSSPV SSPSVSGPA ALVSCLSSQ SSALS | 127 |
| SS-028 | Secretion signal | ATGATGGGGTCCCCAGTGAGT CATCTGCTGGCCGGCTTCTGT GTGTGGGTCGTCTTGGGC | 66 | MMGSPVSH LLAGFCVW VVLG | 128 |
| SS-029 | Secretion signal | ATGGCAAGCATGGCTGCCGTG CTCACCTGGGCTCTGGCTCTT CTTTCAGCGTTTTCGGCCACC CAGGCA | 67 | MASMAAVL TWALALLS AFSATQA | 129 |
| SS-030 | Secretion signal | ATGGTGCTCATGTGGACCAGT GGTGACGCCTTCAAGACGGCC TACTTCCTGCTGAAGGGTGCC CCTCTGCAGTTCTCCGTGTGC GGCCTGCTGCAGGTGCTGGTG GACCTGGCCATCCTGGGGCAG GCCTACGCC | 68 | MVLMWTSG DAFKTAYFL LKGAPLQFS VCGLLQVL VDLAILGQA TA | 130 |
| SS-031 | Secretion signal | ATGGATTTTGTCGCTGGAGCC ATCGGAGGCGTCTGCGGTGTT GCTGTGGGCTACCCCCTGGAC ACGGTGAAGGTCAGGATCCA GACGGAGCCAAAGTACACAG GCATCTGGCACTGCGTCCGGG ATACGTATCACCGAGAGCGCG TGTGGG GCTTCTACCGGGGCCTCTCGC TGCCCGTGTGCACGGTGTCCC TGGTATCTTCC | 69 | MDFVAGAI GGVCGVAV GYPLDTVK VRIQTEPLY TGIWHCVR DTYHRERV WGFYRGLS LPVCTVSLV SS | 131 |

TABLE 9-continued

Signal Peptides

| ID | Description | NUCLEOTIDE SEQUENCE (5'-3') | SEQ ID NO. | ENCODED PEPTIDE | SEQ ID NO. |
|---|---|---|---|---|---|
| SS-032 | Secretion signal | ATGGAGAAGCCCCTCTTCCCA TTAGTGCCTTTGCATTGGTTTG GCTTTGGCTACACAGCACTGG TTGTTTCTGGTGGGATCGTTG GCTATGTAAAAACAGGCAGC GTGCCGTCCCTGGCTGCAGGG CTGCTCTTCGGCAGTCTAGCC | 70 | MEKPLFPLV PLHWFGFG YTALVVSG GIVGYVKTG SVPSLAAGL LFGSLA | 132 |
| SS-033 | Secretion signal | ATGGGTCTGCTCCTTCCCCTG GCACTCTGCATCCTAGTCCTG TGC | 71 | MGLLLPLAL CILVLC | 133 |
| SS-034 | Secretion signal | ATGGGGATCCAGACGAGCCCC GTCCTGCTGGCCTCCCTGGGG GTGGGGCTGGTCACTCTGCTC GGCCTGGCTGTGGGC | 72 | MGIQTSPVL LASLGVGLV TLLGLAVG | 134 |
| SS-035 | Secretion signal | ATGTCGGACCTGCTACTACTG GGCCTGATTGGGGGCCTGACT CTCTTACTGCTGCTGACGCTG CTAGCCTTTGCC | 73 | MSDLLLLGL IGGLTLLLL LTLLAFA | 135 |
| SS-036 | Secretion signal | ATGGAGACTGTGGTGATTGTT GCCATAGGTGTGCTGGCCACC ATGTTTCTGGCTTCGTTTGCAG CCTTGGTGCTGGTTTGCAGGC AG | 74 | METVVIVAI GVLATIFLA SFAALVLVC RQ | 136 |
| SS-037 | Secretion signal | ATGCGCGGCTCTGTGGAGTGC ACCTGGGGTTGGGGGCACTGT GCCCCCAGCCCCTGCTCCTT TGGACTCTACTTCTGTTTGCA GCCCCATTTGGCCTGCTGGGG | 75 | MAGSVECT WGWGHCAP SPLLLWTLL LFAAPFGLLG | 137 |
| SS-038 | Secretion signal | ATGATGCCGTCCCGTACCAAC CTGGCTACTGGAATCCCCAGT AGTAAAGTGAAATATTCAAGG CTCTCCAGCACAGACGATGGC TACATTGACCTTCAGTTTAAG AAAACCCCTCCTAAGATCCCT TATAAGGCCATCGCACTTGCC ACTGTGCTGTTTTTGATTGGC GCC | 76 | MMPSRTNL ATGIPSSKV KYSRLSSTD DGYIDLQFK KTPPKIPYK AIALATVLF LIGA | 138 |
| SS-039 | Secretion signal | ATGGCCCTGCCCCAGATGTGT GACGGGAGCCACTTGGCCTCC ACCCTCCGCTATTGCATGACA GTCAGCGGCACAGTGGTTCTG GTGGCCGGGACGCTCTGCTTC GCT | 77 | MALPQMCD GSHLASTLR YCMTVSGT VVLVAGTL CFA | 139 |
| SS-041 | Vrg-6 | TGAAAAAGTGGTTCGTTGCTG CCGGCATCGGCGCTGCCGGAC TCATGCTCTCCAGCGCCGCCA | 78 | MKKWFVAA GIGAGLLML SSAA | 140 |
| SS-042 | PhoA | ATGAAACAGAGCACCATTGCG CTGGCGCTGCTGCCGCTGCTG TTTACCCCGGTGACCAAAGCG | 79 | MKQSTIALA LLPLLFTPV TKA | 141 |
| SS-043 | OmpA | ATGAAAAAAACCGCGATTGC GATTGCGGTGGCGCTGGCGGG CTTTGCGACCGTGGCGCAGGCG | 80 | MKKTAIAIA VALAGFAT VAQA | 142 |
| SS-044 | STI | ATGAAAAAACTGATGCTGGCG ATTTTTTTTAGCGTGCTGAGCT TTCCGAGCTTTAGCCAGAGC | 81 | MKKLMLAI FFSVLSFPSF SQS | 143 |
| SS-045 | STII | ATGAAAAAAAACATTGCGTTT CTGCTGGCGAGCATGTTTGTG TTTAGCATTGCGACCAACGCG TATGCG | 82 | MKKNIAFLL ASMFVFSIA TNAYA | 144 |

TABLE 9-continued

Signal Peptides

| ID | Description | NUCLEOTIDE SEQUENCE (5'-3') | SEQ ID NO. | ENCODED PEPTIDE | SEQ ID NO. |
|---|---|---|---|---|---|
| SS-046 | Amylase | ATGTTTGCGAAACGCTTTAAA ACCAGCCTGCTGCCGCTGTTT GCGGGCTTTCTGCTGCTGTTTC ATCTGGTGCTGGCGGGCCCGG CGGCGGCGAGC | 83 | MFAKRFKTS LLPLFAGFL LLFHLVLAG PAAAS | 145 |
| SS-047 | Alpha Factor | ATGCGCTTTCCGAGCATTTTT ACCGCGGTGCTGTTTGCGGCG AGCAGCGCGCTGGCG | 84 | MRFPSIFTA VLFAASSALA | 146 |
| SS-048 | Alpha Factor | ATGCGCTTTCCGAGCATTTTT ACCACCGTGCTGTTTGCGGCG AGCAGCGCGCTGGCG | 85 | MRFPSIFTT VLFAASSALA | 147 |
| SS-049 | Alpha Factor | ATGCGCTTTCCGAGCATTTTT ACCAGCGTGCTGTTTGCGGCG AGCAGCGCGCTGGCG | 86 | MRFPSIFTSV LFAASSALA | 148 |
| SS-050 | Alpha Factor | ATGCGCTTTCCGAGCATTTTT ACCCATGTGCTGTTTGCGGCG AGCAGCGCGCTGGCG | 87 | MRFPSIFTH VLFAASSALA | 149 |
| SS-051 | Alpha Factor | ATGCGCTTTCCGAGCATTTTT ACCATTGTGCTGTTTGCGGCG AGCAGCGCGCTGGCG | 88 | MRFPSIFTIV LFAASSALA | 150 |
| SS-052 | Alpha Factor | ATGCGCTTTCCGAGCATTTTT ACCTTTGTGCTGTTTGCGGCG AGCAGCGCGCTGGCG | 89 | MRFPSIFTFV LFAASSALA | 151 |
| SS-053 | Alpha Factor | ATGCGCTTTCCGAGCATTTTT ACCGAAGTGCTGTTTGCGGCG AGCAGCGCGCTGGCG | 90 | MRFPSIFTE VLFAASSALA | 152 |
| SS-054 | Alpha Factor | ATGCGCTTTCCGAGCATTTTT ACCGGCGTGCTGTTTGCGGCG AGCAGCGCGCTGGCG | 91 | MRFPSIFTG VLFAASSALA | 153 |
| SS-055 | Endoglucanase V | ATGCGTTCCTCCCCCCTCCTCC GCTCCGCCGTTGTGGCCGCCC TGCCGGTGTTGGCCCTTGCC | 92 | MRSSPLLRS AVVAALPV LALA | 154 |
| SS-056 | Secretion signal | ATGGGCGCGGCGGCCGTGCGC TGGCACTTGTGCGTGCTGCTG GCCCTGGGCACACGCGGGCG GCTG | 93 | MGAAAVR WHLCVLLA LGTRGRL | 155 |
| SS-057 | Fungal | ATGAGGAGCTCCCTTGTGCTG TTCTTTGTCTCTGCGTGGACG GCCTTGGCCAG | 94 | MRSSLVLFF VSAWTALA | 156 |
| SS-058 | Fibronectin | ATGCTCAGGGGTCCGGGACCC GGGCGGCTGCTGCTGCTAGCA GTCCTGTGCCTGGGGACATCG GTGCGCTGCACCGAAACCGGG AAGAGCAAGAGG | 95 | MLRGPGPG RLLLLAVLC LGTSVRCTE TGKSKR | 157 |
| SS-059 | Fibronectin | ATGCTTAGGGGTCCGGGGCCC GGGCTGCTGCTGCTGGCCGTC CAGCTGGGGACAGCGGTGCCC TCCACG | 96 | MLRGPGPG LLLLAVQCL GTAVPSTGA | 158 |
| SS-060 | Fibronectin | ATGCGCCGGGGGCCCTGACC GGGCTGCTCCTGGTCCTGTGC CTGAGTGTTGTGCTACGTGCA GCCCCTCTGCAACAAGCAAG AAGCGCAGG | 97 | MRRGALTG LLLVLCLSV VLRAAPSAT SKKRR | 159 |

In table 9, SS is secretion signal and MLS is mitochondrial leader signal. The primary constructs or mmRNA of the present invention may be designed to encode any of the signal peptide sequences of SEQ ID NOs 98-159, or fragments or variants thereof. These sequences may be included at the beginning of the polypeptide coding region, in the middle or at the terminus or alternatively into a flanking region. Further, any of the polynucleotide primary constructs of the present invention may also comprise one or more of the sequences defined by SEQ ID NOs 36-97. These may be in the first region or either flanking region.

Additional signal peptide sequences which may be utilized in the present invention include those taught in, for example, databases such as those found at http://www.signalpeptide.de/ or http://proline.bic.nus.edu.sg/spdb/. Those described in U.S. Pat. Nos. 8,124,379; 7,413,875 and 7,385,034 are also within the scope of the invention and the contents of each are incorporated herein by reference in their entirety.

In one embodiment, the modified nucleic acid molecules may include a nucleic acid sequence encoding a nuclear localization signal (NLS) and/or a nuclear export signal (NES). In one aspect, a modified nucleic acid molecules may include a nucleic acid sequence encoding a nuclear localization signal (NLS). The modified nucleic acid molecules encoding a NLS would be able to traffic a polypeptide into the nucleus and deliver a survival or death signal to the nuclear microenvironment. In another aspect, the modified nucleic acid molecules may include a nucleic acid sequence encoding a nuclear export signal such as NES1 and/or NES2. As a nonlimiting example, the modified nucleic acid molecules may encode a NES1, NES2 and a NLS signal and an oncology related polypeptide or a scrambled sequence which is not translatable in order to interact with HIF 1-alpha to alter the transcritome of the cancer cells.

Target Selection

According to the present invention, the primary constructs comprise at least a first region of linked nucleosides encoding at least one polypeptide of interest. The polypeptides of interest or "targets" or proteins and peptides of the present invention are listed in U.S. Provisional Patent Application No. 61/618,862, filed Apr. 2, 2012, entitled Modified Polynucleotides for the Production of Biologics; U.S. Provisional Patent Application No. 61/681,645, filed Aug. 10, 2012, entitled Modified Polynucleotides for the Production of Biologics; U.S. Provisional Patent Application No. 61/737,130, filed Dec. 14, 2012, entitled Modified Polynucleotides for the Production of Biologics; U.S. Provisional Patent Application No. 61/618,866, filed Apr. 2, 2012, entitled Modified Polynucleotides for the Production of Antibodies; U.S. Provisional Patent Application No. 61/681,647, filed Aug. 10, 2012, entitled Modified Polynucleotides for the Production of Antibodies; U.S. Provisional Patent Application No. 61/737,134, filed Dec. 14, 2012, entitled Modified Polynucleotides for the Production of Antibodies; U.S. Provisional Patent Application No. 61/618,868, filed Apr. 2, 2012, entitled Modified Polynucleotides for the Production of Vaccines; U.S. Provisional Patent Application No. 61/681,648, filed Aug. 10, 2012, entitled Modified Polynucleotides for the Production of Vaccines; U.S. Provisional Patent Application No. 61/737,135, filed Dec. 14, 2012, entitled Modified Polynucleotides for the Production of Vaccines; U.S. Provisional Patent Application No. 61/618,870, filed Apr. 2, 2012, entitled Modified Polynucleotides for the Production of Therapeutic Proteins and Peptides; U.S. Provisional Patent Application No. 61/681,649, filed Aug. 10, 2012, entitled Modified Polynucleotides for the Production of Therapeutic Proteins and Peptides; U.S. Provisional Patent Application No. 61/737,139, filed Dec. 14, 2012, Modified Polynucleotides for the Production of Therapeutic Proteins and Peptides; U.S. Provisional Patent Application No. 61/618,873, filed Apr. 2, 2012, entitled Modified Polynucleotides for the Production of Secreted Proteins; U.S. Provisional Patent Application No. 61/681,650, filed Aug. 10, 2012, entitled Modified Polynucleotides for the Production of Secreted Proteins; U.S. Provisional Patent Application No. 61/737,147, filed Dec. 14, 2012, entitled Modified Polynucleotides for the Production of Secreted Proteins; U.S. Provisional Patent Application No. 61/618,878, filed Apr. 2, 2012, entitled Modified Polynucleotides for the Production of Plasma Membrane Proteins; U.S. Provisional Patent Application No. 61/681,654, filed Aug. 10, 2012, entitled Modified Polynucleotides for the Production of Plasma Membrane Proteins; U.S. Provisional Patent Application No. 61/737,152, filed Dec. 14, 2012, entitled Modified Polynucleotides for the Production of Plasma Membrane Proteins; U.S. Provisional Patent Application No. 61/618,885, filed Apr. 2, 2012, entitled Modified Polynucleotides for the Production of Cytoplasmic and Cytoskeletal Proteins; U.S. Provisional Patent Application No. 61/681,658, filed Aug. 10, 2012, entitled Modified Polynucleotides for the Production of Cytoplasmic and Cytoskeletal Proteins; U.S. Provisional Patent Application No. 61/737,155, filed Dec. 14, 2012, entitled Modified Polynucleotides for the Production of Cytoplasmic and Cytoskeletal Proteins; U.S. Provisional Patent Application No. 61/618,896, filed Apr. 2, 2012, entitled Modified Polynucleotides for the Production of Intracellular Membrane Bound Proteins; U.S. Provisional Patent Application No. 61/668,157, filed Jul. 5, 2012, entitled Modified Polynucleotides for the Production of Intracellular Membrane Bound Proteins; U.S. Provisional Patent Application No. 61/681,661, filed Aug. 10, 2012, entitled Modified Polynucleotides for the Production of Intracellular Membrane Bound Proteins; U.S. Provisional Patent Application No. 61/737,160, filed Dec. 14, 2012, entitled Modified Polynucleotides for the Production of Intracellular Membrane Bound Proteins; U.S. Provisional Patent Application No. 61/618,911, filed Apr. 2, 2012, entitled Modified Polynucleotides for the Production of Nuclear Proteins; U.S. Provisional Patent Application No. 61/681,667, filed Aug. 10, 2012, entitled Modified Polynucleotides for the Production of Nuclear Proteins; U.S. Provisional Patent Application No. 61/737,168, filed Dec. 14, 2012, entitled Modified Polynucleotides for the Production of Nuclear Proteins; U.S. Provisional Patent Application No. 61/618,922, filed Apr. 2, 2012, entitled Modified Polynucleotides for the Production of Proteins; U.S. Provisional Patent Application No. 61/681,675, filed Aug. 10, 2012, entitled Modified Polynucleotides for the Production of Proteins; U.S. Provisional Patent Application No. 61/737,174, filed Dec. 14, 2012, entitled Modified Polynucleotides for the Production of Proteins; U.S. Provisional Patent Application No. 61/618,935, filed Apr. 2, 2012, entitled Modified Polynucleotides for the Production of Proteins Associated with Human Disease; U.S. Provisional Patent Application No. 61/681,687, filed Aug. 10, 2012, entitled Modified Polynucleotides for the Production of Proteins Associated with Human Disease; U.S. Provisional Patent Application No. 61/737,184, filed Dec. 14, 2012, entitled Modified Polynucleotides for the Production of Proteins Associated with Human Disease; U.S. Provisional Patent Application No. 61/618,945, filed Apr. 2, 2012, entitled Modified Polynucleotides for the Production of Proteins Associated with Human Disease; U.S. Provisional Patent Application No. 61/681,696, filed Aug. 10, 2012, entitled Modified Polynucleotides for the Production of Proteins Associated with Human Disease; U.S. Provisional Patent Application No. 61/737,191, filed Dec. 14, 2012, entitled Modified Polynucleotides for the Production of Proteins Associated with Human Disease; U.S. Provisional Patent Application No. 61/618,953, filed Apr. 2, 2012, entitled Modified Polynucleotides for the Production of Proteins Associated with Human Disease; U.S. Provisional Patent Application No. 61/681,704, filed Aug. 10, 2012, entitled Modified Polynucleotides for the Production of Proteins Associated with Human Disease; U.S. Provisional Patent Application No. 61/737,203, filed Dec. 14, 2012, entitled Modified Polynucleotides for the Production of Proteins Associated with Human Disease, U.S. Provisional Patent Application No. 61/753,661, entitled Polynucleotides For The Alteration Of Cellular Phenotypes And Microenvironments; International Application No PCT/US2013/030062, filed Mar. 9, 2013, entitled Modified Polynucleotides for the Production of Biologics and Proteins Associated with Human Disease; International Application No PCT/US2013/030063, filed Mar. 9, 2013, entitled Modified Polynucloetides; International Application No. PCT/US2013/030064, entitled Modified Polynucleotides for the Production of Secreted Proteins; International Application No PCT/US2013/030059, filed Mar. 9, 2013, entitled Modified Polynucleotides for the Production of Membrane Proteins; International Application No. PCT/US2013/030066, filed Mar. 9, 2013, entitled Modified Polynucleotides for the Production of Cytoplasmic and Cytoskeletal Proteins; International Application No. PCT/US2013/030067, filed Mar. 9, 2013, entitled Modified Polynucleotides for the Production of Nuclear Proteins; International Application No. PCT/US2013/030060, filed Mar. 9, 2013, entitled Modified Polynucleotides for the Production of Proteins; International Application No. PCT/US2013/030061, filed Mar. 9, 2013, entitled Modified Polynucleotides for the Production of Proteins Associated with Human Disease; International Application No. PCT/US2013/030068, filed Mar. 9, 2013, entitled Modified Polynucleotides for the Production of Cosmetic Proteins and Peptides; International Application No. PCT/US2013/030070, filed Mar. 9, 2013, entitled Modified Polynucleotides for the Production of Oncology-Related Proteins and Peptides; and International Application No. PCT/US2013/031821, filed Mar. 15, 2013, entitled In Vivo Production of Proteins, the contents of each of which are herein incorporated by reference in their entireties.

Protein Cleavage Signals and Sites

In one embodiment, the polypeptides of the present invention may include at least one protein cleavage signal containing at least one protein cleavage site. The protein cleavage site may be located at the N-terminus, the C-terminus, at any space between the N- and the C-termini such as, but not limited to, half-way between the N- and C-termini, between the N-terminus and the half way point, between the half way point and the C-terminus, and combinations thereof.

The polypeptides of the present invention may include, but is not limited to, a proprotein convertase (or prohormone convertase), thrombin or Factor Xa protein cleavage signal. Proprotein convertases are a family of nine proteinases, comprising seven basic amino acid-specific subtilisin-like serine proteinases related to yeast kexin, known as prohormone convertase 1/3 (PC 1/3), PC2, furin, PC4, PC5/6, paired basic amino-acid cleaving enzyme 4 (PACE4) and PC7, and two other subtilases that cleave at non-basic residues, called subtilisin kexin isozyme 1 (SKI-1) and proprotein convertase subtilisin kexin 9 (PCSK9). Non-limiting examples of protein cleavage signal amino acid sequences are listing in Table 10. In Table 10, "X" refers to any amino acid, "n" may be 0, 2, 4 or 6 amino acids and "*" refers to the protein cleavage site. In Table 10, SEQ ID NO: 162 refers to when n=4 and SEQ ID NO: 163 refers to when n=6.

TABLE 10

Protein Cleavage Site Sequences

| Protein Cleavage Signal | Amino Acid Cleavage Sequence | SEQ ID NO |
|---|---|---|
| Proprotein convertase | R-X-X-R* | 160 |
|  | R-X-K/R-R* | 161 |
|  | K/R-Xn-K/R* | 162 or 163 |
| Thrombin | L-V-P-R*-G-S | 164 |
|  | L-V-P-R* | 165 |
|  | A/F/G/I/L/T/V/M-A/F/G/I/L/T/V/W/A-P-R* | 166 |
| Factor Xa | I-E-G-R* | 167 |
|  | I-D-G-R* | 168 |
|  | A-E-G-R* | 169 |
|  | A/F/G/I/L/T/V/M-D/E-G-R* | 170 |

In one embodiment, the primary constructs, modified nucleic acids and the mmRNA of the present invention may be engineered such that the primary construct, modified nucleic acid or mmRNA contains at least one encoded protein cleavage signal. The encoded protein cleavage signal may be located before the start codon, after the start codon, before the coding region, within the coding region such as, but not limited to, half way in the coding region, between the start codon and the half way point, between the half way point and the stop codon, after the coding region, before the stop codon, between two stop codons, after the stop codon and combinations thereof.

In one embodiment, the primary constructs, modified nucleic acids or mmRNA of the present invention may include at least one encoded protein cleavage signal containing at least one protein cleavage site. The encoded protein cleavage signal may include, but is not limited to, a proprotein convertase (or prohormone convertase), thrombin and/or Factor Xa protein cleavage signal. One of skill in the art may use Table 5 above or other known methods to determine the appropriate encoded protein cleavage signal to include in the primary constructs, modified nucleic acids or mmRNA of the present invention. For example, starting with the signal of Table 10 and considering the codons of Table 5 one can design a signal for the primary construct which can produce a protein signal in the resulting polypeptide.

In one embodiment, the polypeptides of the present invention include at least one protein cleavage signal and/or site.

As a non-limiting example, U.S. Pat. No. 7,374,930 and U.S. Pub. No. 20090227660, herein incorporated by reference in their entireties, use a furin cleavage site to cleave the N-terminal methionine of GLP-1 in the expression product from the Golgi apparatus of the cells. In one embodiment, the polypeptides of the present invention include at least one protein cleavage signal and/or site with the proviso that the polypeptide is not GLP-1.

In one embodiment, the primary constructs, modified nucleic acids or mmRNA of the present invention includes at least one encoded protein cleavage signal and/or site.

In one embodiment, the primary constructs, modified nucleic acid or mmRNA of the present invention includes at least one encoded protein cleavage signal and/or site with the proviso that the primary construct, modified nucleic acid or mmRNA does not encode GLP-1.

In one embodiment, the primary constructs, modified nucleic acid or mmRNA of the present invention may include more than one coding region. Where multiple coding regions are present in the primary construct, modified nucleic acid or mmRNA of the present invention, the multiple coding regions may be separated by encoded protein cleavage sites. As a non-limiting example, the primary construct, modified nucleic acid or mmRNA may be signed in an ordered pattern. On such pattern follows AXBY form where A and B are coding regions which may be the same or different coding regions and/or may encode the same or different polypeptides, and X and Y are encoded protein cleavage signals which may encode the same or different protein cleavage signals. A second such pattern follows the form AXYBZ where A and B are coding regions which may be the same or different coding regions and/or may encode the same or different polypeptides, and X, Y and Z are encoded protein cleavage signals which may encode the same or different protein cleavage signals. A third pattern follows the form ABXCY where A, B and C are coding regions which may be the same or different coding regions and/or may encode the same or different polypeptides, and X and Y are encoded protein cleavage signals which may encode the same or different protein cleavage signals.

In on embodiment, the polypeptides, primary constructs, modified nucleic acids and mmRNA can also contain sequences that encode protein cleavage sites so that the polypeptides, primary constructs, modified nucleic acids and mmRNA can be released from a carrier region or a fusion partner by treatment with a specific protease for said protein cleavage site.

Table 11 is a non-exhaustive listing of miRs and miR binding sites (miR BS) and their sequences which may be used with the present invention.

TABLE 11

| Mirs and mir binding sites | | |
|---|---|---|
| microRNA | mir SEQ ID | MIR BS SEQ ID |
| hsa-let-7a-2-3p | 171 | 1192 |
| hsa-let-7a-3p | 172 | 1193 |
| hsa-let-7a-5p | 173 | 1194 |
| hsa-let-7b-3p | 174 | 1195 |
| hsa-let-7b-5p | 175 | 1196 |
| hsa-let-7c | 176 | 1197 |
| hsa-let-7d-3p | 177 | 1198 |
| hsa-let-7d-5p | 178 | 1199 |
| hsa-let-7e-3p | 179 | 1200 |
| hsa-let-7e-5p | 180 | 1201 |
| hsa-let-7f-1-3p | 181 | 1202 |
| hsa-let-7f-2-3p | 182 | 1203 |
| hsa-let-7f-5p | 183 | 1204 |
| hsa-let-7g-3p | 184 | 1205 |
| hsa-let-7g-5p | 185 | 1206 |
| hsa-let-7i-3p | 186 | 1207 |
| hsa-let-7i-5p | 187 | 1208 |
| hsa-miR-1 | 188 | 1209 |
| hsa-miR-100-3p | 189 | 1210 |
| hsa-miR-100-5p | 190 | 1211 |
| hsa-miR-101-3p | 191 | 1212 |
| hsa-miR-101-5p | 192 | 1213 |
| hsa-miR-103a-2-5p | 193 | 1214 |
| hsa-miR-103a-3p | 194 | 1215 |
| hsa-miR-103b | 195 | 1216 |
| hsa-miR-105-3p | 196 | 1217 |
| hsa-miR-105-5p | 197 | 1218 |
| hsa-miR-106a-3p | 198 | 1219 |
| hsa-miR-106a-5p | 199 | 1220 |
| hsa-miR-106b-3p | 200 | 1221 |
| hsa-miR-106b-5p | 201 | 1222 |
| hsa-miR-107 | 202 | 1223 |
| hsa-miR-10a-3p | 203 | 1224 |
| hsa-miR-10a-5p | 204 | 1225 |
| hsa-miR-10b-3p | 205 | 1226 |

TABLE 11-continued

| Mirs and mir binding sites | | |
|---|---|---|
| microRNA | mir SEQ ID | MIR BS SEQ ID |
| hsa-miR-10b-5p | 206 | 1227 |
| hsa-miR-1178-3p | 207 | 1228 |
| hsa-miR-1178-5p | 208 | 1229 |
| hsa-miR-1179 | 209 | 1230 |
| hsa-miR-1180 | 210 | 1231 |
| hsa-miR-1181 | 211 | 1232 |
| hsa-miR-1182 | 212 | 1233 |
| hsa-miR-1183 | 213 | 1234 |
| hsa-miR-1184 | 214 | 1235 |
| hsa-miR-1185-1-3p | 215 | 1236 |
| hsa-miR-1185-2-3p | 216 | 1237 |
| hsa-miR-1185-5p | 217 | 1238 |
| hsa-miR-1193 | 218 | 1239 |
| hsa-miR-1197 | 219 | 1240 |
| hsa-miR-1200 | 220 | 1241 |
| hsa-miR-1202 | 221 | 1242 |
| hsa-miR-1203 | 222 | 1243 |
| hsa-miR-1204 | 223 | 1244 |
| hsa-miR-1205 | 224 | 1245 |
| hsa-miR-1206 | 225 | 1246 |
| hsa-miR-1207-3p | 226 | 1247 |
| hsa-miR-1207-5p | 227 | 1248 |
| hsa-miR-1208 | 228 | 1249 |
| hsa-miR-122-3p | 229 | 1250 |
| hsa-miR-1224-3p | 230 | 1251 |
| hsa-miR-1224-5p | 231 | 1252 |
| hsa-miR-1225-3p | 232 | 1253 |
| hsa-miR-1225-5p | 233 | 1254 |
| hsa-miR-122-5p | 234 | 1255 |
| hsa-miR-1226-3p | 235 | 1256 |
| hsa-miR-1226-5p | 236 | 1257 |
| hsa-miR-1227-3p | 237 | 1258 |
| hsa-miR-1227-5p | 238 | 1259 |
| hsa-miR-1228-3p | 239 | 1260 |
| hsa-miR-1228-5p | 240 | 1261 |
| hsa-miR-1229-3p | 241 | 1262 |
| hsa-miR-1229-5p | 242 | 1263 |
| hsa-miR-1231 | 243 | 1264 |
| hsa-miR-1233-1-5p | 244 | 1265 |
| hsa-miR-1233-3p | 245 | 1266 |
| hsa-miR-1234-3p | 246 | 1267 |
| hsa-miR-1234-5p | 247 | 1268 |
| hsa-miR-1236-3p | 248 | 1269 |
| hsa-miR-1236-5p | 249 | 1270 |
| hsa-miR-1237-3p | 250 | 1271 |
| hsa-miR-1237-5p | 251 | 1272 |
| hsa-miR-1238-3p | 252 | 1273 |
| hsa-miR-1238-5p | 253 | 1274 |
| hsa-miR-1243 | 254 | 1275 |
| hsa-miR-124-3p | 255 | 1276 |
| hsa-miR-1244 | 256 | 1277 |
| hsa-miR-1245a | 257 | 1278 |
| hsa-miR-1245b-3p | 258 | 1279 |
| hsa-miR-1245b-5p | 259 | 1280 |
| hsa-miR-124-5p | 260 | 1281 |
| hsa-miR-1246 | 261 | 1282 |
| hsa-miR-1247-3p | 262 | 1283 |
| hsa-miR-1247-5p | 263 | 1284 |
| hsa-miR-1248 | 264 | 1285 |
| hsa-miR-1249 | 265 | 1286 |
| hsa-miR-1250 | 266 | 1287 |
| hsa-miR-1251 | 267 | 1288 |
| hsa-miR-1252 | 268 | 1289 |
| hsa-miR-1253 | 269 | 1290 |
| hsa-miR-1254 | 270 | 1291 |
| hsa-miR-1255a | 271 | 1292 |
| hsa-miR-1255b-2-3p | 272 | 1293 |
| hsa-miR-1255b-5p | 273 | 1294 |
| hsa-miR-1256 | 274 | 1295 |
| hsa-miR-1257 | 275 | 1296 |
| hsa-miR-1258 | 276 | 1297 |
| hsa-miR-125a-3p | 277 | 1298 |
| hsa-miR-125a-5p | 278 | 1299 |
| hsa-miR-125b-1-3p | 279 | 1300 |
| hsa-miR-125b-2-3p | 280 | 1301 |

TABLE 11-continued

Mirs and mir binding sites

| microRNA | mir SEQ ID | MIR BS SEQ ID |
|---|---|---|
| hsa-miR-125b-5p | 281 | 1302 |
| hsa-miR-1260a | 282 | 1303 |
| hsa-miR-1260b | 283 | 1304 |
| hsa-miR-1261 | 284 | 1305 |
| hsa-miR-1262 | 285 | 1306 |
| hsa-miR-1263 | 286 | 1307 |
| hsa-miR-126-3p | 287 | 1308 |
| hsa-miR-1264 | 288 | 1309 |
| hsa-miR-1265 | 289 | 1310 |
| hsa-miR-126-5p | 290 | 1311 |
| hsa-miR-1266 | 291 | 1312 |
| hsa-miR-1267 | 292 | 1313 |
| hsa-miR-1268a | 293 | 1314 |
| hsa-miR-1268b | 294 | 1315 |
| hsa-miR-1269a | 295 | 1316 |
| hsa-miR-1269b | 296 | 1317 |
| hsa-miR-1270 | 297 | 1318 |
| hsa-miR-1271-3p | 298 | 1319 |
| hsa-miR-1271-5p | 299 | 1320 |
| hsa-miR-1272 | 300 | 1321 |
| hsa-miR-1273a | 301 | 1322 |
| hsa-miR-1273c | 302 | 1323 |
| hsa-miR-1273d | 303 | 1324 |
| hsa-miR-1273e | 304 | 1325 |
| hsa-miR-1273f | 305 | 1326 |
| hsa-miR-1273g-3p | 306 | 1327 |
| hsa-miR-1273g-5p | 307 | 1328 |
| hsa-miR-127-3p | 308 | 1329 |
| hsa-miR-1275 | 309 | 1330 |
| hsa-miR-127-5p | 310 | 1331 |
| hsa-miR-1276 | 311 | 1332 |
| hsa-miR-1277-3p | 312 | 1333 |
| hsa-miR-1277-5p | 313 | 1334 |
| hsa-miR-1278 | 314 | 1335 |
| hsa-miR-1279 | 315 | 1336 |
| hsa-miR-128 | 316 | 1337 |
| hsa-miR-1281 | 317 | 1338 |
| hsa-miR-1282 | 318 | 1339 |
| hsa-miR-1283 | 319 | 1340 |
| hsa-miR-1284 | 320 | 1341 |
| hsa-miR-1285-3p | 321 | 1342 |
| hsa-miR-1285-5p | 322 | 1343 |
| hsa-miR-1286 | 323 | 1344 |
| hsa-miR-1287 | 324 | 1345 |
| hsa-miR-1288 | 325 | 1346 |
| hsa-miR-1289 | 326 | 1347 |
| hsa-miR-1290 | 327 | 1348 |
| hsa-miR-1291 | 328 | 1349 |
| hsa-miR-129-1-3p | 329 | 1350 |
| hsa-miR-1292-3p | 330 | 1351 |
| hsa-miR-129-2-3p | 331 | 1352 |
| hsa-miR-1292-5p | 332 | 1353 |
| hsa-miR-1293 | 333 | 1354 |
| hsa-miR-1294 | 334 | 1355 |
| hsa-miR-1295a | 335 | 1356 |
| hsa-miR-1295b-3p | 336 | 1357 |
| hsa-miR-1295b-5p | 337 | 1358 |
| hsa-miR-129-5p | 338 | 1359 |
| hsa-miR-1296 | 339 | 1360 |
| hsa-miR-1297 | 340 | 1361 |
| hsa-miR-1298 | 341 | 1362 |
| hsa-miR-1299 | 342 | 1363 |
| hsa-miR-1301 | 343 | 1364 |
| hsa-miR-1302 | 344 | 1365 |
| hsa-miR-1303 | 345 | 1366 |
| hsa-miR-1304-3p | 346 | 1367 |
| hsa-miR-1304-5p | 347 | 1368 |
| hsa-miR-1305 | 348 | 1369 |
| hsa-miR-1306-3p | 349 | 1370 |
| hsa-miR-1306-5p | 350 | 1371 |
| hsa-miR-1307-3p | 351 | 1372 |
| hsa-miR-1307-5p | 352 | 1373 |
| hsa-miR-130a-3p | 353 | 1374 |
| hsa-miR-130a-5p | 354 | 1375 |
| hsa-miR-130b-3p | 355 | 1376 |
| hsa-miR-130b-5p | 356 | 1377 |
| hsa-miR-1321 | 357 | 1378 |
| hsa-miR-1322 | 358 | 1379 |
| hsa-miR-1323 | 359 | 1380 |
| hsa-miR-132-3p | 360 | 1381 |
| hsa-miR-1324 | 361 | 1382 |
| hsa-miR-132-5p | 362 | 1383 |
| hsa-miR-133a | 363 | 1384 |
| hsa-miR-133b | 364 | 1385 |
| hsa-miR-134 | 365 | 1386 |
| hsa-miR-1343 | 366 | 1387 |
| hsa-miR-135a-3p | 367 | 1388 |
| hsa-miR-135a-5p | 368 | 1389 |
| hsa-miR-135b-3p | 369 | 1390 |
| hsa-miR-135b-5p | 370 | 1391 |
| hsa-miR-136-3p | 371 | 1392 |
| hsa-miR-136-5p | 372 | 1393 |
| hsa-miR-137 | 373 | 1394 |
| hsa-miR-138-1-3p | 374 | 1395 |
| hsa-miR-138-2-3p | 375 | 1396 |
| hsa-miR-138-5p | 376 | 1397 |
| hsa-miR-139-3p | 377 | 1398 |
| hsa-miR-139-5p | 378 | 1399 |
| hsa-miR-140-3p | 379 | 1400 |
| hsa-miR-140-5p | 380 | 1401 |
| hsa-miR-141-3p | 381 | 1402 |
| hsa-miR-141-5p | 382 | 1403 |
| hsa-miR-142-3p | 383 | 1404 |
| hsa-miR-142-5p | 384 | 1405 |
| hsa-miR-143-3p | 385 | 1406 |
| hsa-miR-143-5p | 386 | 1407 |
| hsa-miR-144-3p | 387 | 1408 |
| hsa-miR-144-5p | 388 | 1409 |
| hsa-miR-145-3p | 389 | 1410 |
| hsa-miR-145-5p | 390 | 1411 |
| hsa-miR-1468 | 391 | 1412 |
| hsa-miR-1469 | 392 | 1413 |
| hsa-miR-146a-3p | 393 | 1414 |
| hsa-miR-146a-5p | 394 | 1415 |
| hsa-miR-146b-3p | 395 | 1416 |
| hsa-miR-146b-5p | 396 | 1417 |
| hsa-miR-1470 | 397 | 1418 |
| hsa-miR-1471 | 398 | 1419 |
| hsa-miR-147a | 399 | 1420 |
| hsa-miR-147b | 400 | 1421 |
| hsa-miR-148a-3p | 401 | 1422 |
| hsa-miR-148a-5p | 402 | 1423 |
| hsa-miR-148b-3p | 403 | 1424 |
| hsa-miR-148b-5p | 404 | 1425 |
| hsa-miR-149-3p | 405 | 1426 |
| hsa-miR-149-5p | 406 | 1427 |
| hsa-miR-150-3p | 407 | 1428 |
| hsa-miR-150-5p | 408 | 1429 |
| hsa-miR-151a-3p | 409 | 1430 |
| hsa-miR-151a-5p | 410 | 1431 |
| hsa-miR-151b | 411 | 1432 |
| hsa-miR-152 | 412 | 1433 |
| hsa-miR-153 | 413 | 1434 |
| hsa-miR-1537 | 414 | 1435 |
| hsa-miR-1538 | 415 | 1436 |
| hsa-miR-1539 | 416 | 1437 |
| hsa-miR-154-3p | 417 | 1438 |
| hsa-miR-154-5p | 418 | 1439 |
| hsa-miR-155-3p | 419 | 1440 |
| hsa-miR-155-5p | 420 | 1441 |
| hsa-miR-1587 | 421 | 1442 |
| hsa-miR-15a-3p | 422 | 1443 |
| hsa-miR-15a-5p | 423 | 1444 |
| hsa-miR-15b-3p | 424 | 1445 |
| hsa-miR-15b-5p | 425 | 1446 |
| hsa-miR-16-1-3p | 426 | 1447 |
| hsa-miR-16-2-3p | 427 | 1448 |
| hsa-miR-16-5p | 428 | 1449 |
| hsa-miR-17-3p | 429 | 1450 |
| hsa-miR-17-5p | 430 | 1451 |

TABLE 11-continued

Mirs and mir binding sites

| microRNA | mir SEQ ID | MIR BS SEQ ID |
|---|---|---|
| hsa-miR-181a-2-3p | 431 | 1452 |
| hsa-miR-181a-3p | 432 | 1453 |
| hsa-miR-181a-5p | 433 | 1454 |
| hsa-miR-181b-3p | 434 | 1455 |
| hsa-miR-181b-5p | 435 | 1456 |
| hsa-miR-181c-3p | 436 | 1457 |
| hsa-miR-181c-5p | 437 | 1458 |
| hsa-miR-181d | 438 | 1459 |
| hsa-miR-182-3p | 439 | 1460 |
| hsa-miR-1825 | 440 | 1461 |
| hsa-miR-182-5p | 441 | 1462 |
| hsa-miR-1827 | 442 | 1463 |
| hsa-miR-183-3p | 443 | 1464 |
| hsa-miR-183-5p | 444 | 1465 |
| hsa-miR-184 | 445 | 1466 |
| hsa-miR-185-3p | 446 | 1467 |
| hsa-miR-185-5p | 447 | 1468 |
| hsa-miR-186-3p | 448 | 1469 |
| hsa-miR-186-5p | 449 | 1470 |
| hsa-miR-187-3p | 450 | 1471 |
| hsa-miR-187-5p | 451 | 1472 |
| hsa-miR-188-3p | 452 | 1473 |
| hsa-miR-188-5p | 453 | 1474 |
| hsa-miR-18a-3p | 454 | 1475 |
| hsa-miR-18a-5p | 455 | 1476 |
| hsa-miR-18b-3p | 456 | 1477 |
| hsa-miR-18b-5p | 457 | 1478 |
| hsa-miR-1908 | 458 | 1479 |
| hsa-miR-1909-3p | 459 | 1480 |
| hsa-miR-1909-5p | 460 | 1481 |
| hsa-miR-190a | 461 | 1482 |
| hsa-miR-190b | 462 | 1483 |
| hsa-miR-1910 | 463 | 1484 |
| hsa-miR-1911-3p | 464 | 1485 |
| hsa-miR-1911-5p | 465 | 1486 |
| hsa-miR-1912 | 466 | 1487 |
| hsa-miR-1913 | 467 | 1488 |
| hsa-miR-191-3p | 468 | 1489 |
| hsa-miR-1914-3p | 469 | 1490 |
| hsa-miR-1914-5p | 470 | 1491 |
| hsa-miR-1915-3p | 471 | 1492 |
| hsa-miR-1915-5p | 472 | 1493 |
| hsa-miR-191-5p | 473 | 1494 |
| hsa-miR-192-3p | 474 | 1495 |
| hsa-miR-192-5p | 475 | 1496 |
| hsa-miR-193a-3p | 476 | 1497 |
| hsa-miR-193a-5p | 477 | 1498 |
| hsa-miR-193b-3p | 478 | 1499 |
| hsa-miR-193b-5p | 479 | 1500 |
| hsa-miR-194-3p | 480 | 1501 |
| hsa-miR-194-5p | 481 | 1502 |
| hsa-miR-195-3p | 482 | 1503 |
| hsa-miR-195-5p | 483 | 1504 |
| hsa-miR-196a-3p | 484 | 1505 |
| hsa-miR-196a-5p | 485 | 1506 |
| hsa-miR-196b-3p | 486 | 1507 |
| hsa-miR-196b-5p | 487 | 1508 |
| hsa-miR-1972 | 488 | 1509 |
| hsa-miR-1973 | 489 | 1510 |
| hsa-miR-197-3p | 490 | 1511 |
| hsa-miR-197-5p | 491 | 1512 |
| hsa-miR-1976 | 492 | 1513 |
| hsa-miR-198 | 493 | 1514 |
| hsa-miR-199a-3p | 494 | 1515 |
| hsa-miR-199a-5p | 495 | 1516 |
| hsa-miR-199b-3p | 496 | 1517 |
| hsa-miR-199b-5p | 497 | 1518 |
| hsa-miR-19a-3p | 498 | 1519 |
| hsa-miR-19a-5p | 499 | 1520 |
| hsa-miR-19b-1-5p | 500 | 1521 |
| hsa-miR-19b-2-5p | 501 | 1522 |
| hsa-miR-19b-3p | 502 | 1523 |
| hsa-miR-200a-3p | 503 | 1524 |
| hsa-miR-200a-5p | 504 | 1525 |
| hsa-miR-200b-3p | 505 | 1526 |
| hsa-miR-200b-5p | 506 | 1527 |
| hsa-miR-200c-3p | 507 | 1528 |
| hsa-miR-200c-5p | 508 | 1529 |
| hsa-miR-202-3p | 509 | 1530 |
| hsa-miR-202-5p | 510 | 1531 |
| hsa-miR-203a | 511 | 1532 |
| hsa-miR-203b-3p | 512 | 1533 |
| hsa-miR-203b-5p | 513 | 1534 |
| hsa-miR-204-3p | 514 | 1535 |
| hsa-miR-204-5p | 515 | 1536 |
| hsa-miR-2052 | 516 | 1537 |
| hsa-miR-2053 | 517 | 1538 |
| hsa-miR-205-3p | 518 | 1539 |
| hsa-miR-2054 | 519 | 1540 |
| hsa-miR-205-5p | 520 | 1541 |
| hsa-miR-206 | 521 | 1542 |
| hsa-miR-208a | 522 | 1543 |
| hsa-miR-208b | 523 | 1544 |
| hsa-miR-20a-3p | 524 | 1545 |
| hsa-miR-20a-5p | 525 | 1546 |
| hsa-miR-20b-3p | 526 | 1547 |
| hsa-miR-20b-5p | 527 | 1548 |
| hsa-miR-210 | 528 | 1549 |
| hsa-miR-2110 | 529 | 1550 |
| hsa-miR-2113 | 530 | 1551 |
| hsa-miR-211-3p | 531 | 1552 |
| hsa-miR-2114-3p | 532 | 1553 |
| hsa-miR-2114-5p | 533 | 1554 |
| hsa-miR-2115-3p | 534 | 1555 |
| hsa-miR-2115-5p | 535 | 1556 |
| hsa-miR-211-5p | 536 | 1557 |
| hsa-miR-2116-3p | 537 | 1558 |
| hsa-miR-2116-5p | 538 | 1559 |
| hsa-miR-2117 | 539 | 1560 |
| hsa-miR-212-3p | 540 | 1561 |
| hsa-miR-212-5p | 541 | 1562 |
| hsa-miR-21-3p | 542 | 1563 |
| hsa-miR-214-3p | 543 | 1564 |
| hsa-miR-214-5p | 544 | 1565 |
| hsa-miR-215 | 545 | 1566 |
| hsa-miR-21-5p | 546 | 1567 |
| hsa-miR-216a-3p | 547 | 1568 |
| hsa-miR-216a-5p | 548 | 1569 |
| hsa-miR-216b | 549 | 1570 |
| hsa-miR-217 | 550 | 1571 |
| hsa-miR-218-1-3p | 551 | 1572 |
| hsa-miR-218-2-3p | 552 | 1573 |
| hsa-miR-218-5p | 553 | 1574 |
| hsa-miR-219-1-3p | 554 | 1575 |
| hsa-miR-219-2-3p | 555 | 1576 |
| hsa-miR-219-5p | 556 | 1577 |
| hsa-miR-221-3p | 557 | 1578 |
| hsa-miR-221-5p | 558 | 1579 |
| hsa-miR-222-3p | 559 | 1580 |
| hsa-miR-222-5p | 560 | 1581 |
| hsa-miR-223-3p | 561 | 1582 |
| hsa-miR-223-5p | 562 | 1583 |
| hsa-miR-22-3p | 563 | 1584 |
| hsa-miR-224-3p | 564 | 1585 |
| hsa-miR-224-5p | 565 | 1586 |
| hsa-miR-22-5p | 566 | 1587 |
| hsa-miR-2276 | 567 | 1588 |
| hsa-miR-2277-3p | 568 | 1589 |
| hsa-miR-2277-5p | 569 | 1590 |
| hsa-miR-2278 | 570 | 1591 |
| hsa-miR-2355-3p | 571 | 1592 |
| hsa-miR-2355-5p | 572 | 1593 |
| hsa-miR-2392 | 573 | 1594 |
| hsa-miR-23a-3p | 574 | 1595 |
| hsa-miR-23a-5p | 575 | 1596 |
| hsa-miR-23b-3p | 576 | 1597 |
| hsa-miR-23b-5p | 577 | 1598 |
| hsa-miR-23c | 578 | 1599 |
| hsa-miR-24-1-5p | 579 | 1600 |
| hsa-miR-24-2-5p | 580 | 1601 |

TABLE 11-continued

Mirs and mir binding sites

| microRNA | mir SEQ ID | MIR BS SEQ ID |
|---|---|---|
| hsa-miR-24-3p | 581 | 1602 |
| hsa-miR-2467-3p | 582 | 1603 |
| hsa-miR-2467-5p | 583 | 1604 |
| hsa-miR-25-3p | 584 | 1605 |
| hsa-miR-25-5p | 585 | 1606 |
| hsa-miR-2681-3p | 586 | 1607 |
| hsa-miR-2681-5p | 587 | 1608 |
| hsa-miR-2682-3p | 588 | 1609 |
| hsa-miR-2682-5p | 589 | 1610 |
| hsa-miR-26a-1-3p | 590 | 1611 |
| hsa-miR-26a-2-3p | 591 | 1612 |
| hsa-miR-26a-5p | 592 | 1613 |
| hsa-miR-26b-3p | 593 | 1614 |
| hsa-miR-26b-5p | 594 | 1615 |
| hsa-miR-27a-3p | 595 | 1616 |
| hsa-miR-27a-5p | 596 | 1617 |
| hsa-miR-27b-3p | 597 | 1618 |
| hsa-miR-27b-5p | 598 | 1619 |
| hsa-miR-28-3p | 599 | 1620 |
| hsa-miR-28-5p | 600 | 1621 |
| hsa-miR-2861 | 601 | 1622 |
| hsa-miR-2909 | 602 | 1623 |
| hsa-miR-296-3p | 603 | 1624 |
| hsa-miR-2964a-3p | 604 | 1625 |
| hsa-miR-2964a-5p | 605 | 1626 |
| hsa-miR-296-5p | 606 | 1627 |
| hsa-miR-297 | 607 | 1628 |
| hsa-miR-298 | 608 | 1629 |
| hsa-miR-299-3p | 609 | 1630 |
| hsa-miR-299-5p | 610 | 1631 |
| hsa-miR-29a-3p | 611 | 1632 |
| hsa-miR-29a-5p | 612 | 1633 |
| hsa-miR-29b-1-5p | 613 | 1634 |
| hsa-miR-29b-2-5p | 614 | 1635 |
| hsa-miR-29b-3p | 615 | 1636 |
| hsa-miR-29c-3p | 616 | 1637 |
| hsa-miR-29c-5p | 617 | 1638 |
| hsa-miR-300 | 618 | 1639 |
| hsa-miR-301a-3p | 619 | 1640 |
| hsa-miR-301a-5p | 620 | 1641 |
| hsa-miR-301b | 621 | 1642 |
| hsa-miR-302a-3p | 622 | 1643 |
| hsa-miR-302a-5p | 623 | 1644 |
| hsa-miR-302b-3p | 624 | 1645 |
| hsa-miR-302b-5p | 625 | 1646 |
| hsa-miR-302c-3p | 626 | 1647 |
| hsa-miR-302c-5p | 627 | 1648 |
| hsa-miR-302d-3p | 628 | 1649 |
| hsa-miR-302d-5p | 629 | 1650 |
| hsa-miR-302e | 630 | 1651 |
| hsa-miR-302f | 631 | 1652 |
| hsa-miR-3064-3p | 632 | 1653 |
| hsa-miR-3064-5p | 633 | 1654 |
| hsa-miR-3065-3p | 634 | 1655 |
| hsa-miR-3065-5p | 635 | 1656 |
| hsa-miR-3074-3p | 636 | 1657 |
| hsa-miR-3074-5p | 637 | 1658 |
| hsa-miR-30a-3p | 638 | 1659 |
| hsa-miR-30a-5p | 639 | 1660 |
| hsa-miR-30b-3p | 640 | 1661 |
| hsa-miR-30b-5p | 641 | 1662 |
| hsa-miR-30c-1-3p | 642 | 1663 |
| hsa-miR-30c-2-3p | 643 | 1664 |
| hsa-miR-30c-5p | 644 | 1665 |
| hsa-miR-30d-3p | 645 | 1666 |
| hsa-miR-30d-5p | 646 | 1667 |
| hsa-miR-30e-3p | 647 | 1668 |
| hsa-miR-30e-5p | 648 | 1669 |
| hsa-miR-3115 | 649 | 1670 |
| hsa-miR-3116 | 650 | 1671 |
| hsa-miR-3117-3p | 651 | 1672 |
| hsa-miR-3117-5p | 652 | 1673 |
| hsa-miR-3118 | 653 | 1674 |
| hsa-miR-3119 | 654 | 1675 |
| hsa-miR-3120-3p | 655 | 1676 |
| hsa-miR-3120-5p | 656 | 1677 |
| hsa-miR-3121-3p | 657 | 1678 |
| hsa-miR-3121-5p | 658 | 1679 |
| hsa-miR-3122 | 659 | 1680 |
| hsa-miR-3123 | 660 | 1681 |
| hsa-miR-3124-3p | 661 | 1682 |
| hsa-miR-3124-5p | 662 | 1683 |
| hsa-miR-3125 | 663 | 1684 |
| hsa-miR-3126-3p | 664 | 1685 |
| hsa-miR-3126-5p | 665 | 1686 |
| hsa-miR-3127-3p | 666 | 1687 |
| hsa-miR-3127-5p | 667 | 1688 |
| hsa-miR-3128 | 668 | 1689 |
| hsa-miR-3129-3p | 669 | 1690 |
| hsa-miR-3129-5p | 670 | 1691 |
| hsa-miR-3130-3p | 671 | 1692 |
| hsa-miR-3130-5p | 672 | 1693 |
| hsa-miR-3131 | 673 | 1694 |
| hsa-miR-3132 | 674 | 1695 |
| hsa-miR-3133 | 675 | 1696 |
| hsa-miR-3134 | 676 | 1697 |
| hsa-miR-3135a | 677 | 1698 |
| hsa-miR-3135b | 678 | 1699 |
| hsa-miR-3136-3p | 679 | 1700 |
| hsa-miR-3136-5p | 680 | 1701 |
| hsa-miR-3137 | 681 | 1702 |
| hsa-miR-3138 | 682 | 1703 |
| hsa-miR-3139 | 683 | 1704 |
| hsa-miR-31-3p | 684 | 1705 |
| hsa-miR-3140-3p | 685 | 1706 |
| hsa-miR-3140-5p | 686 | 1707 |
| hsa-miR-3141 | 687 | 1708 |
| hsa-miR-3142 | 688 | 1709 |
| hsa-miR-3143 | 689 | 1710 |
| hsa-miR-3144-3p | 690 | 1711 |
| hsa-miR-3144-5p | 691 | 1712 |
| hsa-miR-3145-3p | 692 | 1713 |
| hsa-miR-3145-5p | 693 | 1714 |
| hsa-miR-3146 | 694 | 1715 |
| hsa-miR-3147 | 695 | 1716 |
| hsa-miR-3148 | 696 | 1717 |
| hsa-miR-3149 | 697 | 1718 |
| hsa-miR-3150a-3p | 698 | 1719 |
| hsa-miR-3150a-5p | 699 | 1720 |
| hsa-miR-3150b-3p | 700 | 1721 |
| hsa-miR-3150b-5p | 701 | 1722 |
| hsa-miR-3151 | 702 | 1723 |
| hsa-miR-3152-3p | 703 | 1724 |
| hsa-miR-3152-5p | 704 | 1725 |
| hsa-miR-3153 | 705 | 1726 |
| hsa-miR-3154 | 706 | 1727 |
| hsa-miR-3155a | 707 | 1728 |
| hsa-miR-3155b | 708 | 1729 |
| hsa-miR-3156-3p | 709 | 1730 |
| hsa-miR-3156-5p | 710 | 1731 |
| hsa-miR-3157-3p | 711 | 1732 |
| hsa-miR-3157-5p | 712 | 1733 |
| hsa-miR-3158-3p | 713 | 1734 |
| hsa-miR-3158-5p | 714 | 1735 |
| hsa-miR-3159 | 715 | 1736 |
| hsa-miR-31-5p | 716 | 1737 |
| hsa-miR-3160-3p | 717 | 1738 |
| hsa-miR-3160-5p | 718 | 1739 |
| hsa-miR-3161 | 719 | 1740 |
| hsa-miR-3162-3p | 720 | 1741 |
| hsa-miR-3162-5p | 721 | 1742 |
| hsa-miR-3163 | 722 | 1743 |
| hsa-miR-3164 | 723 | 1744 |
| hsa-miR-3165 | 724 | 1745 |
| hsa-miR-3166 | 725 | 1746 |
| hsa-miR-3167 | 726 | 1747 |
| hsa-miR-3168 | 727 | 1748 |
| hsa-miR-3169 | 728 | 1749 |
| hsa-miR-3170 | 729 | 1750 |
| hsa-miR-3171 | 730 | 1751 |

TABLE 11-continued

Mirs and mir binding sites

| microRNA | mir SEQ ID | MIR BS SEQ ID |
|---|---|---|
| hsa-miR-3173-3p | 731 | 1752 |
| hsa-miR-3173-5p | 732 | 1753 |
| hsa-miR-3174 | 733 | 1754 |
| hsa-miR-3175 | 734 | 1755 |
| hsa-miR-3176 | 735 | 1756 |
| hsa-miR-3177-3p | 736 | 1757 |
| hsa-miR-3177-5p | 737 | 1758 |
| hsa-miR-3178 | 738 | 1759 |
| hsa-miR-3179 | 739 | 1760 |
| hsa-miR-3180 | 740 | 1761 |
| hsa-miR-3180-3p | 741 | 1762 |
| hsa-miR-3180-5p | 742 | 1763 |
| hsa-miR-3181 | 743 | 1764 |
| hsa-miR-3182 | 744 | 1765 |
| hsa-miR-3183 | 745 | 1766 |
| hsa-miR-3184-3p | 746 | 1767 |
| hsa-miR-3184-5p | 747 | 1768 |
| hsa-miR-3185 | 748 | 1769 |
| hsa-miR-3186-3p | 749 | 1770 |
| hsa-miR-3186-5p | 750 | 1771 |
| hsa-miR-3187-3p | 751 | 1772 |
| hsa-miR-3187-5p | 752 | 1773 |
| hsa-miR-3188 | 753 | 1774 |
| hsa-miR-3189-3p | 754 | 1775 |
| hsa-miR-3189-5p | 755 | 1776 |
| hsa-miR-3190-3p | 756 | 1777 |
| hsa-miR-3190-5p | 757 | 1778 |
| hsa-miR-3191-3p | 758 | 1779 |
| hsa-miR-3191-5p | 759 | 1780 |
| hsa-miR-3192 | 760 | 1781 |
| hsa-miR-3193 | 761 | 1782 |
| hsa-miR-3194-3p | 762 | 1783 |
| hsa-miR-3194-5p | 763 | 1784 |
| hsa-miR-3195 | 764 | 1785 |
| hsa-miR-3196 | 765 | 1786 |
| hsa-miR-3197 | 766 | 1787 |
| hsa-miR-3198 | 767 | 1788 |
| hsa-miR-3199 | 768 | 1789 |
| hsa-miR-3200-3p | 769 | 1790 |
| hsa-miR-3200-5p | 770 | 1791 |
| hsa-miR-3201 | 771 | 1792 |
| hsa-miR-3202 | 772 | 1793 |
| hsa-miR-320a | 773 | 1794 |
| hsa-miR-320b | 774 | 1795 |
| hsa-miR-320c | 775 | 1796 |
| hsa-miR-320d | 776 | 1797 |
| hsa-miR-320e | 777 | 1798 |
| hsa-miR-323a-3p | 778 | 1799 |
| hsa-miR-323a-5p | 779 | 1800 |
| hsa-miR-323b-3p | 780 | 1801 |
| hsa-miR-323b-5p | 781 | 1802 |
| hsa-miR-32-3p | 782 | 1803 |
| hsa-miR-324-3p | 783 | 1804 |
| hsa-miR-324-5p | 784 | 1805 |
| hsa-miR-325 | 785 | 1806 |
| hsa-miR-32-5p | 786 | 1807 |
| hsa-miR-326 | 787 | 1808 |
| hsa-miR-328 | 788 | 1809 |
| hsa-miR-329 | 789 | 1810 |
| hsa-miR-330-3p | 790 | 1811 |
| hsa-miR-330-5p | 791 | 1812 |
| hsa-miR-331-3p | 792 | 1813 |
| hsa-miR-331-5p | 793 | 1814 |
| hsa-miR-335-3p | 794 | 1815 |
| hsa-miR-335-5p | 795 | 1816 |
| hsa-miR-337-3p | 796 | 1817 |
| hsa-miR-337-5p | 797 | 1818 |
| hsa-miR-338-3p | 798 | 1819 |
| hsa-miR-338-5p | 799 | 1820 |
| hsa-miR-339-3p | 800 | 1821 |
| hsa-miR-339-5p | 801 | 1822 |
| hsa-miR-33a-3p | 802 | 1823 |
| hsa-miR-33a-5p | 803 | 1824 |
| hsa-miR-33b-3p | 804 | 1825 |
| hsa-miR-33b-5p | 805 | 1826 |
| hsa-miR-340-3p | 806 | 1827 |
| hsa-miR-340-5p | 807 | 1828 |
| hsa-miR-342-3p | 808 | 1829 |
| hsa-miR-342-5p | 809 | 1830 |
| hsa-miR-345-3p | 810 | 1831 |
| hsa-miR-345-5p | 811 | 1832 |
| hsa-miR-346 | 812 | 1833 |
| hsa-miR-34a-3p | 813 | 1834 |
| hsa-miR-34a-5p | 814 | 1835 |
| hsa-miR-34b-3p | 815 | 1836 |
| hsa-miR-34b-5p | 816 | 1837 |
| hsa-miR-34c-3p | 817 | 1838 |
| hsa-miR-34c-5p | 818 | 1839 |
| hsa-miR-3529-3p | 819 | 1840 |
| hsa-miR-3529-5p | 820 | 1841 |
| hsa-miR-3591-3p | 821 | 1842 |
| hsa-miR-3591-5p | 822 | 1843 |
| hsa-miR-3605-3p | 823 | 1844 |
| hsa-miR-3605-5p | 824 | 1845 |
| hsa-miR-3606-3p | 825 | 1846 |
| hsa-miR-3606-5p | 826 | 1847 |
| hsa-miR-3607-3p | 827 | 1848 |
| hsa-miR-3607-5p | 828 | 1849 |
| hsa-miR-3609 | 829 | 1850 |
| hsa-miR-3610 | 830 | 1851 |
| hsa-miR-3611 | 831 | 1852 |
| hsa-miR-3612 | 832 | 1853 |
| hsa-miR-3613-3p | 833 | 1854 |
| hsa-miR-3613-5p | 834 | 1855 |
| hsa-miR-361-3p | 835 | 1856 |
| hsa-miR-3614-3p | 836 | 1857 |
| hsa-miR-3614-5p | 837 | 1858 |
| hsa-miR-3615 | 838 | 1859 |
| hsa-miR-361-5p | 839 | 1860 |
| hsa-miR-3616-3p | 840 | 1861 |
| hsa-miR-3616-5p | 841 | 1862 |
| hsa-miR-3617-3p | 842 | 1863 |
| hsa-miR-3617-5p | 843 | 1864 |
| hsa-miR-3618 | 844 | 1865 |
| hsa-miR-3619-3p | 845 | 1866 |
| hsa-miR-3619-5p | 846 | 1867 |
| hsa-miR-3620-3p | 847 | 1868 |
| hsa-miR-3620-5p | 848 | 1869 |
| hsa-miR-3621 | 849 | 1870 |
| hsa-miR-3622a-3p | 850 | 1871 |
| hsa-miR-3622a-5p | 851 | 1872 |
| hsa-miR-3622b-3p | 852 | 1873 |
| hsa-miR-3622b-5p | 853 | 1874 |
| hsa-miR-362-3p | 854 | 1875 |
| hsa-miR-362-5p | 855 | 1876 |
| hsa-miR-363-3p | 856 | 1877 |
| hsa-miR-363-5p | 857 | 1878 |
| hsa-miR-3646 | 858 | 1879 |
| hsa-miR-3648 | 859 | 1880 |
| hsa-miR-3649 | 860 | 1881 |
| hsa-miR-3650 | 861 | 1882 |
| hsa-miR-3651 | 862 | 1883 |
| hsa-miR-3652 | 863 | 1884 |
| hsa-miR-3653 | 864 | 1885 |
| hsa-miR-3654 | 865 | 1886 |
| hsa-miR-3655 | 866 | 1887 |
| hsa-miR-3656 | 867 | 1888 |
| hsa-miR-3657 | 868 | 1889 |
| hsa-miR-3658 | 869 | 1890 |
| hsa-miR-3659 | 870 | 1891 |
| hsa-miR-365a-3p | 871 | 1892 |
| hsa-miR-365a-5p | 872 | 1893 |
| hsa-miR-365b-3p | 873 | 1894 |
| hsa-miR-365b-5p | 874 | 1895 |
| hsa-miR-3660 | 875 | 1896 |
| hsa-miR-3661 | 876 | 1897 |
| hsa-miR-3662 | 877 | 1898 |
| hsa-miR-3663-3p | 878 | 1899 |
| hsa-miR-3663-5p | 879 | 1900 |
| hsa-miR-3664-3p | 880 | 1901 |

TABLE 11-continued

Mirs and mir binding sites

| microRNA | mir SEQ ID | MIR BS SEQ ID |
|---|---|---|
| hsa-miR-3664-5p | 881 | 1902 |
| hsa-miR-3665 | 882 | 1903 |
| hsa-miR-3666 | 883 | 1904 |
| hsa-miR-3667-3p | 884 | 1905 |
| hsa-miR-3667-5p | 885 | 1906 |
| hsa-miR-3668 | 886 | 1907 |
| hsa-miR-3669 | 887 | 1908 |
| hsa-miR-3670 | 888 | 1909 |
| hsa-miR-3671 | 889 | 1910 |
| hsa-miR-3672 | 890 | 1911 |
| hsa-miR-3673 | 891 | 1912 |
| hsa-miR-367-3p | 892 | 1913 |
| hsa-miR-3674 | 893 | 1914 |
| hsa-miR-3675-3p | 894 | 1915 |
| hsa-miR-3675-5p | 895 | 1916 |
| hsa-miR-367-5p | 896 | 1917 |
| hsa-miR-3676-3p | 897 | 1918 |
| hsa-miR-3676-5p | 898 | 1919 |
| hsa-miR-3677-3p | 899 | 1920 |
| hsa-miR-3677-5p | 900 | 1921 |
| hsa-miR-3678-3p | 901 | 1922 |
| hsa-miR-3678-5p | 902 | 1923 |
| hsa-miR-3679-3p | 903 | 1924 |
| hsa-miR-3679-5p | 904 | 1925 |
| hsa-miR-3680-3p | 905 | 1926 |
| hsa-miR-3680-5p | 906 | 1927 |
| hsa-miR-3681-3p | 907 | 1928 |
| hsa-miR-3681-5p | 908 | 1929 |
| hsa-miR-3682-3p | 909 | 1930 |
| hsa-miR-3682-5p | 910 | 1931 |
| hsa-miR-3683 | 911 | 1932 |
| hsa-miR-3684 | 912 | 1933 |
| hsa-miR-3685 | 913 | 1934 |
| hsa-miR-3686 | 914 | 1935 |
| hsa-miR-3687 | 915 | 1936 |
| hsa-miR-3688-3p | 916 | 1937 |
| hsa-miR-3688-5p | 917 | 1938 |
| hsa-miR-3689a-3p | 918 | 1939 |
| hsa-miR-3689a-5p | 919 | 1940 |
| hsa-miR-3689b-3p | 920 | 1941 |
| hsa-miR-3689b-5p | 921 | 1942 |
| hsa-miR-3689c | 922 | 1943 |
| hsa-miR-3689d | 923 | 1944 |
| hsa-miR-3689e | 924 | 1945 |
| hsa-miR-3689f | 925 | 1946 |
| hsa-miR-3690 | 926 | 1947 |
| hsa-miR-3691-3p | 927 | 1948 |
| hsa-miR-3691-5p | 928 | 1949 |
| hsa-miR-3692-3p | 929 | 1950 |
| hsa-miR-3692-5p | 930 | 1951 |
| hsa-miR-369-3p | 931 | 1952 |
| hsa-miR-369-5p | 932 | 1953 |
| hsa-miR-370 | 933 | 1954 |
| hsa-miR-3713 | 934 | 1955 |
| hsa-miR-3714 | 935 | 1956 |
| hsa-miR-371a-3p | 936 | 1957 |
| hsa-miR-371a-5p | 937 | 1958 |
| hsa-miR-371b-3p | 938 | 1959 |
| hsa-miR-371b-5p | 939 | 1960 |
| hsa-miR-372 | 940 | 1961 |
| hsa-miR-373-3p | 941 | 1962 |
| hsa-miR-373-5p | 942 | 1963 |
| hsa-miR-374a-3p | 943 | 1964 |
| hsa-miR-374a-5p | 944 | 1965 |
| hsa-miR-374b-3p | 945 | 1966 |
| hsa-miR-374b-5p | 946 | 1967 |
| hsa-miR-374c-3p | 947 | 1968 |
| hsa-miR-374c-5p | 948 | 1969 |
| hsa-miR-375 | 949 | 1970 |
| hsa-miR-376a-2-5p | 950 | 1971 |
| hsa-miR-376a-3p | 951 | 1972 |
| hsa-miR-376a-5p | 952 | 1973 |
| hsa-miR-376b-3p | 953 | 1974 |
| hsa-miR-376b-5p | 954 | 1975 |
| hsa-miR-376c-3p | 955 | 1976 |
| hsa-miR-376c-5p | 956 | 1977 |
| hsa-miR-377-3p | 957 | 1978 |
| hsa-miR-377-5p | 958 | 1979 |
| hsa-miR-378a-3p | 959 | 1980 |
| hsa-miR-378a-5p | 960 | 1981 |
| hsa-miR-378b | 961 | 1982 |
| hsa-miR-378c | 962 | 1983 |
| hsa-miR-378d | 963 | 1984 |
| hsa-miR-378e | 964 | 1985 |
| hsa-miR-378f | 965 | 1986 |
| hsa-miR-378g | 966 | 1987 |
| hsa-miR-378h | 967 | 1988 |
| hsa-miR-378i | 968 | 1989 |
| hsa-miR-378j | 969 | 1990 |
| hsa-miR-379-3p | 970 | 1991 |
| hsa-miR-379-5p | 971 | 1992 |
| hsa-miR-380-3p | 972 | 1993 |
| hsa-miR-380-5p | 973 | 1994 |
| hsa-miR-381-3p | 974 | 1995 |
| hsa-miR-381-5p | 975 | 1996 |
| hsa-miR-382-3p | 976 | 1997 |
| hsa-miR-382-5p | 977 | 1998 |
| hsa-miR-383 | 978 | 1999 |
| hsa-miR-384 | 979 | 2000 |
| hsa-miR-3907 | 980 | 2001 |
| hsa-miR-3908 | 981 | 2002 |
| hsa-miR-3909 | 982 | 2003 |
| hsa-miR-3910 | 983 | 2004 |
| hsa-miR-3911 | 984 | 2005 |
| hsa-miR-3912 | 985 | 2006 |
| hsa-miR-3913-3p | 986 | 2007 |
| hsa-miR-3913-5p | 987 | 2008 |
| hsa-miR-3914 | 988 | 2009 |
| hsa-miR-3915 | 989 | 2010 |
| hsa-miR-3916 | 990 | 2011 |
| hsa-miR-3917 | 991 | 2012 |
| hsa-miR-3918 | 992 | 2013 |
| hsa-miR-3919 | 993 | 2014 |
| hsa-miR-3920 | 994 | 2015 |
| hsa-miR-3921 | 995 | 2016 |
| hsa-miR-3922-3p | 996 | 2017 |
| hsa-miR-3922-5p | 997 | 2018 |
| hsa-miR-3923 | 998 | 2019 |
| hsa-miR-3924 | 999 | 2020 |
| hsa-miR-3925-3p | 1000 | 2021 |
| hsa-miR-3925-5p | 1001 | 2022 |
| hsa-miR-3926 | 1002 | 2023 |
| hsa-miR-3927-3p | 1003 | 2024 |
| hsa-miR-3927-5p | 1004 | 2025 |
| hsa-miR-3928 | 1005 | 2026 |
| hsa-miR-3929 | 1006 | 2027 |
| hsa-miR-3934-3p | 1007 | 2028 |
| hsa-miR-3934-5p | 1008 | 2029 |
| hsa-miR-3935 | 1009 | 2030 |
| hsa-miR-3936 | 1010 | 2031 |
| hsa-miR-3937 | 1011 | 2032 |
| hsa-miR-3938 | 1012 | 2033 |
| hsa-miR-3939 | 1013 | 2034 |
| hsa-miR-3940-3p | 1014 | 2035 |
| hsa-miR-3940-5p | 1015 | 2036 |
| hsa-miR-3941 | 1016 | 2037 |
| hsa-miR-3942-3p | 1017 | 2038 |
| hsa-miR-3942-5p | 1018 | 2039 |
| hsa-miR-3943 | 1019 | 2040 |
| hsa-miR-3944-3p | 1020 | 2041 |
| hsa-miR-3944-5p | 1021 | 2042 |
| hsa-miR-3945 | 1022 | 2043 |
| hsa-miR-3960 | 1023 | 2044 |
| hsa-miR-3972 | 1024 | 2045 |
| hsa-miR-3973 | 1025 | 2046 |
| hsa-miR-3974 | 1026 | 2047 |
| hsa-miR-3975 | 1027 | 2048 |
| hsa-miR-3976 | 1028 | 2049 |
| hsa-miR-3977 | 1029 | 2050 |
| hsa-miR-3978 | 1030 | 2051 |

TABLE 11-continued

Mirs and mir binding sites

| microRNA | mir SEQ ID | MIR BS SEQ ID |
|---|---|---|
| hsa-miR-409-3p | 1031 | 2052 |
| hsa-miR-409-5p | 1032 | 2053 |
| hsa-miR-410 | 1033 | 2054 |
| hsa-miR-411-3p | 1034 | 2055 |
| hsa-miR-411-5p | 1035 | 2056 |
| hsa-miR-412 | 1036 | 2057 |
| hsa-miR-421 | 1037 | 2058 |
| hsa-miR-422a | 1038 | 2059 |
| hsa-miR-423-3p | 1039 | 2060 |
| hsa-miR-423-5p | 1040 | 2061 |
| hsa-miR-424-3p | 1041 | 2062 |
| hsa-miR-424-5p | 1042 | 2063 |
| hsa-miR-4251 | 1043 | 2064 |
| hsa-miR-4252 | 1044 | 2065 |
| hsa-miR-4253 | 1045 | 2066 |
| hsa-miR-425-3p | 1046 | 2067 |
| hsa-miR-4254 | 1047 | 2068 |
| hsa-miR-4255 | 1048 | 2069 |
| hsa-miR-425-5p | 1049 | 2070 |
| hsa-miR-4256 | 1050 | 2071 |
| hsa-miR-4257 | 1051 | 2072 |
| hsa-miR-4258 | 1052 | 2073 |
| hsa-miR-4259 | 1053 | 2074 |
| hsa-miR-4260 | 1054 | 2075 |
| hsa-miR-4261 | 1055 | 2076 |
| hsa-miR-4262 | 1056 | 2077 |
| hsa-miR-4263 | 1057 | 2078 |
| hsa-miR-4264 | 1058 | 2079 |
| hsa-miR-4265 | 1059 | 2080 |
| hsa-miR-4266 | 1060 | 2081 |
| hsa-miR-4267 | 1061 | 2082 |
| hsa-miR-4268 | 1062 | 2083 |
| hsa-miR-4269 | 1063 | 2084 |
| hsa-miR-4270 | 1064 | 2085 |
| hsa-miR-4271 | 1065 | 2086 |
| hsa-miR-4272 | 1066 | 2087 |
| hsa-miR-4273 | 1067 | 2088 |
| hsa-miR-4274 | 1068 | 2089 |
| hsa-miR-4275 | 1069 | 2090 |
| hsa-miR-4276 | 1070 | 2091 |
| hsa-miR-4277 | 1071 | 2092 |
| hsa-miR-4278 | 1072 | 2093 |
| hsa-miR-4279 | 1073 | 2094 |
| hsa-miR-4280 | 1074 | 2095 |
| hsa-miR-4281 | 1075 | 2096 |
| hsa-miR-4282 | 1076 | 2097 |
| hsa-miR-4283 | 1077 | 2098 |
| hsa-miR-4284 | 1078 | 2099 |
| hsa-miR-4285 | 1079 | 2100 |
| hsa-miR-4286 | 1080 | 2101 |
| hsa-miR-4287 | 1081 | 2102 |
| hsa-miR-4288 | 1082 | 2103 |
| hsa-miR-4289 | 1083 | 2104 |
| hsa-miR-429 | 1084 | 2105 |
| hsa-miR-4290 | 1085 | 2106 |
| hsa-miR-4291 | 1086 | 2107 |
| hsa-miR-4292 | 1087 | 2108 |
| hsa-miR-4293 | 1088 | 2109 |
| hsa-miR-4294 | 1089 | 2110 |
| hsa-miR-4295 | 1090 | 2111 |
| hsa-miR-4296 | 1091 | 2112 |
| hsa-miR-4297 | 1092 | 2113 |
| hsa-miR-4298 | 1093 | 2114 |
| hsa-miR-4299 | 1094 | 2115 |
| hsa-miR-4300 | 1095 | 2116 |
| hsa-miR-4301 | 1096 | 2117 |
| hsa-miR-4302 | 1097 | 2118 |
| hsa-miR-4303 | 1098 | 2119 |
| hsa-miR-4304 | 1099 | 2120 |
| hsa-miR-4305 | 1100 | 2121 |
| hsa-miR-4306 | 1101 | 2122 |
| hsa-miR-4307 | 1102 | 2123 |
| hsa-miR-4308 | 1103 | 2124 |
| hsa-miR-4309 | 1104 | 2125 |
| hsa-miR-4310 | 1105 | 2126 |
| hsa-miR-4311 | 1106 | 2127 |
| hsa-miR-4312 | 1107 | 2128 |
| hsa-miR-4313 | 1108 | 2129 |
| hsa-miR-431-3p | 1109 | 2130 |
| hsa-miR-4314 | 1110 | 2131 |
| hsa-miR-4315 | 1111 | 2132 |
| hsa-miR-431-5p | 1112 | 2133 |
| hsa-miR-4316 | 1113 | 2134 |
| hsa-miR-4317 | 1114 | 2135 |
| hsa-miR-4318 | 1115 | 2136 |
| hsa-miR-4319 | 1116 | 2137 |
| hsa-miR-4320 | 1117 | 2138 |
| hsa-miR-4321 | 1118 | 2139 |
| hsa-miR-4322 | 1119 | 2140 |
| hsa-miR-4323 | 1120 | 2141 |
| hsa-miR-432-3p | 1121 | 2142 |
| hsa-miR-4324 | 1122 | 2143 |
| hsa-miR-4325 | 1123 | 2144 |
| hsa-miR-432-5p | 1124 | 2145 |
| hsa-miR-4326 | 1125 | 2146 |
| hsa-miR-4327 | 1126 | 2147 |
| hsa-miR-4328 | 1127 | 2148 |
| hsa-miR-4329 | 1128 | 2149 |
| hsa-miR-433 | 1129 | 2150 |
| hsa-miR-4330 | 1130 | 2151 |
| hsa-miR-4417 | 1131 | 2152 |
| hsa-miR-4418 | 1132 | 2153 |
| hsa-miR-4419a | 1133 | 2154 |
| hsa-miR-4419b | 1134 | 2155 |
| hsa-miR-4420 | 1135 | 2156 |
| hsa-miR-4421 | 1136 | 2157 |
| hsa-miR-4422 | 1137 | 2158 |
| hsa-miR-4423-3p | 1138 | 2159 |
| hsa-miR-4423-5p | 1139 | 2160 |
| hsa-miR-4424 | 1140 | 2161 |
| hsa-miR-4425 | 1141 | 2162 |
| hsa-miR-4426 | 1142 | 2163 |
| hsa-miR-4427 | 1143 | 2164 |
| hsa-miR-4428 | 1144 | 2165 |
| hsa-miR-4429 | 1145 | 2166 |
| hsa-miR-4430 | 1146 | 2167 |
| hsa-miR-4431 | 1147 | 2168 |
| hsa-miR-4432 | 1148 | 2169 |
| hsa-miR-4433-3p | 1149 | 2170 |
| hsa-miR-4433-5p | 1150 | 2171 |
| hsa-miR-4434 | 1151 | 2172 |
| hsa-miR-4435 | 1152 | 2173 |
| hsa-miR-4436a | 1153 | 2174 |
| hsa-miR-4436b-3p | 1154 | 2175 |
| hsa-miR-4436b-5p | 1155 | 2176 |
| hsa-miR-4437 | 1156 | 2177 |
| hsa-miR-4438 | 1157 | 2178 |
| hsa-miR-4439 | 1158 | 2179 |
| hsa-miR-4440 | 1159 | 2180 |
| hsa-miR-4441 | 1160 | 2181 |
| hsa-miR-4442 | 1161 | 2182 |
| hsa-miR-4443 | 1162 | 2183 |
| hsa-miR-4444 | 1163 | 2184 |
| hsa-miR-4445-3p | 1164 | 2185 |
| hsa-miR-4445-5p | 1165 | 2186 |
| hsa-miR-4446-3p | 1166 | 2187 |
| hsa-miR-4446-5p | 1167 | 2188 |
| hsa-miR-4447 | 1168 | 2189 |
| hsa-miR-4448 | 1169 | 2190 |
| hsa-miR-4449 | 1170 | 2191 |
| hsa-miR-4450 | 1171 | 2192 |
| hsa-miR-4451 | 1172 | 2193 |
| hsa-miR-4452 | 1173 | 2194 |
| hsa-miR-4453 | 1174 | 2195 |
| hsa-miR-4454 | 1175 | 2196 |
| hsa-miR-4455 | 1176 | 2197 |
| hsa-miR-4456 | 1177 | 2198 |
| hsa-miR-4457 | 1178 | 2199 |
| hsa-miR-4458 | 1179 | 2200 |
| hsa-miR-4459 | 1180 | 2201 |

TABLE 11-continued

Mirs and mir binding sites

| microRNA | mir SEQ ID | MIR BS SEQ ID |
| --- | --- | --- |
| hsa-miR-4460 | 1181 | 2202 |
| hsa-miR-4461 | 1182 | 2203 |
| hsa-miR-4462 | 1183 | 2204 |
| hsa-miR-4463 | 1184 | 2205 |
| hsa-miR-4464 | 1185 | 2206 |
| hsa-miR-4465 | 1186 | 2207 |
| hsa-miR-4466 | 1187 | 2208 |
| hsa-miR-4467 | 1188 | 2209 |
| hsa-miR-4468 | 1189 | 2210 |
| hsa-miR-4469 | 1190 | 2211 |
| hsa-miR-4470 | 1191 | 2212 |
| hsa-miR-4471 | 2213 | 3234 |
| hsa-miR-4472 | 2214 | 3235 |
| hsa-miR-4473 | 2215 | 3236 |
| hsa-miR-4474-3p | 2216 | 3237 |
| hsa-miR-4474-5p | 2217 | 3238 |
| hsa-miR-4475 | 2218 | 3239 |
| hsa-miR-4476 | 2219 | 3240 |
| hsa-miR-4477a | 2220 | 3241 |
| hsa-miR-4477b | 2221 | 3242 |
| hsa-miR-4478 | 2222 | 3243 |
| hsa-miR-4479 | 2223 | 3244 |
| hsa-miR-448 | 2224 | 3245 |
| hsa-miR-4480 | 2225 | 3246 |
| hsa-miR-4481 | 2226 | 3247 |
| hsa-miR-4482-3p | 2227 | 3248 |
| hsa-miR-4482-5p | 2228 | 3249 |
| hsa-miR-4483 | 2229 | 3250 |
| hsa-miR-4484 | 2230 | 3251 |
| hsa-miR-4485 | 2231 | 3252 |
| hsa-miR-4486 | 2232 | 3253 |
| hsa-miR-4487 | 2233 | 3254 |
| hsa-miR-4488 | 2234 | 3255 |
| hsa-miR-4489 | 2235 | 3256 |
| hsa-miR-4490 | 2236 | 3257 |
| hsa-miR-4491 | 2237 | 3258 |
| hsa-miR-4492 | 2238 | 3259 |
| hsa-miR-4493 | 2239 | 3260 |
| hsa-miR-4494 | 2240 | 3261 |
| hsa-miR-4495 | 2241 | 3262 |
| hsa-miR-4496 | 2242 | 3263 |
| hsa-miR-4497 | 2243 | 3264 |
| hsa-miR-4498 | 2244 | 3265 |
| hsa-miR-4499 | 2245 | 3266 |
| hsa-miR-449a | 2246 | 3267 |
| hsa-miR-449b-3p | 2247 | 3268 |
| hsa-miR-449b-5p | 2248 | 3269 |
| hsa-miR-449c-3p | 2249 | 3270 |
| hsa-miR-449c-5p | 2250 | 3271 |
| hsa-miR-4500 | 2251 | 3272 |
| hsa-miR-4501 | 2252 | 3273 |
| hsa-miR-4502 | 2253 | 3274 |
| hsa-miR-4503 | 2254 | 3275 |
| hsa-miR-4504 | 2255 | 3276 |
| hsa-miR-4505 | 2256 | 3277 |
| hsa-miR-4506 | 2257 | 3278 |
| hsa-miR-4507 | 2258 | 3279 |
| hsa-miR-4508 | 2259 | 3280 |
| hsa-miR-4509 | 2260 | 3281 |
| hsa-miR-450a-3p | 2261 | 3282 |
| hsa-miR-450a-5p | 2262 | 3283 |
| hsa-miR-450b-3p | 2263 | 3284 |
| hsa-miR-450b-5p | 2264 | 3285 |
| hsa-miR-4510 | 2265 | 3286 |
| hsa-miR-4511 | 2266 | 3287 |
| hsa-miR-4512 | 2267 | 3288 |
| hsa-miR-4513 | 2268 | 3289 |
| hsa-miR-4514 | 2269 | 3290 |
| hsa-miR-4515 | 2270 | 3291 |
| hsa-miR-4516 | 2271 | 3292 |
| hsa-miR-4517 | 2272 | 3293 |
| hsa-miR-4518 | 2273 | 3294 |
| hsa-miR-4519 | 2274 | 3295 |
| hsa-miR-451a | 2275 | 3296 |
| hsa-miR-451b | 2276 | 3297 |
| hsa-miR-4520a-3p | 2277 | 3298 |
| hsa-miR-4520a-5p | 2278 | 3299 |
| hsa-miR-4520b-3p | 2279 | 3300 |
| hsa-miR-4520b-5p | 2280 | 3301 |
| hsa-miR-4521 | 2281 | 3302 |
| hsa-miR-4522 | 2282 | 3303 |
| hsa-miR-4523 | 2283 | 3304 |
| hsa-miR-452-3p | 2284 | 3305 |
| hsa-miR-4524a-3p | 2285 | 3306 |
| hsa-miR-4524a-5p | 2286 | 3307 |
| hsa-miR-4524b-3p | 2287 | 3308 |
| hsa-miR-4524b-5p | 2288 | 3309 |
| hsa-miR-4525 | 2289 | 3310 |
| hsa-miR-452-5p | 2290 | 3311 |
| hsa-miR-4526 | 2291 | 3312 |
| hsa-miR-4527 | 2292 | 3313 |
| hsa-miR-4528 | 2293 | 3314 |
| hsa-miR-4529-3p | 2294 | 3315 |
| hsa-miR-4529-5p | 2295 | 3316 |
| hsa-miR-4530 | 2296 | 3317 |
| hsa-miR-4531 | 2297 | 3318 |
| hsa-miR-4532 | 2298 | 3319 |
| hsa-miR-4533 | 2299 | 3320 |
| hsa-miR-4534 | 2300 | 3321 |
| hsa-miR-4535 | 2301 | 3322 |
| hsa-miR-4536-3p | 2302 | 3323 |
| hsa-miR-4536-5p | 2303 | 3324 |
| hsa-miR-4537 | 2304 | 3325 |
| hsa-miR-4538 | 2305 | 3326 |
| hsa-miR-4539 | 2306 | 3327 |
| hsa-miR-4540 | 2307 | 3328 |
| hsa-miR-454-3p | 2308 | 3329 |
| hsa-miR-454-5p | 2309 | 3330 |
| hsa-miR-455-3p | 2310 | 3331 |
| hsa-miR-455-5p | 2311 | 3332 |
| hsa-miR-4632-3p | 2312 | 3333 |
| hsa-miR-4632-5p | 2313 | 3334 |
| hsa-miR-4633-3p | 2314 | 3335 |
| hsa-miR-4633-5p | 2315 | 3336 |
| hsa-miR-4634 | 2316 | 3337 |
| hsa-miR-4635 | 2317 | 3338 |
| hsa-miR-4636 | 2318 | 3339 |
| hsa-miR-4637 | 2319 | 3340 |
| hsa-miR-4638-3p | 2320 | 3341 |
| hsa-miR-4638-5p | 2321 | 3342 |
| hsa-miR-4639-3p | 2322 | 3343 |
| hsa-miR-4639-5p | 2323 | 3344 |
| hsa-miR-4640-3p | 2324 | 3345 |
| hsa-miR-4640-5p | 2325 | 3346 |
| hsa-miR-4641 | 2326 | 3347 |
| hsa-miR-4642 | 2327 | 3348 |
| hsa-miR-4643 | 2328 | 3349 |
| hsa-miR-4644 | 2329 | 3350 |
| hsa-miR-4645-3p | 2330 | 3351 |
| hsa-miR-4645-5p | 2331 | 3352 |
| hsa-miR-4646-3p | 2332 | 3353 |
| hsa-miR-4646-5p | 2333 | 3354 |
| hsa-miR-4647 | 2334 | 3355 |
| hsa-miR-4648 | 2335 | 3356 |
| hsa-miR-4649-3p | 2336 | 3357 |
| hsa-miR-4649-5p | 2337 | 3358 |
| hsa-miR-4650-3p | 2338 | 3359 |
| hsa-miR-4650-5p | 2339 | 3360 |
| hsa-miR-4651 | 2340 | 3361 |
| hsa-miR-4652-3p | 2341 | 3362 |
| hsa-miR-4652-5p | 2342 | 3363 |
| hsa-miR-4653-3p | 2343 | 3364 |
| hsa-miR-4653-5p | 2344 | 3365 |
| hsa-miR-4654 | 2345 | 3366 |
| hsa-miR-4655-3p | 2346 | 3367 |
| hsa-miR-4655-5p | 2347 | 3368 |
| hsa-miR-4656 | 2348 | 3369 |
| hsa-miR-4657 | 2349 | 3370 |
| hsa-miR-4658 | 2350 | 3371 |
| hsa-miR-4659a-3p | 2351 | 3372 |

TABLE 11-continued

Mirs and mir binding sites

| microRNA | mir SEQ ID | MIR BS SEQ ID |
| --- | --- | --- |
| hsa-miR-4659a-5p | 2352 | 3373 |
| hsa-miR-4659b-3p | 2353 | 3374 |
| hsa-miR-4659b-5p | 2354 | 3375 |
| hsa-miR-466 | 2355 | 3376 |
| hsa-miR-4660 | 2356 | 3377 |
| hsa-miR-4661-3p | 2357 | 3378 |
| hsa-miR-4661-5p | 2358 | 3379 |
| hsa-miR-4662a-3p | 2359 | 3380 |
| hsa-miR-4662a-5p | 2360 | 3381 |
| hsa-miR-4662b | 2361 | 3382 |
| hsa-miR-4663 | 2362 | 3383 |
| hsa-miR-4664-3p | 2363 | 3384 |
| hsa-miR-4664-5p | 2364 | 3385 |
| hsa-miR-4665-3p | 2365 | 3386 |
| hsa-miR-4665-5p | 2366 | 3387 |
| hsa-miR-4666a-3p | 2367 | 3388 |
| hsa-miR-4666a-5p | 2368 | 3389 |
| hsa-miR-4666b | 2369 | 3390 |
| hsa-miR-4667-3p | 2370 | 3391 |
| hsa-miR-4667-5p | 2371 | 3392 |
| hsa-miR-4668-3p | 2372 | 3393 |
| hsa-miR-4668-5p | 2373 | 3394 |
| hsa-miR-4669 | 2374 | 3395 |
| hsa-miR-4670-3p | 2375 | 3396 |
| hsa-miR-4670-5p | 2376 | 3397 |
| hsa-miR-4671-3p | 2377 | 3398 |
| hsa-miR-4671-5p | 2378 | 3399 |
| hsa-miR-4672 | 2379 | 3400 |
| hsa-miR-4673 | 2380 | 3401 |
| hsa-miR-4674 | 2381 | 3402 |
| hsa-miR-4675 | 2382 | 3403 |
| hsa-miR-4676-3p | 2383 | 3404 |
| hsa-miR-4676-5p | 2384 | 3405 |
| hsa-miR-4677-3p | 2385 | 3406 |
| hsa-miR-4677-5p | 2386 | 3407 |
| hsa-miR-4678 | 2387 | 3408 |
| hsa-miR-4679 | 2388 | 3409 |
| hsa-miR-4680-3p | 2389 | 3410 |
| hsa-miR-4680-5p | 2390 | 3411 |
| hsa-miR-4681 | 2391 | 3412 |
| hsa-miR-4682 | 2392 | 3413 |
| hsa-miR-4683 | 2393 | 3414 |
| hsa-miR-4684-3p | 2394 | 3415 |
| hsa-miR-4684-5p | 2395 | 3416 |
| hsa-miR-4685-3p | 2396 | 3417 |
| hsa-miR-4685-5p | 2397 | 3418 |
| hsa-miR-4686 | 2398 | 3419 |
| hsa-miR-4687-3p | 2399 | 3420 |
| hsa-miR-4687-5p | 2400 | 3421 |
| hsa-miR-4688 | 2401 | 3422 |
| hsa-miR-4689 | 2402 | 3423 |
| hsa-miR-4690-3p | 2403 | 3424 |
| hsa-miR-4690-5p | 2404 | 3425 |
| hsa-miR-4691-3p | 2405 | 3426 |
| hsa-miR-4691-5p | 2406 | 3427 |
| hsa-miR-4692 | 2407 | 3428 |
| hsa-miR-4693-3p | 2408 | 3429 |
| hsa-miR-4693-5p | 2409 | 3430 |
| hsa-miR-4694-3p | 2410 | 3431 |
| hsa-miR-4694-5p | 2411 | 3432 |
| hsa-miR-4695-3p | 2412 | 3433 |
| hsa-miR-4695-5p | 2413 | 3434 |
| hsa-miR-4696 | 2414 | 3435 |
| hsa-miR-4697-3p | 2415 | 3436 |
| hsa-miR-4697-5p | 2416 | 3437 |
| hsa-miR-4698 | 2417 | 3438 |
| hsa-miR-4699-3p | 2418 | 3439 |
| hsa-miR-4699-5p | 2419 | 3440 |
| hsa-miR-4700-3p | 2420 | 3441 |
| hsa-miR-4700-5p | 2421 | 3442 |
| hsa-miR-4701-3p | 2422 | 3443 |
| hsa-miR-4701-5p | 2423 | 3444 |
| hsa-miR-4703-3p | 2424 | 3445 |
| hsa-miR-4703-5p | 2425 | 3446 |
| hsa-miR-4704-3p | 2426 | 3447 |
| hsa-miR-4704-5p | 2427 | 3448 |
| hsa-miR-4705 | 2428 | 3449 |
| hsa-miR-4706 | 2429 | 3450 |
| hsa-miR-4707-3p | 2430 | 3451 |
| hsa-miR-4707-5p | 2431 | 3452 |
| hsa-miR-4708-3p | 2432 | 3453 |
| hsa-miR-4708-5p | 2433 | 3454 |
| hsa-miR-4709-3p | 2434 | 3455 |
| hsa-miR-4709-5p | 2435 | 3456 |
| hsa-miR-4710 | 2436 | 3457 |
| hsa-miR-4711-3p | 2437 | 3458 |
| hsa-miR-4711-5p | 2438 | 3459 |
| hsa-miR-4712-3p | 2439 | 3460 |
| hsa-miR-4712-5p | 2440 | 3461 |
| hsa-miR-4713-3p | 2441 | 3462 |
| hsa-miR-4713-5p | 2442 | 3463 |
| hsa-miR-4714-3p | 2443 | 3464 |
| hsa-miR-4714-5p | 2444 | 3465 |
| hsa-miR-4715-3p | 2445 | 3466 |
| hsa-miR-4715-5p | 2446 | 3467 |
| hsa-miR-4716-3p | 2447 | 3468 |
| hsa-miR-4716-5p | 2448 | 3469 |
| hsa-miR-4717-3p | 2449 | 3470 |
| hsa-miR-4717-5p | 2450 | 3471 |
| hsa-miR-4718 | 2451 | 3472 |
| hsa-miR-4719 | 2452 | 3473 |
| hsa-miR-4720-3p | 2453 | 3474 |
| hsa-miR-4720-5p | 2454 | 3475 |
| hsa-miR-4721 | 2455 | 3476 |
| hsa-miR-4722-3p | 2456 | 3477 |
| hsa-miR-4722-5p | 2457 | 3478 |
| hsa-miR-4723-3p | 2458 | 3479 |
| hsa-miR-4723-5p | 2459 | 3480 |
| hsa-miR-4724-3p | 2460 | 3481 |
| hsa-miR-4724-5p | 2461 | 3482 |
| hsa-miR-4725-3p | 2462 | 3483 |
| hsa-miR-4725-5p | 2463 | 3484 |
| hsa-miR-4726-3p | 2464 | 3485 |
| hsa-miR-4726-5p | 2465 | 3486 |
| hsa-miR-4727-3p | 2466 | 3487 |
| hsa-miR-4727-5p | 2467 | 3488 |
| hsa-miR-4728-3p | 2468 | 3489 |
| hsa-miR-4728-5p | 2469 | 3490 |
| hsa-miR-4729 | 2470 | 3491 |
| hsa-miR-4730 | 2471 | 3492 |
| hsa-miR-4731-3p | 2472 | 3493 |
| hsa-miR-4731-5p | 2473 | 3494 |
| hsa-miR-4732-3p | 2474 | 3495 |
| hsa-miR-4732-5p | 2475 | 3496 |
| hsa-miR-4733-3p | 2476 | 3497 |
| hsa-miR-4733-5p | 2477 | 3498 |
| hsa-miR-4734 | 2478 | 3499 |
| hsa-miR-4735-3p | 2479 | 3500 |
| hsa-miR-4735-5p | 2480 | 3501 |
| hsa-miR-4736 | 2481 | 3502 |
| hsa-miR-4737 | 2482 | 3503 |
| hsa-miR-4738-3p | 2483 | 3504 |
| hsa-miR-4738-5p | 2484 | 3505 |
| hsa-miR-4739 | 2485 | 3506 |
| hsa-miR-4740-3p | 2486 | 3507 |
| hsa-miR-4740-5p | 2487 | 3508 |
| hsa-miR-4741 | 2488 | 3509 |
| hsa-miR-4742-3p | 2489 | 3510 |
| hsa-miR-4742-5p | 2490 | 3511 |
| hsa-miR-4743-3p | 2491 | 3512 |
| hsa-miR-4743-5p | 2492 | 3513 |
| hsa-miR-4744 | 2493 | 3514 |
| hsa-miR-4745-3p | 2494 | 3515 |
| hsa-miR-4745-5p | 2495 | 3516 |
| hsa-miR-4746-3p | 2496 | 3517 |
| hsa-miR-4746-5p | 2497 | 3518 |
| hsa-miR-4747-3p | 2498 | 3519 |
| hsa-miR-4747-5p | 2499 | 3520 |
| hsa-miR-4748 | 2500 | 3521 |
| hsa-miR-4749-3p | 2501 | 3522 |

TABLE 11-continued

Mirs and mir binding sites

| microRNA | mir SEQ ID | MIR BS SEQ ID |
|---|---|---|
| hsa-miR-4749-5p | 2502 | 3523 |
| hsa-miR-4750-3p | 2503 | 3524 |
| hsa-miR-4750-5p | 2504 | 3525 |
| hsa-miR-4751 | 2505 | 3526 |
| hsa-miR-4752 | 2506 | 3527 |
| hsa-miR-4753-3p | 2507 | 3528 |
| hsa-miR-4753-5p | 2508 | 3529 |
| hsa-miR-4754 | 2509 | 3530 |
| hsa-miR-4755-3p | 2510 | 3531 |
| hsa-miR-4755-5p | 2511 | 3532 |
| hsa-miR-4756-3p | 2512 | 3533 |
| hsa-miR-4756-5p | 2513 | 3534 |
| hsa-miR-4757-3p | 2514 | 3535 |
| hsa-miR-4757-5p | 2515 | 3536 |
| hsa-miR-4758-3p | 2516 | 3537 |
| hsa-miR-4758-5p | 2517 | 3538 |
| hsa-miR-4759 | 2518 | 3539 |
| hsa-miR-4760-3p | 2519 | 3540 |
| hsa-miR-4760-5p | 2520 | 3541 |
| hsa-miR-4761-3p | 2521 | 3542 |
| hsa-miR-4761-5p | 2522 | 3543 |
| hsa-miR-4762-3p | 2523 | 3544 |
| hsa-miR-4762-5p | 2524 | 3545 |
| hsa-miR-4763-3p | 2525 | 3546 |
| hsa-miR-4763-5p | 2526 | 3547 |
| hsa-miR-4764-3p | 2527 | 3548 |
| hsa-miR-4764-5p | 2528 | 3549 |
| hsa-miR-4765 | 2529 | 3550 |
| hsa-miR-4766-3p | 2530 | 3551 |
| hsa-miR-4766-5p | 2531 | 3552 |
| hsa-miR-4767 | 2532 | 3553 |
| hsa-miR-4768-3p | 2533 | 3554 |
| hsa-miR-4768-5p | 2534 | 3555 |
| hsa-miR-4769-3p | 2535 | 3556 |
| hsa-miR-4769-5p | 2536 | 3557 |
| hsa-miR-4770 | 2537 | 3558 |
| hsa-miR-4771 | 2538 | 3559 |
| hsa-miR-4772-3p | 2539 | 3560 |
| hsa-miR-4772-5p | 2540 | 3561 |
| hsa-miR-4773 | 2541 | 3562 |
| hsa-miR-4774-3p | 2542 | 3563 |
| hsa-miR-4774-5p | 2543 | 3564 |
| hsa-miR-4775 | 2544 | 3565 |
| hsa-miR-4776-3p | 2545 | 3566 |
| hsa-miR-4776-5p | 2546 | 3567 |
| hsa-miR-4777-3p | 2547 | 3568 |
| hsa-miR-4777-5p | 2548 | 3569 |
| hsa-miR-4778-3p | 2549 | 3570 |
| hsa-miR-4778-5p | 2550 | 3571 |
| hsa-miR-4779 | 2551 | 3572 |
| hsa-miR-4780 | 2552 | 3573 |
| hsa-miR-4781-3p | 2553 | 3574 |
| hsa-miR-4781-5p | 2554 | 3575 |
| hsa-miR-4782-3p | 2555 | 3576 |
| hsa-miR-4782-5p | 2556 | 3577 |
| hsa-miR-4783-3p | 2557 | 3578 |
| hsa-miR-4783-5p | 2558 | 3579 |
| hsa-miR-4784 | 2559 | 3580 |
| hsa-miR-4785 | 2560 | 3581 |
| hsa-miR-4786-3p | 2561 | 3582 |
| hsa-miR-4786-5p | 2562 | 3583 |
| hsa-miR-4787-3p | 2563 | 3584 |
| hsa-miR-4787-5p | 2564 | 3585 |
| hsa-miR-4788 | 2565 | 3586 |
| hsa-miR-4789-3p | 2566 | 3587 |
| hsa-miR-4789-5p | 2567 | 3588 |
| hsa-miR-4790-3p | 2568 | 3589 |
| hsa-miR-4790-5p | 2569 | 3590 |
| hsa-miR-4791 | 2570 | 3591 |
| hsa-miR-4792 | 2571 | 3592 |
| hsa-miR-4793-3p | 2572 | 3593 |
| hsa-miR-4793-5p | 2573 | 3594 |
| hsa-miR-4794 | 2574 | 3595 |
| hsa-miR-4795-3p | 2575 | 3596 |
| hsa-miR-4795-5p | 2576 | 3597 |
| hsa-miR-4796-3p | 2577 | 3598 |
| hsa-miR-4796-5p | 2578 | 3599 |
| hsa-miR-4797-3p | 2579 | 3600 |
| hsa-miR-4797-5p | 2580 | 3601 |
| hsa-miR-4798-3p | 2581 | 3602 |
| hsa-miR-4798-5p | 2582 | 3603 |
| hsa-miR-4799-3p | 2583 | 3604 |
| hsa-miR-4799-5p | 2584 | 3605 |
| hsa-miR-4800-3p | 2585 | 3606 |
| hsa-miR-4800-5p | 2586 | 3607 |
| hsa-miR-4801 | 2587 | 3608 |
| hsa-miR-4802-3p | 2588 | 3609 |
| hsa-miR-4802-5p | 2589 | 3610 |
| hsa-miR-4803 | 2590 | 3611 |
| hsa-miR-4804-3p | 2591 | 3612 |
| hsa-miR-4804-5p | 2592 | 3613 |
| hsa-miR-483-3p | 2593 | 3614 |
| hsa-miR-483-5p | 2594 | 3615 |
| hsa-miR-484 | 2595 | 3616 |
| hsa-miR-485-3p | 2596 | 3617 |
| hsa-miR-485-5p | 2597 | 3618 |
| hsa-miR-486-3p | 2598 | 3619 |
| hsa-miR-486-5p | 2599 | 3620 |
| hsa-miR-487a | 2600 | 3621 |
| hsa-miR-487b | 2601 | 3622 |
| hsa-miR-488-3p | 2602 | 3623 |
| hsa-miR-488-5p | 2603 | 3624 |
| hsa-miR-489 | 2604 | 3625 |
| hsa-miR-490-3p | 2605 | 3626 |
| hsa-miR-490-5p | 2606 | 3627 |
| hsa-miR-491-3p | 2607 | 3628 |
| hsa-miR-491-5p | 2608 | 3629 |
| hsa-miR-492 | 2609 | 3630 |
| hsa-miR-493-3p | 2610 | 3631 |
| hsa-miR-493-5p | 2611 | 3632 |
| hsa-miR-494 | 2612 | 3633 |
| hsa-miR-495-3p | 2613 | 3634 |
| hsa-miR-495-5p | 2614 | 3635 |
| hsa-miR-496 | 2615 | 3636 |
| hsa-miR-497-3p | 2616 | 3637 |
| hsa-miR-497-5p | 2617 | 3638 |
| hsa-miR-498 | 2618 | 3639 |
| hsa-miR-4999-3p | 2619 | 3640 |
| hsa-miR-4999-5p | 2620 | 3641 |
| hsa-miR-499a-3p | 2621 | 3642 |
| hsa-miR-499a-5p | 2622 | 3643 |
| hsa-miR-499b-3p | 2623 | 3644 |
| hsa-miR-499b-5p | 2624 | 3645 |
| hsa-miR-5000-3p | 2625 | 3646 |
| hsa-miR-5000-5p | 2626 | 3647 |
| hsa-miR-5001-3p | 2627 | 3648 |
| hsa-miR-5001-5p | 2628 | 3649 |
| hsa-miR-5002-3p | 2629 | 3650 |
| hsa-miR-5002-5p | 2630 | 3651 |
| hsa-miR-5003-3p | 2631 | 3652 |
| hsa-miR-5003-5p | 2632 | 3653 |
| hsa-miR-5004-3p | 2633 | 3654 |
| hsa-miR-5004-5p | 2634 | 3655 |
| hsa-miR-5006-3p | 2635 | 3656 |
| hsa-miR-5006-5p | 2636 | 3657 |
| hsa-miR-5007-3p | 2637 | 3658 |
| hsa-miR-5007-5p | 2638 | 3659 |
| hsa-miR-5008-3p | 2639 | 3660 |
| hsa-miR-5008-5p | 2640 | 3661 |
| hsa-miR-5009-3p | 2641 | 3662 |
| hsa-miR-5009-5p | 2642 | 3663 |
| hsa-miR-500a-3p | 2643 | 3664 |
| hsa-miR-500a-5p | 2644 | 3665 |
| hsa-miR-500b | 2645 | 3666 |
| hsa-miR-5010-3p | 2646 | 3667 |
| hsa-miR-5010-5p | 2647 | 3668 |
| hsa-miR-5011-3p | 2648 | 3669 |
| hsa-miR-5011-5p | 2649 | 3670 |
| hsa-miR-501-3p | 2650 | 3671 |
| hsa-miR-501-5p | 2651 | 3672 |

TABLE 11-continued

Mirs and mir binding sites

| microRNA | mir SEQ ID | MIR BS SEQ ID |
|---|---|---|
| hsa-miR-502-3p | 2652 | 3673 |
| hsa-miR-502-5p | 2653 | 3674 |
| hsa-miR-503-3p | 2654 | 3675 |
| hsa-miR-503-5p | 2655 | 3676 |
| hsa-miR-504 | 2656 | 3677 |
| hsa-miR-5047 | 2657 | 3678 |
| hsa-miR-505-3p | 2658 | 3679 |
| hsa-miR-505-5p | 2659 | 3680 |
| hsa-miR-506-3p | 2660 | 3681 |
| hsa-miR-506-5p | 2661 | 3682 |
| hsa-miR-507 | 2662 | 3683 |
| hsa-miR-508-3p | 2663 | 3684 |
| hsa-miR-508-5p | 2664 | 3685 |
| hsa-miR-5087 | 2665 | 3686 |
| hsa-miR-5088 | 2666 | 3687 |
| hsa-miR-5089-3p | 2667 | 3688 |
| hsa-miR-5089-5p | 2668 | 3689 |
| hsa-miR-5090 | 2669 | 3690 |
| hsa-miR-5091 | 2670 | 3691 |
| hsa-miR-5092 | 2671 | 3692 |
| hsa-miR-5093 | 2672 | 3693 |
| hsa-miR-509-3-5p | 2673 | 3694 |
| hsa-miR-509-3p | 2674 | 3695 |
| hsa-miR-5094 | 2675 | 3696 |
| hsa-miR-5095 | 2676 | 3697 |
| hsa-miR-509-5p | 2677 | 3698 |
| hsa-miR-5096 | 2678 | 3699 |
| hsa-miR-510 | 2679 | 3700 |
| hsa-miR-5100 | 2680 | 3701 |
| hsa-miR-511 | 2681 | 3702 |
| hsa-miR-512-3p | 2682 | 3703 |
| hsa-miR-512-5p | 2683 | 3704 |
| hsa-miR-513a-3p | 2684 | 3705 |
| hsa-miR-513a-5p | 2685 | 3706 |
| hsa-miR-513b | 2686 | 3707 |
| hsa-miR-513c-3p | 2687 | 3708 |
| hsa-miR-513c-5p | 2688 | 3709 |
| hsa-miR-514a-3p | 2689 | 3710 |
| hsa-miR-514a-5p | 2690 | 3711 |
| hsa-miR-514b-3p | 2691 | 3712 |
| hsa-miR-514b-5p | 2692 | 3713 |
| hsa-miR-515-3p | 2693 | 3714 |
| hsa-miR-515-5p | 2694 | 3715 |
| hsa-miR-516a-3p | 2695 | 3716 |
| hsa-miR-516a-5p | 2696 | 3717 |
| hsa-miR-516b-3p | 2697 | 3718 |
| hsa-miR-516b-5p | 2698 | 3719 |
| hsa-miR-517-5p | 2699 | 3720 |
| hsa-miR-517a-3p | 2700 | 3721 |
| hsa-miR-517b-3p | 2701 | 3722 |
| hsa-miR-517c-3p | 2702 | 3723 |
| hsa-miR-5186 | 2703 | 3724 |
| hsa-miR-5187-3p | 2704 | 3725 |
| hsa-miR-5187-5p | 2705 | 3726 |
| hsa-miR-5188 | 2706 | 3727 |
| hsa-miR-5189 | 2707 | 3728 |
| hsa-miR-518a-3p | 2708 | 3729 |
| hsa-miR-518a-5p | 2709 | 3730 |
| hsa-miR-518b | 2710 | 3731 |
| hsa-miR-518c-3p | 2711 | 3732 |
| hsa-miR-518c-5p | 2712 | 3733 |
| hsa-miR-518d-3p | 2713 | 3734 |
| hsa-miR-518d-5p | 2714 | 3735 |
| hsa-miR-518e-3p | 2715 | 3736 |
| hsa-miR-518e-5p | 2716 | 3737 |
| hsa-miR-518f-3p | 2717 | 3738 |
| hsa-miR-518f-5p | 2718 | 3739 |
| hsa-miR-5190 | 2719 | 3740 |
| hsa-miR-5191 | 2720 | 3741 |
| hsa-miR-5192 | 2721 | 3742 |
| hsa-miR-5193 | 2722 | 3743 |
| hsa-miR-5194 | 2723 | 3744 |
| hsa-miR-5195-3p | 2724 | 3745 |
| hsa-miR-5195-5p | 2725 | 3746 |
| hsa-miR-5196-3p | 2726 | 3747 |
| hsa-miR-5196-5p | 2727 | 3748 |
| hsa-miR-5197-3p | 2728 | 3749 |
| hsa-miR-5197-5p | 2729 | 3750 |
| hsa-miR-519a-3p | 2730 | 3751 |
| hsa-miR-519a-5p | 2731 | 3752 |
| hsa-miR-519b-3p | 2732 | 3753 |
| hsa-miR-519b-5p | 2733 | 3754 |
| hsa-miR-519c-3p | 2734 | 3755 |
| hsa-miR-519c-5p | 2735 | 3756 |
| hsa-miR-519d | 2736 | 3757 |
| hsa-miR-519e-3p | 2737 | 3758 |
| hsa-miR-519e-5p | 2738 | 3759 |
| hsa-miR-520a-3p | 2739 | 3760 |
| hsa-miR-520a-5p | 2740 | 3761 |
| hsa-miR-520b | 2741 | 3762 |
| hsa-miR-520c-3p | 2742 | 3763 |
| hsa-miR-520c-5p | 2743 | 3764 |
| hsa-miR-520d-3p | 2744 | 3765 |
| hsa-miR-520d-5p | 2745 | 3766 |
| hsa-miR-520e | 2746 | 3767 |
| hsa-miR-520f | 2747 | 3768 |
| hsa-miR-520g | 2748 | 3769 |
| hsa-miR-520h | 2749 | 3770 |
| hsa-miR-521 | 2750 | 3771 |
| hsa-miR-522-3p | 2751 | 3772 |
| hsa-miR-522-5p | 2752 | 3773 |
| hsa-miR-523-3p | 2753 | 3774 |
| hsa-miR-523-5p | 2754 | 3775 |
| hsa-miR-524-3p | 2755 | 3776 |
| hsa-miR-524-5p | 2756 | 3777 |
| hsa-miR-525-3p | 2757 | 3778 |
| hsa-miR-525-5p | 2758 | 3779 |
| hsa-miR-526a | 2759 | 3780 |
| hsa-miR-526b-3p | 2760 | 3781 |
| hsa-miR-526b-5p | 2761 | 3782 |
| hsa-miR-527 | 2762 | 3783 |
| hsa-miR-532-3p | 2763 | 3784 |
| hsa-miR-532-5p | 2764 | 3785 |
| hsa-miR-539-3p | 2765 | 3786 |
| hsa-miR-539-5p | 2766 | 3787 |
| hsa-miR-541-3p | 2767 | 3788 |
| hsa-miR-541-5p | 2768 | 3789 |
| hsa-miR-542-3p | 2769 | 3790 |
| hsa-miR-542-5p | 2770 | 3791 |
| hsa-miR-543 | 2771 | 3792 |
| hsa-miR-544a | 2772 | 3793 |
| hsa-miR-544b | 2773 | 3794 |
| hsa-miR-545-3p | 2774 | 3795 |
| hsa-miR-545-5p | 2775 | 3796 |
| hsa-miR-548 | 2776 | 3797 |
| hsa-miR-548-3p | 2777 | 3798 |
| hsa-miR-548-5p | 2778 | 3799 |
| hsa-miR-548a | 2779 | 3800 |
| hsa-miR-548a-3p | 2780 | 3801 |
| hsa-miR-548a-5p | 2781 | 3802 |
| hsa-miR-548aa | 2782 | 3803 |
| hsa-miR-548ab | 2783 | 3804 |
| hsa-miR-548ac | 2784 | 3805 |
| hsa-miR-548ad | 2785 | 3806 |
| hsa-miR-548ae | 2786 | 3807 |
| hsa-miR-548ag | 2787 | 3808 |
| hsa-miR-548ah-3p | 2788 | 3809 |
| hsa-miR-548ah-5p | 2789 | 3810 |
| hsa-miR-548ai | 2790 | 3811 |
| hsa-miR-548aj-3p | 2791 | 3812 |
| hsa-miR-548aj-5p | 2792 | 3813 |
| hsa-miR-548ak | 2793 | 3814 |
| hsa-miR-548al | 2794 | 3815 |
| hsa-miR-548am-3p | 2795 | 3816 |
| hsa-miR-548am-5p | 2796 | 3817 |
| hsa-miR-548an | 2797 | 3818 |
| hsa-miR-548ao-3p | 2798 | 3819 |
| hsa-miR-548ao-5p | 2799 | 3820 |
| hsa-miR-548ap-3p | 2800 | 3821 |
| hsa-miR-548ap-5p | 2801 | 3822 |

TABLE 11-continued

Mirs and mir binding sites

| microRNA | mir SEQ ID | MIR BS SEQ ID |
|---|---|---|
| hsa-miR-548aq-3p | 2802 | 3823 |
| hsa-miR-548aq-5p | 2803 | 3824 |
| hsa-miR-548ar-3p | 2804 | 3825 |
| hsa-miR-548ar-5p | 2805 | 3826 |
| hsa-miR-548as-3p | 2806 | 3827 |
| hsa-miR-548as-5p | 2807 | 3828 |
| hsa-miR-548at-3p | 2808 | 3829 |
| hsa-miR-548at-5p | 2809 | 3830 |
| hsa-miR-548au-3p | 2810 | 3831 |
| hsa-miR-548au-5p | 2811 | 3832 |
| hsa-miR-548av-3p | 2812 | 3833 |
| hsa-miR-548av-5p | 2813 | 3834 |
| hsa-miR-548aw | 2814 | 3835 |
| hsa-miR-548ay-3p | 2815 | 3836 |
| hsa-miR-548ay-5p | 2816 | 3837 |
| hsa-miR-548az-3p | 2817 | 3838 |
| hsa-miR-548az-5p | 2818 | 3839 |
| hsa-miR-548b-3p | 2819 | 3840 |
| hsa-miR-548b-5p | 2820 | 3841 |
| hsa-miR-548c-3p | 2821 | 3842 |
| hsa-miR-548c-5p | 2822 | 3843 |
| hsa-miR-548d-3p | 2823 | 3844 |
| hsa-miR-548d-5p | 2824 | 3845 |
| hsa-miR-548e | 2825 | 3846 |
| hsa-miR-548f | 2826 | 3847 |
| hsa-miR-548g-3p | 2827 | 3848 |
| hsa-miR-548g-5p | 2828 | 3849 |
| hsa-miR-548h-3p | 2829 | 3850 |
| hsa-miR-548h-5p | 2830 | 3851 |
| hsa-miR-548i | 2831 | 3852 |
| hsa-miR-548j | 2832 | 3853 |
| hsa-miR-548k | 2833 | 3854 |
| hsa-miR-548l | 2834 | 3855 |
| hsa-miR-548m | 2835 | 3856 |
| hsa-miR-548n | 2836 | 3857 |
| hsa-miR-548o-3p | 2837 | 3858 |
| hsa-miR-548o-5p | 2838 | 3859 |
| hsa-miR-548p | 2839 | 3860 |
| hsa-miR-548q | 2840 | 3861 |
| hsa-miR-548s | 2841 | 3862 |
| hsa-miR-548t-3p | 2842 | 3863 |
| hsa-miR-548t-5p | 2843 | 3864 |
| hsa-miR-548u | 2844 | 3865 |
| hsa-miR-548w | 2845 | 3866 |
| hsa-miR-548y | 2846 | 3867 |
| hsa-miR-548z | 2847 | 3868 |
| hsa-miR-549a | 2848 | 3869 |
| hsa-miR-550a-3-5p | 2849 | 3870 |
| hsa-miR-550a-3p | 2850 | 3871 |
| hsa-miR-550a-5p | 2851 | 3872 |
| hsa-miR-550b-2-5p | 2852 | 3873 |
| hsa-miR-550b-3p | 2853 | 3874 |
| hsa-miR-551a | 2854 | 3875 |
| hsa-miR-551b-3p | 2855 | 3876 |
| hsa-miR-551b-5p | 2856 | 3877 |
| hsa-miR-552 | 2857 | 3878 |
| hsa-miR-553 | 2858 | 3879 |
| hsa-miR-554 | 2859 | 3880 |
| hsa-miR-555 | 2860 | 3881 |
| hsa-miR-556-3p | 2861 | 3882 |
| hsa-miR-556-5p | 2862 | 3883 |
| hsa-miR-557 | 2863 | 3884 |
| hsa-miR-5571-3p | 2864 | 3885 |
| hsa-miR-5571-5p | 2865 | 3886 |
| hsa-miR-5572 | 2866 | 3887 |
| hsa-miR-5579-3p | 2867 | 3888 |
| hsa-miR-5579-5p | 2868 | 3889 |
| hsa-miR-558 | 2869 | 3890 |
| hsa-miR-5580-3p | 2870 | 3891 |
| hsa-miR-5580-5p | 2871 | 3892 |
| hsa-miR-5581-3p | 2872 | 3893 |
| hsa-miR-5581-5p | 2873 | 3894 |
| hsa-miR-5582-3p | 2874 | 3895 |
| hsa-miR-5582-5p | 2875 | 3896 |
| hsa-miR-5583-3p | 2876 | 3897 |
| hsa-miR-5583-5p | 2877 | 3898 |
| hsa-miR-5584-3p | 2878 | 3899 |
| hsa-miR-5584-5p | 2879 | 3900 |
| hsa-miR-5585-3p | 2880 | 3901 |
| hsa-miR-5585-5p | 2881 | 3902 |
| hsa-miR-5586-3p | 2882 | 3903 |
| hsa-miR-5586-5p | 2883 | 3904 |
| hsa-miR-5587-3p | 2884 | 3905 |
| hsa-miR-5587-5p | 2885 | 3906 |
| hsa-miR-5588-3p | 2886 | 3907 |
| hsa-miR-5588-5p | 2887 | 3908 |
| hsa-miR-5589-3p | 2888 | 3909 |
| hsa-miR-5589-5p | 2889 | 3910 |
| hsa-miR-559 | 2890 | 3911 |
| hsa-miR-5590-3p | 2891 | 3912 |
| hsa-miR-5590-5p | 2892 | 3913 |
| hsa-miR-5591-3p | 2893 | 3914 |
| hsa-miR-5591-5p | 2894 | 3915 |
| hsa-miR-561-3p | 2895 | 3916 |
| hsa-miR-561-5p | 2896 | 3917 |
| hsa-miR-562 | 2897 | 3918 |
| hsa-miR-563 | 2898 | 3919 |
| hsa-miR-564 | 2899 | 3920 |
| hsa-miR-566 | 2900 | 3921 |
| hsa-miR-567 | 2901 | 3922 |
| hsa-miR-568 | 2902 | 3923 |
| hsa-miR-5680 | 2903 | 3924 |
| hsa-miR-5681a | 2904 | 3925 |
| hsa-miR-5681b | 2905 | 3926 |
| hsa-miR-5682 | 2906 | 3927 |
| hsa-miR-5683 | 2907 | 3928 |
| hsa-miR-5684 | 2908 | 3929 |
| hsa-miR-5685 | 2909 | 3930 |
| hsa-miR-5686 | 2910 | 3931 |
| hsa-miR-5687 | 2911 | 3932 |
| hsa-miR-5688 | 2912 | 3933 |
| hsa-miR-5689 | 2913 | 3934 |
| hsa-miR-569 | 2914 | 3935 |
| hsa-miR-5690 | 2915 | 3936 |
| hsa-miR-5691 | 2916 | 3937 |
| hsa-miR-5692a | 2917 | 3938 |
| hsa-miR-5692b | 2918 | 3939 |
| hsa-miR-5692c | 2919 | 3940 |
| hsa-miR-5693 | 2920 | 3941 |
| hsa-miR-5694 | 2921 | 3942 |
| hsa-miR-5695 | 2922 | 3943 |
| hsa-miR-5696 | 2923 | 3944 |
| hsa-miR-5697 | 2924 | 3945 |
| hsa-miR-5698 | 2925 | 3946 |
| hsa-miR-5699 | 2926 | 3947 |
| hsa-miR-5700 | 2927 | 3948 |
| hsa-miR-5701 | 2928 | 3949 |
| hsa-miR-5702 | 2929 | 3950 |
| hsa-miR-5703 | 2930 | 3951 |
| hsa-miR-570-3p | 2931 | 3952 |
| hsa-miR-5704 | 2932 | 3953 |
| hsa-miR-5705 | 2933 | 3954 |
| hsa-miR-570-5p | 2934 | 3955 |
| hsa-miR-5706 | 2935 | 3956 |
| hsa-miR-5707 | 2936 | 3957 |
| hsa-miR-5708 | 2937 | 3958 |
| hsa-miR-571 | 2938 | 3959 |
| hsa-miR-572 | 2939 | 3960 |
| hsa-miR-573 | 2940 | 3961 |
| hsa-miR-5739 | 2941 | 3962 |
| hsa-miR-574-3p | 2942 | 3963 |
| hsa-miR-574-5p | 2943 | 3964 |
| hsa-miR-575 | 2944 | 3965 |
| hsa-miR-576-3p | 2945 | 3966 |
| hsa-miR-576-5p | 2946 | 3967 |
| hsa-miR-577 | 2947 | 3968 |
| hsa-miR-578 | 2948 | 3969 |
| hsa-miR-5787 | 2949 | 3970 |
| hsa-miR-579 | 2950 | 3971 |
| hsa-miR-580 | 2951 | 3972 |

TABLE 11-continued

Mirs and mir binding sites

| microRNA | mir SEQ ID | MIR BS SEQ ID |
|---|---|---|
| hsa-miR-581 | 2952 | 3973 |
| hsa-miR-582-3p | 2953 | 3974 |
| hsa-miR-582-5p | 2954 | 3975 |
| hsa-miR-583 | 2955 | 3976 |
| hsa-miR-584-3p | 2956 | 3977 |
| hsa-miR-584-5p | 2957 | 3978 |
| hsa-miR-585 | 2958 | 3979 |
| hsa-miR-586 | 2959 | 3980 |
| hsa-miR-587 | 2960 | 3981 |
| hsa-miR-588 | 2961 | 3982 |
| hsa-miR-589-3p | 2962 | 3983 |
| hsa-miR-589-5p | 2963 | 3984 |
| hsa-miR-590-3p | 2964 | 3985 |
| hsa-miR-590-5p | 2965 | 3986 |
| hsa-miR-591 | 2966 | 3987 |
| hsa-miR-592 | 2967 | 3988 |
| hsa-miR-593-3p | 2968 | 3989 |
| hsa-miR-593-5p | 2969 | 3990 |
| hsa-miR-595 | 2970 | 3991 |
| hsa-miR-596 | 2971 | 3992 |
| hsa-miR-597 | 2972 | 3993 |
| hsa-miR-598 | 2973 | 3994 |
| hsa-miR-599 | 2974 | 3995 |
| hsa-miR-600 | 2975 | 3996 |
| hsa-miR-601 | 2976 | 3997 |
| hsa-miR-602 | 2977 | 3998 |
| hsa-miR-603 | 2978 | 3999 |
| hsa-miR-604 | 2979 | 4000 |
| hsa-miR-605 | 2980 | 4001 |
| hsa-miR-606 | 2981 | 4002 |
| hsa-miR-6068 | 2982 | 4003 |
| hsa-miR-6069 | 2983 | 4004 |
| hsa-miR-607 | 2984 | 4005 |
| hsa-miR-6070 | 2985 | 4006 |
| hsa-miR-6071 | 2986 | 4007 |
| hsa-miR-6072 | 2987 | 4008 |
| hsa-miR-6073 | 2988 | 4009 |
| hsa-miR-6074 | 2989 | 4010 |
| hsa-miR-6075 | 2990 | 4011 |
| hsa-miR-6076 | 2991 | 4012 |
| hsa-miR-6077 | 2992 | 4013 |
| hsa-miR-6078 | 2993 | 4014 |
| hsa-miR-6079 | 2994 | 4015 |
| hsa-miR-608 | 2995 | 4016 |
| hsa-miR-6080 | 2996 | 4017 |
| hsa-miR-6081 | 2997 | 4018 |
| hsa-miR-6082 | 2998 | 4019 |
| hsa-miR-6083 | 2999 | 4020 |
| hsa-miR-6084 | 3000 | 4021 |
| hsa-miR-6085 | 3001 | 4022 |
| hsa-miR-6086 | 3002 | 4023 |
| hsa-miR-6087 | 3003 | 4024 |
| hsa-miR-6088 | 3004 | 4025 |
| hsa-miR-6089 | 3005 | 4026 |
| hsa-miR-609 | 3006 | 4027 |
| hsa-miR-6090 | 3007 | 4028 |
| hsa-miR-610 | 3008 | 4029 |
| hsa-miR-611 | 3009 | 4030 |
| hsa-miR-612 | 3010 | 4031 |
| hsa-miR-6124 | 3011 | 4032 |
| hsa-miR-6125 | 3012 | 4033 |
| hsa-miR-6126 | 3013 | 4034 |
| hsa-miR-6127 | 3014 | 4035 |
| hsa-miR-6128 | 3015 | 4036 |
| hsa-miR-6129 | 3016 | 4037 |
| hsa-miR-613 | 3017 | 4038 |
| hsa-miR-6130 | 3018 | 4039 |
| hsa-miR-6131 | 3019 | 4040 |
| hsa-miR-6132 | 3020 | 4041 |
| hsa-miR-6133 | 3021 | 4042 |
| hsa-miR-6134 | 3022 | 4043 |
| hsa-miR-614 | 3023 | 4044 |
| hsa-miR-615-3p | 3024 | 4045 |
| hsa-miR-615-5p | 3025 | 4046 |
| hsa-miR-616-3p | 3026 | 4047 |
| hsa-miR-6165 | 3027 | 4048 |
| hsa-miR-616-5p | 3028 | 4049 |
| hsa-miR-617 | 3029 | 4050 |
| hsa-miR-618 | 3030 | 4051 |
| hsa-miR-619 | 3031 | 4052 |
| hsa-miR-620 | 3032 | 4053 |
| hsa-miR-621 | 3033 | 4054 |
| hsa-miR-622 | 3034 | 4055 |
| hsa-miR-623 | 3035 | 4056 |
| hsa-miR-624-3p | 3036 | 4057 |
| hsa-miR-624-5p | 3037 | 4058 |
| hsa-miR-625-3p | 3038 | 4059 |
| hsa-miR-625-5p | 3039 | 4060 |
| hsa-miR-626 | 3040 | 4061 |
| hsa-miR-627 | 3041 | 4062 |
| hsa-miR-628-3p | 3042 | 4063 |
| hsa-miR-628-5p | 3043 | 4064 |
| hsa-miR-629-3p | 3044 | 4065 |
| hsa-miR-629-5p | 3045 | 4066 |
| hsa-miR-630 | 3046 | 4067 |
| hsa-miR-631 | 3047 | 4068 |
| hsa-miR-632 | 3048 | 4069 |
| hsa-miR-633 | 3049 | 4070 |
| hsa-miR-634 | 3050 | 4071 |
| hsa-miR-635 | 3051 | 4072 |
| hsa-miR-636 | 3052 | 4073 |
| hsa-miR-637 | 3053 | 4074 |
| hsa-miR-638 | 3054 | 4075 |
| hsa-miR-639 | 3055 | 4076 |
| hsa-miR-640 | 3056 | 4077 |
| hsa-miR-641 | 3057 | 4078 |
| hsa-miR-642a-3p | 3058 | 4079 |
| hsa-miR-642a-5p | 3059 | 4080 |
| hsa-miR-642b-3p | 3060 | 4081 |
| hsa-miR-642b-5p | 3061 | 4082 |
| hsa-miR-643 | 3062 | 4083 |
| hsa-miR-644a | 3063 | 4084 |
| hsa-miR-645 | 3064 | 4085 |
| hsa-miR-646 | 3065 | 4086 |
| hsa-miR-647 | 3066 | 4087 |
| hsa-miR-648 | 3067 | 4088 |
| hsa-miR-649 | 3068 | 4089 |
| hsa-miR-6499-3p | 3069 | 4090 |
| hsa-miR-6499-5p | 3070 | 4091 |
| hsa-miR-650 | 3071 | 4092 |
| hsa-miR-6500-3p | 3072 | 4093 |
| hsa-miR-6500-5p | 3073 | 4094 |
| hsa-miR-6501-3p | 3074 | 4095 |
| hsa-miR-6501-5p | 3075 | 4096 |
| hsa-miR-6502-3p | 3076 | 4097 |
| hsa-miR-6502-5p | 3077 | 4098 |
| hsa-miR-6503-3p | 3078 | 4099 |
| hsa-miR-6503-5p | 3079 | 4100 |
| hsa-miR-6504-3p | 3080 | 4101 |
| hsa-miR-6504-5p | 3081 | 4102 |
| hsa-miR-6505-3p | 3082 | 4103 |
| hsa-miR-6505-5p | 3083 | 4104 |
| hsa-miR-6506-3p | 3084 | 4105 |
| hsa-miR-6506-5p | 3085 | 4106 |
| hsa-miR-6507-3p | 3086 | 4107 |
| hsa-miR-6507-5p | 3087 | 4108 |
| hsa-miR-6508-3p | 3088 | 4109 |
| hsa-miR-6508-5p | 3089 | 4110 |
| hsa-miR-6509-3p | 3090 | 4111 |
| hsa-miR-6509-5p | 3091 | 4112 |
| hsa-miR-651 | 3092 | 4113 |
| hsa-miR-6510-3p | 3093 | 4114 |
| hsa-miR-6510-5p | 3094 | 4115 |
| hsa-miR-6511a-3p | 3095 | 4116 |
| hsa-miR-6511a-5p | 3096 | 4117 |
| hsa-miR-6511b-3p | 3097 | 4118 |
| hsa-miR-6511b-5p | 3098 | 4119 |
| hsa-miR-6512-3p | 3099 | 4120 |

TABLE 11-continued

Mirs and mir binding sites

| microRNA | mir SEQ ID | MIR BS SEQ ID |
|---|---|---|
| hsa-miR-6512-5p | 3100 | 4121 |
| hsa-miR-6513-3p | 3101 | 4122 |
| hsa-miR-6513-5p | 3102 | 4123 |
| hsa-miR-6514-3p | 3103 | 4124 |
| hsa-miR-6514-5p | 3104 | 4125 |
| hsa-miR-6515-3p | 3105 | 4126 |
| hsa-miR-6515-5p | 3106 | 4127 |
| hsa-miR-652-3p | 3107 | 4128 |
| hsa-miR-652-5p | 3108 | 4129 |
| hsa-miR-653 | 3109 | 4130 |
| hsa-miR-654-3p | 3110 | 4131 |
| hsa-miR-654-5p | 3111 | 4132 |
| hsa-miR-655 | 3112 | 4133 |
| hsa-miR-656 | 3113 | 4134 |
| hsa-miR-657 | 3114 | 4135 |
| hsa-miR-658 | 3115 | 4136 |
| hsa-miR-659-3p | 3116 | 4137 |
| hsa-miR-659-5p | 3117 | 4138 |
| hsa-miR-660-3p | 3118 | 4139 |
| hsa-miR-660-5p | 3119 | 4140 |
| hsa-miR-661 | 3120 | 4141 |
| hsa-miR-662 | 3121 | 4142 |
| hsa-miR-663a | 3122 | 4143 |
| hsa-miR-663b | 3123 | 4144 |
| hsa-miR-664a-3p | 3124 | 4145 |
| hsa-miR-664a-5p | 3125 | 4146 |
| hsa-miR-664b-3p | 3126 | 4147 |
| hsa-miR-664b-5p | 3127 | 4148 |
| hsa-miR-665 | 3128 | 4149 |
| hsa-miR-668 | 3129 | 4150 |
| hsa-miR-670 | 3130 | 4151 |
| hsa-miR-671-3p | 3131 | 4152 |
| hsa-miR-6715a-3p | 3132 | 4153 |
| hsa-miR-6715b-3p | 3133 | 4154 |
| hsa-miR-6715b-5p | 3134 | 4155 |
| hsa-miR-671-5p | 3135 | 4156 |
| hsa-miR-6716-3p | 3136 | 4157 |
| hsa-miR-6716-5p | 3137 | 4158 |
| hsa-miR-6717-5p | 3138 | 4159 |
| hsa-miR-6718-5p | 3139 | 4160 |
| hsa-miR-6719-3p | 3140 | 4161 |
| hsa-miR-6720-3p | 3141 | 4162 |
| hsa-miR-6721-5p | 3142 | 4163 |
| hsa-miR-6722-3p | 3143 | 4164 |
| hsa-miR-6722-5p | 3144 | 4165 |
| hsa-miR-6723-5p | 3145 | 4166 |
| hsa-miR-6724-5p | 3146 | 4167 |
| hsa-miR-675-3p | 3147 | 4168 |
| hsa-miR-675-5p | 3148 | 4169 |
| hsa-miR-676-3p | 3149 | 4170 |
| hsa-miR-676-5p | 3150 | 4171 |
| hsa-miR-708-3p | 3151 | 4172 |
| hsa-miR-708-5p | 3152 | 4173 |
| hsa-miR-711 | 3153 | 4174 |
| hsa-miR-7-1-3p | 3154 | 4175 |
| hsa-miR-718 | 3155 | 4176 |
| hsa-miR-7-2-3p | 3156 | 4177 |
| hsa-miR-744-3p | 3157 | 4178 |
| hsa-miR-744-5p | 3158 | 4179 |
| hsa-miR-758-3p | 3159 | 4180 |
| hsa-miR-758-5p | 3160 | 4181 |
| hsa-miR-759 | 3161 | 4182 |
| hsa-miR-7-5p | 3162 | 4183 |
| hsa-miR-760 | 3163 | 4184 |
| hsa-miR-761 | 3164 | 4185 |
| hsa-miR-762 | 3165 | 4186 |
| hsa-miR-764 | 3166 | 4187 |
| hsa-miR-765 | 3167 | 4188 |
| hsa-miR-766-3p | 3168 | 4189 |
| hsa-miR-766-5p | 3169 | 4190 |
| hsa-miR-767-3p | 3170 | 4191 |
| hsa-miR-767-5p | 3171 | 4192 |
| hsa-miR-769-3p | 3172 | 4193 |
| hsa-miR-769-5p | 3173 | 4194 |
| hsa-miR-770-5p | 3174 | 4195 |
| hsa-miR-802 | 3175 | 4196 |
| hsa-miR-873-3p | 3176 | 4197 |
| hsa-miR-873-5p | 3177 | 4198 |
| hsa-miR-874 | 3178 | 4199 |
| hsa-miR-875-3p | 3179 | 4200 |
| hsa-miR-875-5p | 3180 | 4201 |
| hsa-miR-876-3p | 3181 | 4202 |
| hsa-miR-876-5p | 3182 | 4203 |
| hsa-miR-877-3p | 3183 | 4204 |
| hsa-miR-877-5p | 3184 | 4205 |
| hsa-miR-885-3p | 3185 | 4206 |
| hsa-miR-885-5p | 3186 | 4207 |
| hsa-miR-887 | 3187 | 4208 |
| hsa-miR-888-3p | 3188 | 4209 |
| hsa-miR-888-5p | 3189 | 4210 |
| hsa-miR-889 | 3190 | 4211 |
| hsa-miR-890 | 3191 | 4212 |
| hsa-miR-891a | 3192 | 4213 |
| hsa-miR-891b | 3193 | 4214 |
| hsa-miR-892a | 3194 | 4215 |
| hsa-miR-892b | 3195 | 4216 |
| hsa-miR-892c-3p | 3196 | 4217 |
| hsa-miR-892c-5p | 3197 | 4218 |
| hsa-miR-920 | 3198 | 4219 |
| hsa-miR-921 | 3199 | 4220 |
| hsa-miR-922 | 3200 | 4221 |
| hsa-miR-924 | 3201 | 4222 |
| hsa-miR-92a-1-5p | 3202 | 4223 |
| hsa-miR-92a-2-5p | 3203 | 4224 |
| hsa-miR-92a-3p | 3204 | 4225 |
| hsa-miR-92b-3p | 3205 | 4226 |
| hsa-miR-92b-5p | 3206 | 4227 |
| hsa-miR-933 | 3207 | 4228 |
| hsa-miR-93-3p | 3208 | 4229 |
| hsa-miR-934 | 3209 | 4230 |
| hsa-miR-935 | 3210 | 4231 |
| hsa-miR-93-5p | 3211 | 4232 |
| hsa-miR-936 | 3212 | 4233 |
| hsa-miR-937-3p | 3213 | 4234 |
| hsa-miR-937-5p | 3214 | 4235 |
| hsa-miR-938 | 3215 | 4236 |
| hsa-miR-939-3p | 3216 | 4237 |
| hsa-miR-939-5p | 3217 | 4238 |
| hsa-miR-9-3p | 3218 | 4239 |
| hsa-miR-940 | 3219 | 4240 |
| hsa-miR-941 | 3220 | 4241 |
| hsa-miR-942 | 3221 | 4242 |
| hsa-miR-943 | 3222 | 4243 |
| hsa-miR-944 | 3223 | 4244 |
| hsa-miR-95 | 3224 | 4245 |
| hsa-miR-9-5p | 3225 | 4246 |
| hsa-miR-96-3p | 3226 | 4247 |
| hsa-miR-96-5p | 3227 | 4248 |
| hsa-miR-98-3p | 3228 | 4249 |
| hsa-miR-98-5p | 3229 | 4250 |
| hsa-miR-99a-3p | 3230 | 4251 |
| hsa-miR-99a-5p | 3231 | 4252 |
| hsa-miR-99b-3p | 3232 | 4253 |
| hsa-miR-99b-5p | 3233 | 4254 |

As shown in Table 12, microRNAs are differentially expressed in different tissues and cells, and often associated with different types of diseases (e.g. cancer cells). The decision of removal or insertion of microRNA binding sites, or any combination, is dependent on microRNA expression patterns and their profilings in cancer cells. In Table 12, "HCC" represents hepatocellular carcinoma, "ALL" stands for acute lymphoblastsic leukemia, "RCC" stands for renal cell carcinoma, "CLL" stands for chrominc lymphocytic leukemia and "MALT" stands for mucosa-associated lymphoid tissue.

TABLE 12 mirs, tissues/cell expression and diseases

| microRNA | mir SEQ ID | BS SEQ ID | Tissues/cells | Associated disease | Biological function |
|---|---|---|---|---|---|
| hsa-let-7a-2-3p | 171 | 1192 | Embryonic stem cells, lung, myeloid cells | inflammatory, various cancers (lung, cervical, breast, pancreatic, etc) | tumor suppressor, |
| hsa-let-7a-3p | 172 | 1193 | Embryonic stem cells, lung | inflammatory, various cancers (lung, cervical, breast, pancreatic, etc) | tumor suppressor, |
| hsa-let-7a-5p | 173 | 1194 | Embryonic stem cells, lung | inflammatory, various cancers (lung, cervical, breast, pancreatic, etc) | tumor suppressor, |
| hsa-let-7b-3p | 174 | 1195 | epithelial cells, endothelial cells (vascular) | lung cancer, colorectal cancer, cervical cancer, inflammation and immune response after infection | tumor angiogenesis |
| hsa-let-7b-5p | 175 | 1196 | epithelial cells, endothelial cells (vascular) | cervical cancer, inflammation and immune response after infection | tumor angiogenesis |
| hsa-let-7c | 176 | 1197 | dendritic cells | various cacners (cervical, pancreatic, lung, esopphageal, etc) | tumor suppressor, apoptosis |
| hsa-let-7d-3p | 177 | 1198 | embryonic stem cells | associated with various cancer cells | tumor suppressor |
| hsa-let-7d-5p | 178 | 1199 | embryonic stem cells | associated with various cancer cells | tumor suppressor |
| hsa-let-7e-3p | 179 | 1200 | immune cells | various cancer cells, autoimmunity, endotoxin tolerance | tumor suppressor |
| hsa-let-7e-5p | 180 | 1201 | immune cells | various cancer cells | tumor suppressor |
| hsa-let-7f-1-3p | 181 | 1202 | immune cells (T cells) | various cancer cells | tumor suppressor |
| hsa-let-7f-2-3p | 182 | 1203 | immune cells (T cells) | various cancer cells | tumor suppressor |
| hsa-let-7f-5p | 183 | 1204 | immune cells (T cells) | Various cancer cells | tumor suppressor |
| hsa-let-7g-3p | 184 | 1205 | hematopoietic cells, adipose, smooth muscle cells | various cancer cells (lung, breast, etc) | tumor suppressor |
| hsa-let-7g-5p | 185 | 1206 | hematopoietic cells, adipose, smooth muscle cells | various cancer cells (lung, breast, etc) | tumor suppressor |
| hsa-let-7i-3p | 186 | 1207 | immune cells | chronic lymphocyte leukimia | tumor suppressor |
| hsa-let-7i-5p | 187 | 1208 | immune cells | chronic lymphocyte leukimia | tumor suppressor |
| hsa-miR-1 | 188 | 1209 | muscle, heart | | angiogenesis, cell proliferation (myogenesis) |
| hsa-miR-100-3p | 189 | 1210 | hematopoietic cells, endothelial cells | gastric cancer, pancreatic cancer | tumor angiogenesis |
| hsa-miR-100-5p | 190 | 1211 | hematopoietic cells, endothelial cells | gastric cancer, pancreatic cancer | tumor angiogenesis |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-101-3p | 191 | 1212 | endothelial cells | various cancers (breast, non-small cell lung, colon, gastric, pancreatic, bladder, etc); lupus erythematosus | angiogenesis |
| hsa-miR-101-5p | 192 | 1213 | endothelial cells | various cancers (breast, non-small cell lung, colon, gastric, pancreatic, bladder, etc); lupus erythematosus | angiogenesis |
| hsa-miR-103a-2-5p | 193 | 1214 | embryonic stem cells, many tissues/cells | various cancers (endometrial, neuroblastoma, colorectal, breast, liver, etc) | oncogene, cell growth |
| hsa-miR-103a-3p | 194 | 1215 | embryonic stem cells, many tissues/cells | various cancers (endometrial, neuroblastoma, colorectal, breast, liver, etc) | oncogene, cell growth |
| hsa-miR-103b | 195 | 1216 | Many tissues/cells | various cancers (endometrial, neuroblastoma, colorectal, breast, liver, etc) | oncogene, cell growth |
| hsa-miR-105-3p | 196 | 1217 | pancreatic cells | | |
| hsa-miR-105-5p | 197 | 1218 | pancreatic cells | | |
| hsa-miR-106a-3p | 198 | 1219 | osteogenic cells | osteocarcoma, other cancers | cell differentiation |
| hsa-miR-106a-5p | 199 | 1220 | osteogenic cells | osteocarcoma, other cancers | cell differentiation |
| hsa-miR-106b-3p | 200 | 1221 | embryonic stem cells | various cancers (non-small lung cancer, gastric cancer, HCC, gliomas, etc) | oncogene |
| hsa-miR-106b-5p | 201 | 1222 | embryonic stem cells | various cancers (non-small lung cancer, gastric cancer, HCC, gliomas, etc) | oncogene |
| hsa-miR-107 | 202 | 1223 | many tissues, brain hepatocytes/liver | breast cancer, pituitary adenoma, obesity/diabetes | |
| hsa-miR-10a-3p | 203 | 1224 | hematopoeitic cells | acute myeoid leukemia | oncogene, cell growth |
| hsa-miR-10a-5p | 204 | 1225 | hematopoeitic cells | acute myeoid leukemia | oncogene, cell growth |
| hsa-miR-10b-3p | 205 | 1226 | multiple tissues and cells | various cancers (breast, ovarian, glioblastoma, pancreatc ductal adenocarcinoma, gastric, etc) | oncogene |
| hsa-miR-10b-5p | 206 | 1227 | multiple tissues and cells | various cancers (breast, ovarian, glioblastoma, pancreatc ductal adenocarcinoma, gastric, etc) | oncogene |
| hsa-miR-1178-3p | 207 | 1228 | | osteocarcoma | |
| hsa-miR-1178-5p | 208 | 1229 | | osteocarcoma | |
| hsa-miR-1179 | 209 | 1230 | | osteocarcoma | |
| hsa-miR-1180 | 210 | 1231 | discovered in sarcoma, no expression data | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-1181 | 211 | 1232 | | downregulated in ovarian cancer cells, associated with HCV infection in hepatocytes | |
| hsa-miR-1182 | 212 | 1233 | placenta | | |
| hsa-miR-1183 | 213 | 1234 | | associated with rectal cancer | |
| hsa-miR-1184 | 214 | 1235 | Hematopoietic cells | downregulated in oral leukoplakia (OLK) | |
| hsa-miR-1185-1-3p | 215 | 1236 | placenta | | |
| hsa-miR-1185-2-3p | 216 | 1237 | placenta | | |
| hsa-miR-1185-5p | 217 | 1238 | placenta | | |
| hsa-miR-1193 | 218 | 1239 | | melanoma | |
| hsa-miR-1197 | 219 | 1240 | | neublastoma | |
| hsa-miR-1200 | 220 | 1241 | | chronic lynphocytic leukemia | |
| hsa-miR-1202 | 221 | 1242 | | chronic lynphocytic leukemia, downregulated in ovarian cancer cells | |
| hsa-miR-1203 | 222 | 1243 | | in the chromosome 8q24 region, cancer cells | |
| hsa-miR-1204 | 223 | 1244 | | in the chromosome 8q24 region, cancer cells | |
| hsa-miR-1205 | 224 | 1245 | | in the chromosome 8q24 region, cancer cells | |
| hsa-miR-1206 | 225 | 1246 | | in the chromosome 8q24 region, cancer cells | |
| hsa-miR-1207-3p | 226 | 1247 | | in the chromosome 8q24 region, cancer cells | |
| hsa-miR-1207-5p | 227 | 1248 | | in the chromosome 8q24 region, cancer cells | |
| hsa-miR-1208 | 228 | 1249 | | in the chromosome 8q24 region, cancer cells | |
| hsa-miR-122-3p | 229 | 1250 | kidney, liver/hepatocytes | Renal Cell Carcinoma (RCC), cancer cells | lipid metabolism |
| hsa-miR-1224-3p | 230 | 1251 | | Lupus nephritis | |
| hsa-miR-1224-5p | 231 | 1252 | | rectal cancer | |
| hsa-miR-1225-3p | 232 | 1253 | | adrenal pheochromocytomas; upregulated in MITF KnockDown melanocytes | |
| hsa-miR-1225-5p | 233 | 1254 | | prostate cancer | |
| hsa-miR-122-5p | 234 | 1255 | liver/hepatocytes | cancer cells | lipid metabolism |
| hsa-miR-1226-3p | 235 | 1256 | discovered in a mirtron screening | | |
| hsa-miR-1226-5p | 236 | 1257 | discovered in a mirtron screening | | |
| hsa-miR-1227-3p | 237 | 1258 | cartilage/ chondrocytes | | |
| hsa-miR-1227-5p | 238 | 1259 | cartilage/ chondrocytes | | |
| hsa-miR-1228-3p | 239 | 1260 | liver(hepatocytes) | Hepatocellular carcinoma(HCC) | anti-apoptosis |
| hsa-miR-1228-5p | 240 | 1261 | liver(hepatocytes) | Hepatocellular carcinoma(HCC) | anti-apoptosis |
| hsa-miR-1229-3p | 241 | 1262 | discovered in a mirtron screening | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-1229-5p | 242 | 1263 | discovered in a mirtron screening | | |
| hsa-miR-1231 | 243 | 1264 | | HCC | |
| hsa-miR-1233-1-5p | 244 | 1265 | serum | | |
| hsa-miR-1233-3p | 245 | 1266 | serum | | |
| hsa-miR-1234-3p | 246 | 1267 | discovered in embryonic stem cell | | |
| hsa-miR-1234-5p | 247 | 1268 | discovered in embryonic stem cell | | |
| hsa-miR-1236-3p | 248 | 1269 | lymphatic endothelial cells | | target to VEGFR-3 |
| hsa-miR-1236-5p | 249 | 1270 | lymphatic endothelial cells | | target to VEGFR-3 |
| hsa-miR-1237-3p | 250 | 1271 | esophageal cell line KYSE-150R | | |
| hsa-miR-1237-5p | 251 | 1272 | esophageal cell line KYSE-150R | | |
| hsa-miR-1238-3p | 252 | 1273 | | colorectal cancer | |
| hsa-miR-1238-5p | 253 | 1274 | | colorectal cancer | |
| hsa-miR-1243 | 254 | 1275 | discovered in embryonic stem cells | | |
| hsa-miR-124-3p | 255 | 1276 | brain, plasma (exosomal) | glioma | cell differentiation |
| hsa-miR-1244 | 256 | 1277 | discovered in embryonic stem cells | | |
| hsa-miR-1245a | 257 | 1278 | discovered in embryonic stem cells | | |
| hsa-miR-1245b-3p | 258 | 1279 | discovered in embryonic stem cells | | |
| hsa-miR-1245b-5p | 259 | 1280 | discovered in embryonic stem cells | | |
| hsa-miR-124-5p | 260 | 1281 | brain, Plasma (circulating) | upregulated in heart dysfunction, glioma | cell differentiation |
| hsa-miR-1246 | 261 | 1282 | embryonic stem cells, epithelial cells | | |
| hsa-miR-1247-3p | 262 | 1283 | embryoid body cells | | |
| hsa-miR-1247-5p | 263 | 1284 | embryoid body cells | | |
| hsa-miR-1248 | 264 | 1285 | | | component of SnoRNAs |
| hsa-miR-1249 | 265 | 1286 | liver(hepatocytes) | | |
| hsa-miR-1250 | 266 | 1287 | oligodendrocytes | | |
| hsa-miR-1251 | 267 | 1288 | discovered in embryonic stem cells | | |
| hsa-miR-1252 | 268 | 1289 | discovered in embryonic stem cells | | |
| hsa-miR-1253 | 269 | 1290 | discovered in embryonic stem cells | | |
| hsa-miR-1254 | 270 | 1291 | embryonic stem cells | | |
| hsa-miR-1255a | 271 | 1292 | discovered in embryonic stem cells | | |
| hsa-miR-1255b-2-3p | 272 | 1293 | discovered in embryonic stem cells | | |
| hsa-miR-1255b-5p | 273 | 1294 | discovered in embryonic stem cells | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-1256 | 274 | 1295 | discovered in embryonic stem cells | prostate cancer | |
| hsa-miR-1257 | 275 | 1296 | discovered in embryonic stem cells | liposarcoma (soft tissue sarcoma) | |
| hsa-miR-1258 | 276 | 1297 | discovered in embryonic stem cells | breast cancer and lung cancer | |
| hsa-miR-125a-3p | 277 | 1298 | brain, hematopoietic cells | various cancer (prostate, HCC, etc) | cell proliferation and differentiation |
| hsa-miR-125a-5p | 278 | 1299 | brain, hematopoietic cells | various cancer (prostate, HCC, etc) | cell proliferation and differentiation |
| hsa-miR-125b-1-3p | 279 | 1300 | hematopoietic cells (monocytes), brain(neuron) | various cancer (prostate, HCC, etc) | oncogene, cell differentiation |
| hsa-miR-125b-2-3p | 280 | 1301 | hematopoietic cells (monocytes), brain(neuron) | various cancer (prostate, HCC, etc) | oncogene, cell differentiation |
| hsa-miR-125b-5p | 281 | 1302 | hematopoietic cells, brain (neuron) | various cancer (cutaneous T cell lymphoma, prostate, HCC, etc) | oncogene, cell differentiation |
| hsa-miR-1260a | 282 | 1303 | periodontal tissue | | |
| hsa-miR-1260b | 283 | 1304 | periodontal tissue | | |
| hsa-miR-1261 | 284 | 1305 | embryonic stem cells | | |
| hsa-miR-1262 | 285 | 1306 | embryoid body cells | | |
| hsa-miR-1263 | 286 | 1307 | discovered in embryonic stem cells | | |
| hsa-miR-126-3p | 287 | 1308 | endothelial cells, lung | B-lieage ALL | angiogenesis |
| hsa-miR-1264 | 288 | 1309 | discovered in embryonic stem cells | | |
| hsa-miR-1265 | 289 | 1310 | discovered in embryonic stem cells | | |
| hsa-miR-126-5p | 290 | 1311 | endothelial cells, lung | breast cancer, B-lieage ALL | angiogenesis |
| hsa-miR-1266 | 291 | 1312 | embryonic stem cells | | |
| hsa-miR-1267 | 292 | 1313 | discovered in embryonic stem cells | | |
| hsa-miR-1268a | 293 | 1314 | embryonic stem cells | | |
| hsa-miR-1268b | 294 | 1315 | embryonic stem cells | | |
| hsa-miR-1269a | 295 | 1316 | embryoid body cells | | |
| hsa-miR-1269b | 296 | 1317 | embryoid body cells | | |
| hsa-miR-1270 | 297 | 1318 | discovered in embryonic stem cells | | |
| hsa-miR-1271-3p | 298 | 1319 | brain | Hepatocellular carcinoma(HCC) | Suppress GPC-3 in HCC |
| hsa-miR-1271-5p | 299 | 1320 | brain | Hepatocellular carcinoma(HCC) | Suppress GPC-3 in HCC |
| hsa-miR-1272 | 300 | 1321 | embryonic stem cells | | |
| hsa-miR-1273a | 301 | 1322 | discovered in embryonic stem cells | | |
| hsa-miR-1273c | 302 | 1323 | | colorectal cancer | |
| hsa-miR-1273d | 303 | 1324 | discovered in embryonic stem cells | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-1273e | 304 | 1325 | | solid tumor cells | |
| hsa-miR-1273f | 305 | 1326 | | cervical cancer | |
| hsa-miR-1273g-3p | 306 | 1327 | | cervical cancer | |
| hsa-miR-1273g-5p | 307 | 1328 | | cervical cancer | |
| hsa-miR-127-3p | 308 | 1329 | lung, placenta | | |
| hsa-miR-1275 | 309 | 1330 | embryonic stem cells | gastric carcinoma | |
| hsa-miR-127-5p | 310 | 1331 | lung, placenta(islet) | | |
| hsa-miR-1276 | 311 | 1332 | discovered in embryonic stem cells | | |
| hsa-miR-1277-3p | 312 | 1333 | embryoid body cells | | |
| hsa-miR-1277-5p | 313 | 1334 | embryoid body cells | | |
| hsa-miR-1278 | 314 | 1335 | discovered in embryonic stem cells | | |
| hsa-miR-1279 | 315 | 1336 | monocytes | | |
| hsa-miR-128 | 316 | 1337 | glioblast, brain | B-lieage ALL | target to neurofibromin1 in neuron |
| hsa-miR-1281 | 317 | 1338 | | muscle invasive bladder cancer | |
| hsa-miR-1282 | 318 | 1339 | discovered in embryonic stem cells | | |
| hsa-miR-1283 | 319 | 1340 | placenta | | |
| hsa-miR-1284 | 320 | 1341 | | lung cancer | |
| hsa-miR-1285-3p | 321 | 1342 | | various cancer cells | inhibit P53 expression |
| hsa-miR-1285-5p | 322 | 1343 | | various cancer cells | inhibit P53 expression |
| hsa-miR-1286 | 323 | 1344 | smooth muscle | esophageal cancer | |
| hsa-miR-1287 | 324 | 1345 | embryoid body cells | breast cancer | |
| hsa-miR-1288 | 325 | 1346 | discovered in embryonic stem cells | | |
| hsa-miR-1289 | 326 | 1347 | multiple cell types | | |
| hsa-miR-1290 | 327 | 1348 | embryoid body cells | gastric carcinoma | |
| hsa-miR-1291 | 328 | 1349 | hepatocytes | | component of SnoRNAs |
| hsa-miR-129-1-3p | 329 | 1350 | multiple cell types | HCC cancer cells | |
| hsa-miR-1292-3p | 330 | 1351 | | | |
| hsa-miR-129-2-3p | 331 | 1352 | multiple cell types | various cancer cells | |
| hsa-miR-1292-5p | 332 | 1353 | | | |
| hsa-miR-1293 | 333 | 1354 | discovered in embryonic stem cells | | |
| hsa-miR-1294 | 334 | 1355 | discovered in embryonic stem cells | | |
| hsa-miR-1295a | 335 | 1356 | | tumor cells (follicular lymphoma) | |
| hsa-miR-1295b-3p | 336 | 1357 | | tumor cells (follicular lymphoma) | |
| hsa-miR-1295b-5p | 337 | 1358 | | tumor cells (follicular lymphoma) | |
| hsa-miR-129-5p | 338 | 1359 | liver(hepatocytes) | HCC, thyroid cancer | cell death in cancer cell |
| hsa-miR-1296 | 339 | 1360 | | breast cancer | |
| hsa-miR-1297 | 340 | 1361 | discovered in embryonic stem cells | | |
| hsa-miR-1298 | 341 | 1362 | | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-1299 | 342 | 1363 | discovered in embryonic stem cells | | |
| hsa-miR-1301 | 343 | 1364 | | breast cancer | |
| hsa-miR-1302 | 344 | 1365 | | | |
| hsa-miR-1303 | 345 | 1366 | hepatocyte | colorectal cancer, liver cancer | |
| hsa-miR-1304-3p | 346 | 1367 | | | dental development |
| hsa-miR-1304-5p | 347 | 1368 | | | dental development |
| hsa-miR-1305 | 348 | 1369 | discovered in embryonic stem cells | | |
| hsa-miR-1306-3p | 349 | 1370 | discovered in embryonic stem cells | | |
| hsa-miR-1306-5p | 350 | 1371 | discovered in embryonic stem cells | | |
| hsa-miR-1307-3p | 351 | 1372 | discovered in embryonic stem cells | | |
| hsa-miR-1307-5p | 352 | 1373 | discovered in embryonic stem cells | | |
| hsa-miR-130a-3p | 353 | 1374 | lung, monocytes, vascular endothelial cells | various cancers (basal cell carcinoma, HCC, ovarian, etc), drug resistance | pro-angiogenic |
| hsa-miR-130a-5p | 354 | 1375 | lung, monocytes, vascular endothelial cells | various cancers (basal cell carcinoma, HCC, ovarian, etc), drug resistance | pro-angiogenic |
| hsa-miR-130b-3p | 355 | 1376 | Lung, epidermal cells (keratinocytes) | various cancers (gastric, rena cell carcinoma) | cell proliferation/ senescence |
| hsa-miR-130b-5p | 356 | 1377 | Lung, epidermal cells (keratinocytes) | various cancers (gastric, rena cell carcinoma) | cell proliferation/ senescence |
| hsa-miR-1321 | 357 | 1378 | | neuroblastoma | |
| hsa-miR-1322 | 358 | 1379 | | neuroblastoma | |
| hsa-miR-1323 | 359 | 1380 | placenta | neuroblastoma | |
| hsa-miR-132-3p | 360 | 1381 | Brain(neuron), immune cells | | |
| hsa-miR-1324 | 361 | 1382 | | neuroblastoma | |
| hsa-miR-132-5p | 362 | 1383 | brain(neuron), immune cells | | |
| hsa-miR-133a | 363 | 1384 | muscle, heart, epithelial cells (lung) | heart failure, esophageal cancer | myogenesis |
| hsa-miR-133b | 364 | 1385 | muscle, heart, epithelial cells (lung) | heart failure, esophageal cancer | myogenesis |
| hsa-miR-134 | 365 | 1386 | lung (epithelial) | non-samll cell lung cancer, pulmonary embolism | |
| hsa-miR-1343 | 366 | 1387 | | breast cancer cells | |
| hsa-miR-135a-3p | 367 | 1388 | brain, other tissues | various cancer cells (lung, breast, colorectal, HCC, etc) | tumor suppressor |
| hsa-miR-135a-5p | 368 | 1389 | brain, other tissues | various cancer cells (lung, breast, colorectal, HCC, etc) | tumor suppressor |
| hsa-miR-135b-3p | 369 | 1390 | brain, placenta, other tissues | various cancers (gastric, mammary, neuroblastomas, pancreatic, etc) | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-135b-5p | 370 | 1391 | brain, placenta, other tissues | various cancers (gastric, mammary, neuroblastomas, pancreatic, etc) | |
| hsa-miR-136-3p | 371 | 1392 | stem cells, placenta | glioma | tumor suppressor |
| hsa-miR-136-5p | 372 | 1393 | stem cells, placenta | glioma | tumor suppressor |
| hsa-miR-137 | 373 | 1394 | brain | various cancers (glioblastoma, breast, gastric etc), Alzheimer's disease | inhibiting cancer cell proliferation and migration |
| hsa-miR-138-1-3p | 374 | 1395 | stem cells, epidermal cells (keratinocytes) | arious cancer cells, downregulated in HCC | cell proliferation/ senescence |
| hsa-miR-138-2-3p | 375 | 1396 | stem cells | arious cancer cells, downregulated in HCC | |
| hsa-miR-138-5p | 376 | 1397 | stem cells | arious cancer cells, downregulated in HCC | |
| hsa-miR-139-3p | 377 | 1398 | hematocytes, brain | various cancer cells (colorectal, gastric, ovarian) | repress cancer metastasis |
| hsa-miR-139-5p | 378 | 1399 | hematocytes, brain | various cancer cells (colorectal, gastric, ovarian) | repress cancer metastasis |
| hsa-miR-140-3p | 379 | 1400 | airway smooth muscle | Virus infection, cancers | |
| hsa-miR-140-5p | 380 | 1401 | cartilage (chondrocytes) | csncers | |
| hsa-miR-141-3p | 381 | 1402 | Many tissues/cells | various cancer cells (HCC, prostate, kidney, etc) | cell differentiation |
| hsa-miR-141-5p | 382 | 1403 | Many tissues/cells | various cancer cells (HCC, prostate, kidney, etc) | cell differentiation |
| hsa-miR-142-3p | 383 | 1404 | meyloid cells, hematopoiesis, APC cells | | immune response |
| hsa-miR-142-5p | 384 | 1405 | meyloid cells, hematopoiesis, APC cells | | immune response |
| hsa-miR-143-3p | 385 | 1406 | vascular smooth muscle | pre-B-cell acute lymphocytic leukemia, virus infection | |
| hsa-miR-143-5p | 386 | 1407 | vascular smooth muscle, T-cells | virus infection | |
| hsa-miR-144-3p | 387 | 1408 | erythroid | various cancers (lung, colorectal, etc) | cell differentiation |
| hsa-miR-144-5p | 388 | 1409 | erythroid | various cancers (lung, colorectal, etc) | cell differentiation |
| hsa-miR-145-3p | 389 | 1410 | kidney, cartilage, vascular smooth muscle | T-cell lupus | tumor suppressor |
| hsa-miR-145-5p | 390 | 1411 | kidney, cartilage, vascular smooth muscle | T-cell lupus | tumor suppressor |
| hsa-miR-1468 | 391 | 1412 | | lung cancer | |
| hsa-miR-1469 | 392 | 1413 | | tumor cell(follicular lymphoma), rectal cancer | |
| hsa-miR-146a-3p | 393 | 1414 | immune cells, hematopoiesis | various cancers, endotoxin tolerance | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-146a-5p | 394 | 1415 | immune cells, hematopoiesis | various cancers, endotoxin tolerance | |
| hsa-miR-146b-3p | 395 | 1416 | immune cells | various cancers | |
| hsa-miR-146b-5p | 396 | 1417 | Embryonic stem cells | various cancers (glioma) | tumor invation, migration |
| hsa-miR-1470 | 397 | 1418 | | | |
| hsa-miR-1471 | 398 | 1419 | | tumor cell(follicular lymphoma), rectal cancer | |
| hsa-miR-147a | 399 | 1420 | Macrophage | inflammatory response | |
| hsa-miR-147b | 400 | 1421 | Macrophage | inflammatory response | |
| hsa-miR-148a-3p | 401 | 1422 | hematopoietic cells | CLL, T-lineage ALL | |
| hsa-miR-148a-5p | 402 | 1423 | hematopoietic cells | CLL, T-lineage ALL | |
| hsa-miR-148b-3p | 403 | 1424 | neuron | | |
| hsa-miR-148b-5p | 404 | 1425 | neuron | | |
| hsa-miR-149-3p | 405 | 1426 | heart, brain | various cancers (glioma, colorectal, gastric, etc) | |
| hsa-miR-149-5p | 406 | 1427 | heart, brain | various cancers (glioma, colorectal, gastric, etc) | |
| hsa-miR-150-3p | 407 | 1428 | hematopoietic cells (lymphoid) | circulating plasma (acute myeloid leukemia) | |
| hsa-miR-150-5p | 408 | 1429 | hematopoietic cells (lymphoid) | circulating plasma (acute myeloid leukemia) | |
| hsa-miR-151a-3p | 409 | 1430 | neuron, fetal liver | | |
| hsa-miR-151a-5p | 410 | 1431 | neuron, fetal liver | | |
| hsa-miR-151b | 411 | 1432 | immune cells (B-cells) | | |
| hsa-miR-152 | 412 | 1433 | liver | | |
| hsa-miR-153 | 413 | 1434 | brain | | |
| hsa-miR-1537 | 414 | 1435 | | | |
| hsa-miR-1538 | 415 | 1436 | blood | Cancer cells | |
| hsa-miR-1539 | 416 | 1437 | esophageal cell line KYSE-150R | | |
| hsa-miR-154-3p | 417 | 1438 | embryonic stem cells | | |
| hsa-miR-154-5p | 418 | 1439 | embryonic stem cells | | |
| hsa-miR-155-3p | 419 | 1440 | T/B cells, monocytes, breast | various cancers (CLL, B cell lymphoma, breast, lung, ovarian, cervical, colorectal, prostate) | |
| hsa-miR-155-5p | 420 | 1441 | T/B cells, monocytes, breast | various cancers (CLL, B cell lymphoma, breast, lung, ovarian, cervical, colorectal, prostate) | |
| hsa-miR-1587 | 421 | 1442 | identified in B-cells | | |
| hsa-miR-15a-3p | 422 | 1443 | blood, lymphocyte, hematopoietic tissues (spleen) | | cell cycle, proliferation |
| hsa-miR-15a-5p | 423 | 1444 | blood, lymphocyte, hematopoietic tissues (spleen) | | cell cycle, proliferation |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-15b-3p | 424 | 1445 | blood, lymphocyte, hematopoietic tissues (spleen) | | cell cycle, proliferation |
| hsa-miR-15b-5p | 425 | 1446 | blood, lymphocyte, hematopoietic tissues (spleen) | | cell cycle, proliferation |
| hsa-miR-16-1-3p | 426 | 1447 | embryonic stem cells, blood, hematopoietic tissues (spleen) | | |
| hsa-miR-16-2-3p | 427 | 1448 | blood, lymphocyte, hematopoietic tissues (spleen) | | |
| hsa-miR-16-5p | 428 | 1449 | Many tissues, blood | | |
| hsa-miR-17-3p | 429 | 1450 | embryonic stem cells, endothelial cells, | | tumor angiogenesis |
| hsa-miR-17-5p | 430 | 1451 | endothelial cells, kidney, breast; | | tumor angiogenesis |
| hsa-miR-181a-2-3p | 431 | 1452 | glioblast, stem cells | | |
| hsa-miR-181a-3p | 432 | 1453 | glioblast, myeloid cells, Embryonic stem cells | | |
| hsa-miR-181a-5p | 433 | 1454 | glioblast, myeloid cells, Embryonic stem cells | | |
| hsa-miR-181b-3p | 434 | 1455 | glioblast, Embryonic stem cells, epidermal (keratinocytes) | | cell proliferation/ senescence |
| hsa-miR-181b-5p | 435 | 1456 | glioblast, Embryonic stem cells, epidermal (keratinocytes) | | cell proliferation/ senescence |
| hsa-miR-181c-3p | 436 | 1457 | brain, stem cells/progenitor | variou cance cells (gliobasltoma, basal cell carcinoma, prostate) | cell differentiation |
| hsa-miR-181c-5p | 437 | 1458 | brain, stem cells/progenitor | variou cance cells (gliobasltoma, basal cell carcinoma, prostate) | cell differentiation |
| hsa-miR-181d | 438 | 1459 | glia cells | | |
| hsa-miR-182-3p | 439 | 1460 | immune cells | autoimmune | immune response |
| hsa-miR-1825 | 440 | 1461 | discovered in a MiRDeep screening | | |
| hsa-miR-182-5p | 441 | 1462 | lung, immune cells | autoimmune | immune response |
| hsa-miR-1827 | 442 | 1463 | | small cell lung cancer | |
| hsa-miR-183-3p | 443 | 1464 | brain | | |
| hsa-miR-183-5p | 444 | 1465 | brain | | |
| hsa-miR-184 | 445 | 1466 | blood, tongue, pancreas (islet) | | |
| hsa-miR-185-3p | 446 | 1467 | | | |
| hsa-miR-185-5p | 447 | 1468 | | | |
| hsa-miR-186-3p | 448 | 1469 | osteoblasts, heart | various cancer cells | |
| hsa-miR-186-5p | 449 | 1470 | osteoblasts, heart | various cancer cells | |
| hsa-miR-187-3p | 450 | 1471 | | thyroid tumor | |
| hsa-miR-187-5p | 451 | 1472 | | thyroid tumor | |
| hsa-miR-188-3p | 452 | 1473 | irway smooth muscle, central nervous system | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-188-5p | 453 | 1474 | irway smooth muscle, central nervous system | | |
| hsa-miR-18a-3p | 454 | 1475 | endothelial cells, lung | | |
| hsa-miR-18a-5p | 455 | 1476 | endothelial cells, lung | | |
| hsa-miR-18b-3p | 456 | 1477 | lung | | |
| hsa-miR-18b-5p | 457 | 1478 | lung | | |
| hsa-miR-1908 | 458 | 1479 | | breast cancer | |
| hsa-miR-1909-3p | 459 | 1480 | | rectal cancer | |
| hsa-miR-1909-5p | 460 | 1481 | | rectal cancer | |
| hsa-miR-190a | 461 | 1482 | brain | | |
| hsa-miR-190b | 462 | 1483 | brain | | |
| hsa-miR-1910 | 463 | 1484 | embryonic stem cells | | |
| hsa-miR-1911-3p | 464 | 1485 | embryonic stem cells, neural precursor | | |
| hsa-miR-1911-5p | 465 | 1486 | embryonic stem cells, neural precursor | | |
| hsa-miR-1912 | 466 | 1487 | embryonic stem cells, neural precursor | | |
| hsa-miR-1913 | 467 | 1488 | embryonic stem cells | | |
| hsa-miR-191-3p | 468 | 1489 | | chroninc lymphocyte leukimia, B-lieage ALL | |
| hsa-miR-1914-3p | 469 | 1490 | embryonic stem cells | | |
| hsa-miR-1914-5p | 470 | 1491 | embryonic stem cells | | |
| hsa-miR-1915-3p | 471 | 1492 | embryonic stem cells | | |
| hsa-miR-1915-5p | 472 | 1493 | embryonic stem cells | | |
| hsa-miR-191-5p | 473 | 1494 | | chroninc lymphocyte leukimia, B-lieage ALL | |
| hsa-miR-192-3p | 474 | 1495 | kidney | | |
| hsa-miR-192-5p | 475 | 1496 | kidney | | |
| hsa-miR-193a-3p | 476 | 1497 | many tissues/cells | various cancer cells (lung, osteoblastoma, ALL, follicular lymphoma, etc) | tumor suppressor, proliferation |
| hsa-miR-193a-5p | 477 | 1498 | many tissues/cells | various cancer cells (lung, osteoblastoma, ALL, follicular lymphoma, etc) | tumor suppressor, proliferation |
| hsa-miR-193b-3p | 478 | 1499 | many tissues/ cells, semen | arious cancer cells (prostate, breast, melanoma, myeloma, non small cell lung, etc)follicular lymphoma) | tumor suppressor |
| hsa-miR-193b-5p | 479 | 1500 | many tissues/cells, semen | arious cancer cells (prostate, breast, melanoma, myeloma, non small cell lung, etc)follicular lymphoma) | tumor suppressor |
| hsa-miR-194-3p | 480 | 1501 | kidney, liver | various cancers | |
| hsa-miR-194-5p | 481 | 1502 | kidney, liver | various cancers | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-195-3p | 482 | 1503 | breast, pancreas (islet) | | |
| hsa-miR-195-5p | 483 | 1504 | breast, pancreas (islet) | | |
| hsa-miR-196a-3p | 484 | 1505 | pancreatic cells, endometrial tissues, mesenchymal stem cells | various cancer cells (pancreatic, osteosarcoma, endometrial, AML etc) | oncogenic, tumor suppressor |
| hsa-miR-196a-5p | 485 | 1506 | pancreatic cells, endometrial tissues, mesenchymal stem cells | various cancer cells (pancreatic, osteosarcoma, endometrial, AML etc) | oncogenic, tumor suppressor |
| hsa-miR-196b-3p | 486 | 1507 | endometrial tissues | glioblastoma | apoptosis |
| hsa-miR-196b-5p | 487 | 1508 | endometrial tissues | glioblastoma | apoptosis |
| hsa-miR-1972 | 488 | 1509 | | acute lymphoblastic leukemia | |
| hsa-miR-1973 | 489 | 1510 | | acute lymphoblastic leukemia | |
| hsa-miR-197-3p | 490 | 1511 | blood (myeloid), other tissues/cells | various cancers (thyroid tumor, leukemia, etc) | |
| hsa-miR-197-5p | 491 | 1512 | blood (myeloid), other tissues/cells | various cancers (thyroid tumor, leukemia, etc) | |
| hsa-miR-1976 | 492 | 1513 | | acute lymphoblastic leukemia | |
| hsa-miR-198 | 493 | 1514 | central nevous system(CNS) | | |
| hsa-miR-199a-3p | 494 | 1515 | liver, embryoid body cells, cardiomyocytes | | |
| hsa-miR-199a-5p | 495 | 1516 | liver, cardiomyocytes | | |
| hsa-miR-199b-3p | 496 | 1517 | liver, osteoblast | various cancers | osteogenesis |
| hsa-miR-199b-5p | 497 | 1518 | liver, osteoblast | various cancers | osteogenesis |
| hsa-miR-19a-3p | 498 | 1519 | endothelial cells | | tumor angiogenesis |
| hsa-miR-19a-5p | 499 | 1520 | endothelial cells | | tumor angiogenesis |
| hsa-miR-19b-1-5p | 500 | 1521 | endothelial cells | | tumor angiogenesis |
| hsa-miR-19b-2-5p | 501 | 1522 | endothelial cells | | tumor angiogenesis |
| hsa-miR-19b-3p | 502 | 1523 | endothelial cells | | tumor angiogenesis |
| hsa-miR-200a-3p | 503 | 1524 | epithelial cells, many other tissues | various cancers (breast, cervical, bladder, etc) | tumor progression and metastasis |
| hsa-miR-200a-5p | 504 | 1525 | epithelial cells, many other tissues | various cancers (breast, cervical, bladder, etc) | tumor progression and metastasis |
| hsa-miR-200b-3p | 505 | 1526 | epithelial cells, many other tissues | | tumor progression and metastasis |
| hsa-miR-200b-5p | 506 | 1527 | epithelial cells, many other tissues | | tumor progression and metastasis |
| hsa-miR-200c-3p | 507 | 1528 | epithelial cells, many other tissues, embryonic stem cells | | tumor progression and metastasis |
| hsa-miR-200c-5p | 508 | 1529 | epithelial cells, many other tissues, embryonic stem cells | | tumor progression and metastasis |
| hsa-miR-202-3p | 509 | 1530 | blood | lymphomagenesis, other cancers | |
| hsa-miR-202-5p | 510 | 1531 | blood | lymphomagenesis, other cancers | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-203a | 511 | 1532 | skin (epithelium) | psoriasis, autoimmune | |
| hsa-miR-203b-3p | 512 | 1533 | skin specific (epithelium) | psoriasis, autoimmune | |
| hsa-miR-203b-5p | 513 | 1534 | skin specific (epithelium) | psoriasis, autoimmune | |
| hsa-miR-204-3p | 514 | 1535 | adipose, other tissues/cells, kidney | various cancers | tumor metastasis |
| hsa-miR-204-5p | 515 | 1536 | adipose, other tissues/cells, kidney | various cancers | tumor metastasis |
| hsa-miR-2052 | 516 | 1537 | | | |
| hsa-miR-2053 | 517 | 1538 | | | |
| hsa-miR-205-3p | 518 | 1539 | blood(plasma) | various cancer cells (breast, glioma, melanoma, endometrial, etc) | |
| hsa-miR-2054 | 519 | 1540 | | | |
| hsa-miR-205-5p | 520 | 1541 | blood(plasma) | various cancer cells (breast, glioma, melanoma, endometrial, etc) | |
| hsa-miR-206 | 521 | 1542 | muscle (cardiac and skeletal) | | myogenesis |
| hsa-miR-208a | 522 | 1543 | heart(cardiomyocyte), muscle | cardiac defects | |
| hsa-miR-208b | 523 | 1544 | heart(cardiomyocyte), muscle | cardiac defects | |
| hsa-miR-20a-3p | 524 | 1545 | endothelial cells, kidney, osteogenic cells | | |
| hsa-miR-20a-5p | 525 | 1546 | endothelial cells, kidney, osteogenic cells | | |
| hsa-miR-20b-3p | 526 | 1547 | osteogenic cells | | |
| hsa-miR-20b-5p | 527 | 1548 | osteogenic cells | | |
| hsa-miR-210 | 528 | 1549 | kidney, heart, vascular endothelial cells | RCC, B-cell lymphocytes | angiogenesis |
| hsa-miR-2110 | 529 | 1550 | | rectal cancer | |
| hsa-miR-2113 | 530 | 1551 | embryonic stem cells | | |
| hsa-miR-211-3p | 531 | 1552 | melanocytes | melanoma and other cancers | |
| hsa-miR-2114-3p | 532 | 1553 | ovary, female reproductuve tract | | |
| hsa-miR-2114-5p | 533 | 1554 | ovary, female reproductuve tract | | |
| hsa-miR-2115-3p | 534 | 1555 | female reproductive tract | ovarian cancer | |
| hsa-miR-2115-5p | 535 | 1556 | female reproductive tract | ovarian cancer | |
| hsa-miR-211-5p | 536 | 1557 | melanocytes | melanoma and other cancers | |
| hsa-miR-2116-3p | 537 | 1558 | | live cancer(hepatocytes) and ovarian cancer | |
| hsa-miR-2116-5p | 538 | 1559 | | live cancer(hepatocytes) and ovarian cancer | |
| hsa-miR-2117 | 539 | 1560 | | ovarian cancer | |
| hsa-miR-212-3p | 540 | 1561 | brain(neuron), spleen | lymphoma | |
| hsa-miR-212-5p | 541 | 1562 | brain(neuron), spleen | lymphoma | |
| hsa-miR-21-3p | 542 | 1563 | glioblast, Blood (meyloid cells), liver, vascular endothelial cells | autoimmune, heart diseases, cancers | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-214-3p | 543 | 1564 | immune cerlls, pancreas | varioua cancers (melanoma, pancreatic, ovarian) | immune response |
| hsa-miR-214-5p | 544 | 1565 | immune cells, pancreas | varioua cancers (melanoma, pancreatic, ovarian) | immune response |
| hsa-miR-215 | 545 | 1566 | many tissues/cells | various cancers (renal, colon, osteosarcoma) | cell cycle arrest/p53 inducible |
| hsa-miR-21-5p | 546 | 1567 | blood (myeloid cells), liver, endothelial cells | autoimmune, heart diseases, cancers | |
| hsa-miR-216a-3p | 547 | 1568 | kidney, pancreas | | |
| hsa-miR-216a-5p | 548 | 1569 | kidney, pancreas | | |
| hsa-miR-216b | 549 | 1570 | | cancers | senescence |
| hsa-miR-217 | 550 | 1571 | endothelial cells | various cancer cells (pancreas, kidney, breast) | |
| hsa-miR-218-1-3p | 551 | 1572 | endothelial cells | various cancer cells (gastric tumor, bladder, cervical, etc) | |
| hsa-miR-218-2-3p | 552 | 1573 | | various cancer cells (gastric tumor, bladder, cervical, etc) | |
| hsa-miR-218-5p | 553 | 1574 | | various cancer cells (gastric tumor, bladder, cervical, etc) | |
| hsa-miR-219-1-3p | 554 | 1575 | brain, oligodendrocytes | | |
| hsa-miR-219-2-3p | 555 | 1576 | brain, oligodendrocytes | | |
| hsa-miR-219-5p | 556 | 1577 | brain, oligodendrocytes | | |
| hsa-miR-221-3p | 557 | 1578 | endothelial cells, immune cells | leukemia and other cancers | angiogenesis/ vasculogenesis |
| hsa-miR-221-5p | 558 | 1579 | endothelial cells, immune cells | leukemia and other cancers | angiogenesis/ vasculogenesis |
| hsa-miR-222-3p | 559 | 1580 | endothelial cells | various cancers | angiogenesis |
| hsa-miR-222-5p | 560 | 1581 | endothelial cells | various cancers | angiogenesis |
| hsa-miR-223-3p | 561 | 1582 | meyloid cells | leukemia | |
| hsa-miR-223-5p | 562 | 1583 | meyloid cells | leukemia | |
| hsa-miR-22-3p | 563 | 1584 | many tissues/cells | various cancers | tumorigenesis |
| hsa-miR-224-3p | 564 | 1585 | blood(plasma), ovary | cancers and inflammation | |
| hsa-miR-224-5p | 565 | 1586 | blood(plasma), ovary | cancers and inflammation | |
| hsa-miR-22-5p | 566 | 1587 | many tissues/cells | Various cancers | tumorigenesis |
| hsa-miR-2276 | 567 | 1588 | | breast cancer | |
| hsa-miR-2277-3p | 568 | 1589 | female reproductive tract | | |
| hsa-miR-2277-5p | 569 | 1590 | female reproductive tract | | |
| hsa-miR-2278 | 570 | 1591 | | breast cancer | |
| hsa-miR-2355-3p | 571 | 1592 | embryonic stem cells | | |
| hsa-miR-2355-5p | 572 | 1593 | embryonic stem cells | | |
| hsa-miR-2392 | 573 | 1594 | identified in B-cells | | |
| hsa-miR-23a-3p | 574 | 1595 | brain(astrocyte), endothelial cells, blood(erythroid) | Cancers | |
| hsa-miR-23a-5p | 575 | 1596 | brain(astrocyte), endothelial cells, blood(erythroid) | cancers | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-23b-3p | 576 | 1597 | blood, meyloid cells | cancers (renal cancer, glioblastoma, prostate, etc) and autoimmune | |
| hsa-miR-23b-5p | 577 | 1598 | blood, meyloid cells | cancers(glioblastoma, prostate, etc) and autoimmune | |
| hsa-miR-23c | 578 | 1599 | | cervical cancer | |
| hsa-miR-24-1-5p | 579 | 1600 | lung, meyloid cells | | |
| hsa-miR-24-2-5p | 580 | 1601 | lung, meyloid cells | | |
| hsa-miR-24-3p | 581 | 1602 | lung, meyloid cells | | |
| hsa-miR-2467-3p | 582 | 1603 | | breast cancer | |
| hsa-miR-2467-5p | 583 | 1604 | | breast cancer | |
| hsa-miR-25-3p | 584 | 1605 | embryonic stem cells, airway smooth muscle | | |
| hsa-miR-25-5p | 585 | 1606 | embryonic stem cells, airway smooth muscle | | |
| hsa-miR-2681-3p | 586 | 1607 | | breast cancer | |
| hsa-miR-2681-5p | 587 | 1608 | | breast cancer | |
| hsa-miR-2682-3p | 588 | 1609 | | | |
| hsa-miR-2682-5p | 589 | 1610 | | | |
| hsa-miR-26a-1-3p | 590 | 1611 | embryonic stem cells, blood, other tissues | CLL and other cancers | cell cycle and differentiation |
| hsa-miR-26a-2-3p | 591 | 1612 | blood, other tissues | CLL and other cancers | cell cycle and differentiation |
| hsa-miR-26a-5p | 592 | 1613 | blood, other tissues | CLL and other cancers | cell cycle and differentiation |
| hsa-miR-26b-3p | 593 | 1614 | hematopoietic cells | | |
| hsa-miR-26b-5p | 594 | 1615 | hematopoietic cells | | |
| hsa-miR-27a-3p | 595 | 1616 | meyloid cells | various cancer cells | |
| hsa-miR-27a-5p | 596 | 1617 | meyloid cells | various cancer cells | |
| hsa-miR-27b-3p | 597 | 1618 | meyloid cells, vascular endothelial cells | various cancer cells | pro-angiogenic |
| hsa-miR-27b-5p | 598 | 1619 | meyloid cells, vascular endothelial cells | various cancer cells | pro-angiogenic |
| hsa-miR-28-3p | 599 | 1620 | blood(immune cells) | B/T cell lymphoma | |
| hsa-miR-28-5p | 600 | 1621 | blood(immune cells) | B/T cell lymphoma | |
| hsa-miR-2861 | 601 | 1622 | osteoblasts | basal cell carcinoma | |
| hsa-miR-2909 | 602 | 1623 | T-Lymphocytes | | |
| hsa-miR-296-3p | 603 | 1624 | kidney, heart, lung, entothelial cells | | angiogenesis |
| hsa-miR-2964a-3p | 604 | 1625 | | | |
| hsa-miR-2964a-5p | 605 | 1626 | | | |
| hsa-miR-296-5p | 606 | 1627 | lung, liver, endothelial cells | | angiogenesis |
| hsa-miR-297 | 607 | 1628 | oocyte and prostate | | |
| hsa-miR-298 | 608 | 1629 | | breast cancer | |
| hsa-miR-299-3p | 609 | 1630 | | myeloid leukaemia, hepatoma, breast cancer | |
| hsa-miR-299-5p | 610 | 1631 | | myeloid leukaemia, hepatoma, breast cancer | |
| hsa-miR-29a-3p | 611 | 1632 | immuno system | CLL, other cancers, neurodegenerative disease | tumor suppression, immune modulation |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-29a-5p | 612 | 1633 | immuno system | CLL, other cancers, neurodegenerative disease | tumor suppression, immune modulation |
| hsa-miR-29b-1-5p | 613 | 1634 | immuno system | CLL, other cancers, neurodegenerative disease | tumor suppression, immune modulation |
| hsa-miR-29b-2-5p | 614 | 1635 | immuno system | CLL, other cancers | tumor suppression, immune modulation |
| hsa-miR-29b-3p | 615 | 1636 | immuno system | CLL, other cancers | tumor suppression, immune modulation |
| hsa-miR-29c-3p | 616 | 1637 | immuno system | CLL, other cancers | tumor suppression, immune modulation |
| hsa-miR-29c-5p | 617 | 1638 | immuno system | CLL, other cancers | tumor suppression, immune modulation |
| hsa-miR-300 | 618 | 1639 | osteoblast | Bladder cancer | |
| hsa-miR-301a-3p | 619 | 1640 | embryonic stem cells | | |
| hsa-miR-301a-5p | 620 | 1641 | embryonic stem cells | | |
| hsa-miR-301b | 621 | 1642 | | esophageal adenocarcinoma, colonic cancer | |
| hsa-miR-302a-3p | 622 | 1643 | embryonic stem cells, lipid metabolism | | lipid metabolism |
| hsa-miR-302a-5p | 623 | 1644 | embryonic stem cells, lipid metabolism | | lipid metabolism |
| hsa-miR-302b-3p | 624 | 1645 | embryonic stem cells | | |
| hsa-miR-302b-5p | 625 | 1646 | embryonic stem cells | | |
| hsa-miR-302c-3p | 626 | 1647 | embryonic stem cells | | |
| hsa-miR-302c-5p | 627 | 1648 | embryonic stem cells | | |
| hsa-miR-302d-3p | 628 | 1649 | embryonic stem cells | | |
| hsa-miR-302d-5p | 629 | 1650 | embryonic stem cells | | |
| hsa-miR-302e | 630 | 1651 | embryoid body cells | | |
| hsa-miR-302f | 631 | 1652 | | gastric cancer | |
| hsa-miR-3064-3p | 632 | 1653 | | | |
| hsa-miR-3064-5p | 633 | 1654 | | | |
| hsa-miR-3065-3p | 634 | 1655 | oligodendrocytes | anti-virus response | |
| hsa-miR-3065-5p | 635 | 1656 | oligodendrocytes | solid tumors | |
| hsa-miR-3074-3p | 636 | 1657 | | various cancer(melanoma, breast) | |
| hsa-miR-3074-5p | 637 | 1658 | | various cancer(melanoma, breast) | |
| hsa-miR-30a-3p | 638 | 1659 | kidney, pancreatic cells | various cancers | autophagy |
| hsa-miR-30a-5p | 639 | 1660 | CNS(prefrontal cortex), other tissues | glioma, colon carcinoma | autophagy |
| hsa-miR-30b-3p | 640 | 1661 | kidney, adipose, CNS(prefrontal cortex) | | |
| hsa-miR-30b-5p | 641 | 1662 | kidney, adipose, CNS(prefrontal cortex) | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-30c-1-3p | 642 | 1663 | kidney, adipose, CNS(prefrontal cortex) | | |
| hsa-miR-30c-2-3p | 643 | 1664 | kidney, adipose, CNS(prefrontal cortex) | | |
| hsa-miR-30c-5p | 644 | 1665 | kidney, adipose, CNS(prefrontal cortex) | | |
| hsa-miR-30d-3p | 645 | 1666 | CNS (prefrontal cortex | | |
| hsa-miR-30d-5p | 646 | 1667 | CNS (prefrontal cortex, embryoid body cells | | |
| hsa-miR-30e-3p | 647 | 1668 | myeloid cells, glia cells | | |
| hsa-miR-30e-5p | 648 | 1669 | myeloid cells, glia cells | | |
| hsa-miR-3115 | 649 | 1670 | | various cancer (melanoma, breast tumor) | |
| hsa-miR-3116 | 650 | 1671 | discovered in the melanoma miRNAome | | |
| hsa-miR-3117-3p | 651 | 1672 | discovered in the melanoma miRNAome | | |
| hsa-miR-3117-5p | 652 | 1673 | discovered in the melanoma miRNAome | | |
| hsa-miR-3118 | 653 | 1674 | discovered in the melanoma miRNAome | | |
| hsa-miR-3119 | 654 | 1675 | discovered in the melanoma miRNAome | | |
| hsa-miR-3120-3p | 655 | 1676 | discovered in the melanoma miRNAome | breast tumor | |
| hsa-miR-3120-5p | 656 | 1677 | discovered in the melanoma miRNAome | breast tumor | |
| hsa-miR-3121-3p | 657 | 1678 | discovered in the melanoma miRNAome | breast tumor | |
| hsa-miR-3121-5p | 658 | 1679 | discovered in the melanoma miRNAome | breast tumor | |
| hsa-miR-3122 | 659 | 1680 | discovered in the melanoma miRNAome | | |
| hsa-miR-3123 | 660 | 1681 | discovered in the melanoma miRNAome | | |
| hsa-miR-3124-3p | 661 | 1682 | discovered in the melanoma miRNAome, ovary | breast tumor | |
| hsa-miR-3124-5p | 662 | 1683 | discovered in the melanoma miRNAome, ovary | breast tumor | |
| hsa-miR-3125 | 663 | 1684 | discovered in the melanoma miRNAome | | |
| hsa-miR-3126-3p | 664 | 1685 | discovered in the melanoma miRNAome, ovary | breast tumor | |
| hsa-miR-3126-5p | 665 | 1686 | discovered in the melanoma miRNAome, ovary | breast tumor | |
| hsa-miR-3127-3p | 666 | 1687 | discovered in the melanoma miRNAome | breast tumor | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-3127-5p | 667 | 1688 | discovered in the melanoma miRNAome | breast tumor | |
| hsa-miR-3128 | 668 | 1689 | discovered in the melanoma miRNAome | breast tumor | |
| hsa-miR-3129-3p | 669 | 1690 | discovered in the melanoma miRNAome, ovary | breast tumor | |
| hsa-miR-3129-5p | 670 | 1691 | discovered in the melanoma miRNAome, ovary | breast tumor | |
| hsa-miR-3130-3p | 671 | 1692 | discovered in the melanoma miRNAome, ovary | breast tumor | |
| hsa-miR-3130-5p | 672 | 1693 | discovered in the melanoma miRNAome, ovary | breast tumor | |
| hsa-miR-3131 | 673 | 1694 | discovered in the melanoma miRNAome | breast tumor | |
| hsa-miR-3132 | 674 | 1695 | discovered in the melanoma miRNAome | | |
| hsa-miR-3133 | 675 | 1696 | discovered in the melanoma miRNAome | | |
| hsa-miR-3134 | 676 | 1697 | discovered in the melanoma miRNAome | | |
| hsa-miR-3135a | 677 | 1698 | discovered in the melanoma miRNAome | | |
| hsa-miR-3135b | 678 | 1699 | discovered in B cells | | |
| hsa-miR-3136-3p | 679 | 1700 | discovered in the melanoma miRNAome | lymphoblastic leukaemia and breast tumor | |
| hsa-miR-3136-5p | 680 | 1701 | discovered in the melanoma miRNAome | lymphoblastic leukaemia and breast tumor | |
| hsa-miR-3137 | 681 | 1702 | discovered in the melanoma miRNAome | | |
| hsa-miR-3138 | 682 | 1703 | discovered in the melanoma miRNAome, ovary | | |
| hsa-miR-3139 | 683 | 1704 | discovered in the melanoma miRNAome | | |
| hsa-miR-31-3p | 684 | 1705 | | | |
| hsa-miR-3140-3p | 685 | 1706 | discovered in the melanoma miRNAome, ovary | lymphoblastic leukaemia and breast tumor | |
| hsa-miR-3140-5p | 686 | 1707 | discovered in the melanoma miRNAome, ovary | lymphoblastic leukaemia and breast tumor | |
| hsa-miR-3141 | 687 | 1708 | discovered in the melanoma miRNAome | | |
| hsa-miR-3142 | 688 | 1709 | discovered in the melanoma miRNAome; immune cells | | |
| hsa-miR-3143 | 689 | 1710 | discovered in the melanoma miRNAome | breast tumor | |
| hsa-miR-3144-3p | 690 | 1711 | discovered in the melanoma miRNAome, ovary | | |
| hsa-miR-3144-5p | 691 | 1712 | discovered in the melanoma miRNAome, ovary | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-3145-3p | 692 | 1713 | discovered in the melanoma miRNAome | breast tumor | |
| hsa-miR-3145-5p | 693 | 1714 | discovered in the melanoma miRNAome | breast tumor | |
| hsa-miR-3146 | 694 | 1715 | discovered in the melanoma miRNAome | breast tumor | |
| hsa-miR-3147 | 695 | 1716 | discovered in the melanoma miRNAome | | |
| hsa-miR-3148 | 696 | 1717 | discovered in the melanoma miRNAome | | |
| hsa-miR-3149 | 697 | 1718 | discovered in the melanoma miRNAome, ovary | | |
| hsa-miR-3150a-3p | 698 | 1719 | discovered in the melanoma miRNAome | breast tumor | |
| hsa-miR-3150a-5p | 699 | 1720 | discovered in the melanoma miRNAome | breast tumor | |
| hsa-miR-3150b-3p | 700 | 1721 | discovered in the melanoma miRNAome | breast tumor and lymphoblastic leukaemia | |
| hsa-miR-3150b-5p | 701 | 1722 | discovered in the melanoma miRNAome | breast tumor and lymphoblastic leukaemia | |
| hsa-miR-3151 | 702 | 1723 | discovered in the melanoma miRNAome | lymphoblastic leukaemia | |
| hsa-miR-3152-3p | 703 | 1724 | discovered in the melanoma miRNAome, ovary | breast tumor | |
| hsa-miR-3152-5p | 704 | 1725 | discovered in the melanoma miRNAome, ovary | breast tumor | |
| hsa-miR-3153 | 705 | 1726 | discovered in the melanoma miRNAome | | |
| hsa-miR-3154 | 706 | 1727 | discovered in the melanoma miRNAome | lymphoblastic leukaemia | |
| hsa-miR-3155a | 707 | 1728 | discovered in the melanoma miRNAome | | |
| hsa-miR-3155b | 708 | 1729 | discovered in B cells | | |
| hsa-miR-3156-3p | 709 | 1730 | discovered in the melanoma miRNAome | breast tumor | |
| hsa-miR-3156-5p | 710 | 1731 | discovered in the melanoma miRNAome | breast tumor | |
| hsa-miR-3157-3p | 711 | 1732 | discovered in the melanoma miRNAome | breast tumor | |
| hsa-miR-3157-5p | 712 | 1733 | discovered in the melanoma miRNAome | breast tumor | |
| hsa-miR-3158-3p | 713 | 1734 | discovered in the melanoma miRNAome, ovary | breast tumor | |
| hsa-miR-3158-5p | 714 | 1735 | discovered in the melanoma miRNAome, ovary | breast tumor | |
| hsa-miR-3159 | 715 | 1736 | discovered in the melanoma miRNAome | | |
| hsa-miR-31-5p | 716 | 1737 | | various cancer cells (breast, lung, prostate) | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-3160-3p | 717 | 1738 | discovered in the melanoma miRNAome | breast tumor | |
| hsa-miR-3160-5p | 718 | 1739 | discovered in the melanoma miRNAome | breast tumor | |
| hsa-miR-3161 | 719 | 1740 | discovered in the melanoma miRNAome | | |
| hsa-miR-3162-3p | 720 | 1741 | discovered in the melanoma miRNAome | breast tumor | |
| hsa-miR-3162-5p | 721 | 1742 | discovered in the melanoma miRNAome | breast tumor | |
| hsa-miR-3163 | 722 | 1743 | discovered in the melanoma miRNAome | | |
| hsa-miR-3164 | 723 | 1744 | discovered in the melanoma miRNAome | | |
| hsa-miR-3165 | 724 | 1745 | discovered in the melanoma miRNAome | breast tumor | |
| hsa-miR-3166 | 725 | 1746 | discovered in the melanoma miRNAome | | |
| hsa-miR-3167 | 726 | 1747 | discovered in the melanoma miRNAome, ovary | | |
| hsa-miR-3168 | 727 | 1748 | discovered in the melanoma miRNAome | | |
| hsa-miR-3169 | 728 | 1749 | discovered in the melanoma miRNAome | | |
| hsa-miR-3170 | 729 | 1750 | discovered in the melanoma miRNAome | breast tumor | |
| hsa-miR-3171 | 730 | 1751 | discovered in the melanoma miRNAome, ovary | | |
| hsa-miR-3173-3p | 731 | 1752 | discovered in the melanoma miRNAome | breast tumor | |
| hsa-miR-3173-5p | 732 | 1753 | discovered in the melanoma miRNAome | breast tumor | |
| hsa-miR-3174 | 733 | 1754 | discovered in the melanoma miRNAome | | |
| hsa-miR-3175 | 734 | 1755 | discovered in the melanoma miRNAome, ovary | breast tumor | |
| hsa-miR-3176 | 735 | 1756 | discovered in the melanoma miRNAome | breast tumor | |
| hsa-miR-3177-3p | 736 | 1757 | discovered in the melanoma miRNAome | breast tumor and lymphoblastic leukaemia | |
| hsa-miR-3177-5p | 737 | 1758 | discovered in the melanoma miRNAome | breast tumor and lymphoblastic leukaemia | |
| hsa-miR-3178 | 738 | 1759 | discovered in the melanoma miRNAome | | |
| hsa-miR-3179 | 739 | 1760 | discovered in the melanoma miRNAome | | |
| hsa-miR-3180 | 740 | 1761 | discovered in the melanoma miRNAome, ovary | breast tumor | |
| hsa-miR-3180-3p | 741 | 1762 | discovered in breast tumor | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-3180-5p | 742 | 1763 | discovered in breast tumor | | |
| hsa-miR-3181 | 743 | 1764 | discovered in the melanoma miRNAome | | |
| hsa-miR-3182 | 744 | 1765 | discovered in the melanoma miRNAome | | |
| hsa-miR-3183 | 745 | 1766 | discovered in the melanoma miRNAome | | |
| hsa-miR-3184-3p | 746 | 1767 | discovered in the melanoma miRNAome | | |
| hsa-miR-3184-5p | 747 | 1768 | discovered in the melanoma miRNAome | | |
| hsa-miR-3185 | 748 | 1769 | discovered in the melanoma miRNAome | | |
| hsa-miR-3186-3p | 749 | 1770 | discovered in the melanoma miRNAome, ovary | | |
| hsa-miR-3186-5p | 750 | 1771 | discovered in the melanoma miRNAome, ovary | | |
| hsa-miR-3187-3p | 751 | 1772 | discovered in the melanoma miRNAome | breast tumor | |
| hsa-miR-3187-5p | 752 | 1773 | discovered in the melanoma miRNAome | breast tumor | |
| hsa-miR-3188 | 753 | 1774 | discovered in the melanoma miRNAome | | |
| hsa-miR-3189-3p | 754 | 1775 | discovered in the melanoma miRNAome | breast tumor | |
| hsa-miR-3189-5p | 755 | 1776 | discovered in the melanoma miRNAome | breast tumor | |
| hsa-miR-3190-3p | 756 | 1777 | discovered in the melanoma miRNAome | lymphoblastic leukaemia | |
| hsa-miR-3190-5p | 757 | 1778 | discovered in the melanoma miRNAome | lymphoblastic leukaemia | |
| hsa-miR-3191-3p | 758 | 1779 | discovered in the melanoma miRNAome | | |
| hsa-miR-3191-5p | 759 | 1780 | discovered in the melanoma miRNAome | | |
| hsa-miR-3192 | 760 | 1781 | discovered in the melanoma miRNAome | breast tumor | |
| hsa-miR-3193 | 761 | 1782 | discovered in the melanoma miRNAome | | |
| hsa-miR-3194-3p | 762 | 1783 | discovered in the melanoma miRNAome | breast tumor | |
| hsa-miR-3194-5p | 763 | 1784 | discovered in the melanoma miRNAome | breast tumor | |
| hsa-miR-3195 | 764 | 1785 | discovered in the melanoma miRNAome | | |
| hsa-miR-3196 | 765 | 1786 | | basal cell carcinoma | |
| hsa-miR-3197 | 766 | 1787 | discovered in the melanoma miRNAome | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-3198 | 767 | 1788 | discovered in the melanoma miRNAome | breast tumor | |
| hsa-miR-3199 | 768 | 1789 | discovered in the melanoma miRNAome | | |
| hsa-miR-3200-3p | 769 | 1790 | discovered in the melanoma miRNAome, ovary | breast tumor | |
| hsa-miR-3200-5p | 770 | 1791 | discovered in the melanoma miRNAome, ovary | breast tumor | |
| hsa-miR-3201 | 771 | 1792 | discovered in the melanoma miRNAome, | | |
| hsa-miR-3202 | 772 | 1793 | discovered in the melanoma miRNAome, epithelial cell BEAS2B | | |
| hsa-miR-320a | 773 | 1794 | blood, heart(myocardiac) | colon cancer cells, heart disease | |
| hsa-miR-320b | 774 | 1795 | central nevous system | | |
| hsa-miR-320c | 775 | 1796 | chondrocyte | | cartilage metabolism |
| hsa-miR-320d | 776 | 1797 | | cancer stem cells | |
| hsa-miR-320e | 777 | 1798 | neural cells | | |
| hsa-miR-323a-3p | 778 | 1799 | neurons | myeloid leukaemia, mudulla thyroid carcinoma | |
| hsa-miR-323a-5p | 779 | 1800 | neurons | myeloid leukaemia, mudulla thyroid carcinoma | |
| hsa-miR-323b-3p | 780 | 1801 | | myeloid leukaemia | |
| hsa-miR-323b-5p | 781 | 1802 | | myeloid leukaemia | |
| hsa-miR-32-3p | 782 | 1803 | blood, glia | various cancers (lung, kidney, prostate, etc), virus infection | |
| hsa-miR-324-3p | 783 | 1804 | kidney | | |
| hsa-miR-324-5p | 784 | 1805 | neurons | tumor cells | |
| hsa-miR-325 | 785 | 1806 | neurons, placenta | | |
| hsa-miR-32-5p | 786 | 1807 | blood, glia | various cancers (lung, kidney, prostate, etc), virus infection | |
| hsa-miR-326 | 787 | 1808 | neurons | tumor cells | |
| hsa-miR-328 | 788 | 1809 | neuron, blood | tumor cells | |
| hsa-miR-329 | 789 | 1810 | brain and platele | | |
| hsa-miR-330-3p | 790 | 1811 | | various cancers (prostate, glioblastoma, colorectal) | |
| hsa-miR-330-5p | 791 | 1812 | | various cancers (prostate, glioblastoma, colorectal) | |
| hsa-miR-331-3p | 792 | 1813 | | gastric cancer | |
| hsa-miR-331-5p | 793 | 1814 | lymphocytes | | |
| hsa-miR-335-3p | 794 | 1815 | kidney, breast | RCC, multiple myeloma | |
| hsa-miR-335-5p | 795 | 1816 | kidney, breast | RCC, multiple myeloma | |
| hsa-miR-337-3p | 796 | 1817 | lung | gastric cancer | |
| hsa-miR-337-5p | 797 | 1818 | lung | | |
| hsa-miR-338-3p | 798 | 1819 | epithelial cells, oligodendrocytes | gastric, rectal cancer cells, osteosarcoma | |
| hsa-miR-338-5p | 799 | 1820 | oligodendrocytes | gastric cancer | |
| hsa-miR-339-3p | 800 | 1821 | immune cell | | |
| hsa-miR-339-5p | 801 | 1822 | immune cell | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-33a-3p | 802 | 1823 | pancreatic islet, lipid metabolism | | lipid metabolism |
| hsa-miR-33a-5p | 803 | 1824 | pancreatic islet, lipid metabolism | | lipid metabolism |
| hsa-miR-33b-3p | 804 | 1825 | lipid metabolism | | lipid metabolism |
| hsa-miR-33b-5p | 805 | 1826 | lipid metabolism | | lipid metabolism |
| hsa-miR-340-3p | 806 | 1827 | | various cancers | |
| hsa-miR-340-5p | 807 | 1828 | embryoid body cells | | |
| hsa-miR-342-3p | 808 | 1829 | brain, circulating plasma | multiple myeloma, other cancers | |
| hsa-miR-342-5p | 809 | 1830 | circulating plasma | multiple myeloma, other cancers | |
| hsa-miR-345-3p | 810 | 1831 | hematopoietic cells | follicular lymphoma, other cancers | |
| hsa-miR-345-5p | 811 | 1832 | hematopoietic cells | follicular lymphoma, other cancers | |
| hsa-miR-346 | 812 | 1833 | immume cells | cancers and autoimmune | |
| hsa-miR-34a-3p | 813 | 1834 | breast, meyloid cells, ciliated epithelial cells | gastric cancer, CLL, other | tumor suppressor, p53 inducible |
| hsa-miR-34a-5p | 814 | 1835 | breast, meyloid cells, ciliated epithelial cells | gastric cancer, CLL, other | tumor suppressor, p53 inducible |
| hsa-miR-34b-3p | 815 | 1836 | ciliated epithelial cells | various cancers | tumor suppressor, p53 inducible |
| hsa-miR-34b-5p | 816 | 1837 | ciliated epithelial cells | various cancers | tumor suppressor, p53 inducible |
| hsa-miR-34c-3p | 817 | 1838 | ciliated epithelial cells, placenta | various cancers | tumor suppressor, p53 inducible |
| hsa-miR-34c-5p | 818 | 1839 | ciliated epithelial cells, placenta | various cancers | tumor suppressor, p53 inducible |
| hsa-miR-3529-3p | 819 | 1840 | discovered in breast tumor | | |
| hsa-miR-3529-5p | 820 | 1841 | discovered in breast tumor | | |
| hsa-miR-3591-3p | 821 | 1842 | discovered in breast tumor | | |
| hsa-miR-3591-5p | 822 | 1843 | discovered in breast tumor | | |
| hsa-miR-3605-3p | 823 | 1844 | discovered in reprodcutive tracts | | |
| hsa-miR-3605-5p | 824 | 1845 | discovered in reprodcutive tracts | | |
| hsa-miR-3606-3p | 825 | 1846 | discovered in cervical tumors | | |
| hsa-miR-3606-5p | 826 | 1847 | discovered in cervical tumors | | |
| hsa-miR-3607-3p | 827 | 1848 | discovered in cervical tumors | | |
| hsa-miR-3607-5p | 828 | 1849 | discovered in cervical tumors | | |
| hsa-miR-3609 | 829 | 1850 | discovered in cervical tumors | | |
| hsa-miR-3610 | 830 | 1851 | discovered in cervical tumors | | |
| hsa-miR-3611 | 831 | 1852 | discovered in cervical tumors | | |
| hsa-miR-3612 | 832 | 1853 | discovered in cervical tumors | | |
| hsa-miR-3613-3p | 833 | 1854 | discovered in cervical tumors | | |
| hsa-miR-3613-5p | 834 | 1855 | discovered in cervical tumors | | |
| hsa-miR-361-3p | 835 | 1856 | blood, endothelial cells | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-3614-3p | 836 | 1857 | discovered in cervical and breast tumors | | |
| hsa-miR-3614-5p | 837 | 1858 | discovered in cervical and breast tumors | | |
| hsa-miR-3615 | 838 | 1859 | discovered in cervical tumors | | |
| hsa-miR-361-5p | 839 | 1860 | endothelial cells | | |
| hsa-miR-3616-3p | 840 | 1861 | discovered in cervical tumors | | |
| hsa-miR-3616-5p | 841 | 1862 | discovered in cervical tumors | | |
| hsa-miR-3617-3p | 842 | 1863 | discovered in cervical tumors and psoriasis | | |
| hsa-miR-3617-5p | 843 | 1864 | discovered in cervical tumors and psoriasis | | |
| hsa-miR-3618 | 844 | 1865 | discovered in cervical tumors | | |
| hsa-miR-3619-3p | 845 | 1866 | discovered in breast tumors | | |
| hsa-miR-3619-5p | 846 | 1867 | discovered in breast tumors | | |
| hsa-miR-3620-3p | 847 | 1868 | discovered in cervical tumors | | |
| hsa-miR-3620-5p | 848 | 1869 | discovered in cervical tumors | | |
| hsa-miR-3621 | 849 | 1870 | discovered in cervical tumors | | |
| hsa-miR-3622a-3p | 850 | 1871 | discovered in breast tumors | | |
| hsa-miR-3622a-5p | 851 | 1872 | discovered in breast tumors | | |
| hsa-miR-3622b-3p | 852 | 1873 | discovered in cervical tumors | | |
| hsa-miR-3622b-5p | 853 | 1874 | discovered in cervical tumors | | |
| hsa-miR-362-3p | 854 | 1875 | | melanoma | |
| hsa-miR-362-5p | 855 | 1876 | | melanoma | |
| hsa-miR-363-3p | 856 | 1877 | kidney stem cell, blood cells | | |
| hsa-miR-363-5p | 857 | 1878 | kidney stem cell, blood cells | | |
| hsa-miR-3646 | 858 | 1879 | discovered in solid tumor | | |
| hsa-miR-3648 | 859 | 1880 | discovered in solid tumor | | |
| hsa-miR-3649 | 860 | 1881 | discovered in solid tumor | | |
| hsa-miR-3650 | 861 | 1882 | discovered in solid tumor | | |
| hsa-miR-3651 | 862 | 1883 | discovered in solid tumor | | |
| hsa-miR-3652 | 863 | 1884 | discovered in solid tumor | | |
| hsa-miR-3653 | 864 | 1885 | discovered in solid tumor | | |
| hsa-miR-3654 | 865 | 1886 | discovered in solid tumor | | |
| hsa-miR-3655 | 866 | 1887 | discovered in solid tumor | | |
| hsa-miR-3656 | 867 | 1888 | discovered in solid tumor | | |
| hsa-miR-3657 | 868 | 1889 | discovered in solid tumor | | |
| hsa-miR-3658 | 869 | 1890 | discovered in solid tumor | | |
| hsa-miR-3659 | 870 | 1891 | discovered in breast tumors | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-365a-3p | 871 | 1892 | | various cancer cells (Immune cells, lung, colon, endometriotic) | apoptosis |
| hsa-miR-365a-5p | 872 | 1893 | | various cancer cells (Immune cells, lung, colon, endometriotic)) | apoptosis |
| hsa-miR-365b-3p | 873 | 1894 | | various cancers (retinoblastoma, colon, endometriotic) | apoptosis |
| hsa-miR-365b-5p | 874 | 1895 | | various cancers (colon, endometriotic) | apoptosis |
| hsa-miR-3660 | 875 | 1896 | discovered in breast tumors | | |
| hsa-miR-3661 | 876 | 1897 | discovered in breast tumors | | |
| hsa-miR-3662 | 877 | 1898 | — | | |
| hsa-miR-3663-3p | 878 | 1899 | — | | |
| hsa-miR-3663-5p | 879 | 1900 | — | | |
| hsa-miR-3664-3p | 880 | 1901 | discovered in breast tumors | | |
| hsa-miR-3664-5p | 881 | 1902 | discovered in breast tumors | | |
| hsa-miR-3665 | 882 | 1903 | brain | | |
| hsa-miR-3666 | 883 | 1904 | brain | | |
| hsa-miR-3667-3p | 884 | 1905 | discovered in peripheral blood | | |
| hsa-miR-3667-5p | 885 | 1906 | discovered in peripheral blood | | |
| hsa-miR-3668 | 886 | 1907 | discovered in peripheral blood | | |
| hsa-miR-3669 | 887 | 1908 | discovered in peripheral blood | | |
| hsa-miR-3670 | 888 | 1909 | discovered in peripheral blood | | |
| hsa-miR-3671 | 889 | 1910 | discovered in peripheral blood | | |
| hsa-miR-3672 | 890 | 1911 | discovered in peripheral blood | | |
| hsa-miR-3673 | 891 | 1912 | discovered in peripheral blood | | |
| hsa-miR-367-3p | 892 | 1913 | embryonic stem cells | | reprogramming |
| hsa-miR-3674 | 893 | 1914 | discovered in peripheral blood | | |
| hsa-miR-3675-3p | 894 | 1915 | discovered in peripheral blood | | |
| hsa-miR-3675-5p | 895 | 1916 | discovered in peripheral blood | | |
| hsa-miR-367-5p | 896 | 1917 | embryonic stem cells | | reprogramming |
| hsa-miR-3676-3p | 897 | 1918 | discovered in peripheral blood | | |
| hsa-miR-3676-5p | 898 | 1919 | discovered in peripheral blood | | |
| hsa-miR-3677-3p | 899 | 1920 | discovered in peripheral blood | | |
| hsa-miR-3677-5p | 900 | 1921 | discovered in peripheral blood | | |
| hsa-miR-3678-3p | 901 | 1922 | discovered in peripheral blood | | |
| hsa-miR-3678-5p | 902 | 1923 | discovered in peripheral blood | | |
| hsa-miR-3679-3p | 903 | 1924 | discovered in peripheral blood | | |
| hsa-miR-3679-5p | 904 | 1925 | discovered in peripheral blood | | |
| hsa-miR-3680-3p | 905 | 1926 | discovered in peripheral blood | | |
| hsa-miR-3680-5p | 906 | 1927 | discovered in peripheral blood | | |
| hsa-miR-3681-3p | 907 | 1928 | discovered in peripheral blood | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-3681-5p | 908 | 1929 | discovered in peripheral blood | | |
| hsa-miR-3682-3p | 909 | 1930 | discovered in peripheral blood | | |
| hsa-miR-3682-5p | 910 | 1931 | discovered in peripheral blood | | |
| hsa-miR-3683 | 911 | 1932 | discovered in peripheral blood | | |
| hsa-miR-3684 | 912 | 1933 | discovered in peripheral blood | | |
| hsa-miR-3685 | 913 | 1934 | discovered in peripheral blood | | |
| hsa-miR-3686 | 914 | 1935 | discovered in peripheral blood | | |
| hsa-miR-3687 | 915 | 1936 | discovered in peripheral blood | | |
| hsa-miR-3688-3p | 916 | 1937 | discovered in breast tumor | | |
| hsa-miR-3688-5p | 917 | 1938 | discovered in breast tumor | | |
| hsa-miR-3689a-3p | 918 | 1939 | discovered in female reproductuve tract | | |
| hsa-miR-3689a-5p | 919 | 1940 | discovered in female reproductuve tract and peripheral blood | | |
| hsa-miR-3689b-3p | 920 | 1941 | discovered in female reproductuve tract and peripheral blood | | |
| hsa-miR-3689b-5p | 921 | 1942 | discovered in female reproductuve tract | | |
| hsa-miR-3689c | 922 | 1943 | discovered in B cells | | |
| hsa-miR-3689d | 923 | 1944 | discovered in B cells | | |
| hsa-miR-3689e | 924 | 1945 | discovered in B cells | | |
| hsa-miR-3689f | 925 | 1946 | discovered in B cells | | |
| hsa-miR-3690 | 926 | 1947 | discovered in peripheral blood | | |
| hsa-miR-3691-3p | 927 | 1948 | discovered in peripheral blood | | |
| hsa-miR-3691-5p | 928 | 1949 | discovered in peripheral blood | | |
| hsa-miR-3692-3p | 929 | 1950 | discovered in peripheral blood | | |
| hsa-miR-3692-5p | 930 | 1951 | discovered in peripheral blood | | |
| hsa-miR-369-3p | 931 | 1952 | stem cells | | reprogramming |
| hsa-miR-369-5p | 932 | 1953 | stem cells | | reprogramming |
| hsa-miR-370 | 933 | 1954 | | acute meyloid leukaemia and other cancers | tumor suppressor, lipid metabolism |
| hsa-miR-3713 | 934 | 1955 | discovered in neuroblastoma | | |
| hsa-miR-3714 | 935 | 1956 | discovered in neuroblastoma | | |
| hsa-miR-371a-3p | 936 | 1957 | serum | | |
| hsa-miR-371a-5p | 937 | 1958 | serum | | |
| hsa-miR-371b-3p | 938 | 1959 | serum | | |
| hsa-miR-371b-5p | 939 | 1960 | serum | | |
| hsa-miR-372 | 940 | 1961 | hematopoietic cells, lung, placental (blood) | | |
| hsa-miR-373-3p | 941 | 1962 | | breast cancer | |
| hsa-miR-373-5p | 942 | 1963 | | breast cancer | |
| hsa-miR-374a-3p | 943 | 1964 | muscle (myoblasts) | breast and lung cancer | myogenic differentiation |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-374a-5p | 944 | 1965 | muscle (myoblasts) | breast and lung cancer | myogenic differentiation |
| hsa-miR-374b-3p | 945 | 1966 | muscle (myoblasts) | | myogenic differentiation |
| hsa-miR-374b-5p | 946 | 1967 | muscle (myoblasts) | | myogenic differentiation |
| hsa-miR-374c-3p | 947 | 1968 | muscle (myoblasts) | | myogenic differentiation |
| hsa-miR-374c-5p | 948 | 1969 | muscle (myoblasts) | | myogenic differentiation |
| hsa-miR-375 | 949 | 1970 | pancreas (islet) | | |
| hsa-miR-376a-2-5p | 950 | 1971 | regulatory miRs for hematopoietic cells (erythroid, platelet, lympho) | | |
| hsa-miR-376a-3p | 951 | 1972 | regulatory miRs for hematopoietic cells (erythroid, platelet, lympho) | | |
| hsa-miR-376a-5p | 952 | 1973 | regulatory miRs for hematopoietic cells (erythroid, platelet, lympho) | | |
| hsa-miR-376b-3p | 953 | 1974 | blood | various cancer cells | autophagy |
| hsa-miR-376b-5p | 954 | 1975 | blood | various cancer cells | autophagy |
| hsa-miR-376c-3p | 955 | 1976 | trophoblast | various cancer cells | cell proliferatio |
| hsa-miR-376c-5p | 956 | 1977 | trophoblast | various cancer cells | cell proliferatio |
| hsa-miR-377-3p | 957 | 1978 | hematopoietic cells | | |
| hsa-miR-377-5p | 958 | 1979 | hematopoietic cells | | |
| hsa-miR-378a-3p | 959 | 1980 | ovary, lipid metabolism | | |
| hsa-miR-378a-5p | 960 | 1981 | ovary, placenta/ trophoblast, lipid metabolism | | |
| hsa-miR-378b | 961 | 1982 | lipid metabolism | | |
| hsa-miR-378c | 962 | 1983 | lipid metabolism | | |
| hsa-miR-378d | 963 | 1984 | lipid metabolism | | |
| hsa-miR-378e | 964 | 1985 | lipid metabolism | | |
| hsa-miR-378f | 965 | 1986 | lipid metabolism | | |
| hsa-miR-378g | 966 | 1987 | lipid metabolism | | |
| hsa-miR-378h | 967 | 1988 | lipid metabolism | | |
| hsa-miR-378i | 968 | 1989 | lipid metabolism | | |
| hsa-miR-378j | 969 | 1990 | lipid metabolism | | |
| hsa-miR-379-3p | 970 | 1991 | | various cancers (breast, hepatocytes, colon) | |
| hsa-miR-379-5p | 971 | 1992 | | various cancers (breast, hepatocytes, colon) | |
| hsa-miR-380-3p | 972 | 1993 | brain | neuroblastoma | |
| hsa-miR-380-5p | 973 | 1994 | brain, embryonic stem cells | neuroblastoma | |
| hsa-miR-381-3p | 974 | 1995 | chondrogenesis, lung, brain | | |
| hsa-miR-381-5p | 975 | 1996 | chondrogenesis, lung, brain | | |
| hsa-miR-382-3p | 976 | 1997 | renal epithelial cells | | |
| hsa-miR-382-5p | 977 | 1998 | renal epithelial cells | | |
| hsa-miR-383 | 978 | 1999 | testes, brain (medulla) | | |
| hsa-miR-384 | 979 | 2000 | epithelial cells | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-3907 | 980 | 2001 | discovered in female reproductive tract | | |
| hsa-miR-3908 | 981 | 2002 | discovered in female reproductive tract | | |
| hsa-miR-3909 | 982 | 2003 | discovered in female reproductive tract | | |
| hsa-miR-3910 | 983 | 2004 | discovered in female reproductive tract | | |
| hsa-miR-3911 | 984 | 2005 | discovered in breast tumor and female reproductive tract | | |
| hsa-miR-3912 | 985 | 2006 | discovered in female reproductive tract | | |
| hsa-miR-3913-3p | 986 | 2007 | discovered in breast tumor and female reproductive tract | | |
| hsa-miR-3913-5p | 987 | 2008 | discovered in breast tumor and female reproductive tract | | |
| hsa-miR-3914 | 988 | 2009 | discovered in breast tumor and female reproductive tract | | |
| hsa-miR-3915 | 989 | 2010 | discovered in female reproductive tract | | |
| hsa-miR-3916 | 990 | 2011 | discovered in female reproductive tract | | |
| hsa-miR-3917 | 991 | 2012 | discovered in female reproductive tract | | |
| hsa-miR-3918 | 992 | 2013 | discovered in female reproductive tract | | |
| hsa-miR-3919 | 993 | 2014 | discovered in female reproductive tract | | |
| hsa-miR-3920 | 994 | 2015 | discovered in female reproductive tract | | |
| hsa-miR-3921 | 995 | 2016 | discovered in female reproductive tract | | |
| hsa-miR-3922-3p | 996 | 2017 | discovered in breast tumor and female reproductive tract | | |
| hsa-miR-3922-5p | 997 | 2018 | discovered in breast tumor and female reproductive tract | | |
| hsa-miR-3923 | 998 | 2019 | discovered in female reproductive tract | | |
| hsa-miR-3924 | 999 | 2020 | discovered in female reproductive tract | | |
| hsa-miR-3925-3p | 1000 | 2021 | discovered in breast tumor and female reproductive tract | | |
| hsa-miR-3925-5p | 1001 | 2022 | discovered in breast tumor and female reproductive tract | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-3926 | 1002 | 2023 | discovered in female reproductive tract | | |
| hsa-miR-3927-3p | 1003 | 2024 | discovered in female reproductive tract and psoriasis | | |
| hsa-miR-3927-5p | 1004 | 2025 | discovered in female reproductive tract and psoriasis | | |
| hsa-miR-3928 | 1005 | 2026 | discovered in female reproductive tract | | |
| hsa-miR-3929 | 1006 | 2027 | discovered in female reproductive tract | | |
| hsa-miR-3934-3p | 1007 | 2028 | discovered in abnormal skin (psoriasis) | | |
| hsa-miR-3934-5p | 1008 | 2029 | discovered in abnormal skin (psoriasis) | | |
| hsa-miR-3935 | 1009 | 2030 | | | |
| hsa-miR-3936 | 1010 | 2031 | discovered in breast tumor and lymphoblastic leukaemia | | |
| hsa-miR-3937 | 1011 | 2032 | | | |
| hsa-miR-3938 | 1012 | 2033 | | | |
| hsa-miR-3939 | 1013 | 2034 | | | |
| hsa-miR-3940-3p | 1014 | 2035 | discovered in breast tumor | | |
| hsa-miR-3940-5p | 1015 | 2036 | discovered in breast tumor | | |
| hsa-miR-3941 | 1016 | 2037 | | | |
| hsa-miR-3942-3p | 1017 | 2038 | discovered in breast tumor and lymphoblastic leukaemia | | |
| hsa-miR-3942-5p | 1018 | 2039 | discovered in breast tumor and lymphoblastic leukaemia | | |
| hsa-miR-3943 | 1019 | 2040 | | | |
| hsa-miR-3944-3p | 1020 | 2041 | discovered in breast tumor | | |
| hsa-miR-3944-5p | 1021 | 2042 | discovered in breast tumor | | |
| hsa-miR-3945 | 1022 | 2043 | | | |
| hsa-miR-3960 | 1023 | 2044 | osteoblast | | |
| hsa-miR-3972 | 1024 | 2045 | discovered in Acute Myeloid Leukaemia | | |
| hsa-miR-3973 | 1025 | 2046 | discovered in Acute Myeloid Leukaemia | | |
| hsa-miR-3974 | 1026 | 2047 | discovered in Acute Myeloid Leukaemia | | |
| hsa-miR-3975 | 1027 | 2048 | discovered in Acute Myeloid Leukaemia | | |
| hsa-miR-3976 | 1028 | 2049 | discovered in Acute Myeloid Leukaemia | | |
| hsa-miR-3977 | 1029 | 2050 | discovered in Acute Myeloid Leukaemia | | |
| hsa-miR-3978 | 1030 | 2051 | discovered in Acute Myeloid Leukaemia | | |
| hsa-miR-409-3p | 1031 | 2052 | | gastric cancer | |
| hsa-miR-409-5p | 1032 | 2053 | | gastric cancer | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-410 | 1033 | 2054 | brain | glioma | |
| hsa-miR-411-3p | 1034 | 2055 | | Glioblastoma others | |
| hsa-miR-411-5p | 1035 | 2056 | | Glioblastoma others | |
| hsa-miR-412 | 1036 | 2057 | | upregulated in lung cancer | |
| hsa-miR-421 | 1037 | 2058 | endothelial cells | gastric cancer, HCC | |
| hsa-miR-422a | 1038 | 2059 | circulating microRNA (in plasma) | | |
| hsa-miR-423-3p | 1039 | 2060 | embryonic stem cells | | |
| hsa-miR-423-5p | 1040 | 2061 | heart, embryonic stem cells | | |
| hsa-miR-424-3p | 1041 | 2062 | endothelial cells | various cancers(e.g B-lieage ALL), cardiac diseases | pro-angiogenic |
| hsa-miR-424-5p | 1042 | 2063 | endothelial cells | various cancers(e.g B-lieage ALL), cardiac diseases | pro-angiogenic |
| hsa-miR-4251 | 1043 | 2064 | discovered in embryonic stem cells and neural precusors | | |
| hsa-miR-4252 | 1044 | 2065 | discovered in embryonic stem cells and neural precusors | | |
| hsa-miR-4253 | 1045 | 2066 | discovered in embryonic stem cells and neural precusors | | |
| hsa-miR-425-3p | 1046 | 2067 | brain | ovarian cancer, brain tumor | |
| hsa-miR-4254 | 1047 | 2068 | discovered in embryonic stem cells and neural precusors | | |
| hsa-miR-4255 | 1048 | 2069 | discovered in embryonic stem cells and neural precusors | | |
| hsa-miR-425-5p | 1049 | 2070 | brain | B-lieage ALL, brain tumor | |
| hsa-miR-4256 | 1050 | 2071 | discovered in embryonic stem cells and neural precusors | | |
| hsa-miR-4257 | 1051 | 2072 | discovered in embryonic stem cells and neural precusors | | |
| hsa-miR-4258 | 1052 | 2073 | discovered in embryonic stem cells and neural precusors | | |
| hsa-miR-4259 | 1053 | 2074 | discovered in embryonic stem cells and neural precusors | | |
| hsa-miR-4260 | 1054 | 2075 | discovered in embryonic stem cells and neural precusors | | |
| hsa-miR-4261 | 1055 | 2076 | discovered in embryonic stem cells and neural precusors | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-4262 | 1056 | 2077 | discovered in embryonic stem cells and neural precusors | | |
| hsa-miR-4263 | 1057 | 2078 | discovered in embryonic stem cells and neural precusors | | |
| hsa-miR-4264 | 1058 | 2079 | discovered in embryonic stem cells and neural precusors | | |
| hsa-miR-4265 | 1059 | 2080 | discovered in embryonic stem cells and neural precusors | | |
| hsa-miR-4266 | 1060 | 2081 | discovered in embryonic stem cells and neural precusors | | |
| hsa-miR-4267 | 1061 | 2082 | discovered in embryonic stem cells and neural precusors | | |
| hsa-miR-4268 | 1062 | 2083 | discovered in embryonic stem cells and neural precusors | | |
| hsa-miR-4269 | 1063 | 2084 | discovered in embryonic stem cells and neural precusors | | |
| hsa-miR-4270 | 1064 | 2085 | discovered in embryonic stem cells and neural precusors | | |
| hsa-miR-4271 | 1065 | 2086 | discovered in embryonic stem cells and neural precusors | | |
| hsa-miR-4272 | 1066 | 2087 | discovered in embryonic stem cells and neural precusors | | |
| hsa-miR-4273 | 1067 | 2088 | | | |
| hsa-miR-4274 | 1068 | 2089 | discovered in embryonic stem cells and neural precusors | | |
| hsa-miR-4275 | 1069 | 2090 | discovered in embryonic stem cells and neural precusors | | |
| hsa-miR-4276 | 1070 | 2091 | discovered in embryonic stem cells and neural precusors | | |
| hsa-miR-4277 | 1071 | 2092 | discovered in embryonic stem cells and neural precusors | | |
| hsa-miR-4278 | 1072 | 2093 | discovered in embryonic stem cells and neural precusors | | |
| hsa-miR-4279 | 1073 | 2094 | discovered in embryonic stem cells and neural precusors | | |
| hsa-miR-4280 | 1074 | 2095 | discovered in embryonic stem cells and neural precusors | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-4281 | 1075 | 2096 | discovered in embryonic stem cells and neural precusors | | |
| hsa-miR-4282 | 1076 | 2097 | discovered in embryonic stem cells and neural precusors | | |
| hsa-miR-4283 | 1077 | 2098 | discovered in embryonic stem cells and neural precusors | | |
| hsa-miR-4284 | 1078 | 2099 | discovered in embryonic stem cells and neural precusors | | |
| hsa-miR-4285 | 1079 | 2100 | discovered in embryonic stem cells and neural precusors | | |
| hsa-miR-4286 | 1080 | 2101 | discovered in embryonic stem cells and neural precusors | | |
| hsa-miR-4287 | 1081 | 2102 | discovered in embryonic stem cells and neural precusors | | |
| hsa-miR-4288 | 1082 | 2103 | discovered in embryonic stem cells and neural precusors | | |
| hsa-miR-4289 | 1083 | 2104 | discovered in embryonic stem cells and neural precusors | | |
| hsa-miR-429 | 1084 | 2105 | Epithelial cells | various cancers (colorectal, endometrial, gastric, ovarian etc) | |
| hsa-miR-4290 | 1085 | 2106 | discovered in embryonic stem cells and neural precusors | | |
| hsa-miR-4291 | 1086 | 2107 | discovered in embryonic stem cells and neural precusors | | |
| hsa-miR-4292 | 1087 | 2108 | discovered in embryonic stem cells and neural precusors | | |
| hsa-miR-4293 | 1088 | 2109 | discovered in embryonic stem cells and neural precusors | | |
| hsa-miR-4294 | 1089 | 2110 | discovered in embryonic stem cells and neural precusors | | |
| hsa-miR-4295 | 1090 | 2111 | discovered in embryonic stem cells and neural precusors | | |
| hsa-miR-4296 | 1091 | 2112 | discovered in embryonic stem cells and neural precusors | | |
| hsa-miR-4297 | 1092 | 2113 | discovered in embryonic stem cells and neural precusors | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-4298 | 1093 | 2114 | discovered in embryonic stem cells and neural precusors | | |
| hsa-miR-4299 | 1094 | 2115 | discovered in embryonic stem cells and neural precusors | | |
| hsa-miR-4300 | 1095 | 2116 | discovered in embryonic stem cells and neural precusors | | |
| hsa-miR-4301 | 1096 | 2117 | discovered in embryonic stem cells and neural precusors | | |
| hsa-miR-4302 | 1097 | 2118 | discovered in embryonic stem cells and neural precusors | | |
| hsa-miR-4303 | 1098 | 2119 | discovered in embryonic stem cells and neural precusors | | |
| hsa-miR-4304 | 1099 | 2120 | discovered in embryonic stem cells and neural precusors | | |
| hsa-miR-4305 | 1100 | 2121 | discovered in embryonic stem cells and neural precusors | | |
| hsa-miR-4306 | 1101 | 2122 | discovered in embryonic stem cells and neural precusors | | |
| hsa-miR-4307 | 1102 | 2123 | discovered in embryonic stem cells and neural precusors | | |
| hsa-miR-4308 | 1103 | 2124 | discovered in embryonic stem cells and neural precusors | | |
| hsa-miR-4309 | 1104 | 2125 | discovered in embryonic stem cells and neural precusors | | |
| hsa-miR-4310 | 1105 | 2126 | discovered in embryonic stem cells and neural precusors | | |
| hsa-miR-4311 | 1106 | 2127 | discovered in embryonic stem cells and neural precusors | | |
| hsa-miR-4312 | 1107 | 2128 | discovered in embryonic stem cells and neural precusors | | |
| hsa-miR-4313 | 1108 | 2129 | discovered in embryonic stem cells and neural precusors | | |
| hsa-miR-431-3p | 1109 | 2130 | | Cancers (follicular lymphoma) | |
| hsa-miR-4314 | 1110 | 2131 | discovered in embryonic stem cells and neural precusors | | |
| hsa-miR-4315 | 1111 | 2132 | discovered in embryonic stem cells and neural precusors | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-431-5p | 1112 | 2133 | | Cancers (follicular lymphoma) | |
| hsa-miR-4316 | 1113 | 2134 | discovered in embryonic stem cells and neural precusors | | |
| hsa-miR-4317 | 1114 | 2135 | discovered in embryonic stem cells and neural precusors | | |
| hsa-miR-4318 | 1115 | 2136 | discovered in embryonic stem cells and neural precusors | | |
| hsa-miR-4319 | 1116 | 2137 | discovered in embryonic stem cells and neural precusors | | |
| hsa-miR-4320 | 1117 | 2138 | discovered in embryonic stem cells and neural precusors | | |
| hsa-miR-4321 | 1118 | 2139 | discovered in embryonic stem cells and neural precusors | | |
| hsa-miR-4322 | 1119 | 2140 | discovered in embryonic stem cells and neural precusors | | |
| hsa-miR-4323 | 1120 | 2141 | discovered in embryonic stem cells and neural precusors | | |
| hsa-miR-432-3p | 1121 | 2142 | myoblast | | myogenic differentiation |
| hsa-miR-4324 | 1122 | 2143 | discovered in embryonic stem cells and neural precusors | | |
| hsa-miR-4325 | 1123 | 2144 | discovered in embryonic stem cells and neural precusors | | |
| hsa-miR-432-5p | 1124 | 2145 | myoblast | | myogenic differentiation |
| hsa-miR-4326 | 1125 | 2146 | discovered in embryonic stem cells and neural precusors | | |
| hsa-miR-4327 | 1126 | 2147 | discovered in embryonic stem cells and neural precusors | | |
| hsa-miR-4328 | 1127 | 2148 | discovered in embryonic stem cells and neural precusors | | |
| hsa-miR-4329 | 1128 | 2149 | discovered in embryonic stem cells and neural precusors | | |
| hsa-miR-433 | 1129 | 2150 | | various diseases (cancer, Parkinson's, Chondrodysplasia) | |
| hsa-miR-4330 | 1130 | 2151 | discovered in embryonic stem cells and neural precusors | | |
| hsa-miR-4417 | 1131 | 2152 | discovered in B cells | | |
| hsa-miR-4418 | 1132 | 2153 | discovered in B cells | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-4419a | 1133 | 2154 | discovered in B cells | | |
| hsa-miR-4419b | 1134 | 2155 | discovered in B cells | | |
| hsa-miR-4420 | 1135 | 2156 | discovered in B cells | | |
| hsa-miR-4421 | 1136 | 2157 | discovered in B cells | | |
| hsa-miR-4422 | 1137 | 2158 | discovered in breast tumor and B cells | | |
| hsa-miR-4423-3p | 1138 | 2159 | discovered in breast tumor, B cells and skin(psoriasis) | | |
| hsa-miR-4423-5p | 1139 | 2160 | discovered in breast tumor B cells and skin(psoriasis) | | |
| hsa-miR-4424 | 1140 | 2161 | discovered in B cells | | |
| hsa-miR-4425 | 1141 | 2162 | discovered in B cells | | |
| hsa-miR-4426 | 1142 | 2163 | discovered in B cells | | |
| hsa-miR-4427 | 1143 | 2164 | discovered in B cells | | |
| hsa-miR-4428 | 1144 | 2165 | discovered in B cells | | |
| hsa-miR-4429 | 1145 | 2166 | discovered in B cells | | |
| hsa-miR-4430 | 1146 | 2167 | discovered in B cells | | |
| hsa-miR-4431 | 1147 | 2168 | discovered in B cells | | |
| hsa-miR-4432 | 1148 | 2169 | discovered in B cells | | |
| hsa-miR-4433-3p | 1149 | 2170 | discovered in B cells | | |
| hsa-miR-4433-5p | 1150 | 2171 | discovered in B cells | | |
| hsa-miR-4434 | 1151 | 2172 | discovered in B cells | | |
| hsa-miR-4435 | 1152 | 2173 | discovered in B cells | | |
| hsa-miR-4436a | 1153 | 2174 | discovered in breast tumor and B cells | | |
| hsa-miR-4436b-3p | 1154 | 2175 | discovered in breast tumor | | |
| hsa-miR-4436b-5p | 1155 | 2176 | discovered in breast tumor | | |
| hsa-miR-4437 | 1156 | 2177 | discovered in B cells | | |
| hsa-miR-4438 | 1157 | 2178 | discovered in B cells | | |
| hsa-miR-4439 | 1158 | 2179 | discovered in B cells | | |
| hsa-miR-4440 | 1159 | 2180 | discovered in B cells | | |
| hsa-miR-4441 | 1160 | 2181 | discovered in B cells | | |
| hsa-miR-4442 | 1161 | 2182 | discovered in B cells | | |
| hsa-miR-4443 | 1162 | 2183 | discovered in B cells | | |
| hsa-miR-4444 | 1163 | 2184 | discovered in B cells | | |
| hsa-miR-4445-3p | 1164 | 2185 | discovered in B cells | | |
| hsa-miR-4445-5p | 1165 | 2186 | discovered in B cells | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-4446-3p | 1166 | 2187 | discovered in breast tumor and B cells | | |
| hsa-miR-4446-5p | 1167 | 2188 | discovered in breast tumor and B cells | | |
| hsa-miR-4447 | 1168 | 2189 | discovered in B cells | | |
| hsa-miR-4448 | 1169 | 2190 | discovered in B cells | | |
| hsa-miR-4449 | 1170 | 2191 | discovered in B cells | | |
| hsa-miR-4450 | 1171 | 2192 | discovered in B cells | | |
| hsa-miR-4451 | 1172 | 2193 | discovered in B cells | | |
| hsa-miR-4452 | 1173 | 2194 | discovered in B cells | | |
| hsa-miR-4453 | 1174 | 2195 | discovered in B cells | | |
| hsa-miR-4454 | 1175 | 2196 | discovered in B cells | | |
| hsa-miR-4455 | 1176 | 2197 | discovered in B cells | | |
| hsa-miR-4456 | 1177 | 2198 | discovered in B cells | | |
| hsa-miR-4457 | 1178 | 2199 | discovered in B cells | | |
| hsa-miR-4458 | 1179 | 2200 | discovered in B cells | | |
| hsa-miR-4459 | 1180 | 2201 | discovered in B cells | | |
| hsa-miR-4460 | 1181 | 2202 | discovered in B cells | | |
| hsa-miR-4461 | 1182 | 2203 | discovered in B cells | | |
| hsa-miR-4462 | 1183 | 2204 | discovered in B cells | | |
| hsa-miR-4463 | 1184 | 2205 | discovered in B cells | | |
| hsa-miR-4464 | 1185 | 2206 | discovered in B cells | | |
| hsa-miR-4465 | 1186 | 2207 | discovered in B cells | | |
| hsa-miR-4466 | 1187 | 2208 | discovered in B cells | | |
| hsa-miR-4467 | 1188 | 2209 | discovered in breast tumor and B cells | | |
| hsa-miR-4468 | 1189 | 2210 | discovered in B cells | | |
| hsa-miR-4469 | 1190 | 2211 | discovered in breast tumor and B cells | | |
| hsa-miR-4470 | 1191 | 2212 | discovered in B cells | | |
| hsa-miR-4471 | 2213 | 3234 | discovered in breast tumor and B cells | | |
| hsa-miR-4472 | 2214 | 3235 | discovered in B cells | | |
| hsa-miR-4473 | 2215 | 3236 | discovered in B cells | | |
| hsa-miR-4474-3p | 2216 | 3237 | discovered in breast tumor, lymphoblastic leukaemia and B cells | | |
| hsa-miR-4474-5p | 2217 | 3238 | discovered in breast tumor, lymphoblastic leukaemia and B cells | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-4475 | 2218 | 3239 | discovered in B cells | | |
| hsa-miR-4476 | 2219 | 3240 | discovered in B cells | | |
| hsa-miR-4477a | 2220 | 3241 | discovered in B cells | | |
| hsa-miR-4477b | 2221 | 3242 | discovered in B cells | | |
| hsa-miR-4478 | 2222 | 3243 | discovered in B cells | | |
| hsa-miR-4479 | 2223 | 3244 | discovered in B cells | | |
| hsa-miR-448 | 2224 | 3245 | liver(hepatocytes) | HCC | |
| hsa-miR-4480 | 2225 | 3246 | discovered in B cells | | |
| hsa-miR-4481 | 2226 | 3247 | discovered in B cells | | |
| hsa-miR-4482-3p | 2227 | 3248 | discovered in B cells | | |
| hsa-miR-4482-5p | 2228 | 3249 | discovered in B cells | | |
| hsa-miR-4483 | 2229 | 3250 | discovered in B cells | | |
| hsa-miR-4484 | 2230 | 3251 | discovered in B cells | | |
| hsa-miR-4485 | 2231 | 3252 | discovered in B cells | | |
| hsa-miR-4486 | 2232 | 3253 | discovered in B cells | | |
| hsa-miR-4487 | 2233 | 3254 | discovered in B cells | | |
| hsa-miR-4488 | 2234 | 3255 | discovered in B cells | | |
| hsa-miR-4489 | 2235 | 3256 | discovered in breast tumor and B cells | | |
| hsa-miR-4490 | 2236 | 3257 | discovered in B cells | | |
| hsa-miR-4491 | 2237 | 3258 | discovered in B cells | | |
| hsa-miR-4492 | 2238 | 3259 | discovered in B cells | | |
| hsa-miR-4493 | 2239 | 3260 | discovered in B cells | | |
| hsa-miR-4494 | 2240 | 3261 | discovered in B cells | | |
| hsa-miR-4495 | 2241 | 3262 | discovered in B cells | | |
| hsa-miR-4496 | 2242 | 3263 | discovered in B cells | | |
| hsa-miR-4497 | 2243 | 3264 | discovered in B cells | | |
| hsa-miR-4498 | 2244 | 3265 | discovered in B cells | | |
| hsa-miR-4499 | 2245 | 3266 | discovered in B cells | | |
| hsa-miR-449a | 2246 | 3267 | chondrocytes, ciliated epithelial cells | lung, colonic, ovarian cancer | cell cycle progression and proliferation |
| hsa-miR-449b-3p | 2247 | 3268 | ciliated epithelial cells, other tissues | various cancer cells | cell cycle progression and proliferation |
| hsa-miR-449b-5p | 2248 | 3269 | ciliated epithelial cells, other tissues | various cancer cells | cell cycle progression and proliferation |
| hsa-miR-449c-3p | 2249 | 3270 | | epithelial ovarian cancer cells | |
| hsa-miR-449c-5p | 2250 | 3271 | | epithelial ovarian cancer cells | |
| hsa-miR-4500 | 2251 | 3272 | discovered in B cells | | |
| hsa-miR-4501 | 2252 | 3273 | discovered in B cells | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-4502 | 2253 | 3274 | discovered in B cells | | |
| hsa-miR-4503 | 2254 | 3275 | discovered in B cells | | |
| hsa-miR-4504 | 2255 | 3276 | discovered in B cells | | |
| hsa-miR-4505 | 2256 | 3277 | discovered in B cells | | |
| hsa-miR-4506 | 2257 | 3278 | discovered in B cells | | |
| hsa-miR-4507 | 2258 | 3279 | discovered in B cells | | |
| hsa-miR-4508 | 2259 | 3280 | discovered in B cells | | |
| hsa-miR-4509 | 2260 | 3281 | discovered in B cells | | |
| hsa-miR-450a-3p | 2261 | 3282 | | | |
| hsa-miR-450a-5p | 2262 | 3283 | | | |
| hsa-miR-450b-3p | 2263 | 3284 | | | |
| hsa-miR-450b-5p | 2264 | 3285 | | | |
| hsa-miR-4510 | 2265 | 3286 | discovered in B cells | | |
| hsa-miR-4511 | 2266 | 3287 | discovered in B cells | | |
| hsa-miR-4512 | 2267 | 3288 | discovered in B cells | | |
| hsa-miR-4513 | 2268 | 3289 | discovered in B cells | | |
| hsa-miR-4514 | 2269 | 3290 | discovered in B cells | | |
| hsa-miR-4515 | 2270 | 3291 | discovered in B cells | | |
| hsa-miR-4516 | 2271 | 3292 | discovered in B cells | | |
| hsa-miR-4517 | 2272 | 3293 | discovered in B cells | | |
| hsa-miR-4518 | 2273 | 3294 | discovered in B cells | | |
| hsa-miR-4519 | 2274 | 3295 | discovered in B cells | | |
| hsa-miR-451a | 2275 | 3296 | heart, central nevous system, epithelial cells | | |
| hsa-miR-451b | 2276 | 3297 | heart, central nevous system, epithelial cells | | |
| hsa-miR-4520a-3p | 2277 | 3298 | discovered in breast tumor and B cells, skin(psoriasis) | | |
| hsa-miR-4520a-5p | 2278 | 3299 | discovered in breast tumor and B cells, skin(psoriasis) | | |
| hsa-miR-4520b-3p | 2279 | 3300 | discovered in breast tumor | | |
| hsa-miR-4520b-5p | 2280 | 3301 | discovered in breast tumor | | |
| hsa-miR-4521 | 2281 | 3302 | discovered in B cells | | |
| hsa-miR-4522 | 2282 | 3303 | discovered in B cells | | |
| hsa-miR-4523 | 2283 | 3304 | discovered in B cells | | |
| hsa-miR-452-3p | 2284 | 3305 | myoblast | bladder cancer and others | |
| hsa-miR-4524a-3p | 2285 | 3306 | discovered in breast tumor and B cells, skin(psoriasis) | | |
| hsa-miR-4524a-5p | 2286 | 3307 | discovered in breast tumor and B cells, skin(psoriasis) | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-4524b-3p | 2287 | 3308 | discovered in breast tumor and B cells, skin(psoriasis) | | |
| hsa-miR-4524b-5p | 2288 | 3309 | discovered in breast tumor and B cells, skin(psoriasis) | | |
| hsa-miR-4525 | 2289 | 3310 | discovered in B cells | | |
| hsa-miR-452-5p | 2290 | 3311 | myoblast | bladder cancer and others | |
| hsa-miR-4526 | 2291 | 3312 | discovered in breast tumor and B cells | | |
| hsa-miR-4527 | 2292 | 3313 | discovered in B cells | | |
| hsa-miR-4528 | 2293 | 3314 | discovered in B cells | | |
| hsa-miR-4529-3p | 2294 | 3315 | discovered in breast tumor and B cells | | |
| hsa-miR-4529-5p | 2295 | 3316 | discovered in breast tumor and B cells | | |
| hsa-miR-4530 | 2296 | 3317 | discovered in B cells | | |
| hsa-miR-4531 | 2297 | 3318 | discovered in B cells | | |
| hsa-miR-4532 | 2298 | 3319 | discovered in B cells | | |
| hsa-miR-4533 | 2299 | 3320 | discovered in B cells | | |
| hsa-miR-4534 | 2300 | 3321 | discovered in B cells | | |
| hsa-miR-4535 | 2301 | 3322 | discovered in B cells | | |
| hsa-miR-4536-3p | 2302 | 3323 | discovered in B cells | | |
| hsa-miR-4536-5p | 2303 | 3324 | discovered in B cells | | |
| hsa-miR-4537 | 2304 | 3325 | discovered in B cells | | |
| hsa-miR-4538 | 2305 | 3326 | discovered in B cells | | |
| hsa-miR-4539 | 2306 | 3327 | discovered in B cells | | |
| hsa-miR-4540 | 2307 | 3328 | discovered in B cells | | |
| hsa-miR-454-3p | 2308 | 3329 | embryoid body cells, central nevous system, monocytes | | |
| hsa-miR-454-5p | 2309 | 3330 | embryoid body cells, central nevous system, monocytes | | |
| hsa-miR-455-3p | 2310 | 3331 | | basal cell carcinoma, other cancers | |
| hsa-miR-455-5p | 2311 | 3332 | | basal cell carcinoma, other cancers | |
| hsa-miR-4632-3p | 2312 | 3333 | discovred in breast tumor | | |
| hsa-miR-4632-5p | 2313 | 3334 | discovered in breast tumor | | |
| hsa-miR-4633-3p | 2314 | 3335 | discovered in breast tumor | | |
| hsa-miR-4633-5p | 2315 | 3336 | discovered in breast tumor | | |
| hsa-miR-4634 | 2316 | 3337 | discovered in breast tumor | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-4635 | 2317 | 3338 | discovered in breast tumor | | |
| hsa-miR-4636 | 2318 | 3339 | discovered in breast tumor | | |
| hsa-miR-4637 | 2319 | 3340 | discovered in breast tumor and lymphoblastic leukaemia | | |
| hsa-miR-4638-3p | 2320 | 3341 | discovered in breast tumor | | |
| hsa-miR-4638-5p | 2321 | 3342 | discovered in breast tumor | | |
| hsa-miR-4639-3p | 2322 | 3343 | discovered in breast tumor | | |
| hsa-miR-4639-5p | 2323 | 3344 | discovered in breast tumor | | |
| hsa-miR-4640-3p | 2324 | 3345 | discovered in breast tumor | | |
| hsa-miR-4640-5p | 2325 | 3346 | discovered in breast tumor | | |
| hsa-miR-4641 | 2326 | 3347 | discovered in breast tumor | | |
| hsa-miR-4642 | 2327 | 3348 | discovered in breast tumor | | |
| hsa-miR-4643 | 2328 | 3349 | discovered in breast tumor | | |
| hsa-miR-4644 | 2329 | 3350 | discovered in breast tumor | | |
| hsa-miR-4645-3p | 2330 | 3351 | discovered in breast tumor | | |
| hsa-miR-4645-5p | 2331 | 3352 | discovered in breast tumor | | |
| hsa-miR-4646-3p | 2332 | 3353 | discovered in breast tumor | | |
| hsa-miR-4646-5p | 2333 | 3354 | discovered in breast tumor | | |
| hsa-miR-4647 | 2334 | 3355 | discovered in breast tumor | | |
| hsa-miR-4648 | 2335 | 3356 | discovered in breast tumor | | |
| hsa-miR-4649-3p | 2336 | 3357 | discovered in breast tumor | | |
| hsa-miR-4649-5p | 2337 | 3358 | discovered in breast tumor | | |
| hsa-miR-4650-3p | 2338 | 3359 | discovered in breast tumor | | |
| hsa-miR-4650-5p | 2339 | 3360 | discovered in breast tumor | | |
| hsa-miR-4651 | 2340 | 3361 | discovered in breast tumor | | |
| hsa-miR-4652-3p | 2341 | 3362 | discovered in breast tumor | | |
| hsa-miR-4652-5p | 2342 | 3363 | discovered in breast tumor | | |
| hsa-miR-4653-3p | 2343 | 3364 | discovered in breast tumor | | |
| hsa-miR-4653-5p | 2344 | 3365 | discovered in breast tumor | | |
| hsa-miR-4654 | 2345 | 3366 | discovered in breast tumor | | |
| hsa-miR-4655-3p | 2346 | 3367 | discovered in breast tumor | | |
| hsa-miR-4655-5p | 2347 | 3368 | discovered in breast tumor | | |
| hsa-miR-4656 | 2348 | 3369 | discovered in breast tumor | | |
| hsa-miR-4657 | 2349 | 3370 | discovered in breast tumor | | |
| hsa-miR-4658 | 2350 | 3371 | discovered in breast tumor | | |
| hsa-miR-4659a-3p | 2351 | 3372 | discovered in breast tumor | | |
| hsa-miR-4659a-5p | 2352 | 3373 | discovered in breast tumor | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-4659b-3p | 2353 | 3374 | discovered in breast tumor | | |
| hsa-miR-4659b-5p | 2354 | 3375 | discovered in breast tumor | | |
| hsa-miR-466 | 2355 | 3376 | | | |
| hsa-miR-4660 | 2356 | 3377 | discovered in breast tumor | | |
| hsa-miR-4661-3p | 2357 | 3378 | discovered in breast tumor | | |
| hsa-miR-4661-5p | 2358 | 3379 | discovered in breast tumor | | |
| hsa-miR-4662a-3p | 2359 | 3380 | discovered in breast tumor, psoriasis | | |
| hsa-miR-4662a-5p | 2360 | 3381 | discovered in breast tumor, psoriasis | | |
| hsa-miR-4662b | 2361 | 3382 | discovered in breast tumor | | |
| hsa-miR-4663 | 2362 | 3383 | discovered in breast tumor | | |
| hsa-miR-4664-3p | 2363 | 3384 | discovered in breast tumor | | |
| hsa-miR-4664-5p | 2364 | 3385 | discovered in breast tumor | | |
| hsa-miR-4665-3p | 2365 | 3386 | discovered in breast tumor | | |
| hsa-miR-4665-5p | 2366 | 3387 | discovered in breast tumor | | |
| hsa-miR-4666a-3p | 2367 | 3388 | discovered in breast tumor | | |
| hsa-miR-4666a-5p | 2368 | 3389 | discovered in breast tumor | | |
| hsa-miR-4666b | 2369 | 3390 | | | |
| hsa-miR-4667-3p | 2370 | 3391 | discovered in breast tumor | | |
| hsa-miR-4667-5p | 2371 | 3392 | discovered in breast tumor | | |
| hsa-miR-4668-3p | 2372 | 3393 | discovered in breast tumor | | |
| hsa-miR-4668-5p | 2373 | 3394 | discovered in breast tumor | | |
| hsa-miR-4669 | 2374 | 3395 | discovered in breast tumor | | |
| hsa-miR-4670-3p | 2375 | 3396 | discovered in breast tumor | | |
| hsa-miR-4670-5p | 2376 | 3397 | discovered in breast tumor | | |
| hsa-miR-4671-3p | 2377 | 3398 | discovered in breast tumor | | |
| hsa-miR-4671-5p | 2378 | 3399 | discovered in breast tumor | | |
| hsa-miR-4672 | 2379 | 3400 | discovered in breast tumor | | |
| hsa-miR-4673 | 2380 | 3401 | discovered in breast tumor | | |
| hsa-miR-4674 | 2381 | 3402 | discovered in breast tumor | | |
| hsa-miR-4675 | 2382 | 3403 | discovered in breast tumor | | |
| hsa-miR-4676-3p | 2383 | 3404 | discovered in breast tumor | | |
| hsa-miR-4676-5p | 2384 | 3405 | discovered in breast tumor | | |
| hsa-miR-4677-3p | 2385 | 3406 | discovered in breast tumor, psoriasis | | |
| hsa-miR-4677-5p | 2386 | 3407 | discovered in breast tumor, psoriasis | | |
| hsa-miR-4678 | 2387 | 3408 | discovered in breast tumor | | |
| hsa-miR-4679 | 2388 | 3409 | discovered in breast tumor | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-4680-3p | 2389 | 3410 | discovered in breast tumor | | |
| hsa-miR-4680-5p | 2390 | 3411 | discovered in breast tumor | | |
| hsa-miR-4681 | 2391 | 3412 | discovered in breast tumor | | |
| hsa-miR-4682 | 2392 | 3413 | discovered in breast tumor | | |
| hsa-miR-4683 | 2393 | 3414 | discovered in breast tumor | | |
| hsa-miR-4684-3p | 2394 | 3415 | discovered in breast tumor | | |
| hsa-miR-4684-5p | 2395 | 3416 | discovered in breast tumor | | |
| hsa-miR-4685-3p | 2396 | 3417 | discovered in breast tumor | | |
| hsa-miR-4685-5p | 2397 | 3418 | discovered in breast tumor | | |
| hsa-miR-4686 | 2398 | 3419 | discovered in breast tumor | | |
| hsa-miR-4687-3p | 2399 | 3420 | discovered in breast tumor | | |
| hsa-miR-4687-5p | 2400 | 3421 | discovered in breast tumor | | |
| hsa-miR-4688 | 2401 | 3422 | discovered in breast tumor | | |
| hsa-miR-4689 | 2402 | 3423 | discovered in breast tumor | | |
| hsa-miR-4690-3p | 2403 | 3424 | discovered in breast tumor | | |
| hsa-miR-4690-5p | 2404 | 3425 | discovered in breast tumor | | |
| hsa-miR-4691-3p | 2405 | 3426 | discovered in breast tumor | | |
| hsa-miR-4691-5p | 2406 | 3427 | discovered in breast tumor | | |
| hsa-miR-4692 | 2407 | 3428 | discovered in breast tumor | | |
| hsa-miR-4693-3p | 2408 | 3429 | discovered in breast tumor | | |
| hsa-miR-4693-5p | 2409 | 3430 | discovered in breast tumor | | |
| hsa-miR-4694-3p | 2410 | 3431 | discovered in breast tumor | | |
| hsa-miR-4694-5p | 2411 | 3432 | discovered in breast tumor | | |
| hsa-miR-4695-3p | 2412 | 3433 | discovered in breast tumor | | |
| hsa-miR-4695-5p | 2413 | 3434 | discovered in breast tumor | | |
| hsa-miR-4696 | 2414 | 3435 | discovered in breast tumor | | |
| hsa-miR-4697-3p | 2415 | 3436 | discovered in breast tumor | | |
| hsa-miR-4697-5p | 2416 | 3437 | discovered in breast tumor | | |
| hsa-miR-4698 | 2417 | 3438 | discovered in breast tumor | | |
| hsa-miR-4699-3p | 2418 | 3439 | discovered in breast tumor | | |
| hsa-miR-4699-5p | 2419 | 3440 | discovered in breast tumor | | |
| hsa-miR-4700-3p | 2420 | 3441 | discovered in breast tumor | | |
| hsa-miR-4700-5p | 2421 | 3442 | discovered in breast tumor | | |
| hsa-miR-4701-3p | 2422 | 3443 | discovered in breast tumor | | |
| hsa-miR-4701-5p | 2423 | 3444 | discovered in breast tumor | | |
| hsa-miR-4703-3p | 2424 | 3445 | discovered in breast tumor | | |
| hsa-miR-4703-5p | 2425 | 3446 | discovered in breast tumor | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-4704-3p | 2426 | 3447 | discovered in breast tumor | | |
| hsa-miR-4704-5p | 2427 | 3448 | discovered in breast tumor | | |
| hsa-miR-4705 | 2428 | 3449 | discovered in breast tumor | | |
| hsa-miR-4706 | 2429 | 3450 | discovered in breast tumor | | |
| hsa-miR-4707-3p | 2430 | 3451 | discovered in breast tumor | | |
| hsa-miR-4707-5p | 2431 | 3452 | discovered in breast tumor | | |
| hsa-miR-4708-3p | 2432 | 3453 | discovered in breast tumor | | |
| hsa-miR-4708-5p | 2433 | 3454 | discovered in breast tumor | | |
| hsa-miR-4709-3p | 2434 | 3455 | discovered in breast tumor | | |
| hsa-miR-4709-5p | 2435 | 3456 | discovered in breast tumor | | |
| hsa-miR-4710 | 2436 | 3457 | discovered in breast tumor | | |
| hsa-miR-4711-3p | 2437 | 3458 | discovered in breast tumor | | |
| hsa-miR-4711-5p | 2438 | 3459 | discovered in breast tumor | | |
| hsa-miR-4712-3p | 2439 | 3460 | discovered in breast tumor | | |
| hsa-miR-4712-5p | 2440 | 3461 | discovered in breast tumor | | |
| hsa-miR-4713-3p | 2441 | 3462 | discovered in breast tumor | | |
| hsa-miR-4713-5p | 2442 | 3463 | discovered in breast tumor | | |
| hsa-miR-4714-3p | 2443 | 3464 | discovered in breast tumor | | |
| hsa-miR-4714-5p | 2444 | 3465 | discovered in breast tumor | | |
| hsa-miR-4715-3p | 2445 | 3466 | discovered in breast tumor | | |
| hsa-miR-4715-5p | 2446 | 3467 | discovered in breast tumor | | |
| hsa-miR-4716-3p | 2447 | 3468 | discovered in breast tumor | | |
| hsa-miR-4716-5p | 2448 | 3469 | discovered in breast tumor | | |
| hsa-miR-4717-3p | 2449 | 3470 | discovered in breast tumor | | |
| hsa-miR-4717-5p | 2450 | 3471 | discovered in breast tumor | | |
| hsa-miR-4718 | 2451 | 3472 | discovered in breast tumor | | |
| hsa-miR-4719 | 2452 | 3473 | discovered in breast tumor | | |
| hsa-miR-4720-3p | 2453 | 3474 | discovered in breast tumor | | |
| hsa-miR-4720-5p | 2454 | 3475 | discovered in breast tumor | | |
| hsa-miR-4721 | 2455 | 3476 | discovered in breast tumor | | |
| hsa-miR-4722-3p | 2456 | 3477 | discovered in breast tumor | | |
| hsa-miR-4722-5p | 2457 | 3478 | discovered in breast tumor | | |
| hsa-miR-4723-3p | 2458 | 3479 | discovered in breast tumor | | |
| hsa-miR-4723-5p | 2459 | 3480 | discovered in breast tumor | | |
| hsa-miR-4724-3p | 2460 | 3481 | discovered in breast tumor | | |
| hsa-miR-4724-5p | 2461 | 3482 | discovered in breast tumor | | |
| hsa-miR-4725-3p | 2462 | 3483 | discovered in breast tumor | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-4725-5p | 2463 | 3484 | discovered in breast tumor | | |
| hsa-miR-4726-3p | 2464 | 3485 | discovered in breast tumor | | |
| hsa-miR-4726-5p | 2465 | 3486 | discovered in breast tumor | | |
| hsa-miR-4727-3p | 2466 | 3487 | discovered in breast tumor | | |
| hsa-miR-4727-5p | 2467 | 3488 | discovered in breast tumor | | |
| hsa-miR-4728-3p | 2468 | 3489 | discovered in breast tumor | | |
| hsa-miR-4728-5p | 2469 | 3490 | discovered in breast tumor | | |
| hsa-miR-4729 | 2470 | 3491 | discovered in breast tumor | | |
| hsa-miR-4730 | 2471 | 3492 | discovered in breast tumor | | |
| hsa-miR-4731-3p | 2472 | 3493 | discovered in breast tumor | | |
| hsa-miR-4731-5p | 2473 | 3494 | discovered in breast tumor | | |
| hsa-miR-4732-3p | 2474 | 3495 | discovered in breast tumor | | |
| hsa-miR-4732-5p | 2475 | 3496 | discovered in breast tumor | | |
| hsa-miR-4733-3p | 2476 | 3497 | discovered in breast tumor | | |
| hsa-miR-4733-5p | 2477 | 3498 | discovered in breast tumor | | |
| hsa-miR-4734 | 2478 | 3499 | discovered in breast tumor | | |
| hsa-miR-4735-3p | 2479 | 3500 | discovered in breast tumor | | |
| hsa-miR-4735-5p | 2480 | 3501 | discovered in breast tumor | | |
| hsa-miR-4736 | 2481 | 3502 | discovered in breast tumor | | |
| hsa-miR-4737 | 2482 | 3503 | discovered in breast tumor | | |
| hsa-miR-4738-3p | 2483 | 3504 | discovered in breast tumor | | |
| hsa-miR-4738-5p | 2484 | 3505 | discovered in breast tumor | | |
| hsa-miR-4739 | 2485 | 3506 | discovered in breast tumor | | |
| hsa-miR-4740-3p | 2486 | 3507 | discovered in breast tumor | | |
| hsa-miR-4740-5p | 2487 | 3508 | discovered in breast tumor | | |
| hsa-miR-4741 | 2488 | 3509 | discovered in breast tumor, psoriasis | | |
| hsa-miR-4742-3p | 2489 | 3510 | discovered in breast tumor, psoriasis | | |
| hsa-miR-4742-5p | 2490 | 3511 | discovered in breast tumor | | |
| hsa-miR-4743-3p | 2491 | 3512 | discovered in breast tumor | | |
| hsa-miR-4743-5p | 2492 | 3513 | discovered in breast tumor | | |
| hsa-miR-4744 | 2493 | 3514 | discovered in breast tumor | | |
| hsa-miR-4745-3p | 2494 | 3515 | discovered in breast tumor | | |
| hsa-miR-4745-5p | 2495 | 3516 | discovered in breast tumor | | |
| hsa-miR-4746-3p | 2496 | 3517 | discovered in breast tumor | | |
| hsa-miR-4746-5p | 2497 | 3518 | discovered in breast tumor | | |
| hsa-miR-4747-3p | 2498 | 3519 | discovered in breast tumor | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-4747-5p | 2499 | 3520 | discovered in breast tumor | | |
| hsa-miR-4748 | 2500 | 3521 | discovered in breast tumor | | |
| hsa-miR-4749-3p | 2501 | 3522 | discovered in breast tumor | | |
| hsa-miR-4749-5p | 2502 | 3523 | discovered in breast tumor | | |
| hsa-miR-4750-3p | 2503 | 3524 | discovered in breast tumor | | |
| hsa-miR-4750-5p | 2504 | 3525 | discovered in breast tumor | | |
| hsa-miR-4751 | 2505 | 3526 | discovered in breast tumor | | |
| hsa-miR-4752 | 2506 | 3527 | discovered in breast tumor | | |
| hsa-miR-4753-3p | 2507 | 3528 | discovered in breast tumor | | |
| hsa-miR-4753-5p | 2508 | 3529 | discovered in breast tumor | | |
| hsa-miR-4754 | 2509 | 3530 | discovered in breast tumor | | |
| hsa-miR-4755-3p | 2510 | 3531 | discovered in breast tumor | | |
| hsa-miR-4755-5p | 2511 | 3532 | discovered in breast tumor | | |
| hsa-miR-4756-3p | 2512 | 3533 | discovered in breast tumor | | |
| hsa-miR-4756-5p | 2513 | 3534 | discovered in breast tumor | | |
| hsa-miR-4757-3p | 2514 | 3535 | discovered in breast tumor | | |
| hsa-miR-4757-5p | 2515 | 3536 | discovered in breast tumor | | |
| hsa-miR-4758-3p | 2516 | 3537 | discovered in breast tumor | | |
| hsa-miR-4758-5p | 2517 | 3538 | discovered in breast tumor | | |
| hsa-miR-4759 | 2518 | 3539 | discovered in breast tumor | | |
| hsa-miR-4760-3p | 2519 | 3540 | discovered in breast tumor | | |
| hsa-miR-4760-5p | 2520 | 3541 | discovered in breast tumor | | |
| hsa-miR-4761-3p | 2521 | 3542 | discovered in breast tumor | | |
| hsa-miR-4761-5p | 2522 | 3543 | discovered in breast tumor | | |
| hsa-miR-4762-3p | 2523 | 3544 | discovered in breast tumor | | |
| hsa-miR-4762-5p | 2524 | 3545 | discovered in breast tumor | | |
| hsa-miR-4763-3p | 2525 | 3546 | discovered in breast tumor | | |
| hsa-miR-4763-5p | 2526 | 3547 | discovered in breast tumor | | |
| hsa-miR-4764-3p | 2527 | 3548 | discovered in breast tumor | | |
| hsa-miR-4764-5p | 2528 | 3549 | discovered in breast tumor | | |
| hsa-miR-4765 | 2529 | 3550 | discovered in breast tumor | | |
| hsa-miR-4766-3p | 2530 | 3551 | discovered in breast tumor | | |
| hsa-miR-4766-5p | 2531 | 3552 | discovered in breast tumor | | |
| hsa-miR-4767 | 2532 | 3553 | discovered in breast tumor | | |
| hsa-miR-4768-3p | 2533 | 3554 | discovered in breast tumor | | |
| hsa-miR-4768-5p | 2534 | 3555 | discovered in breast tumor | | |
| hsa-miR-4769-3p | 2535 | 3556 | discovered in breast tumor | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-4769-5p | 2536 | 3557 | discovered in breast tumor | | |
| hsa-miR-4770 | 2537 | 3558 | discovered in breast tumor | | |
| hsa-miR-4771 | 2538 | 3559 | discovered in breast tumor | | |
| hsa-miR-4772-3p | 2539 | 3560 | discovered in breast tumor, blood monoclear cells | energy metabolism/ obesity | |
| hsa-miR-4772-5p | 2540 | 3561 | discovered in breast tumor, blood monoclear cells | energy metabolism/ obesity | |
| hsa-miR-4773 | 2541 | 3562 | discovered in breast tumor | | |
| hsa-miR-4774-3p | 2542 | 3563 | discovered in breast tumor and Lymphoblastic leukemia | | |
| hsa-miR-4774-5p | 2543 | 3564 | discovered in breast tumor and Lymphoblastic leukemia | | |
| hsa-miR-4775 | 2544 | 3565 | discovered in breast tumor | | |
| hsa-miR-4776-3p | 2545 | 3566 | discovered in breast tumor | | |
| hsa-miR-4776-5p | 2546 | 3567 | discovered in breast tumor | | |
| hsa-miR-4777-3p | 2547 | 3568 | discovered in breast tumor | | |
| hsa-miR-4777-5p | 2548 | 3569 | discovered in breast tumor | | |
| hsa-miR-4778-3p | 2549 | 3570 | discovered in breast tumor | | |
| hsa-miR-4778-5p | 2550 | 3571 | discovered in breast tumor | | |
| hsa-miR-4779 | 2551 | 3572 | discovered in breast tumor | | |
| hsa-miR-4780 | 2552 | 3573 | discovered in breast tumor | | |
| hsa-miR-4781-3p | 2553 | 3574 | discovered in breast tumor | | |
| hsa-miR-4781-5p | 2554 | 3575 | discovered in breast tumor | | |
| hsa-miR-4782-3p | 2555 | 3576 | discovered in breast tumor | | |
| hsa-miR-4782-5p | 2556 | 3577 | discovered in breast tumor | | |
| hsa-miR-4783-3p | 2557 | 3578 | discovered in breast tumor | | |
| hsa-miR-4783-5p | 2558 | 3579 | discovered in breast tumor | | |
| hsa-miR-4784 | 2559 | 3580 | discovered in breast tumor | | |
| hsa-miR-4785 | 2560 | 3581 | discovered in breast tumor | | |
| hsa-miR-4786-3p | 2561 | 3582 | discovered in breast tumor | | |
| hsa-miR-4786-5p | 2562 | 3583 | discovered in breast tumor | | |
| hsa-miR-4787-3p | 2563 | 3584 | discovered in breast tumor | | |
| hsa-miR-4787-5p | 2564 | 3585 | discovered in breast tumor | | |
| hsa-miR-4788 | 2565 | 3586 | discovered in breast tumor | | |
| hsa-miR-4789-3p | 2566 | 3587 | discovered in breast tumor | | |
| hsa-miR-4789-5p | 2567 | 3588 | discovered in breast tumor | | |
| hsa-miR-4790-3p | 2568 | 3589 | discovered in breast tumor | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-4790-5p | 2569 | 3590 | discovered in breast tumor | | |
| hsa-miR-4791 | 2570 | 3591 | discovered in breast tumor | | |
| hsa-miR-4792 | 2571 | 3592 | discovered in breast tumor | | |
| hsa-miR-4793-3p | 2572 | 3593 | discovered in breast tumor | | |
| hsa-miR-4793-5p | 2573 | 3594 | discovered in breast tumor | | |
| hsa-miR-4794 | 2574 | 3595 | discovered in breast tumor | | |
| hsa-miR-4795-3p | 2575 | 3596 | discovered in breast tumor | | |
| hsa-miR-4795-5p | 2576 | 3597 | discovered in breast tumor | | |
| hsa-miR-4796-3p | 2577 | 3598 | discovered in breast tumor | | |
| hsa-miR-4796-5p | 2578 | 3599 | discovered in breast tumor | | |
| hsa-miR-4797-3p | 2579 | 3600 | discovered in breast tumor | | |
| hsa-miR-4797-5p | 2580 | 3601 | discovered in breast tumor | | |
| hsa-miR-4798-3p | 2581 | 3602 | discovered in breast tumor | | |
| hsa-miR-4798-5p | 2582 | 3603 | discovered in breast tumor | | |
| hsa-miR-4799-3p | 2583 | 3604 | discovered in breast tumor | | |
| hsa-miR-4799-5p | 2584 | 3605 | discovered in breast tumor | | |
| hsa-miR-4800-3p | 2585 | 3606 | discovered in breast tumor | | |
| hsa-miR-4800-5p | 2586 | 3607 | discovered in breast tumor | | |
| hsa-miR-4801 | 2587 | 3608 | discovered in breast tumor | | |
| hsa-miR-4802-3p | 2588 | 3609 | discovered in breast tumor, psoriasis | | |
| hsa-miR-4802-5p | 2589 | 3610 | discovered in breast tumor, psoriasis | | |
| hsa-miR-4803 | 2590 | 3611 | discovered in breast tumor | | |
| hsa-miR-4804-3p | 2591 | 3612 | discovered in breast tumor | | |
| hsa-miR-4804-5p | 2592 | 3613 | discovered in breast tumor | | |
| hsa-miR-483-3p | 2593 | 3614 | | aderonocortical carcinoma, rectal/pancreatic cancer, proliferation of wounded epithelial cells | oncogenic |
| hsa-miR-483-5p | 2594 | 3615 | cartilage (chondrocyte), fetal brain | aderonocortical carcinoma | angiogenesis |
| hsa-miR-484 | 2595 | 3616 | | | mitochondrial network |
| hsa-miR-485-3p | 2596 | 3617 | | | |
| hsa-miR-485-5p | 2597 | 3618 | | ovarian epithelial tumor | |
| hsa-miR-486-3p | 2598 | 3619 | erythroid cells | various cancers | |
| hsa-miR-486-5p | 2599 | 3620 | stem cells (adipose) | various cancers | |
| hsa-miR-487a | 2600 | 3621 | | laryngeal carcinoma | |
| hsa-miR-487b | 2601 | 3622 | | neuroblastoma, pulmonary carcinogenesis | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-488-3p | 2602 | 3623 | | prostate cancer, others | |
| hsa-miR-488-5p | 2603 | 3624 | | prostate cancer, others | |
| hsa-miR-489 | 2604 | 3625 | mesenchymal stem cells | osteogenesis | |
| hsa-miR-490-3p | 2605 | 3626 | | neuroblastoma, terine leiomyoma (ULM)/muscle | |
| hsa-miR-490-5p | 2606 | 3627 | | neuroblastoma, terine leiomyoma (ULM)/muscle | |
| hsa-miR-491-3p | 2607 | 3628 | | various cancers, brain disease | pro-apoptosis |
| hsa-miR-491-5p | 2608 | 3629 | | various cancers, brain disease | pro-apoptosis |
| hsa-miR-492 | 2609 | 3630 | | | |
| hsa-miR-493-3p | 2610 | 3631 | myeloid cells, pancreas (islet) | | |
| hsa-miR-493-5p | 2611 | 3632 | myeloid cells, pancreas (islet) | | |
| hsa-miR-494 | 2612 | 3633 | epithelial cells | various cancers | cell cycle |
| hsa-miR-495-3p | 2613 | 3634 | platelet | various cancers (gastric, MLL leukemia, pancreatic etc) and inflammation | |
| hsa-miR-495-5p | 2614 | 3635 | platelet | various cancers (gastric, MLL leukemia, pancreatic etc) and inflammation | |
| hsa-miR-496 | 2615 | 3636 | Blood | | |
| hsa-miR-497-3p | 2616 | 3637 | | various cancers (breast, colorectal, etc) | tumor supressor/pro-apoptosis |
| hsa-miR-497-5p | 2617 | 3638 | | various cancers (breast, colorectal, etc) | tumor supressor/pro-apoptosis |
| hsa-miR-498 | 2618 | 3639 | | autoimmuno (e.g. rheumatoid arthritis) | |
| hsa-miR-4999-3p | 2619 | 3640 | | | |
| hsa-miR-4999-5p | 2620 | 3641 | | | |
| hsa-miR-499a-3p | 2621 | 3642 | heart, cardiac stem cells | cardiovascular disease | cardiomyocyte differentiation |
| hsa-miR-499a-5p | 2622 | 3643 | heart, cardiac stem cells | cardiovascular disease | cardiomyocyte differentiation |
| hsa-miR-499b-3p | 2623 | 3644 | heart, cardiac stem cells | cardiovascular disease | cardiomyocyte differentiation |
| hsa-miR-499b-5p | 2624 | 3645 | heart, cardiac stem cells | cardiovascular disease | cardiomyocyte differentiation |
| hsa-miR-5000-3p | 2625 | 3646 | discovered in lymphoblastic leukaemia | | |
| hsa-miR-5000-5p | 2626 | 3647 | discovered in lymphoblastic leukaemia | | |
| hsa-miR-5001-3p | 2627 | 3648 | | | |
| hsa-miR-5001-5p | 2628 | 3649 | | | |
| hsa-miR-5002-3p | 2629 | 3650 | | | |
| hsa-miR-5002-5p | 2630 | 3651 | | | |
| hsa-miR-5003-3p | 2631 | 3652 | | | |
| hsa-miR-5003-5p | 2632 | 3653 | | | |
| hsa-miR-5004-3p | 2633 | 3654 | | | |
| hsa-miR-5004-5p | 2634 | 3655 | | | |
| hsa-miR-5006-3p | 2635 | 3656 | discovered in lymphoblastic leukaemia | | |
| hsa-miR-5006-5p | 2636 | 3657 | discovered in lymphoblastic leukaemia | | |
| hsa-miR-5007-3p | 2637 | 3658 | | | |
| hsa-miR-5007-5p | 2638 | 3659 | | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-5008-3p | 2639 | 3660 | | | |
| hsa-miR-5008-5p | 2640 | 3661 | | | |
| hsa-miR-5009-3p | 2641 | 3662 | | | |
| hsa-miR-5009-5p | 2642 | 3663 | | | |
| hsa-miR-500a-3p | 2643 | 3664 | | | |
| hsa-miR-500a-5p | 2644 | 3665 | | | |
| hsa-miR-500b | 2645 | 3666 | Blood (plasma) | | |
| hsa-miR-5010-3p | 2646 | 3667 | | abnormal skin (psoriasis) | |
| hsa-miR-5010-5p | 2647 | 3668 | | abnormal skin (psoriasis) | |
| hsa-miR-5011-3p | 2648 | 3669 | | | |
| hsa-miR-5011-5p | 2649 | 3670 | | | |
| hsa-miR-501-3p | 2650 | 3671 | | | |
| hsa-miR-501-5p | 2651 | 3672 | | | |
| hsa-miR-502-3p | 2652 | 3673 | | various cancers (hepatocellular, ovarian, breast) | |
| hsa-miR-502-5p | 2653 | 3674 | | various cancers (hepatocellular, ovarian, breast) | |
| hsa-miR-503-3p | 2654 | 3675 | ovary | | |
| hsa-miR-503-5p | 2655 | 3676 | ovary | | |
| hsa-miR-504 | 2656 | 3677 | | glioblastoma | |
| hsa-miR-5047 | 2657 | 3678 | | | |
| hsa-miR-505-3p | 2658 | 3679 | | breast cancer | |
| hsa-miR-505-5p | 2659 | 3680 | | breast cancer | |
| hsa-miR-506-3p | 2660 | 3681 | | various cancers | |
| hsa-miR-506-5p | 2661 | 3682 | | various cancers | |
| hsa-miR-507 | 2662 | 3683 | | | |
| hsa-miR-508-3p | 2663 | 3684 | | renal cell carcinoma | |
| hsa-miR-508-5p | 2664 | 3685 | endothelial progenitor cells (EPCs) | | |
| hsa-miR-5087 | 2665 | 3686 | | | |
| hsa-miR-5088 | 2666 | 3687 | | | |
| hsa-miR-5089-3p | 2667 | 3688 | | | |
| hsa-miR-5089-5p | 2668 | 3689 | | | |
| hsa-miR-5090 | 2669 | 3690 | | | |
| hsa-miR-5091 | 2670 | 3691 | | | |
| hsa-miR-5092 | 2671 | 3692 | | | |
| hsa-miR-5093 | 2672 | 3693 | | | |
| hsa-miR-509-3-5p | 2673 | 3694 | testis | | |
| hsa-miR-509-3p | 2674 | 3695 | | renal cell carcinoma, brain disease | |
| hsa-miR-5094 | 2675 | 3696 | | | |
| hsa-miR-5095 | 2676 | 3697 | | cervical cancer | |
| hsa-miR-509-5p | 2677 | 3698 | | metabolic syndrome, brain disease | |
| hsa-miR-5096 | 2678 | 3699 | | cervical cance | |
| hsa-miR-510 | 2679 | 3700 | brain | | |
| hsa-miR-5100 | 2680 | 3701 | discoverd in Salivary gland | | |
| hsa-miR-511 | 2681 | 3702 | dendritic cells and macrophages | | |
| hsa-miR-512-3p | 2682 | 3703 | embryonic stem cells, placenta | | |
| hsa-miR-512-5p | 2683 | 3704 | embryonic stem cells, placenta, | | |
| hsa-miR-513a-3p | 2684 | 3705 | | lung carcinoma | |
| hsa-miR-513a-5p | 2685 | 3706 | endothelial cells | | |
| hsa-miR-513b | 2686 | 3707 | | follicular lymphoma | |
| hsa-miR-513c-3p | 2687 | 3708 | | | |
| hsa-miR-513c-5p | 2688 | 3709 | | | |
| hsa-miR-514a-3p | 2689 | 3710 | | | |
| hsa-miR-514a-5p | 2690 | 3711 | | | |
| hsa-miR-514b-3p | 2691 | 3712 | | various cancer cells | |
| hsa-miR-514b-5p | 2692 | 3713 | | various cancer cells | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-515-3p | 2693 | 3714 | | | |
| hsa-miR-515-5p | 2694 | 3715 | placenta | | |
| hsa-miR-516a-3p | 2695 | 3716 | frontal cortex | | |
| hsa-miR-516a-5p | 2696 | 3717 | placenta | | |
| hsa-miR-516b-3p | 2697 | 3718 | | | |
| hsa-miR-516b-5p | 2698 | 3719 | | | |
| hsa-miR-517-5p | 2699 | 3720 | placenta | | |
| hsa-miR-517a-3p | 2700 | 3721 | placenta | | |
| hsa-miR-517b-3p | 2701 | 3722 | placenta | | |
| hsa-miR-517c-3p | 2702 | 3723 | placenta | | |
| hsa-miR-5186 | 2703 | 3724 | discovered in lymphoblastic leukaemia | | |
| hsa-miR-5187-3p | 2704 | 3725 | discovered in lymphoblastic leukaemia, skin (psoriasis) | | |
| hsa-miR-5187-5p | 2705 | 3726 | discovered in lymphoblastic leukaemia, skin (psoriasis) | | |
| hsa-miR-5188 | 2706 | 3727 | discovered in lymphoblastic leukaemia | | |
| hsa-miR-5189 | 2707 | 3728 | discovered in lymphoblastic leukaemia | | |
| hsa-miR-518a-3p | 2708 | 3729 | | HCC | |
| hsa-miR-518a-5p | 2709 | 3730 | | various cancer cells | |
| hsa-miR-518b | 2710 | 3731 | placenta | HCC | cell cycle progression |
| hsa-miR-518c-3p | 2711 | 3732 | placenta | | |
| hsa-miR-518c-5p | 2712 | 3733 | placenta | | |
| hsa-miR-518d-3p | 2713 | 3734 | | | |
| hsa-miR-518d-5p | 2714 | 3735 | | | |
| hsa-miR-518e-3p | 2715 | 3736 | | HCC | cell cycle progression |
| hsa-miR-518e-5p | 2716 | 3737 | | HCC | cell cycle progression |
| hsa-miR-518f-3p | 2717 | 3738 | placenta | | |
| hsa-miR-518f-5p | 2718 | 3739 | placenta | | |
| hsa-miR-5190 | 2719 | 3740 | discovered in lymphoblastic leukaemia | | |
| hsa-miR-5191 | 2720 | 3741 | discovered in lymphoblastic leukaemia | | |
| hsa-miR-5192 | 2721 | 3742 | discovered in lymphoblastic leukaemia | | |
| hsa-miR-5193 | 2722 | 3743 | discovered in lymphoblastic leukaemia | | |
| hsa-miR-5194 | 2723 | 3744 | discovered in lymphoblastic leukaemia | | |
| hsa-miR-5195-3p | 2724 | 3745 | discovered in lymphoblastic leukaemia | | |
| hsa-miR-5195-5p | 2725 | 3746 | discovered in lymphoblastic leukaemia | | |
| hsa-miR-5196-3p | 2726 | 3747 | discovered in lymphoblastic leukaemia | | |
| hsa-miR-5196-5p | 2727 | 3748 | discovered in lymphoblastic leukaemia | | |
| hsa-miR-5197-3p | 2728 | 3749 | discovered in lymphoblastic leukaemia | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-5197-5p | 2729 | 3750 | discovered in lymphoblastic leukaemia | | |
| hsa-miR-519a-3p | 2730 | 3751 | placenta | HCC | |
| hsa-miR-519a-5p | 2731 | 3752 | placenta | HCC | |
| hsa-miR-519b-3p | 2732 | 3753 | | breast cancer | |
| hsa-miR-519b-5p | 2733 | 3754 | | breast cancer | |
| hsa-miR-519c-3p | 2734 | 3755 | | | |
| hsa-miR-519c-5p | 2735 | 3756 | | | |
| hsa-miR-519d | 2736 | 3757 | placenta | | |
| hsa-miR-519e-3p | 2737 | 3758 | placenta | | |
| hsa-miR-519e-5p | 2738 | 3759 | placenta | | |
| hsa-miR-520a-3p | 2739 | 3760 | placenta | | |
| hsa-miR-520a-5p | 2740 | 3761 | placenta | | |
| hsa-miR-520b | 2741 | 3762 | | breast cancer | |
| hsa-miR-520c-3p | 2742 | 3763 | | gastric cancer, breast tumor | |
| hsa-miR-520c-5p | 2743 | 3764 | | breast tumor | |
| hsa-miR-520d-3p | 2744 | 3765 | | various cancer cells | |
| hsa-miR-520d-5p | 2745 | 3766 | | various cancer cells | |
| hsa-miR-520e | 2746 | 3767 | | hepatoma | tomor suppressor |
| hsa-miR-520f | 2747 | 3768 | | breast cancer | |
| hsa-miR-520g | 2748 | 3769 | | HCC, bladder cancer, breast cancer | |
| hsa-miR-520h | 2749 | 3770 | placental specific | | |
| hsa-miR-521 | 2750 | 3771 | | prostate cancer | |
| hsa-miR-522-3p | 2751 | 3772 | | HCC | |
| hsa-miR-522-5p | 2752 | 3773 | | HCC | |
| hsa-miR-523-3p | 2753 | 3774 | | | |
| hsa-miR-523-5p | 2754 | 3775 | | | |
| hsa-miR-524-3p | 2755 | 3776 | | colon cancer stem cells | |
| hsa-miR-524-5p | 2756 | 3777 | placental specific | gliomas | |
| hsa-miR-525-3p | 2757 | 3778 | placental specific | HCC | |
| hsa-miR-525-5p | 2758 | 3779 | placental specific | | |
| hsa-miR-526a | 2759 | 3780 | placental specific | | |
| hsa-miR-526b-3p | 2760 | 3781 | placental specific | | |
| hsa-miR-526b-5p | 2761 | 3782 | placental specific | | |
| hsa-miR-527 | 2762 | 3783 | | | |
| hsa-miR-532-3p | 2763 | 3784 | | ALL | |
| hsa-miR-532-5p | 2764 | 3785 | | ALL | |
| hsa-miR-539-3p | 2765 | 3786 | | | |
| hsa-miR-539-5p | 2766 | 3787 | | | |
| hsa-miR-541-3p | 2767 | 3788 | | | |
| hsa-miR-541-5p | 2768 | 3789 | | | |
| hsa-miR-542-3p | 2769 | 3790 | monocytes | | |
| hsa-miR-542-5p | 2770 | 3791 | | basal cell carcinoma, neuroblastoma | |
| hsa-miR-543 | 2771 | 3792 | | | |
| hsa-miR-544a | 2772 | 3793 | | osteocarcoma | |
| hsa-miR-544b | 2773 | 3794 | | osteocarcoma | |
| hsa-miR-545-3p | 2774 | 3795 | | | |
| hsa-miR-545-5p | 2775 | 3796 | | rectal cancer | |
| hsa-miR-548 | 2776 | 3797 | | | |
| hsa-miR-548-3p | 2777 | 3798 | | | |
| hsa-miR-548-5p | 2778 | 3799 | | | |
| hsa-miR-548a | 2779 | 3800 | identified in colorectal microRNAome | | |
| hsa-miR-548a-3p | 2780 | 3801 | identified in colorectal microRNAome | | |
| hsa-miR-548a-5p | 2781 | 3802 | identified in colorectal microRNAome | | |
| hsa-miR-548aa | 2782 | 3803 | identified in cervical tumor | | |
| hsa-miR-548ab | 2783 | 3804 | discovered in B-cells | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-548ac | 2784 | 3805 | discovered in B-cells | | |
| hsa-miR-548ad | 2785 | 3806 | discovered in B-cells | | |
| hsa-miR-548ae | 2786 | 3807 | discovered in B-cells | | |
| hsa-miR-548ag | 2787 | 3808 | discovered in B-cells | | |
| hsa-miR-548ah-3p | 2788 | 3809 | discovered in B-cells | | |
| hsa-miR-548ah-5p | 2789 | 3810 | discovered in B-cells | | |
| hsa-miR-548ai | 2790 | 3811 | discovered in B-cells | | |
| hsa-miR-548aj-3p | 2791 | 3812 | discovered in B-cells | | |
| hsa-miR-548aj-5p | 2792 | 3813 | discovered in B-cells | | |
| hsa-miR-548ak | 2793 | 3814 | discovered in B-cells | | |
| hsa-miR-548al | 2794 | 3815 | discovered in B-cells | | |
| hsa-miR-548am-3p | 2795 | 3816 | discovered in B-cells | | |
| hsa-miR-548am-5p | 2796 | 3817 | discovered in B-cells | | |
| hsa-miR-548an | 2797 | 3818 | discovered in B-cells | | |
| hsa-miR-548ao-3p | 2798 | 3819 | | | |
| hsa-miR-548ao-5p | 2799 | 3820 | | | |
| hsa-miR-548ap-3p | 2800 | 3821 | | | |
| hsa-miR-548ap-5p | 2801 | 3822 | | | |
| hsa-miR-548aq-3p | 2802 | 3823 | | | |
| hsa-miR-548aq-5p | 2803 | 3824 | | | |
| hsa-miR-548ar-3p | 2804 | 3825 | | | |
| hsa-miR-548ar-5p | 2805 | 3826 | | | |
| hsa-miR-548as-3p | 2806 | 3827 | | | |
| hsa-miR-548as-5p | 2807 | 3828 | | | |
| hsa-miR-548at-3p | 2808 | 3829 | | prostate cancer | |
| hsa-miR-548at-5p | 2809 | 3830 | | prostate cancer | |
| hsa-miR-548au-3p | 2810 | 3831 | | | |
| hsa-miR-548au-5p | 2811 | 3832 | | | |
| hsa-miR-548av-3p | 2812 | 3833 | | | |
| hsa-miR-548av-5p | 2813 | 3834 | | | |
| hsa-miR-548aw | 2814 | 3835 | | prostate cancer | |
| hsa-miR-548ay-3p | 2815 | 3836 | discovered in abnormal skin (psoriasis) | | |
| hsa-miR-548ay-5p | 2816 | 3837 | discovered in abnormal skin (psoriasis) | | |
| hsa-miR-548az-3p | 2817 | 3838 | discovered in abnormal skin (psoriasis) | | |
| hsa-miR-548az-5p | 2818 | 3839 | discovered in abnormal skin (psoriasis) | | |
| hsa-miR-548b-3p | 2819 | 3840 | identified in colorectal microRNAome | | |
| hsa-miR-548b-5p | 2820 | 3841 | immune cells, frontal cortex | | |
| hsa-miR-548c-3p | 2821 | 3842 | identified in colorectal microRNAome | | |
| hsa-miR-548c-5p | 2822 | 3843 | immune cells, frontal cortex | | |
| hsa-miR-548d-3p | 2823 | 3844 | identified in colorectal microRNAome | | |
| hsa-miR-548d-5p | 2824 | 3845 | identified in colorectal microRNAome | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-548e | 2825 | 3846 | embryonic stem cells | | |
| hsa-miR-548f | 2826 | 3847 | embryonic stem cells | | |
| hsa-miR-548g-3p | 2827 | 3848 | embryonic stem cells | | |
| hsa-miR-548g-5p | 2828 | 3849 | embryonic stem cells | | |
| hsa-miR-548h-3p | 2829 | 3850 | embryonic stem cells | | |
| hsa-miR-548h-5p | 2830 | 3851 | embryonic stem cells | | |
| hsa-miR-548i | 2831 | 3852 | embryonic stem cells, immune cells | | |
| hsa-miR-548j | 2832 | 3853 | immune cells | | |
| hsa-miR-548k | 2833 | 3854 | embryonic stem cells | | |
| hsa-miR-548l | 2834 | 3855 | embryonic stem cells | | |
| hsa-miR-548m | 2835 | 3856 | embryonic stem cells | | |
| hsa-miR-548n | 2836 | 3857 | embryonic stem cells, immune cells | | |
| hsa-miR-548o-3p | 2837 | 3858 | embryonic stem cells | | |
| hsa-miR-548o-5p | 2838 | 3859 | embryonic stem cells | | |
| hsa-miR-548p | 2839 | 3860 | embryonic stem cells | | |
| hsa-miR-548q | 2840 | 3861 | | ovarian cancer cells | |
| hsa-miR-548s | 2841 | 3862 | discovered in the melanoma MicroRNAome | | |
| hsa-miR-548t-3p | 2842 | 3863 | discovered in the melanoma MicroRNAome | | |
| hsa-miR-548t-5p | 2843 | 3864 | discovered in the melanoma MicroRNAome | | |
| hsa-miR-548u | 2844 | 3865 | discovered in the melanoma MicroRNAome | | |
| hsa-miR-548w | 2845 | 3866 | discovered in the melanoma MicroRNAome | | |
| hsa-miR-548y | 2846 | 3867 | / | | |
| hsa-miR-548z | 2847 | 3868 | discovered in cervical tumor | | |
| hsa-miR-549a | 2848 | 3869 | discovered in a colorectal MicroRNAome | | |
| hsa-miR-550a-3-5p | 2849 | 3870 | | Hepatocellular Carcinoma | |
| hsa-miR-550a-3p | 2850 | 3871 | | Hepatocellular Carcinoma | |
| hsa-miR-550a-5p | 2851 | 3872 | | Hepatocellular Carcinoma | |
| hsa-miR-550b-2-5p | 2852 | 3873 | discovered in cervical tumor | | |
| hsa-miR-550b-3p | 2853 | 3874 | discovered in cervical tumor | | |
| hsa-miR-551a | 2854 | 3875 | | gastric cancer | |
| hsa-miR-551b-3p | 2855 | 3876 | hepatocytes | | |
| hsa-miR-551b-5p | 2856 | 3877 | hepatocytes | | |
| hsa-miR-552 | 2857 | 3878 | discovered in a colorectal MicroRNAome | | |
| hsa-miR-553 | 2858 | 3879 | discovered in a colorectal MicroRNAome | | |
| hsa-miR-554 | 2859 | 3880 | discovered in a colorectal MicroRNAome | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-555 | 2860 | 3881 | discovered in a colorectal MicroRNAome | | |
| hsa-miR-556-3p | 2861 | 3882 | discovered in a colorectal MicroRNAome | | |
| hsa-miR-556-5p | 2862 | 3883 | discovered in a colorectal MicroRNAome | | |
| hsa-miR-557 | 2863 | 3884 | liver(hepatocytes) | | |
| hsa-miR-5571-3p | 2864 | 3885 | discoveredd in Salivary gland | | |
| hsa-miR-5571-5p | 2865 | 3886 | discoveredd in Salivary gland | | |
| hsa-miR-5572 | 2866 | 3887 | discoveredd in Salivary gland | | |
| hsa-miR-5579-3p | 2867 | 3888 | | | |
| hsa-miR-5579-5p | 2868 | 3889 | | | |
| hsa-miR-558 | 2869 | 3890 | | neuroblastoma | |
| hsa-miR-5580-3p | 2870 | 3891 | | | |
| hsa-miR-5580-5p | 2871 | 3892 | | | |
| hsa-miR-5581-3p | 2872 | 3893 | | | |
| hsa-miR-5581-5p | 2873 | 3894 | | | |
| hsa-miR-5582-3p | 2874 | 3895 | | | |
| hsa-miR-5582-5p | 2875 | 3896 | | | |
| hsa-miR-5583-3p | 2876 | 3897 | | | |
| hsa-miR-5583-5p | 2877 | 3898 | | | |
| hsa-miR-5584-3p | 2878 | 3899 | | | |
| hsa-miR-5584-5p | 2879 | 3900 | | | |
| hsa-miR-5585-3p | 2880 | 3901 | | | |
| hsa-miR-5585-5p | 2881 | 3902 | | | |
| hsa-miR-5586-3p | 2882 | 3903 | | | |
| hsa-miR-5586-5p | 2883 | 3904 | | | |
| hsa-miR-5587-3p | 2884 | 3905 | | | |
| hsa-miR-5587-5p | 2885 | 3906 | | | |
| hsa-miR-5588-3p | 2886 | 3907 | | | |
| hsa-miR-5588-5p | 2887 | 3908 | | | |
| hsa-miR-5589-3p | 2888 | 3909 | | | |
| hsa-miR-5589-5p | 2889 | 3910 | | | |
| hsa-miR-559 | 2890 | 3911 | | | |
| hsa-miR-5590-3p | 2891 | 3912 | | | |
| hsa-miR-5590-5p | 2892 | 3913 | | | |
| hsa-miR-5591-3p | 2893 | 3914 | | | |
| hsa-miR-5591-5p | 2894 | 3915 | | | |
| hsa-miR-561-3p | 2895 | 3916 | | multiple myeloma | |
| hsa-miR-561-5p | 2896 | 3917 | | multiple myeloma | |
| hsa-miR-562 | 2897 | 3918 | | | |
| hsa-miR-563 | 2898 | 3919 | discovered in a colorectal MicroRNAome | | |
| hsa-miR-564 | 2899 | 3920 | | Chronic myeloid leukemia | |
| hsa-miR-566 | 2900 | 3921 | | MALT lymphoma/ lymphocyte | |
| hsa-miR-567 | 2901 | 3922 | | colorectal cancer | |
| hsa-miR-568 | 2902 | 3923 | discovered in a colorectal MicroRNAome | | |
| hsa-miR-5680 | 2903 | 3924 | | Associated with metastatic prostate cancer | |
| hsa-miR-5681a | 2904 | 3925 | | Associated with metastatic prostate cancer | |
| hsa-miR-5681b | 2905 | 3926 | | Associated with metastatic prostate cancer | |
| hsa-miR-5682 | 2906 | 3927 | | Associated with metastatic prostate cancer | |
| hsa-miR-5683 | 2907 | 3928 | | Associated with metastatic prostate cancer | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-5684 | 2908 | 3929 | | Associated with metastatic prostate cancer | |
| hsa-miR-5685 | 2909 | 3930 | | Associated with metastatic prostate cancer | |
| hsa-miR-5686 | 2910 | 3931 | | Associated with metastatic prostate cancer | |
| hsa-miR-5687 | 2911 | 3932 | | Associated with metastatic prostate cancer | |
| hsa-miR-5688 | 2912 | 3933 | | Associated with metastatic prostate cancer | |
| hsa-miR-5689 | 2913 | 3934 | | Associated with metastatic prostate cancer | |
| hsa-miR-569 | 2914 | 3935 | | | |
| hsa-miR-5690 | 2915 | 3936 | | Associated with metastatic prostate cancer | |
| hsa-miR-5691 | 2916 | 3937 | | Associated with metastatic prostate cancer | |
| hsa-miR-5692a | 2917 | 3938 | | Associated with metastatic prostate cancer | |
| hsa-miR-5692b | 2918 | 3939 | | Associated with metastatic prostate cancer | |
| hsa-miR-5692c | 2919 | 3940 | | Associated with metastatic prostate cancer | |
| hsa-miR-5693 | 2920 | 3941 | | Associated with metastatic prostate cancer | |
| hsa-miR-5694 | 2921 | 3942 | | Associated with metastatic prostate cancer | |
| hsa-miR-5695 | 2922 | 3943 | | Associated with metastatic prostate cancer | |
| hsa-miR-5696 | 2923 | 3944 | | Associated with metastatic prostate cancer | |
| hsa-miR-5697 | 2924 | 3945 | | Associated with metastatic prostate cancer | |
| hsa-miR-5698 | 2925 | 3946 | | Associated with metastatic prostate cancer | |
| hsa-miR-5699 | 2926 | 3947 | | Associated with metastatic prostate cancer | |
| hsa-miR-5700 | 2927 | 3948 | | Associated with metastatic prostate cancer | |
| hsa-miR-5701 | 2928 | 3949 | | Associated with metastatic prostate cancer | |
| hsa-miR-5702 | 2929 | 3950 | | Associated with metastatic prostate cancer | |
| hsa-miR-5703 | 2930 | 3951 | | Associated with metastatic prostate cancer | |
| hsa-miR-570-3p | 2931 | 3952 | | follicular lymphoma | |
| hsa-miR-5704 | 2932 | 3953 | | Associated with metastatic prostate cancer | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-5705 | 2933 | 3954 | | Associated with metastatic prostate cancer | |
| hsa-miR-570-5p | 2934 | 3955 | | follicular lymphoma | |
| hsa-miR-5706 | 2935 | 3956 | | Associated with metastatic prostate cancer | |
| hsa-miR-5707 | 2936 | 3957 | | Associated with metastatic prostate cancer | |
| hsa-miR-5708 | 2937 | 3958 | | Associated with metastatic prostate cancer | |
| hsa-miR-571 | 2938 | 3959 | frontal cortex | | |
| hsa-miR-572 | 2939 | 3960 | circulating microRNA (in plasma) | basal cell carcinoma | |
| hsa-miR-573 | 2940 | 3961 | discovered in the colorectal MicroRNAome | | |
| hsa-miR-5739 | 2941 | 3962 | endothelial cells | | |
| hsa-miR-574-3p | 2942 | 3963 | blood (myeloid cells) | follicular lymphoma | |
| hsa-miR-574-5p | 2943 | 3964 | semen | | |
| hsa-miR-575 | 2944 | 3965 | | gastric cancer | |
| hsa-miR-576-3p | 2945 | 3966 | discovered in a colorectal MicroRNAome | | |
| hsa-miR-576-5p | 2946 | 3967 | cartilage/chondrocyte | | |
| hsa-miR-577 | 2947 | 3968 | discovered in a colorectal MicroRNAome | | |
| hsa-miR-578 | 2948 | 3969 | discovered in a colorectal MicroRNAome | | |
| hsa-miR-5787 | 2949 | 3970 | fibroblast | | |
| hsa-miR-579 | 2950 | 3971 | | | |
| hsa-miR-580 | 2951 | 3972 | | breast cancer | |
| hsa-miR-581 | 2952 | 3973 | liver(hepatocytes) | | |
| hsa-miR-582-3p | 2953 | 3974 | cartilage/chondrocyte | bladder cancer | |
| hsa-miR-582-5p | 2954 | 3975 | | bladder cancer | |
| hsa-miR-583 | 2955 | 3976 | | rectal cancer cells | |
| hsa-miR-584-3p | 2956 | 3977 | | tumor cells (follicular lymphoma, rectal cancer cells) | |
| hsa-miR-584-5p | 2957 | 3978 | | tumor cells (follicular lymphoma, rectal cancer cells) | |
| hsa-miR-585 | 2958 | 3979 | | oral squamous cell carcinoma | |
| hsa-miR-586 | 2959 | 3980 | discovered in a colorectal MicroRNAome | | |
| hsa-miR-587 | 2960 | 3981 | discovered in a colorectal MicroRNAome | | |
| hsa-miR-588 | 2961 | 3982 | discovered in a colorectal MicroRNAome | | |
| hsa-miR-589-3p | 2962 | 3983 | mesothelial cells | | |
| hsa-miR-589-5p | 2963 | 3984 | mesothelial cells | | |
| hsa-miR-590-3p | 2964 | 3985 | cardiomyocytes | | Cell cycle progression |
| hsa-miR-590-5p | 2965 | 3986 | cardiomyocytes | | Cell cycle progression |
| hsa-miR-591 | 2966 | 3987 | | neuroblastoma | |
| hsa-miR-592 | 2967 | 3988 | | hepatocellular carcinoma | |
| hsa-miR-593-3p | 2968 | 3989 | | esophageal cancer | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-593-5p | 2969 | 3990 | | esophageal cancer | |
| hsa-miR-595 | 2970 | 3991 | | heart failure | |
| hsa-miR-596 | 2971 | 3992 | | ependymoma, cancers | |
| hsa-miR-597 | 2972 | 3993 | discovered in a colorectal MicroRNAome | | |
| hsa-miR-598 | 2973 | 3994 | Blood (lymphocytes) | | |
| hsa-miR-599 | 2974 | 3995 | | Multiple sclerosis | |
| hsa-miR-600 | 2975 | 3996 | discovered in a colorectal MicroRNAome | | |
| hsa-miR-601 | 2976 | 3997 | | various cancers (colonrectal, gastric) | |
| hsa-miR-602 | 2977 | 3998 | oocyte | | |
| hsa-miR-603 | 2978 | 3999 | | | |
| hsa-miR-604 | 2979 | 4000 | discovered in a colorectal MicroRNAome | | |
| hsa-miR-605 | 2980 | 4001 | discovered in a colorectal MicroRNAome | | |
| hsa-miR-606 | 2981 | 4002 | discovered in a colorectal MicroRNAome | | |
| hsa-miR-6068 | 2982 | 4003 | discovered in endothelial cells | | |
| hsa-miR-6069 | 2983 | 4004 | discovered in endothelial cells | | |
| hsa-miR-607 | 2984 | 4005 | discovered in a colorectal MicroRNAome | | |
| hsa-miR-6070 | 2985 | 4006 | discovered in a colorectal MicroRNAome | | |
| hsa-miR-6071 | 2986 | 4007 | discovered in endothelial cells | | |
| hsa-miR-6072 | 2987 | 4008 | discovered in endothelial cells | | |
| hsa-miR-6073 | 2988 | 4009 | discovered in endothelial cells | | |
| hsa-miR-6074 | 2989 | 4010 | discovered in endothelial cells | | |
| hsa-miR-6075 | 2990 | 4011 | discovered in endothelial cells | | |
| hsa-miR-6076 | 2991 | 4012 | discovered in endothelial cells | | |
| hsa-miR-6077 | 2992 | 4013 | discovered in endothelial cells | | |
| hsa-miR-6078 | 2993 | 4014 | discovered in endothelial cells | | |
| hsa-miR-6079 | 2994 | 4015 | discovered in endothelial cells | | |
| hsa-miR-608 | 2995 | 4016 | | various cancers | |
| hsa-miR-6080 | 2996 | 4017 | discovered in endothelial cells | | |
| hsa-miR-6081 | 2997 | 4018 | discovered in endothelial cells | | |
| hsa-miR-6082 | 2998 | 4019 | discovered in endothelial cells | | |
| hsa-miR-6083 | 2999 | 4020 | discovered in endothelial cells | | |
| hsa-miR-6084 | 3000 | 4021 | discovered in endothelial cells | | |
| hsa-miR-6085 | 3001 | 4022 | discovered in endothelial cells | | |
| hsa-miR-6086 | 3002 | 4023 | embryonic stem cells | | |
| hsa-miR-6087 | 3003 | 4024 | embryonic stem cells | | |
| hsa-miR-6088 | 3004 | 4025 | embryonic stem cells | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-6089 | 3005 | 4026 | embryonic stem cells | | |
| hsa-miR-609 | 3006 | 4027 | discovered in a colorectal MicroRNAome | | |
| hsa-miR-6090 | 3007 | 4028 | embryonic stem cells | | |
| hsa-miR-610 | 3008 | 4029 | | gastric cancer | |
| hsa-miR-611 | 3009 | 4030 | | Renal cell carcinoma | |
| hsa-miR-612 | 3010 | 4031 | | AM leukemia | |
| hsa-miR-6124 | 3011 | 4032 | | | |
| hsa-miR-6125 | 3012 | 4033 | | | |
| hsa-miR-6126 | 3013 | 4034 | | | |
| hsa-miR-6127 | 3014 | 4035 | | | |
| hsa-miR-6128 | 3015 | 4036 | | | |
| hsa-miR-6129 | 3016 | 4037 | | | |
| hsa-miR-613 | 3017 | 4038 | lipid metabolism | | |
| hsa-miR-6130 | 3018 | 4039 | | | |
| hsa-miR-6131 | 3019 | 4040 | | | |
| hsa-miR-6132 | 3020 | 4041 | | | |
| hsa-miR-6133 | 3021 | 4042 | | | |
| hsa-miR-6134 | 3022 | 4043 | | | |
| hsa-miR-614 | 3023 | 4044 | circulating micrRNAs (in Plasma) | | |
| hsa-miR-615-3p | 3024 | 4045 | | | |
| hsa-miR-615-5p | 3025 | 4046 | | | |
| hsa-miR-616-3p | 3026 | 4047 | | prostate cancer | |
| hsa-miR-6165 | 3027 | 4048 | | | Pro-apoptotic factor |
| hsa-miR-616-5p | 3028 | 4049 | | prostate cancer | |
| hsa-miR-617 | 3029 | 4050 | | | |
| hsa-miR-618 | 3030 | 4051 | | | |
| hsa-miR-619 | 3031 | 4052 | discovered in a colorectal MicroRNAome | | |
| hsa-miR-620 | 3032 | 4053 | discovered in a colorectal MicroRNAome | | |
| hsa-miR-621 | 3033 | 4054 | | | |
| hsa-miR-622 | 3034 | 4055 | | | |
| hsa-miR-623 | 3035 | 4056 | | | |
| hsa-miR-624-3p | 3036 | 4057 | chondrocyte | | |
| hsa-miR-624-5p | 3037 | 4058 | chondrocyte | | |
| hsa-miR-625-3p | 3038 | 4059 | liver(hepatocytes), circulating (blood) | various cancers | |
| hsa-miR-625-5p | 3039 | 4060 | liver(hepatocytes), circulating (blood) | various cancers | |
| hsa-miR-626 | 3040 | 4061 | discovered in the colorectal MicroRNAome | | |
| hsa-miR-627 | 3041 | 4062 | | colorectal cancer | |
| hsa-miR-628-3p | 3042 | 4063 | | neuroblastoma | |
| hsa-miR-628-5p | 3043 | 4064 | | neuroblastoma | |
| hsa-miR-629-3p | 3044 | 4065 | | B-lineage ALL, T cell lupus, RCC/kidney | |
| hsa-miR-629-5p | 3045 | 4066 | | B-lineage ALL, T cell lupus, RCC/kidney | |
| hsa-miR-630 | 3046 | 4067 | chondrocytes | rectal cancer | |
| hsa-miR-631 | 3047 | 4068 | discovered in the colorectal MicroRNAom | | |
| hsa-miR-632 | 3048 | 4069 | | myelodysplastic syndromes | |
| hsa-miR-633 | 3049 | 4070 | | multiple sclerosis | |
| hsa-miR-634 | 3050 | 4071 | cartilage/ chondrocyte | | |
| hsa-miR-635 | 3051 | 4072 | discovered in the colorectal MicroRNAome | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-636 | 3052 | 4073 | | myelodysplastic syndromes | |
| hsa-miR-637 | 3053 | 4074 | discovered in the colorectal MicroRNAome | | |
| hsa-miR-638 | 3054 | 4075 | | Lupus nephritis, basal cell carcinoma | |
| hsa-miR-639 | 3055 | 4076 | discovered in the colorectal MicroRNAome | | |
| hsa-miR-640 | 3056 | 4077 | | Chronic lymphocytic leukemia | |
| hsa-miR-641 | 3057 | 4078 | cartilage/chondrocyte | | |
| hsa-miR-642a-3p | 3058 | 4079 | adipocyte | | |
| hsa-miR-642a-5p | 3059 | 4080 | discovered in the colorectal MicroRNAome | | |
| hsa-miR-642b-3p | 3060 | 4081 | discovered in a cervial tumo | | |
| hsa-miR-642b-5p | 3061 | 4082 | discovered in a cervial tumo | | |
| hsa-miR-643 | 3062 | 4083 | discovered in the colorectal MicroRNAome | | |
| hsa-miR-644a | 3063 | 4084 | | | |
| hsa-miR-645 | 3064 | 4085 | | ovarian cancer | |
| hsa-miR-646 | 3065 | 4086 | | | |
| hsa-miR-647 | 3066 | 4087 | | prostate and lung cancer | |
| hsa-miR-648 | 3067 | 4088 | circulating micrRNAs (in Plasma) | | |
| hsa-miR-649 | 3068 | 4089 | Serum | | |
| hsa-miR-6499-3p | 3069 | 4090 | discovered in abnormal skin (psoriasis) | | |
| hsa-miR-6499-5p | 3070 | 4091 | discovered in abnormal skin (psoriasis) | | |
| hsa-miR-650 | 3071 | 4092 | | melanoma | |
| hsa-miR-6500-3p | 3072 | 4093 | discovered in abnormal skin (psoriasis) | | |
| hsa-miR-6500-5p | 3073 | 4094 | discovered in abnormal skin (psoriasis) | | |
| hsa-miR-6501-3p | 3074 | 4095 | discovered in abnormal skin (psoriasis) | | |
| hsa-miR-6501-5p | 3075 | 4096 | discovered in abnormal skin (psoriasis) | | |
| hsa-miR-6502-3p | 3076 | 4097 | discovered in abnormal skin (psoriasis) | | |
| hsa-miR-6502-5p | 3077 | 4098 | discovered in abnormal skin (psoriasis) | | |
| hsa-miR-6503-3p | 3078 | 4099 | discovered in abnormal skin (psoriasis) | | |
| hsa-miR-6503-5p | 3079 | 4100 | discovered in abnormal skin (psoriasis) | | |
| hsa-miR-6504-3p | 3080 | 4101 | discovered in abnormal skin (psoriasis) | | |
| hsa-miR-6504-5p | 3081 | 4102 | discovered in abnormal skin (psoriasis) | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-6505-3p | 3082 | 4103 | discovered in abnormal skin (psoriasis) | | |
| hsa-miR-6505-5p | 3083 | 4104 | discovered in abnormal skin (psoriasis) | | |
| hsa-miR-6506-3p | 3084 | 4105 | discovered in abnormal skin (psoriasis) | | |
| hsa-miR-6506-5p | 3085 | 4106 | discovered in abnormal skin (psoriasis) | | |
| hsa-miR-6507-3p | 3086 | 4107 | discovered in abnormal skin (psoriasis) | | |
| hsa-miR-6507-5p | 3087 | 4108 | discovered in abnormal skin (psoriasis) | | |
| hsa-miR-6508-3p | 3088 | 4109 | discovered in abnormal skin (psoriasis) | | |
| hsa-miR-6508-5p | 3089 | 4110 | discovered in abnormal skin (psoriasis) | | |
| hsa-miR-6509-3p | 3090 | 4111 | discovered in abnormal skin (psoriasis) | | |
| hsa-miR-6509-5p | 3091 | 4112 | discovered in abnormal skin (psoriasis) | | |
| hsa-miR-651 | 3092 | 4113 | discovered in the colorectal MicroRNAome | lung cancer | |
| hsa-miR-6510-3p | 3093 | 4114 | discovered in abnormal skin (psoriasis) | | |
| hsa-miR-6510-5p | 3094 | 4115 | discovered in abnormal skin (psoriasis) | | |
| hsa-miR-6511a-3p | 3095 | 4116 | discovered in abnormal skin (psoriasis) and epididymis | | |
| hsa-miR-6511a-5p | 3096 | 4117 | discovered in abnormal skin (psoriasis) and epididymis | | |
| hsa-miR-6511b-3p | 3097 | 4118 | discovered in epididymis | | |
| hsa-miR-6511b-5p | 3098 | 4119 | discovered in epididymis | | |
| hsa-miR-6512-3p | 3099 | 4120 | discovered in abnormal skin (psoriasis) | | |
| hsa-miR-6512-5p | 3100 | 4121 | discovered in abnormal skin (psoriasis) | | |
| hsa-miR-6513-3p | 3101 | 4122 | discovered in abnormal skin (psoriasis) | | |
| hsa-miR-6513-5p | 3102 | 4123 | discovered in abnormal skin (psoriasis) | | |
| hsa-miR-6514-3p | 3103 | 4124 | discovered in abnormal skin (psoriasis) | | |
| hsa-miR-6514-5p | 3104 | 4125 | discovered in abnormal skin (psoriasis) | | |
| hsa-miR-6515-3p | 3105 | 4126 | discovered in abnormal skin (psoriasis) and epididymis | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-6515-5p | 3106 | 4127 | discovered in abnormal skin (psoriasis) and epididymis | | |
| hsa-miR-652-3p | 3107 | 4128 | | rectal cancer cells | |
| hsa-miR-652-5p | 3108 | 4129 | | rectal cancer cells | |
| hsa-miR-653 | 3109 | 4130 | Discovered in the colorectal MicroRNAome | | |
| hsa-miR-654-3p | 3110 | 4131 | Discovered in the colorectal MicroRNAome | | |
| hsa-miR-654-5p | 3111 | 4132 | bone marrow | prostate cancer | |
| hsa-miR-655 | 3112 | 4133 | | | |
| hsa-miR-656 | 3113 | 4134 | | various cancers | |
| hsa-miR-657 | 3114 | 4135 | oligodendrocytes | diabetes | |
| hsa-miR-658 | 3115 | 4136 | | gastric cancer | |
| hsa-miR-659-3p | 3116 | 4137 | myoblast | | |
| hsa-miR-659-5p | 3117 | 4138 | myoblast | | |
| hsa-miR-660-3p | 3118 | 4139 | myoblast | | |
| hsa-miR-660-5p | 3119 | 4140 | myoblast | | |
| hsa-miR-661 | 3120 | 4141 | | breast cancer | |
| hsa-miR-662 | 3121 | 4142 | endothelial progenitor cells, oocytes | | |
| hsa-miR-663a | 3122 | 4143 | | follicular lymphoma, Lupus nephritis | |
| hsa-miR-663b | 3123 | 4144 | | follicular lymphoma, Lupus nephritis | |
| hsa-miR-664a-3p | 3124 | 4145 | embryonic stem cells | | component of SnoRNAs |
| hsa-miR-664a-5p | 3125 | 4146 | embryonic stem cells | | component of SnoRNAs |
| hsa-miR-664b-3p | 3126 | 4147 | embryonic stem cells | | component of SnoRNAs |
| hsa-miR-664b-5p | 3127 | 4148 | embryonic stem cells | | component of SnoRNAs |
| hsa-miR-665 | 3128 | 4149 | | breast cancer | |
| hsa-miR-668 | 3129 | 4150 | keratinocytes | | senescence |
| hsa-miR-670 | 3130 | 4151 | | | |
| hsa-miR-671-3p | 3131 | 4152 | | | |
| hsa-miR-6715a-3p | 3132 | 4153 | discovered in epididymis | | |
| hsa-miR-6715b-3p | 3133 | 4154 | discovered in epididymis | | |
| hsa-miR-6715b-5p | 3134 | 4155 | discovered in epididymis | | |
| hsa-miR-671-5p | 3135 | 4156 | | rectal cancer, prolactinomas | |
| hsa-miR-6716-3p | 3136 | 4157 | discovered in epididymis | | |
| hsa-miR-6716-5p | 3137 | 4158 | discovered in epididymis | | |
| hsa-miR-6717-5p | 3138 | 4159 | discovered in epididymis | | |
| hsa-miR-6718-5p | 3139 | 4160 | discovered in epididymis | | |
| hsa-miR-6719-3p | 3140 | 4161 | discovered in epididymis | | |
| hsa-miR-6720-3p | 3141 | 4162 | discovered in epididymis | | |
| hsa-miR-6721-5p | 3142 | 4163 | discovered in epididymis | | |
| hsa-miR-6722-3p | 3143 | 4164 | discovered in epididymis | | |
| hsa-miR-6722-5p | 3144 | 4165 | discovered in epididymis | | |
| hsa-miR-6723-5p | 3145 | 4166 | discovered in epididymis | | |
| hsa-miR-6724-5p | 3146 | 4167 | discovered in epididymis | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-675-3p | 3147 | 4168 | | adrenocortical tumor | |
| hsa-miR-675-5p | 3148 | 4169 | | adrenocortical tumor | |
| hsa-miR-676-3p | 3149 | 4170 | discovered in female reproductuve tract | | |
| hsa-miR-676-5p | 3150 | 4171 | discovered in female reproductuve tract | | |
| hsa-miR-708-3p | 3151 | 4172 | | Various cancers (lung, bladder, pancreatic, ALL) | |
| hsa-miR-708-5p | 3152 | 4173 | | Various cancers (lung, bladder, pancreatic, ALL) | |
| hsa-miR-711 | 3153 | 4174 | | cutaneous T-cell lymphomas | |
| hsa-miR-7-1-3p | 3154 | 4175 | Glioblast, brain, prancreas | | |
| hsa-miR-718 | 3155 | 4176 | blood | | |
| hsa-miR-7-2-3p | 3156 | 4177 | brain, pancreas | | |
| hsa-miR-744-3p | 3157 | 4178 | heart | | |
| hsa-miR-744-5p | 3158 | 4179 | embryonic stem cells, heart | | |
| hsa-miR-758-3p | 3159 | 4180 | cholesterol regulation and brain | | |
| hsa-miR-758-5p | 3160 | 4181 | cholesterol regulation and brain | | |
| hsa-miR-759 | 3161 | 4182 | | | |
| hsa-miR-7-5p | 3162 | 4183 | brain | | |
| hsa-miR-760 | 3163 | 4184 | | colonrectal and breast cancer | |
| hsa-miR-761 | 3164 | 4185 | | | |
| hsa-miR-762 | 3165 | 4186 | corneal epithelial cells | | |
| hsa-miR-764 | 3166 | 4187 | osteoblast | | |
| hsa-miR-765 | 3167 | 4188 | | rectal cancer | |
| hsa-miR-766-3p | 3168 | 4189 | embryonic stem cells | | |
| hsa-miR-766-5p | 3169 | 4190 | embryonic stem cells | | |
| hsa-miR-767-3p | 3170 | 4191 | | | |
| hsa-miR-767-5p | 3171 | 4192 | | | |
| hsa-miR-769-3p | 3172 | 4193 | | | |
| hsa-miR-769-5p | 3173 | 4194 | | | |
| hsa-miR-770-5p | 3174 | 4195 | | | |
| hsa-miR-802 | 3175 | 4196 | brain, epithelial cells, hepatocytes | down symdrome | |
| hsa-miR-873-3p | 3176 | 4197 | | | |
| hsa-miR-873-5p | 3177 | 4198 | | | |
| hsa-miR-874 | 3178 | 4199 | | cervical cancer, lung cancer, carcinoma | |
| hsa-miR-875-3p | 3179 | 4200 | | | |
| hsa-miR-875-5p | 3180 | 4201 | | | |
| hsa-miR-876-3p | 3181 | 4202 | | | |
| hsa-miR-876-5p | 3182 | 4203 | | | |
| hsa-miR-877-3p | 3183 | 4204 | | | |
| hsa-miR-877-5p | 3184 | 4205 | | | |
| hsa-miR-885-3p | 3185 | 4206 | embryonic stem cells | | |
| hsa-miR-885-5p | 3186 | 4207 | embryonic stem cells | | |
| hsa-miR-887 | 3187 | 4208 | | | |
| hsa-miR-888-3p | 3188 | 4209 | | | |
| hsa-miR-888-5p | 3189 | 4210 | | | |
| hsa-miR-889 | 3190 | 4211 | | | |
| hsa-miR-890 | 3191 | 4212 | epididymis | | |
| hsa-miR-891a | 3192 | 4213 | epididymis | osteosarcoma | |
| hsa-miR-891b | 3193 | 4214 | epididymis | | |
| hsa-miR-892a | 3194 | 4215 | epididymis | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-892b | 3195 | 4216 | epididymis | | |
| hsa-miR-892c-3p | 3196 | 4217 | discovered in epididymis | | |
| hsa-miR-892c-5p | 3197 | 4218 | discovered in epididymis | | |
| hsa-miR-920 | 3198 | 4219 | human testis | | |
| hsa-miR-921 | 3199 | 4220 | human testis | muscle invasive bladder cancer | |
| hsa-miR-922 | 3200 | 4221 | human testis, neuronal tissues | multiple sclerosis, Alcoholic liver disease | |
| hsa-miR-924 | 3201 | 4222 | human testis | | |
| hsa-miR-92a-1-5p | 3202 | 4223 | endothelial cells | | |
| hsa-miR-92a-2-5p | 3203 | 4224 | endothelial cells | | |
| hsa-miR-92a-3p | 3204 | 4225 | endothelial cells, CNS | | |
| hsa-miR-92b-3p | 3205 | 4226 | endothelial cells, heart | | |
| hsa-miR-92b-5p | 3206 | 4227 | endothelial cells, heart | | |
| hsa-miR-933 | 3207 | 4228 | discovered in cervical cancer | | |
| hsa-miR-93-3p | 3208 | 4229 | embryonic stem cells | basal cell carcinoma | |
| hsa-miR-934 | 3209 | 4230 | discovered in cervical cancer | | |
| hsa-miR-935 | 3210 | 4231 | blood monoclear cells | energy metabolism/ obesity, medullablastoma/ neural stem cells | |
| hsa-miR-93-5p | 3211 | 4232 | embryonic stem cells | | |
| hsa-miR-936 | 3212 | 4233 | skin | | |
| hsa-miR-937-3p | 3213 | 4234 | | cervical cancer | |
| hsa-miR-937-5p | 3214 | 4235 | | cervical cancer | |
| hsa-miR-938 | 3215 | 4236 | | Various cancer cells | |
| hsa-miR-939-3p | 3216 | 4237 | hepatocytes | | |
| hsa-miR-939-5p | 3217 | 4238 | hepatocytes | | |
| hsa-miR-9-3p | 3218 | 4239 | brain | Cancers and brain diseases | |
| hsa-miR-940 | 3219 | 4240 | identified in Cervical cancer | | |
| hsa-miR-941 | 3220 | 4241 | Embryonic stem cells | | |
| hsa-miR-942 | 3221 | 4242 | | lung cancer | |
| hsa-miR-943 | 3222 | 4243 | identified in Cervical cancer | | |
| hsa-miR-944 | 3223 | 4244 | | various cancers (cervical, pancreatic, colonrectal) | |
| hsa-miR-95 | 3224 | 4245 | | various cancers (pancreatic, glioblastoma, colorectal etc) | |
| hsa-miR-9-5p | 3225 | 4246 | brain | Cancers and brain disease | |
| hsa-miR-96-3p | 3226 | 4247 | stem cells | various cancers (prostate, lymphoma, HCC, etc) and inflammation | |
| hsa-miR-96-5p | 3227 | 4248 | stem cells | various cancers (prostate, lymphoma, HCC, etc) and inflammation | |
| hsa-miR-98-3p | 3228 | 4249 | | various cancer cells | apoptosis |
| hsa-miR-98-5p | 3229 | 4250 | | various cancer cells | apoptosis |
| hsa-miR-99a-3p | 3230 | 4251 | hemapoietic cells | | |
| hsa-miR-99a-5p | 3231 | 4252 | hemapoietic cells | | |

TABLE 12-continued mirs, tissues/cell expression and diseases

| microRNA | mir SEQ ID | BS SEQ ID | Tissues/cells | Associated disease | Biological function |
|---|---|---|---|---|---|
| hsa-miR-99b-3p | 3232 | 4253 | hemapoietic cells, embryonic stem cells | | |
| hsa-miR-99b-5p | 3233 | 4254 | hemapoietic cells, embryonic stem cells | | |

MicroRNAs that are enriched in specific types of immune cells are listed in Table 13. Furthermore, novel miroRNAs are discovered in the immune cells in the art through micro-array hybridization and microtome analysis (Jima D D et al, Blood, 2010, 116:e118-e127; Vaz C et al., BMC Genomics, 2010, 11,288, the content of each of which is incorporated herein by reference in its entirety). In Table 13, "HCC" represents hepatocellular carcinoma, "ALL" stands for acute lymphoblastsic leukemia and "CLL" stands for chrominc lymphocytic leukemia.

TABLE 13 microRNAs in immune cells

| microRNA | mir SEQ ID | BS SEQ ID | tissues/cells with MicroRNAs | associated diseases | biological functions/targets |
|---|---|---|---|---|---|
| hsa-let-7a-2-3p | 171 | 1192 | embryonic stem cells, lung, myeloid cells | inflammatory, various cancers (lung, cervical, breast, pancreatic, etc) | tumor suppressor, target to c-myc |
| hsa-let-7a-3p | 172 | 1193 | embryonic stem cell, lung, myeloid cells | inflammatory, various cancers (lung, cervical, breast, pancreatic, etc) | tumor suppressor, target to c-myc |
| hsa-let-7a-5p | 173 | 1194 | embryonic stem cells, lung, myeloid cells | inflammatory, various cancers (lung, cervical, breast, pancreatic, etc) | tumor suppressor, target to c-myc |
| hsa-let-7c | 176 | 1197 | dendritic cells | various cacners (cervical, pancreatic, lung, esopphageal, etc) | tumor suppressor apoptosis (target to BCL-xl) |
| hsa-let-7e-3p | 179 | 1200 | immune cells | various cancer cells, autoimmunity TLR signal pathway in endotoxin tolerance | tumor suppressor |
| hsa-let-7e-5p | 180 | 1201 | immune cells | associated with various cancer cells | tumor suppressor |
| hsa-let-7f-1-3p | 181 | 1202 | immune cells (T cells) | associated with various cancer cells | tumor suppressor |
| hsa-let-7f-2-3p | 182 | 1203 | immune cells (T cells) | associated with various cancer cells | tumor suppressor |
| hsa-let-7f-5p | 183 | 1204 | immune cells (T cells) | associated with various cancer cells | tumor suppressor |
| hsa-let-7g-3p | 184 | 1205 | hematopoietic cells, adipose, smooth muscle cells | various cancer cells (lung, breast, etc) | tumor suppressor (target to NFkB, LOX1 |
| hsa-let-7g-5p | 185 | 1206 | hematopoietic cells, adipose, smooth muscle cells | various cancer cells (lung, breast, etc) | tumor suppressor (target to NFkB, LOX1 |
| hsa-let-7i-3p | 186 | 1207 | immune cells | chronic lymphocyte leukimia | tumor suppressor |

TABLE 13-continued microRNAs in immune cells

| microRNA | mir SEQ ID | BS SEQ ID | tissues/cells with MicroRNAs | associated diseases | biological functions/targets |
|---|---|---|---|---|---|
| hsa-let-7i-5p | 187 | 1208 | immune cells | chronic lymphocyte leukimia | tumor suppressor |
| hsa-miR-10a-3p | 203 | 1224 | hematopoeitic cells | acute myeoid leukemia | oncogene, cell growth |
| hsa-miR-10a-5p | 204 | 1225 | hematopoietic cells | acute myeloid leukemia | oncogene, cell growth |
| hsa-miR-1184 | 214 | 1235 | Hematopoietic cells | downregulated in oral leukoplakia (OLK) | predited in the intron 22 of F8 gene |
| hsa-miR-125b-1-3p | 279 | 1300 | hematopoietic cells (monocytes), brain (neuron) | various cancer (ALL, prostate, HCC, etc); TLR signal pathway in endotoxin tolerance | oncogene, cell differentiation |
| hsa-miR-125b-2-3p | 280 | 1301 | hematopoietic cells (monocytes), brain (neuron) | various cancer (ALL, prostate, HCC etc); TLR signal pathway in endotoxin tolerance | oncogene cell differentiation |
| hsa-miR-125b-5p | 281 | 1302 | hematopoietic cells, brain (neuron) | various cancer (Cutaneous T cell lymphomas, prostate, HCC, etc); TLR signal pathway in endotoxin tolerance | oncogene cell differentiation |
| hsa-miR-1279 | 315 | 1336 | monocytes | | |
| hsa-miR-130a-3p | 353 | 1374 | lung, monocytes, vascular endothelial cells | various cancers (basal cell carcinoma, HCC, ovarian, etc), drug resistance | pro-angiogenic |
| hsa-miR-130a-5p | 354 | 1375 | lung, monocytes, vasscular endothelial cells | various cancers (basal cell carcinoma, HCC, ovarian, etc), drug resistance | pro-angiogenic |
| hsa-miR-132-3p | 360 | 1381 | brain(neuron), immune cells | | |
| hsa-miR-132-5p | 362 | 1383 | brain(neuron), immune cells | | |
| hsa-miR-142-3p | 383 | 1404 | meyloid cells, hematopoiesis, APC cells | | tumor suppressor, immune response |
| hsa-miR-142-5p | 384 | 1405 | meyloid cells, hematopoiesis, APC cells | | immune response |
| hsa-miR-143-5p | 386 | 1407 | vascular smooth muscle, T-cells | increased in serum after virus infection | |
| hsa-miR-146a-3p | 393 | 1414 | immune cells, hematopoiesis, cartilage, | associated with CLL, TLR signal pathway in endotoxin tolerance | |
| hsa-miR-146a-5p | 394 | 1415 | immune cells, hematopoiesis, cartilage, | associated with CLL, TLR signal pathway in endotoxin tolerance | |
| hsa-miR-146b-3p | 395 | 1416 | immune cells | cancers (thyroid carcimona) | immune response |
| hsa-miR-146b-5p | 396 | 1417 | embryoid body cells | thyroid cancer, associated with CLL | tumor invation, migration |
| hsa-miR-147a | 399 | 1420 | Macrophage | inflammatory response | |

TABLE 13-continued microRNAs in immune cells

| microRNA | mir SEQ ID | BS SEQ ID | tissues/cells with MicroRNAs | associated diseases | biological functions/targets |
|---|---|---|---|---|---|
| hsa-miR-147b | 400 | 1421 | Macrophage | inflammatory response | |
| hsa-miR-148a-3p | 401 | 1422 | hematopoietic cells | associated with CLL, T-lineage ALL | |
| hsa-miR-148a-5p | 402 | 1423 | hematopoietic cells | associated with CLL, T-lineage ALL | |
| hsa-miR-150-3p | 407 | 1428 | hematopoitic cells (lymphoid) | circulating plasma (acute myeloid leukemia) | |
| hsa-miR-150-5p | 408 | 1429 | hematopoitic cells (lymphoid) | circulating plasma (acute myeloid leukemia) | |
| hsa-miR-151b | 411 | 1432 | immune cells (B-cells) | | |
| hsa-miR-155-3p | 419 | 1440 | T/B cells, monocytes, breast | associated with CLL, TLR signal pathway in endotoxin tolerance; upregulated in B cell lymphoma(CLL) and other cancers (breast, lung, ovarian, cervical, colorectal, prostate) | |
| hsa-miR-155-5p | 420 | 1441 | T/B cells, monocytes, breast | associated with CLL, TLR signal pathway in endotoxin tolerance, upregulated in B cell lymphoma (CLL) and other cancers (breast, lung, ovarian, cervical, colorectal, prostate) | |
| hsa-miR-15a-3p | 422 | 1443 | blood, lymphocyte, hematopoietic tissues (spleen) | chronic lymphocytic leukemia | |
| hsa-miR-15a-5p | 423 | 1444 | blood, lymphocyte, hematopoietic tissues (spleen) | chronic lymphocytic leukemia | |
| hsa-miR-15b-3p | 424 | 1445 | blood, lymphocyte, hematopoietic tissues (spleen) | | cell cycle, proliferation |
| hsa-miR-15b-5p | 425 | 1446 | blood, lymphocyte, hematopoietic tissues (spleen) | | cell cycle, proliferation |
| hsa-miR-16-1-3p | 426 | 1447 | embryonic stem cells, blood, hematopoietic tissues (spleen) | chronic lymphocytic leukemia | |
| hsa-miR-16-2-3p | 427 | 1448 | blood, lymphocyte, hematopoietic tissues (spleen) | | |
| hsa-miR-16-5p | 428 | 1449 | blood, lymphocyte, hematopoietic tissues | | |

TABLE 13-continued microRNAs in immune cells

| microRNA | mir SEQ ID | BS SEQ ID | tissues/cells with MicroRNAs | associated diseases | biological functions/targets |
|---|---|---|---|---|---|
| hsa-miR-181a-3p | 432 | 1453 | glioblast, myeloid cells, Embryonic stem cells | | |
| hsa-miR-181a-5p | 433 | 1454 | glioblast, myeloid cells, Embryonic stem cells | | |
| hsa-miR-182-3p | 439 | 1460 | immune cells | colonrectal cancer, autoimmne | immune response |
| hsa-miR-182-5p | 441 | 1462 | lung, immune cells | autoimmune | immune response |
| hsa-miR-197-3p | 490 | 1511 | blood (myeloid), other tissues | various cancers (thyroid tumor, leukemia, etc) | |
| hsa-miR-197-5p | 491 | 1512 | blood (myeloid), other tissues | various cancers (thyroid tumor, leukemia, etc) | |
| hsa-miR-21-3p | 542 | 1563 | glioblast, Blood (meyloid cells), liver, vascular endothelial cells | autoimmune, heart diseases, cancers | |
| hsa-miR-214-3p | 543 | 1564 | immune cells, pancreas | varioua cancers (melanoma, pancreatic, ovarian) | immune response |
| hsa-miR-214-5p | 544 | 1565 | immune cells, pancreas | varioua cancers (melanoma, pancreatic, ovarian) | immune response |
| hsa-miR-21-5p | 546 | 1567 | blood (myeloid cells), liver, endothelial cells | autoimmune, heart diseases, cancers | |
| hsa-miR-221-3p | 557 | 1578 | endothelial cells, immune cells | breast cancer, upregulated in thyroid cell transformation induced by HMGA1, TLR signal pathway in endotoxin tolerance, upregulated in T cell ALL | angiogenesis/ vasculogenesis |
| hsa-miR-221-5p | 558 | 1579 | endothelial cells, immune cells | breast cancer, upregulated in thyroid cell transformation induced by HMGA1, TLR signal pathway in endotoxin tolerance, upregulated in T cell ALL | angiogenesis/ vasculogenesis |
| hsa-miR-223-3p | 561 | 1582 | meyloid cells | associated with CLL | |
| hsa-miR-223-5p | 562 | 1583 | meyloid cells | associated with CLL | |
| hsa-miR-23b-3p | 576 | 1597 | blood, myeloid cells | cancers (renal cancer, glioblastoma, prostate, etc) and autoimmune | |
| hsa-miR-23b-5p | 577 | 1598 | blood, myeloid cells | cancers(glioblastoma, prostate, etc) and autoimmune | |
| hsa-miR-24-1-5p | 579 | 1600 | lung, myeloid cells | | |
| hsa-miR-24-2-5p | 580 | 1601 | lung, myeloid cells | | |
| hsa-miR-24-3p | 581 | 1602 | lung, myeloid cells | | |

TABLE 13-continued microRNAs in immune cells

| microRNA | mir SEQ ID | BS SEQ ID | tissues/cells with MicroRNAs | associated diseases | biological functions/targets |
|---|---|---|---|---|---|
| hsa-miR-26a-1-3p | 590 | 1611 | embryonic stem cells, blood (T cells) | chronic lymphocyte leukemia and other cancers | cell cycle and differentiation |
| hsa-miR-26a-2-3p | 591 | 1612 | blood (Tcells), other tissues | chronic lymphocyte leukemia and other cancers | cell cycle and differentiation |
| hsa-miR-26a-5p | 592 | 1613 | blood (Tcells), other tissues | chronic lymphocyte leukemia and other cancers | cell cycle and differentiation |
| hsa-miR-26b-3p | 593 | 1614 | hematopoietic cells | | |
| hsa-miR-26b-5p | 594 | 1615 | hematopoietic cells | | |
| hsa-miR-27a-3p | 595 | 1616 | myeloid cells | various cancer cells | |
| hsa-miR-27a-5p | 596 | 1617 | myeloid cells | various cancer cells | |
| hsa-miR-27b-3p | 597 | 1618 | myeloid cells, vascular endothelial cells | various cancer cells | pro-angiogenic |
| hsa-miR-28-3p | 599 | 1620 | blood(immune cells) | B/T cell lymphoma | |
| hsa-miR-28-5p | 600 | 1621 | blood(immune cells) | B/T cell lymphoma | |
| hsa-miR-2909 | 602 | 1623 | T-Lymphocytes | | |
| hsa-miR-29a-3p | 611 | 1632 | immuno system, colonrectun | various cancers, neurodegenerative disease | tumor suppression, immune modulation (mir-29 family) |
| hsa-miR-29a-5p | 612 | 1633 | immuno system, colonrectun | various cancers, neurodegenerative disease | adaptive immunity |
| hsa-miR-29b-1-5p | 613 | 1634 | immuno system | associated with CLL, other cancers, neurodegenerative disease | adaptive immunity |
| hsa-miR-29b-2-5p | 614 | 1635 | immuno system | associated with CLL, other cancers, | adaptive immunity |
| hsa-miR-29b-3p | 615 | 1636 | immuno system | associated with CLL, other cancers | adaptive immunity |
| hsa-miR-29c-3p | 616 | 1637 | immuno system | associated with CLL, other cancers | adaptive immunity |
| hsa-miR-29c-5p | 617 | 1638 | immuno system | associated with CLL, other cancers | adaptive immunity |
| hsa-miR-30e-3p | 647 | 1668 | myeloid cells, glia cells | | |
| hsa-miR-30e-5p | 648 | 1669 | myeloid cells, glia cells | | |
| hsa-miR-331-5p | 793 | 1814 | lymphocytes | | |
| hsa-miR-339-3p | 800 | 1821 | immune cells | | |
| hsa-miR-339-5p | 801 | 1822 | immune cells | | |
| hsa-miR-345-3p | 810 | 1831 | hematopoietic cells | increased in follicular lymphoma(53), other cancers | |
| hsa-miR-345-5p | 811 | 1832 | hematopoietic cells | increased in follicular lymphoma(53) | |
| hsa-miR-346 | 812 | 1833 | immume cells | cancers and autoimmune | |
| hsa-miR-34a-3p | 813 | 1834 | breast, myeloid cells, ciliated epithelial cells | gastric cancer, CLL, other | tumor suppressor, p53 inducible |

TABLE 13-continued microRNAs in immune cells

| microRNA | mir SEQ ID | BS SEQ ID | tissues/cells with MicroRNAs | associated diseases | biological functions/targets |
|---|---|---|---|---|---|
| hsa-miR-34a-5p | 814 | 1835 | breast, myeloid cells, ciliated epithelial cells | gastric cancer, CLL, other | tumor suppressor, p53 inducible |
| hsa-miR-363-3p | 856 | 1877 | kidney stem cell, blood cells | | |
| hsa-miR-363-5p | 857 | 1878 | kidney stem cell, blood cells | | |
| hsa-miR-372 | 940 | 1961 | hematopoietic cells, lung, placental (blood) | | |
| hsa-miR-377-3p | 957 | 1978 | hematopoietic cells | | |
| hsa-miR-377-5p | 958 | 1979 | hematopoietic cells | | |
| hsa-miR-493-3p | 2610 | 3631 | myeloid cells, pancreas (islet) | | |
| hsa-miR-493-5p | 2611 | 3632 | myeloid cells, pancreas (islet) | | |
| hsa-miR-542-3p | 2769 | 3790 | monocytes | | targets to survivin, introduce growth arrest |
| hsa-miR-548b-5p | 2820 | 3841 | immune cells frontal cortex | | |
| hsa-miR-548c-5p | 2822 | 3843 | immune cells frontal cortex | | |
| hsa-miR-548i | 2831 | 3852 | embryonic stem cells (41), immune cells | | |
| hsa-miR-548j | 2832 | 3853 | immune cells | | |
| hsa-miR-548n | 2836 | 3857 | embryonic stem cells, immune cells | | |
| hsa-miR-574-3p | 2942 | 3963 | blood (myeloid cells) | increased in follicular lymphoma(53) | |
| hsa-miR-598 | 2973 | 3994 | in blood lymphocytes (PBL) | | |
| hsa-miR-935 | 3210 | 4231 | identified in human cervical cancer blood mononuclear cells | associated with energy metabolism/obesity, medullablastoma/ neural stem cells | |
| hsa-miR-99a-3p | 3230 | 4251 | hemapoietic cells | | |
| hsa-miR-99a-5p | 3231 | 4252 | hemapoietic cells, plasma (exosome) | | |
| hsa-miR-99b-3p | 3232 | 4253 | hemapoietic cells, Embryonic stem cells, | | |
| hsa-miR-99b-5p | 3233 | 4254 | hemapoietic cells, Embryonic stem cells, plasma(exosome) | | |

III. Modifications

Herein, in a nucleotide, nucleoside polynucleotide (such as the nucleic acids of the invention, e.g., modified RNA, modified nucleic acid molecule, modified RNAs, nucleic acid and modified nucleic acids), the terms "modification" or, as appropriate, "modified" refer to modification with respect to A, G, U or C ribonucleotides. Generally, herein, these terms are not intended to refer to the ribonucleotide modifications in naturally occurring 5'-terminal mRNA cap moieties. In a polypeptide, the term "modification" refers to a modification as compared to the canonical set of 20 amino acids.

The modifications may be various distinct modifications. In some embodiments, where the nucleic acids or modified RNA, the coding region, the flanking regions and/or the terminal regions may contain one, two, or more (optionally different) nucleoside or nucleotide modifications. In some embodiments, a modified nucleic acids or modified RNA introduced to a cell may exhibit reduced degradation in the cell, as compared to an unmodified nucleic acid or modified RNA.

The polynucleotide, primary construct, nucleic acids or modified RNA can include any useful modification, such as to the sugar, the nucleobase, or the internucleoside linkage (e.g. to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications according to the present invention may be modifications of ribonucleic acids (RNAs) to deoxyribonucleic acids (DNAs), e.g., the substitution of the 2'OH of the ribofuranysyl ring to 2'H, threose nucleic acids (TNAs), glycol nucleic acids (GNAs), peptide nucleic acids (PNAs), locked nucleic acids (LNAs) or hybrids thereof). Additional modifications are described herein.

As described herein, the polynucleotides, primary construct, nucleic acids or modified RNA of the invention do not substantially induce an innate immune response of a cell into which the polynucleotides, primary constructs, nucleic acids or modified RNA (e.g., mRNA) is introduced. Features of an induced innate immune response include 1) increased expression of pro-inflammatory cytokines, 2) activation of intracellular PRRs (RIG-I, MDA5, etc, and/or 3) termination or reduction in protein translation.

In certain embodiments, it may desirable for a modified nucleic acid molecule introduced into the cell to be degraded intracellulary. For example, degradation of a modified nucleic acid molecule may be preferable if precise timing of protein production is desired. Thus, in some embodiments, the invention provides a modified nucleic acid molecule containing a degradation domain, which is capable of being acted on in a directed manner within a cell. In another aspect, the present disclosure provides polynucleotides, primary constructs, nucleic acids or modified RNA comprising a nucleoside or nucleotide that can disrupt the binding of a major groove interacting, e.g. binding, partner with the polynucleotides, primary constructs, nucleic acids or modified RNA (e.g., where the modified nucleotide has decreased binding affinity to major groove interacting partner, as compared to an unmodified nucleotide).

The polynucleotides, primary constructs, nucleic acids or modified RNA can optionally include other agents (e.g., RNAi-inducing agents, RNAi agents, siRNAs, shRNAs, miRNAs, antisense RNAs, ribozymes, catalytic DNA, tRNA, RNAs that induce triple helix formation, aptamers, vectors, etc.). In some embodiments, the polynucleotides, primary constructs, nucleic acids or modified RNA may include one or more messenger RNAs (mRNAs) having one or more modified nucleoside or nucleotides (i.e., modified mRNA molecules). Details for these nucleic acids or modified RNA follow.

Modified mRNA Molecules

The polynucleotides, primary constructs, nucleic acids or modified RNA of the invention includes a first region of linked nucleosides encoding a polypeptide of interest, a first flanking region located at the 5' terminus of the first region, and a second flanking region located at the 3' terminus of the first region. The first region of linked nucleosides may be a translatable region.

In some embodiments, the polynucleotide, primary construct, or mmRNA (e.g., the first region, first flanking region, or second flanking region) includes n number of linked nucleosides having any base, sugar, backbone, building block or other structure or formula, including but not limited to those of Formulas I through IX or any substructures thereof as described in International Application PCT/US 12/58519 filed Oct. 3, 2012, the contents of which are incorporated herein by reference in their entirety. Such structures include modifications to the sugar, nucleobase, internucleoside linkage, or combinations thereof.

Combinations of chemical modifications include those taught in including but not limited to those described in International Application PCT/US 12/58519 filed Oct. 3, 2012, the contents of which are incorporated herein by reference in their entirety.

The synthesis of polynucleotides, primary constructs or mmRNA of the present invention may be according to the methods described in International Application PCT/US12/58519 filed Oct. 3, 2012, the contents of which are incorporated herein by reference in their entirety.

In some embodiments, the nucleobase selected from the group consisting of cytosine, guanine, adenine, and uracil.

In some embodiments, the modified nucleobase is a modified uracil. Exemplary nucleobases and nucleosides having a modified uracil include pseudouridine ($\psi$), pyridin-4-one ribonucleoside, 5-aza-uridine, 6-aza-uridine, 2-thio-5-aza-uridine, 2-thiouridine ($s^2U$), 4-thio-uridine ($s^4U$), 4-thio-pseudouridine, 2-thio-pseudouridine, 5-hydroxyuridine (ho$^5$U), 5-aminoallyl-uridine, 5-halo-uridine (e.g., 5-iodo-uridineor 5-bromo-uridine), 3-methyluridine (m$^3$U), 5-methoxy-uridine (mo$^5$U), uridine 5-oxyacetic acid (cmo$^5$U), uridine 5-oxyacetic acid methyl ester (mcmo$^5$U), 5-carboxymethyl-uridine (cm$^5$U), 1-carboxymethyl-pseudouridine, 5-carboxyhydroxymethyl-uridine (chm$^5$U), 5-carboxyhydroxymethyl-uridine methyl ester (mchm$^5$U), 5-methoxycarbonylmethyl-uridine (mcm$^5$U), 5-methoxycarbonylmethyl-2-thio-uridine (mcm$^5$ s$^2$U), 5-aminomethyl-2-thio-uridine (nm$^5$s$^2$U), 5-methylaminomethyl-uridine (mnm$^5$U), 5-methylaminomethyl-2-thio-uridine (mnm$^5$s$^2$U), 5-methyl aminomethyl-2-seleno-uridine (mnm$^5$ se$^2$U), 5-carbamoylmethyl-uridine (ncm$^5$U), 5-carboxymethylaminomethyl-uridine (cmnm$^5$U), 5-carboxymethylaminomethyl-2-thio-uridine (cmnm$^5$s$^2$U), 5-propynyl-uridine, 1-propynyl-pseudouridine, 5-taurinomethyluridine ($\tau$m$^5$U), 1-taurinomethyl-pseudouridine, 5-taurinomethyl-2-thio-uridine ($\tau$m$^5$ s$^2$U), 1-taurinomethyl-4-thio-pseudouridine, 5-methyl-uridine (m$^5$U, i.e., having the nucleobase deoxythymine), 1-methyl-pseudouridine (m$^1\psi$), 5-methyl-2-thio-uridine (m$^5$ s$^2$U), 1-methyl-4-thio-pseudouridine (m$^1$s$^4\psi$), 4-thio-1-methyl-pseudouridine, 3-methyl-pseudouridine (m$^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m$^5$D), 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine (acp$^3$U), 1-methyl-3-(3-amino-3-carboxypropyl)pseudouridine (acp$^3$ $\psi$), 5-(isopentenylaminomethyl)uridine (inm$^5$U), 5-(isopentenylaminomethyl)-2-thio-uridine (inm$^5$ s$^2$U), $\alpha$-thio-uridine, 2'-O-methyl-uridine (Um), 5,2'-O-dimethyl-uridine (m$^5$Um), 2'-O-methyl-pseudouridine ($\psi$m), 2-thio-2'-O-methyl-uridine (s$^2$Um), 5-methoxycarbonylmethyl-2'-O-methyl-uridine (mcm$^5$Um), 5-carbamoylmethyl-2'-O-methyl-uridine (ncm$^5$Um), 5-carboxymethyl aminomethyl-2'-O-methyl-uridine (cmnm$^5$Um), 3,2'-O-dimethyl-uridine (m$^3$Um), and 5-(isopentenylaminomethyl)-2'-O-methyl-uridine (inm$^5$Um), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino) uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine (m$^3$C), N4-acetyl-cytidine (ac$^4$C), 5-formylcytidine (f$^5$C), N4-methylcytidine (m⁴C), 5-methyl-cytidine (m⁵C), 5-halo-cytidine (e.g., 5-iodo-cytidine), 5-hydroxymethylcytidine (hm⁵C), 1-methyl-pseudoisocytidine, pyrrolo-cytidine, pyrrolo-pseudoisocytidine, 2-thio-cytidine (s²C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k₂C), α-thio-cytidine, 2'-O-methyl-cytidine (Cm), 5,2'-O-dimethyl-cytidine (m⁵Cm), N4-acetyl-2'-O-methyl-cytidine (ac⁴Cm), N4,2'-O-dimethyl-cytidine (m⁴Cm), 5-formyl-2'-O-methyl-cytidine (f⁵Cm), N4,N4,2'-O-trimethyl-cytidine (m⁴₂Cm), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include 2-aminopurine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyladenosine (m¹A), 2-methyl-adenine (m²A), N6-methyladenosine (m⁶A), 2-methylthio-N6-methyl-adenosine (ms²m⁶A), N6-isopentenyladenosine (i⁶A), 2-methylthio-N6-isopentenyl-adenosine (ms²i⁶A), N6-(cis-hydroxyisopentenyl)adenosine (io⁶A), 2-methylthio-N6-(cis-hydroxyisopentenyl)adenosine (ms²io⁶A), N6-glycinylcarbamoyladenosine (g⁶A), N6-threonylcarbamoyladenosine (t⁶A), N6-methyl-N6-threonylcarbamoyl-adenosine (m⁶t⁶A), 2-methylthio-N6-threonyl carbamoyladenosine (ms²g⁶A), N6,N6-dimethyl-adenosine (m⁶₂A), N6-hydroxynorvalylcarbamoyl-adenosine (hn⁶A), 2-methylthio-N6-hydroxynorvalylcarbamoyl-adenosine (ms²hn⁶A), N6-acetyl-adenosine (ac⁶A), 7-methyladenine, 2-methylthio-adenine, 2-methoxy-adenine, α-thio-adenosine, 2'-O-methyl-adenosine (Am), N6,2'-O-dimethyl-adenosine (m⁶Am), N6,N6,2'-O-trimethyl-adenosine (m⁶₂Am), 1,2'-O-dimethyl-adenosine (m¹Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include inosine (I), 1-methyl-inosine (m¹I), wyosine (imG), methylwyosine (mimG), 4-demethyl-wyosine (imG-14), isowyosine (imG2), wybutosine (yW), peroxywybutosine (o₂yW), hydroxywybutosine (OHyW), undermodified hydroxywybutosine (OHyW*), 7-deaza-guanosine, queuosine (Q), epoxyqueuosine (oQ), galactosyl-queuosine (galQ), mannosyl-queuosine (manQ), 7-cyano-7-deaza-guanosine (preQo), 7-aminomethyl-7-deaza-guanosine (preQ₁), archaeosine (G⁺), 7-deaza-8-aza-guanosine, 6-thio-guanosine, 6-thio-7-deaza-guanosine, 6-thio-7-deaza-8-aza-guanosine, 7-methyl-guanosine (m⁷G), 6-thio-7-methyl-guanosine, 7-methyl-inosine, 6-methoxy-guanosine, 1-methylguanosine (m G), N2-methyl-guanosine (m²G), N2,N2-dimethyl-guanosine (m²₂G), N2,7-dimethyl-guanosine (m²,⁷G), N2, N2,7-dimethyl-guanosine (m²,²,⁷G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m²Gm), N2,N2-dimethyl-2'-O-methyl-guanosine (m²₂Gm), 1-methyl-2'-O-methyl-guanosine (m Gm), N2,7-dimethyl-2'-O-methyl-guanosine (m²,⁷Gm), 2'-O-methyl-inosine (Im), 1,2'-O-dimethyl-inosine (m¹Im), 2'-O-ribosylguanosine (phosphate) (Gr(p)), 1-thio-guanosine, 06-methyl-guanosine, 2'-F-ara-guanosine, and 2'-F-guanosine.

Phosphorothioate DNA and RNA have increased nuclease resistance and subsequently a longer half-life in a cellular environment. Phosphorothioate linked nucleic acids are expected to also reduce the innate immune response through weaker binding/activation of cellular innate immune molecules.

The nucleobase of the nucleotide can be independently selected from a purine, a pyrimidine, a purine or pyrimidine analog. For example, the nucleobase can each be independently selected from adenine, cytosine, guanine, uracil, or hypoxanthine. In another embodiment, the nucleobase can also include, for example, naturally-occurring and synthetic derivatives of a base, including pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; and 1,3,5 triazine. When the nucleotides are depicted using the shorthand A, G, C, T or U, each letter refers to the representative base and/or derivatives thereof, e.g., A includes adenine or adenine analogs, e.g., 7-deaza adenine).

Modifications on the Internucleoside Linkage

The modified nucleotides, which may be incorporated into a nucleic acid or modified RNA molecule, can be modified on the internucleoside linkage (e.g., phosphate backbone). Herein, in the context of the polynucleotides, primary constructs, nucleic acids or modified RNA backbone, the phrases "phosphate" and "phosphodiester" are used interchangeably. Backbone phosphate groups can be modified by replacing one or more of the oxygen atoms with a different substituent. Further, the modified nucleosides and nucleotides can include the wholesale replacement of an unmodified phosphate moiety with another internucleoside linkage as described herein. Examples of modified phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates).

The α-thio substituted phosphate moiety is provided to confer stability to RNA and DNA polymers through the unnatural phosphorothioate backbone linkages. Phosphorothioate DNA and RNA have increased nuclease resistance and subsequently a longer half-life in a cellular environment. While not wishing to be bound by theory, phosphorothioate linked polynucleotides, primary constructs, nucleic acids or modified RNA molecules are expected to also reduce the innate immune response through weaker binding/activation of cellular innate immune molecules.

In specific embodiments, a modified nucleoside includes an alpha-thio-nucleoside (e.g., 5'-O-(1-thiophosphate)-adenosine, 5'-O-(1-thiophosphate)-cytidine (α-thio-cytidine), 5'-O-(1-thiophosphate)-guanosine, 5'-O-(1-thiophosphate)-uridine, or 5'-O-(1-thiophosphate)-pseudouridine).

Other internucleoside linkages that may be employed according to the present invention, including internucleoside linkages which do not contain a phosphorous atom, are described herein below.

Combinations of Modified Sugars, Nucleobases, and Internucleoside Linkages

The nucleic acids or modified RNA of the invention can include a combination of modifications to the sugar, the nucleobase, and/or the internucleoside linkage. These combinations can include any one or more modifications described herein. For examples, any of the nucleotides described herein in Formulas (Ia), (Ia-1)-(Ia-3), (Ib)-(If), (IIa)-(IIp), (IIb-1), (IIb-2), (IIc-1)-(IIc-2), (IIn-1), (IIn-2), (IVa)-(IVl), and (IXa)-(IXr) can be combined with any of the nucleobases described herein (e.g., in Formulas (b1)-(b43) or any other described herein).

Synthesis of Nucleic Acids or Modified RNA Molecules (Modified RNAs)

Nucleic acids for use in accordance with the invention may be prepared according to any useful technique as described herein or any available technique including, but not limited to chemical synthesis, enzymatic synthesis, which is generally termed in vitro transcription, enzymatic or chemical cleavage of a longer precursor, etc. Methods of synthesizing RNAs are known in the art (see, e.g., Gait, M. J. (ed.) *Oligonucleotide synthesis: a practical approach*, Oxford [Oxfordshire], Washington, D.C.: IRL Press, 1984; and Herdewijn, P. (ed.) *Oligonucleotide synthesis: methods and applications*, Methods in Molecular Biology, v. 288 (Clifton, N.J.) Totowa, N.J.: Humana Press, 2005; both of which are incorporated herein by reference).

The modified nucleosides and nucleotides used in the synthesis of modified RNAs disclosed herein can be prepared from readily available starting materials using the following general methods and procedures. It is understood that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Preparation of modified nucleosides and nucleotides used in the manufacture or synthesis of modified RNAs of the present invention can involve the protection and deprotection of various chemical groups. The need for protection and deprotection, and the selection of appropriate protecting groups can be readily determined by one skilled in the art.

The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents, which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of modified nucleosides and nucleotides can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

Modified nucleosides and nucleotides (e.g., building block molecules) can be prepared according to the synthetic methods described in Ogata et al., J. Org. Chem. 74:2585-2588 (2009); Purmal et al., Nucl. Acids Res. 22(1): 72-78, (1994); Fukuhara et al., Biochemistry, 1(4): 563-568 (1962); and Xu et al., Tetrahedron, 48(9): 1729-1740 (1992), each of which are incorporated by reference in their entirety.

Modified nucleosides and nucleotides (e.g., building block molecules) can be prepared according to the synthetic methods described in Ogata et al., J. Org. Chem. 74:2585-2588 (2009); Purmal et al., Nucl. Acids Res. 22(1): 72-78, (1994); Fukuhara et al., Biochemistry, 1(4): 563-568 (1962); and Xu et al., Tetrahedron, 48(9): 1729-1740 (1992), each of which are incorporated by reference in their entirety.

The modified nucleic acids of the invention may or may not be uniformly modified along the entire length of the molecule. Different nucleotide modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially decreased. A modification may also be a 5' or 3' terminal modification. The nucleic acids may contain at a minimum one and at maximum 100% modified nucleotides, or any intervening percentage, such as at least 50% modified nucleotides, at least 80% modified nucleotides, or at least 90% modified nucleotides. For example, one or more or all types of nucleotide (e.g., purine or pyrimidine, or any one or more or all of A, G, U, C) may or may not be uniformly modified in a nucleic acids or modified RNA of the invention, or in a given predetermined sequence region thereof. In some embodiments, all nucleotides X in a nucleic acids or modified RNA of the invention (or in a given sequence region thereof) are modified, wherein X may any one of nucleotides A, G, U, C, or any one of the combinations A+G, A+U, A+C, G+U, G+C, U+C, A+G+U, A+G+C, G+U+C or A+G+C.

Different sugar modifications, nucleotide modifications, and/or internucleoside linkages (e.g., backbone structures) may exist at various positions in the nucleic acids or modified RNA. One of ordinary skill in the art will appreciate that the nucleotide analogs or other modification(s) may be located at any position(s) of a nucleic acid or modified RNA such that the function of the nucleic acids or modified RNA is not substantially decreased. A modification may also be a 5' or 3' terminal modification. The nucleic acids or modified RNA may contain from about 1% to about 100% modified nucleotides (either in relation to overall nucleotide content, or in relation to one or more types of nucleotide, i.e. any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, the nucleic acids or modified RNA includes a modified pyrimidine (e.g., a modified uracil/uridine/U or modified cytosine/cytidine/C). In some embodiments, the uracil or uridine (generally: U) in the nucleic acids or modified RNA molecule may be replaced with from about 1% to about 100% of a modified uracil or modified uridine (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100% of a modified uracil or modified uridine). The modified uracil or uridine can be replaced by a compound having a single unique structure or by a plurality of compounds having different structures (e.g., 2, 3, 4 or more unique structures, as described herein). In some embodiments, the cytosine or cytidine (generally: C) in the nucleic acid or modified RNA molecule may be replaced with from about 1% to about 100% of a modified cytosine or modified cytidine (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100% of a modified cytosine or modified cytidine). The modified cytosine or cytidine can be replaced by a compound having a single unique structure or by a plurality of compounds having different structures (e.g., 2, 3, 4 or more unique structures, as described herein).

Other components of the nucleic acid are optional, and are beneficial in some embodiments. For example, a 5' untranslated region (UTR) and/or a 3'UTR are provided, wherein either or both may independently contain one or more different nucleotide modifications. In such embodiments, nucleotide modifications may also be present in the translatable region. Also provided are nucleic acids containing a Kozak sequence which may include an IRES sequence or not include an IRES sequence (See e.g., the polynucleotides described in Table 30 in Example 31).

Additionally, provided are nucleic acids containing one or more intronic nucleotide sequences capable of being excised from the nucleic acid.

Combinations of Nucleotides

Further examples of modified nucleotides and modified nucleotide combinations are provided below in Table 14. These combinations of modified nucleotides can be used to form the nucleic acids or modified RNA of the invention. Unless otherwise noted, the modified nucleotides may be completely substituted for the natural nucleotides of the nucleic acids or modified RNA of the invention. As a non-limiting example, the natural nucleotide uridine may be substituted with a modified nucleoside described herein. In another non-limiting example, the natural nucleotide uridine may be partially substituted (e.g., about 0.1%, 1%, 5%, 10%, 15%, 20%, 25%, 30%, 35%, 40%, 45%, 50%, 55%, 60%, 65%, 70%, 75%, 80%, 85%, 90%, 95% or 99.9%) with at least one of the modified nucleoside disclosed herein.

TABLE 14

Chemical Modifications

| Modified Nucleotide | Modified Nucleotide Combination |
|---|---|
| 6-aza-cytidine | α-thio-cytidine/5-iodo-uridine |
| 2-thio-cytidine | α-thio-cytidine/N1-methyl-pseudo-uridine |
| α-thio-cytidine | α-thio-cytidine/α-thio-uridine |
| Pseudo-iso-cytidine | α-thio-cytidine/5-methyl-uridine |
| 5-aminoallyl-uridine | α-thio-cytidine/pseudo-uridine |
| 5-iodo-uridine | Pseudo-iso-cytidine/5-iodo-uridine |
| N1-methyl-pseudouridine | Pseudo-iso-cytidine/N1-methyl-pseudo-uridine |
| 5,6-dihydrouridine | Pseudo-iso-cytidine/α-thio-uridine |
| α-thio-uridine | Pseudo-iso-cytidine/5-methyl-uridine |
| 4-thio-uridine | Pseudo-iso-cytidine/Pseudo-uridine |
| 6-aza-uridine | |

TABLE 14-continued

Chemical Modifications

| Modified Nucleotide | Modified Nucleotide Combination |
| --- | --- |
| 5-hydroxy-uridine | Pyrrolo-cytidine/5-iodo-uridine |
| Deoxy-thymidine | Pyrrolo-cytidine/N1-methyl-pseudo-uridine |
| Pseudo-uridine | Pyrrolo-cytidine/α-thio-uridine |
| Inosine | Pyrrolo-cytidine/5-methyl-uridine |
| α-thio-guanosine | Pyrrolo-cytidine/Pseudo-uridine |
| 8-oxo-guanosine | 5-methyl-cytidine/5-iodo-uridine |
| O6-methyl-guanosine | 5-methyl-cytidine/N1-methyl-pseudo-uridine |
| 7-deaza-guanosine | 5-methyl-cytidine/α-thio-uridine |
| No modification | 5-methyl-cytidine/5-methyl-uridine |
| N1-methyl-adenosine | 5-methyl-cytidine/Pseudo-uridine |
| 2-amino-6-Chloro-purine | |
| N6-methyl-2-amino-purine | about 25% of cytosines are Pseudo-iso-cytidine |
| 6-Chloro-purine | about 25% of uridines are N1-methyl-pseudo-uridine |
| N6-methyl-adenosine | 25% N1-Methyl-pseudo-uridine/75%-pseudo-uridine |
| α-thio-adenosine | |
| 8-azido-adenosine | |
| 7-deaza-adenosine | about 50% of the cytosines are pyrrolo-cytidine |
| Pyrrolo-cytidine | 5-methyl-cytidine/5-iodo-uridine |
| 5-methyl-cytidine | 5-methyl-cytidine/N1-methyl-pseudouridine |
| N4-acetyl-cytidine | 5-methyl-cytidine/α-thio-uridine |
| 5-methyl-uridine | 5-methyl-cytidine/5-methyl-uridine |
| 5-iodo-cytidine | 5-methyl-cytidine/pseudouridine |
| | about 25% of cytosines are 5-methyl-cytidine |
| | about 50% of cytosines are 5-methyl-cytidine |
| | 5-methyl-cytidine/5-methoxy-uridine |
| | 5-methyl-cytidine/5-bromo-uridine |
| | 5-methyl-cytidine/2-thio-uridine |
| | 5-methyl-cytidine/about 50% of uridines are 2-thio-uridine |
| | about 50% of uridines are 5-methyl-cytidine/about 50% of uridines are 2-thio-uridine |
| | N4-acetyl-cytidine/5-iodo-uridine |
| | N4-acetyl-cytidine/N1-methyl-pseudouridine |
| | N4-acetyl-cytidine/α-thio-uridine |
| | N4-acetyl-cytidine/5-methyl-uridine |
| | N4-acetyl-cytidine/pseudouridine |
| | about 50% of cytosines are N4-acetyl-cytidine |
| | about 25% of cytosines are N4-acetyl-cytidine |
| | N4-acetyl-cytidine/5-methoxy-uridine |
| | N4-acetyl-cytidine/5-bromo-uridine |
| | N4-acetyl-cytidine/2-thio-uridine |
| | about 50% of cytosines are N4-acetyl-cytidine/about 50% of uridines are 2-thio-uridine |
| | pseudoisocytidine/about 50% of uridines are N1-methyl-pseudouridine and about 50% of uridines are pseudouridine |
| | pseudoisocytidine/about 25% of uridines are N1-methyl-pseudouridine and about 25% of uridines are pseudouridine (e.g., 25% N1-methyl-pseudouridine/75% pseudouridine) |
| | about 50% of the cytosines are α-thio-cytidine |

Certain modified nucleotides and nucleotide combinations have been explored by the current inventors. These findings are described in U.S. Provisional Application No. 61/404,413, filed on Oct. 1, 2010, entitled Engineered Nucleic Acids and Methods of Use Thereof, U.S. patent application Ser. No. 13/251,840, filed on Oct. 3, 2011, entitled Modified Nucleotides, and Nucleic Acids, and Uses Thereof, now abandoned, U.S. patent application Ser. No. 13/481,127, filed on May 25, 2012, entitled Modified Nucleotides, and Nucleic Acids, and Uses Thereof, International Patent Publication No WO2012045075, filed on Oct. 3, 2011, entitled Modified Nucleosides, Nucleotides, And Nucleic Acids, and Uses Thereof, U.S. Patent Publication No US20120237975 filed on Oct. 3, 2011, entitled Engineered Nucleic Acids and Method of Use Thereof, and International Patent Publication No WO2012045082, which are incorporated by reference in their entireties.

Further examples of modified nucleotide combinations are provided below in Table 15. These combinations of modified nucleotides can be used to form the nucleic acids of the invention.

TABLE 15

Chemical Modifications

| Modified Nucleotide | Modified Nucleotide Combination |
| --- | --- |
| modified cytidine having one or more nucleobases of Formula (b10) | modified cytidine with (b10)/pseudouridine |
| | modified cytidine with (b10)/N1-methyl-pseudouridine |
| | modified cytidine with (b10)/5-methoxy-uridine |
| | modified cytidine with (b10)/5-methyl-uridine |
| | modified cytidine with (b10)/5-bromo-uridine |
| | modified cytidine with (b10)/2-thio-uridine |
| | about 50% of cytidine substituted with modified cytidine (b10)/about 50% of uridines are 2-thio-uridine |
| modified cytidine having one or more nucleobases of Formula (b32) | modified cytidine with (b32)/pseudouridine |
| | modified cytidine with (b32)/N1-methyl-pseudouridine |
| | modified cytidine with (b32)/5-methoxy-uridine |
| | modified cytidine with (b32)/5-methyl-uridine |
| | modified cytidine with (b32)/5-bromo-uridine |

TABLE 15-continued

Chemical Modifications

| Modified Nucleotide | Modified Nucleotide Combination |
|---|---|
| | modified cytidine with (b32)/2-thio-uridine about 50% of cytidine substituted with modified cytidine (b32)/about 50% of uridines are 2-thio-uridine |
| modified uridine having one or more nucleobases of Formula (b1) | modified uridine with (b1)/N4-acetyl-cytidine |
| | modified uridine with (b1)/5-methyl-cytidine |
| modified uridine having one or more nucleobases of Formula (b8) | modified uridine with (b8)/N4-acetyl-cytidine |
| | modified uridine with (b8)/5-methyl-cytidine |
| modified uridine having one or more nucleobases of Formula (b28) | modified uridine with (b28)/N4-acetyl-cytidine |
| | modified uridine with (b28)/5-methyl-cytidine |
| modified uridine having one or more nucleobases of Formula (b29) | modified uridine with (b29)/N4-acetyl-cytidine |
| | modified uridine with (b29)/5-methyl-cytidine |
| modified uridine having one or more nucleobases of Formula (b30) | modified uridine with (b30)/N4-acetyl-cytidine |
| | modified uridine with (b30)/5-methyl-cytidine |

In some embodiments, at least 25% of the cytosines are replaced by a compound of Formula (b10)-(b14), (b24), (b25), or (b32)-(b35) (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of, e.g., a compound of Formula (b10) or (b32)).

In some embodiments, at least 25% of the uracils are replaced by a compound of Formula (b1)-(b9), (b21)-(b23), or (b28)-(b31) (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of, e.g., a compound of Formula (b1), (b8), (b28), (b29), or (b30)).

In some embodiments, at least 25% of the cytosines are replaced by a compound of Formula (b10)-(b14), (b24), (b25), or (b32)-(b35) (e.g. Formula (b10) or (b32)), and at least 25% of the uracils are replaced by a compound of Formula (b11)-(b9), (b21)-(b23), or (b28)-(b31) (e.g. Formula (b1), (b8), (b28), (b29), or (b30)) (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

Modifications Including Linker and a Payload

Payload

The methods and compositions described herein are useful for delivering a payload to a biological target. The payload can be used, e.g., for labeling (e.g., a detectable agent such as a fluorophore), or for therapeutic purposes (e.g., a cytotoxin or other therapeutic agent).

Payload: Therapeutic Agents

In some embodiments the payload is a therapeutic agent such as a cytotoxin, radioactive ion, chemotherapeutic, or other therapeutic agent. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Radioactive ions include, but are not limited to iodine (e.g., iodine 125 or iodine 131), strontium 89, phosphorous, palladium, cesium, iridium, phosphate, cobalt, yttrium 90, Samarium 153 and praseodymium. Other therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

Payload: Detectable Agents

Examples of detectable substances include various organic small molecules, inorganic compounds, nanoparticles, enzymes or enzyme substrates, fluorescent materials, luminescent materials, bioluminescent materials, chemiluminescent materials, radioactive materials, and contrast agents. Such optically-detectable labels include for example, without limitation, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5' 5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]-naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodarnine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Cyanine-3 (Cy3); Cyanine-5 (Cy5); Cyanine-5.5 (Cy5.5), Cyanine-7 (Cy7); IRD 700; IRD 800; Alexa 647; La Jolta Blue; phthalo cyanine; and naphthalo cyanine. In some embodiments, the detectable label is a fluorescent dye, such as Cy5 and Cy3.

Examples luminescent material includes luminol; examples of bioluminescent materials include luciferase, luciferin, and aequorin.

Examples of suitable radioactive material include $^{18}$F, $^{67}$Ga, $^{81m}$Kr, $^{82}$Rb, $^{111}$In, $^{123}$I, $^{133}$Xe, $^{201}$Tl, $^{125}$I, $^{35}$S, $^{14}$C, or $^{3}$H, $^{99m}$Tc (e.g., as pertechnetate (technetate(VII), TcO$_4^-$) either directly or indirectly, or other radioisotope detectable by direct counting of radioemission or by scintillation counting.

In addition, contrast agents, e.g., contrast agents for MRI or NMR, for X-ray CT, Raman imaging, optical coherence tomography, absorption imaging, ultrasound imaging, or thermal imaging can be used. Exemplary contrast agents include gold (e.g., gold nanoparticles), gadolinium (e.g., chelated Gd), iron oxides (e.g., superparamagnetic iron oxide (SPIO), monocrystalline iron oxide nanoparticles (MI-ONs), and ultrasmall superparamagnetic iron oxide (US-PIO)), manganese chelates (e.g., Mn-DPDP), barium sulfate, iodinated contrast media (iohexol), microbubbles, or perfluorocarbons can also be used.

In some embodiments, the detectable agent is a non-detectable pre-cursor that becomes detectable upon activation. Examples include fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE (VisEn Medical)).

When the compounds are enzymatically labeled with, for example, horseradish peroxidase, alkaline phosphatase, or luciferase, the enzymatic label is detected by determination of conversion of an appropriate substrate to product.

In vitro assays in which these compositions can be used include enzyme linked immunosorbent assays (ELISAs), immunoprecipitations, immunofluorescence, enzyme immunoassay (EIA), radioimmunoassay (RIA), and Western blot analysis.

Labels other than those described herein are contemplated by the present disclosure, including other optically-detectable labels. Labels can be attached to the modified nucleotide of the present disclosure at any position using standard chemistries such that the label can be removed from the incorporated base upon cleavage of the cleavable linker.

Payload: Cell Penetrating Payloads

In some embodiments, the modified nucleotides and modified nucleic acids can also include a payload that can be a cell penetrating moiety or agent that enhances intracellular delivery of the compositions. For example, the compositions can include a cell-penetrating peptide sequence that facilitates delivery to the intracellular space, e.g., HIV-derived TAT peptide, penetratins, transportans, or hCT derived cell-penetrating peptides, see, e.g., Caron et al., (2001) Mol Ther. 3(3):310-8; Langel, Cell-Penetrating Peptides: Processes and Applications (CRC Press, Boca Raton Fla. 2002); El-Andaloussi et al., (2005) Curr Pharm Des. 11(28):3597-611; and Deshayes et al., (2005) Cell Mol Life Sci. 62(16):1839-49. The compositions can also be formulated to include a cell penetrating agent, e.g., liposomes, which enhance delivery of the compositions to the intracellular space.

Payload: Biological Targets

The modified nucleotides and modified nucleic acids described herein can be used to deliver a payload to any biological target for which a specific ligand exists or can be generated. The ligand can bind to the biological target either covalently or non-covalently.

Exemplary biological targets include biopolymers, e.g., antibodies, nucleic acids such as RNA and DNA, proteins, enzymes; exemplary proteins include enzymes, receptors, and ion channels. In some embodiments the target is a tissue- or cell-type specific marker, e.g., a protein that is expressed specifically on a selected tissue or cell type. In some embodiments, the target is a receptor, such as, but not limited to, plasma membrane receptors and nuclear receptors; more specific examples include G-protein-coupled receptors, cell pore proteins, transporter proteins, surface-expressed antibodies, HLA proteins, MHC proteins and growth factor receptors.

Synthesis of Modified Nucleotides

The modified nucleosides and nucleotides disclosed herein can be prepared from readily available starting materials using the following general methods and procedures. It is understood that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Preparation of modified nucleosides and nucleotides can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 2d. Ed., Wiley & Sons, 1991, which is incorporated herein by reference in its entirety.

The reactions of the processes described herein can be carried out in suitable solvents, which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of modified nucleosides and nucleotides can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

Length

Generally, the length of a modified mRNA of the present invention is greater than 30 nucleotides in length. In another embodiment, the RNA molecule is greater than 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 60 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1800 nucleotides. In another embodiment, the length is at least 2000 nucleotides. In another embodiment, the length is at least 2500 nucleotides. In another embodiment, the length is at least 3000 nucleotides. In another embodiment, the length is at least 4000 nucleotides. In another embodiment, the length is at least 5000 nucleotides, or greater than 5000 nucleotides. In another embodiment, the length is at least 5000 nucleotides, or greater than 6000 nucleotides. In another embodiment, the length is at least 7000 nucleotides, or greater than 7000 nucleotides. In another embodiment, the length is at least 8000 nucleotides, or greater than 8000 nucleotides. In another embodiment, the length is at least 9000 nucleotides, or greater than 9000 nucleotides. In another embodiment, the length is at least 10,000 nucleotides, or greater than 10,000 nucleotides.

Use of Modified RNAs

Prevention or Reduction of Innate Cellular Immune Response Activation

The term "innate immune response" includes a cellular response to exogenous single stranded nucleic acids, generally of viral or bacterial origin, which involves the induction of cytokine expression and release, particularly the interferons, and cell death. Protein synthesis is also reduced during the innate cellular immune response. While it is advantageous to eliminate the innate immune response in a cell, the invention provides modified mRNAs that substantially reduce the immune response, including interferon signaling, without entirely eliminating such a response. In some embodiments, the immune response is reduced by 10%, 20%, 30%, 40%, 50%, 60%, 70%, 80%, 90%, 95%, 99%, 99.9%, or greater than 99.9% as compared to the immune response induced by a corresponding unmodified nucleic acid. Such a reduction can be measured by expression or activity level of Type 1 interferons or the expression of interferon-regulated genes such as the toll-like receptors (e.g., TLR7 and TLR8). Reduction of innate immune response can also be measured by decreased cell death following one or more administrations of modified RNAs to a cell population; e.g., cell death is 10%, 25%, 50%, 75%, 85%, 90%, 95%, or over 95% less than the cell death frequency observed with a corresponding unmodified nucleic acid. Moreover, cell death may affect fewer than 50%, 40%, 30%, 20%, 10%, 5%, 1%, 0.1%, 0.01% or fewer than 0.01% of cells contacted with the modified nucleic acids.

The invention provides for the repeated introduction (e.g., transfection) of modified nucleic acids into a target cell population, e.g., in vitro, ex vivo, or in vivo. The step of contacting the cell population may be repeated one or more times (such as two, three, four, five or more than five times). In some embodiments, the step of contacting the cell population with the modified nucleic acids is repeated a number of times sufficient such that a predetermined efficiency of protein translation in the cell population is achieved. Given the reduced cytotoxicity of the target cell population provided by the nucleic acid modifications, such repeated transfections are achievable in a diverse array of cell types.

Major Groove Interacting Partners

As described herein, the phrase "major groove interacting partner" refers to RNA recognition receptors that detect and respond to RNA ligands through interactions, e.g. binding, with the major groove face of a nucleotide or nucleic acid. As such, RNA ligands comprising modified nucleotides or nucleic acids such as the modified RNAs as described herein decrease interactions with major groove binding partners, and therefore decrease an innate immune response.

Example major groove interacting, e.g. binding, partners include, but are not limited to the following nucleases and helicases. Within membranes, TLRs (Toll-like Receptors) 3, 7, and 8 can respond to single- and double-stranded RNAs. Within the cytoplasm, members of the superfamily 2 class of DEX(D/H) helicases and ATPases can sense RNAs to initiate antiviral responses. These helicases include the RIG-I (retinoic acid-inducible gene I) and MDA5 (melanoma differentiation-associated gene 5). Other examples include laboratory of genetics and physiology 2 (LGP2), HIN-200 domain containing proteins, or Helicase-domain containing proteins.

RNA Binding Proteins

In some embodiments of the present invention, RNA binding proteins are provided. RNA binding proteins may be provided as proteins and/or as nucleic acids encoding such proteins. RNA binding proteins play a multitude of roles in regulating RNA stability and protein translation. A/U rich elements in the 3' UTR of mRNAs leads to formation of secondary structures which are bound by A/U Rich Binding Protiens (AREBPs) resulting in increased or decreased mRNA stability (Fan, X. C. et al., Overexpression of HuR, a nuclear-cytoplasmic shuttling protein, increases the in vivo stability of ARE-containing mRNAs. EMBO J. 1998 Jun. 15; 17(12):3448-60). HuR is a stabilizing AREBP. To increase the stability of the mRNA of interest, an mRNA encoding HuR can be co-transfected or co-injected along with the mRNA of interest into the cells or into the tissue. These proteins can also be tethered to the mRNA of interest in vitro and then administered to the cells together. Poly A tail binding protein, PABP interacts with eukaryotic translation initiation factor eIF4G to stimulate translational initiation. Co-administration of mRNAs encoding these RBPs along with the mRNA drug and/or tethering these proteins to the mRNA drug in vitro and administering the protein-bound mRNA into the cells can increase the translational efficiency of the mRNA. The same concept can be extended to co-administration of mRNA along with mRNAs encoding various translation factors and facilitators as well as with the proteins themselves to influence RNA stability and/or translational efficiency.

Polypeptide Variants

Provided are nucleic acids that encode variant polypeptides, which have a certain identity with a reference polypeptide sequence. The term "identity" as known in the art, refers to a relationship between the sequences of two or more peptides, as determined by comparing the sequences. In the art, "identity" also means the degree of sequence relatedness between peptides, as determined by the number of matches between strings of two or more amino acid residues.

"Identity" measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

In some embodiments, the polypeptide variant has the same or a similar activity as the reference polypeptide. Alternatively, the variant has an altered activity (e.g., increased or decreased) relative to a reference polypeptide. Generally, variants of a particular polynucleotide or polypeptide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular reference polynucleotide or polypeptide as determined by sequence alignment programs and parameters described herein and known to those skilled in the art.

As recognized by those skilled in the art, protein fragments, functional protein domains, and homologous proteins are also considered to be within the scope of this invention. For example, provided herein is any protein fragment of a reference protein (meaning a polypeptide sequence at least one amino acid residue shorter than a reference polypeptide sequence but otherwise identical) 10, 20, 30, 40, 50, 60, 70, 80, 90, 100 or greater than 100 amino acids in length In another example, any protein that includes a stretch of about 20, about 30, about 40, about 50, or about 100 amino acids which are about 40%, about 50%, about 60%, about 70%, about 80%, about 90%, about 95%, or about 100% identical to any of the sequences described herein can be utilized in accordance with the invention. In certain embodiments, a protein sequence to be utilized in accordance with the invention includes 2, 3, 4, 5, 6, 7, 8, 9, 10, or more mutations as shown in any of the sequences provided or referenced herein.

Polypeptide Libraries

Also provided are polynucleotide libraries containing nucleoside modifications, wherein the polynucleotides individually contain a first nucleic acid sequence encoding a polypeptide, such as an antibody, protein binding partner, scaffold protein, and other polypeptides known in the art. Preferably, the polynucleotides are mRNA in a form suitable for direct introduction into a target cell host, which in turn synthesizes the encoded polypeptide.

In certain embodiments, multiple variants of a protein, each with different amino acid modification(s), are produced and tested to determine the best variant in terms of pharmacokinetics, stability, biocompatibility, and/or biological activity, or a biophysical property such as expression level. Such a library may contain 10, $10^2$, $10^3$, $10^4$, $10^5$, $10^6$, $10^7$, $10^8$, $10^9$, or over $10^9$ possible variants (including substitutions, deletions of one or more residues, and insertion of one or more residues).

Polypeptide-Nucleic Acid Complexes

Proper protein translation involves the physical aggregation of a number of polypeptides and nucleic acids associated with the mRNA. Provided by the invention are complexes containing conjugates of protein and nucleic acids, containing a translatable mRNA having one or more nucleoside modifications (e.g., at least two different nucleoside modifications) and one or more polypeptides bound to the mRNA. Generally, the proteins are provided in an amount effective to prevent or reduce an innate immune response of a cell into which the complex is introduced.

Targeting Moieties

In embodiments of the invention, modified nucleic acids are provided to express a protein-binding partner or a receptor on the surface of the cell, which functions to target the cell to a specific tissue space or to interact with a specific moiety, either in vivo or in vitro. Suitable protein-binding partners include antibodies and functional fragments thereof, scaffold proteins, or peptides. Additionally, modified nucleic acids can be employed to direct the synthesis and extracellular localization of lipids, carbohydrates, or other biological moieties.

As described herein, a useful feature of the modified nucleic acids of the invention is the capacity to reduce the innate immune response of a cell to an exogenous nucleic acid. Provided are methods for performing the titration, reduction or elimination of the immune response in a cell or a population of cells. In some embodiments, the cell is contacted with a first composition that contains a first dose of a first exogenous nucleic acid including a translatable region and at least one nucleoside modification, and the level of the innate immune response of the cell to the first exogenous nucleic acid is determined. Subsequently, the cell is contacted with a second composition, which includes a second dose of the first exogenous nucleic acid, the second dose containing a lesser amount of the first exogenous nucleic acid as compared to the first dose.

Alternatively, the cell is contacted with a first dose of a second exogenous nucleic acid. The second exogenous nucleic acid may contain one or more modified nucleosides, which may be the same or different from the first exogenous nucleic acid or, alternatively, the second exogenous nucleic acid may not contain modified nucleosides. The steps of contacting the cell with the first composition and/or the second composition may be repeated one or more times.

Additionally, efficiency of protein production (e.g., protein translation) in the cell is optionally determined, and the cell may be re-transfected with the first and/or second composition repeatedly until a target protein production efficiency is achieved.

In one embodiment, the 3' end of the modified nucleic acids described herein may include a sequence for targeting the modified nucleic acid to a desired location within the cell such as, but not limited to, microvesicles within a cell. The sequence for targeting may be "zip code-like" in its function as it can be recognized by the cellular machinery that can traffic molecules to various places within the cell. Non-limiting examples of sequences for targeting nucleic acids are described in International Patent Publication No. WO2013109713, the contents of which are herein incorporated by reference in its entirety. Zip-code like sequences and miR-1289 have been shown by Bolukbasi et al. to enrich mRNA in microvesicles (Mol. Ther. Nuc. Acid 2012 1, e10; the contents of which are herein incorporated by reference in its entirety) as both zipcodes and microRNA have a role in post-transcriptional regulation of mRNA.

In one embodiment, the sequence for targeting the modified nucleic acid is SEQ ID NO: 22, SEQ ID NO: 38 or a concatomer of at least one SEQ ID NO: 22 and at least one SEQ ID NO: 38 as described in International Patent Publicatoin No. WO2013109713, the contents of which are herein incorporated by reference in its entirety.

Vaccines

As described herein, provided are mRNAs having sequences that are substantially not translatable. Such mRNA is effective as a vaccine when administered to a mammalian subject.

Also provided are modified nucleic acids that contain one or more noncoding regions. Such modified nucleic acids are generally not translated, but are capable of binding to and sequestering one or more translational machinery component such as a ribosomal protein or a transfer RNA (tRNA), thereby effectively reducing protein expression in the cell. The modified nucleic acid may contain a small nucleolar RNA (sno-RNA), micro RNA (miRNA), small interfering RNA (siRNA) or Piwi-interacting RNA (piRNA).

Additionally, certain modified nucleosides, or combinations thereof, when introduced into modified nucleic acids activate the innate immune response. Such activating modified nucleic acids, e.g., modified RNAs, are useful as adjuvants when combined with polypeptide or other vaccines. In certain embodiments, the activated modified mRNAs contain a translatable region which encodes for a polypeptide sequence useful as a vaccine, thus providing the ability to be a self-adjuvant.

Therapeutic Agents

The modified nucleic acids (modified RNAs) and the proteins translated from the modified nucleic acids described herein can be used as therapeutic agents. For example, a modified nucleic acid described herein can be administered to a subject, wherein the modified nucleic acid is translated in vivo to produce a therapeutic peptide in the subject. Provided are compositions, methods, kits, and reagents for treatment or prevention of disease or conditions in humans and other mammals. The active therapeutic agents of the invention include modified nucleic acids, cells containing modified nucleic acids or polypeptides translated from the modified nucleic acids, polypeptides translated from modified nucleic acids, and cells contacted with cells containing modified nucleic acids or polypeptides translated from the modified nucleic acids.

In certain embodiments, provided are combination therapeutics containing one or more modified nucleic acids containing translatable regions that encode for a protein or proteins that boost a mammalian subject's immunity along with a protein that induces antibody-dependent cellular toxicity. For example, provided are therapeutics containing one or more nucleic acids that encode trastuzumab and granulocyte-colony stimulating factor (G-CSF). In particular, such combination therapeutics are useful in Her2+ breast cancer patients who develop induced resistance to trastuzumab. (See, e.g., Albrecht, Immunotherapy. 2(6): 795-8 (2010)).

Provided are methods of inducing translation of a recombinant polypeptide in a cell population using the modified nucleic acids described herein. Such translation can be in vivo, ex vivo, in culture, or in vitro. The cell population is contacted with an effective amount of a composition containing a nucleic acid that has at least one nucleoside modification, and a translatable region encoding the recombinant polypeptide. The population is contacted under conditions such that the nucleic acid is localized into one or more cells of the cell population and the recombinant polypeptide is translated in the cell from the nucleic acid.

An effective amount of the composition is provided based, at least in part, on the target tissue, target cell type, means of administration, physical characteristics of the nucleic acid (e.g., size, and extent of modified nucleosides), and other determinants. In general, an effective amount of the composition provides efficient protein production in the cell, preferably more efficient than a composition containing a corresponding unmodified nucleic acid. Increased efficiency may be demonstrated by increased cell transfection (i.e., the percentage of cells transfected with the nucleic acid), increased protein translation from the nucleic acid, decreased nucleic acid degradation (as demonstrated, e.g., by increased duration of protein translation from a modified nucleic acid), or reduced innate immune response of the host cell.

Aspects of the invention are directed to methods of inducing in vivo translation of a recombinant polypeptide in a mammalian subject in need thereof. Therein, an effective amount of a composition containing a nucleic acid that has at least one nucleoside modification and a translatable region encoding the recombinant polypeptide is administered to the subject using the delivery methods described herein. The nucleic acid is provided in an amount and under other conditions such that the nucleic acid is localized into a cell of the subject and the recombinant polypeptide is translated in the cell from the nucleic acid. The cell in which the nucleic acid is localized, or the tissue in which the cell is present, may be targeted with one or more than one rounds of nucleic acid administration.

Other aspects of the invention relate to transplantation of cells containing modified nucleic acids to a mammalian subject. Administration of cells to mammalian subjects is known to those of ordinary skill in the art, such as local implantation (e.g., topical or subcutaneous administration), organ delivery or systemic injection (e.g., intravenous injection or inhalation), as is the formulation of cells in pharmaceutically acceptable carrier. Compositions containing modified nucleic acids are formulated for administration intramuscularly, transarterially, intraocularly, vaginally, rectally, intraperitoneally, intravenously, intranasally, subcutaneously, endoscopically, transdermally, or intrathecally. In some embodiments, the composition is formulated for extended release.

The subject to whom the therapeutic agent is administered suffers from or is at risk of developing a disease, disorder, or deleterious condition. Provided are methods of identifying, diagnosing, and classifying subjects on these bases, which may include clinical diagnosis, biomarker levels, genome-wide association studies (GWAS), and other methods known in the art.

In certain embodiments, the administered modified nucleic acid directs production of one or more recombinant polypeptides that provide a functional activity which is substantially absent in the cell in which the recombinant polypeptide is translated. For example, the missing functional activity may be enzymatic, structural, or gene regulatory in nature. In related embodiments, the administered modified nucleic acid directs production of one or more recombinant polypeptides that increases (e.g., synergistically) a functional activity which is present but substantially deficient in the cell in which the recombinant polypeptide is translated.

In other embodiments, the administered modified nucleic acid directs production of one or more recombinant polypeptides that replace a polypeptide (or multiple polypeptides) that is substantially absent in the cell in which the recombinant polypeptide is translated. Such absence may be due to genetic mutation of the encoding gene or regulatory pathway thereof. In some embodiments, the recombinant polypeptide increases the level of an endogenous protein in the cell to a desirable level; such an increase may bring the level of the endogenous protein from a subnormal level to a normal level, or from a normal level to a super-normal level.

Alternatively, the recombinant polypeptide functions to antagonize the activity of an endogenous protein present in, on the surface of, or secreted from the cell. Usually, the activity of the endogenous protein is deleterious to the subject, for example, do to mutation of the endogenous protein resulting in altered activity or localization. Additionally, the recombinant polypeptide antagonizes, directly or indirectly, the activity of a biological moiety present in, on the surface of, or secreted from the cell. Examples of antagonized biological moieties include lipids (e.g., cholesterol), a lipoprotein (e.g., low density lipoprotein), a nucleic acid, a carbohydrate, a protein toxin such as shiga and tetanus toxins, or a small molecule toxin such as botulinum, cholera, and diphtheria toxins. Additionally, the antagonized biological molecule may be an endogenous protein that exhibits an undesirable activity, such as a cytotoxic or cytostatic activity. The recombinant proteins described herein are engineered for localization within the cell, potentially within a specific compartment such as the nucleus, or are engineered for secretion from the cell or translocation to the plasma membrane of the cell.

Therapeutics

Provided are methods for treating or preventing a symptom of diseases characterized by missing or aberrant protein activity, by replacing the missing protein activity or overcoming the aberrant protein activity. Because of the rapid initiation of protein production following introduction of modified mRNAs, as compared to viral DNA vectors, the compounds of the present invention are particularly advantageous in treating acute diseases such as sepsis, stroke, and myocardial infarction. Moreover, the lack of transcriptional regulation of the modified mRNAs of the invention is advantageous in that accurate titration of protein production is achievable.

In some embodiments, modified mRNAs and their encoded polypeptides in accordance with the present invention may be used for therapeutic purposes. In some embodiments, modified mRNAs and their encoded polypeptides in accordance with the present invention may be used for treatment of any of a variety of diseases, disorders, and/or conditions, including but not limited to one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc.

Diseases characterized by dysfunctional or aberrant protein activity include cystic fibrosis, sickle cell anemia, epidermolysis bullosa, amyotrophic lateral sclerosis, and glucose-6-phosphate dehydrogenase deficiency. The present invention provides a method for treating such conditions or diseases in a subject by introducing nucleic acid or cell-based therapeutics containing the modified nucleic acids provided herein, wherein the modified nucleic acids encode for a protein that antagonizes or otherwise overcomes the aberrant protein activity present in the cell of the subject. Specific examples of a dysfunctional protein are the missense mutation variants of the cystic fibrosis transmembrane conductance regulator (CFTR) gene, which produce a dysfunctional protein variant of CFTR protein, which causes cystic fibrosis.

Diseases characterized by missing (or substantially diminished such that proper protein function does not occur) protein activity include cystic fibrosis, Niemann-Pick type C, β thalassemia major, Duchenne muscular dystrophy, Hurler Syndrome, Hunter Syndrome, and Hemophilia A. Such proteins may not be present, or are essentially nonfunctional. The present invention provides a method for treating such conditions or diseases in a subject by introducing nucleic acid or cell-based therapeutics containing the modified nucleic acids provided herein, wherein the modified nucleic acids encode for a protein that replaces the protein activity missing from the target cells of the subject. Specific examples of a dysfunctional protein are the nonsense mutation variants of the cystic fibrosis transmembrane conductance regulator (CFTR) gene, which produce a nonfunctional protein variant of CFTR protein, which causes cystic fibrosis.

Thus, provided are methods of treating cystic fibrosis in a mammalian subject by contacting a cell of the subject with a modified nucleic acid having a translatable region that encodes a functional CFTR polypeptide, under conditions such that an effective amount of the CTFR polypeptide is present in the cell. Preferred target cells are epithelial, endothelial and mesothelial cells, such as the lung, and methods of administration are determined in view of the target tissue; i.e., for lung delivery, the RNA molecules are formulated for administration by inhalation.

In another embodiment, the present invention provides a method for treating hyperlipidemia in a subject, by introducing into a cell population of the subject with a modified mRNA molecule encoding Sortilin, a protein recently characterized by genomic studies, thereby ameliorating the hyperlipidemia in a subject. The SORT1 gene encodes a trans-Golgi network (TGN) transmembrane protein called Sortilin. Genetic studies have shown that one of five individuals has a single nucleotide polymorphism, rs12740374, in the 1p13 locus of the SORT1 gene that predisposes them to having low levels of low-density lipoprotein (LDL) and very-low-density lipoprotein (VLDL). Each copy of the minor allele, present in about 30% of people, alters LDL cholesterol by 8 mg/dL, while two copies of the minor allele, present in about 5% of the population, lowers LDL cholesterol 16 mg/dL. Carriers of the minor allele have also been shown to have a 40% decreased risk of myocardial infarction. Functional in vivo studies in mice describes that overexpression of SORT1 in mouse liver tissue led to significantly lower LDL-cholesterol levels, as much as 80% lower, and that silencing SORT1 increased LDL cholesterol approximately 200% (Musunuru K et al. From noncoding variant to phenotype via SORT1 at the 1p13 cholesterol locus. *Nature* 2010; 466: 714-721, herein incorporated by reference in its entirety).

Modulation of Cell Fate

Provided are methods of inducing an alteration in cell fate in a target mammalian cell. The target mammalian cell may be a precursor cell and the alteration may involve driving differentiation into a lineage, or blocking such differentiation. Alternatively, the target mammalian cell may be a differentiated cell, and the cell fate alteration includes driving de-differentiation into a pluripotent precursor cell, or blocking such de-differentiation, such as the dedifferentiation of cancer cells into cancer stem cells. In situations where a change in cell fate is desired, effective amounts of mRNAs encoding a cell fate inductive polypeptide is introduced into a target cell under conditions such that an alteration in cell fate is induced. In some embodiments, the modified mRNAs are useful to reprogram a subpopulation of cells from a first phenotype to a second phenotype. Such a reprogramming may be temporary or permanent.

Optionally, the reprogramming induces a target cell to adopt an intermediate phenotype.

Additionally, the methods of the present invention are particularly useful to generate induced pluripotent stem cells (iPS cells) because of the high efficiency of transfection, the ability to re-transfect cells, and the tenability of the amount of recombinant polypeptides produced in the target cells. Further, the use of iPS cells generated using the methods described herein is expected to have a reduced incidence of teratoma formation.

Also provided are methods of reducing cellular differentiation in a target cell population. For example, a target cell population containing one or more precursor cell types is contacted with a composition having an effective amount of a modified mRNA encoding a polypeptide, under conditions such that the polypeptide is translated and reduces the differentiation of the precursor cell. In non-limiting embodiments, the target cell population contains injured tissue in a mammalian subject or tissue affected by a surgical procedure. The precursor cell is, e.g., a stromal precursor cell, a neural precursor cell, or a mesenchymal precursor cell.

In a specific embodiment, provided are modified nucleic acids that encode one or more differentiation factors Gata4, Mef2c and Tbx4. These mRNA-generated factors are introduced into fibroblasts and drive the reprogramming into cardiomyocytes. Such a reprogramming can be performed in vivo, by contacting an mRNA-containing patch or other material to damaged cardiac tissue to facilitate cardiac regeneration. Such a process promotes cardiomyocyte genesis as opposed to fibrosis.

Targeting of Pathogenic Organisms; Purification of Biological Materials

Provided herein are methods for targeting pathogenic microorganisms, such as bacteria, yeast, protozoa, helminthes and the like, using modified mRNAs that encode cytostatic or cytotoxic polypeptides. Preferably the mRNA introduced into the target pathogenic organism contains modified nucleosides or other nucleic acid sequence modifications that the mRNA is translated exclusively, or preferentially, in the target pathogenic organism, to reduce possible off-target effects of the therapeutic. Such methods are useful for removing pathogenic organisms from biological material, including blood, semen, eggs, and transplant materials including embryos, tissues, and organs.

Targeting Diseased Cells

Provided herein are methods for targeting pathogenic or diseased cells, particularly cancer cells, using modified mRNAs that encode cytostatic or cytotoxic polypeptides. Preferably the mRNA introduced into the target pathogenic cell contains modified nucleosides or other nucleic acid sequence modifications that the mRNA is translated exclusively, or preferentially, in the target pathogenic cell, to reduce possible off-target effects of the therapeutic. Alternatively, the invention provides targeting moieties that are capable of targeting the modified mRNAs to preferentially bind to and enter the target pathogenic cell.

Protein Production

The methods provided herein are useful for enhancing protein product yield in a cell culture process. In a cell culture containing a plurality of host cells, introduction of the modified mRNAs described herein results in increased protein production efficiency relative to a corresponding unmodified nucleic acid. Such increased protein production efficiency can be demonstrated, e.g., by showing increased cell transfection, increased protein translation from the nucleic acid, decreased nucleic acid degradation, and/or reduced innate immune response of the host cell. Protein production can be measured by ELISA, and protein activity can be measured by various functional assays known in the art. The protein production may be generated in a continuous or a fed-batch mammalian process.

Additionally, it is useful to optimize the expression of a specific polypeptide in a cell line or collection of cell lines of potential interest, particularly an engineered protein such as a protein variant of a reference protein having a known activity. In one embodiment, provided is a method of optimizing expression of an engineered protein in a target cell, by providing a plurality of target cell types, and independently contacting with each of the plurality of target cell types a modified mRNA encoding an engineered polypeptide. Additionally, culture conditions may be altered to increase protein production efficiency. Subsequently, the presence and/or level of the engineered polypeptide in the plurality of target cell types is detected and/or quantitated, allowing for the optimization of an engineered polypeptide's expression by selection of an efficient target cell and cell culture conditions relating thereto. Such methods are particularly useful when the engineered polypeptide contains one or more post-translational modifications or has substantial tertiary structure, situations which often complicate efficient protein production.

Gene Silencing

The modified mRNAs described herein are useful to silence (i.e., prevent or substantially reduce) expression of one or more target genes in a cell population. A modified mRNA encoding a polypeptide capable of directing sequence-specific histone H3 methylation is introduced into the cells in the population under conditions such that the polypeptide is translated and reduces gene transcription of a target gene via histone H3 methylation and subsequent heterochromatin formation. In some embodiments, the silencing mechanism is performed on a cell population present in a mammalian subject. By way of non-limiting example, a useful target gene is a mutated Janus Kinase-2 family member, wherein the mammalian subject expresses the mutant target gene suffers from a myeloproliferative disease resulting from aberrant kinase activity.

Co-administration of modified mRNAs and siRNAs are also provided herein. As demonstrated in yeast, sequence-specific trans silencing is an effective mechanism for altering cell function. Fission yeast require two RNAi complexes for siRNA-mediated heterochromatin assembly: the RNA-induced transcriptional silencing (RITS) complex and the RNA-directed RNA polymerase complex (RDRC) (Motamedi et al. Cell 2004, 119, 789-802). In fission yeast, the RITS complex contains the siRNA binding Argonaute family protein Ago1, a chromodomain protein Chp1, and Tas3. The fission yeast RDRC complex is composed of an RNA-dependent RNA Polymerase Rdpl, a putative RNA helicase Hrr1, and a polyA polymerase family protein Cid12. These two complexes require the Dicer ribonuclease and Clr4 histone H3 methyltransferase for activity. Together, Ago1 binds siRNA molecules generated through Dicer-mediated cleavage of Rdpl co-transcriptionally generated dsRNA transcripts and allows for the sequence-specific direct association of Chp1, Tas3, Hrr1, and Clr4 to regions of DNA destined for methylation and histone modification and subsequent compaction into transcriptionally silenced heterochromatin. While this mechanism functions in cis- with centromeric regions of DNA, sequence-specific trans silencing is possible through co-transfection with double-stranded siRNAs for specific regions of DNA and concomitant RNAi-directed silencing of the siRNA ribonuclease Eri1 (Buhler et al. Cell 2006, 125, 873-886, herein incorporated by reference in its entirety).

Modulation of Biological Pathways

The rapid translation of modified mRNAs introduced into cells provides a desirable mechanism of modulating target biological pathways. Such modulation includes antagonism or agonism of a given pathway. In one embodiment, a method is provided for antagonizing a biological pathway in a cell by contacting the cell with an effective amount of a composition comprising a modified nucleic acid encoding a recombinant polypeptide, under conditions such that the nucleic acid is localized into the cell and the recombinant polypeptide is capable of being translated in the cell from the nucleic acid, wherein the recombinant polypeptide inhibits the activity of a polypeptide functional in the biological pathway. Exemplary biological pathways are those defective in an autoimmune or inflammatory disorder such as multiple sclerosis, rheumatoid arthritis, psoriasis, lupus erythematosus, ankylosing spondylitis colitis, or Crohn's disease; in particular, antagonism of the IL-12 and IL-23 signaling pathways are of particular utility. (See Kikly K, Liu L, Na S, Sedgwick J D (2006) Curr. Opin. Immunol. 18 (6): 670-5, herein incorporated by reference in its entirety).

Further, provided are modified nucleic acids encoding an antagonist for chemokine receptors; chemokine receptors CXCR-4 and CCR-5 are required for, e.g., HIV entry into host cells (Arenzana-Seisdedos F et al, (1996) Nature. October 3; 383(6599):400, herein incorporated by reference in its entirety).

Alternatively, provided are methods of agonizing a biological pathway in a cell by contacting the cell with an effective amount of a modified nucleic acid encoding a recombinant polypeptide under conditions such that the nucleic acid is localized into the cell and the recombinant polypeptide is capable of being translated in the cell from the nucleic acid, and the recombinant polypeptide induces the activity of a polypeptide functional in the biological pathway. Exemplary agonized biological pathways include pathways that modulate cell fate determination. Such agonization is reversible or, alternatively, irreversible.

Cellular Nucleic Acid Delivery

Methods of the present invention enhance nucleic acid delivery into a cell population, in vivo, ex vivo, or in culture. For example, a cell culture containing a plurality of host cells (e.g., eukaryotic cells such as yeast or mammalian cells) is contacted with a composition that contains an enhanced nucleic acid having at least one nucleoside modification and, optionally, a translatable region. The composition also generally contains a transfection reagent or other compound that increases the efficiency of enhanced nucleic acid uptake into the host cells. The enhanced nucleic acid exhibits enhanced retention in the cell population, relative to a corresponding unmodified nucleic acid. The retention of the enhanced nucleic acid is greater than the retention of the unmodified nucleic acid. In some embodiments, it is at least about 50%, 75%, 90%, 95%, 100%, 150%, 200% or more than 200% greater than the retention of the unmodified nucleic acid. Such retention advantage may be achieved by one round of transfection with the enhanced nucleic acid, or may be obtained following repeated rounds of transfection.

In some embodiments, the enhanced nucleic acid is delivered to a target cell population with one or more additional nucleic acids. Such delivery may be at the same time, or the enhanced nucleic acid is delivered prior to delivery of the one or more additional nucleic acids. The additional one or more nucleic acids may be modified nucleic acids or unmodified nucleic acids. It is understood that the initial presence of the enhanced nucleic acids does not substantially induce an innate immune response of the cell population and, moreover, that the innate immune response will not be activated by the later presence of the unmodified nucleic acids. In this regard, the enhanced nucleic acid may not itself contain a translatable region, if the protein desired to be present in the target cell population is translated from the unmodified nucleic acids.

IV. Pharmaceutical Compositions

Formulation, Administration, Delivery and Dosing

The present invention provides polynucleotides, modified nucleic acid, enhanced modified RNA and ribonucleic acid compositions and complexes in combination with one or more pharmaceutically acceptable excipients. Pharmaceutical compositions may optionally comprise one or more additional active substances, e.g. therapeutically and/or prophylactically active substances. General considerations in the formulation and/or manufacture of pharmaceutical agents may be found, for example, in *Remington: The Science and Practice of Pharmacy* $21^{st}$ ed., Lippincott Williams & Wilkins, 2005 (incorporated herein by reference).

In one embodiment, provided are formulations containing an effective amount of a ribonucleic acid (e.g., an mRNA or a nucleic acid containing an mRNA) engineered to avoid an innate immune response of a cell into which the ribonucleic acid enters. The ribonucleic acid generally includes a nucleotide sequence encoding a polypeptide of interest.

In some embodiments, compositions are administered to humans, human patients or subjects. For the purposes of the present disclosure, the phrase "active ingredient" generally refers to a modified nucleic acid, an enhanced nucleic acid or a ribonucleic acid to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient Formulations The polynucleotides, modified nucleic acid, enhanced modified RNA and ribonucleic acid of the invention can be formulated using one or more excipients to: (1) increase stability; (2) increase cell transfection; (3) permit the sustained or delayed release (e.g., from a depot formulation of the modified nucleic acids, enhanced modified RNA or ribonucleic acids); (4) alter the biodistribution (e.g., target the modified nucleic acids, enhanced modified RNA or ribonucleic acids to specific tissues or cell types); (5) increase the translation of encoded protein in vivo; and/or (6) alter the release profile of encoded protein in vivo. In addition to traditional excipients such as any and all solvents, dispersion media, diluents, or other liquid vehicles, dispersion or suspension aids, surface active agents, isotonic agents, thickening or emulsifying agents, preservatives, excipients of the present invention can include, without limitation, lipidoids, liposomes, lipid nanoparticles, polymers, lipoplexes, core-shell nanoparticles, peptides, proteins, cells transfected with polynucleotides, modified nucleic acid, enhanced modified RNA and ribonucleic acid (e.g., for transplantation into a subject), hyaluronidase, nanoparticle mimics and combinations thereof.

Accordingly, the formulations of the invention can include one or more excipients, each in an amount that together increases the stability of the polynucleotide, modified nucleic acid, enhanced modified RNA or ribonucleic acid, increases cell transfection by the polynucleotides, modified nucleic acid, enhanced modified RNA or ribonucleic acid, increases the expression of polynucleotides, modified nucleic acid, enhanced modified RNA or ribonucleic acid encoded protein, and/or alters the release profile of the polynucleotides, modified nucleic acid, enhanced modified RNA or ribonucleic acid encoded proteins. Further, the polynucleotides, modified nucleic acid, enhanced modified RNA or ribonucleic acid of the present invention may be formulated using self-assembled nucleic acid nanoparticles.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

The polynucleotides, modified nucleic acid, enhanced modified RNA and ribonucleic acid of the invention may be formulated for delivery in the tissues and/or organs of a subject. Organs may include, but are not limited to, the heart, lung, brain, liver, basal ganglia, brain stem medulla, midbrain, pons, cerebellum, cerebral cortex, hypothalamus, eye, pituitary, thyroid, parathyroid, esophagus, thymus, adrenal glands, appendix, bladder, gallbladder, intestines (e.g., large intestine and small intestine), kidney, pancreas, spleen, stomach, skin, prostate, testes, ovaries, uterus, adrenal glands, anus, bronchi, ears, esophagus, genitals, larynx (voice box), lymph nodes, meninges, mouth, nose, parathyroid glands, pituitary gland, rectum, salivary glands, spinal cord, thymus gland, tongue, trachea, ureters, urethra, colon. Tissues may include, but are not limited to, heart valves, bone, vein, middle ear, muscle (cardiac, smooth or skeletal) cartilage, tendon or ligaments. As a non-limiting example, the polynucleotides, modified nucleic acid, enhanced modified RNA and ribonucleic acid may be formulated in a lipid nanoparticle and delivered to an organ such as, but not limited, to the liver, spleen, kidney or lung. In another non-limiting example, the polynucleotides, modified nucleic acids, enhanced modified RNA and ribonucleic acid may be formulated in a lipid nanoparticle comprising the cationic lipid DLin-KC2-DMA and delivered to an organ such as, but not limited to, the liver, spleen, kidney or lung.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient may generally be equal to the dosage of the active ingredient which would be administered to a subject and/or a convenient fraction of such a dosage including, but not limited to, one-half or one-third of such a dosage.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient.

In some embodiments, the modified mRNA formulations described herein may contain at least one modified mRNA. The formulations may contain 1, 2, 3, 4 or 5 modified mRNA. In one embodiment the formulation may contain modified mRNA encoding proteins selected from categories such as, but not limited to, human proteins, veterinary proteins, bacterial proteins, biological proteins, antibodies, immunogenic proteins, therapeutic peptides and proteins, secreted proteins, plasma membrane proteins, cytoplasmic and cytoskeletal proteins, intracellular membrane bound proteins, nuclear proteins, proteins associated with human disease and/or proteins associated with non-human diseases. In one embodiment, the formulation contains at least three modified mRNA encoding proteins. In one embodiment, the formulation contains at least five modified mRNA encoding proteins.

Pharmaceutical formulations may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, Md., 2006; incorporated herein by reference). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

In some embodiments, the particle size of the lipid nanoparticle may be increased and/or decreased. The change in particle size may be able to help counter biological reaction such as, but not limited to, inflammation or may increase the biological effect of the modified mRNA delivered to mammals.

Pharmaceutically acceptable excipients used in the manufacture of pharmaceutical compositions include, but are not limited to, inert diluents, surface active agents and/or emulsifiers, preservatives, buffering agents, lubricating agents, and/or oils. Such excipients may optionally be included in the pharmaceutical formulations of the invention Lipidoid The synthesis of lipidoids has been extensively described and formulations containing these compounds are particularly suited for delivery of polynucleotides, modified nucleic acids, enhanced modified RNA and ribonucleic acids (see Mahon et al., Bioconjug Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

While these lipidoids have been used to effectively deliver double stranded small interfering RNA molecules in rodents and non-human primates (see Akinc et al., Nat Biotechnol. 2008 26:561-569; Frank-Kamenetsky et al., Proc Natl Acad Sci USA. 2008 105:11915-11920; Akinc et al., Mol Ther. 2009 17:872-879; Love et al., Proc Natl Acad Sci USA. 2010 107:1864-1869; Leuschner et al., Nat Biotechnol. 2011 29:1005-1010; all of which is incorporated herein in their entirety), the present disclosure describes their formulation and use in delivering single stranded polynucleotide, modified nucleic acids, enhanced modified RNA and ribonucleic acids. Complexes, micelles, liposomes or particles can be prepared containing these lipidoids and therefore, can result in an effective delivery of the polynucleotides, modified nucleic acids, enhanced modified RNA and ribonucleic acids, as judged by the production of an encoded protein, following the injection of a lipidoid formulation via localized and/or systemic routes of administration. Lipidoid complexes of polynucleotides, modified nucleic acids, enhanced modified RNA and ribonucleic acids can be administered by various means including, but not limited to, intravenous, intramuscular, or subcutaneous routes.

In vivo delivery of nucleic acids may be affected by many parameters, including, but not limited to, the formulation composition, nature of particle PEGylation, degree of loading, oligonucleotide to lipid ratio, and biophysical parameters such as particle size (Akinc et al., Mol Ther. 2009 17:872-879; herein incorporated by reference in its entirety). As an example, small changes in the anchor chain length of poly(ethylene glycol) (PEG) lipids may result in significant effects on in vivo efficacy. Formulations with the different lipidoids, including, but not limited to penta[3-(1-laurylaminopropionyl)]-triethylenetetramine hydrochloride (TETA-5LAP; aka 98N12-5, see Murugaiah et al., Analytical Biochemistry, 401:61 (2010)), C12-200 (including derivatives and variants), and MD1, can be tested for in vivo activity.

The lipidoid referred to herein as "98N12-5" is disclosed by Akinc et al., Mol Ther. 2009 17:872-879 and is incorporated by reference in its entirety.

The lipidoid referred to herein as "C12-200" is disclosed by Love et al., Proc Natl Acad Sci USA. 2010 107:1864-1869 and Liu and Huang, Molecular Therapy. 2010 669-670; both of which are herein incorporated by reference in their entirety. The lipidoid formulations can include particles comprising either 3 or 4 or more components in addition to polynucleotide, modified nucleic acids, enhanced modified RNA and ribonucleic acids. As an example, formulations with certain lipidoids, include, but are not limited to, 98N12-5 and may contain 42% lipidoid, 48% cholesterol and 10% PEG (C14 alkyl chain length). As another example, formulations with certain lipidoids, include, but are not limited to, C12-200 and may contain 50% lipidoid, 10% disteroylphosphatidyl choline, 38.5% cholesterol, and 1.5% PEG-DMG.

In one embodiment, a modified nucleic acids, enhanced modified RNA or ribonucleic acids formulated with a lipidoid for systemic intravenous administration can target the liver. For example, a final optimized intravenous formulation using modified nucleic acids, enhanced modified RNA or ribonucleic acids, and comprising a lipid molar composition of 42% 98N12-5, 48% cholesterol, and 10% PEG-lipid with a final weight ratio of about 7.5 to 1 total lipid to polynucleotide, modified nucleic acids, enhanced modified RNA or ribonucleic acids, and a C14 alkyl chain length on the PEG lipid, with a mean particle size of roughly 50-60 nm, can result in the distribution of the formulation to be greater than 90% to the liver. (see, Akinc et al., Mol Ther.

2009 17:872-879; herein incorporated in its entirety). In another example, an intravenous formulation using a C12-200 (see U.S. provisional application 61/175,770 and published international application WO2010129709, each of which is herein incorporated by reference in their entirety) lipidoid may have a molar ratio of 50/10/38.5/1.5 of C12-200/disteroylphosphatidyl choline/cholesterol/PEG-DMG, with a weight ratio of 7 to 1 total lipid to polynucleotide, modified nucleic acids, enhanced modified RNA or ribonucleic acids, and a mean particle size of 80 nm may be effective to deliver polynucleotides, modified nucleic acids, enhanced modified RNA or ribonucleic acids to hepatocytes (see, Love et al., Proc Natl Acad Sci USA. 2010 107:1864-1869 herein incorporated by reference). In another embodiment, an MD1 lipidoid-containing formulation may be used to effectively deliver polynucleotides, modified nucleic acids, enhanced modified RNA or ribonucleic acids to hepatocytes in vivo. The characteristics of optimized lipidoid formulations for intramuscular or subcutaneous routes may vary significantly depending on the target cell type and the ability of formulations to diffuse through the extracellular matrix into the blood stream. While a particle size of less than 150 nm may be desired for effective hepatocyte delivery due to the size of the endothelial fenestrae (see, Akinc et al., Mol Ther. 2009 17:872-879 herein incorporated by reference), use of a lipidoid-formulated polynucleotides, modified nucleic acids, enhanced modified RNA or ribonucleic acids to deliver the formulation to other cells types including, but not limited to, endothelial cells, myeloid cells, and muscle cells may not be similarly size-limited. Use of lipidoid formulations to deliver siRNA in vivo to other non-hepatocyte cells such as myeloid cells and endothelium has been reported (see Akinc et al., Nat Biotechnol. 2008 26:561-569; Leuschner et al., Nat Biotechnol. 2011 29:1005-1010; Cho et al. Adv. Funct. Mater. 2009 19:3112-3118; 8$^{th}$ International Judah Folkman Conference, Cambridge, Mass. Oct. 8-9, 2010 herein incorporated by reference in its entirety). Effective delivery to myeloid cells, such as monocytes, lipidoid formulations may have a similar component molar ratio. Different ratios of lipidoids and other components including, but not limited to, disteroylphosphatidyl choline, cholesterol and PEG-DMG, may be used to optimize the formulation of the polynucleotides, modified nucleic acids, enhanced modified RNA or ribonucleic acids for delivery to different cell types including, but not limited to, hepatocytes, myeloid cells, muscle cells, etc. For example, the component molar ratio may include, but is not limited to, 50% C12-200, 10% disteroylphosphatidyl choline, 38.5% cholesterol, and %1.5 PEG-DMG (see Leuschner et al., Nat Biotechnol 2011 29:1005-1010; herein incorporated by reference in its entirety). The use of lipidoid formulations for the localized delivery of nucleic acids to cells (such as, but not limited to, adipose cells and muscle cells) via either subcutaneous or intramuscular delivery, may not require all of the formulation components desired for systemic delivery, and as such may comprise only the lipidoid and the polynucleotides, modified nucleic acids, enhanced modified RNA or ribonucleic acids.

Combinations of different lipidoids may be used to improve the efficacy of polynucleotides, modified nucleic acids, enhanced modified RNA or ribonucleic acids directed protein production as the lipidoids may be able to increase cell transfection by the polynucleotides, modified nucleic acid, or modified nucleic acids, enhanced modified RNA or ribonucleic acids; and/or increase the translation of encoded protein (see Whitehead et al., Mol. Ther. 2011, 19:1688-1694, herein incorporated by reference in its entirety).

Liposomes, Lipoplexes, and Lipid Nanoparticles

The polynucleotides, modified nucleic acids, enhanced modified RNA or ribonucleic acids of the invention can be formulated using one or more liposomes, lipoplexes, or lipid nanoparticles. In one embodiment, pharmaceutical compositions of polynucleotides, modified nucleic acids, enhanced modified RNA or ribonucleic acids include liposomes. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

In one embodiment, pharmaceutical compositions described herein may include, without limitation, liposomes such as those formed from 1,2-dioleyloxy-N,N-dimethylaminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (US20100324120; herein incorporated by reference in its entirety) and liposomes which may deliver small molecule drugs such as, but not limited to, DOXIL® from Janssen Biotech, Inc. (Horsham, Pa.). In one embodiment, pharmaceutical compositions described herein may include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles *Hum Gene Ther.* 2008 19:125-132; all of which are incorporated herein in their entireties.) The original manufacture method by Wheeler et al. was a detergent dialysis method, which was later improved by Jeffs et al. and is referred to as the spontaneous vesicle formation method. The liposome formulations are composed of 3 to 4 lipid components in addition to the polynucleotides, modified nucleic acids, enhanced modified RNA or ribonucleic acids.

As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. As another example, certain liposome formulations may contain, but are not limited to, 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethylaminopropane (DLenDMA), as described by Heyes et al.

In one embodiment, pharmaceutical compositions may include liposomes which may be formed to deliver polynucleotides, modified nucleic acids, enhanced modified RNA and ribonucleic acids which may encode at least one immunogen. The polynucleotides, modified nucleic acids, enhanced modified RNA and ribonucleic acids may be encapsulated by the liposome and/or it may be contained in an aqueous core which may then be encapsulated by the liposome (see International Pub. Nos. WO2012031046, WO2012031043, WO2012030901 and WO2012006378; each of which is herein incorporated by reference in their entirety). In another polynucleotides, embodiment, the modified nucleic acids, enhanced modified RNA and ribonucleic acids which may encode an immunogen may be formulated in a cationic oil-in-water emulsion where the emulsion particle comprises an oil core and a cationic lipid which can interact with the polynucleotides, modified nucleic acids, enhanced modified RNA and ribonucleic acids anchoring the molecule to the emulsion particle (see International Pub. No. WO2012006380). In yet another embodiment, the lipid formulation may include at least cationic lipid, a lipid which may enhance transfection and a least one lipid which contains a hydrophilic head group linked to a lipid moiety (International Pub. No. WO2011076807 and U.S. Pub. No. 20110200582; each of which is herein incorporated by reference in their entirety). In another embodiment, the polynucleotides, modified nucleic acids, enhanced modified RNA or ribonucleic acids encoding an immunogen may be formulated in a lipid vesicle which may have crosslinks between functionalized lipid bilayers (see U.S. Pub. No. 20120177724, herein incorporated by reference in its entirety).

In one embodiment, the polynucleotides, modified nucleic acids, enhanced modified RNA or ribonucleic acids may be formulated in a lipid vesicle which may have crosslinks between functionalized lipid bilayers.

In one embodiment, the polynucleotides, modified nucleic acids, enhanced modified RNA or ribonucleic acids may be formulated in a lipid-polycation complex. The formation of the lipid-polycation complex may be accomplished by methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine. In another embodiment, the polynucleotide, modified nucleic acids, enhanced modified RNA or ribonucleic acids may be formulated in a lipid-polycation complex which may further include a neutral lipid such as, but not limited to, cholesterol or dioleoyl phosphatidylethanolamine (DOPE).

The liposome formulation may be influenced by, but not limited to, the selection of the cationic lipid component, the degree of cationic lipid saturation, the nature of the PEGylation, ratio of all components and biophysical parameters such as size. In one example by Semple et al. (Semple et al. Nature Biotech. 2010 28:172-176), the liposome formulation was composed of 57.1% cationic lipid, 7.1% dipalmitoylphosphatidylcholine, 34.3% cholesterol, and 1.4% PEG-c-DMA. As another example, changing the composition of the cationic lipid could more effectively deliver siRNA to various antigen presenting cells (Basha et al. Mol Ther. 2011 19:2186-2200; herein incorporated by reference in its entirety).

In some embodiments, the ratio of PEG in the LNP formulations may be increased or decreased and/or the carbon chain length of the PEG lipid may be modified from C14 to C18 to alter the pharmacokinetics and/or biodistribution of the LNP formulations. As a non-limiting example, LNP formulations may contain 1-5% of the lipid molar ratio of PEG-c-DOMG as compared to the cationic lipid, DSPC and cholesterol. In another embodiment the PEG-c-DOMG may be replaced with a PEG lipid such as, but not limited to, PEG-DSG (1,2-Distearoyl-sn-glycerol, methoxypolyethylene glycol) or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In one embodiment, the cationic lipid may be selected from, but not limited to, a cationic lipid described in International Publication Nos. WO2012040184, WO2011153120, WO2011149733, WO2011090965, WO2011043913, WO2011022460, WO2012061259, WO2012054365, WO2012044638, WO2010080724, WO201021865 and WO2008103276, U.S. Pat. Nos. 7,893, 302 and 7,404,969 and US Patent Publication No. US20100036115; each of which is herein incorporated by reference in their entirety. In another embodiment, the cationic lipid may be selected from, but not limited to, formula A described in International Publication Nos. WO2012040184, WO2011153120, WO2011149733, WO2011090965, WO2011043913, WO2011022460, WO2012061259, WO2012054365 and WO2012044638; each of which is herein incorporated by reference in their entirety. In yet another embodiment, the cationic lipid may be selected from, but not limited to, formula CLI-CLXXIX of International Publication No. WO2008103276, formula CLI-CLXXIX of U.S. Pat. No. 7,893,302, formula CLI-CLXXXII of U.S. Pat. No. 7,404,969 and formula I-VI of US Patent Publication No. US20100036115; each of which is herein incorporated by reference in their entirety. As a non-limiting example, the cationic lipid may be selected from (20Z,23Z)—N,N-dimethylnonacosa-20,23-dien-10-amine, (17Z,20Z)—N,N-dimemylhexacosa-17,20-dien-9-amine, (1 Z, 19Z)—N5N-dimethylpentacosa~16, 19-dien-8-amine, (13Z,16Z)—N,N-dimethyldocosa-13J16-dien-5-amine, (12Z,15Z)-NJN-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21 Z)—N,N-dimethylheptacosa-18,21-dien-8-amine, (17Z,20Z)—N,N-dimethylhexacosa-17,20-dien-7-amine, (16Z; 19Z)—N,N-dimethylpentacosa-16,19-dien-6-amine, (22Z,25Z)—N,N-dimethylhentriaconta-22,25-dien-10-amine, (21 Z,24Z)—N; N-dimethyltriaconta-21,24-dien-9-amine, (18Z)—N,N-dimetiylheptacos-18-en-10-amine, (17Z)—N,N-dimethylhexacos-17-en-9-amine, (19Z,22Z)—NJN-dimethyloctacosa-19,22-dien-7-amine, N,N-dimethylheptacosan-10-amine, (20Z,23Z)—N-ethyl-N-methylnonacosa-20J23-dien-10-amine, 1-[(11Z,14Z)-1-nonylicosa-11, 14-dien-1-yl]pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12, 15-dien-1-amine, (13Z,16Z)—N,N-dimethyl-3-nonyldocosa-13, 16-dien-1-amine, N,N-dimethyl-1-[(1 S,2R)-2-octylcyclopropyl]eptadecan-8-amine, 1-[(1 S,2R)-2-hexylcyclopropyl]-N,N-dimethylnonadecan-10-amine, N,N-dimethyl-1-[(1 S,2R)-2-octylcyclopropyl]nonadecan-10-amine, N,N-dimethyl-21-[(1S,2R)-2-octylcyclopropyl] henicosan-10-amine, N,N-dimethyl-1-[(1 S,2S)-2-{[(1R, 2R)-2-pentylcyclopropyl]methyl}cyclopropyl]nonadecan-10-amine, N,N-dimethyl-1-[(1 S,2R)-2-octylcyclopropyl] hexadecan-8-amine, N,N-dimethyH-[(1R,2S)-2-undecylcyclopropyl]tetradecan-5-amine, N,N-dimethyl-3-{7-[(1 S,2R)-2-octylcyclopropyl]heptyl}dodecan-1-amine, 1-[(1R,2S)-2-heptylcyclopropyl]-N,N-dimethyloctadecan-9-amine, 1-[(1 S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy) methyl] ethyl}pyrrolidine, (2S)—N,N-dimethyl-1-[(9Z,12Z)-octadeca-9,12-dien-1-yloxy]-3-[(5Z)-oct-5-en-1-yloxy] propan-2-amine, 1-{2-[(9Z,12Z)-octadeca-9,12-dien-1-yloxy]-1-[(octyloxy) methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy) propan-2-amine (Compound 9); (2S)—N,N-dimethyl-1-[(6Z,9Z,12Z)-octadeca-6,9,12-trien-1-yloxy]-3-(octyloxy) propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13, 16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoylo ctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z, 12Z)-octadeca-9,12-dien-1-yloxy]propan-2-amine, N,N-dimethyl-1-(octyloxy)-3-({8-[(1 S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl] oxy}-3-(octyloxy)propan-2-amine and (11E,20Z,23Z)—N; N-dimethylnonacosa-11,20,2-trien-10-amine or a pharmaceutically acceptable salt or stereoisomer thereof.

In one embodiment, the cationic lipid may be synthesized by methods known in the art and/or as described in International Publication Nos. WO2012040184, WO2011153120, WO2011149733, WO2011090965, WO2011043913, WO2011022460, WO2012061259, WO2012054365, WO2012044638, WO2010080724 and WO201021865; each of which is herein incorporated by reference in their entirety.

In one embodiment, the LNP formulation may contain PEG-c-DOMG 3% lipid molar ratio. In another embodiment, the LNP formulation may contain PEG-c-DOMG 1.5% lipid molar ratio.

In one embodiment, the LNP formulation may contain PEG-DMG 2000 (1,2-dimyristoyl-sn-glycero-3-phophoethanolamine-N-[methoxy(polyethylene glycol)-2000). In one embodiment, the LNP formulation may contain PEG-DMG 2000, a cationic lipid known in the art and at least one other component. In another embodiment, the LNP formulation may contain PEG-DMG 2000, a cationic lipid known in the art, DSPC and cholesterol. As a non-limiting example, the LNP formulation may contain PEG-DMG 2000, DLin-DMA, DSPC and cholesterol. As another non-limiting example the LNP formulation may contain PEG-DMG 2000, DLin-DMA, DSPC and cholesterol in a molar ratio of 2:40:10:48 (see Geall et al., Nonviral delivery of self-amplifying RNA vaccines, PNAS 2012; PMID: 22908294).

In one embodiment, the LNP formulation may be formulated by the methods described in International Publication Nos. WO2011127255 or WO2008103276, each of which is herein incorporated by reference in their entirety. As a non-limiting example, modified RNA described herein may be encapsulated in LNP formulations as described in WO2011127255 and/or WO2008103276; each of which is herein incorporated by reference in their entirety.

In one embodiment, LNP formulations described herein may comprise a polycationic composition. As a non-limiting example, the polycationic composition may be selected from formula 1-60 of US Patent Publication No. US20050222064; herein incorporated by reference in its entirety. In another embodiment, the LNP formulations comprising a polycationic composition may be used for the delivery of the modified RNA described herein in vivo and/or in vitro.

In one embodiment, the LNP formulations described herein may additionally comprise a permeability enhancer molecule. Non-limiting permeability enhancer molecules are described in US Patent Publication No. US20050222064; herein incorporated by reference in its entirety.

In one embodiment, the pharmaceutical compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713)) and hyaluronan-coated liposomes (Quiet Therapeutics, Israel).

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In one embodiment, the internal ester linkage may be located on either side of the saturated carbon. Non-limiting examples of reLNPs include, rates of permeation and/or fluorescent microscopy techniques including, but not limited to, fluorescence recovery after photobleaching (FRAP) and high resolution multiple particle tracking (MPT).

The lipid nanoparticle engineered to penetrate mucus may comprise a polymeric material (i.e. a polymeric core) and/or

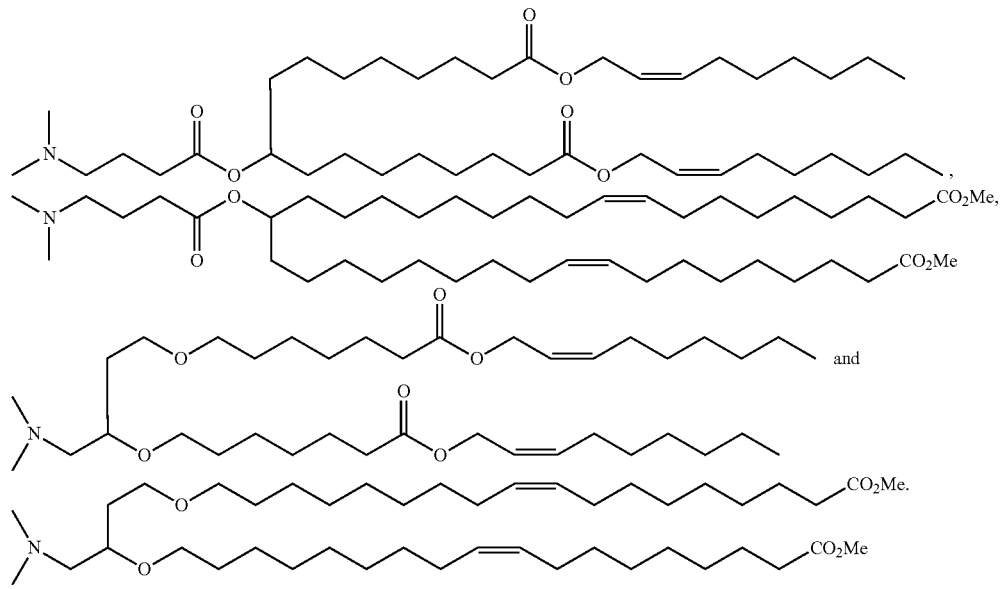

In one embodiment, an immune response may be elicited by delivering a lipid nanoparticle which may include a nanospecies, a polymer and an immunogen. (U.S. Publication No. 20120189700 and International Publication No. WO2012099805; each of which is herein incorporated by reference in their entirety). The polymer may encapsulate the nanospecies or partially encapsulate the nanospecies. The immunogen may be a recombinant protein, a modified RNA described herein. In one embodiment, the lipid nanoparticle may be formulated for use in a vaccine such as, but not limited to, against a pathogen.

Lipid nanoparticles may be engineered to alter the surface properties of particles so the lipid nanoparticles may penetrate the mucosal barrier. Mucus is located on mucosal tissue such as, but not limted to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles may be removed from the mucosla tissue within seconds or within a few hours. Large polymeric nanoparticles (200 nm-500 nm in diameter) which have been coated densely with a low molecular weight polyethylene glycol (PEG) diffused through mucus only 4 to 6-fold lower than the same particles diffusing in water (Lai et al. PNAS 2007 104(5):1482-487; Lai et al. Adv Drug Deliv Rev. 2009 61(2): 158-171; each of which is herein incorporated by reference in their entirety). The transport of nanoparticles may be determined using a polymer-vitamin conjugate and/or a tri-block co-polymer. The polymeric material may include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates. The polymeric material may be biodegradable and/or biocompatible. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropyl cellulose, carboxymethylcellulose, polymers of acrylic acids, such as poly(methyl(meth)acrylate) (PMMA), poly(ethyl(meth) acrylate), poly(butyl(meth)acrylate), poly(isobutyl(meth)

acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), and trimethylene carbonate, polyvinylpyrrolidone. The lipid nanoparticle may be coated or associated with a co-polymer such as, but not limited to, a block co-polymer, and (poly(ethylene glycol))-(poly(propylene oxide))-(poly(ethylene glycol)) triblock copolymer (see US Publication 20120121718 and US Publication 20100003337; each of which is herein incorporated by reference in their entirety). The co-polymer may be a polymer that is generally regarded as safe (GRAS) and the formation of the lipid nanoparticle may be in such a way that no new chemical entities are created. For example, the lipid nanoparticle may comprise poloxamers coating PLGA nanoparticles without forming new chemical entities which are still able to rapidly penetrate human mucus (Yang et al. Angew. Chem. Int. Ed. 2011 50:2597-2600; herein incorporated by reference in its entirety).

The vitamin of the polymer-vitamin conjugate may be vitamin E. The vitamin portion of the conjugate may be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

The lipid nanoparticle engineered to penetrate mucus may include surface altering agents such as, but not limited to, polynucleotides, modified nucleic acids, enhanced modified RNA, ribonucleic acids, anionic protein (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4 dornase alfa, neltenexine, erdosteine) and various DNases including rhDNase. The surface altering agent may be embedded or enmeshed in the particle's surface or disposed (e.g., by coating, adsorption, covalent linkage, or other process) on the surface of the lipid nanoparticle. (see US Publication 20100215580 and US Publication 20080166414; each of which is herein incorporated by reference in their entirety).

The mucus penetrating lipid nanoparticles may comprise at least one polynucleotide, modified nucleic acids, enhanced modified RNA or ribonucleic acids described herein. The modified nucleic acids, enhanced modified RNA or ribonucleic acids may be encapsulated in the lipid nanoparticle and/or disposed on the surface of the particle. The polynucleotide, modified nucleic acids, enhanced modified RNA or ribonucleic acids may be covalently coupled to the lipid nanoparticle. Formulations of mucus penetrating lipid nanoparticles may comprise a plurality of nanoparticles. Further, the formulations may contain particles which may interact with the mucus and alter the structural and/or adhesive properties of the surrounding mucus to decrease mucoadhesion which may increase the delivery of the mucus penetrating lipid nanoparticles to the mucosal tissue.

In one embodiment, the polynucleotide, modified nucleic acids, enhanced modified RNA or ribonucleic acids is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In one embodiment such formulations may also be constructed or compositions altered such that they passively or actively are directed to different cell types in vivo, including but not limited to hepatocytes, immune cells, tumor cells, endothelial cells, antigen presenting cells, and leukocytes (Akinc et al. Mol Ther. 2010 18:1357-1364; Song et al., Nat Biotechnol. 2005 23:709-717; Judge et al., J Clin Invest. 2009 119:661-673; Kaufmann et al., Microvasc Res 2010 80:286-293; Santel et al., Gene Ther 2006 13:1222-1234; Santel et al., Gene Ther 2006 13:1360-1370; Gutbier et al., Pulm Pharmacol. Ther. 2010 23:334-344; Basha et al., Mol. Ther. 2011 19:2186-2200; Fenske and Cullis, Expert Opin Drug Deliv. 2008 5:25-44; Peer et al., Science. 2008 319: 627-630; Peer and Lieberman, Gene Ther. 2011 18:1127-1133; all of which are incorporated herein by reference in its entirety). One example of passive targeting of formulations to liver cells includes the DLin-DMA, DLin-KC2-DMA and MC3-based lipid nanoparticle formulations which have been shown to bind to apolipoprotein E and promote binding and uptake of these formulations into hepatocytes in vivo (Akinc et al. Mol Ther. 2010 18:1357-1364; herein incorporated by reference in its entirety). Formulations can also be selectively targeted through expression of different ligands on their surface as exemplified by, but not limited by, folate, transferrin, N-acetylgalactosamine (GalNAc), and antibody targeted approaches (Kolhatkar et al., Curr Drug Discov Technol. 2011 8:197-206; Musacchio and Torchilin, Front Biosci. 2011 16:1388-1412; Yu et al., Mol Membr Biol. 2010 27:286-298; Patil et al., Crit Rev Ther Drug Carrier Syst. 2008 25:1-61; Benoit et al., Biomacromolecules. 2011 12:2708-2714 Zhao et al., Expert Opin Drug Deliv. 2008 5:309-319; Akinc et al., Mol Ther. 2010 18:1357-1364; Srinivasan et al., Methods Mol Biol. 2012 820:105-116; Ben-Arie et al., Methods Mol Biol. 2012 757:497-507; Peer 2010 J Control Release. 20:63-68; Peer et al., Proc Natl Acad Sci USA. 2007 104:4095-4100; Kim et al., Methods Mol Biol. 2011 721:339-353; Subramanya et al., Mol Ther. 2010 18:2028-2037; Song et al., Nat Biotechnol. 2005 23:709-717; Peer et al., Science. 2008 319:627-630; Peer and Lieberman, Gene Ther. 2011 18:1127-1133; all of which are incorporated herein by reference in its entirety).

In one embodiment, the polynucleotide, modified nucleic acids, enhanced modified RNA or ribonucleic acids is formulated as a solid lipid nanoparticle. A solid lipid nanoparticle (SLN) may be spherical with an average diameter between 10 to 1000 nm. SLN possess a solid lipid core matrix that can solubilize lipophilic molecules and may be stabilized with surfactants and/or emulsifiers. In a further embodiment, the lipid nanoparticle may be a self-assembly lipid-polymer nanoparticle (see Zhang et al., ACS Nano, 2008, 2 (8), pp 1696-1702; herein incorporated by reference in its entirety).

Liposomes, lipoplexes, or lipid nanoparticles may be used to improve the efficacy of polynucleotides, modified nucleic acids, enhanced modified RNA or ribonucleic acids directed protein production as these formulations may be able to increase cell transfection by the polynucleotides, modified nucleic acids, enhanced modified RNA or ribonucleic acids; and/or increase the translation of encoded protein. One such example involves the use of lipid encapsulation to enable the effective systemic delivery of polyplex plasmid DNA (Heyes et al., Mol Ther. 2007 15:713-720; herein incorporated by reference in its entirety). The liposomes, lipoplexes, or lipid nanoparticles may also be used to increase the stability of the polynucleotides, modified nucleic acids, enhanced modified RNA or ribonucleic acids.

In one embodiment, the polynucleotide, modified nucleic acids, enhanced modified RNA or ribonucleic acids of the present invention can be formulated for controlled release and/or targeted delivery. As used herein, "controlled release" refers to a pharmaceutical composition or compound release profile that conforms to a particular pattern of release to effect a therapeutic outcome. In one embodiment, the polynucleotide, modified nucleic acids, enhanced modified RNA or ribonucleic acids may be encapsulated into a delivery agent described herein and/or known in the art for controlled release and/or targeted delivery. As used herein, the term "encapsulate" means to enclose, surround or encase. As it relates to the formulation of the compounds of the invention, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the invention may be enclosed, surrounded or encased within the delivery agent. "Partially encapsulation" means that less than 10, 10, 20, 30, 40 50 or less of the pharmaceutical composition or compound of the invention may be enclosed, surrounded or encased within the delivery agent. Advantageously, encapsulation may be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the invention are encapsulated in the delivery agent.

In another embodiment, the polynucleotides, modified nucleic acids, enhanced modified RNA or ribonucleic acids may be encapsulated into a lipid nanoparticle or a rapidly eliminating lipid nanoparticle and the lipid nanoparticles or a rapidly eliminating lipid nanoparticle may then be encapsulated into a polymer, hydrogel and/or surgical sealant described herein and/or known in the art. As a non-limiting example, the polymer, hydrogel or surgical sealant may be PLGA, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc Deerfield, Ill.), PEG-based sealants, and COSEAL® (Baxter International, Inc Deerfield, Ill.).

In one embodiment, the lipid nanoparticle may be encapsulated into any polymer or hydrogel known in the art which may form a gel when injected into a subject. As another non-limiting example, the lipid nanoparticle may be encapsulated into a polymer matrix which may be biodegradable.

In one embodiment, the polynucleotides, modified nucleic acids, enhanced modified RNA or ribonucleic acids formulation for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In one embodiment, the controlled release and/or targeted delivery formulation may comprise at least one degradable polyester which may contain polycationic side chains. Degradeable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In one embodiment, the modified nucleic acids, enhanced modified RNA or ribonucleic acids of the present invention may be encapsulated in a therapeutic nanoparticle. Therapeutic nanoparticles may be formulated by methods described herein and known in the art such as, but not limited to, International Pub Nos. WO2010005740, WO2010030763, WO2010005721, WO2010005723, WO2012054923, US Pub. Nos. US20110262491, US20100104645, US20100087337, US20100068285, US20110274759, US20100068286, and U.S. Pat. No. 8,206, 747; each of which is herein incorporated by reference in their entirety. In another embodiment, therapeutic polymer nanoparticles may be identified by the methods described in US Pub No. US20120140790, herein incorporated by reference in its entirety.

In one embodiment, the therapeutic nanoparticle may be formulated for sustained release. As used herein, "sustained release" refers to a pharmaceutical composition or compound that conforms to a release rate over a specific period of time. The period of time may include, but is not limited to, hours, days, weeks, months and years. As a non-limiting example, the sustained release nanoparticle may comprise a polymer and a therapeutic agent such as, but not limited to, the polynucleotides, modified nucleic acids, enhanced modified RNA or ribonucleic acids of the present invention (see International Pub No. 2010075072 and US Pub No. US20100216804 and US20110217377, each of which is herein incorporated by reference in their entirety).

In one embodiment, the therapeutic nanoparticles may be formulated to be target specific. As a non-limiting example, the therapeutic nanoparticles may include a corticosteroid (see International Pub. No. WO2011084518). In one embodiment, the therapeutic nanoparticles may be formulated to be cancer specific. As a non-limiting example, the therapeutic nanoparticles may be formulated in nanoparticles described in International Pub No. WO2008121949, WO2010005726, WO2010005725, WO2011084521 and US Pub No. US20100069426, US20120004293 and US20100104655, each of which is herein incorporated by reference in their entirety.

In one embodiment, the nanoparticles of the present invention may comprise a polymeric matrix. As a non-limiting example, the nanoparticle may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In one embodiment, the diblock copolymer may include PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In one embodiment, the therapeutic nanoparticle comprises a diblock copolymer. As a non-limiting example the therapeutic nanoparticle comprises a PLGA-PEG block copolymer (see US Pub. No. US20120004293 and U.S. Pat. No. 8,236,330, each of which is herein incorporated by reference in their entirety). In another non-limiting example, the therapeutic nanoparticle is a stealth nanoparticle comprising a diblock copolymer of PEG and PLA or PEG and PLGA (see U.S. Pat. No. 8,246,968, herein incorporated by reference in its entirety).

In one embodiment, the therapeutic nanoparticle may comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), polycyanoacrylates and combinations thereof.

In one embodiment, the therapeutic nanoparticles may comprise at least one cationic polymer described herein and/or known in the art.

In one embodiment, the therapeutic nanoparticles may comprise at least one amine-containing polymer such as, but not limited to polylysine, polyethylene imine, poly(amidoamine) dendrimers and combinations thereof.

In one embodiment, the therapeutic nanoparticles may comprise at least one degradable polyester which may contain polycationic side chains. Degradeable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In another embodiment, the therapeutic nanoparticle may include a conjugation of at least one targeting ligand.

In one embodiment, the therapeutic nanoparticle may be formulated in an aqueous solution which may be used to target cancer (see International Pub No. WO2011084513 and US Pub No. US20110294717, each of which is herein incorporated by reference in their entirety).

In one embodiment, the polynucleotides, modified nucleic acids, enhanced modified RNA or ribonucleic acids may be encapsulated in, linked to and/or associated with synthetic nanocarriers. The synthetic nanocarriers may be formulated using methods known in the art and/or described herein. As a non-limiting example, the synthetic nanocarriers may be formulated by the methods described in International Pub Nos. WO2010005740, WO2010030763 and US Pub. Nos. US20110262491, US20100104645 and US20100087337, each of which is herein incorporated by reference in their entirety. In another embodiment, the synthetic nanocarrier formulations may be lyophilized by methods described in International Pub. No. WO2011072218 and U.S. Pat. No. 8,211,473; each of which is herein incorporated by reference in their entirety.

In one embodiment, the synthetic nanocarriers may contain reactive groups to release the modified nucleic acids, enhanced modified RNA or ribonucleic acids described herein (see International Pub. No. WO20120952552 and US Pub No. US20120171229, each of which is herein incorporated by reference in their entirety).

In one embodiment, the synthetic nanocarriers may contain an immunostimulatory agent to enhance the immune response from delivery of the synthetic nanocarrier. As a non-limiting example, the synthetic nanocarrier may comprise a Th1 immunostimulatory agent which may enhance a Th1-based response of the immune system (see International Pub No. WO2010123569 and US Pub. No. US20110223201, each of which is herein incorporated by reference in its entirety).

In one embodiment, the synthetic nanocarriers may be formulated for targeted release. In one embodiment, the synthetic nanocarrier is formulated to release the polynucleotides, modified nucleic acids, enhanced modified RNA or ribonucleic acids at a specified pH and/or after a desired time interval. As a non-limiting example, the synthetic nanoparticle may be formulated to release the modified nucleic acids, enhanced modified RNA or ribonucleic acids after 24 hours and/or at a pH of 4.5 (see International Pub. Nos. WO2010138193 and WO2010138194 and US Pub Nos. US20110020388 and US20110027217, each of which is herein incorporated by reference in their entirety).

In one embodiment, the synthetic nanocarriers may be formulated for controlled and/or sustained release of the polynucleotides, modified nucleic acids, enhanced modified RNA or ribonucleic acids described herein. As a non-limiting example, the synthetic nanocarriers for sustained release may be formulated by methods known in the art, described herein and/or as described in International Pub No. WO2010138192 and US Pub No. 20100303850, each of which is herein incorporated by reference in their entirety.

In one embodiment, the synthetic nanocarrier may be formulated for use as a vaccine. In one embodiment, the synthetic nanocarrier may encapsulate at least one modified nucleic acids, enhanced modified RNA or ribonucleic acids which encodes at least one antigen. As a non-limiting example, the synthetic nanocarrier may include at least one antigen and an excipient for a vaccine dosage form (see International Pub No. WO2011150264 and US Pub No. US20110293723, each of which is herein incorporated by reference in their entirety). As another non-limiting example, a vaccine dosage form may include at least two synthetic nanocarriers with the same or different antigens and an excipient (see International Pub No. WO2011150249 and US Pub No. US20110293701, each of which is herein incorporated by reference in their entirety). The vaccine dosage form may be selected by methods described herein, known in the art and/or described in International Pub No. WO2011150258 and US Pub No. US20120027806, each of which is herein incorporated by reference in their entirety).

In one embodiment, the synthetic nanocarrier may comprise at least one polynucleotide, modified nucleic acids, enhanced modified RNA or ribonucleic acids which encodes at least one adjuvant. In another embodiment, the synthetic nanocarrier may comprise at least one modified nucleic acids, enhanced modified RNA or ribonucleic acids and an adjuvant. As a non-limiting example, the synthetic nanocarrier comprising and adjuvant may be formulated by the methods described in International Pub No. WO2011150240 and US Pub No. US20110293700, each of which is herein incorporated by reference in its entirety.

In one embodiment, the synthetic nanocarrier may encapsulate at least one polynucleotide, modified nucleic acids, enhanced modified RNA or ribonucleic acids which encodes a peptide, fragment or region from a virus. As a non-limiting example, the synthetic nanocarrier may include, but is not limited to, the nanocarriers described in International Pub No. WO2012024621, WO201202629, WO2012024632 and US Pub No. US20120064110, US20120058153 and US20120058154, each of which is herein incorporated by reference in their entirety.

Polymers, Biodegradable Nanoparticles, and Core-Shell Nanoparticles

The polynucleotides, modified nucleic acids, enhanced modified RNA or ribonucleic acids of the invention can be formulated using natural and/or synthetic polymers. Non-limiting examples of polymers which may be used for delivery include, but are not limited to, Dynamic POLYCONJUGATE™ formulations from MIRUS® Bio (Madison, Wis.) and Roche Madison (Madison, Wis.), PHASERX™ polymer formulations such as, without limitation, SMARTT POLYMER TECHNOLOGY™ (Seattle, Wash.), DMRI/DOPE, poloxamer, VAXFECTIN® adjuvant from Vical (San Diego, Calif.), chitosan, cyclodextrin from Calando Pharmaceuticals (Pasadena, Calif.), dendrimers and poly(lactic-co-glycolic acid) (PLGA) polymers, RONDEL™ (RNAi/Oligonucleotide Nanoparticle Delivery) polymers (Arrowhead Research Corporation, Pasadena, Calif.) and pH responsive co-block polymers such as, but not limited to, PHASERX™ (Seattle, Wash.).

A non-limiting example of PLGA formulations include, but are not limited to, PLGA injectable depots (e.g., ELIGARD® which is formed by dissolving PLGA in 66% N-methyl-2-pyrrolidone (NMP) and the remainder being aqueous solvent and leuprolide. Once injected, the PLGA and leuprolide peptide precipitates into the subcutaneous space).

Many of these polymer approaches have demonstrated efficacy in delivering oligonucleotides in vivo into the cell cytoplasm (reviewed in deFougerolles Hum Gene Ther. 2008 19:125-132; herein incorporated by reference in its entirety). Two polymer approaches that have yielded robust in vivo delivery of nucleic acids, in this case with small interfering RNA (siRNA), are dynamic polyconjugates and cyclodextrin-based nanoparticles. The first of these delivery approaches uses dynamic polyconjugates and has been shown in vivo in mice to effectively deliver siRNA and silence endogenous target mRNA in hepatocytes (Rozema et al., Proc Natl Acad Sci USA. 2007 104:12982-12887). This particular approach is a multicomponent polymer system whose key features include a membrane-active polymer to which nucleic acid, in this case siRNA, is covalently coupled via a disulfide bond and where both PEG (for charge masking) and N-acetylgalactosamine (for hepatocyte targeting) groups are linked via pH-sensitive bonds (Rozema et al., Proc Natl Acad Sci USA. 2007 104:12982-12887). On binding to the hepatocyte and entry into the endosome, the polymer complex disassembles in the low-pH environment, with the polymer exposing its positive charge, leading to endosomal escape and cytoplasmic release of the siRNA from the polymer. Through replacement of the N-acetylgalactosamine group with a mannose group, it was shown one could alter targeting from asialoglycoprotein receptor-expressing hepatocytes to sinusoidal endothelium and Kupffer cells. Another polymer approach involves using transferrin-targeted cyclodextrin-containing polycation nanoparticles. These nanoparticles have demonstrated targeted silencing of the EWS-FLI1 gene product in transferrin receptor-expressing Ewing's sarcoma tumor cells (Hu-Lieskovan et al., Cancer Res. 2005 65: 8984-8982) and siRNA formulated in these nanoparticles was well tolerated in non-human primates (Heidel et al., Proc Natl Acad Sci USA 2007 104: 5715-21). Both of these delivery strategies incorporate rational approaches using both targeted delivery and endosomal escape mechanisms.

The polymer formulation can permit the sustained or delayed release of polynucleotides, modified nucleic acids, enhanced modified RNA or ribonucleic acids (e.g., following intramuscular or subcutaneous injection). The altered release profile for the polynucleotides, modified nucleic acids, enhanced modified RNA or ribonucleic acids can result in, for example, translation of an encoded protein over an extended period of time. The polymer formulation may also be used to increase the stability of the polynucleotide, modified nucleic acids, enhanced modified RNA or ribonucleic acids. Biodegradable polymers have been previously used to protect nucleic acids other than modified nucleic acids, enhanced modified RNA or ribonucleic acids from degradation and been shown to result in sustained release of payloads in vivo (Rozema et al., Proc Natl Acad Sci USA. 2007 104:12982-12887; Sullivan et al., Expert Opin Drug Deliv. 2010 7:1433-1446; Convertine et al., Biomacromolecules. 2010 Oct. 1; Chu et al., Acc Chem Res. 2012 Jan. 13; Manganiello et al., Biomaterials. 2012 33:2301-2309; Benoit et al., Biomacromolecules. 2011 12:2708-2714; Singha et al., Nucleic Acid Ther. 2011 2:133-147; deFougerolles Hum Gene Ther. 2008 19:125-132; Schaffert and Wagner, Gene Ther. 2008 16:1131-1138; Chaturvedi et al., Expert Opin Drug Deliv. 2011 8:1455-1468; Davis, Mol Pharm. 2009 6:659-668; Davis, Nature 2010 464:1067-1070; herein incorporated by reference in its entirety).

In one embodiment, the pharmaceutical compositions may be sustained release formulations. In a further embodiment, the sustained release formulations may be for subcutaneous delivery. Sustained release formulations may include, but are not limited to, PLGA microspheres, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc Deerfield, Ill.), PEG-based sealants, and COSEAL® (Baxter International, Inc Deerfield, Ill.).

As a non-limiting example modified mRNA may be formulated in PLGA microspheres by preparing the PLGA microspheres with tunable release rates (e.g., days and weeks) and encapsulating the modified mRNA in the PLGA microspheres while maintaining the integrity of the modified mRNA during the encapsulation process. EVAc are non-biodegradeable, biocompatible polymers which are used extensively in pre-clinical sustained release implant applications (e.g., extended release products Ocusert a pilocarpine ophthalmic insert for glaucoma or progestasert a sustained release progesterone intrauterine device; transdermal delivery systems Testoderm, Duragesic and Selegiline; catheters). Poloxamer F-407 NF is a hydrophilic, non-ionic surfactant triblock copolymer of polyoxyethylene-polyoxypropylene-polyoxyethylene having a low viscosity at temperatures less than 5° C. and forms a solid gel at temperatures greater than 15° C. PEG-based surgical sealants comprise two synthetic PEG components mixed in a delivery device which can be prepared in one minute, seals in 3 minutes and is reabsorbed within 30 days. GELSITE® and natural polymers are capable of in-situ gelation at the site of administration. They have been shown to interact with protein and peptide therapeutic candidates through ionic interaction to provide a stabilizing effect.

Polymer formulations can also be selectively targeted through expression of different ligands as exemplified by, but not limited by, folate, transferrin, and N-acetylgalactosamine (GalNAc) (Benoit et al., Biomacromolecules. 2011 12:2708-2714; Rozema et al., Proc Natl Acad Sci USA. 2007 104:12982-12887; Davis, Mol Pharm. 2009 6:659-668; Davis, Nature 2010 464:1067-1070; each of which is herein incorporated by reference in its entirety).

The polynucleotides, modified nucleic acids, enhanced modified RNA or ribonucleic acids of the invention may be formulated with or in a polymeric compound. The polymer may include at least one polymer such as, but not limited to, polyethenes, polyethylene glycol (PEG), poly(1-lysine) (PLL), PEG grafted to PLL, cationic lipopolymer, biodegradable cationic lipopolymer, polyethyleneimine (PEI), cross-linked branched poly(alkylene imines), a polyamine derivative, a modified poloxamer, a biodegradable polymer, biodegradable block copolymer, biodegradable random copolymer, biodegradable polyester copolymer, biodegradable polyester block copolymer, biodegradable polyester block random copolymer, linear biodegradable copolymer, poly[α-(4-aminobutyl)-L-glycolic acid) (PAGA), biodegradable cross-linked cationic multi-block copolymers, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester), acrylic polymers, amine-containing polymers or combinations thereof.

As a non-limiting example, the polynucleotides, modified nucleic acids, enhanced modified RNA or ribonucleic acids of the invention may be formulated with the polymeric compound of PEG grafted with PLL as described in U.S. Pat. No. 6,177,274 herein incorporated by reference in its entirety. The formulation may be used for transfecting cells in vitro or for in vivo delivery of the modified nucleic acids, enhanced modified RNA or ribonucleic acids. In another example, the polynucleotides, modified nucleic acids, enhanced modified RNA or ribonucleic acids may be suspended in a solution or medium with a cationic polymer, in a dry pharmaceutical composition or in a solution that is capable of being dried as described in U.S. Pub. Nos. 20090042829 and 20090042825 each of which are herein incorporated by reference in their entireties.

As another non-limiting example the polynucleotides, modified nucleic acids, enhanced modified RNA or ribonucleic acids of the invention may be formulated with a PLGA-PEG block copolymer (see US Pub. No. US20120004293 and U.S. Pat. No. 8,236,330, each of which are herein incorporated by reference in their entireties). As a non-limiting example, the polynucleotides, modified nucleic acids, enhanced modified RNA or ribonucleic acids of the invention may be formulated with a diblock copolymer of PEG and PLA or PEG and PLGA (see U.S. Pat. No. 8,246,968, herein incorporated by reference in its entirety).

A polyamine derivative may be used to deliver nucleic acids or to treat and/or prevent a disease or to be included in an implantable or injectable device (U.S. Pub. No. 20100260817 herein incorporated by reference in its entirety). As a non-limiting example, a pharmaceutical composition may include the modified nucleic acids, enhanced modified RNA or ribonucleic acids and the polyamine derivative described in U.S. Pub. No. 20100260817 (the contents of which are incorporated herein by reference in its entirety).

The polynucleotides, modified nucleic acids, enhanced modified RNA or ribonucleic acids of the invention may be formulated with at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), polycyanoacrylates and combinations thereof.

In one embodiment, the polynucleotides, modified nucleic acids, enhanced modified RNA or ribonucleic acids of the present invention may be formulated with at least one polymer described in International Publication Nos. WO2011115862, WO2012082574 and WO2012068187, each of which are herein incorporated by reference in their entireties. In another embodiment, the polynucleotides, modified nucleic acids, enhanced modified RNA or ribonucleic acids of the present invention may be formulated with a polymer of formula Z as described in WO2011115862, herein incorporated by reference in its entirety. In yet another embodiment, the polynucleotides, modified nucleic acids, enhanced modified RNA or ribonucleic acids may be formulated with a polymer of formula Z, Z' or Z" as described in WO2012082574 or WO2012068187, each of which are herein incorporated by reference in their entireties. The polymers formulated with the modified RNA of the present invention may be synthesized by the methods described in WO2012082574 or WO2012068187, each of which are herein incorporated by reference in their entireties.

Formulations of polynucleotides, modified nucleic acids, enhanced modified RNA or ribonucleic acids of the invention may include at least one amine-containing polymer such as, but not limited to polylysine, polyethylene imine, poly (amidoamine) dendrimers or combinations thereof.

For example, the polynucleotides, modified nucleic acids, enhanced modified RNA or ribonucleic acids of the invention may be formulated in a pharmaceutical compound including a poly(alkylene imine), a biodegradable cationic lipopolymer, a biodegradable block copolymer, a biodegradable polymer, or a biodegradable random copolymer, a biodegradable polyester block copolymer, a biodegradable polyester polymer, a biodegradable polyester random copolymer, a linear biodegradable copolymer, PAGA, a biodegradable cross-linked cationic multi-block copolymer or combinations thereof. The biodegradable cationic lipopolymer may be made by methods known in the art and/or described in U.S. Pat. No. 6,696,038, U.S. App. Nos. 20030073619 and 20040142474 each of which is herein incorporated by reference in their entireties. The poly(alkylene imine) may be made using methods known in the art and/or as described in U.S. Pub. No. 20100004315, herein incorporated by reference in its entirety. The biodegradabale polymer, biodegradable block copolymer, the biodegradable random copolymer, biodegradable polyester block copolymer, biodegradable polyester polymer, or biodegradable polyester random copolymer may be made using methods known in the art and/or as described in U.S. Pat. Nos. 6,517,869 and 6,267,987, the contents of which are each incorporated herein by reference in its entirety. The linear biodegradable copolymer may be made using methods known in the art and/or as described in U.S. Pat. No. 6,652,886. The PAGA polymer may be made using methods known in the art and/or as described in U.S. Pat. No. 6,217,912 herein incorporated by reference in its entirety. The PAGA polymer may be copolymerized to form a copolymer or block copolymer with polymers such as but not limited to, poly-L-lysine, polyargine, polyornithine, histones, avidin, protamines, polylactides and poly(lactide-coglycolides). The biodegradable cross-linked cationic multiblock copolymers may be made my methods known in the art and/or as described in U.S. Pat. No. 8,057,821 or U.S. Pub. No. 2012009145 each of which are herein incorporated by reference in their entireties. For example, the multi-block copolymers may be synthesized using linear polyethyleneimine (LPEI) blocks which have distinct patterns as compared to branched polyethyleneimines. Further, the composition or pharmaceutical composition may be made by the methods known in the art, described herein, or as described in U.S. Pub. No. 20100004315 or U.S. Pat. Nos. 6,267,987 and 6,217,912 each of which are herein incorporated by reference in their entireties.

The polynucleotides, modified nucleic acids, enhanced modified RNA or ribonucleic acids of the invention may be formulated with at least one degradable polyester which may contain polycationic side chains. Degradeable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In one embodiment, the polymers described herein may be conjugated to a lipid-terminating PEG. As a non-limiting example, PLGA may be conjugated to a lipid-terminating PEG forming PLGA-DSPE-PEG. As another non-limiting example, PEG conjugates for use with the present invention are described in International Publication No. WO2008103276, herein incorporated by reference in its entirety.

In one embodiment, the polynucleotides, modified RNA described herein may be conjugated with another compound. Non-limiting examples of conjugates are described in U.S. Pat. Nos. 7,964,578 and 7,833,992, each of which are herein incorporated by reference in their entireties. In another embodiment, modified RNA of the present invention may be conjugated with conjugates of formula 1-122 as described in U.S. Pat. Nos. 7,964,578 and 7,833,992, each of which are herein incorporated by reference in their entireties.

As described in U.S. Pub. No. 20100004313, herein incorporated by reference in its entirety, a gene delivery composition may include a nucleotide sequence and a poloxamer. For example, the polynucleotide, modified nucleic acids, enhanced modified RNA or ribonucleic acids of the present invention may be used in a gene delivery composition with the poloxamer described in U.S. Pub. No. 20100004313.

In one embodiment, the polymer formulation of the present invention may be stabilized by contacting the polymer formulation, which may include a cationic carrier, with a cationic lipopolymer which may be covalently linked to cholesterol and polyethylene glycol groups. The polymer formulation may be contacted with a cationic lipopolymer using the methods described in U.S. Pub. No. 20090042829 herein incorporated by reference in its entirety. The cationic carrier may include, but is not limited to, polyethylenimine, poly(trimethylenimine), poly(tetramethylenimine), polypropylenimine, aminoglycoside-polyamine, dideoxy-diamino-b-cyclodextrin, spermine, spermidine, poly(2-dimethylamino)ethyl methacrylate, poly(lysine), poly(histidine), poly(arginine), cationized gelatin, dendrimers, chitosan, 1,2-Dioleoyl-3-Trimethylammonium-Propane (DOTAP), N-[1-(2,3-dioleoyloxy)propyl]-N,N,N-trimethylammonium chloride (DOTMA), 1-[2-(oleoyloxy)ethyl]-2-oleyl-3-(2-hydroxyethyl)imidazolinium chloride (DOTIM), 2,3-dioleyloxy-N-[2(sperminecarboxamido)ethyl]-N,N-dimethyl-1-propanaminium trifluoroacetate (DOSPA), 3B—[N—(N',N'-Dimethyl aminoethane)-carbamoyl]Cholesterol Hydrochloride (DC-Cholesterol HCl) diheptadecylamidoglycyl spermidine (DOGS), N,N-distearyl-N,N-dimethyl-ammonium bromide (DDAB), N-(1,2-dimyristyloxyprop-3-yl)-N,N-dimethyl-N-hydroxyethyl ammonium bromide (DMRIE), N,N-dioleyl-N,N-dimethylammonium chloride DODAC) and combinations thereof.

The polynucleotides, modified nucleic acids, enhanced modified RNA or ribonucleic acids of the invention can also be formulated as a nanoparticle using a combination of polymers, lipids, and/or other biodegradable agents, such as, but not limited to, calcium phosphate. Components may be combined in a core-shell, hybrid, and/or layer-by-layer architecture, to allow for fine-tuning of the nanoparticle so to deliver the modified nucleic acids, enhanced modified RNA or ribonucleic acids may be enhanced (Wang et al., Nat Mater. 2006 5:791-796; Fuller et al., Biomaterials. 2008 29:1526-1532; DeKoker et al., Adv Drug Deliv Rev. 2011 63:748-761; Endres et al., Biomaterials. 2011 32:7721-7731; Su et al., Mol Pharm. 2011 Jun. 6; 8(3):774-87; herein incorporated by reference in its entirety).

Biodegradable calcium phosphate nanoparticles in combination with lipids and/or polymers have been shown to deliver polynucleotides, modified nucleic acids, enhanced modified RNA or ribonucleic acids in vivo. In one embodiment, a lipid coated calcium phosphate nanoparticle, which may also contain a targeting ligand such as anisamide, may be used to deliver the polynucleotides, modified nucleic acids, enhanced modified RNA or ribonucleic acids of the present invention. For example, to effectively deliver siRNA in a mouse metastatic lung model a lipid coated calcium phosphate nanoparticle was used (Li et al., J Contr Rel. 2010 142: 416-421; Li et al., J Contr Rel. 2012 158:108-114; Yang et al., Mol Ther. 2012 20:609-615). This delivery system combines both a targeted nanoparticle and a component to enhance the endosomal escape, calcium phosphate, in order to improve delivery of the siRNA.

In one embodiment, calcium phosphate with a PEG-polyanion block copolymer may be used to deliver polynucleotides, modified nucleic acids, enhanced modified RNA or ribonucleic acids (Kazikawa et al., J Contr Rel. 2004 97:345-356; Kazikawa et al., J Contr Rel. 2006 111: 368-370).

In one embodiment, a PEG-charge-conversional polymer (Pitella et al., Biomaterials. 2011 32:3106-3114) may be used to form a nanoparticle to deliver the polynucleotides, modified nucleic acids, enhanced modified RNA or ribonucleic acids of the present invention. The PEG-charge-conversional polymer may improve upon the PEG-polyanion block copolymers by being cleaved into a polycation at acidic pH, thus enhancing endosomal escape.

The use of core-shell nanoparticles has additionally focused on a high-throughput approach to synthesize cationic cross-linked nanogel cores and various shells (Siegwart et al., Proc Natl Acad Sci USA. 2011 108:12996-13001). The complexation, delivery, and internalization of the polymeric nanoparticles can be precisely controlled by altering the chemical composition in both the core and shell components of the nanoparticle. For example, the core-shell nanoparticles may efficiently deliver siRNA to mouse hepatocytes after they covalently attach cholesterol to the nanoparticle.

In one embodiment, a hollow lipid core comprising a middle PLGA layer and an outer neutral lipid layer containing PEG may be used to delivery of the polynucleotide, modified nucleic acids, enhanced modified RNA or ribonucleic acids of the present invention. As a non-limiting example, in mice bearing a luciferase-expressing tumor, it was determined that the lipid-polymer-lipid hybrid nanoparticle significantly suppressed luciferase expression, as compared to a conventional lipoplex (Shi et al, Angew Chem Int Ed. 2011 50:7027-7031).

Peptides and Proteins

The polynucleotides, modified nucleic acids, enhanced modified RNA or ribonucleic acids of the invention can be formulated with peptides and/or proteins in order to increase transfection of cells by the modified nucleic acids, enhanced modified RNA or ribonucleic acids. In one embodiment, peptides such as, but not limited to, cell penetrating peptides and proteins and peptides that enable intracellular delivery may be used to deliver pharmaceutical formulations. A non-limiting example of a cell penetrating peptide which may be used with the pharmaceutical formulations of the present invention includes a cell-penetrating peptide sequence attached to polycations that facilitates delivery to the intracellular space, e.g., HIV-derived TAT peptide, penetratins, transportans, or hCT derived cell-penetrating peptides (see, e.g., Caron et al., Mol. Ther. 3(3):310-8 (2001); Langel, Cell-Penetrating Peptides: Processes and Applications (CRC Press, Boca Raton Fla., 2002); El-Andaloussi et al., Curr. Pharm. Des. 11(28):3597-611 (2003); and Deshayes et al., Cell. Mol. Life Sci. 62(16):1839-49 (2005), all of which are incorporated herein by reference). The compositions can also be formulated to include a cell penetrating agent, e.g., liposomes, which enhance delivery of the compositions to the intracellular space. Modified nucleic acids, enhanced modified RNA or ribonucleic acids of the invention may be complexed to peptides and/or proteins such as, but not limited to, peptides and/or proteins from Aileron Therapeutics (Cambridge, Mass.) and Permeon Biologics (Cambridge, Mass.) in order to enable intracellular delivery (Cronican et al., ACS Chem. Biol. 2010 5:747-752; McNaughton et al., Proc. Natl. Acad. Sci. USA 2009 106:6111-6116; Sawyer, Chem Biol Drug Des. 2009 73:3-6; Verdine and Hilinski, Methods Enzymol. 2012; 503:3-33; all of which are herein incorporated by reference in its entirety).

In one embodiment, the cell-penetrating polypeptide may comprise a first domain and a second domain. The first domain may comprise a supercharged polypeptide. The second domain may comprise a protein-binding partner. As used herein, "protein-binding partner" includes, but are not limited to, antibodies and functional fragments thereof, scaffold proteins, or peptides. The cell-penetrating polypeptide may further comprise an intracellular binding partner for the protein-binding partner. The cell-penetrating polypeptide may be capable of being secreted from a cell where the modified nucleic acids, enhanced modified RNA or ribonucleic acids may be introduced.

Formulations of the including peptides or proteins may be used to increase cell transfection by the polynucleotides, modified nucleic acids, enhanced modified RNA or ribonucleic acids, alter the biodistribution of the polynucleotides, modified nucleic acids, enhanced modified RNA or ribonucleic acids (e.g., by targeting specific tissues or cell types), and/or increase the translation of encoded protein.

Cells

The polynucleotides, modified nucleic acids, enhanced modified RNA or ribonucleic acids of the invention can be transfected ex vivo into cells, which are subsequently transplanted into a subject. As non-limiting examples, the pharmaceutical compositions may include red blood cells to deliver modified RNA to liver and myeloid cells, virosomes to deliver modified RNA in virus-like particles (VLPs), and electroporated cells such as, but not limited to, from MAXCYTE® (Gaithersburg, Md.) and from ERYTECH® (Lyon, France) to deliver modified RNA. Examples of use of red blood cells, viral particles and electroporated cells to deliver payloads other than polynucleotides, modified nucleic acids, enhanced modified RNA or ribonucleic acids have been documented (Godfrin et al., Expert Opin Biol Ther. 2012 12:127-133; Fang et al., Expert Opin Biol Ther. 2012 12:385-389; Hu et al., Proc Natl Acad Sci USA. 2011 108:10980-10985; Lund et al., Pharm Res. 2010 27:400-420; Huckriede et al., J Liposome Res. 2007; 17:39-47; Cusi, Hum Vaccin. 2006 2:1-7; de Jonge et al., Gene Ther. 2006 13:400-411; all of which are herein incorporated by reference in its entirety). The modified RNA may be delivered in synthetic VLPs synthesized by the methods described in International Pub No. WO2011085231 and US Pub No. 20110171248, each of which are herein incorporated by reference in their entireties.

Cell-based formulations of the polynucleotides, modified nucleic acids, enhanced modified RNA or ribonucleic acids of the invention may be used to ensure cell transfection (e.g., in the cellular carrier), alter the biodistribution of the modified nucleic acids, enhanced modified RNA or ribonucleic acids (e.g., by targeting the cell carrier to specific tissues or cell types), and/or increase the translation of encoded protein.

Introduction into Cells

A variety of methods are known in the art and suitable for introduction of nucleic acid into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion.

The technique of sonoporaiton, or cellular sonication, is the use of sound (e.g., ultrasonic frequencies) for modifying the permeability of the cell plasma membrane. Sonoporation methods are known to those in the art and are taught for example as it relates to bacteria in US Patent Publication 20100196983 and as it relates to other cell types in, for example, US Patent Publication 20100009424, each of which are incorporated herein by reference in their entirety.

Electroporation techniques are also well known in the art. In one embodiment, modified nucleic acids, enhanced modified RNA or ribonucleic acids may be delivered by electroporation as described in Example 11.

Hyaluronidase

The intramuscular or subcutaneous localized injection of polynucleotides, modified nucleic acids, enhanced modified RNA or ribonucleic acids of the invention can include hyaluronidase, which catalyzes the hydrolysis of hyaluronan. By catalyzing the hydrolysis of hyaluronan, a constituent of the interstitial barrier, hyaluronidase lowers the viscosity of hyaluronan, thereby increasing tissue permeability (Frost, Expert Opin. Drug Deliv. (2007) 4:427-440; herein incorporated by reference in its entirety). It is useful to speed their dispersion and systemic distribution of encoded proteins produced by transfected cells. Alternatively, the hyaluronidase can be used to increase the number of cells exposed to a modified nucleic acids, enhanced modified RNA or ribonucleic acids of the invention administered intramuscularly or subcutaneously.

Nanoparticle Mimics

The polynucleotides, modified nucleic acids, enhanced modified RNA or ribonucleic acids of the invention may be encapsulated within and/or absorbed to a nanoparticle mimic. A nanoparticle mimic can mimic the delivery function organisms or particles such as, but not limited to, pathogens, viruses, bacteria, fungus, parasites, prions and cells. As a non-limiting example the polynucleotides, modified nucleic acids, enhanced modified RNA or ribonucleic acids of the invention may be encapsulated in a non-viron particle which can mimic the delivery function of a virus (see International Pub. No. WO2012006376 herein incorporated by reference in its entirety).

Nanotubes

The polynucleotides, modified nucleic acids, enhanced modified RNA or ribonucleic acids of the invention can be attached or otherwise bound to at least one nanotube such as, but not limited to, rosette nanotubes, rosette nanotubes having twin bases with a linker, carbon nanotubes and/or single-walled carbon nanotubes, The polynucleotides, modified nucleic acids, enhanced modified RNA or ribonucleic acids may be bound to the nanotubes through forces such as, but not limited to, steric, ionic, covalent and/or other forces.

In one embodiment, the nanotube can release one or more polynucleotides, modified nucleic acids, enhanced modified RNA or ribonucleic acids into cells. The size and/or the surface structure of at least one nanotube may be altered so as to govern the interaction of the nanotubes within the body and/or to attach or bind to the polynucleotides, modified nucleic acids, enhanced modified RNA or ribonucleic acids disclosed herein. In one embodiment, the building block and/or the functional groups attached to the building block of the at least one nanotube may be altered to adjust the dimensions and/or properties of the nanotube. As a non-limiting example, the length of the nanotubes may be altered to hinder the nanotubes from passing through the holes in the walls of normal blood vessels but still small enough to pass through the larger holes in the blood vessels of tumor tissue.

In one embodiment, at least one nanotube may also be coated with delivery enhancing compounds including polymers, such as, but not limited to, polyethylene glycol. In another embodiment, at least one nanotube and/or the modified mRNA may be mixed with pharmaceutically acceptable excipients and/or delivery vehicles.

In one embodiment, the polynucleotides or modified mRNA are attached and/or otherwise bound to at least one rosette nanotube. The rosette nanotubes may be formed by a process known in the art and/or by the process described in International Publication No. WO2012094304, herein incorporated by reference in its entirety. At least one modified mRNA may be attached and/or otherwise bound to at least one rosette nanotube by a process as described in International Publication No. WO2012094304, herein incorporated by reference in its entirety, where rosette nanotubes or modules forming rosette nanotubes are mixed in aqueous media with at least one modified mRNA under conditions which may cause at least one modified mRNA to attach or otherwise bind to the rosette nanotubes.

Conjugates

The polynucleotides, modified nucleic acids, enhanced modified RNA or ribonucleic acids of the invention include conjugates, such as a modified nucleic acids, enhanced modified RNA or ribonucleic acids covalently linked to a carrier or targeting group, or including two encoding regions that together produce a fusion protein (e.g., bearing a targeting group and therapeutic protein or peptide).

The conjugates of the invention include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Representative U.S. patents that teach the preparation of polynucleotide conjugates, particularly to RNA, include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; each of which is herein incorporated by reference in their entireties.

In one embodiment, the conjugate of the present invention may function as a carrier for the polynucleotide, modified nucleic acids, enhanced modified RNA or ribonucleic acids of the present invention. The conjugate may comprise a cationic polymer such as, but not limited to, polyamine, polylysine, polyalkylenimine, and polyethylenimine which may be grafted to with poly(ethylene glycol). As a non-limiting example, the conjugate may be similar to the polymeric conjugate and the method of synthesizing the polymeric conjugate described in U.S. Pat. No. 6,586,524 herein incorporated by reference in its entirety.

The conjugates can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Targeting groups may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, or an activator of p38 MAP kinase.

The targeting group can be any ligand that is capable of targeting a specific receptor. Examples include, without limitation, folate, GalNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein.

In one embodiment, pharmaceutical compositions of the present invention may include chemical modifications such as, but not limited to, modifications similar to locked nucleic acids.

Representative U.S. Patents that teach the preparation of locked nucleic acid (LNA) such as those from Santaris, include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include modified nucleic acids, enhanced modified RNA or ribonucleic acids with phosphorothioate backbones and oligonucleosides with other modified backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$—[wherein the native phosphodiester backbone is represented as —O—P(O)$_2$—O—$CH_2$—] of the above-referenced U.S. Pat. No. 5,489,677, and the amide backbones of the above-referenced U.S. Pat. No. 5,602,240. In some embodiments, the polynucletotides featured herein have morpholino backbone structures of the above-referenced U.S. Pat. No. 5,034,506.

Modifications at the 2' position may also aid in delivery. Preferably, modifications at the 2' position are not located in a polypeptide-coding sequence, i.e., not in a translatable region. Modifications at the 2' position may be located in a 5'UTR, a 3'UTR and/or a tailing region. Modifications at the 2' position can include one of the following at the 2' position: H (i.e., 2'-deoxy); F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$)$_n$OCH$_3$, O($CH_2$)$_n$NH$_2$, O($CH_2$)$_n$CH$_3$, O($CH_2$)$_n$ONH$_2$, and O($CH_2$)$_n$ON[($CH_2$)$_n$CH$_3$)]$_2$, where n and m are from 1 to about 10. In other embodiments, the modified nucleic acids, enhanced modified RNA or ribonucleic acids include one of the following at the 2' position: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties, or a group for improving the pharmacodynamic properties, and other substituents having similar properties. In some embodiments, the modification includes a 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH$_2$)$_2$ON(CH$_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$, also described in examples herein below. Other modifications include 2'-methoxy (2'-OCH$_3$), 2'-aminopropoxy (2'-OCH$_2$CH$_2$NH$_2$) and 2'-fluoro (2'-F). Similar modifications may also be made at other positions, particularly the 3' position of the sugar on the 3' terminal nucleotide or in 2'-5' linked dsRNAs and the 5' position of 5' terminal nucleotide. Polynucleotides of the invention may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920 and each of which is herein incorporated by reference.

In still other embodiments, the polynucleotides, modified nucleic acids, enhanced modified RNA or ribonucleic acids is covalently conjugated to a cell penetrating polypeptide. The cell-penetrating peptide may also include a signal sequence. The conjugates of the invention can be designed to have increased stability; increased cell transfection; and/or altered the biodistribution (e.g., targeted to specific tissues or cell types).

Self-Assembled Nucleic Acid Nanoparticles

Self-assembled nanoparticles have a well-defined size which may be precisely controlled as the nucleic acid strands may be easily reprogrammable. For example, the optimal particle size for a cancer-targeting nanodelivery carrier is 20-100 nm as a diameter greater than 20 nm avoids renal clearance and enhances delivery to certain tumors through enhanced permeability and retention effect. Using self-assembled nucleic acid nanoparticles a single uniform population in size and shape having a precisely controlled spatial orientation and density of cancer-targeting ligands for enhanced delivery. As a non-limiting example, oligonucleotide nanoparticles were prepared using programmable self-assembly of short DNA fragments and therapeutic siRNAs. These nanoparticles are molecularly identical with controllable particle size and target ligand location and density. The DNA fragments and siRNAs self-assembled into a one-step reaction to generate DNA/siRNA tetrahedral nanoparticles for targeted in vivo delivery. (Lee et al., Nature Nanotechnology 2012 7:389-393).

Excipients

Pharmaceutical formulations may additionally comprise a pharmaceutically acceptable excipient, which, as used herein, includes, but are not limited to, any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Various excipients for formulating pharmaceutical compositions and techniques for preparing the composition are known in the art (see *Remington: The Science and Practice of Pharmacy*, 21$^{st}$ Edition, A. R. Gennaro, Lippincott, Williams & Wilkins, Baltimore, Md., 2006; incorporated herein by reference). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

In some embodiments, a pharmaceutically acceptable excipient may be at least 95%, at least 96%, at least 97%, at least 98%, at least 99%, or 100% pure. In some embodiments, an excipient may be approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. The composition may also include excipients such as cocoa butter and suppository waxes, coloring agents, coating agents, sweetening, flavoring, and/or perfuming agents.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM®[magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN®20], polyoxyethylene sorbitan [TWEEN®60], polyoxyethylene sorbitan monooleate [TWEEN®80], sorbitan monopalmitate [SPAN®40], sorbitan monostearate [Span®60], sorbitan tristearate [Span®65], glyceryl monooleate, sorbitan monooleate [SPAN®80]), polyoxyethylene esters (e.g. polyoxyethylene monostearate [MYRJ®45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ®30]), poly (vinyl-pyrrolidone), diethylene glycol monolaurate, triethanolamine oleate, sodium oleate, potassium oleate, ethyl oleate, oleic acid, ethyl laurate, sodium lauryl sulfate, PLUORINC® F 68, POLOXAMER®188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethyl cellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL®115, GERMABEN® II, NEOLONE™, KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Excipients such as cocoa butter and suppository waxes, coloring agents, coating agents, sweetening, flavoring, and/or perfuming agents can be present in the composition, according to the judgment of the formulator.

Delivery

The present disclosure encompasses the delivery of polynucleotides, modified nucleic acids, enhanced modified RNA or ribonucleic acids for any of therapeutic, pharmaceutical, diagnostic or imaging by any appropriate route taking into consideration likely advances in the sciences of drug delivery. Delivery may be naked or formulated.

Naked Delivery

The polynucleotides, modified nucleic acids, enhanced modified RNA or ribonucleic acids of the present invention may be delivered to a cell naked. As used herein in, "naked" refers to delivering polynucleotides, modified nucleic acids, enhanced modified RNA or ribonucleic acids free from agents which promote transfection. For example, the polynucleotides, modified nucleic acids, enhanced modified RNA or ribonucleic acids delivered to the cell may contain no modifications. The naked polynucleotides, modified nucleic acids, enhanced modified RNA or ribonucleic acids may be delivered to the cell using routes of administration known in the art and described herein.

Formulated Delivery

The polynucleotides, modified nucleic acids, enhanced modified RNA or ribonucleic acids of the present invention may be formulated, using the methods described herein. The formulations may contain polynucleotides, modified nucleic acids, enhanced modified RNA or ribonucleic acids which may be modified and/or unmodified. The formulations may further include, but are not limited to, cell penetration agents, a pharmaceutically acceptable carrier, a delivery agent, a bioerodible or biocompatible polymer, a solvent, and a sustained-release delivery depot. The formulated polynucleotides, modified nucleic acids or enhanced modified nucleic acids may be delivered to the cell using routes of administration known in the art and described herein.

The compositions may also be formulated for direct delivery to an organ or tissue in any of several ways in the art including, but not limited to, direct soaking or bathing, via a catheter, by gels, powder, ointments, creams, gels, lotions, and/or drops, by using substrates such as fabric or biodegradable materials coated or impregnated with the compositions, and the like.

In certain embodiments, the formulations include one or more cell penetration agents, e.g., transfection agents. In one specific embodiment, a ribonucleic acid is mixed or admixed with a transfection agent (or mixture thereof) and the resulting mixture is employed to transfect cells. Preferred transfection agents are cationic lipid compositions, particularly monovalent and polyvalent cationic lipid compositions, more particularly "LIPOFECTIN," "LIPOFECTACE," "LIPOFECTAMINE," "CELLFECTIN," DMRIE-C, DMRIE, DOTAP, DOSPA, and DOSPER, and dendrimer compositions, particularly G5-G10 dendrimers, including dense star dendrimers, PAMAM dendrimers, grafted dendrimers, and dendrimers known as dendrigrafts and "SUPERFECT." In a second specific transfection method, a ribonucleic acid is conjugated to a nucleic acid-binding group, for example a polyamine and more particularly a spermine, which is then introduced into the cell or admixed with a transfection agent (or mixture thereof) and the resulting mixture is employed to transfect cells. In a third specific embodiment, a mixture of one or more transfection-enhancing peptides, proteins, or protein fragments, including fusagenic peptides or proteins, transport or trafficking peptides or proteins, receptor-ligand peptides or proteins, or nuclear localization peptides or proteins and/or their modified analogs (e.g., spermine modified peptides or proteins) or combinations thereof are mixed with and complexed with a ribonucleic acid to be introduced into a cell, optionally being admixed with transfection agent and the resulting mixture is employed to transfect cells. Further, a component of a transfection agent (e.g., lipids, cationic lipids or dendrimers) is covalently conjugated to selected peptides, proteins, or protein fragments directly or via a linking or spacer group. Of particular interest in this embodiment are peptides or proteins that are fusagenic, membrane-permeabilizing, transport or trafficking, or which function for cell-targeting. The peptide- or protein-transfection agent complex is combined with a ribonucleic acid and employed for transfection.

In certain embodiments, the formulations include a pharmaceutically acceptable carrier that causes the effective amount of polynucleotide, modified nucleic acid, or ribonucleic acid to be substantially retained in a target tissue containing the cell.

Administration

The polynucleotides, modified nucleic acids, enhanced modified RNA or ribonucleic acids of the present invention may be administered by any route which results in a therapeutically effective outcome. These include, but are not limited to enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops.

In one embodiment, provided are compositions for generation of an in vivo depot containing a polynucleotide, modified nucleic acid or engineered ribonucleotide. For example, the composition contains a bioerodible, biocompatible polymer, a solvent present in an amount effective to plasticize the polymer and form a gel therewith, and a polynucleotide, modified nucleic acid or engineered ribonucleic acid. In certain embodiments the composition also includes a cell penetration agent as described herein. In other embodiments, the composition also contains a thixotropic amount of a thixotropic agent mixable with the polymer so as to be effective to form a thixotropic composition. Further compositions include a stabilizing agent, a bulking agent, a chelating agent, or a buffering agent.

In other embodiments, provided are sustained-release delivery depots, such as for administration of a polynucleotide, modified nucleic acid, or engineered ribonucleic acid an environment (meaning an organ or tissue site) in a patient. Such depots generally contain an engineered ribonucleic acid and a flexible chain polymer where both the engineered ribonucleic acid and the flexible chain polymer are entrapped within a porous matrix of a crosslinked matrix protein. Usually, the pore size is less than 1 mm, such as 900 nm, 800 nm, 700 nm, 600 nm, 500 nm, 400 nm, 300 nm, 200 nm, 100 nm, or less than 100 nm. Usually the flexible chain polymer is hydrophilic. Usually the flexible chain polymer has a molecular weight of at least 50 kDa, such as 75 kDa, 100 kDa, 150 kDa, 200 kDa, 250 kDa, 300 kDa, 400 kDa, 500 kDa, or greater than 500 kDa. Usually the flexible chain polymer has a persistence length of less than 10%, such as 9, 8, 7, 6, 5, 4, 3, 2, 1 or less than 1% of the persistence length of the matrix protein. Usually the flexible chain polymer has a charge similar to that of the matrix protein. In some embodiments, the flexible chain polymer alters the effective pore size of a matrix of crosslinked matrix protein to a size capable of sustaining the diffusion of the engineered ribonucleic acid from the matrix into a surrounding tissue comprising a cell into which the polynucleotide, modified nucleic acid, engineered ribonucleic acid is capable of entering.

In specific embodiments, compositions may be administered in a way which allows them cross the blood-brain barrier, vascular barrier, or other epithelial barrier. Non-limiting routes of administration for the polynucleotides, modified nucleic acids, enhanced modified RNA or ribonucleic acids of the present invention are described below.

The present invention provides methods comprising administering polynucleotides, modified mRNAs and their encoded proteins or complexes in accordance with the invention to a subject in need thereof. Nucleic acids, proteins or complexes, or pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like. Compositions in accordance with the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective, prophylactially effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Parenteral and Injectable Administration

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are prepared by entrapping the drug in liposomes or microemulsions which are compatible with body tissues.

Rectal and Vaginal Administration

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Oral Administration

Solid dosage forms for oral administration include capsules, tablets, pills, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g. carboxymethylcellulose, alginates, gelatin, polyvinylpyrrolidinone, sucrose, and acacia), humectants (e.g. glycerol), disintegrating agents (e.g. agar, calcium carbonate, potato or tapioca starch, alginic acid, certain silicates, and sodium carbonate), solution retarding agents (e.g. paraffin), absorption accelerators (e.g. quaternary ammonium compounds), wetting agents (e.g. cetyl alcohol and glycerol monostearate), absorbents (e.g. kaolin and bentonite clay), and lubricants (e.g. talc, calcium stearate, magnesium stearate, solid polyethylene glycols, sodium lauryl sulfate), and mixtures thereof. In the case of capsules, tablets and pills, the dosage form may comprise buffering agents.

Topical or Transdermal Administration

As described herein, compositions containing the polynucleotides, modified nucleic acids, enhanced modified RNA or ribonucleic acids of the invention may be formulated for administration topically. The skin may be an ideal target site for delivery as it is readily accessible. Gene expression may be restricted not only to the skin, potentially avoiding nonspecific toxicity, but also to specific layers and cell types within the skin.

The site of cutaneous expression of the delivered compositions will depend on the route of nucleic acid delivery. Three routes are commonly considered to deliver polynucleotides, modified nucleic acids, enhanced modified RNA or ribonucleic acids to the skin: (i) topical application (e.g. for local/regional treatment); (ii) intradermal injection (e.g. for local/regional treatment); and (iii) systemic delivery (e.g. for treatment of dermatologic diseases that affect both cutaneous and extracutaneous regions). Polynucleotides, modified nucleic acids, enhanced modified RNA or ribonucleic acids can be delivered to the skin by several different approaches known in the art. Most topical delivery approaches have been shown to work for delivery of DNA, such as but not limited to, topical application of non-cationic liposome-DNA complex, cationic liposome-DNA complex, particle-mediated (gene gun), puncture-mediated gene transfections, and viral delivery approaches. After delivery of the nucleic acid, gene products have been detected in a number of different skin cell types, including, but not limited to, basal keratinocytes, sebaceous gland cells, dermal fibroblasts and dermal macrophages.

In one embodiment, the invention provides for a variety of dressings (e.g., wound dressings) or bandages (e.g., adhesive bandages) for conveniently and/or effectively carrying out methods of the present invention. Typically dressing or bandages may comprise sufficient amounts of pharmaceutical compositions and/or polynucleotides, modified nucleic acids, enhanced modified RNA or ribonucleic acids described herein to allow a user to perform multiple treatments of a subject(s).

In one embodiment, the invention provides for the polynucleotides, modified nucleic acids, enhanced modified RNA or ribonucleic acids compositions to be delivered in more than one injection.

In one embodiment, before topical and/or transdermal administration at least one area of tissue, such as skin, may be subjected to a device and/or solution which may increase permeability. In one embodiment, the tissue may be subjected to an abrasion device to increase the permeability of the skin (see U.S. Patent Publication No. 20080275468, herein incorporated by reference in its entirety). In another embodiment, the tissue may be subjected to an ultrasound enhancement device. An ultrasound enhancement device may include, but is not limited to, the devices described in U.S. Publication No. 20040236268 and U.S. Pat. Nos. 6,491,657 and 6,234,990; each of which are herein incorporated by reference in their entireties. Methods of enhancing the permeability of tissue are described in U.S. Publication Nos. 20040171980 and 20040236268 and U.S. Pat. No. 6,190,315; each of which are herein incorporated by reference in their entireties.

In one embodiment, a device may be used to increase permeability of tissue before delivering formulations of modified mRNA described herein. The permeability of skin may be measured by methods known in the art and/or described in U.S. Pat. No. 6,190,315, herein incorporated by reference in its entirety. As a non-limiting example, a modified mRNA formulation may be delivered by the drug delivery methods described in U.S. Pat. No. 6,190,315, herein incorporated by reference in its entirety.

In another non-limiting example tissue may be treated with a eutectic mixture of local anesthetics (EMLA) cream before, during and/or after the tissue may be subjected to a device which may increase permeability. Katz et al. (Anesth Analg (2004); 98:371-76; herein incorporated by reference in its entirety) showed that using the EMLA cream in combination with a low energy, an onset of superficial cutaneous analgesia was seen as fast as 5 minutes after a pretreatment with a low energy ultrasound.

In one embodiment, enhancers may be applied to the tissue before, during, and/or after the tissue has been treated to increase permeability. Enhancers include, but are not limited to, transport enhancers, physical enhancers, and cavitation enhancers. Non-limiting examples of enhancers are described in U.S. Pat. No. 6,190,315, herein incorporated by reference in its entirety.

In one embodiment, a device may be used to increase permeability of tissue before delivering formulations of modified mRNA described herein, which may further contain a substance that invokes an immune response. In another non-limiting example, a formulation containing a substance to invoke an immune response may be delivered by the methods described in U.S. Publication Nos. 20040171980 and 20040236268; each of which are herein incorporated by reference in their entireties.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required. Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions.

Topically-administrable formulations may, for example, comprise from about 0.1% to about 10% (w/w) active ingredient, although the concentration of active ingredient may be as high as the solubility limit of the active ingredient in the solvent. Formulations for topical administration may further comprise one or more of the additional ingredients described herein.

Depot Administration

As described herein, in some embodiments, the composition is formulated in depots for extended release. Generally, a specific organ or tissue (a "target tissue") is targeted for administration.

In some aspects of the invention, the nucleic acids (particularly ribonucleic acids encoding polypeptides) are spatially retained within or proximal to a target tissue. Provided are method of providing a composition to a target tissue of a mammalian subject by contacting the target tissue (which contains one or more target cells) with the composition under conditions such that the composition, in particular the nucleic acid component(s) of the composition, is substantially retained in the target tissue, meaning that at least 10, 20, 30, 40, 50, 60, 70, 80, 85, 90, 95, 96, 97, 98, 99, 99.9, 99.99 or greater than 99.99% of the composition is retained in the target tissue. Advantageously, retention is determined by measuring the amount of the nucleic acid present in the composition that enters one or more target cells. For example, at least 1, 5, 10, 20, 30, 40, 50, 60, 70, 80, 85, 90, 95, 96, 97, 98, 99, 99.9, 99.99 or greater than 99.99% of the nucleic acids administered to the subject are present intracellularly at a period of time following administration. For example, intramuscular injection to a mammalian subject is performed using an aqueous composition containing a ribonucleic acid and a transfection reagent, and retention of the composition is determined by measuring the amount of the ribonucleic acid present in the muscle cells.

Aspects of the invention are directed to methods of providing a composition to a target tissue of a mammalian subject, by contacting the target tissue (containing one or more target cells) with the composition under conditions such that the composition is substantially retained in the target tissue. In another embodiment, a polynucleotide, ribonucleic acid engineered to avoid an innate immune response of a cell into which the ribonucleic acid enters, where the ribonucleic acid contains a nucleotide sequence encoding a polypeptide of interest, under conditions such that the polypeptide of interest is produced in at least one target cell. The compositions generally contain a cell penetration agent, although "naked" nucleic acid (such as nucleic acids without a cell penetration agent or other agent) is also contemplated, and a pharmaceutically acceptable carrier.

In some circumstances, the amount of a protein produced by cells in a tissue is desirably increased. Preferably, this increase in protein production is spatially restricted to cells within the target tissue. Thus, provided are methods of increasing production of a protein of interest in a tissue of a mammalian subject. A composition is provided that contains a ribonucleic acid that is engineered to avoid an innate immune response of a cell into which the ribonucleic acid enters and encodes the polypeptide of interest and the composition is characterized in that a unit quantity of composition has been determined to produce the polypeptide of interest in a substantial percentage of cells contained within a predetermined volume of the target tissue.

In some embodiments, the composition includes a plurality of different ribonucleic acids, where one or more than one of the ribonucleic acids is engineered to avoid an innate immune response of a cell into which the ribonucleic acid enters, and where one or more than one of the ribonucleic acids encodes a polypeptide of interest. Optionally, the composition also contains a cell penetration agent to assist in the intracellular delivery of the ribonucleic acid. A determination is made of the dose of the composition required to produce the polypeptide of interest in a substantial percentage of cells contained within the predetermined volume of the target tissue (generally, without inducing significant production of the polypeptide of interest in tissue adjacent to the predetermined volume, or distally to the target tissue). Subsequent to this determination, the determined dose is introduced directly into the tissue of the mammalian subject.

In one embodiment, the invention provides for the polynucleotides, modified nucleic acids, enhanced modified RNA or ribonucleic acids to be delivered in more than one injection or by split dose injections.

In one embodiment, the invention may be retained near target tissue using a small disposable drug reservoir or patch pump. Non-limiting examples of patch pumps include those manufactured and/or sold by BD®, (Franklin Lakes, N.J.), Insulet Corporation (Bedford, Mass.), SteadyMed Therapeutics (San Francisco, Calif.), Medtronic (Minneapolis, Minn.), UniLife (York, Pa.), Valeritas (Bridgewater, N.J.), and SpringLeaf Therapeutics (Boston, Mass.).

Pulmonary Administration

A pharmaceutical composition may be prepared, packaged, and/or sold in a formulation suitable for pulmonary administration via the buccal cavity. Such a formulation may comprise dry particles which comprise the active ingredient and which have a diameter in the range from about 0.5 nm to about 7 nm or from about 1 nm to about 6 nm. Such compositions are suitably in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and active ingredient may constitute 0.1% to 20% (w/w) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm.

Intranasal, Nasal and Buccal Administration

Formulations described herein as being useful for pulmonary delivery are useful for intranasal delivery of a pharmaceutical composition. Another formulation suitable for intranasal administration is a coarse powder comprising the active ingredient and having an average particle from about 0.2 µm to 500 µm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein Ophthalmic Administration A pharmaceutical composition may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of any additional ingredients described herein. Other ophthalmically-administrable formulations which are useful include those which comprise the active ingredient in microcrystalline form and/or in a liposomal preparation. Ear drops and/or eye drops are contemplated as being within the scope of this invention.

Payload Administration: Detectable Agents and Therapeutic Agents

The polynucleotides, modified nucleic acids, enhanced modified RNA or ribonucleic acids described herein can be used in a number of different scenarios in which delivery of a substance (the "payload") to a biological target is desired, for example delivery of detectable substances for detection of the target, or delivery of a therapeutic agent. Detection methods can include, but are not limited to, both imaging in vitro and in vivo imaging methods, e.g., immunohistochemistry, bioluminescence imaging (BLI), Magnetic Resonance Imaging (MRI), positron emission tomography (PET), electron microscopy, X-ray computed tomography, Raman imaging, optical coherence tomography, absorption imaging, thermal imaging, fluorescence reflectance imaging, fluorescence microscopy, fluorescence molecular tomographic imaging, nuclear magnetic resonance imaging, X-ray imaging, ultrasound imaging, photoacoustic imaging, lab assays, or in any situation where tagging/staining/imaging is required.

The polynucleotides, modified nucleic acids, enhanced modified RNA or ribonucleic acids can be designed to include both a linker and a payload in any useful orientation. For example, a linker having two ends is used to attach one end to the payload and the other end to the nucleobase, such as at the C-7 or C-8 positions of the deaza-adenosine or deaza-guanosine or to the N-3 or C-5 positions of cytosine or uracil. The polynucleotide of the invention can include more than one payload (e.g., a label and a transcription inhibitor), as well as a cleavable linker.

In one embodiment, the modified nucleotide is a modified 7-deaza-adenosine triphosphate, where one end of a cleavable linker is attached to the C7 position of 7-deaza-adenine, the other end of the linker is attached to an inhibitor (e.g., to the C5 position of the nucleobase on a cytidine), and a label (e.g., Cy5) is attached to the center of the linker (see, e.g., compound 1 of A*pCp C5 Parg Capless in FIG. 5 and columns 9 and 10 of U.S. Pat. No. 7,994,304, incorporated herein by reference). Upon incorporation of the modified 7-deaza-adenosine triphosphate to an encoding region, the resulting polynucleotide having a cleavable linker attached to a label and an inhibitor (e.g., a polymerase inhibitor). Upon cleavage of the linker (e.g., with reductive conditions to reduce a linker having a cleavable disulfide moiety), the label and inhibitor are released. Additional linkers and payloads (e.g., therapeutic agents, detectable labels, and cell penetrating payloads) are described herein.

For example, the polynucleotides, modified nucleic acids, enhanced modified RNA or ribonucleic acids described herein can be used in reprogramming induced pluripotent stem cells (iPS cells), which can directly track cells that are transfected compared to total cells in the cluster. In another example, a drug that may be attached to the modified nucleic acids, enhanced modified RNA or ribonucleic acids via a linker and may be fluorescently labeled can be used to track the drug in vivo, e.g. intracellularly. Other examples include, but are not limited to, the use of polynucleotides, modified nucleic acids, enhanced modified RNA or ribonucleic acids in reversible drug delivery into cells.

The polynucleotides, modified modified nucleic acids, enhanced modified RNA or ribonucleic acids described herein can be used in intracellular targeting of a payload, e.g., detectable or therapeutic agent, to specific organelle. Exemplary intracellular targets can include, but are not limited to, the nuclear localization for advanced mRNA processing, or a nuclear localization sequence (NLS) linked to the mRNA containing an inhibitor.

In addition, the polynucleotides, modified nucleic acids, enhanced modified RNA or ribonucleic acids described herein can be used to deliver therapeutic agents to cells or tissues, e.g., in living animals. For example, the polynucleotides, modified nucleic acids, enhanced modified RNA or ribonucleic acids described herein can be used to deliver highly polar chemotherapeutics agents to kill cancer cells. The polynucleotides, modified nucleic acids, enhanced modified RNA or ribonucleic acids attached to the therapeutic agent through a linker can facilitate member permeation allowing the therapeutic agent to travel into a cell to reach an intracellular target.

In another example, the polynucleotides, modified nucleic acids, enhanced modified RNA or ribonucleic acids can be attached to the polynucleotides, modified nucleic acids, enhanced modified RNA or ribonucleic acids a viral inhibitory peptide (VIP) through a cleavable linker. The cleavable linker can release the VIP and dye into the cell. In another example, the polynucleotides, modified nucleic acids, enhanced modified RNA or ribonucleic acids can be attached through the linker to an ADP-ribosylate, which is responsible for the actions of some bacterial toxins, such as cholera toxin, diphtheria toxin, and pertussis toxin. These toxin proteins are ADP-ribosyltransferases that modify target proteins in human cells. For example, cholera toxin ADP-ribosylates G proteins modifies human cells by causing massive fluid secretion from the lining of the small intestine, which results in life-threatening diarrhea.

In some embodiments, the payload may be a therapeutic agent such as a cytotoxin, radioactive ion, chemotherapeutic, or other therapeutic agent. A cytotoxin or cytotoxic agent includes any agent that may be detrimental to cells. Examples include, but are not limited to, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020 incorporated herein in its entirety), rachelmycin (CC-1065, see U.S. Pat. Nos. 5,475,092, 5,585,499, and 5,846,545, all of which are incorporated herein by reference), and analogs or homologs thereof. Radioactive ions include, but are not limited to iodine (e.g., iodine 125 or iodine 131), strontium 89, phosphorous, palladium, cesium, iridium, phosphate, cobalt, yttrium 90, samarium 153, and praseodymium. Other therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, rachelmycin (CC-1065), melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In some embodiments, the payload may be a detectable agent, such as various organic small molecules, inorganic compounds, nanoparticles, enzymes or enzyme substrates, fluorescent materials, luminescent materials (e.g., luminol), bioluminescent materials (e.g., luciferase, luciferin, and aequorin), chemiluminescent materials, radioactive materials (e.g., $^{18}$F, $^{67}$Ga, $^{81m}$Kr, $^{82}$Rb, $^{111}$In, $^{123}$I, $^{133}$Xe, $^{201}$Tl, $^{125}$I, $^{35}$S, $^{14}$C, $^{3}$H, or $^{99m}$Tc (e.g., as pertechnetate (technetate (VII), TcO$_4^-$)), and contrast agents (e.g., gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons). Such optically-detectable labels include for example, without limitation, 4-acetamido-4'-isothiocyanatostilbene-2,2'disulfonic acid; acridine and derivatives (e.g., acridine and acridine isothiocyanate); 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives (e.g., coumarin, 7-amino-4-methylcoumarin (AMC, Coumarin 120), and 7-amino-4-trifluoromethylcoumarin (Coumarin 151)); cyanine dyes; cyanosine; 4',6-diaminidino-2-phenylindole (DAPI); 5' 5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]-naphthalene-1-sulfonyl chloride (DNS, dansylchloride); 4-dimethylaminophenylazophenyl-4'-isothiocyanate (DABITC); eosin and derivatives (e.g., eosin and eosin isothiocyanate); erythrosin and derivatives (e.g., erythrosin B and erythrosin isothiocyanate); ethidium; fluorescein and derivatives (e.g., 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, X-rhodamine-5-(and-6)-isothiocyanate (QFITC or XRITC), and fluorescamine); 2-[2-[3-[[1,3-dihydro-1,1-dimethyl-3-(3-sulfopropyl)-2H-benz[e]indol-2-ylidene]ethylidene]-2-[4-(ethoxycarbonyl)-

1-piperazinyl]-1-cyclopenten-1-yl]ethenyl]-1,1-dimethyl-3-(3-sulforpropyl)-1H-benz[e]indolium hydroxide, inner salt, compound with n,n-diethylethanamine (1:1) (IR144); 5-chloro-2-[2-[3-[(5-chloro-3-ethyl-2(3H)-benzothiazol-ylidene)ethylidene]-2-(diphenylamino)-1-cyclopenten-1-yl] ethenyl]-3-ethyl benzothiazolium perchlorate (IR140); Malachite Green isothiocyanate; 4-methylumbelliferone orthocresolphthalein; nitrotyrosine; pararosaniline; Phenol Red; B-phycoerythrin; o-phthaldialdehyde; pyrene and derivatives (e.g., pyrene, pyrene butyrate, and succinimidyl 1-pyrene); butyrate quantum dots; Reactive Red 4 (Ciba-cron™ Brilliant Red 3B-A); rhodamine and derivatives (e.g., 6-carboxy-X-rhodamine (ROX), 6-carboxyrhodamine (R6G), lissamine rhodamine B sulfonyl chloride rhodarnine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'tetramethyl-6-carboxyrhodamine (TAMRA) tetramethyl rhodamine, and tetramethyl rhodamine isothiocyanate (TRITC)); riboflavin; rosolic acid; terbium chelate derivatives; Cyanine-3 (Cy3); Cyanine-5 (Cy5); cyanine-5.5 (Cy5.5), Cyanine-7 (Cy7); IRD 700; IRD 800; Alexa 647; La Jolta Blue; phthalo cyanine; and naphthalo cyanine.

In some embodiments, the detectable agent may be a non-detectable pre-cursor that becomes detectable upon activation (e.g., fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE® (VisEn Medical))). In vitro assays in which the enzyme labeled compositions can be used include, but are not limited to, enzyme linked immunosorbent assays (ELISAs), immunoprecipitation assays, immunofluorescence, enzyme immunoassays (EIA), radioimmunoassays (RIA), and Western blot analysis. Combination The modified nucleic acids, enhanced modified RNA or ribonucleic acids may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that may improve their bioavailability, reduce and/or modify their metabolism, inhibit their excretion, and/or modify their distribution within the body. As a non-limiting example, the modified nucleic acids, enhanced modified RNA or ribonucleic acids may be used in combination with a pharmaceutical agent for the treatment of cancer or to control hyperproliferative cells. In U.S. Pat. No. 7,964,571, herein incorporated by reference in its entirety, a combination therapy for the treatment of solid primary or metastasized tumor is described using a pharmaceutical composition including a DNA plasmid encoding for interleukin-12 with a lipopolymer and also administering at least one anticancer agent or chemotherapeutic. Further, the modified nucleic acids, enhanced modified RNA or ribonucleic acids of the present invention that encodes anti-proliferative molecules may be in a pharmaceutical composition with a lipopolymer (see e.g., U.S. Pub. No. 20110218231, herein incorporated by reference in its entirety, claiming a pharmaceutical composition comprising a DNA plasmid encoding an anti-proliferative molecule and a lipopolymer) which may be administered with at least one chemotherapeutic or anticancer agent.

Payload Administration: Cell Penetrating Payload

In some embodiments, the polynucleotides, modified nucleotides and modified nucleic acid molecules, which are incorporated into a nucleic acid, e.g., RNA or mRNA, can also include a payload that can be a cell penetrating moiety or agent that enhances intracellular delivery of the compositions. For example, the compositions can include, but are not limited to, a cell-penetrating peptide sequence that facilitates delivery to the intracellular space, e.g., HIV-derived TAT peptide, penetratins, transportans, or hCT derived cell-penetrating peptides, see, e.g., Caron et al., (2001) Mol Ther. 3(3):310-8; Langel, Cell-Penetrating Peptides: Processes and Applications (CRC Press, Boca Raton Fla. 2002); El-Andaloussi et al., (2005) Curr Pharm Des. 11(28):3597-611; and Deshayes et al., (2005) Cell Mol Life Sci. 62(16):1839-49; all of which are incorporated herein by reference. The compositions can also be formulated to include a cell penetrating agent, e.g., liposomes, which enhance delivery of the compositions to the intracellular space.

Payload Administration: Biological Target

The modified nucleotides and modified nucleic acid molecules described herein, which are incorporated into a nucleic acid, e.g., RNA or mRNA, can be used to deliver a payload to any biological target for which a specific ligand exists or can be generated. The ligand can bind to the biological target either covalently or non-covalently.

Examples of biological targets include, but are not limited to, biopolymers, e.g., antibodies, nucleic acids such as RNA and DNA, proteins, enzymes; examples of proteins include, but are not limited to, enzymes, receptors, and ion channels. In some embodiments the target may be a tissue- or a cell-type specific marker, e.g., a protein that is expressed specifically on a selected tissue or cell type. In some embodiments, the target may be a receptor, such as, but not limited to, plasma membrane receptors and nuclear receptors; more specific examples include, but are not limited to, G-protein-coupled receptors, cell pore proteins, transporter proteins, surface-expressed antibodies, HLA proteins, MHC proteins and growth factor receptors.

Dosing

The present invention provides methods comprising administering modified mRNAs and their encoded proteins or complexes in accordance with the invention to a subject in need thereof. Nucleic acids, proteins or complexes, or pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like. Compositions in accordance with the invention are typically formulated in dosage unit form for ease of administration and uniformity of dosage. It will be understood, however, that the total daily usage of the compositions of the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In certain embodiments, compositions in accordance with the present invention may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

According to the present invention, it has been discovered that administration of modified nucleic acids, enhanced modified RNA or ribonucleic acids in split-dose regimens produce higher levels of proteins in mammalian subjects. As used herein, a "split dose" is the division of single unit dose or total daily dose into two or more doses, e.g, two or more administrations of the single unit dose. As used herein, a "single unit dose" is a dose of any therapeutic administered in one dose/at one time/single route/single point of contact, i.e., single administration event. As used herein, a "total daily dose" is an amount given or prescribed in 24 hr period. It may be administered as a single unit dose. In one embodiment, the modified nucleic acids, enhanced modified RNA or ribonucleic acids of the present invention are administered to a subject in split doses. The modified nucleic acids, enhanced modified RNA or ribonucleic acids may be formulated in buffer only or in a formulation described herein.

Dosage Forms

A pharmaceutical composition described herein can be formulated into a dosage form described herein, such as a topical, intranasal, intratracheal, or injectable (e.g., intravenous, intraocular, intravitreal, intramuscular, intracardiac, intraperitoneal, subcutaneous).

Liquid Dosage Forms

Liquid dosage forms for parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art including, but not limited to, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. In certain embodiments for parenteral administration, compositions may be mixed with solubilizing agents such as CREMOPHOR®, alcohols, oils, modified oils, glycols, polysorbates, cyclodextrins, polymers, and/or combinations thereof.

Injectable

Injectable preparations, for example, sterile injectable aqueous or oleaginous suspensions may be formulated according to the known art and may include suitable dispersing agents, wetting agents, and/or suspending agents. Sterile injectable preparations may be sterile injectable solutions, suspensions, and/or emulsions in nontoxic parenterally acceptable diluents and/or solvents, for example, a solution in 1,3-butanediol. Among the acceptable vehicles and solvents that may be employed include, but are not limited to, are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it may be desirable to slow the absorption of the active ingredient from subcutaneous or intramuscular injection. This may be accomplished by the use of a liquid suspension of crystalline or amorphous material with poor water solubility. The rate of absorption of modified mRNA then depends upon its rate of dissolution which, in turn, may depend upon crystal size and crystalline form. Alternatively, delayed absorption of a parenterally administered modified mRNA may be accomplished by dissolving or suspending the modified mRNA in an oil vehicle. Injectable depot forms are made by forming microencapsule matrices of the modified mRNA in biodegradable polymers such as polylactide-polyglycolide. Depending upon the ratio of modified mRNA to polymer and the nature of the particular polymer employed, the rate of modified mRNA release can be controlled. Examples of other biodegradable polymers include, but are not limited to, poly(orthoesters) and poly (anhydrides). Depot injectable formulations may be prepared by entrapping the modified mRNA in liposomes or microemulsions which are compatible with body tissues.

Pulmonary

Formulations described herein as being useful for pulmonary delivery may also be use for intranasal delivery of a pharmaceutical composition. Another formulation suitable for intranasal administration may be a coarse powder comprising the active ingredient and having an average particle from about 0.2 μm to 500 μm. Such a formulation may be administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, contain about 0.1% to 20% (w/w) active ingredient, where the balance may comprise an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

General considerations in the formulation and/or manufacture of pharmaceutical agents may be found, for example, in Remington: The Science and Practice of Pharmacy 21$^{st}$ ed., Lippincott Williams & Wilkins, 2005 (incorporated herein by reference in its entirety).

Coatings or Shells

Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Kits

The invention provides a variety of kits for conveniently and/or effectively carrying out methods of the present invention. Typically kits will comprise sufficient amounts and/or numbers of components to allow a user to perform multiple treatments of a subject(s) and/or to perform multiple experiments.

In one aspect, the present invention provides kits for protein production, comprising a first modified nucleic acids, enhanced modified RNA or ribonucleic acids comprising a translatable region. The kit may further comprise packaging and instructions and/or a delivery agent to form a formulation composition. The delivery agent may comprise a saline, a buffered solution, a lipidoid or any delivery agent disclosed herein.

In one embodiment, the buffer solution may include sodium chloride, calcium chloride, phosphate and/or EDTA. In another embodiment, the buffer solution may include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium. In a further embodiment, the buffer solutions may be precipitated or it may be lyophilized. The amount of each component may be varied to enable consistent, reproducible higher concentration saline or simple buffer formulations. The components may also be varied in order to increase the stability of modified RNA in the buffer solution over a period of time and/or under a variety of conditions.

In one aspect, the present invention provides kits for protein production, comprising: a modified nucleic acids, enhanced modified RNA or ribonucleic acids comprising a translatable region, provided in an amount effective to produce a desired amount of a protein encoded by the translatable region when introduced into a target cell; a second modified nucleic acids, enhanced modified RNA or ribonucleic acids comprising an inhibitory nucleic acid, provided in an amount effective to substantially inhibit the innate immune response of the cell; and packaging and instructions.

In one aspect, the present invention provides kits for protein production, comprising a modified nucleic acids, enhanced modified RNA or ribonucleic acids comprising a translatable region, wherein the nucleic acid exhibits reduced degradation by a cellular nuclease, and packaging and instructions.

In one aspect, the present invention provides kits for protein production, comprising a modified nucleic acids, enhanced modified RNA or ribonucleic acids comprising a translatable region, wherein the nucleic acid exhibits reduced degradation by a cellular nuclease, and a mammalian cell suitable for translation of the translatable region of the first nucleic acid Devices The present invention provides for devices which may incorporate modified nucleic acids, enhanced modified RNA or ribonucleic acids that encode polypeptides of interest. These devices contain in a stable formulation the reagents to synthesize a nucleic acid in a formulation available to be immediately delivered to a subject in need thereof, such as a human patient. Non-limiting examples of such a polypeptide of interest include a growth factor and/or angiogenesis stimulator for wound healing, a peptide antibiotic to facilitate infection control, and an antigen to rapidly stimulate an immune response to a newly identified virus.

In some embodiments the device is self-contained, and is optionally capable of wireless remote access to obtain instructions for synthesis and/or analysis of the generated modified nucleic acids, enhanced modified RNA or ribonucleic acids. The device is capable of mobile synthesis of at least one modified nucleic acids, enhanced modified RNA or ribonucleic acids and preferably an unlimited number of different modified nucleic acids, enhanced modified RNA or ribonucleic acids. In certain embodiments, the device is capable of being transported by one or a small number of individuals. In other embodiments, the device is scaled to fit on a benchtop or desk. In other embodiments, the device is scaled to fit into a suitcase, backpack or similarly sized object. In another embodiment, the device may be a point of care or handheld device. In further embodiments, the device is scaled to fit into a vehicle, such as a car, truck or ambulance, or a military vehicle such as a tank or personnel carrier. The information necessary to generate a ribonucleic acid encoding polypeptide of interest is present within a computer readable medium present in the device.

In one embodiment, a device may be used to assess levels of a protein which has been administered in the form of a modified nucleic acids, enhanced modified RNA or ribonucleic acids. The device may comprise a blood, urine or other biofluidic test.

In some embodiments, the device is capable of communication (e.g., wireless communication) with a database of nucleic acid and polypeptide sequences. The device contains at least one sample block for insertion of one or more sample vessels. Such sample vessels are capable of accepting in liquid or other form any number of materials such as template DNA, nucleotides, enzymes, buffers, and other reagents. The sample vessels are also capable of being heated and cooled by contact with the sample block. The sample block is generally in communication with a device base with one or more electronic control units for the at least one sample block. The sample block preferably contains a heating module, such heating molecule capable of heating and/or cooling the sample vessels and contents thereof to temperatures between about −20 C and above +100 C. The device base is in communication with a voltage supply such as a battery or external voltage supply. The device also contains means for storing and distributing the materials for RNA synthesis.

Optionally, the sample block contains a module for separating the synthesized nucleic acids. Alternatively, the device contains a separation module operably linked to the sample block. Preferably the device contains a means for analysis of the synthesized nucleic acid. Such analysis includes sequence identity (demonstrated such as by hybridization), absence of non-desired sequences, measurement of integrity of synthesized mRNA (such has by microfluidic viscometry combined with spectrophotometry), and concentration and/or potency of modified nucleic acids, enhanced modified RNA or ribonucleic acids (such as by spectrophotometry).

In certain embodiments, the device is combined with a means for detection of pathogens present in a biological material obtained from a subject, e.g., the IBIS PLEX-ID system (Abbott, Abbott Park, Ill.) for microbial identification.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable.

Alternatively or additionally, conventional syringes may be used in the classical mantoux method of intradermal administration.

In some embodiments, the device may be a pump or comprise a catheter for administration of compounds or compositions of the invention across the blood brain barrier. Such devices include but are not limited to a pressurized olfactory delivery device, iontophoresis devices, multi-layered microfluidic devices, and the like. Such devices may be portable or stationary. They may be implantable or externally tethered to the body or combinations thereof.

Devices for administration may be employed to deliver the modified nucleic acids, enhanced modified RNA or ribonucleic acids of the present invention according to single, multi- or split-dosing regimens taught herein. Such devices are described below.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

According to the present invention, these multi-administration devices may be utilized to deliver the single, multi- or split doses contemplated herein.

A method for delivering therapeutic agents to a solid tissue has been described by Bahrami et al. and is taught for example in US Patent Publication 20110230839, the contents of which are incorporated herein by reference in their entirety. According to Bahrami, an array of needles is incorporated into a device which delivers a substantially equal amount of fluid at any location in said solid tissue along each needle's length.

A device for delivery of biological material across the biological tissue has been described by Kodgule et al. and is taught for example in US Patent Publication 20110172610, the contents of which are incorporated herein by reference in their entirety. According to Kodgule, multiple hollow microneedles made of one or more metals and having outer diameters from about 200 microns to about 350 microns and lengths of at least 100 microns are incorporated into the device which delivers peptides, proteins, carbohydrates, nucleic acid molecules, lipids and other pharmaceutically active ingredients or combinations thereof.

A delivery probe for delivering a therapeutic agent to a tissue has been described by Gunday et al. and is taught for example in US Patent Publication 20110270184, the contents of which are incorporated herein by reference in their entirety. According to Gunday, multiple needles are incorporated into the device which moves the attached capsules between an activated position and an inactivated position to force the agent out of the capsules through the needles.

A multiple-injection medical apparatus has been described by Assaf and is taught for example in US Patent Publication 20110218497, the contents of which are incorporated herein by reference in their entirety. According to Assaf, multiple needles are incorporated into the device which has a chamber connected to one or more of said needles and a means for continuously refilling the chamber with the medical fluid after each injection.

In one embodiment, the modified nucleic acids, enhanced modified RNA or ribonucleic acids are administered subcutaneously or intramuscularly via at least 3 needles to three different, optionally adjacent, sites simultaneously, or within a 60 minutes period (e.g., administration to 4, 5, 6, 7, 8, 9, or 10 sites simultaneously or within a 60 minute period). The split doses can be administered simultaneously to adjacent tissue using the devices described in U.S. Patent Publication Nos. 20110230839 and 20110218497, each of which is incorporated herein by reference.

An at least partially implantable system for injecting a substance into a patient's body, in particular a penis erection stimulation system has been described by Forsell and is taught for example in US Patent Publication 20110196198, the contents of which are incorporated herein by reference in their entirety. According to Forsell, multiple needles are incorporated into the device which is implanted along with one or more housings adjacent the patient's left and right corpora cavernosa. A reservoir and a pump are also implanted to supply drugs through the needles.

A method for the transdermal delivery of a therapeutic effective amount of iron has been described by Berenson and is taught for example in US Patent Publication 20100130910, the contents of which are incorporated herein by reference in their entirety. According to Berenson, multiple needles may be used to create multiple micro channels in stratum corneum to enhance transdermal delivery of the ionic iron on an iontophoretic patch.

A method for delivery of biological material across the biological tissue has been described by Kodgule et al and is taught for example in US Patent Publication 20110196308, the contents of which are incorporated herein by reference in their entirety. According to Kodgule, multiple biodegradable microneedles containing a therapeutic active ingredient are incorporated in a device which delivers proteins, carbohydrates, nucleic acid molecules, lipids and other pharmaceutically active ingredients or combinations thereof.

A transdermal patch comprising a botulinum toxin composition has been described by Donovan and is taught for example in US Patent Publication 20080220020, the contents of which are incorporated herein by reference in their entirety. According to Donovan, multiple needles are incorporated into the patch which delivers botulinum toxin under stratum corneum through said needles which project through the stratum corneum of the skin without rupturing a blood vessel.

A small, disposable drug reservoir, or patch pump, which can hold approximately 0.2 to 15 mL of liquid formulations can be placed on the skin and deliver the formulation continuously subcutaneously using a small bore needed (e.g., 26 to 34 gauge). As non-limiting examples, the patch pump may be 50 mm by 76 mm by 20 mm spring loaded having a 30 to 34 gauge needle (BD™ Microinfuser, Franklin Lakes N.J.), 41 mm by 62 mm by 17 mm with a 2 mL reservoir used for drug delivery such as insulin (OMNIPOD®, Insulet Corporation Bedford, Mass.), or 43-60 mm diameter, 10 mm thick with a 0.5 to 10 mL reservoir (PATCHPUMP®, SteadyMed Therapeutics, San Francisco, Calif.). Further, the patch pump may be battery powered and/or rechargeable.

A cryoprobe for administration of an active agent to a location of cryogenic treatment has been described by Toubia and is taught for example in US Patent Publication 20080140061, the contents of which are incorporated herein by reference in their entirety. According to Toubia, multiple needles are incorporated into the probe which receives the active agent into a chamber and administers the agent to the tissue.

A method for treating or preventing inflammation or promoting healthy joints has been described by Stock et al and is taught for example in US Patent Publication 20090155186, the contents of which are incorporated herein by reference in their entirety. According to Stock, multiple needles are incorporated in a device which administers compositions containing signal transduction modulator compounds.

A multi-site injection system has been described by Kimmell et al. and is taught for example in US Patent Publication 20100256594, the contents of which are incorporated herein by reference in their entirety. According to Kimmell, multiple needles are incorporated into a device which delivers a medication into a stratum corneum through the needles.

A method for delivering interferons to the intradermal compartment has been described by Dekker et al. and is taught for example in US Patent Publication 20050181033, the contents of which are incorporated herein by reference in their entirety. According to Dekker, multiple needles having an outlet with an exposed height between 0 and 1 mm are incorporated into a device which improves pharmacokinetics and bioavailability by delivering the substance at a depth between 0.3 mm and 2 mm.

A method for delivering genes, enzymes and biological agents to tissue cells has described by Desai and is taught for example in US Patent Publication 20030073908, the contents of which are incorporated herein by reference in their entirety. According to Desai, multiple needles are incorporated into a device which is inserted into a body and delivers a medication fluid through said needles.

A method for treating cardiac arrhythmias with fibroblast cells has been described by Lee et al and is taught for example in US Patent Publication 20040005295, the contents of which are incorporated herein by reference in their entirety. According to Lee, multiple needles are incorporated into the device which delivers fibroblast cells into the local region of the tissue.

A method using a magnetically controlled pump for treating a brain tumor has been described by Shachar et al. and is taught for example in U.S. Pat. No. 7,799,012 (method) and U.S. Pat. No. 7,799,016 (device), the contents of which are incorporated herein by reference in their entirety. According Shachar, multiple needles were incorporated into the pump which pushes a medicating agent through the needles at a controlled rate.

Methods of treating functional disorders of the bladder in mammalian females have been described by Versi et al. and are taught for example in U.S. Pat. No. 8,029,496, the contents of which are incorporated herein by reference in their entirety. According to Versi, an array of micro-needles is incorporated into a device which delivers a therapeutic agent through the needles directly into the trigone of the bladder.

A micro-needle transdermal transport device has been described by Angel et al and is taught for example in U.S. Pat. No. 7,364,568, the contents of which are incorporated herein by reference in their entirety. According to Angel, multiple needles are incorporated into the device which transports a substance into a body surface through the needles which are inserted into the surface from different directions. The micro-needle transdermal transport device may be a solid micro-needle system or a hollow micro-needle system. As a non-limiting example, the solid micro-needle system may have up to a 0.5 mg capacity, with 300-1500 solid micro-needles per $cm^2$ about 150-700 m tall coated with a drug. The micro-needles penetrate the stratum corneum and remain in the skin for short duration (e.g., 20 seconds to 15 minutes). In another example, the hollow micro-needle system has up to a 3 mL capacity to deliver liquid formulations using 15-20 microneedles per cm2 being approximately 950 μm tall. The micro-needles penetrate the skin to allow the liquid formulations to flow from the device into the skin. The hollow micro-needle system may be worn from 1 to 30 minutes depending on the formulation volume and viscocity.

A device for subcutaneous infusion has been described by Dalton et al and is taught for example in U.S. Pat. No. 7,150,726, the contents of which are incorporated herein by reference in their entirety. According to Dalton, multiple needles are incorporated into the device which delivers fluid through the needles into a subcutaneous tissue.

A device and a method for intradermal delivery of vaccines and gene therapeutic agents through microcannula have been described by Mikszta et al. and are taught for example in U.S. Pat. No. 7,473,247, the contents of which are incorporated herein by reference in their entirety. According to Mitszta, at least one hollow micro-needle is incorporated into the device which delivers the vaccines to the subject's skin to a depth of between 0.025 mm and 2 mm.

A method of delivering insulin has been described by Pettis et al and is taught for example in U.S. Pat. No. 7,722,595, the contents of which are incorporated herein by reference in their entirety. According to Pettis, two needles are incorporated into a device wherein both needles insert essentially simultaneously into the skin with the first at a depth of less than 2.5 mm to deliver insulin to intradermal compartment and the second at a depth of greater than 2.5 mm and less than 5.0 mm to deliver insulin to subcutaneous compartment.

Cutaneous injection delivery under suction has been described by Kochamba et al. and is taught for example in U.S. Pat. No. 6,896,666, the contents of which are incorporated herein by reference in their entirety. According to Kochamba, multiple needles in relative adjacency with each other are incorporated into a device which injects a fluid below the cutaneous layer.

A device for withdrawing or delivering a substance through the skin has been described by Down et al and is taught for example in U.S. Pat. No. 6,607,513, the contents of which are incorporated herein by reference in their entirety. According to Down, multiple skin penetrating members which are incorporated into the device have lengths of about 100 microns to about 2000 microns and are about 30 to 50 gauge.

A device for delivering a substance to the skin has been described by Palmer et al and is taught for example in U.S. Pat. No. 6,537,242, the contents of which are incorporated herein by reference in their entirety. According to Palmer, an array of micro-needles is incorporated into the device which uses a stretching assembly to enhance the contact of the needles with the skin and provides a more uniform delivery of the substance.

A perfusion device for localized drug delivery has been described by Zamoyski and is taught for example in U.S. Pat. No. 6,468,247, the contents of which are incorporated herein by reference in their entirety. According to Zamoyski, multiple hypodermic needles are incorporated into the device which injects the contents of the hypodermics into a tissue as said hypodermics are being retracted.

A method for enhanced transport of drugs and biological molecules across tissue by improving the interaction between micro-needles and human skin has been described by Prausnitz et al. and is taught for example in U.S. Pat. No. 6,743,211, the contents of which are incorporated herein by reference in their entirety. According to Prausnitz, multiple micro-needles are incorporated into a device which is able to present a more rigid and less deformable surface to which the micro-needles are applied.

A device for intraorgan administration of medicinal agents has been described by Ting et al and is taught for example in U.S. Pat. No. 6,077,251, the contents of which are incorporated herein by reference in their entirety. According to Ting, multiple needles having side openings for enhanced administration are incorporated into a device which by extending and retracting said needles from and into the needle chamber forces a medicinal agent from a reservoir into said needles and injects said medicinal agent into a target organ.

A multiple needle holder and a subcutaneous multiple channel infusion port has been described by Brown and is taught for example in U.S. Pat. No. 4,695,273, the contents of which are incorporated herein by reference in their entirety. According to Brown, multiple needles on the needle holder are inserted through the septum of the infusion port and communicate with isolated chambers in said infusion port.

A dual hypodermic syringe has been described by Horn and is taught for example in U.S. Pat. No. 3,552,394, the contents of which are incorporated herein by reference in their entirety. According to Horn, two needles incorporated into the device are spaced apart less than 68 mm and may be of different styles and lengths, thus enabling injections to be made to different depths.

A syringe with multiple needles and multiple fluid compartments has been described by Hershberg and is taught for example in U.S. Pat. No. 3,572,336, the contents of which are incorporated herein by reference in their entirety. According to Hershberg, multiple needles are incorporated into the syringe which has multiple fluid compartments and is capable of simultaneously administering incompatible drugs which are not able to be mixed for one injection.

A surgical instrument for intradermal injection of fluids has been described by Eliscu et al. and is taught for example in U.S. Pat. No. 2,588,623, the contents of which are incorporated herein by reference in their entirety. According to Eliscu, multiple needles are incorporated into the instrument which injects fluids intradermally with a wider disperse.

An apparatus for simultaneous delivery of a substance to multiple breast milk ducts has been described by Hung and is taught for example in EP 1818017, the contents of which are incorporated herein by reference in their entirety. According to Hung, multiple lumens are incorporated into the device which inserts though the orifices of the ductal networks and delivers a fluid to the ductal networks.

A catheter for introduction of medications to the tissue of a heart or other organs has been described by Tkebuchava and is taught for example in WO2006138109, the contents of which are incorporated herein by reference in their entirety. According to Tkebuchava, two curved needles are incorporated which enter the organ wall in a flattened trajectory.

Devices for delivering medical agents have been described by Mckay et al. and are taught for example in WO2006118804, the content of which are incorporated herein by reference in their entirety. According to Mckay, multiple needles with multiple orifices on each needle are incorporated into the devices to facilitate regional delivery to a tissue, such as the interior disc space of a spinal disc.

A method for directly delivering an immunomodulatory substance into an intradermal space within a mammalian skin has been described by Pettis and is taught for example in WO2004020014, the contents of which are incorporated herein by reference in their entirety. According to Pettis, multiple needles are incorporated into a device which delivers the substance through the needles to a depth between 0.3 mm and 2 mm.

Methods and devices for administration of substances into at least two compartments in skin for systemic absorption and improved pharmacokinetics have been described by Pettis et al. and are taught for example in WO2003094995, the contents of which are incorporated herein by reference in their entirety. According to Pettis, multiple needles having lengths between about 300 µm and about 5 mm are incorporated into a device which delivers to intradermal and subcutaneous tissue compartments simultaneously.

A drug delivery device with needles and a roller has been described by Zimmerman et al. and is taught for example in WO2012006259, the contents of which are incorporated herein by reference in their entirety. According to Zimmerman, multiple hollow needles positioned in a roller are incorporated into the device which delivers the content in a reservoir through the needles as the roller rotates.

Methods and Devices Utilizing Catheters and/or Lumens

Methods and devices using catheters and lumens may be employed to administer the modified nucleic acids, enhanced modified RNA or ribonucleic acids of the present invention on a single, multi- or split dosing schedule. Such methods and devices are described below.

A catheter-based delivery of skeletal myoblasts to the myocardium of damaged hearts has been described by Jacoby et al and is taught for example in US Patent Publication 20060263338, the contents of which are incorporated herein by reference in their entirety. According to Jacoby, multiple needles are incorporated into the device at least part of which is inserted into a blood vessel and delivers the cell composition through the needles into the localized region of the subject's heart.

An apparatus for treating asthma using neurotoxin has been described by Deem et al and is taught for example in US Patent Publication 20060225742, the contents of which are incorporated herein by reference in their entirety. According to Deem, multiple needles are incorporated into the device which delivers neurotoxin through the needles into the bronchial tissue.

A method for administering multiple-component therapies has been described by Nayak and is taught for example in U.S. Pat. No. 7,699,803, the contents of which are incorporated herein by reference in their entirety. According to Nayak, multiple injection cannulas may be incorporated into a device wherein depth slots may be included for controlling the depth at which the therapeutic substance is delivered within the tissue.

A surgical device for ablating a channel and delivering at least one therapeutic agent into a desired region of the tissue has been described by McIntyre et al and is taught for example in U.S. Pat. No. 8,012,096, the contents of which are incorporated herein by reference in their entirety. According to McIntyre, multiple needles are incorporated into the device which dispenses a therapeutic agent into a region of tissue surrounding the channel and is particularly well suited for transmyocardial revascularization operations.

Methods of treating functional disorders of the bladder in mammalian females have been described by Versi et al and are taught for example in U.S. Pat. No. 8,029,496, the contents of which are incorporated herein by reference in their entirety. According to Versi, an array of micro-needles is incorporated into a device which delivers a therapeutic agent through the needles directly into the trigone of the bladder.

A device and a method for delivering fluid into a flexible biological barrier have been described by Yeshurun et al. and are taught for example in U.S. Pat. No. 7,998,119 (device) and U.S. Pat. No. 8,007,466 (method), the contents of which are incorporated herein by reference in their entirety. According to Yeshurun, the micro-needles on the device penetrate and extend into the flexible biological barrier and fluid is injected through the bore of the hollow micro-needles.

A method for epicardially injecting a substance into an area of tissue of a heart having an epicardial surface and disposed within a torso has been described by Bonner et al and is taught for example in U.S. Pat. No. 7,628,780, the contents of which are incorporated herein by reference in their entirety. According to Bonner, the devices have elongate shafts and distal injection heads for driving needles into tissue and injecting medical agents into the tissue through the needles.

A device for sealing a puncture has been described by Nielsen et al and is taught for example in U.S. Pat. No. 7,972,358, the contents of which are incorporated herein by reference in their entirety. According to Nielsen, multiple needles are incorporated into the device which delivers a closure agent into the tissue surrounding the puncture tract.

A method for myogenesis and angiogenesis has been described by Chiu et al. and is taught for example in U.S. Pat. No. 6,551,338, the contents of which are incorporated herein by reference in their entirety. According to Chiu, 5 to 15 needles having a maximum diameter of at least 1.25 mm and a length effective to provide a puncture depth of 6 to 20 mm are incorporated into a device which inserts into proximity with a myocardium and supplies an exogeneous angiogenic or myogenic factor to said myocardium through the conduits which are in at least some of said needles.

A method for the treatment of prostate tissue has been described by Bolmsj et al. and is taught for example in U.S. Pat. No. 6,524,270, the contents of which are incorporated herein by reference in their entirety. According to Bolmsj, a device comprising a catheter which is inserted through the urethra has at least one hollow tip extendible into the surrounding prostate tissue. An astringent and analgesic medicine is administered through said tip into said prostate tissue.

A method for infusing fluids to an intraosseous site has been described by Findlay et al. and is taught for example in U.S. Pat. No. 6,761,726, the contents of which are incorporated herein by reference in their entirety. According to Findlay, multiple needles are incorporated into a device which is capable of penetrating a hard shell of material covered by a layer of soft material and delivers a fluid at a predetermined distance below said hard shell of material.

A device for injecting medications into a vessel wall has been described by Vigil et al. and is taught for example in U.S. Pat. No. 5,713,863, the contents of which are incorporated herein by reference in their entirety. According to Vigil, multiple injectors are mounted on each of the flexible tubes in the device which introduces a medication fluid through a multi-lumen catheter, into said flexible tubes and out of said injectors for infusion into the vessel wall.

A catheter for delivering therapeutic and/or diagnostic agents to the tissue surrounding a bodily passageway has been described by Faxon et al. and is taught for example in U.S. Pat. No. 5,464,395, the contents of which are incorporated herein by reference in their entirety. According to Faxon, at least one needle cannula is incorporated into the catheter which delivers the desired agents to the tissue through said needles which project outboard of the catheter.

Balloon catheters for delivering therapeutic agents have been described by Orr and are taught for example in WO2010024871, the contents of which are incorporated herein by reference in their entirety. According to Orr, multiple needles are incorporated into the devices which deliver the therapeutic agents to different depths within the tissue.

Methods and Devices Utilizing Electrical Current

Methods and devices utilizing electric current may be employed to deliver the modified nucleic acids, enhanced modified RNA or ribonucleic acids of the present invention according to the single, multi- or split dosing regimens taught herein. Such methods and devices are described below.

An electro collagen induction therapy device has been described by Marquez and is taught for example in US Patent Publication 20090137945, the contents of which are incorporated herein by reference in their entirety. According to Marquez, multiple needles are incorporated into the device which repeatedly pierce the skin and draw in the skin a portion of the substance which is applied to the skin first.

An electrokinetic system has been described by Etheredge et al. and is taught for example in US Patent Publication 20070185432, the contents of which are incorporated herein by reference in their entirety. According to Etheredge, micro-needles are incorporated into a device which drives by an electrical current the medication through the needles into the targeted treatment site.

An iontophoresis device has been described by Matsumura et al. and is taught for example in U.S. Pat. No. 7,437,189, the contents of which are incorporated herein by reference in their entirety. According to Matsumura, multiple needles are incorporated into the device which is capable of delivering ionizable drug into a living body at higher speed or with higher efficiency.

Intradermal delivery of biologically active agents by needle-free injection and electroporation has been described by Hoffmann et al and is taught for example in U.S. Pat. No. 7,171,264, the contents of which are incorporated herein by reference in their entirety. According to Hoffmann, one or more needle-free injectors are incorporated into an electroporation device and the combination of needle-free injection and electroporation is sufficient to introduce the agent into cells in skin, muscle or mucosa.

A method for electropermeabilization-mediated intracellular delivery has been described by Lundkvist et al. and is taught for example in U.S. Pat. No. 6,625,486, the contents of which are incorporated herein by reference in their entirety. According to Lundkvist, a pair of needle electrodes is incorporated into a catheter. Said catheter is positioned into a body lumen followed by extending said needle electrodes to penetrate into the tissue surrounding said lumen. Then the device introduces an agent through at least one of said needle electrodes and applies electric field by said pair of needle electrodes to allow said agent pass through the cell membranes into the cells at the treatment site.

A delivery system for transdermal immunization has been described by Levin et al. and is taught for example in WO2006003659, the contents of which are incorporated herein by reference in their entirety. According to Levin, multiple electrodes are incorporated into the device which applies electrical energy between the electrodes to generate micro channels in the skin to facilitate transdermal delivery.

A method for delivering RF energy into skin has been described by Schomacker and is taught for example in WO2011163264, the contents of which are incorporated herein by reference in their entirety. According to Schomacker, multiple needles are incorporated into a device which applies vacuum to draw skin into contact with a plate so that needles insert into skin through the holes on the plate and deliver RF energy.

Definitions

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

About: As used herein, the term "about" means +/−10% of the recited value.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Auxotrophic: As used herein, the term "auxotrophic" refers to mRNA that comprises at least one feature that triggers or induces the degradation or inactivation of the mRNA such that the protein expression is substantially prevented or reduced in a selected tissue or organ.

Bifunctional: As used herein, the term "bifunctional" refers to any substance, molecule or moiety which is capable of or maintains at least two functions. The functions may effect the same outcome or a different outcome. The structure that produces the function may be the same or different. For example, bifunctional modified RNAs of the present invention may encode a cytotoxic peptide (a first function) while those nucleosides which comprise the encoding RNA are, in and of themselves, cytotoxic (second function). In this example, delivery of the bifunctional modified RNA to a cancer cell would produce not only a peptide or protein molecule which may ameliorate or treat the cancer but would also deliver a cytotoxic payload of nucleosides to the cell should degradation, instead of translation of the modified RNA, occur.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological affect on that organism, is considered to be biologically active. In particular embodiments, a nucleic acid molecule of the present invention may be considered biologically active if even a portion of the nucleic acid molecule is biologically active or mimics an activity considered biologically relevant.

Chemical terms: The following provides the definition of various chemical terms from "acyl" to "thiol."

The term "acyl," as used herein, represents a hydrogen or an alkyl group (e.g., a haloalkyl group), as defined herein, that is attached to the parent molecular group through a carbonyl group, as defined herein, and is exemplified by formyl (i.e., a carboxyaldehyde group), acetyl, propionyl, butanoyl and the like. Exemplary unsubstituted acyl groups include from 1 to 7, from 1 to 11, or from 1 to 21 carbons. In some embodiments, the alkyl group is further substituted with 1, 2, 3, or 4 substituents as described herein.

The term "acylamino," as used herein, represents an acyl group, as defined herein, attached to the parent molecular group though an amino group, as defined herein (i.e., —N($R^{N1}$)—C(O)—R, where R is H or an optionally substituted $C_{1-6}$, $C_{1-10}$, or $C_{1-20}$ alkyl group and $R^{N1}$ is as defined herein). Exemplary unsubstituted acylamino groups include from 1 to 41 carbons (e.g., from 1 to 7, from 1 to 13, from 1 to 21, from 2 to 7, from 2 to 13, from 2 to 21, or from 2 to 41 carbons). In some embodiments, the alkyl group is further substituted with 1, 2, 3, or 4 substituents as described herein, and/or the amino group is —$NH_2$ or —$NHR^{N1}$, wherein $R^{N1}$ is, independently, OH, $NO_2$, $NH_2$, $NR^{N2}_2$, $SO_2OR^{N2}$, $SO_2RN^2$, $SOR^{N2}$, alkyl, or aryl, and each $R^{N2}$ can be H, alkyl, or aryl.

The term "acyloxy," as used herein, represents an acyl group, as defined herein, attached to the parent molecular group though an oxygen atom (i.e., —O—C(O)—R, where R is H or an optionally substituted $C_{1-6}$, $C_{1-10}$, or $C_{1-20}$ alkyl group). Exemplary unsubstituted acyloxy groups include from 1 to 21 carbons (e.g., from 1 to 7 or from 1 to 11 carbons). In some embodiments, the alkyl group is further substituted with 1, 2, 3, or 4 substituents as described herein, and/or the amino group is —$NH_2$ or —$NHR^{N1}$, wherein $R^{N1}$ is, independently, OH, $NO_2$, $NH_2$, $NR^{N2}_2$, $SO_2OR^{N2}$, $SO_2RN^2$, $SOR^{N2}$, alkyl, or aryl, and each $R^{N2}$ can be H, alkyl, or aryl.

The term "alkaryl," as used herein, represents an aryl group, as defined herein, attached to the parent molecular group through an alkylene group, as defined herein. Exemplary unsubstituted alkaryl groups are from 7 to 30 carbons (e.g., from 7 to 16 or from 7 to 20 carbons, such as $C_{1-6}$ alk-$C_{6-10}$ aryl, $C_{1-10}$ alk-$C_{6-10}$ aryl, or $C_{1-20}$ alk-$C_{6-10}$ aryl). In some embodiments, the alkylene and the aryl each can be further substituted with 1, 2, 3, or 4 substituent groups as defined herein for the respective groups. Other groups preceded by the prefix "alk-" are defined in the same manner, where "alk" refers to a $C_{1-6}$ alkylene, unless otherwise noted, and the attached chemical structure is as defined herein.

The term "alkcycloalkyl" represents a cycloalkyl group, as defined herein, attached to the parent molecular group through an alkylene group, as defined herein (e.g., an alkylene group of from 1 to 4, from 1 to 6, from 1 to 10, or form 1 to 20 carbons). In some embodiments, the alkylene and the cycloalkyl each can be further substituted with 1, 2, 3, or 4 substituent groups as defined herein for the respective group.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, 2-butenyl, and the like. Alkenyls include both cis and trans isomers. Alkenyl groups may be optionally substituted with 1, 2, 3, or 4 substituent groups that are selected, independently, from amino, aryl, cycloalkyl, or heterocyclyl (e.g., heteroaryl), as defined herein, or any of the exemplary alkyl substituent groups described herein.

The term "alkenyloxy" represents a chemical substituent of formula —OR, where R is a $C_{2-20}$ alkenyl group (e.g., $C_{2-6}$ or $C_{2-10}$ alkenyl), unless otherwise specified. Exemplary alkenyloxy groups include ethenyloxy, propenyloxy, and the like. In some embodiments, the alkenyl group can be further substituted with 1, 2, 3, or 4 substituent groups as defined herein (e.g., a hydroxy group).

The term "alkheteroaryl" refers to a heteroaryl group, as defined herein, attached to the parent molecular group through an alkylene group, as defined herein. Exemplary unsubstituted alkheteroaryl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heteroaryl, $C_{1-10}$ alk-$C_{1-12}$ heteroaryl, or $C_{1-20}$ alk-$C_{1-12}$ heteroaryl). In some embodiments, the alkylene and the heteroaryl each can be further substituted with 1, 2, 3, or 4 substituent groups as defined herein for the respective group. Alkheteroaryl groups are a subset of alkheterocyclyl groups.

The term "alkheterocyclyl" represents a heterocyclyl group, as defined herein, attached to the parent molecular group through an alkylene group, as defined herein. Exemplary unsubstituted alkheterocyclyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heterocyclyl, $C_{1-10}$ alk-$C_{1-12}$ heterocyclyl, or $C_{1-20}$ alk-$C_{1-12}$ heterocyclyl). In some embodiments, the alkylene and the heterocyclyl each can be further substituted with 1, 2, 3, or 4 substituent groups as defined herein for the respective group.

The term "alkoxy" represents a chemical substituent of formula —OR, where R is a $C_{1-20}$ alkyl group (e.g., $C_{1-6}$ or $C_{1-10}$ alkyl), unless otherwise specified. Exemplary alkoxy groups include methoxy, ethoxy, propoxy (e.g., n-propoxy and isopropoxy), t-butoxy, and the like. In some embodiments, the alkyl group can be further substituted with 1, 2, 3, or 4 substituent groups as defined herein (e.g., hydroxy or alkoxy).

The term "alkoxyalkoxy" represents an alkoxy group that is substituted with an alkoxy group. Exemplary unsubstituted alkoxyalkoxy groups include between 2 to 40 carbons (e.g., from 2 to 12 or from 2 to 20 carbons, such as $C_{1-6}$ alkoxy-$C_{1-6}$ alkoxy, $C_{1-10}$ alkoxy-$C_{1-10}$ alkoxy, or $C_{1-20}$ alkoxy-$C_{1-20}$ alkoxy). In some embodiments, the each alkoxy group can be further substituted with 1, 2, 3, or 4 substituent groups as defined herein.

The term "alkoxyalkyl" represents an alkyl group that is substituted with an alkoxy group. Exemplary unsubstituted alkoxyalkyl groups include between 2 to 40 carbons (e.g., from 2 to 12 or from 2 to 20 carbons, such as $C_{1-6}$ alkoxy-$C_{1-6}$ alkyl, $C_{1-10}$ alkoxy-$C_{1-10}$ alkyl, or $C_{1-20}$ alkoxy-$C_{1-20}$ alkyl). In some embodiments, the alkyl and the alkoxy each can be further substituted with 1, 2, 3, or 4 substituent groups as defined herein for the respective group.

The term "alkoxycarbonyl," as used herein, represents an alkoxy, as defined herein, attached to the parent molecular group through a carbonyl atom (e.g., —C(O)—OR, where R is H or an optionally substituted $C_{1-6}$, $C_{1-10}$, or $C_{1-20}$ alkyl group). Exemplary unsubstituted alkoxycarbonyl include from 1 to 21 carbons (e.g., from 1 to 11 or from 1 to 7 carbons). In some embodiments, the alkoxy group is further substituted with 1, 2, 3, or 4 substituents as described herein.

The term "alkoxycarbonylalkoxy," as used herein, represents an alkoxy group, as defined herein, that is substituted with an alkoxycarbonyl group, as defined herein (e.g., —O-alkyl-C(O)—OR, where R is an optionally substituted $C_{1-6}$, $C_{1-10}$, or $C_{1-20}$ alkyl group). Exemplary unsubstituted alkoxycarbonylalkoxy include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkoxy, $C_{1-10}$ alkoxycarbonyl-$C_{1-10}$ alkoxy, or $C_{1-20}$ alkoxycarbonyl-$C_{1-20}$ alkoxy). In some embodiments, each alkoxy group is further independently substituted with 1, 2, 3, or 4 substituents, as described herein (e.g., a hydroxy group).

The term "alkoxycarbonylalkyl," as used herein, represents an alkyl group, as defined herein, that is substituted with an alkoxycarbonyl group, as defined herein (e.g., -alkyl-C(O)—OR, where R is an optionally substituted $C_{1-20}$, $C_{1-10}$, or $C_{1-6}$ alkyl group). Exemplary unsubstituted alkoxycarbonylalkyl include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkyl, $C_{1-10}$ alkoxycarbonyl-$C_{1-10}$ alkyl, or $C_{1-20}$ alkoxycarbonyl-$C_{1-20}$ alkyl). In some embodiments, each alkyl and alkoxy group is further independently substituted with 1, 2, 3, or 4 substituents as described herein (e.g., a hydroxy group).

The term "alkyl," as used herein, is inclusive of both straight chain and branched chain saturated groups from 1 to 20 carbons (e.g., from 1 to 10 or from 1 to 6), unless otherwise specified. Alkyl groups are exemplified by methyl, ethyl, n- and iso-propyl, n-, sec-, iso- and tert-butyl, neopentyl, and the like, and may be optionally substituted with one, two, three, or, in the case of alkyl groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —NH$_2$) or a substituted amino (i.e., —N($R^{N1}$)$_2$, where $R^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy; (9) nitro; (10) oxo (e.g., carboxyaldehyde or acyl); (11) $C_{1-7}$ spirocyclyl; (12) thioalkoxy; (13) thiol; (14) —CO$_2$$R^{A'}$, where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (15) —C(O)NR$^{B'}$R$^{C'}$, where each of R$^{B'}$ and R$^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —SO$_2$R$^{D'}$, where R$^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) —SO$_2$NR$^{E'}$R$^{F'}$, where each of R$^{E'}$ and R$^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —C(O)R$^{G'}$, where R$^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) —NR$^{H'}$C(O)R$^{I'}$, wherein R$^{H'}$ is selected from the group consisting of (a1) hydrogen and (b1) $C_{1-6}$ alkyl, and R$^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) —NR$^{J'}$C(O)OR$^{K'}$, wherein R$^{J'}$ is selected from the group consisting of (a1) hydrogen and (b1) $C_{1-6}$ alkyl, and R$^{K'}$ is selected from the group consisting of (a2) $C_{1-20}$ alkyl (e.g., $C_{1-6}$ alkyl), (b2) $C_{2}$-20 alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein. For example, the alkylene group of a $C_1$-alkaryl can be further substituted with an oxo group to afford the respective aryloyl substituent.

The term "alkylene" and the prefix "alk-," as used herein, represent a saturated divalent hydrocarbon group derived from a straight or branched chain saturated hydrocarbon by the removal of two hydrogen atoms, and is exemplified by methylene, ethylene, isopropylene, and the like. The term "$C_{x-y}$ alkylene" and the prefix "$C_{x-y}$ alk-" represent alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., $C_{1-6}$, $C_{1-10}$, $C_{2-20}$, $C_{2-6}$, $C_{2-10}$, or $C_{2-20}$ alkylene). In some embodiments, the alkylene can be further substituted with 1, 2, 3, or 4 substituent groups as defined herein for an alkyl group.

The term "alkylsulfinyl," as used herein, represents an alkyl group attached to the parent molecular group through an —S(O)— group. Exemplary unsubstituted alkylsulfinyl groups are from 1 to 6, from 1 to 10, or from 1 to 20 carbons. In some embodiments, the alkyl group can be further substituted with 1, 2, 3, or 4 substituent groups as defined herein.

The term "alkylsulfinylalkyl," as used herein, represents an alkyl group, as defined herein, substituted by an alkylsulfinyl group. Exemplary unsubstituted alkylsulfinyl-alkyl groups are from 2 to 12, from 2 to 20, or from 2 to 40 carbons. In some embodiments, each alkyl group can be further substituted with 1, 2, 3, or 4 substituent groups as defined herein.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, 1-propynyl, and the like. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

The term "alkynyloxy" represents a chemical substituent of formula —OR, where R is a $C_{2-20}$ alkynyl group (e.g., $C_{2-6}$ or $C_{2-10}$ alkynyl), unless otherwise specified. Exemplary alkynyloxy groups include ethynyloxy, propynyloxy, and the like. In some embodiments, the alkynyl group can be further substituted with 1, 2, 3, or 4 substituent groups as defined herein (e.g., a hydroxy group).

The term "amidine," as used herein, represents a —C(=NH)NH$_2$ group.

The term "amino," as used herein, represents —N(R$^{N1}$)$_2$, wherein each R$^{N1}$ is, independently, H, OH, NO$_2$, N(R$^{N2}$)$_2$, SO$_2$OR$^{N2}$, SO$_2$RN$^2$, SOR$^{N2}$, an N-protecting group, alkyl, alkenyl, alkynyl, alkoxy, aryl, alkaryl, cycloalkyl, alkcycloalkyl, carboxyalkyl, sulfoalkyl, heterocyclyl (e.g., heteroaryl), or alkheterocyclyl (e.g., alkheteroaryl), wherein each of these recited R$^{N1}$ groups can be optionally substituted, as defined herein for each group; or two R$^{N1}$ combine to form a heterocyclyl or an N-protecting group, and wherein each R$^{N2}$ is, independently, H, alkyl, or aryl. The amino groups of the invention can be an unsubstituted amino (i.e., —NH$_2$) or a substituted amino (i.e., —N(R$^{N1}$)$_2$). In a preferred embodiment, amino is —NH$_2$ or —NHR$^{N1}$, wherein R$^{N1}$ is, independently, OH, NO$_2$, NH$_2$, NR$^{N2}_2$, SO$_2$OR$^{N2}$, SO$_2$RN$^2$, SOR$^{N2}$, alkyl, carboxyalkyl, sulfoalkyl, or aryl, and each R$^{N2}$ can be H, $C_{1-20}$ alkyl (e.g., $C_{1-6}$ alkyl), or $C_{6-10}$ aryl.

The term "amino acid," as described herein, refers to a molecule having a side chain, an amino group, and an acid group (e.g., a carboxy group of —CO$_2$H or a sulfo group of —SO$_3$H), wherein the amino acid is attached to the parent molecular group by the side chain, amino group, or acid group (e.g., the side chain). In some embodiments, the amino acid is attached to the parent molecular group by a carbonyl group, where the side chain or amino group is attached to the carbonyl group. Exemplary side chains include an optionally substituted alkyl, aryl, heterocyclyl, alkaryl, alkheterocyclyl, aminoalkyl, carbamoylalkyl, and carboxyalkyl. Exemplary amino acids include alanine, arginine, asparagine, aspartic acid, cysteine, glutamic acid, glutamine, glycine, histidine, hydroxynorvaline, isoleucine, leucine, lysine, methionine, norvaline, ornithine, phenylalanine, proline, pyrrolysine, selenocysteine, serine, taurine, threonine, tryptophan, tyrosine, and valine. Amino acid groups may be optionally substituted with one, two, three, or, in the case of amino acid groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —NH$_2$) or a substituted amino (i.e., —N(R$^{N1}$)$_2$, where R$^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy; (9) nitro; (10) oxo (e.g., carboxyaldehyde or acyl); (11) $C_{1-7}$ spirocyclyl; (12) thioalkoxy; (13) thiol; (14) —CO$_2$R$^{A'}$, where R$^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (15) —C(O)NR$^{B'}$R$^{C'}$, where each of R$^{B'}$ and R$^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —SO$_2$R$^{D'}$, where R$^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) —SO$_2$NR$^{E'}$R$^{F'}$, where each of R$^{E'}$ and R$^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —C(O)R$^{G'}$, where R$^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (19) —NR$^{H'}$C(O)R$^{I'}$, wherein R$^{H'}$ is selected from the group consisting of (a1) hydrogen and (b1) $C_{1-6}$ alkyl, and R$^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (20) —NR$^{J'}$C(O)OR$^{K'}$, wherein R$^{J'}$ is selected from the group consisting of (a1) hydrogen and (b1) $C_{1-6}$ alkyl, and R$^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein.

The term "aminoalkoxy," as used herein, represents an alkoxy group, as defined herein, substituted by an amino group, as defined herein. The alkyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy).

The term "aminoalkyl," as used herein, represents an alkyl group, as defined herein, substituted by an amino group, as defined herein. The alkyl and amino each can be further substituted with 1, 2, 3, or 4 substituent groups as described herein for the respective group (e.g., $CO_2R^{A'}$, where $R^{A'}$ is selected from the group consisting of (a) $C_1$-6 alkyl, (b) $C_{6-10}$ aryl, (c) hydrogen, and (d) $C_{1-6}$ alk-$C_{6-10}$ aryl, e.g., carboxy).

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, anthracenyl, phenanthrenyl, fluorenyl, indanyl, indenyl, and the like, and may be optionally substituted with 1, 2, 3, 4, or 5 substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) alkyl, (b) $C_{6-10}$ aryl, and (c) alk-$C_{6-10}$ aryl; (20) —$(CH_2)_qSO_2NR^{E'}R^{E'}$, where q is an integer from zero to four and where each of $R^{E'}$ and $R^{E'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) $C_{2-20}$ alkenyl; and (27) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "arylalkoxy," as used herein, represents an alkaryl group, as defined herein, attached to the parent molecular group through an oxygen atom. Exemplary unsubstituted alkoxyalkyl groups include from 7 to 30 carbons (e.g., from 7 to 16 or from 7 to 20 carbons, such as $C_{6-10}$ aryl-$C_{1-6}$ alkoxy, $C_{6-10}$ aryl-$C_{1-10}$ alkoxy, or $C_{6-10}$ aryl-$C_{1-20}$ alkoxy).

In some embodiments, the arylalkoxy group can be substituted with 1, 2, 3, or 4 substituents as defined herein.

The term "aryloxy" represents a chemical substituent of formula —OR', where R' is an aryl group of 6 to 18 carbons, unless otherwise specified. In some embodiments, the aryl group can be substituted with 1, 2, 3, or 4 substituents as defined herein.

The term "aryloyl," as used herein, represents an aryl group, as defined herein, that is attached to the parent molecular group through a carbonyl group. Exemplary unsubstituted aryloyl groups are of 7 to 11 carbons. In some embodiments, the aryl group can be substituted with 1, 2, 3, or 4 substituents as defined herein.

The term "azido" represents an —$N_3$ group, which can also be represented as —N=N=N.

The term "bicyclic," as used herein, refer to a structure having two rings, which may be aromatic or non-aromatic. Bicyclic structures include spirocyclyl groups, as defined herein, and two rings that share one or more bridges, where such bridges can include one atom or a chain including two, three, or more atoms. Exemplary bicyclic groups include a bicyclic carbocyclyl group, where the first and second rings are carbocyclyl groups, as defined herein; a bicyclic aryl groups, where the first and second rings are aryl groups, as defined herein; bicyclic heterocyclyl groups, where the first ring is a heterocyclyl group and the second ring is a carbocyclyl (e.g., aryl) or heterocyclyl (e.g., heteroaryl) group; and bicyclic heteroaryl groups, where the first ring is a heteroaryl group and the second ring is a carbocyclyl (e.g., aryl) or heterocyclyl (e.g., heteroaryl) group. In some embodiments, the bicyclic group can be substituted with 1, 2, 3, or 4 substituents as defined herein for cycloalkyl, heterocyclyl, and aryl groups.

The terms "carbocyclic" and "carbocyclyl," as used herein, refer to an optionally substituted $C_{3-12}$ monocyclic, bicyclic, or tricyclic structure in which the rings, which may be aromatic or non-aromatic, are formed by carbon atoms. Carbocyclic structures include cycloalkyl, cycloalkenyl, and aryl groups.

The term "carbamoyl," as used herein, represents —C(O)—N($R^{N1}$)$_2$, where the meaning of each $R^{N1}$ is found in the definition of "amino" provided herein.

The term "carbamoylalkyl," as used herein, represents an alkyl group, as defined herein, substituted by a carbamoyl group, as defined herein. The alkyl group can be further substituted with 1, 2, 3, or 4 substituent groups as described herein.

The term "carbamyl," as used herein, refers to a carbamate group having the structure —$NR^{N1}C(=O)OR$ or —$OC(=O)N(R^{N1})_2$, where the meaning of each $R^{N1}$ is found in the definition of "amino" provided herein, and R is alkyl, cycloalkyl, alkcycloalkyl, aryl, alkaryl, heterocyclyl (e.g., heteroaryl), or alkheterocyclyl (e.g., alkheteroaryl), as defined herein.

The term "carbonyl," as used herein, represents a C(O) group, which can also be represented as C=O.

The term "carboxyaldehyde" represents an acyl group having the structure —CHO.

The term "carboxy," as used herein, means —$CO_2H$.

The term "carboxyalkoxy," as used herein, represents an alkoxy group, as defined herein, substituted by a carboxy group, as defined herein. The alkoxy group can be further substituted with 1, 2, 3, or 4 substituent groups as described herein for the alkyl group.

The term "carboxyalkyl," as used herein, represents an alkyl group, as defined herein, substituted by a carboxy group, as defined herein. The alkyl group can be further substituted with 1, 2, 3, or 4 substituent groups as described herein.

The term "cyano," as used herein, represents an —CN group.

The term "cycloalkoxy" represents a chemical substituent of formula —OR, where R is a $C_{3-8}$ cycloalkyl group, as defined herein, unless otherwise specified. The cycloalkyl group can be further substituted with 1, 2, 3, or 4 substituent groups as described herein. Exemplary unsubstituted cycloalkoxy groups are from 3 to 8 carbons. In some embodiment, the cycloalkyl group can be further substituted with 1, 2, 3, or 4 substituent groups as described herein.

The term "cycloalkyl," as used herein represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, bicyclo[2.2.1.]heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like. The cycloalkyl groups of this invention can be optionally substituted with: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{6-10}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) $C_{6-10}$ alkyl, (b) $C_{6-10}$ aryl, and (c) $C_{1-6}$ alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{6-10}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) oxo; (27) $C_{2-20}$ alkenyl; and (28) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "diastereomer," as used herein means stereoisomers that are not mirror images of one another and are non-superimposable on one another.

The term "effective amount" of an agent, as used herein, is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "halo," as used herein, represents a halogen selected from bromine, chlorine, iodine, or fluorine.

The term "haloalkoxy," as used herein, represents an alkoxy group, as defined herein, substituted by a halogen group (i.e., F, Cl, Br, or I). A haloalkoxy may be substituted with one, two, three, or, in the case of alkyl groups of two carbons or more, four halogens. Haloalkoxy groups include perfluoroalkoxys (e.g., —$OCF_3$), —$OCHF_2$, —$OCH_2F$, —$OCCl_3$, —$OCH_2CH_2Br$, —$OCH_2CH(CH_2CH_2Br)CH_3$, and —$OCHICH_3$. In some embodiments, the haloalkoxy group can be further substituted with 1, 2, 3, or 4 substituent groups as described herein for alkyl groups.

The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens. Haloalkyl groups include perfluoroalkyls (e.g., —$CF_3$), —$CHF_2$, —$CH_2F$, —$CCl_3$, —$CH_2CH_2Br$, —$CH_2CH(CH_2CH_2Br)CH_3$, and —$CHICH_3$. In some embodiments, the haloalkyl group can be further substituted with 1, 2, 3, or 4 substituent groups as described herein for alkyl groups.

The term "heteroalkylene," as used herein, refers to an alkylene group, as defined herein, in which one or two of the constituent carbon atoms have each been replaced by nitrogen, oxygen, or sulfur. In some embodiments, the heteroalkylene group can be further substituted with 1, 2, 3, or 4 substituent groups as described herein for alkylene groups.

The term "heteroaryl," as used herein, represents that subset of heterocyclyls, as defined herein, which are aromatic: i.e., they contain 4n+2 pi electrons within the mono- or multicyclic ring system. Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiment, the heteroaryl is substituted with 1, 2, 3, or 4 substituents groups as defined for a heterocyclyl group.

The term "heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, benzothienyl, and the like, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3,7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl. Heterocyclic groups also include groups of the formula

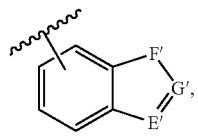

where

E' is selected from the group consisting of —N— and —CH—; F' is selected from the group consisting of —N=CH—, —NH—CH$_2$—, —NH—C(O)—, —NH—, —CH=N—, —CH$_2$—NH—, —C(O)—NH—, —CH=CH—, —CH$_2$—, —CH$_2$CH$_2$—, —CH$_2$O—, —OCH$_2$—, —O—, and —S—; and G' is selected from the group consisting of —CH— and —N—. Any of the heterocyclyl groups mentioned herein may be optionally substituted with one, two, three, four or five substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., C2-12 heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —(CH$_2$)$_q$CO$_2$R$^{A'}$, where q is an integer from zero to four, and R$^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —(CH$_2$)$_q$CONR$^{B'}$R$^{C'}$, where q is an integer from zero to four and where R$^{B'}$ and R$^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —(CH$_2$)$_q$SO$_2$R$^{D'}$, where q is an integer from zero to four and where R$^{D'}$ is selected from the group consisting of (a) $C_{1-6}$ alkyl, (b) $C_{6-10}$ aryl, and (c) $C_{1-6}$ alk-$C_{6-10}$ aryl; (20) —(CH$_2$)$_q$SO$_2$NR$^{E'}$R$^{F'}$, where q is an integer from zero to four and where each of R$^{E'}$ and R$^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) arylalkoxy; (25) $C_{1-6}$ alk-$C_{1-12}$ heterocyclyl (e.g., $C_{1-6}$ alk-$C_{1-12}$ heteroaryl); (26) oxo; (27) ($C_{1-12}$ heterocyclyl)imino; (28) $C_{2-20}$ alkenyl; and (29) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "(heterocyclyl)imino," as used herein, represents a heterocyclyl group, as defined herein, attached to the parent molecular group through an imino group. In some embodiments, the heterocyclyl group can be substituted with 1, 2, 3, or 4 substituent groups as defined herein.

The term "(heterocyclyl)oxy," as used herein, represents a heterocyclyl group, as defined herein, attached to the parent molecular group through an oxygen atom. In some embodiments, the heterocyclyl group can be substituted with 1, 2, 3, or 4 substituent groups as defined herein.

The term "(heterocyclyl)oyl," as used herein, represents a heterocyclyl group, as defined herein, attached to the parent molecular group through a carbonyl group. In some embodiments, the heterocyclyl group can be substituted with 1, 2, 3, or 4 substituent groups as defined herein.

The term "hydrocarbon," as used herein, represents a group consisting only of carbon and hydrogen atoms.

The term "hydroxy," as used herein, represents an —OH group.

The term "hydroxyalkenyl," as used herein, represents an alkenyl group, as defined herein, substituted by one to three hydroxy groups, with the proviso that no more than one hydroxy group may be attached to a single carbon atom of the alkyl group, and is exemplified by dihydroxypropenyl, hydroxyisopentenyl, and the like.

The term "hydroxyalkyl," as used herein, represents an alkyl group, as defined herein, substituted by one to three hydroxy groups, with the proviso that no more than one hydroxy group may be attached to a single carbon atom of the alkyl group, and is exemplified by hydroxymethyl, dihydroxypropyl, and the like.

The term "isomer," as used herein, means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "N-protected amino," as used herein, refers to an amino group, as defined herein, to which is attached one or two N-protecting groups, as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarb onyl, 2-nitro-4, 5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups, such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —NO$_2$ group.

The term "oxo" as used herein, represents =O.

The term "perfluoroalkyl," as used herein, represents an alkyl group, as defined herein, where each hydrogen radical bound to the alkyl group has been replaced by a fluoride radical. Perfluoroalkyl groups are exemplified by trifluoromethyl, pentafluoroethyl, and the like.

The term "perfluoroalkoxy," as used herein, represents an alkoxy group, as defined herein, where each hydrogen radical bound to the alkoxy group has been replaced by a fluoride radical. Perfluoroalkoxy groups are exemplified by trifluoromethoxy, pentafluoroethoxy, and the like.

The term "spirocyclyl," as used herein, represents a C$_{2-7}$ alkylene diradical, both ends of which are bonded to the same carbon atom of the parent group to form a spirocyclic group, and also a C$_{1-6}$ heteroalkylene diradical, both ends of which are bonded to the same atom. The heteroalkylene radical forming the spirocyclyl group can containing one, two, three, or four heteroatoms independently selected from the group consisting of nitrogen, oxygen, and sulfur. In some embodiments, the spirocyclyl group includes one to seven carbons, excluding the carbon atom to which the diradical is attached. The spirocyclyl groups of the invention may be optionally substituted with 1, 2, 3, or 4 substituents provided herein as optional substituents for cycloalkyl and/or heterocyclyl groups.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

The term "sulfoalkyl," as used herein, represents an alkyl group, as defined herein, substituted by a sulfo group of —SO$_3$H. In some embodiments, the alkyl group can be further substituted with 1, 2, 3, or 4 substituent groups as described herein.

The term "sulfonyl," as used herein, represents an —S(O)$_2$— group.

The term "thioalkaryl," as used herein, represents a chemical substituent of formula —SR, where R is an alkaryl group. In some embodiments, the alkaryl group can be further substituted with 1, 2, 3, or 4 substituent groups as described herein.

The term "thioalkheterocyclyl," as used herein, represents a chemical substituent of formula —SR, where R is an alkheterocyclyl group. In some embodiments, the alkheterocyclyl group can be further substituted with 1, 2, 3, or 4 substituent groups as described herein.

The term "thioalkoxy," as used herein, represents a chemical substituent of formula —SR, where R is an alkyl group, as defined herein. In some embodiments, the alkyl group can be further substituted with 1, 2, 3, or 4 substituent groups as described herein.

The term "thiol" represents an —SH group.

Compound. As used herein, the term "compound," as used herein, is meant to include all stereoisomers, geometric isomers, tautomers, and isotopes of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an oligonucleotide or polypeptide or may apply to a portion, region or feature thereof. Conservation of sequence may apply to the entire length of an oligonucleotide or polypeptide or may apply to a portion, region or feature thereof.

Delivery: As used herein, "delivery" refers to the act or manner of delivering a compound, substance, entity, moiety, cargo or payload.

Delivery Agent: As used herein, "delivery agent" refers to any substance which facilitates, at least in part, the in vivo delivery of a modified nucleic acid to targeted cells.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels may be located at any position in the peptides or proteins disclosed herein. They may be within the amino acids, the peptides, or proteins, or located at the N- or C-termini.

Device: As used herein, the term "device" means a piece of equipment designed to serve a special purpose. The device may comprise many features such as, but not limited to, components, electrical (e.g., wiring and circuits), storage modules and analysis modules.

Disease: As used herein, the term "disease" refers to an abnormal condition affecting the body of an organism often showing specific bodily symptoms.

Disorder: As used herein, the term "disorder," refers to a disruption of or an interference with normal functions or established systems of the body.

Digest: As used herein, the term "digest" means to break apart into smaller pieces or components. When referring to polypeptides or proteins, digestion results in the production of peptides.

Encoded protein cleavage signal: As used herein, "encoded protein cleavage signal" refers to the nucleotide sequence which encodes a protein cleavage signal.

Engineered. As used herein, embodiments of the invention are "engineered" when they are designed to have a feature or property, whether structural or chemical, that varies from a starting point, wild type or native molecule.

Exosome: As used herein, "exosome" is a vesicle secreted by mammalian cells or a complex involved in RNA degradation.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Feature: As used herein, a "feature" refers to a characteristic, a property, or a distinctive element.

Formulation: As used herein, a "formulation" includes at least a modified nucleic acid and a delivery agent.

Fragment: A "fragment," as used herein, refers to a portion. For example, fragments of proteins may comprise polypeptides obtained by digesting full-length protein isolated from cultured cells.

Functional: As used herein, a "functional" biological molecule is a biological molecule in a form in which it exhibits a property and/or activity by which it is characterized.

Heterologous: As used herein, the term "heterologous" in reference to an untranslated region such as a 5'UTR or 3'UTR means a region of nucleic acid, particularly untranslated nucleic acid which is not naturally found with the coding region encoded on the same or instant polynucleotide, primary construct or mmRNA. Homologous UTRs for example would represent those UTRs which are naturally found associated with the coding region of the mRNA, such as the wild type UTR.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% similar. The term "homologous" necessarily refers to a comparison between at least two sequences (polynucleotide or polypeptide sequences).

In accordance with the invention, two polynucleotide sequences are considered to be homologous if the polypeptides they encode are at least about 50% identical, at least about 60% identical, at least about 70% identical, at least about 80% identical, or at least about 90% identical for at least one stretch of at least about 20 amino acids.

In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the invention, two protein sequences are considered to be homologous if the proteins are at least about 50% identical, at least about 60% identical, at least about 70% identical, at least about 80% identical, or at least about 90% identical for at least one stretch of at least about 20 amino acids.

Identity: As used herein, the term "identity" refers to the overall relatedness between polymeric molecules, e.g., between oligonucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Atschul, S. F. et al., *J. Molec. Biol.,* 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

Linker: As used herein, a linker refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker may be of sufficient length as to not interfere with incorporation into a nucleic acid sequence. The linker can be used for any useful purpose, such as to form modified mRNA multimers (e.g., through linkage of two or more modified nucleic acids) or modified mRNA conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers, Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Modified: As used herein "modified" refers to a changed state or structure of a molecule of the invention. Molecules may be modified in many ways including chemically, structurally, and functionally. In one embodiment, the mRNA molecules of the present invention are modified by the introduction of non-natural nucleosides and/or nucleotides.

Naturally occurring: As used herein, "naturally occurring" means existing in nature without artificial aid.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Patient: As used herein, "patient" refers to a subject who may seek or be in need of treatment, requires treatment, is receiving treatment, will receive treatment, or a subject who is under care by a trained professional for a particular disease or condition.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional. Peptide: As used herein, "peptide" is less than or equal to 50 amino acids long, e.g., about 5, 10, 15, 20, 25, 30, 35, 40, 45, or 50 amino acids long.

Peptide: As used herein, "peptide" is less than or equal to 50 amino acids long, e.g., about 5, 10, 15, 20, 25, 30, 35, 40, 45, or 50 amino acids long.

Pharmaceutical composition: The phrase "pharmaceutical composition" refers to a composition that alters the etiology of a disease, disorder and/or condition.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418 and *Journal of Pharmaceutical Science*, 66, 2 (1977), each of which is incorporated herein by reference in its entirety.

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Physicochemical: As used herein, "physicochemical" means of or relating to a physical and/or chemical property.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestested in some way and which release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference in their entirety.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Pseudouridine: As used herein, pseudouridine refers to the C-glycoside isomer of the nucleoside uridine. A "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methyl-pseudouridine (m$^1\psi$), 1-methyl-4-thio-pseudouridine (m$^1$s$^4\psi$), 4-thio-1-methyl-pseudouridine, 3-methyl-pseudouridine (m$^3\psi$), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thio-pseudouridine, N1-methyl-pseudouridine, 1-methyl-3-(3-amino-3-carboxypropyl)pseudouridine (acp$^3\psi$), and 2'-O-methyl-pseudouridine ($\psi$m).

Purified: As used herein, "purify," "purified," "purification" means to make substantially pure or clear from unwanted components, material defilement, admixture or imperfection.

Reducing the effect: As used herein, the phrase "reducing the effect" when referring to symptoms, means reducing, eliminating or alleviating the symptom in the subject. It does not necessarily mean that the symptom will, in fact, be completely eliminated, reduced or alleviated.

Sample. As used herein, the term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Sample. As used herein, the term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Seed: As used herein with respect to micro RNA (miRNA), a miRNA "seed" is a sequence with nucleotide identity at positions 2-8 of the mature miRNA. In one embodiment, a miRNA seed comprises positions 2-7 of the mature miRNA.

Side effect: As used herein, the phrase "side effect" refers to a secondary effect of treatment.

Signal Peptide Sequences: As used herein, the phrase "signal peptide sequences" refers to a sequence which can direct the transport or localization of a protein.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Split dose: As used herein, a "split dose" is the division of single unit dose or total daily dose into two or more doses.

Stable: As used herein "stable" refers to a compound that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term means within 15 seconds.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Symptom: As used herein, the term "symptom" is a signal of a disease, disorder and/or condition. For example, symptoms may be felt or noticed by the subject who has them but may not be easily accessed by looking at a subject's outward appearance or behaviors. Examples of symptoms include, but are not limited to, weakness, aches and pains, fever, fatigue, weight loss, blood clots, increased blood calcium levels, low white blood cell count, short of breath, dizziness, headaches, hyperpigmentation, jaundice, erthema, pruritis, excessive hair growth, change in bowel habits, change in bladder function, long-lasting sores, white patches inside the mouth, white spots on the tongue, unusual bleeding or discharge, thickening or lump on parts of the body, indigestion, trouble swallowing, changes in warts or moles, change in new skin and nagging cough or hoarseness.

Synthetic: The term "synthetic" means produced, prepared, and/or manufactured by the hand of man. Synthesis of polynucleotides or polypeptides or other molecules of the present invention may be chemical or enzymatic.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Terminal region: As used herein, the term "terminal region" refers to a region on the 5' or 3' end of a region of linked nucleosides encoding a polypeptide of interest or coding region.

Terminally optimized: The term "terminally optimized" when referring to nucleic acids means the terminal regions of the nucleic acid are improved over the native terminal regions.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to a disease, disorder, and/or condition, to treat, improve symptoms of, diagnose, prevent, and/or delay the onset of the disease, disorder, and/or condition.

Therapeutically effective outcome: As used herein, "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to a disease, disorder, and/or condition, to treat, improve symptoms of, diagnose, prevent, and/or delay the onset of the disease, disorder, and/or condition.

Total daily dose: As used herein, a "total daily dose" is an amount given or prescribed in 24 hr period. It may be administered as a single unit dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Treating: As used herein, the term "treating" refers to partially or completely alleviating, ameliorating, improving, relieving, delaying onset of, inhibiting progression of, reducing severity of, and/or reducing incidence of one or more symptoms or features of a particular disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

EXAMPLES

Example 1. Modified mRNA Production

Modified mRNAs according to the invention are made using standard laboratory methods and materials.

Figure 3:
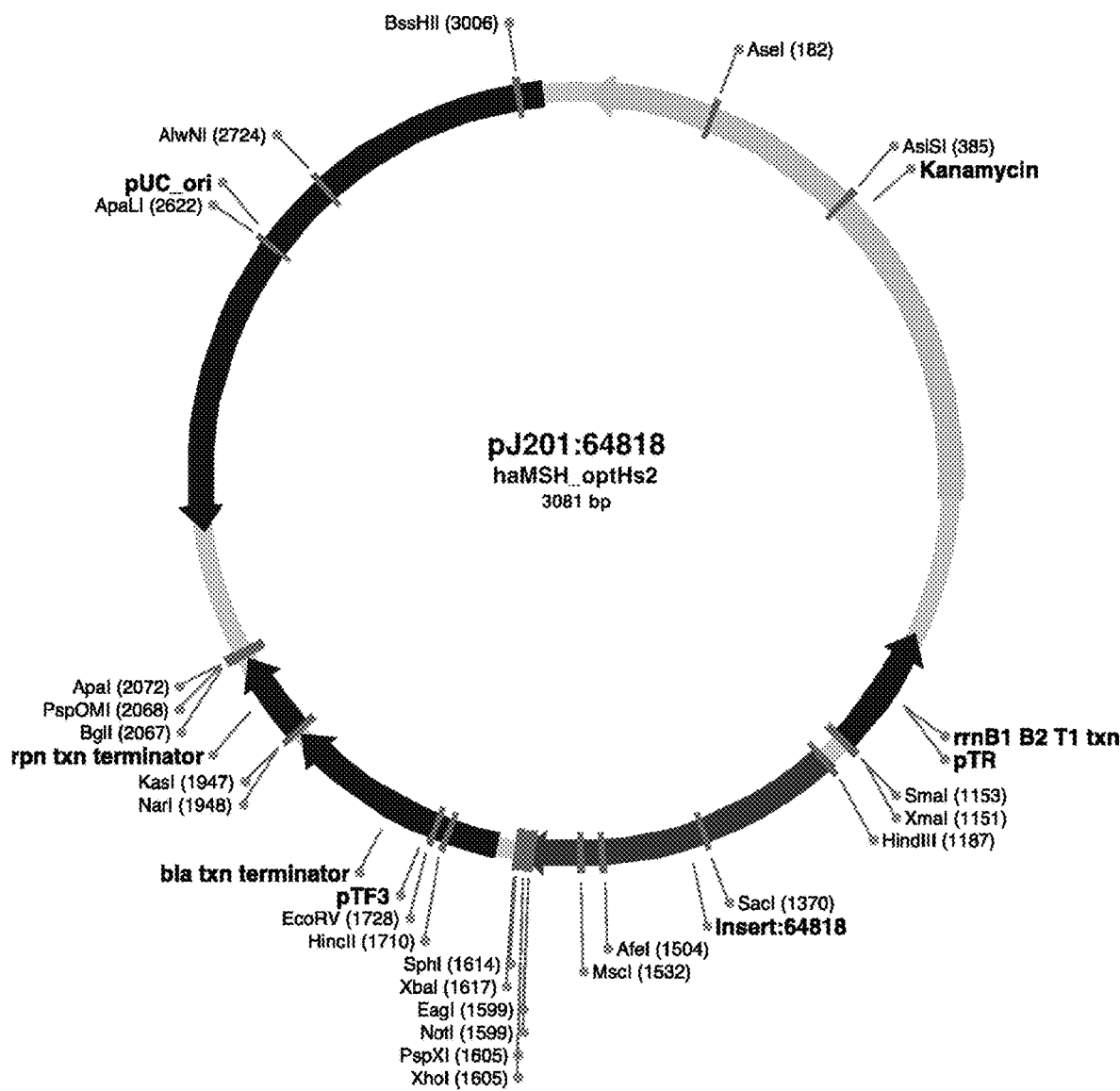
FIG. 3 is a clone map useful in the present invention.

The open reading frame with various upstream or downstream regions ((3-globin, tags, etc.) is ordered from DNA2.0 (Menlo Park, Calif.) and typically contains a multiple cloning site with XbaI recognition. Upon receipt of the construct, it is reconstituted and transformed into chemically competent E. coli. For the present invention, NEB DH5-alpha Competent E. coli are used. A typical clone map is shown in FIG. 3. Transformations are performed according to NEB instructions using 100 ng of plasmid. The protocol is as follows:
1. Thaw a tube of NEB 5-alpha Competent E. coli cells on ice for 10 minutes.
2. Add 1-5 µl containing 1 pg-100 ng of plasmid DNA to the cell mixture. Carefully flick the tube 4-5 times to mix cells and DNA. Do not vortex.
3. Place the mixture on ice for 30 minutes. Do not mix.
4. Heat shock at 42° C. for exactly 30 seconds. Do not mix.
5. Place on ice for 5 minutes. Do not mix.
6. Pipette 950 µl of room temperature SOC into the mixture.
7. Place at 37° C. for 60 minutes. Shake vigorously (250 rpm) or rotate.
8. Warm selection plates to 37° C.
9. Mix the cells thoroughly by flicking the tube and inverting.
10. Spread 50-100 µl of each dilution onto a selection plate and incubate overnight at 37° C. Alternatively, incubate at 30° C. for 24-36 hours or 25° C. for 48 hours.

A single colony is then used to inoculate 5 ml of LB growth media using the appropriate antibiotic and then allowed to grow (250 RPM, 37° C.) for 5 hours. This is then used to inoculate a 200 ml culture medium and allowed to grow overnight under the same conditions.

To isolate the plasmid (up to 850 µg), a maxi prep is performed using the Invitrogen PureLink™ HiPure Maxiprep Kit (Carlsbad, Calif.), following the manufacturer's instructions.

In order to generate cDNA for In Vitro Transcription (IVT), the plasmid is first linearized using a restriction enzyme such as XbaI. A typical restriction digest with XbaI will comprise the following: Plasmid1.0 Gig; 10× Buffer 1.0 µl; XbaI1.5 µl; dH$_2$0

Up to 10 µl; incubated at 37° C. for 1 hr. If performing at lab scale (<5 µg), the reaction is cleaned up using Invitrogen's PureLink™ PCR Micro Kit (Carlsbad, Calif.) per manufacturer's instructions. Larger scale purifications may need to be done with a product that has a larger load capacity such as Invitrogen's standard PureLink PCR Kit (Carlsbad, Calif.). Following the cleanup, the linearized vector is quantified using the NanoDrop and analyzed to confirm linearization using agarose gel electrophoresis.

As a non-limiting example, G-CSF may represent the polypeptide of interest. Sequences used in the steps outlined in Examples 1-5 are shown in Table 16. It should be noted that the start codon (ATG) has been underlined in each sequence of Table 16.

TABLE 16

G-CSF Sequences

| SEQ ID NO | Description |
|---|---|
| 4255 | cDNAsequence:<br>ATGGCTGGACCTGCCACCCAGAGCCCCATGAAGCTGATGGCCCTGCAG<br>CTGCTGCTGTGGCACAGTGCACTCTGGACAGTGCAGGAAGCCACCCCC<br>CTGGGCCCTGCCAGCTCCCTGCCCCAGAGCTTCCTGCTCAAGTGCTTAG<br>AGCAAGTGAGGAAGATCCAGGGCGATGGCGCAGCGCTCCAGGAGAAG<br>CTGTGTGCCACCTACAAGCTGTGCCACCCCGAGGAGCTGGTGCTGCTCG<br>GACACTCTCTGGGCATCCCCTGGGCTCCCCTGAGCAGCTGCCCCAGCCA<br>GGCCCTGCAGCTGGCAGGCTGCTTGAGCCAACTCCATAGCGGCCTTTTC<br>CTCTACCAGGGGCTCCTGCAGGCCCTGGAAGGGATCTCCCCCGAGTTG<br>GGTCCCACCTTGGACACACTGCAGCTGGACGTCGCCGACTTTGCCACCA<br>CCATCTGGCAGCAGATGGAAGAACTGGGAATGGCCCCTGCCCTGCAGC<br>CCACCCAGGGTGCCATGCCGGCCTTCGCCTCTGCTTTCCAGCGCCGGGC<br>AGGAGGGGTCCTGGTTGCCTCCCATCTGCAGAGCTTCCTGGAGGTGTCG<br>TACCGCGTTCTACGCCACCTTGCCCAGCCCTGA |
| 4256 | cDNA having T7 polymerase site, AfeI and Xba restriction site:<br>TAATACGACTCACTATA<br>GGGAAATAAGAGAGAAAAGAAGAGTAAGAAGAAATATAAGAGCCACC<br>ATGGCTGGACCTGCCACCCAGAGCCCCATGAAGCTGATGGCCCTGCAG<br>CTGCTGCTGTGGCACAGTGCACTCTGGACAGTGCAGGAAGCCACCCCC<br>CTGGGCCCTGCCAGCTCCCTGCCCCAGAGCTTCCTGCTCAAGTGCTTAG<br>AGCAAGTGAGGAAGATCCAGGGCGATGGCGCAGCGCTCCAGGAGAAG<br>CTGTGTGCCACCTACAAGCTGTGCCACCCCGAGGAGCTGGTGCTGCTCG<br>GACACTCTCTGGGCATCCCCTGGGCTCCCCTGAGCAGCTGCCCCAGCCA<br>GGCCCTGCAGCTGGCAGGCTGCTTGAGCCAACTCCATAGCGGCCTTTTC<br>CTCTACCAGGGGCTCCTGCAGGCCCTGGAAGGGATCTCCCCCGAGTTG<br>GGTCCCACCTTGGACACACTGCAGCTGGACGTCGCCGACTTTGCCACCA<br>CCATCTGGCAGCAGATGGAAGAACTGGGAATGGCCCCTGCCCTGCAGC<br>CCACCCAGGGTGCCATGCCGGCCTTCGCCTCTGCTTTCCAGCGCCGGGC<br>AGGAGGGGTCCTGGTTGCCTCCCATCTGCAGAGCTTCCTGGAGGTGTCG<br>TACCGCGTTCTACGCCACCTTGCCCAGCCCTGA<br>AGCGCTGCCTTCTGCGGGGCTTGCCTTCTGGCCATGCCCTTCTTCTCTCC<br>CTTGCACCTGTACCTCTTGGTCTTTGAATAAAGCCTGAGTAGGAAGGCG<br>GCCGCTCGAGCATGCATCTAGA |
| 4257 | Optimized sequence; containing T7 polymerase site, AfeI and Xba restriction site<br>TAATACGACTCACTATA<br>GGGAAATAAGAGAGAAAAGAAGAGTAAGAAGAAATATAAGAGCCACC<br>ATGGCCGGTCCCGCGACCCAAAGCCCCATGAAACTTATGGCCCTGCAG<br>TTGCTGCTTTGGCACTCGGCCCTCTGGACAGTCCAAGAAGCGACTCCTC<br>TCGGACCTGCCTCATCGTTGCCGCAGTCATTCCTTTTGAAGTGTCTGGA<br>GCAGGTGCGAAAGATTCAGGGCGATGGAGCCGCACTCCAAGAGAAGC |

TABLE 16-continued

G-CSF Sequences

SEQ ID NO | Description
---|---
 | TCTGCGCGACATACAAACTTTGCCATCCCGAGGAGCTCGTACTGCTCGG
 | GCACAGCTTGGGGATTCCCTGGGCTCCTCTCTCGTCCTGTCCGTCGCAG
 | GCTTTGCAGTTGGCAGGGTGCCTTTCCCAGCTCCACTCCGGTTTGTTCTT
 | GTATCAGGGACTGCTGCAAGCCCTTGAGGGAATCTCGCCAGAATTGGG
 | CCCGACGCTGGACACGTTGCAGCTCGACGTGGCGGATTTCGCAACAAC
 | CATCTGGCAGCAGATGGAGGAACTGGGGATGGCACCCGCGCTGCAGCC
 | CACGCAGGGGGCAATGCCGGCCTTTGCGTCCGCGTTTCAGCGCAGGGC
 | GGGTGGAGTCCTCGTAGCGAGCCACCTTCAATCATTTTTGGAAGTCTCG
 | TACCGGGTGCTGAGACATCTTGCGCAGCCGTGA
 | AGCGCTGCCTTCTGCGGGGCTTGCCTTCTGGCCATGCCCTTCTTCTCTCC
 | CTTGCACCTGTACCTCTTGGTCTTTGAATAAAGCCTGAGTAGGAAGGCG
 | GCCGCTCGAGCATGCATCTAGA
4258 | mRNA sequence (transcribed)
 | GGGAAAUAAGAGAGAAAAGAAGAGUAAGAAGAAAUAUAAGAGCCACC
 | <u>AUG</u>GCCGGUCCCGCGACCCAAAGCCCCAUGAAACUUAUGGCCCUGCA
 | GUUGCUGCUUUGGCACUCGGCCCUCUGGACAGUCCAAGAAGCGACUC
 | CUCUCGGACCUGCCUCAUCGUUGCCGCAGUCAUUCCUUUUGAAGUGU
 | CUGGAGCAGGUGCGAAAGAUUCAGGGCGAUGGAGCCGCACUCCAAGA
 | GAAGCUCUGCGCGACAUACAAACUUUGCCAUCCCGAGGAGCUCGUAC
 | UGCUCGGGCACAGCUUGGGGAUUCCCUGGGCUCCUCUCUCGUCCUGU
 | CCGUCGCAGGCUUUGCAGUUGGCAGGGUGCCUUUCCCAGCUCCACUC
 | CGGUUUGUUCUUGUAUCAGGGACUGCUGCAAGCCCUUGAGGGAAUC
 | UCGCCAGAAUUGGGCCCGACGCUGGACACGUUGCAGCUCGACGUGGC
 | GGAUUUCGCAACAACCAUCUGGCAGCAGAUGGAGGAACUGGGGAUG
 | GCACCCGCGCUGCAGCCCACGCAGGGGGCAAUGCCGGCCUUUGCGUC
 | CGCGUUUCAGCGCAGGGCGGGUGGAGUCCUCGUAGCGAGCCACCUUC
 | AAUCAUUUUUGGAAGUCUCGUACCGGGUGCUGAGACAUCUUGCGCA
 | GCCGUGA
 | AGCGCUGCCUUCUGCGGGGCUUGCCUUCUGGCCAUGCCCUUCUUCUC
 | UCCCUUGCACCUGUACCUCUUGGUCUUUGAAUAAAGCCUGAGUAGGA
 | AG Example 2: PCR for cDNA Production PCR procedures for the preparation of cDNA is performed using 2×KAPA HiFi™ HotStart ReadyMix by Kapa Biosystems (Woburn, Mass.). This system includes 2× KAPA ReadyMix 12.5 µl; Forward Primer (10 uM) 0.75 µl; Reverse Primer (10 uM) 0.75 µl; Template cDNA 100 ng; and dH$_2$0 diluted to 25.0 µl. The reaction conditions are at 95° C. for 5 min. and 25 cycles of 98° C. 20 sec, then 58° C. 15 sec, then 72° C. 45 sec, then 72° C. 5 min. then 4° C. to termination.

The reverse primer of the instant invention incorporates a poly-T$_{120}$ for a poly-A$_{120}$ in the mRNA. Other reverse primers with longer or shorter poly(T) tracts can be used to adjust the length of the poly(A) tail in the mRNA.

The reaction is cleaned up using Invitrogen's PureLink™ PCR Micro Kit (Carlsbad, Calif.) per manufacturer's instructions (up to 5 µg). Larger reactions will require a cleanup using a product with a larger capacity. Following the cleanup, the cDNA is quantified using the NanoDrop and analyzed by agarose gel electrophoresis to confirm the cDNA is the expected size. The cDNA is then submitted for sequencing analysis before proceeding to the in vitro transcription reaction.

Example 3. In Vitro Transcription

The in vitro transcription reaction generates mRNA containing modified nucleotides or modified RNA. The input nucleotide triphosphate (NTP) mix is made in-house using natural and un-natural NTPs.

A typical in vitro transcription reaction includes the following:

1. Template cDNA 1.0 µg
2. 10× transcription buffer (400 mM Tris-HCl pH 8.0, 190 mM MgCl2, 50 mM DTT, 10 mM Spermidine) 2.0 µl
3. Custom NTPs (25 mM each) 7.2 µl
4. RNase Inhibitor 20 U
5. T7 RNA polymerase 3000 U
6. dH$_2$0 Up to 20.0 µl. and
7. Incubation at 37° C. for 3 hr-5 hrs.

The crude IVT mix may be stored at 4° C. overnight for cleanup the next day. 1 U of RNase-free DNase is then used to digest the original template. After 15 minutes of incubation at 37° C., the mRNA is purified using Ambion's MEGAclear™ Kit (Austin, Tex.) following the manufacturer's instructions. This kit can purify up to 500 µg of RNA. Following the cleanup, the RNA is quantified using the NanoDrop and analyzed by agarose gel electrophoresis to confirm the RNA is the proper size and that no degradation of the RNA has occurred.

Example 4. Enzymatic Capping of mRNA

Capping of the mRNA is performed as follows where the mixture includes: IVT RNA 60 µg-180 g and dH$_2$0 up to 72 µl. The mixture is incubated at 65° C. for 5 minutes to denature RNA, then transfer immediately to ice.

The protocol then involves the mixing of 10× Capping Buffer (0.5 M Tris-HCl (pH 8.0), 60 mM KCl, 12.5 mM MgCl2)(10.0 µl); 20 mM GTP (5.0 µl); 20 mM S-Adenosyl Methionine (2.5 µl); RNase Inhibitor (100 U); 2'-O-Methyltransferase (400 U); Vaccinia capping enzyme (Guanylyl transferase) (40 U); dH$_2$0 (Up to 28 µl); and incubation at 37° C. for 30 minutes for 60 µg RNA or up to 2 hours for 180 µg of RNA.

The mRNA is then purified using Ambion's MEGAclear™ Kit (Austin, Tex.) following the manufacturer's instructions. Following the cleanup, the RNA is quantified using the NanoDrop (ThermoFisher, Waltham, Mass.) and analyzed by agarose gel electrophoresis to confirm the RNA is the proper size and that no degradation of the RNA has occurred. The RNA product may also be sequenced by running a reverse-transcription-PCR to generate the cDNA for sequencing.

Example 5. PolyA Tailing Reaction

Without a poly-T in the cDNA, a poly-A tailing reaction must be performed before cleaning the final product. This is done by mixing Capped IVT RNA (100 µl); RNase Inhibitor (20 U); 10× Tailing Buffer (0.5 M Tris-HCl (pH 8.0), 2.5 M NaCl, 100 mM MgCl2)(12.0 µl); 20 mM ATP (6.0 µl); Poly-A Polymerase (20 U); dH$_2$0 up to 123.5 µl and incubation at 37° C. for 30 min. If the poly-A tail is already in the transcript, then the tailing reaction may be skipped and proceed directly to cleanup with Ambion's MEGAclear™ kit (up to 500 µg). Poly-A Polymerase is preferably a recombinant enzyme expressed in yeast.

For studies performed and described herein, the poly-A tail is encoded in the IVT template to comprise 160 nucleotides in length. However, it should be understood that the processivity or integrity of the polyA tailing reaction may not always result in exactly 160 nucleotides. Hence polyA tails of approximately 160 nucleotides, e.g, about 150-165, 155, 156, 157, 158, 159, 160, 161, 162, 163, 164 or 165 are within the scope of the invention.

Example 6. Natural 5' Caps and 5' Cap Analogues

5'-capping of modified RNA may be completed concomitantly during the in vitro-transcription reaction using the following chemical RNA cap analogs to generate the 5'-guanosine cap structure according to manufacturer protocols: 3'-O-Me-m7G(5')ppp(5')G; G(5')ppp(5')A; G(5')ppp(5')G; m7G(5')ppp(5')A; m7G(5')ppp(5')G (New England BioLabs, Ipswich, Mass.). 5'-capping of modified RNA may be completed post-transcriptionally using a Vaccinia Virus Capping Enzyme to generate the "Cap 0" structure: m7G(5')ppp(5')G (New England BioLabs, Ipswich, Mass.). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes are preferably derived from a recombinant source.

When transfected into mammalian cells, the modified mRNAs may have a stability of between 12-18 hours or more than 18 hours, e.g., 24, 36, 48, 60, 72 or greater than 72 hours.

Example 7. Chemical Cap Vs. Enzymatically-Derived Cap Protein Expression Assay

Synthetic mRNAs encoding human G-CSF containing the ARCA cap analog or the Cap1 structure can be transfected into human primary keratinocytes at equal concentrations. 6, 12, 24 and 36 hours post-transfection the amount of G-CSF secreted into the culture medium can be assayed by ELISA. Synthetic mRNAs that secrete higher levels of G-CSF into the medium would correspond to a synthetic mRNA with a higher translationally-competent Cap structure.

Example 8. Chemical Cap Vs. Enzymatically-Derived Cap Purity Analysis

Synthetic mRNAs encoding human G-CSF containing the ARCA cap analog or the Cap1 structure crude synthesis products can be compared for purity using denaturing Agarose-Urea gel electrophoresis or HPLC analysis. Synthetic mRNAs with a single, consolidated band by electrophoresis correspond to the higher purity product compared to a synthetic mRNA with multiple bands or streaking bands. Synthetic mRNAs with a single HPLC peak would also correspond to a higher purity product. The capping reaction with a higher efficiency would provide a more pure mRNA population.

Example 9. Chemical Cap Vs. Enzymatically-Derived Cap Cytokine Analysis

Synthetic mRNAs encoding human G-CSF containing the ARCA cap analog or the Cap1 structure can be transfected into human primary keratinocytes at multiple concentrations. 6, 12, 24 and 36 hours post-transfection the amount of pro-inflammatory cytokines such as TNF-alpha and IFN-beta secreted into the culture medium can be assayed by ELISA. Synthetic mRNAs that secrete higher levels of pro-inflammatory cytokines into the medium would correspond to a synthetic mRNA containing an immune-activating cap structure.

Example 10. Chemical Cap Vs. Enzymatically-Derived Cap Capping Reaction Efficiency Synthetic mRNAs encoding human G-CSF containing the ARCA cap analog or the Cap1 structure can be analyzed for capping reaction efficiency by LC-MS after capped mRNA nuclease treatment. Nuclease treatment of capped mRNAs would yield a mixture of free nucleotides and the capped 5'-5-triphosphate cap structure detectable by LC-MS. The amount of capped product on the LC-MS spectra can be expressed as a percent of total mRNA from the reaction and would correspond to capping reaction efficiency. The Cap structure with a higher capping reaction efficiency would have a higher amount of capped product by LC-MS.

Example 11. Agarose Gel Electrophoresis of Modified RNA or RT PCR Products

Individual modRNAs (200-400 ng in a 20 µl volume) or reverse transcribed PCR products (200-400 ng) are loaded into a well on a non-denaturing 1.2% Agarose E-Gel (Invitrogen, Carlsbad, Calif.) and run for 12-15 minutes according to the manufacturer protocol.

Example 12. Nanodrop Modified RNA Quantification and UV Spectral Data

Modified RNAs in TE buffer (1 µl) are used for Nanodrop UV absorbance readings to quantitate the yield of each modified RNA from an in vitro transcription reaction.

Example 13. In Vitro Transcription of Modified RNA Containing Varying Poly-A Tail Lengths Modified mRNAs were made using standard laboratory methods and materials for in vitro transcription with the exception that the nucleotide mix contains modified nucleotides. Modified mRNAs of the present example included 5-methycytosine and pseudouridine. The open reading frame (ORF) of the gene of interest is flanked by a 5' untranslated region (UTR) containing a strong Kozak translational initiation signal and an alpha-globin 3' UTR terminating with an oligo(dT) sequence for templated addition of a polyA tail for modified RNAs not incorporating Adenosine analogs. Adenosine-containing modRNAs are synthesized without an oligo (dT) sequence to allow for post-transcription poly (A) polymerase poly-(A) tailing. Poly-a tail lengths of 0 nts, 80 nts, 120 nts, 160 nts were generated for human G-CSF. G-CSF sequences include the cDNA sequence (SEQ ID NO: 4257), the mRNA sequence (SEQ ID NO: 4258) and the protein sequence (SEQ ID NO: 4259). Detection of G-CSF may be performed by the primer probe sets for cDNA including the forward primer TTG GAC CCT CGT ACA GAA GCT AAT ACG (SEQ ID NO: 4260), a reverse primer for template Poly(A) tailing T$_{(120)}$CT TCC TAC TCA GGC TTT ATT CAA AGA CCA (SEQ ID NO: 4261) and a reverse primer for post-transcriptional Poly(A) polymerase tailing CTT CCT ACT CAG GCT TTA TTC AAA GAC CA (SED ID NO: 4262). Detection may also be performed by G-CSF modified nucleic acid molecule reverse-transcriptase polymerase chain reaction (RT-PCR) forward primer TGG CCG GTC CCG CGA CCC AA (SEQ ID NO: 4263) and reverse primer GCT TCA CGG CTG CGC AAG AT (SEQ ID NO: 4264).

Synthesized reverse primers were designed and ordered from IDT. The reverse primers incorporate a poly-T40, poly-T80, poly-T120, poly-T160 for a poly-A40, poly-A80, poly-A120, and poly-A160 respectively. The Human Embryonic Kidney (HEK) 293 were grown in Eagles' Minimal Essential Medium (EMEM) and 10% Fetal Bovine Serum (FBS) until they reached a confluence of 80-90%. Approximately 80,000 cells were transfected with 100 ng and 500 ng of modified RNA complexed with RNAiMax from Invitrogen (Carlsbad, Calif.) in a 24-well plate. The RNA:RNAiMax complex was formed by first incubating the RNAiMax with EMEM in a 5× volumetric dilution for 10 minutes at room temperature.

Figure 4:
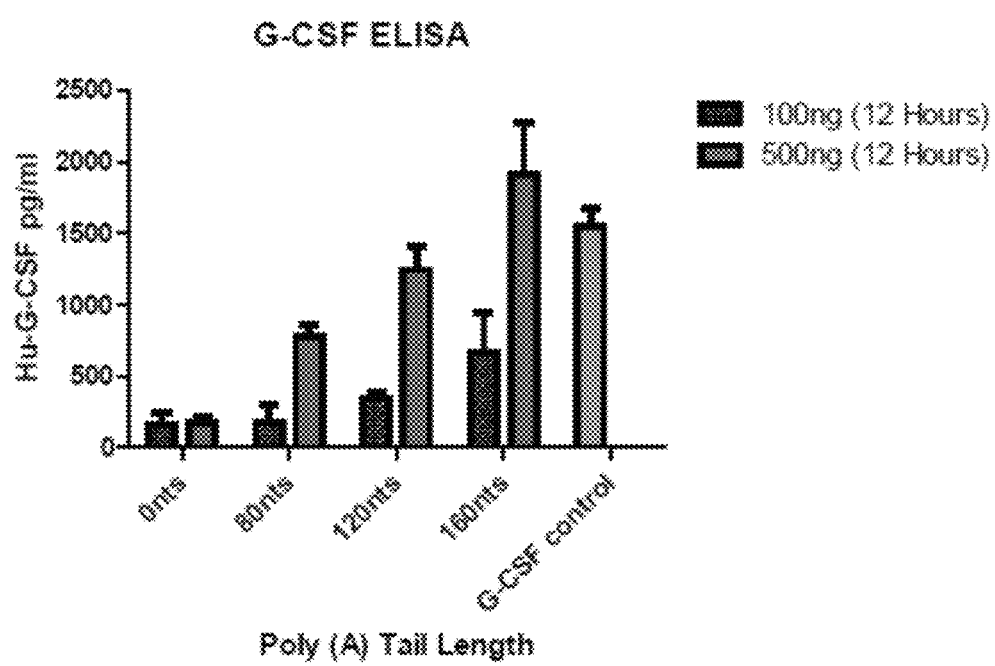
FIG. 4 is a histogram showing the improved protein production from modified mRNAs of the present invention having increasingly longer poly-A tails at two concentrations.

The RNA vial was then mixed with the RNAiMAX vial and incubated for 20-30 at room temperature before being added to the cells in a drop-wise fashion. Recombinant Human G-CSF was added at 2 ng/mL to the control cell culture wells. The concentration of secreted Human G-CSF was measured at 12 hours post-transfection. FIG. 4 shows the histogram for the Enzyme-linked immunosorbent assay (ELISA) for Human G-CSF from HEK293 cells transfected with human G-CSF modified RNA that had varying poly-A tail lengths: 0nts, 80 nts, 120 nts, 160 nts. We observed increased protein expression with the 160 nts poly-A tail.

From the data it can be determined that longer poly-A tails produce more protein and that this activity is dose dependent.

Example 14. Expression of Modified Nucleic Acid with microRNA Binding Site

Human embryonic kidney epithelial cells (HEK293A) and primary human hepatocytes (Hepatocytes) were seeded at a density of 200,000 per well in 500 ul cell culture medium (InVitro GRO medium from Celsis, Chicago, Ill.). G-CSF mRNA having an alpha-globin 3'UTR (G-CSF alpha) (cDNA sequence is shown in SEQ ID NO: 4265; mRNA sequence is shown in SEQ ID NO: 4266; polyA tail of approximately 160 nucleotides not shown in sequence; 5'Cap, Cap1; fully modified with 5-methylcytidine and pseudouridine) G-CSF mRNA having an alpha-globin 3'UTR and a miR-122 binding site (G-CSF miR-122) (cDNA sequence is shown in SEQ ID NO: 4267; mRNA sequence is shown in SEQ ID NO: 4268; polyA tail of approximately 160 nucleotides not shown in sequence; 5'Cap, Cap1; fully modified with 5-methylcytidine and pseudouridine) or G-CSF mRNA having an alpha-globin 3'UTR with four miR-122 binding sites with the seed deleted (G-CSF no seed) (cDNA sequence is shown in SEQ ID NO: 4269; mRNA sequence is shown in SEQ ID NO: 4270; polyA tail of approximately 160 nucleotides not shown in sequence; 5'Cap, Cap1; fully modified with 5-methylcytidine and pseudouridine) was tested at a concentration of 250 ng per well in 24 well plates. The expression of G-CSF was measured by ELISA and the results are shown in Table 17

TABLE 17

| miR-122 Binding Sites | HEK293A Protein Expression (ng/mL) | Hepatocytes Protein Expression (ng/mL) |
| --- | --- | --- |
| G-CSF alpha | 99.85 | 8.18 |
| G-CSF miR-122 | 87.67 | 0 |
| G-CSF no seed | 200.2 | 8.05 |

Since HEK293 cells do not express miR-122 there was no down-regulation of G-CSF protein from the sequence containing miR-122. Whereas, the human hepatocytes express high levels of miR-122 and there was a drastic down-regulation of G-CSF protein observed when the G-CSF sequence contained the miR-122 target sequence. Consequently, the mRNA functioned as an auxotrophic mRNA.

Example 15. Directed SAR of Pseudouridine and N1-Methyl PseudoUridine

With the recent focus on the pyrimidine nucleoside pseudouridine, a series of structure-activity studies were designed to investigate mRNA containing modifications to pseudouridine or N1-methyl-pseudourdine.

The study was designed to explore the effect of chain length, increased lipophilicity, presence of ring structures, and alteration of hydrophobic or hydrophilic interactions when modifications were made at the N1 position, C6 position, the 2-position, the 4-position and on the phosphate backbone. Stability is also investigated.

To this end, modifications involving alkylation, cycloalkylation, alkyl-cycloalkylation, arylation, alkyl-arylation, alkylation moieties with amino groups, alkylation moieties with carboxylic acid groups, and alkylation moieties containing amino acid charged moieties are investigated. The degree of alkylation is generally $C_1$-$C_6$. Examples of the chemistry modifications include those listed in Table 18 and 19.

TABLE 18

Pseudouridine and N1-methyl Pseudo Uridine SAR

| Chemistry Modification | Compound # | Naturally occuring |
|---|---|---|
| N1-Modifications | | |
| N1-Ethyl-pseudo-UTP | 1 | N |
| N1-Propyl-pseudo-UTP | 2 | N |
| N1-iso-propyl-pseudo-UTP | 3 | N |
| N1-(2,2,2-Trifluoroethyl)-pseudo-UTP | 4 | N |
| N1-Cyclopropyl-pseudo-UTP | 5 | N |
| N1-Cyclopropylmethyl-pseudo-UTP | 6 | N |
| N1-Phenyl-pseudo-UTP | 7 | N |
| N1-Benzyl-pseudo-UTP | 8 | N |
| N1-Aminomethyl-pseudo-UTP | 9 | N |
| P seudo-UTP-N1-2-ethanoic acid | 10 | N |
| N 1-(3-Amino-3-carboxypropyl)pseudo-UTP | 11 | N |
| N1-Methyl-3-(3-amino-3-carboxy-propyl)pseudo-UTP | 12 | Y |
| C-6 Modifications | | |
| 6-Methyl-pseudo-UTP | 13 | N |
| 6-Trifluoromethyl-pseudo-UTP | 14 | N |
| 6-Methoxy-pseudo-UTP | 15 | N |
| 6-Phenyl-pseudo-UTP | 16 | N |
| 6-Iodo-pseudo-UTP | 17 | N |
| 6-Bromo-pseudo-UTP | 18 | N |
| 6-Chloro-pseudo-UTP | 19 | N |
| 6-Fluoro-pseudo-UTP | 20 | N |
| 2- or 4-position Modifications | | |
| 4-Thio-pseudo-UTP | 21 | N |
| 2-Thio-pseudo-UTP | 22 | N |
| Phosphate backbone Modifications | | |
| Alpha-thio-pseudo-UTP | 23 | N |
| N1-Me-alpha-thio-pseudo-UTP | 24 | N |

TABLE 19

Pseudouridine and N1-methyl Pseudo Uridine SAR

| Chemistry Modification | Compound # | Naturally occuring |
|---|---|---|
| N1-Methyl-pseudo-UTP | 1 | Y |
| N1-Butyl-pseudo-UTP | 2 | N |
| N1-tert-Butyl-pseudo-UTP | 3 | N |
| N1-Pentyl-pseudo-UTP | 4 | N |
| N1-Hexyl-pseudo-UTP | 5 | N |
| N1-Trifluoromethyl-pseudo-UTP | 6 | Y |
| N1-Cyclobutyl-pseudo-UTP | 7 | N |
| N1-Cyclopentyl-pseudo-UTP | 8 | N |
| N1-Cyclohexyl-pseudo-UTP | 9 | N |
| N1-Cycloheptyl-pseudo-UTP | 10 | N |
| N1-Cyclooctyl-pseudo-UTP | 11 | N |
| N1-Cyclobutylmethyl-pseudo-UTP | 12 | N |
| N1-Cyclopentylmethyl-pseudo-UTP | 13 | N |
| N1-Cyclohexylmethyl-pseudo-UTP | 14 | N |
| N1-Cycloheptylmethyl-pseudo-UTP | 15 | N |
| N1-Cyclooctylmethyl-pseudo-UTP | 16 | N |
| N1-p-tolyl-pseudo-UTP | 17 | N |
| N1-(2,4,6-Trimethyl-phenyl)pseudo-UTP | 18 | N |
| N1-(4-Methoxy-phenyl)pseudo-UTP | 19 | N |
| N1-(4-Amino-phenyl)pseudo-UTP | 20 | N |
| N1(4-Nitro-phenyl)pseudo-UTP | 21 | N |
| Pseudo-UTP-N1-p-benzoic acid | 22 | N |
| N1-(4-Methyl-benzyl)pseudo-UTP | 24 | N |
| N1-(2,4,6-Trimethyl-benzyl)pseudo-UTP | 23 | N |
| N1-(4-Methoxy-benzyl)pseudo-UTP | 25 | N |
| N1-(4-Amino-benzyl)pseudo-UTP | 26 | N |
| N1-(4-Nitro-benzyl)pseudo-UTP | 27 | N |
| Pseudo-UTP-N1-methyl-p-benzoic acid | 28 | N |
| N1-(2-Amino-ethyl)pseudo-UTP | 29 | N |
| N1-(3-Amino-propyl)pseudo-UTP | 30 | N |
| N1-(4-Amino-butyl)pseudo-UTP | 31 | N |
| N1-(5-Amino-pentyl)pseudo-UTP | 32 | N |
| N1-(6-Amino-hexyl)pseudo-UTP | 33 | N |
| Pseudo-UTP-N1-3-propionic acid | 34 | N |
| Pseudo-UTP-N1-4-butanoic acid | 35 | N |
| Pseudo-UTP-N1-5-pentanoic acid | 36 | N |
| Pseudo-UTP-N1-6-hexanoic acid | 37 | N |
| Pseudo-UTP-N1-7-heptanoic acid | 38 | N |
| N1-(2-Amino-2-carboxyethyl)pseudo-UTP | 39 | N |
| N1-(4-Amino-4-carboxybutyl)pseudo-UTP | 40 | N |
| N3-Alkyl-pseudo-UTP | 41 | N |
| 6-Ethyl-pseudo-UTP | 42 | N |
| 6-Propyl-pseudo-UTP | 43 | N |
| 6-iso-Propyl-pseudo-UTP | 44 | N |
| 6-Butyl-pseudo-UTP | 45 | N |
| 6-tert-Butyl-pseudo-UTP | 46 | N |
| 6-(2,2,2-Trifluoroethyl)-pseudo-UTP | 47 | N |
| 6-Ethoxy-pseudo-UTP | 48 | N |
| 6-Trifluoromethoxy-pseudo-UTP | 49 | N |
| 6-Phenyl-pseudo-UTP | 50 | N |
| 6-(Substituted-Phenyl)-pseudo-UTP | 51 | N |
| 6-Cyano-pseudo-UTP | 52 | N |
| 6-Azido-pseudo-UTP | 53 | N |
| 6-Amino-pseudo-UTP | 54 | N |
| 6-Ethylcarboxylate-pseudo-UTP | 54b | N |
| 6-Hydroxy-pseudo-UTP | 55 | N |
| 6-Methylamino-pseudo-UTP | 55b | N |
| 6-Dimethylamino-pseudo-UTP | 57 | N |
| 6-Hydroxyamino-pseudo-UTP | 59 | N |
| 6-Formyl-pseudo-UTP | 60 | N |
| 6-(4-Morpholino)-pseudo-UTP | 61 | N |
| 6-(4-Thiomorpholino)-pseudo-UTP | 62 | N |
| N1-Me-4-thio-pseudo-UTP | 63 | N |
| N1-Me-2-thio-pseudo-UTP | 64 | N |
| 1,6-Dimethyl-pseudo-UTP | 65 | N |
| 1-Methyl-6-trifluoromethyl-pseudo-UTP | 66 | N |
| 1-Methyl-6-ethyl-pseudo-UTP | 67 | N |
| 1-Methyl-6-propyl-pseudo-UTP | 68 | N |
| 1-Methyl-6-iso-propyl-pseudo-UTP | 69 | N |
| 1-Methyl-6-butyl-pseudo-UTP | 70 | N |
| 1-Methyl-6-tert-butyl-pseudo-UTP | 71 | N |
| 1-Methyl-6-(2,2,2-Trifluoroethyl)pseudo-UTP | 72 | N |
| 1-Methyl-6-iodo-pseudo-UTP | 73 | N |
| 1-Methyl-6-bromo-pseudo-UTP | 74 | N |
| 1-Methyl-6-chloro-pseudo-UTP | 75 | N |
| 1-Methyl-6-fluoro-pseudo-UTP | 76 | N |
| 1-Methyl-6-methoxy-pseudo-UTP | 77 | N |
| 1-Methyl-6-ethoxy-pseudo-UTP | 78 | N |
| 1-Methyl-6-trifluoromethoxy-pseudo-UTP | 79 | N |
| 1-Methyl-6-phenyl-pseudo-UTP | 80 | N |
| 1-Methyl-6-(substituted phenyl)pseudo-UTP | 81 | N |
| 1-Methyl-6-cyano-pseudo-UTP | 82 | N |
| 1-Methyl-6-azido-pseudo-UTP | 83 | N |
| 1-Methyl-6-amino-pseudo-UTP | 84 | N |
| 1-Methyl-6-ethylcarboxylate-pseudo-UTP | 85 | N |
| 1-Methyl-6-hydroxy-pseudo-UTP | 86 | N |
| 1-Methyl-6-methylamino-pseudo-UTP | 87 | N |
| 1-Methyl-6-dimethylamino-pseudo-UTP | 88 | N |
| 1-Methyl-6-hydroxyamino-pseudo-UTP | 89 | N |
| 1-Methyl-6-formyl-pseudo-UTP | 90 | N |
| 1-Methyl-6-(4-morpholino)-pseudo-UTP | 91 | N |
| 1-Methyl-6-(4-thiomorpholino)-pseudo-UTP | 92 | N |
| 1-Alkyl-6-vinyl-pseudo-UTP | 93 | N |
| 1-Alkyl-6-allyl-pseudo-UTP | 94 | N |
| 1-Alkyl-6-homoallyl-pseudo-UTP | 95 | N |
| 1-Alkyl-6-ethynyl-pseudo-UTP | 96 | N |
| 1-Alkyl-6-(2-propynyl)-pseudo-UTP | 97 | N |
| 1-Alkyl-6-(1-propynyl)-pseudo-UTP | 98 | N |

Example 16. Incorporation of Naturally and Non-Naturally Occurring Nucleosides

Naturally and non-naturally occurring nucleosides are incorporated into mRNA encoding a polypeptide of interest.

Examples of these are given in Tables 20 and 21. Certain commercially available nucleoside triphosphates (NTPs) are investigated in the polynucleotides of the invention. A selection of these are given in Table 20. The resultant mRNA are then examined for their ability to produce protein, induce cytokines, and/or produce a therapeutic outcome.

TABLE 20

Naturally and non-naturally occurring nucleosides

| Chemistry Modification | Compound # | Naturally occuring |
|---|---|---|
| N4-Methyl-Cytosine | 1 | Y |
| N4,N4-Dimethyl-2'-OMe-Cytosine | 2 | Y |
| 5-Oxyacetic acid-methyl ester-Uridine | 3 | Y |
| N3-Methyl-pseudo-Uridine | 4 | Y |
| 5-Hydroxymethyl-Cytosine | 5 | Y |
| 5-Trifluoromethyl-Cytosine | 6 | N |
| 5-Trifluoromethyl-Uridine | 7 | N |
| 5-Methyl-amino-methyl-Uridine | 8 | Y |
| 5-Carboxy-methyl-amino-methyl-Uridine | 9 | Y |
| 5-Carboxymethylaminomethyl-2'-OMe-Uridine | 10 | Y |
| 5-Carboxymethylaminomethyl-2-thio-Uridine | 11 | Y |
| 5-Methylaminomethyl-2-thio-Uridine | 12 | Y |
| 5-Methoxy-carbonyl-methyl-Uridine | 13 | Y |
| 5-Methoxy-carbonyl-methyl-2'-OMe-Uridine | 14 | Y |
| 5-Oxyacetic acid- Uridine | 15 | Y |
| 3-(3-Amino-3-carboxypropyl)-Uridine | 16 | Y |
| 5-(carboxyhydroxymethyl)uridine methyl ester | 17 | Y |
| 5-(carboxyhydroxymethyl)uridine | 18 | Y |

TABLE 21

Non-naturally occurring nucleoside triphosphates

| Chemistry Modification | Compound # | Naturally occuring |
|---|---|---|
| N1-Me-GTP | 1 | N |
| 2'-OMe-2-Amino-ATP | 2 | N |
| 2'-OMe-pseudo-UTP | 3 | Y |
| 2'-OMe-6-Me-UTP | 4 | N |
| 2'-Azido-2'-deoxy-ATP | 5 | N |
| 2'-Azido-2'-deoxy-GTP | 6 | N |
| 2'-Azido-2'-deoxy-UTP | 7 | N |
| 2'-Azido-2'-deoxy-CTP | 8 | N |
| 2'-Amino-2'-deoxy-ATP | 9 | N |
| 2'-Amino-2'-deoxy-GTP | 10 | N |
| 2'-Amino-2'-deoxy-UTP | 11 | N |
| 2'-Amino-2'-deoxy-CTP | 12 | N |
| 2-Amino-ATP | 13 | N |
| 8-Aza-ATP | 14 | N |
| Xanthosine-5'-TP | 15 | N |
| 5-Bromo-CTP | 16 | N |
| 2'-F-5-Methyl-2'-deoxy-UTP | 17 | N |
| 5-Aminoallyl-CTP | 18 | N |
| 2-Amino-riboside-TP | 19 | N |

Example 17. Incorporation of Modifications to the Nucleobase and Carbohydrate (Sugar)

Naturally and non-naturally occurring nucleosides are incorporated into mRNA encoding a polypeptide of interest. Commercially available nucleosides and NTPs having modifications to both the nucleobase and carbohydrate (sugar) are examined for their ability to be incorporated into mRNA and to produce protein, induce cytokines, and/or produce a therapeutic outcome. Examples of these nucleosides are given in Tables 22 and 23.

TABLE 22

Combination modifications

| Chemistry Modification | Compound # |
|---|---|
| 5-iodo-2'-fluoro-deoxyuridine | 1 |
| 5-iodo-cytidine | 6 |
| 2'-bromo-deoxyuridine | 7 |
| 8-bromo-adenosine | 8 |
| 8-bromo-guanosine | 9 |
| 2,2'-anhydro-cytidine hydrochloride | 10 |
| 2,2'-anhydro-uridine | 11 |
| 2'-Azido-deoxyuridine | 12 |
| 2-amino-adenosine | 13 |
| N4-Benzoyl-cytidine | 14 |
| N4-Amino-cytidine | 15 |
| 2'-O-Methyl-N4-Acetyl-cytidine | 16 |
| 2'Fluoro-N4-Acetyl-cytidine | 17 |
| 2'Fluor-N4-Bz-cytidine | 18 |
| 2'O-methyl-N4-Bz-cytidine | 19 |
| 2'O-methyl-N6-Bz-deoxyadenosine | 20 |
| 2'Fluoro-N6-Bz-deoxyadenosine | 21 |
| N2-isobutyl-guanosine | 22 |
| 2'Fluro-N2-isobutyl-guanosine | 23 |
| 2'O-methyl-N2-isobutyl-guanosine | 24 |

TABLE 23

Naturally occuring combinations

| Name | Compound # | Naturally occurring |
|---|---|---|
| 5-Methoxycarbonylmethyl-2-thiouridine TP | 1 | Y |
| 5-Methylaminomethyl-2-thiouridine TP | 2 | Y |
| 5-Crbamoylmethyluridine TP | 3 | Y |
| 5-Carbamoylmethyl-2'-O-methyluridine TP | 4 | Y |
| 1-Methyl-3-(3-amino-3-carboxypropyl) pseudouridine TP | 5 | Y |
| 5-Methylaminomethyl-2-selenouridine TP | 6 | Y |
| 5-Carboxymethyluridine TP | 7 | Y |
| 5-Methyldihydrouridine TP | 8 | Y |
| lysidine TP | 9 | Y |
| 5-Taurinomethyluridine TP | 10 | Y |
| 5-Taurinomethyl-2-thiouridine TP | 11 | Y |
| 5-(iso-Pentenylaminomethyl)uridine TP | 12 | Y |
| 5-(iso-Pentenylaminomethyl)- 2-thiouridine TP | 13 | Y |
| 5-(iso-Pentenylaminomethyl)-2'-O-methyluridine TP | 14 | Y |
| N4-Acetyl-2'-O-methylcytidine TP | 15 | Y |
| N4,2'-O-Dimethylcytidine TP | 16 | Y |
| 5-Formyl-2'-O-methylcytidine TP | 17 | Y |
| 2'-O-Methylpseudouridine TP | 18 | Y |
| 2-Thio-2'-O-methyluridine TP | 19 | Y |
| 3,2'-O-Dimethyluridine TP | 20 | Y |

In the tables "UTP" stands for uridine triphosphate, "GTP" stands for guanosine triphosphate, "ATP" stands for adenosine triphosphate, "CTP" stands for cytosine triphosphate, "TP" stands for triphosphate and "Bz" stands for benzyl.

Example 18. Signal Sequence Exchange Study

Several variants of mmRNAs encoding human Granulocyte colony stimulating factor (G-CSF) (mRNA sequence shown in SEQ ID NO: 4258; polyA tail of approximately 160 nucleotides not shown in sequence; 5'cap, Cap1) were synthesized using modified nucleotides pseudouridine and 5-methylcytidine (pseudo-U/5mC). These variants included the G-CSF constructs encoding either the wild-type N terminal secretory signal peptide sequence (MAGPATQSPMKLMALQLLLWHSALWTVQEA; SEQ ID NO: 4271), no secretory signal peptide sequence, or secretory signal peptide sequences taken from other mRNAs. These included sequences where the wild type GCSF signal peptide sequence was replaced with the signal peptide sequence of either:

human α-1-anti trypsin (AAT) (MMPSSVSWGILLLAGLCCLV

PVSLA; SEQ ID NO: 4272), human Factor IX (FIX)

(MQRVNMIMAESPSLITICLLGYLLSAECTVFLDHENANKILNR

PKR; SEQ ID NO: 4273), human Prolactin (Prolac) (M

KGSLLLLLVSNLLLCQSVAP; SEQ ID NO: 4274), or human Albumin (Alb) (MKWVTFISLLFLFSSAYSRGVFRR;

SEQ ID NO: 4275).

250 ng of modified mRNA encoding each G-CSF variant was transfected into HEK293A (293A in the table), mouse myoblast (MM in the table) (C2C12, CRL-1772, ATCC) and rat myoblast (RM in the table) (L6 line, CRL-1458, ATCC) cell lines in a 24 well plate using 1 ul of Lipofectamine 2000 (Life Technologies), each well containing 300,000 cells. The supernatants were harvested after 24 hrs and the secreted G-CSF protein was analyzed by ELISA using the Human G-CSF ELISA kit (Life Technologies). The data shown in Table 24 reveal that cells transfected with G-CSF mmRNA encoding the Albumin signal peptide secrete at least 12 fold more G-CSF protein than its wild type counterpart.

TABLE 24

Signal Peptide Exchange

| Signal peptides | 293A (pg/ml) | MM (pg/ml) | RM (pg/ml) |
|---|---|---|---|
| G-CSF Natural | 9650 | 3450 | 6050 |
| α-1-anti trypsin | 9950 | 5000 | 8475 |
| Factor IX | 11675 | 6175 | 11675 |
| Prolactin | 7875 | 1525 | 9800 |
| Albumin | 122050 | 81050 | 173300 |
| No Signal peptide | 0 | 0 | 0 |

Example 19. 3' Untranslated Regions

A 3' UTR may be provided a flanking region. Multiple 3' UTRs may be included in the flanking region and may be the same or of different sequences. Any portion of the flanking regions, including none, may be codon optimized and any may independently contain one or more different structural or chemical modifications, before and/or after codon optimization.

Shown in Table 7 is a listing of 3'-untranslated regions of the invention. Variants of 3' UTRs may be utilized wherein one or more nucleotides are added or removed to the termini, including A, T, C or G.

Example 20. Alteration of Polynucleotide Trafficking: NLS and NES

Two nuclear export signals (NES) which may be incorporated into the polynucleotides of the present invention includes those reported by Muller, et al (Traffic, 2009, 10: 514-527) and are associated with signaling via the gene COMMD1. These are NES1, PVAIIELEL (SEQ ID NO 4276) and NES2, VNQILKTLSE (SEQ ID NO 4277).

Nuclear localization signals may also be used. One such sequence is PKKKRKV (SEQ ID NO: 4278).

Cell lines or mice are administered one or more polynucleotides having a NLS or NES encoded therein. Upon administration the polynucleotide is trafficked to an alternate location, e.g., into the nucleus using the NLS. The polypeptide having the NLS would be trafficked to the nucleus where it would deliver either a survival or death signal to the nuclear microenvironment. Polypeptides which may be localized to the nucleus include those with altered binding properties for DNA which will function to alter the expression profile of the cell in a therapeutically beneficial manner for the cell, tissue or organism.

In one experiment, the polynucleotide encodes a COMMD1 mut1/mut 2+ NLS (e.g., both NES signals disrupted plus a NLS added) following the methods of Muller et al, (Traffic 2009; 10: 514-527) and van de Sluis et al, (J Clin Invest. 2010; 120 (6):2119-2130). The signal sequence may encode a polypeptide or a scrambled sequence which is not translatable. The signal sequence encoded would interact with HIF 1-alpha to alter the transcritome of the cancer cells.

The experiment is repeated under normal and hypoxic conditions.

Once identified the HIF 1-alpha dependent polynucleotide is tested in cancer cell lines clonal survival or a marker of apoptosis is measured and compared to control or mock treated cells.

Example 21. miRNA Binding Sites (BS) Useful as Sensor Sequences in Polynucleotides miRNA-binding sites are used in the 3'UTR of mRNA therapeutics to direct cytotoxic or cytoprotective mRNA therapeutics to specific cells (normal and/or cancerous).

A strong apoptotic signal (i.e., AIFsh—Apoptosis Inducing Factor short isoform) is encoded as the polypeptide or "signal" and is encoded along with a series of 3'UTR miR binding sites, such as that for mir-122a, that would make the polynucleotide relatively much more stable in cancerous cells than in normal cells.

Experiments comparing cancer vs. normal hepatic cell lines where the cancer cell lines have a specific miR signature are performed in vitro. SNU449 or HEP3B (human derived HCC cell lines) are used because both have been shown to have "undetectable miR-122a", whereas normal hepatocytes should have very high miR-122a levels. First a cancer cell is selected which is sensitive to AIFsh polynucleotide (i.e., it results in apoptosis).

Three miR-122a binding sites are encoded into the 3'UTR of an mRNA sequence for AIFsh and the study arms include 2 cell lines (normal hepatocyte, SNU449 or HEP3B)×5 treatments (vehicle alone, polynucleotide untranslatabe, polynucleotide AIFsh (no miR BS in 3'UTR), 3'UTR [miR122a BS x3]-polynucleotide untranslatable, 3'UTR [miR122a BS x3]-polynucleotide AIFsh).

The expected result would be significant apoptosis in the face of polynucleotide AIFsh in both normal and cancer (HEP3B or SNU449) cell lines in the absence of any 3'UTR-miR122a BS. However, a significant difference in the relative apoptosis of normal vs. cancer cell lines in the face of 3'UTR [miR122a BS x3]-polynucleotide AIFsh.

Reversibility of the effect is shown with the co-administration of miR122a to the cancer cell line (e.g., through some transduction of the miR122a activity back into the cancer cell line).

In vivo animal studies are then performed using any of the models disclosed herein or a commercially available orthotopic HCC model.

Example 22. Cell Lines for the Study of Polynucleotides

Polynucleotides of the present invention and formulations comprising the polynucleotides of the present invention or described in International application No PCT/US2012/69610, herein incorporated by reference in its entirety, may be investigated in any number of cancer or normal cell lines. Cell lines useful in the present invention include those from ATCC (Manassas, Va.) and are listed in Table 25.

TABLE 25

Cell lines

| ATCC Number | Hybridoma or Cell line Description | Name |
|---|---|---|
| CCL-171 | *Homo sapiens* (human) Source: Organ: lung Disease: normal Cell Type: fibroblast | MRC-5 |
| CCL-185 | *Homo sapiens* (human) Source: Organ: lung Disease: carcinoma | A549 |
| CCL-248 | *Homo sapiens* (human) Source: Organ: colon Disease: colorectal carcinoma Derived from metastatic site: lung | T84 |
| CCL-256 | *Homo sapiens* (human) Source: Organ: lung Disease: adenocarcinoma; non-small cell lung cancer Derived from metastatic site: pleural effusion | NCI-H2126 [H2126] |
| CCL-257 | *Homo sapiens* (human) Source: Organ: lung Disease: carcinoma; classic small cell lung cancer | NCI-H1688 [H1688] |
| CCL-75 | *Homo sapiens* (human) Source: Organ: lung Disease: normal Cell Type: fibroblast | WI-38 |
| CCL-75.1 | *Homo sapiens* (human) Source: Organ: lung Cell Type: fibroblastSV40 transformed | WI-38 VA-13 subline 2RA |
| CCL-95.1 | *Homo sapiens* (human) Source: Organ: lung Cell Type: SV40 transformed | WI-26 VA4 |
| CRL-10741 | *Homo sapiens* (human) Source: Organ: liver Disease: hepatocellular carcinoma | C3A [HepG2/C3A, derivative of Hep G2 (ATCC HB-8065)] |
| CRL-11233 | *Homo sapiens* (human) Source: Organ: liver Tissue: left lobe Cell Type: epithelialimmortalized with SV40 large T antigen | THLE-3 |
| CRL-11351 | *Homo sapiens* (human) Source: Organ: lung Disease: carcinoma; small cell lung cancer; multidrug resistant Cell Type: epithelial | H69AR |
| CRL-1848 | *Homo sapiens* (human) Source: Organ: lung Disease: mucoepidermoid pulmonary carcinoma | NCI-H292 [H292] |
| CRL-1918 | *Homo sapiens* (human) Source: Organ: pancreas Disease: ductal adenocarcinoma; cystic fibrosis Derived from metastatic site: liver metastasis | CFPAC-1 |
| CRL-1973 | *Homo sapiens* (human) Source: Organ: testis Disease: malignant pluripotent embryonal carcinoma Derived from metastatic site: lung | NTERA-2 cl.D1 [NT2/D1] |
| CRL-2049 | *Homo sapiens* (human) Source: Organ: lung Disease: carcinoma; small cell lung cancer | DMS 79 |
| CRL-2062 | *Homo sapiens* (human) Source: Organ: lung Disease: carcinoma; small cell lung cancer | DMS 53 |
| CRL-2064 | *Homo sapiens* (human) Source: Organ: lung Disease: carcinoma; small cell lung cancer Derived from metastatic site: liver | DMS 153 |
| CRL-2066 | *Homo sapiens* (human) Source: Organ: lung Disease: carcinoma; small cell lung cancer | DMS 114 |
| CRL-2081 | *Homo sapiens* (human) Source: Disease: biphasic mesothelioma Derived from metastatic site: lung | MSTO-211H |
| CRL-2170 | *Homo sapiens* (human) Source: Organ: lung Disease: alveolar cell carcinoma | SW 1573 [SW-1573, SW1573] |
| CRL-2177 | *Homo sapiens* (human) Source: Organ: lung Disease: carcinoma; small cell lung cancer | SW 1271 [SW-1271, SW1271] |
| CRL-2195 | *Homo sapiens* (human) Source: Organ: lung Disease: carcinoma; small cell lung cancer Cell Type: large cell, variant; | SHP-77 |
| CRL-2233 | *Homo sapiens* (human) Source: Organ: liver Disease: hepatocellular carcinoma | SNU-398 |
| CRL-2234 | *Homo sapiens* (human) Source: Organ: liver Tumor Stage: grade II-III/IV Disease: hepatocellular carcinoma | SNU-449 |

TABLE 25-continued

Cell lines

| ATCC Number | Hybridoma or Cell line Description | Name |
|---|---|---|
| CRL-2235 | *Homo sapiens* (human) Source: Organ: liver Tumor Stage: grade III/IV Disease: hepatocellular carcinoma | SNU-182 |
| CRL-2236 | *Homo sapiens* (human) Source: Organ: liver Tumor Stage: grade II-IV/V Disease: hepatocellular carcinoma | SNU-475 |
| CRL-2237 | *Homo sapiens* (human) Source: Organ: liver Tumor Stage: grade IV/V Disease: pleomorphic hepatocellular carcinoma | SNU-387 |
| CRL-2238 | *Homo sapiens* (human) Source: Organ: liver Tumor Stage: grade III/IV Disease: pleomorphic hepatocellular carcinoma | SNU-423 |
| CRL-2503 | *Homo sapiens* (human) Source: Organ: lung Tissue: bronchus Disease: normal | NL20 |
| CRL-2504 | *Homo sapiens* (human) Source: Organ: lung Tissue: bronchus Disease: normal | NL20-TA [NL20T-A] |
| CRL-2706 | *Homo sapiens* (human) Source: Organ: liver Tissue: left lobe Cell Type: epithelialSV40 transformed | THLE-2 |
| CRL-2741 | *Homo sapiens* (human) Source: Organ: lung Tissue: bronchus Cell Type: epithelialHPV-16 E6/E7 transformed | HBE135-E6E7 |
| CRL-2868 | *Homo sapiens* (human) Source: Organ: lung Disease: adenocarcinoma Cell Type: epithelial | HCC827 |
| CRL-2871 | *Homo sapiens* (human) Source: Organ: lung Disease: adenocarcinoma Derived from metastatic site: pleural effusion Cell Type: epithelial | HCC4006 |
| CRL-5800 | *Homo sapiens* (human) Source: Organ: lung Disease: adenocarcinoma; non-small cell lung cancer | NCI-H23 [H23] |
| CRL-5803 | *Homo sapiens* (human) Source: Organ: lung Disease: carcinoma; non-small cell lung cancer Derived from metastatic site: lymph node | NCI-H1299 |
| CRL-5804 | *Homo sapiens* (human) Source: Organ: lung Disease: carcinoma; classic small cell lung cancer Derived from metastatic site: pleural effusion | NCI-H187 [H187] |
| CRL-5807 | *Homo sapiens* (human) Source: Organ: lung Tissue: bronchiole; alveolus Disease: bronchioalveolar carcinoma; non-small cell lung cancer | NCI-H358 [H-358, H358] |
| CRL-5808 | *Homo sapiens* (human) Source: Organ: lung Tumor Stage: stage E Disease: carcinoma; classic small cell lung cancer Derived from metastatic site: pleural effusion | NCI-H378 [H378] |
| CRL-5810 | *Homo sapiens* (human) Source: Organ: lung Tumor Stage: stage 2 Disease: adenocarcinoma; non-small cell lung cancer | NCI-H522 [H522] |
| CRL-5811 | *Homo sapiens* (human) Source: Organ: lung Tumor Stage: stage E Disease: carcinoma; variant small cell lung cancer Derived from metastatic site: bone marrow | NCI-H526 [H526] |
| CRL-5815 | *Homo sapiens* (human) Source: Organ: lung Tissue: bronchus Disease: carcinoid | NCI-H727 [H727] |
| CRL-5816 | *Homo sapiens* (human) Source: Organ: lung Tumor Stage: stage 2 Disease: carcinoma; non-small cell lung cancer | NCI-H810 [H810] |
| CRL-5817 | *Homo sapiens* (human) Source: Organ: lung Tumor Stage: stage E Disease: carcinoma; classic small cell lung cancer Derived from metastatic site: lymph node | NCI-H889 [H889] |
| CRL-5818 | *Homo sapiens* (human) Source: Organ: lung Disease: carcinoma; non-small cell lung cancer Derived from metastatic site: lymph node | NCI-H1155 H1155] |

TABLE 25-continued

Cell lines

| ATCC Number | Hybridoma or Cell line Description | Name |
|---|---|---|
| CRL-5819 | *Homo sapiens* (human) Source: Organ: lung<br>Disease: papillary adenocarcinoma<br>Derived from metastatic site: lymph node | NCI-H1404 [H1404] |
| CRL-5822 | *Homo sapiens* (human) Source: Organ: stomach<br>Disease: gastric carcinoma<br>Derived from metastatic site: liver | NCI-N87 [N87] |
| CRL-5823 | *Homo sapiens* (human) Source: Organ: lung<br>Tumor Stage: stage E<br>Disease: carcinoma; variant small cell lung cancer<br>Derived from metastatic site: pleural effusion | NCI-H196 [H196] |
| CRL-5824 | *Homo sapiens* (human) Source: Organ: lung<br>Tumor Stage: stage E<br>Disease: carcinoma; small cell lung cancer<br>Derived from metastatic site: bone marrow | NCI-H211 [H211] |
| CRL-5825 | *Homo sapiens* (human) Source: Organ: lung<br>Tumor Stage: stage E<br>Disease: carcinoma; classic small cell lung cancer<br>Derived from metastatic site: pleural effusion | NCI-H220 [H220] |
| CRL-5828 | *Homo sapiens* (human) Source: Organ: lung<br>Tumor Stage: stage E<br>Disease: carcinoma; classic small cell lung cancer<br>Derived from metastatic site: brain | NCI-H250 [H250] |
| CRL-5831 | *Homo sapiens* (human) Source: Organ: lung<br>Tumor Stage: stage L<br>Disease: carcinoma; variant small cell lung cancer<br>Derived from metastatic site: lymph node | NCI-H524 [H524] |
| CRL-5834 | *Homo sapiens* (human) Source: Organ: lung<br>Tumor Stage: stage 3A<br>Disease: adenosquamous carcinoma; non-small cell lung cancer<br>Derived from metastatic site: pleural effusion | NCI-H647 [H647] |
| CRL-5835 | *Homo sapiens* (human) Source: Organ: lung<br>Disease: bronchioalveolar carcinoma; non-small cell lung cancer<br>Derived from metastatic site: lymph node | NCI-H650 [H650] |
| CRL-5836 | *Homo sapiens* (human) Source: Organ: lung<br>Tumor Stage: stage E<br>Disease: carcinoma; classic small cell lung cancer<br>Derived from metastatic site: bone marrow | NCI-H711 [H711] |
| CRL-5837 | *Homo sapiens* (human) Source: Organ: lung<br>Tumor Stage: stage E<br>Disease: carcinoma; classic small cell lung cancer<br>Derived from metastatic site: bone marrow | NCI-H719 [H719] |
| CRL-5840 | *Homo sapiens* (human) Source: Organ: lung<br>Tumor Stage: stage E<br>Disease: carcinoma; classic small cell lung cancer<br>Derived from metastatic site: lymph node | NCI-H740 [H740] |
| CRL-5841 | *Homo sapiens* (human) Source: Organ: lung<br>Tumor Stage: stage E<br>Disease: carcinoma; classic small cell lung cancer<br>Derived from metastatic site: lymph node | NCI-H748 [H748] |
| CRL-5842 | *Homo sapiens* (human) Source: Organ: lung<br>Tumor Stage: stage E<br>Disease: carcinoma; classic small cell lung cancer<br>Derived from metastatic site: soft tissue | NCI-H774 [H774] |
| CRL-5844 | *Homo sapiens* (human) Source: Organ: lung<br>Tumor stage: 3B<br>Disease: adenocarcinoma; non-small cell lung cancer<br>Derived from metastatic site: lymph node | NCI-H838 [H838] |
| CRL-5845 | *Homo sapiens* (human) Source: Organ: lung<br>Tumor Stage: stage L<br>Disease: carcinoma; variant small cell lung cancer<br>Derived from metastatic site: lymph node | NCI-H841 [H841] |

TABLE 25-continued

Cell lines

| ATCC Number | Hybridoma or Cell line Description | Name |
|---|---|---|
| CRL-5846 | *Homo sapiens* (human) Source: Organ: lung<br>Tumor Stage: stage L<br>Disease: carcinoma; classic small cell lung cancer<br>Derived from metastatic site: pleural effusion | NCI-H847 [H847] |
| CRL-5849 | *Homo sapiens* (human) Source: Organ: lung<br>Tumor Stage: stage L<br>Disease: carcinoma; classic small cell lung cancer<br>Derived from metastatic site: pleural effusion | NCI-H865 [H865] |
| CRL-5850 | *Homo sapiens* (human) Source: Organ: lung<br>Tumor Stage: stage 4<br>Disease: adenocarcinoma; non-small cell lung cancer<br>Derived from metastatic site: lymph node | NCI-H920 [H920] |
| CRL-5853 | *Homo sapiens* (human) Source: Organ: lung<br>Disease: carcinoma; small cell lung cancer<br>Derived from metastatic site: pleural effusion | NCI-H1048 [H1048] |
| CRL-5855 | *Homo sapiens* (human) Source: Organ: lung<br>Tumor Stage: stage E<br>Disease: carcinoma; classic small cell lung cancer<br>Derived from metastatic site: bone marrow | NCI-H1092 [H1092] |
| CRL-5856 | *Homo sapiens* (human) Source: Organ: lung<br>Tumor Stage: stage E<br>Disease: carcinoma; classic small cell lung cancer<br>Derived from metastatic site: lymph node | NCI-H1105 [H1105] |
| CRL-5858 | *Homo sapiens* (human) Source: Organ: lung<br>Tumor Stage: stage L<br>Disease: carcinoma; small cell lung cancer<br>Derived from metastatic site: lymph node | NCI-H1184 [H1184] |
| CRL-5859 | *Homo sapiens* (human) Source: Organ: lung<br>Tumor Stage: stage E<br>Disease: carcinoma; small cell lung cancer<br>Derived from metastatic site: bone marrow | NCI-H1238 [H1238] |
| CRL-5864 | *Homo sapiens* (human) Source: Organ: lung<br>Disease: carcinoma; small cell lung cancer<br>Derived from metastatic site: cervix | NCI-H1341 [H1341] |
| CRL-5867 | *Homo sapiens* (human) Source: Organ: lung<br>Tumor Stage: stage 3A<br>Disease: carcinoma; non-small cell lung cancer<br>Derived from metastatic site: lymph node | NCI-H1385 [H1385] |
| CRL-5869 | *Homo sapiens* (human) Source: Organ: lung<br>Tumor Stage: stage E<br>Disease: carcinoma; classic small cell lung cancer | NCI-H1417 [H1417] |
| CRL-5870 | *Homo sapiens* (human) Source: Organ: lung<br>Disease: adenocarcinoma; non-small cell lung cancer | NCI-H1435 [H1435] |
| CRL-5871 | *Homo sapiens* (human) Source: Organ: lung<br>Tumor Stage: stage E<br>Disease: carcinoma; classic small cell lung cancer<br>Derived from metastatic site: lymph node | NCI-H1436 [H1436] |
| CRL-5872 | *Homo sapiens* (human) Source: Organ: lung<br>Tumor Stage: stage 1<br>Disease: adenocarcinoma; non-small cell lung cancer<br>Derived from metastatic site: pleural effusion | NCI-H1437 [H1437] |
| CRL-5874 | *Homo sapiens* (human) Source: Organ: lung<br>Tumor Stage: stage E<br>Disease: carcinoma; small cell lung cancer<br>Derived from metastatic site: pleural effusion | NCI-H1522 [H1522] |
| CRL-5875 | *Homo sapiens* (human) Source: Organ: lung<br>Disease: adenocarcinoma; non-small cell lung cancer | NCI-H1563 [H1563] |
| CRL-5876 | *Homo sapiens* (human) Source: Organ: lung<br>Disease: adenocarcinoma; non-small cell lung cancer<br>Derived from metastatic site: lymph node | NCI-H1568 [H1568] |
| CRL-5877 | *Homo sapiens* (human) Source: Organ: lung<br>Tumor Stage: stage 4<br>Disease: adenocarcinoma<br>Derived from metastatic site: soft tissue | NCI-H1573 [H1573] |

TABLE 25-continued

Cell lines

| ATCC Number | Hybridoma or Cell line Description | Name |
|---|---|---|
| CRL-5878 | *Homo sapiens* (human) Source: Organ: lung<br>Tumor Stage: stage 4<br>Disease: non-small cell lung cancer<br>Cell Type: large cell; | NCI-H1581<br>[H1581] |
| CRL-5879 | *Homo sapiens* (human) Source: Tumor Stage: stage E<br>Disease: carcinoma; small cell lung cancer<br>Derived from metastatic site: bone marrow | NCI-H1618<br>[H1618] |
| CRL-5881 | *Homo sapiens* (human) Source: Organ: lung<br>Tumor Stage: stage 3B<br>Disease: adenocarcinoma; non-small cell lung cancer<br>Derived from metastatic site: lymph node | NCI-H1623<br>[H1623] |
| CRL-5883 | *Homo sapiens* (human) Source: Organ: lung<br>Tumor Stage: stage 3B<br>Disease: adenocarcinoma; bronchoalveolar carcinoma<br>Derived from metastatic site: pleural effusion | NCI-H1650 [H-1650, H1650] |
| CRL-5884 | *Homo sapiens* (human) Source: Organ: lung<br>Disease: adenocarcinoma; non-small cell lung cancer | NCI-H1651<br>[H1651] |
| CRL-5885 | *Homo sapiens* (human) Source: Organ: lung<br>Disease: adenocarcinoma; bronchoalveolar carcinoma<br>Derived from metastatic site: pleural effusion | NCI-H1666 [H-1666, H1666] |
| CRL-5886 | *Homo sapiens* (human) Source: Organ: lung<br>Tumor Stage: stage L<br>Disease: carcinoma; classic small cell lung cancer | NCI-H1672<br>[H1672] |
| CRL-5887 | *Homo sapiens* (human) Source: Organ: lung<br>Tumor Stage: stage 3B<br>Disease: adenocarcinoma; non-small cell lung cancer<br>Derived from metastatic site: lymph node | NCI-H1693<br>[H1693] |
| CRL-5888 | *Homo sapiens* (human) Source: Organ: lung<br>Tumor Stage: stage E<br>Disease: carcinoma; classic small cell lung cancer<br>Derived from metastatic site: ascites | NCI-H1694<br>[H1694] |
| CRL-5889 | *Homo sapiens* (human) Source: Organ: lung<br>Tumor Stage: stage 1<br>Disease: non-small cell lung cancer<br>Cell Type: squamous cell; | NCI-H1703<br>[H1703] |
| CRL-5891 | *Homo sapiens* (human) Source: Organ: lung<br>Disease: adenocarcinoma; non-small cell lung cancer | NCI-H1734 [H-1734, H1734] |
| CRL-5892 | *Homo sapiens* (human) Source: Organ: lung<br>Tumor Stage: stage 4<br>Disease: adenocarcinoma; non-small cell lung cancer<br>Derived from metastatic site: liver | NCI-H1755<br>[H1755] |
| CRL-5892 | *Homo sapiens* (human) Source: Organ: lung<br>Tumor Stage: stage 4<br>Disease: adenocarcinoma; non-small cell lung cancer<br>Derived from metastatic site: liver | NCI-H1755<br>[H1755] |
| CRL-5893 | *Homo sapiens* (human) Source: Organ: lung<br>Tumor Stage: stage 4<br>Disease: carcinoma; non-small cell lung cancer<br>Derived from metastatic site: lymph node<br>Cell Type: neuroendocrine; | NCI-H1770<br>[H1770] |
| CRL-5896 | *Homo sapiens* (human) Source: Organ: lung<br>Disease: adenocarcinoma; non-small cell lung cancer | NCI-H1793<br>[H1793] |
| CRL-5898 | *Homo sapiens* (human) Source: Organ: lung<br>Tumor Stage: stage L<br>Disease: carcinoma; classic small cell lung cancer | NCI-H1836<br>[H1836] |
| CRL-5899 | *Homo sapiens* (human) Source: Organ: lung<br>Disease: adenocarcinoma; non-small cell lung cancer | NCI-H1838<br>[H1838] |

TABLE 25-continued

Cell lines

| ATCC Number | Hybridoma or Cell line Description | Name |
|---|---|---|
| CRL-5900 | *Homo sapiens* (human) Source: Organ: lung Tumor Stage: stage 4 Disease: non-small cell lung cancer Derived from metastatic site: pleural effusion Cell Type: squamous cell; | NCI-H1869 [H1869] |
| CRL-5902 | *Homo sapiens* (human) Source: Organ: lung Tumor Stage: stage E Disease: carcinoma; classic small cell lung cancer Derived from metastatic site: lymph node | NCI-H1876 [H1876] |
| CRL-5903 | *Homo sapiens* (human) Source: Organ: lung Tumor Stage: stage E Disease: carcinoma; small cell lung cancer Derived from metastatic site: bone marrow | NCI-H1882 [H1882] |
| CRL-5904 | *Homo sapiens* (human) Source: Organ: lung Tumor Stage: stage 4 Disease: poorly differentiated carcinoma; non-small cell lung cancer Derived from metastatic site: brain Cell Type: large cell; | NCI-H1915 [H1915] |
| CRL-5906 | *Homo sapiens* (human) Source: Organ: lung Tumor Stage: stage L Disease: carcinoma; classic small cell lung cancer Derived from metastatic site: lymph node | NCI-H1930 [H1930] |
| CRL-5907 | *Homo sapiens* (human) Source: Organ: lung Tumor Stage: stage 3B Disease: adenocarcinoma; non-small cell lung cancer Derived from metastatic site: soft tissue | NCI-H1944 [H1944] |
| CRL-5908 | *Homo sapiens* (human) Source: Organ: lung Disease: adenocarcinoma; non-small cell lung cancer | NCI-H1975 [H-1975, H1975] |
| CRL-5909 | *Homo sapiens* (human) Source: Organ: lung Tumor Stage: stage 3A Disease: adenocarcinoma; non-small cell lung cancer Derived from metastatic site: lymph node | NCI-H1993 [H1993] |
| CRL-5912 | *Homo sapiens* (human) Source: Organ: lung Tumor Stage: stage 3A Disease: adenocarcinoma; non-small cell lung cancer Derived from metastatic site: lymph node | NCI-H2023 [H2023] |
| CRL-5913 | *Homo sapiens* (human) Source: Organ: lung Tumor Stage: stage E Disease: carcinoma; small cell lung cancer Derived from metastatic site: lymph node | NCI-H2029 [H2029] |
| CRL-5914 | *Homo sapiens* (human) Source: Organ: lung Disease: adenocarcinoma; non-small cell lung cancer Derived from metastatic site: lymph node | NCI-H2030 [H2030] |
| CRL-5917 | *Homo sapiens* (human) Source: Organ: lung Tumor Stage: stage 1 Disease: mixed; small cell lung cancer; adenocarcinoma; squamous cell carcinoma | NCI-H2066 [H2066] |
| CRL-5918 | *Homo sapiens* (human) Source: Organ: lung Tumor Stage: stage 3A Disease: adenocarcinoma; non-small cell lung cancer | NCI-H2073 [H2073] |
| CRL-5920 | *Homo sapiens* (human) Source: Organ: lung Tumor Stage: stage E Disease: carcinoma; classic small cell lung cancer Derived from metastatic site: pleural effusion | NCI-H2081 [H2081] |
| CRL-5921 | *Homo sapiens* (human) Source: Organ: lung Disease: adenocarcinoma; non-small cell lung cancer | NCI-H2085 [H2085] |
| CRL-5922 | *Homo sapiens* (human) Source: Organ: lung Tumor Stage: stage 1 Disease: adenocarcinoma; non-small cell lung cancer Derived from metastatic site: lymph node | NCI-H2087 [H2087] |

TABLE 25-continued

Cell lines

| ATCC Number | Hybridoma or Cell line Description | Name |
|---|---|---|
| CRL-5923 | *Homo sapiens* (human) Source: Organ: lung<br>Tissue: neuroendocrine<br>Tumor Stage: stage 4<br>Disease: non-small cell lung cancer<br>Derived from metastatic site: lymph node | NCI-H2106<br>[H2106] |
| CRL-5924 | *Homo sapiens* (human) Source: Organ: lung<br>Disease: non-small cell lung cancer<br>Derived from metastatic site: pleural effusion | NCI-H2110<br>[H2110] |
| CRL-5926 | *Homo sapiens* (human) Source: Organ: lung<br>Disease: non-small cell lung cancer | NCI-H2135<br>[H2135] |
| CRL-5927 | *Homo sapiens* (human) Source: Organ: lung<br>Tumor Stage: stage E<br>Disease: carcinoma; small cell lung cancer<br>Derived from metastatic site: lymph node | NCI-H2141<br>[H2141] |
| CRL-5929 | *Homo sapiens* (human) Source: Organ: lung<br>Tumor Stage: stage E<br>Disease: carcinoma; small cell lung cancer<br>Derived from metastatic site: pleural effusion | NCI-H2171<br>[H2171] |
| CRL-5930 | *Homo sapiens* (human) Source: Organ: lung<br>Disease: non-small cell lung cancer | NCI-H2172<br>[H2172] |
| CRL-5931 | *Homo sapiens* (human) Source: Organ: lung<br>Tumor Stage: stage E<br>Disease: carcinoma; small cell lung cancer<br>Derived from metastatic site: bone marrow | NCI-H2195<br>[H2195] |
| CRL-5932 | *Homo sapiens* (human) Source: Organ: lung<br>Tumor Stage: stage E<br>Disease: carcinoma; small cell lung cancer<br>Derived from metastatic site: bone marrow | NCI-H2196<br>[H2196] |
| CRL-5933 | *Homo sapiens* (human) Source: Organ: lung<br>Tumor Stage: stage E<br>Disease: carcinoma; small cell lung cancer<br>Derived from metastatic site: lymph node | NCI-H2198<br>[H2198] |
| CRL-5934 | *Homo sapiens* (human) Source: Organ: lung<br>Tumor Stage: stage E<br>Disease: carcinoma; small cell lung cancer | NCI-H2227<br>[H2227] |
| CRL-5935 | *Homo sapiens* (human) Source: Organ: lung<br>Disease: adenocarcinoma; non-small cell lung cancer | NCI-H2228<br>[H2228] |
| CRL-5938 | *Homo sapiens* (human) Source: Organ: lung<br>Tumor Stage: stage 1<br>Disease: mixed; small cell lung cancer; adenocarcinoma; squamous cell carcinoma | NCI-H2286<br>[H2286] |
| CRL-5939 | *Homo sapiens* (human) Source: Organ: lung<br>Disease: adenocarcinoma; non-small cell lung cancer<br>Derived from metastatic site: lymph node | NCI-H2291<br>[H2291] |
| CRL-5940 | *Homo sapiens* (human) Source: Organ: lung<br>Tumor Stage: stage L<br>Disease: carcinoma; small cell lung cancer<br>Derived from metastatic site: lymph node | NCI-H2330<br>[H2330] |
| CRL-5941 | *Homo sapiens* (human) Source: Organ: lung<br>Tumor Stage: stage 3A<br>Disease: adenocarcinoma; non-small cell lung cancer | NCI-H2342<br>[H2342] |
| CRL-5942 | *Homo sapiens* (human) Source: Organ: lung<br>Tumor Stage: stage 1<br>Disease: adenocarcinoma; non-small cell lung cancer | NCI-H2347<br>[H2347] |
| CRL-5944 | *Homo sapiens* (human) Source: Organ: lung<br>Tumor Stage: stage 4<br>Disease: adenocarcinoma; non-small cell lung cancer<br>Derived from metastatic site: ascites | NCI-H2405<br>[H2405] |
| CRL-5945 | *Homo sapiens* (human) Source: Organ: lung<br>Disease: non-small cell lung cancer | NCI-H2444<br>[H2444] |
| CRL-5975 | *Homo sapiens* (human) Source: Organ: lung<br>Disease: carcinoid | UMC-11 |
| CRL-5976 | *Homo sapiens* (human) Source: Organ: lung<br>Tumor Stage: stage E<br>Disease: carcinoma; small cell lung cancer<br>Derived from metastatic site: lymph node | NCI-H64 [H64] |
| CRL-5978 | *Homo sapiens* (human) Source: Organ: lung<br>Tumor Stage: stage E<br>Disease: carcinoma; small cell lung cancer<br>Derived from metastatic site: liver | NCI-H735 [H735] |

TABLE 25-continued

Cell lines

| ATCC Number | Hybridoma or Cell line Description | Name |
|---|---|---|
| CRL-5978 | *Homo sapiens* (human) Source: Organ: lung<br>Tumor Stage: stage E<br>Disease: carcinoma; small cell lung cancer<br>Derived from metastatic site: liver | NCI-H735 [H735] |
| CRL-5982 | *Homo sapiens* (human) Source: Organ: lung<br>Tumor Stage: stage L<br>Disease: carcinoma; small cell lung cancer | NCI-H1963 [H1963] |
| CRL-5983 | *Homo sapiens* (human) Source: Organ: lung<br>Tumor Stage: stage E<br>Disease: carcinoma; small cell lung cancer<br>Derived from metastatic site: bone marrow | NCI-H2107 [H2107] |
| CRL-5984 | *Homo sapiens* (human) Source: Organ: lung<br>Tumor Stage: stage E<br>Disease: carcinoma; small cell lung cancer<br>Derived from metastatic site: bone marrow | NCI-H2108 [H2108] |
| CRL-5985 | *Homo sapiens* (human) Source: Organ: lung<br>Tumor Stage: stage 4<br>Disease: adenocarcinoma; non-small cell lung cancer<br>Derived from metastatic site: pleural effusion | NCI-H2122 [H2122] |
| CRL-7343 | *Homo sapiens* (human) Source: Organ: lung<br>Disease: cancer | Hs 573.T |
| CRL-7344 | *Homo sapiens* (human) Source: Organ: lung | Hs 573.Lu |
| CRL-8024 | *Homo sapiens* (human) Source: Organ: liver<br>Disease: hepatoma<br>Cell Type: Alexander cells; | PLC/PRF/5 |
| CRL-9609 | *Homo sapiens* (human) Source: Organ: lung<br>Tissue: bronchus<br>Disease: normal<br>Cell Type: epithelial virus transformed | BEAS-2B |
| HB-8065 | *Homo sapiens* (human) Source: Organ: liver<br>Disease: hepatocellular carcinoma | HepG2 |
| HTB-105 | *Homo sapiens* (human) Source: Organ: testes<br>Disease: embryonal carcinoma, malignant<br>Derived from metastatic site: lung | Tera-1 |
| HTB-106 | *Homo sapiens* (human) Source: Disease:<br>malignant embryonal carcinoma<br>Derived from metastatic site: lung | Tera-2 |
| HTB-119 | *Homo sapiens* (human) Source: Organ: lung<br>Disease: carcinoma; small cell lung cancer | NCI-H69 [H69] |
| HTB-120 | *Homo sapiens* (human) Source: Organ: lung<br>Disease: carcinoma; small cell lung cancer<br>Derived from metastatic site: pleural effusion | NCI-H128 [H128] |
| HTB-168 | *Homo sapiens* (human) Source: Organ: lung<br>Tissue: bronchus<br>Disease: bronchogenic carcinoma | ChaGo-K-1 |
| HTB-171 | *Homo sapiens* (human) Source: Organ: lung<br>Disease: carcinoma; small cell lung cancer<br>Derived from metastatic site: pleural effusion | NCI-H446 [H446] |
| HTB-172 | *Homo sapiens* (human) Source: Organ: lung<br>Disease: carcinoma; small cell lung cancer<br>Derived from metastatic site: bone marrow | NCI-H209 [H209] |
| HTB-173 | *Homo sapiens* (human) Source: Organ: lung<br>Disease: carcinoma; small cell lung cancer<br>Derived from metastatic site: bone marrow | NCI-H146 [H146] |
| HTB-174 | *Homo sapiens* (human) Source: Organ: lung<br>Disease: papillary adenocarcinoma | NCI-H441 [H441] |
| HTB-175 | *Homo sapiens* (human) Source: Organ: lung<br>Disease: carcinoma; small cell lung cancer<br>Derived from metastatic site: pleural effusion | NCI-H82 [H82] |
| HTB-177 | *Homo sapiens* (human) Source: Organ: lung<br>Disease: carcinoma; large cell lung cancer<br>Derived from metastatic site: pleural effusion | NCI-H460 [H460] |
| HTB-178 | *Homo sapiens* (human) Source: Organ: lung<br>Disease: adenosquamous carcinoma | NCI-H596 [H596] |
| HTB-179 | *Homo sapiens* (human) Source: Organ: lung<br>Disease: adenocarcinoma<br>Derived from metastatic site: pleural effusion | NCI-H676B [H676B] |
| HTB-180 | *Homo sapiens* (human) Source: Organ: lung<br>Disease: carcinoma; small cell lung cancer<br>Derived from metastatic site: bone marrow | NCI-H345 [H345] |
| HTB-181 | *Homo sapiens* (human) Source: Organ: lung<br>Disease: papillary adenocarcinoma<br>Derived from metastatic site: lymph node | NCI-H820 [H820] |

TABLE 25-continued

Cell lines

| ATCC Number | Hybridoma or Cell line Description | Name |
|---|---|---|
| HTB-182 | *Homo sapiens* (human) Source: Organ: lung Disease: squamous cell carcinoma | NCI-H520 [H520] |
| HTB-183 | *Homo sapiens* (human) Source: Organ: lung Disease: carcinoma; large cell lung cancer Derived from metastatic site: lymph node | NCI-H661 [H661] |
| HTB-184 | *Homo sapiens* (human) Source: Organ: lung Disease: carcinoma; small cell lung cancer; extrapulmonary origin Derived from metastatic site: adrenal gland | NCI-H510A [H510A, NCI-H510] |
| HTB-52 | *Homo sapiens* (human) Source: Organ: liver Tissue: ascites Disease: adenocarcinoma | SK-HEP-1 |
| HTB-53 | *Homo sapiens* (human) Source: Organ: lung Disease: carcinoma | A-427 |
| HTB-54 | *Homo sapiens* (human) Source: Organ: lung Tumor Stage: grade III Disease: epidermoid carcinoma Derived from metastatic site: pleura | Calu-1 |
| HTB-55 | *Homo sapiens* (human) Source: Organ: lung Disease: adenocarcinoma Derived from metastatic site: pleural effusion | Calu-3 |
| HTB-56 | *Homo sapiens* (human) Source: Organ: unknown, probably lung Disease: anaplastic carcinoma | Calu-6 |
| HTB-57 | *Homo sapiens* (human) Source: Organ: lung Disease: adenocarcinoma | SK-LU-1 |
| HTB-58 | *Homo sapiens* (human) Source: Organ: lung Disease: squamous cell carcinoma Derived from metastatic site: pleural effusion | SK-MES-1 |
| HTB-59 | *Homo sapiens* (human) Source: Organ: lung Tumor Stage: grade IV Disease: squamous cell carcinoma | SW 900 [SW-900, SW900] |
| HTB-64 | *Homo sapiens* (human) Source: Disease: malignant melanoma Derived from metastatic site: lung | Malme-3M |
| HTB-79 | *Homo sapiens* (human) Source: Organ: pancreas Disease: adenocarcinoma Derived from metastatic site: liver | Capan-1 |

Example 23. RNA Binding Proteins

RNA binding proteins may be provided as proteins and/or as nucleic acids encoding such proteins. RNA binding proteins play a multitude of roles in regulating RNA stability and protein translation. In some embodiments, RNA binding proteins are provided in protein and/or nucleic acid form with elements of the present invention. Such RNA binding proteins include, but are not limited to those listed (along with the ENSG number, identifying the corresponding gene as well as one or more ENST number, identifying transcriptional variants of each) in Table 26.

TABLE 26

RNA binding proteins

| Protein No. | RNA binding protein | ENSG | ENST | ENST SEQ ID NO | ENSP | ENSP SEQ ID NO |
|---|---|---|---|---|---|---|
| 1 | AU RNA binding protein/enoyl-CoA hydratase | 148090 | 422391 | 4279 | 402026 | 4632 |
| 2 | AU RNA binding protein/enoyl-CoA hydratase | 148090 | 303617 | 4280 | 307334 | 4633 |
| 3 | AU RNA binding protein/enoyl-CoA hydratase | 148090 | 375731 | 4281 | 364883 | 4634 |
| 4 | cold inducible RNA binding protein | 99622 | 320936 | 4282 | 322887 | 4635 |
| 5 | cold inducible RNA binding protein | 99622 | 444172 | 4283 | 407512 | 4636 |
| 6 | cold inducible RNA binding protein | 99622 | 413636 | 4284 | 412831 | 4637 |
| 7 | cold shock domain containing C2, RNA binding | 172346 | 306149 | 4285 | 302485 | 4638 |

TABLE 26-continued

| | RNA binding proteins | | | | | |
|---|---|---|---|---|---|---|
| Protein No. | RNA binding protein | ENSG | ENST | ENST SEQ ID NO | ENSP | ENSP SEQ ID NO |
| 8 | heterogeneous nuclear ribonucleoprotein D (AU-rich element RNA binding protein 1, 37 kDa) | 138668 | 543098 | 4286 | 439380 | 4639 |
| 9 | heterogeneous nuclear ribonucleoprotein D (AU-rich element RNA binding protein 1, 37 kDa) | 138668 | 313899 | 4287 | 313199 | 4640 |
| 10 | heterogeneous nuclear ribonucleoprotein D (AU-rich element RNA binding protein 1, 37 kDa) | 138668 | 541060 | 4288 | 437416 | 4641 |
| 11 | heterogeneous nuclear ribonucleoprotein D (AU-rich element RNA binding protein 1, 37 kDa) | 138668 | 503822 | 4289 | 422615 | 4642 |
| 12 | heterogeneous nuclear ribonucleoprotein D (AU-rich element RNA binding protein 1, 37 kDa) | 138668 | 507010 | 4290 | 421952 | 4643 |
| 13 | heterogeneous nuclear ribonucleoprotein D (AU-rich element RNA binding protein 1, 37 kDa) | 138668 | 353341 | 4291 | 313327 | 4644 |
| 14 | heterogeneous nuclear ribonucleoprotein D (AU-rich element RNA binding protein 1, 37 kDa) | 138668 | 514671 | 4292 | 426446 | 4645 |
| 15 | heterogeneous nuclear ribonucleoprotein D (AU-rich element RNA binding protein 1, 37 kDa) | 138668 | 352301 | 4293 | 305860 | 4646 |
| 16 | heterogeneous nuclear ribonucleoprotein D (AU-rich element RNA binding protein 1, 37 kDa) | 138668 | 307213 | 4294 | 307544 | 4647 |
| 17 | insulin-like growth factor 2 mRNA binding protein 1 | 159217 | 290341 | 4295 | 290341 | 4648 |
| 18 | insulin-like growth factor 2 mRNA binding protein 2 | 73792 | 382199 | 4296 | 371634 | 4649 |
| 19 | insulin-like growth factor 2 mRNA binding protein 2 | 73792 | 421047 | 4297 | 413787 | 4650 |
| 20 | insulin-like growth factor 2 mRNA binding protein 2 | 73792 | 346192 | 4298 | 320204 | 4651 |
| 21 | insulin-like growth factor 2 mRNA binding protein 3 | 136231 | 258729 | 4299 | 258729 | 4652 |
| 22 | KH domain containing, RNA binding, signal transduction associated 1 | 121774 | 327300 | 4300 | 313829 | 4653 |
| 23 | KH domain containing, RNA binding, signal transduction associated 1 | 121774 | 492989 | 4301 | 417731 | 4654 |
| 24 | KH domain containing, RNA binding, signal transduction associated 1 | 121774 | 355201 | 4302 | 347336 | 4655 |
| 25 | KH domain containing, RNA binding, signal transduction associated 2 | 112232 | 281156 | 4303 | 281156 | 4656 |
| 26 | KH domain containing, RNA binding, signal transduction associated 2 | 112232 | 539571 | 4304 | 443437 | 4657 |
| 27 | KH domain containing, RNA binding, signal transduction associated 3 | 131773 | 355849 | 4305 | 348108 | 4658 |
| 28 | QKI, KH domain containing, RNA binding | 112531 | 361752 | 4306 | 355094 | 4659 |
| 29 | QKI, KH domain containing, RNA binding | 112531 | 275262 | 4307 | 275262 | 4660 |
| 30 | QKI, KH domain containing, RNA binding | 112531 | 392127 | 4308 | 375973 | 4661 |
| 31 | QKI, KH domain containing, RNA binding | 112531 | 361195 | 4309 | 354867 | 4662 |

TABLE 26-continued

| | RNA binding proteins | | | | | |
|---|---|---|---|---|---|---|
| Protein No. | RNA binding protein | ENSG | ENST | ENST SEQ ID NO | ENSP | ENSP SEQ ID NO |
| 32 | QKI, KH domain containing, RNA binding | 112531 | 453779 | 4310 | 408775 | 4663 |
| 33 | RALY RNA binding protein-like | 184672 | 522613 | 4311 | 427787 | 4664 |
| 34 | RALY RNA binding protein-like | 184672 | 523850 | 4312 | 428807 | 4665 |
| 35 | RALY RNA binding protein-like | 184672 | 521695 | 4313 | 428667 | 4666 |
| 36 | RALY RNA binding protein-like | 184672 | 521268 | 4314 | 430367 | 4667 |
| 37 | RALY RNA binding protein-like | 184672 | 517988 | 4315 | 428711 | 4668 |
| 38 | RALY RNA binding protein-like | 184672 | 522455 | 4316 | 430394 | 4669 |
| 39 | RD RNA binding protein | 204356 | 375425 | 4317 | 364574 | 4670 |
| 40 | RD RNA binding protein | 204356 | 444811 | 4318 | 388400 | 4671 |
| 41 | RD RNA binding protein | 204356 | 441998 | 4319 | 397914 | 4672 |
| 42 | RD RNA binding protein | 204356 | 375429 | 4320 | 364578 | 4673 |
| 43 | RD RNA binding protein | 204356 | 426722 | 4321 | 394340 | 4674 |
| 44 | RD RNA binding protein | 204356 | 454913 | 4322 | 409389 | 4675 |
| 45 | RD RNA binding protein | 206268 | 411745 | 4323 | 410872 | 4676 |
| 46 | RD RNA binding protein | 206268 | 456281 | 4324 | 396971 | 4677 |
| 47 | RD RNA binding protein | 206268 | 440478 | 4325 | 407528 | 4678 |
| 48 | RD RNA binding protein | 206268 | 383174 | 4326 | 372660 | 4679 |
| 49 | RD RNA binding protein | 206268 | 551833 | 4327 | 447903 | 4680 |
| 50 | RD RNA binding protein | 206268 | 458622 | 4328 | 409139 | 4681 |
| 51 | RD RNA binding protein | 206357 | 548056 | 4329 | 449897 | 4682 |
| 52 | RD RNA binding protein | 206357 | 434518 | 4330 | 409269 | 4683 |
| 53 | RD RNA binding protein | 206357 | 449057 | 4331 | 393793 | 4684 |
| 54 | RD RNA binding protein | 206357 | 383343 | 4332 | 372834 | 4685 |
| 55 | RD RNA binding protein | 206357 | 420039 | 4333 | 411487 | 4686 |
| 56 | RD RNA binding protein | 206357 | 425810 | 4334 | 403630 | 4687 |
| 57 | RD RNA binding protein | 229363 | 549252 | 4335 | 450250 | 4688 |
| 58 | RD RNA binding protein | 229363 | 448628 | 4336 | 394879 | 4689 |
| 59 | RD RNA binding protein | 229363 | 424762 | 4337 | 415567 | 4690 |
| 60 | RD RNA binding protein | 229363 | 418423 | 4338 | 395175 | 4691 |
| 61 | RD RNA binding protein | 229363 | 418059 | 4339 | 401342 | 4692 |
| 62 | RD RNA binding protein | 229363 | 453084 | 4340 | 393794 | 4693 |
| 63 | RD RNA binding protein | 231044 | 443464 | 4341 | 393103 | 4694 |
| 64 | RD RNA binding protein | 231044 | 548988 | 4342 | 449910 | 4695 |
| 65 | RD RNA binding protein | 231044 | 429857 | 4343 | 403623 | 4696 |
| 66 | RD RNA binding protein | 231044 | 437732 | 4344 | 397565 | 4697 |
| 67 | RD RNA binding protein | 231044 | 424967 | 4345 | 411724 | 4698 |
| 68 | RD RNA binding protein | 231044 | 420837 | 4346 | 414014 | 4699 |
| 69 | RD RNA binding protein | 233801 | 456263 | 4347 | 407630 | 4700 |
| 70 | RD RNA binding protein | 233801 | 452147 | 4348 | 401745 | 4701 |
| 71 | RD RNA binding protein | 233801 | 457397 | 4349 | 393005 | 4702 |
| 72 | RD RNA binding protein | 233801 | 552869 | 4350 | 447844 | 4703 |
| 73 | RD RNA binding protein | 233801 | 425721 | 4351 | 390689 | 4704 |
| 74 | RD RNA binding protein | 233801 | 435435 | 4352 | 396604 | 4705 |
| 75 | RNA binding motif (RNP1, RRM) protein 3 | 102317 | 430348 | 4353 | 412764 | 4706 |
| 76 | RNA binding motif (RNP1, RRM) protein 3 | 102317 | 376759 | 4354 | 365950 | 4707 |
| 77 | RNA binding motif (RNP1, RRM) protein 3 | 102317 | 376755 | 4355 | 365946 | 4708 |
| 78 | RNA binding motif (RNP1, RRM) protein 3 | 102317 | 354480 | 4356 | 346473 | 4709 |
| 79 | RNA binding motif protein 10 | 182872 | 377604 | 4357 | 366829 | 4710 |
| 80 | RNA binding motif protein 10 | 182872 | 329236 | 4358 | 328848 | 4711 |
| 81 | RNA binding motif protein 10 | 182872 | 345781 | 4359 | 329659 | 4712 |
| 82 | RNA binding motif protein 11 | 185272 | 400577 | 4360 | 383421 | 4713 |
| 83 | RNA binding motif protein 12 | 244462 | 359646 | 4361 | 352668 | 4714 |
| 84 | RNA binding motif protein 12 | 244462 | 374104 | 4362 | 363217 | 4715 |
| 85 | RNA binding motif protein 12 | 244462 | 374114 | 4363 | 363228 | 4716 |
| 86 | RNA binding motif protein 12 | 244462 | 431148 | 4364 | 392642 | 4717 |
| 87 | RNA binding motif protein 12 | 244462 | 424458 | 4365 | 411036 | 4718 |
| 88 | RNA binding motif protein 12 | 244462 | 435161 | 4366 | 411692 | 4719 |
| 89 | RNA binding motif protein 12 | 244462 | 349942 | 4367 | 339879 | 4720 |
| 90 | RNA binding motif protein 12B | 183808 | 518597 | 4368 | 428269 | 4721 |
| 91 | RNA binding motif protein 12B | 183808 | 399300 | 4369 | 382239 | 4722 |
| 92 | RNA binding motif protein 12B | 183808 | 520560 | 4370 | 429807 | 4723 |
| 93 | RNA binding motif protein 12B | 183808 | 521947 | 4371 | 430466 | 4724 |
| 94 | RNA binding motif protein 12B | 183808 | 517700 | 4372 | 427729 | 4725 |
| 95 | RNA binding motif protein 12B | 183808 | 519109 | 4373 | 430474 | 4726 |
| 96 | RNA binding motif protein 14 | 239306 | 310137 | 4374 | 311747 | 4727 |
| 97 | RNA binding motif protein 15 | 162775 | 369784 | 4375 | 358799 | 4728 |
| 98 | RNA binding motif protein 15B | 179837 | 323686 | 4376 | 313890 | 4729 |
| 99 | RNA binding motif protein 15B | 179837 | 536338 | 4377 | 444388 | 4730 |

TABLE 26-continued

| | RNA binding proteins | | | | | |
|---|---|---|---|---|---|---|
| Protein No. | RNA binding protein | ENSG | ENST | ENST SEQ ID NO | ENSP | ENSP SEQ ID NO |
| 100 | RNA binding motif protein 15B | 179837 | 541145 | 4378 | 443941 | 4731 |
| 101 | RNA binding motif protein 15B | 179837 | 540284 | 4379 | 437933 | 4732 |
| 102 | RNA binding motif protein 17 | 134453 | 447032 | 4380 | 406024 | 4733 |
| 103 | RNA binding motif protein 17 | 134453 | 437845 | 4381 | 395448 | 4734 |
| 104 | RNA binding motif protein 17 | 134453 | 372795 | 4382 | 361881 | 4735 |
| 105 | RNA binding motif protein 17 | 134453 | 418631 | 4383 | 402303 | 4736 |
| 106 | RNA binding motif protein 17 | 134453 | 432931 | 4384 | 408214 | 4737 |
| 107 | RNA binding motif protein 17 | 134453 | 379888 | 4385 | 369218 | 4738 |
| 108 | RNA binding motif protein 17 | 134453 | 446108 | 4386 | 388638 | 4739 |
| 109 | RNA binding motif protein 18 | 119446 | 417201 | 4387 | 409315 | 4740 |
| 110 | RNA binding motif protein 19 | 122965 | 545145 | 4388 | 442053 | 4741 |
| 111 | RNA binding motif protein 19 | 122965 | 261741 | 4389 | 261741 | 4742 |
| 112 | RNA binding motif protein 19 | 122965 | 392561 | 4390 | 376344 | 4743 |
| 113 | RNA binding motif protein 20 | 203867 | 539821 | 4391 | 446400 | 4744 |
| 114 | RNA binding motif protein 20 | 203867 | 369519 | 4392 | 358532 | 4745 |
| 115 | RNA binding motif protein 22 | 86589 | 447771 | 4393 | 412118 | 4746 |
| 116 | RNA binding motif protein 22 | 86589 | 199814 | 4394 | 199814 | 4747 |
| 117 | RNA binding motif protein 22 | 86589 | 540000 | 4395 | 441594 | 4748 |
| 118 | RNA binding motif protein 23 | 100461 | 399922 | 4396 | 382806 | 4749 |
| 119 | RNA binding motif protein 23 | 100461 | 359890 | 4397 | 352956 | 4750 |
| 120 | RNA binding motif protein 23 | 100461 | 346528 | 4398 | 339220 | 4751 |
| 121 | RNA binding motif protein 23 | 100461 | 554618 | 4399 | 451448 | 4752 |
| 122 | RNA binding motif protein 23 | 100461 | 553876 | 4400 | 450672 | 4753 |
| 123 | RNA binding motif protein 23 | 100461 | 557571 | 4401 | 452382 | 4754 |
| 124 | RNA binding motif protein 23 | 100461 | 557549 | 4402 | 450558 | 4755 |
| 125 | RNA binding motif protein 23 | 100461 | 338980 | 4403 | 345496 | 4756 |
| 126 | RNA binding motif protein 23 | 100461 | 554256 | 4404 | 452583 | 4757 |
| 127 | RNA binding motif protein 23 | 100461 | 557464 | 4405 | 451403 | 4758 |
| 128 | RNA binding motif protein 23 | 100461 | 555691 | 4406 | 452538 | 4759 |
| 129 | RNA binding motif protein 23 | 100461 | 556862 | 4407 | 452557 | 4760 |
| 130 | RNA binding motif protein 23 | 100461 | 555676 | 4408 | 451364 | 4761 |
| 131 | RNA binding motif protein 24 | 112183 | 379052 | 4409 | 368341 | 4762 |
| 132 | RNA binding motif protein 24 | 112183 | 318204 | 4410 | 319551 | 4763 |
| 133 | RNA binding motif protein 24 | 112183 | 425446 | 4411 | 396898 | 4764 |
| 134 | RNA binding motif protein 25 | 119707 | 525161 | 4412 | 434004 | 4765 |
| 135 | RNA binding motif protein 25 | 119707 | 525321 | 4413 | 436868 | 4766 |
| 136 | RNA binding motif protein 25 | 119707 | 531500 | 4414 | 434333 | 4767 |
| 137 | RNA binding motif protein 25 | 119707 | 261973 | 4415 | 261973 | 4768 |
| 138 | RNA binding motif protein 25 | 119707 | 527432 | 4416 | 431150 | 4769 |
| 139 | RNA binding motif protein 25 | 119707 | 526754 | 4417 | 436225 | 4770 |
| 140 | RNA binding motif protein 25 | 119707 | 540173 | 4418 | 437934 | 4771 |
| 141 | RNA binding motif protein 26 | 139746 | 267229 | 4419 | 267229 | 4772 |
| 142 | RNA binding motif protein 26 | 139746 | 327303 | 4420 | 327080 | 4773 |
| 143 | RNA binding motif protein 26 | 139746 | 438724 | 4421 | 390222 | 4774 |
| 144 | RNA binding motif protein 27 | 91009 | 265271 | 4422 | 265271 | 4775 |
| 145 | RNA binding motif protein 28 | 106344 | 223073 | 4423 | 223073 | 4776 |
| 146 | RNA binding motif protein 33 | 184863 | 438356 | 4424 | 405793 | 4777 |
| 147 | RNA binding motif protein 33 | 184863 | 287912 | 4425 | 287912 | 4778 |
| 148 | RNA binding motif protein 33 | 184863 | 401878 | 4426 | 384160 | 4779 |
| 149 | RNA binding motif protein 33 | 184863 | 341148 | 4427 | 341583 | 4780 |
| 150 | RNA binding motif protein 34 | 188739 | 408888 | 4428 | 386226 | 4781 |
| 151 | RNA binding motif protein 34 | 188739 | 400947 | 4429 | 383731 | 4782 |
| 152 | RNA binding motif protein 34 | 188739 | 429912 | 4430 | 413409 | 4783 |
| 153 | RNA binding motif protein 34 | 188739 | 366606 | 4431 | 355565 | 4784 |
| 154 | RNA binding motif protein 38 | 132819 | 356208 | 4432 | 348538 | 4785 |
| 155 | RNA binding motif protein 38 | 132819 | 440234 | 4433 | 407848 | 4786 |
| 156 | RNA binding motif protein 38 | 132819 | 371219 | 4434 | 360263 | 4787 |
| 157 | RNA binding motif protein 39 | 131051 | 253363 | 4435 | 253363 | 4788 |
| 158 | RNA binding motif protein 39 | 131051 | 407261 | 4436 | 384541 | 4789 |
| 159 | RNA binding motif protein 39 | 131051 | 361162 | 4437 | 354437 | 4790 |
| 160 | RNA binding motif protein 39 | 131051 | 448303 | 4438 | 394824 | 4791 |
| 161 | RNA binding motif protein 39 | 131051 | 374038 | 4439 | 363150 | 4792 |
| 162 | RNA binding motif protein 39 | 131051 | 528062 | 4440 | 436747 | 4793 |
| 163 | RNA binding motif protein 39 | 131051 | 338163 | 4441 | 344581 | 4794 |
| 164 | RNA binding motif protein 39 | 131051 | 434927 | 4442 | 393493 | 4795 |
| 165 | RNA binding motif protein 4 | 173933 | 532968 | 4443 | 432020 | 4796 |
| 166 | RNA binding motif protein 4 | 173933 | 408993 | 4444 | 386561 | 4797 |
| 167 | RNA binding motif protein 4 | 173933 | 409406 | 4445 | 386894 | 4798 |
| 168 | RNA binding motif protein 4 | 173933 | 483858 | 4446 | 435821 | 4799 |
| 169 | RNA binding motif protein 4 | 173933 | 310092 | 4447 | 309166 | 4800 |
| 170 | RNA binding motif protein 41 | 89682 | 434854 | 4448 | 405522 | 4801 |
| 171 | RNA binding motif protein 41 | 89682 | 372479 | 4449 | 361557 | 4802 |
| 172 | RNA binding motif protein 41 | 89682 | 372487 | 4450 | 361565 | 4803 |

TABLE 26-continued

| | RNA binding proteins | | | | | |
|---|---|---|---|---|---|---|
| Protein No. | RNA binding protein | ENSG | ENST | ENST SEQ ID NO | ENSP | ENSP SEQ ID NO |
| 173 | RNA binding motif protein 41 | 89682 | 372482 | 4451 | 361560 | 4804 |
| 174 | RNA binding motif protein 41 | 89682 | 203616 | 4452 | 203616 | 4805 |
| 175 | RNA binding motif protein 42 | 126254 | 262633 | 4453 | 262633 | 4806 |
| 176 | RNA binding motif protein 42 | 126254 | 360475 | 4454 | 353663 | 4807 |
| 177 | RNA binding motif protein 43 | 184898 | 331426 | 4455 | 331211 | 4808 |
| 178 | RNA binding motif protein 44 | 177483 | 316997 | 4456 | 321179 | 4809 |
| 179 | RNA binding motif protein 44 | 177483 | 409864 | 4457 | 386727 | 4810 |
| 180 | RNA binding motif protein 45 | 155636 | 286070 | 4458 | 286070 | 4811 |
| 181 | RNA binding motif protein 45 | 155636 | 455903 | 4459 | 415940 | 4812 |
| 182 | RNA binding motif protein 46 | 151962 | 281722 | 4460 | 281722 | 4813 |
| 183 | RNA binding motif protein 47 | 163694 | 295971 | 4461 | 295971 | 4814 |
| 184 | RNA binding motif protein 47 | 163694 | 381793 | 4462 | 371212 | 4815 |
| 185 | RNA binding motif protein 47 | 163694 | 511902 | 4463 | 425111 | 4816 |
| 186 | RNA binding motif protein 47 | 163694 | 515053 | 4464 | 422564 | 4817 |
| 187 | RNA binding motif protein 47 | 163694 | 511598 | 4465 | 424019 | 4818 |
| 188 | RNA binding motif protein 47 | 163694 | 513473 | 4466 | 421589 | 4819 |
| 189 | RNA binding motif protein 47 | 163694 | 505414 | 4467 | 423527 | 4820 |
| 190 | RNA binding motif protein 47 | 163694 | 514782 | 4468 | 426542 | 4821 |
| 191 | RNA binding motif protein 47 | 163694 | 319592 | 4469 | 320108 | 4822 |
| 192 | RNA binding motif protein 47 | 163694 | 507180 | 4470 | 423398 | 4823 |
| 193 | RNA binding motif protein 47 | 163694 | 381795 | 4471 | 371214 | 4824 |
| 194 | RNA binding motif protein 47 | 163694 | 505220 | 4472 | 425507 | 4825 |
| 195 | RNA binding motif protein 48 | 127993 | 509224 | 4473 | 442073 | 4826 |
| 196 | RNA binding motif protein 48 | 127993 | 450580 | 4474 | 401920 | 4827 |
| 197 | RNA binding motif protein 48 | 127993 | 265732 | 4475 | 265732 | 4828 |
| 198 | RNA binding motif protein 4B | 173914 | 525754 | 4476 | 433071 | 4829 |
| 199 | RNA binding motif protein 4B | 173914 | 310046 | 4477 | 310471 | 4830 |
| 200 | RNA binding motif protein 5 | 3756 | 469838 | 4478 | 419534 | 4831 |
| 201 | RNA binding motif protein 5 | 3756 | 347869 | 4479 | 343054 | 4832 |
| 202 | RNA binding motif protein 5 | 3756 | 441305 | 4480 | 390711 | 4833 |
| 203 | RNA binding motif protein 5 | 3756 | 543047 | 4481 | 442591 | 4834 |
| 204 | RNA binding motif protein 5 | 3756 | 536082 | 4482 | 445347 | 4835 |
| 205 | RNA binding motif protein 5 | 3756 | 417905 | 4483 | 406119 | 4836 |
| 206 | RNA binding motif protein 5 | 3756 | 437500 | 4484 | 394622 | 4837 |
| 207 | RNA binding motif protein 5 | 3756 | 544851 | 4485 | 439808 | 4838 |
| 208 | RNA binding motif protein 5 | 3756 | 539538 | 4486 | 440744 | 4839 |
| 209 | RNA binding motif protein 6 | 4534 | 422955 | 4487 | 392939 | 4840 |
| 210 | RNA binding motif protein 6 | 4534 | 442092 | 4488 | 393530 | 4841 |
| 211 | RNA binding motif protein 6 | 4534 | 425608 | 4489 | 408665 | 4842 |
| 212 | RNA binding motif protein 6 | 4534 | 443081 | 4490 | 396466 | 4843 |
| 213 | RNA binding motif protein 6 | 4534 | 416583 | 4491 | 390202 | 4844 |
| 214 | RNA binding motif protein 6 | 4534 | 433811 | 4492 | 389763 | 4845 |
| 215 | RNA binding motif protein 6 | 4534 | 539992 | 4493 | 443165 | 4846 |
| 216 | RNA binding motif protein 6 | 4534 | 266022 | 4494 | 266022 | 4847 |
| 217 | RNA binding motif protein 7 | 76053 | 540163 | 4495 | 439918 | 4848 |
| 218 | RNA binding motif protein 8A | 131795 | 369307 | 4496 | 358313 | 4849 |
| 219 | RNA binding motif protein 8A | 131795 | 330165 | 4497 | 333001 | 4850 |
| 220 | RNA binding motif protein, X-linked | 147274 | 449161 | 4498 | 415250 | 4851 |
| 221 | RNA binding motif protein, X-linked | 147274 | 320676 | 4499 | 359645 | 4852 |
| 222 | RNA binding motif protein, X-linked | 147274 | 419968 | 4500 | 405117 | 4853 |
| 223 | RNA binding motif protein, X-linked | 147274 | 431446 | 4501 | 411989 | 4854 |
| 224 | RNA binding motif protein, X-linked 2 | 134597 | 305536 | 4502 | 339090 | 4855 |
| 225 | RNA binding motif protein, X-linked 2 | 134597 | 370947 | 4503 | 359985 | 4856 |
| 226 | RNA binding motif protein, X-linked 2 | 134597 | 538614 | 4504 | 437425 | 4857 |
| 227 | RNA binding motif protein, X-linked-like 1 | 213516 | 399794 | 4505 | 446099 | 4858 |
| 228 | RNA binding motif protein, X-linked-like 1 | 213516 | 321792 | 4506 | 318415 | 4859 |
| 229 | RNA binding motif protein, X-linked-like 2 | 170748 | 306904 | 4507 | 304139 | 4860 |
| 230 | RNA binding motif protein, X-linked-like 3 | 175718 | 424776 | 4508 | 417451 | 4861 |
| 231 | RNA binding motif protein, Y-linked, family 1, member A1 | 234414 | 382707 | 4509 | 372154 | 4862 |
| 232 | RNA binding motif protein, Y-linked, family 1, member A1 | 234414 | 439108 | 4510 | 388006 | 4863 |

TABLE 26-continued

| Protein No. | RNA binding protein | ENSG | ENST | ENST SEQ ID NO | ENSP | ENSP SEQ ID NO |
|---|---|---|---|---|---|---|
| 233 | RNA binding motif protein, Y-linked, family 1, member A1 | 234414 | 303902 | 4511 | 303712 | 4864 |
| 234 | RNA binding motif protein, Y-linked, family 1, member B | 242875 | 383020 | 4512 | 372484 | 4865 |
| 235 | RNA binding motif protein, Y-linked, family 1, member D | 244395 | 418956 | 4513 | 399181 | 4866 |
| 236 | RNA binding motif protein, Y-linked, family 1, member D | 244395 | 382680 | 4514 | 372127 | 4867 |
| 237 | RNA binding motif protein, Y-linked, family 1, member D | 244395 | 382677 | 4515 | 372124 | 4868 |
| 238 | RNA binding motif protein, Y-linked, family 1, member E | 242389 | 382658 | 4516 | 372104 | 4869 |
| 239 | RNA binding motif protein, Y-linked, family 1, member E | 242389 | 382659 | 4517 | 372105 | 4870 |
| 240 | RNA binding motif protein, Y-linked, family 1, member E | 242389 | 382673 | 4518 | 372119 | 4871 |
| 241 | RNA binding motif protein, Y-linked, family 1, member F | 169800 | 303766 | 4519 | 307155 | 4872 |
| 242 | RNA binding motif protein, Y-linked, family 1, member F | 169800 | 454978 | 4520 | 406005 | 4873 |
| 243 | RNA binding motif protein, Y-linked, family 1, member J | 226941 | 414629 | 4521 | 405745 | 4874 |
| 244 | RNA binding motif protein, Y-linked, family 1, member J | 226941 | 250831 | 4522 | 250831 | 4875 |
| 245 | RNA binding motif protein, Y-linked, family 1, member J | 226941 | 445779 | 4523 | 389621 | 4876 |
| 246 | RNA binding motif, single stranded interacting protein 1 | 153250 | 348849 | 4524 | 294904 | 4877 |
| 247 | RNA binding motif, single stranded interacting protein 1 | 153250 | 428519 | 4525 | 389016 | 4878 |
| 248 | RNA binding motif, single stranded interacting protein 1 | 153250 | 409075 | 4526 | 386347 | 4879 |
| 249 | RNA binding motif, single stranded interacting protein 1 | 153250 | 409972 | 4527 | 387280 | 4880 |
| 250 | RNA binding motif, single stranded interacting protein 1 | 153250 | 392753 | 4528 | 376508 | 4881 |
| 251 | RNA binding motif, single stranded interacting protein 1 | 153250 | 409289 | 4529 | 386571 | 4882 |
| 252 | RNA binding motif, single stranded interacting protein 2 | 76067 | 262031 | 4530 | 262031 | 4883 |
| 253 | RNA binding motif, single stranded interacting protein 3 | 144642 | 434693 | 4531 | 395592 | 4884 |
| 254 | RNA binding motif, single stranded interacting protein 3 | 144642 | 383767 | 4532 | 373277 | 4885 |
| 255 | RNA binding motif, single stranded interacting protein 3 | 144642 | 383766 | 4533 | 373276 | 4886 |
| 256 | RNA binding motif, single stranded interacting protein 3 | 144642 | 456853 | 4534 | 400519 | 4887 |
| 257 | RNA binding motif, single stranded interacting protein 3 | 144642 | 396583 | 4535 | 379828 | 4888 |
| 258 | RNA binding motif, single stranded interacting protein 3 | 144642 | 273139 | 4536 | 273139 | 4889 |
| 259 | RNA binding protein S1, serine-rich domain | 205937 | 320225 | 4537 | 315859 | 4890 |
| 260 | RNA binding protein S1, serine-rich domain | 205937 | 301730 | 4538 | 301730 | 4891 |
| 261 | RNA binding protein S1, serine-rich domain | 205937 | 397086 | 4539 | 380275 | 4892 |
| 262 | RNA binding protein with multiple splicing | 157110 | 320203 | 4540 | 318102 | 4893 |
| 263 | RNA binding protein with multiple splicing | 157110 | 287771 | 4541 | 287771 | 4894 |
| 264 | RNA binding protein with multiple splicing | 157110 | 339877 | 4542 | 340176 | 4895 |
| 265 | RNA binding protein with multiple splicing | 157110 | 538486 | 4543 | 445406 | 4896 |
| 266 | RNA binding protein with multiple splicing | 157110 | 397323 | 4544 | 380486 | 4897 |
| 267 | RNA binding protein with multiple splicing 2 | 166831 | 300069 | 4545 | 300069 | 4898 |

TABLE 26-continued

| | RNA binding proteins | | | | | |
|---|---|---|---|---|---|---|
| Protein No. | RNA binding protein | ENSG | ENST | ENST SEQ ID NO | ENSP | ENSP SEQ ID NO |
| 268 | RNA binding protein, autoantigenic (hnRNP-associated with lethal yellow homolog (mouse)) | 125970 | 246194 | 4546 | 246194 | 4899 |
| 269 | RNA binding protein, autoantigenic (hnRNP-associated with lethal yellow homolog (mouse)) | 125970 | 442805 | 4547 | 415973 | 4900 |
| 270 | RNA binding protein, autoantigenic (hnRNP-associated with lethal yellow homolog (mouse)) | 125970 | 448364 | 4548 | 413638 | 4901 |
| 271 | RNA binding protein, autoantigenic (hnRNP-associated with lethal yellow homolog (mouse)) | 125970 | 413297 | 4549 | 403744 | 4902 |
| 272 | RNA binding protein, autoantigenic (hnRNP-associated with lethal yellow homolog (mouse)) | 125970 | 375114 | 4550 | 364255 | 4903 |
| 273 | RNA binding protein, fox-1 homolog (C. elegans) 1 | 78328 | 311745 | 4551 | 309117 | 4904 |
| 274 | RNA binding protein, fox-1 homolog (C. elegans) 1 | 78328 | 550418 | 4552 | 450031 | 4905 |
| 275 | RNA binding protein, fox-1 homolog (C. elegans) 1 | 78328 | 355637 | 4553 | 347855 | 4906 |
| 276 | RNA binding protein, fox-1 homolog (C. elegans) 1 | 78328 | 553186 | 4554 | 447753 | 4907 |
| 277 | RNA binding protein, fox-1 homolog (C. elegans) 1 | 78328 | 436368 | 4555 | 402745 | 4908 |
| 278 | RNA binding protein, fox-1 homolog (C. elegans) 1 | 78328 | 352951 | 4556 | 322925 | 4909 |
| 279 | RNA binding protein, fox-1 homolog (C. elegans) 1 | 78328 | 340209 | 4557 | 344196 | 4910 |
| 280 | RNA binding protein, fox-1 homolog (C. elegans) 1 | 78328 | 547338 | 4558 | 447717 | 4911 |
| 281 | RNA binding protein, fox-1 homolog (C. elegans) 1 | 78328 | 547372 | 4559 | 446842 | 4912 |
| 282 | RNA binding protein, fox-1 homolog (C. elegans) 1 | 78328 | 551752 | 4560 | 447281 | 4913 |
| 283 | RNA binding protein, fox-1 homolog (C. elegans) 2 | 100320 | 397303 | 4561 | 380470 | 4914 |
| 284 | RNA binding protein, fox-1 homolog (C. elegans) 2 | 100320 | 397305 | 4562 | 380472 | 4915 |
| 285 | RNA binding protein, fox-1 homolog (C. elegans) 2 | 100320 | 338644 | 4563 | 342831 | 4916 |
| 286 | RNA binding protein, fox-1 homolog (C. elegans) 2 | 100320 | 408983 | 4564 | 386177 | 4917 |
| 287 | RNA binding protein, fox-1 homolog (C. elegans) 2 | 100320 | 438146 | 4565 | 413035 | 4918 |
| 288 | RNA binding protein, fox-1 homolog (C. elegans) 2 | 100320 | 359369 | 4566 | 352328 | 4919 |
| 289 | RNA binding protein, fox-1 homolog (C. elegans) 2 | 100320 | 262829 | 4567 | 262829 | 4920 |
| 290 | RNA binding protein, fox-1 homolog (C. elegans) 2 | 100320 | 405409 | 4568 | 384944 | 4921 |
| 291 | RNA binding protein, fox-1 homolog (C. elegans) 2 | 100320 | 449924 | 4569 | 391670 | 4922 |
| 292 | RNA binding protein, fox-1 homolog (C. elegans) 2 | 100320 | 414461 | 4570 | 407855 | 4923 |
| 293 | RNA binding protein, fox-1 homolog (C. elegans) 2 | 100320 | 416721 | 4571 | 405651 | 4924 |
| 294 | RNA binding protein, fox-1 homolog (C. elegans) 3 | 167281 | 415831 | 4572 | 408395 | 4925 |
| 295 | RNA binding protein, fox-1 homolog (C. elegans) 3 | 167281 | 453134 | 4573 | 393262 | 4926 |
| 296 | S1 RNA binding domain 1 | 68784 | 535761 | 4574 | 263736 | 4927 |
| 297 | S1 RNA binding domain 1 | 68784 | 263736 | 4575 | 441272 | 4928 |
| 298 | SERPINE1 mRNA binding protein 1 | 142864 | 370995 | 4576 | 360034 | 4929 |
| 299 | SERPINE1 mRNA binding protein 1 | 142864 | 361219 | 4577 | 354591 | 4930 |

TABLE 26-continued

| | RNA binding proteins | | | | | |
|---|---|---|---|---|---|---|
| Protein No. | RNA binding protein | ENSG | ENST | ENST SEQ ID NO | ENSP | ENSP SEQ ID NO |
| 300 | SERPINE1 mRNA binding protein 1 | 142864 | 370994 | 4578 | 360033 | 4931 |
| 301 | SERPINE1 mRNA binding protein 1 | 142864 | 370990 | 4579 | 360029 | 4932 |
| 302 | signal recognition particle 14 kDa (homologous Alu RNA binding protein) | 140319 | 267884 | 4580 | 267884 | 4933 |
| 303 | spermatid perinuclear RNA binding protein | 165209 | 407982 | 4581 | 384292 | 4934 |
| 304 | spermatid perinuclear RNA binding protein | 165209 | 348403 | 4582 | 321347 | 4935 |
| 305 | spermatid perinuclear RNA binding protein | 165209 | 479114 | 4583 | 431531 | 4936 |
| 306 | spermatid perinuclear RNA binding protein | 165209 | 447404 | 4584 | 415968 | 4937 |
| 307 | spermatid perinuclear RNA binding protein | 165209 | 360998 | 4585 | 354271 | 4938 |
| 308 | SRA stem-loop interacting RNA binding protein | 119705 | 557342 | 4586 | 450909 | 4939 |
| 309 | staufen, RNA binding protein, homolog 1 (Drosophila) | 124214 | 371856 | 4587 | 360922 | 4940 |
| 310 | staufen, RNA binding protein, homolog 1 (Drosophila) | 124214 | 360426 | 4588 | 353604 | 4941 |
| 311 | staufen, RNA binding protein, homolog 1 (Drosophila) | 124214 | 371828 | 4589 | 360893 | 4942 |
| 312 | staufen, RNA binding protein, homolog 1 (Drosophila) | 124214 | 371805 | 4590 | 360870 | 4943 |
| 313 | staufen, RNA binding protein, homolog 1 (Drosophila) | 124214 | 371802 | 4591 | 360867 | 4944 |
| 314 | staufen, RNA binding protein, homolog 1 (Drosophila) | 124214 | 456866 | 4592 | 398785 | 4945 |
| 315 | staufen, RNA binding protein, homolog 1 (Drosophila) | 124214 | 347458 | 4593 | 323443 | 4946 |
| 316 | staufen, RNA binding protein, homolog 1 (Drosophila) | 124214 | 340954 | 4594 | 345425 | 4947 |
| 317 | staufen, RNA binding protein, homolog 1 (Drosophila) | 124214 | 371792 | 4595 | 360857 | 4948 |
| 318 | staufen, RNA binding protein, homolog 1 (Drosophila) | 124214 | 437404 | 4596 | 416779 | 4949 |
| 319 | staufen, RNA binding protein, homolog 2 (Drosophila) | 40341 | 355780 | 4597 | 348026 | 4950 |
| 320 | staufen, RNA binding protein, homolog 2 (Drosophila) | 40341 | 524300 | 4598 | 428756 | 4951 |
| 321 | staufen, RNA binding protein, homolog 2 (Drosophila) | 40341 | 524104 | 4599 | 430611 | 4952 |
| 322 | staufen, RNA binding protein, homolog 2 (Drosophila) | 40341 | 522695 | 4600 | 428456 | 4953 |
| 323 | staufen, RNA binding protein, homolog 2 (Drosophila) | 40341 | 522509 | 4601 | 427977 | 4954 |
| 324 | staufen, RNA binding protein, homolog 2 (Drosophila) | 40341 | 521736 | 4602 | 428737 | 4955 |
| 325 | staufen, RNA binding protein, homolog 2 (Drosophila) | 40341 | 521447 | 4603 | 428829 | 4956 |
| 326 | TAR (HIV-1) RNA binding protein 1 | 59588 | 40877 | 4604 | 40877 | 4957 |
| 327 | TAR (HIV-1) RNA binding protein 2 | 139546 | 456234 | 4605 | 416077 | 4958 |
| 328 | TAR (HIV-1) RNA binding protein 2 | 139546 | 266987 | 4606 | 266987 | 4959 |
| 329 | TIA1 cytotoxic granule-associated RNA binding protein | 116001 | 433529 | 4607 | 401371 | 4960 |
| 330 | TIA1 cytotoxic granule-associated RNA binding protein | 116001 | 477807 | 4608 | 445092 | 4961 |
| 331 | TIA1 cytotoxic granule-associated RNA binding protein | 116001 | 415783 | 4609 | 404023 | 4962 |
| 332 | TIA1 cytotoxic granule-associated RNA binding protein-like 1 | 151923 | 412524 | 4610 | 403573 | 4963 |
| 333 | TIA1 cytotoxic granule-associated RNA binding protein-like 1 | 151923 | 436547 | 4611 | 394902 | 4964 |

TABLE 26-continued

RNA binding proteins

| Protein No. | RNA binding protein | ENSG | ENST | ENST SEQ ID NO | ENSP | ENSP SEQ ID NO |
|---|---|---|---|---|---|---|
| 334 | TIA1 cytotoxic granule-associated RNA binding protein-like 1 | 151923 | 369086 | 4612 | 358082 | 4965 |
| 335 | TIA1 cytotoxic granule-associated RNA binding protein-like 1 | 151923 | 369093 | 4613 | 358089 | 4966 |
| 336 | TIA1 cytotoxic granule-associated RNA binding protein-like 1 | 151923 | 369092 | 4614 | 358088 | 4967 |
| 337 | zinc finger CCHC-type and RNA binding motif 1 | 139168 | 266529 | 4615 | 266529 | 4968 |
| 338 | zinc finger RNA binding protein | 56097 | 265069 | 4616 | 265069 | 4969 |
| 339 | zinc finger RNA binding protein | 56097 | 416900 | 4617 | 393243 | 4970 |
| 340 | zinc finger RNA binding protein | 56097 | 382126 | 4618 | 371560 | 4971 |
| 341 | zinc finger RNA binding protein 2 | 105278 | 439086 | 4619 | 388567 | 4972 |
| 342 | zinc finger RNA binding protein 2 | 105278 | 262961 | 4620 | 262961 | 4973 |
| 343 | zinc finger RNA binding protein 2 | 105278 | 438164 | 4621 | 388974 | 4974 |
| 344 | cold shock domain containing E1, RNA-binding | 9307 | 261443 | 4622 | 261443 | 4975 |
| 345 | cold shock domain containing E1, RNA-binding | 9307 | 339438 | 4623 | 342408 | 4976 |
| 346 | cold shock domain containing E1, RNA-binding | 9307 | 358528 | 4624 | 351329 | 4977 |
| 347 | cold shock domain containing E1, RNA-binding | 9307 | 369530 | 4625 | 358543 | 4978 |
| 348 | cold shock domain containing E1, RNA-binding | 9307 | 438362 | 4626 | 407724 | 4979 |
| 349 | cold shock domain containing E1, RNA-binding | 9307 | 525878 | 4627 | 431562 | 4980 |
| 350 | cold shock domain containing E1, RNA-binding | 9307 | 525970 | 4628 | 432805 | 4981 |
| 351 | cold shock domain containing E1, RNA-binding | 9307 | 530886 | 4629 | 431297 | 4982 |
| 352 | cold shock domain containing E1, RNA-binding | 9307 | 534389 | 4630 | 435185 | 4983 |
| 353 | cold shock domain containing E1, RNA-binding | 9307 | 534699 | 4631 | 432958 | 4984 |

HuR is a stabilizing AREBP. To increase the stability of the mRNA of interest, an mRNA encoding HuR can be co-transfected or co-injected along with the mRNA of interest into the cells or into the tissue. These proteins can also be tethered to the mRNA of interest in vitro and then administered to the cells together. Poly A tail binding protein, PABP interacts with eukaryotic translation initiation factor eIF4G to stimulate translational initiation. Co-administration of mRNAs encoding these RBPs along with the mRNA drug and/or tethering these proteins to the mRNA drug in vitro and administering the protein-bound mRNA into the cells can increase the translational efficiency of the mRNA. The same concept can be extended to co-administration of mRNA along with mRNAs encoding various translation factors and facilitators as well as with the proteins themselves to influence RNA stability and/or translational efficiency.

Example 24. Expression of Modified Nucleic Acid with microRNA Binding Site

Human embryonic kidney epithelial cells (HEK293A), antigen presenting cells or cell lines with highly expressed mir-142/146, such as monocyte-derived dendritic cells (MDDC) or PBMC, are seeded at a density of 200,000 per well in 500 ul cell culture medium (InVitro GRO medium from Celsis, Chicago, Ill.). G-CSF mRNA (mRNA sequence is shown in SEQ ID NO: 4258; polyA tail of at least 140 nucleotides not shown in sequence; 5'Cap, Cap1) G-CSF mRNA having a miR-142-5p binding site (G-CSF miR-142-5p) (cDNA sequence is shown in SEQ ID NO: 4985; mRNA sequence is shown in SEQ ID NO: 4986, polyA tail of at least 140 nucleotides not shown in sequence; 5'Cap, Cap1), G-CSF mRNA having a seed sequence from miR-142-5p binding site (G-CSF miR-142-5p-seed) (cDNA sequence is shown in SEQ ID NO: 4987; mRNA sequence is shown in SEQ ID NO: 4988; polyA tail of at least 140 nucleotides not shown in sequence; 5'Cap, Cap1) G-CSF mRNA having a miR-142-5p binding site without the seed sequence (G-CSF miR-142-5p-seedless) (cDNA sequence is shown in SEQ ID NO: 4989, mRNA sequence is shown in SEQ ID NO: 4990; polyA tail of at least 140 nucleotides not shown in sequence; 5'Cap, Cap1) G-CSF mRNA having a miR-142-3p binding site (G-CSF miR-142-3p) (cDNA sequence is shown in SEQ ID NO: 4991; mRNA sequence is shown in SEQ ID NO: 4992; polyA tail of at least 140 nucleotides not shown in sequence; 5'Cap, Cap1) G-CSF mRNA having a seed sequence from miR-142-3p binding site (G-CSF miR-142-3p-seed) (cDNA sequence is shown in SEQ ID NO: 4993; mRNA sequence is shown in SEQ ID NO: 4994; polyA tail of at least 140 nucleotides not shown in sequence; 5'Cap, Cap1) G-CSF mRNA having a miR-142-3p binding site without the seed sequence (G-CSF miR-142-3p-seedless) (DNA sequence is shown in SEQ ID NO: 4995; mRNA sequence is shown in SEQ ID NO: 4996; polyA tail of at least 140 nucleotides not shown in sequence; 5'Cap, Cap1) G-CSF mRNA having a miR-146a binding site (G-CSF miR-146a) (cDNA sequence is shown in SEQ ID NO: 4997; mRNA sequence is shown in SEQ ID NO: 4998; polyA tail of at least 140 nucleotides not shown in sequence; 5'Cap, Cap1) G-CSF mRNA having a seed sequence from miR-146a binding site (G-CSF miR-146a-seed) (cDNA sequence is shown in SEQ ID NO:4999; mRNA sequence is shown in SEQ ID NO: 5000; polyA tail at least 140 nucleotides not shown in sequence; 5'Cap,Cap1) or G-CSF mRNA having a miR-146a binding site without the seed sequence (G-CSF miR-146a-seedless) (cDNA sequence is shown in SEQ ID NO: 5001; mRNA sequence is shown in SEQ ID NO: 5002; polyA tail at least nucleotides not shown in sequence; 5'Cap, Cap1) are tested at a concentration of 250 ng per well in 24 well plates. The mRNA sequences are evaluated with various chemical modifications described herein and/or known in the art including, fully modified with 5-methylcytidine and pseudouridine, fully modified with 5-methylcytidine and 1-methylpseudouridine, fully modified with pseudouridine, fully modified with 1-methylpseudouridine and where 25% of the uridine residues are modified with 2-thiouridine and 25% of the cytosine residues are modified with 5-methylcytidine. The expression of G-CSF in each sample is measured by ELISA.

Shown in Table 27 are the DNA and mRNA G-CSF sequences with the miR binding sites described above. In the table, the start codon of each sequence is underlined.

TABLE 27

G-CSF Constructs with miR binding sites

| SEQ ID NO. | Description | SEQ |
|---|---|---|
| 4985 | DNA sequence having the T7 polymerase site and restriction sites: G-CSF miR-142-5p | TAATACGACTCACTATA GGGAAATAAGAGAGAAAAGAAGAGTAAGAAGAAATATAAGAG CCACCATGGCCGGTCCCGCGACCCAAAGCCCCATGAAACTTAT GGCCCTGCAGTTGCTGCTTTGGCACTCGGCCCTCTGGACAGTCC AAGAAGCGACTCCTCTCGGACCTGCCTCATCGTTGCCGCAGTCA TTCCTTTTGAAGTGTCTGGAGCAGGTGCGAAAGATTCAGGGCG ATGGAGCCGCACTCCAAGAGAAGCTCTGCGCGACATACAAACT TTGCCATCCCGAGGAGCTCGTACTGCTCGGGCACAGCTTGGGG ATTCCCTGGGCTCCTCTCTCGTCCTGTCCGTCGCAGGCTTTGCA GTTGGCAGGGTGCCTTTCCCAGCTCCACTCCGGTTTGTTCTTGT ATCAGGGACTGCTGCAAGCCCTTGAGGGAATCTCGCCAGAATT GGGCCCGACGCTGGACACGTTGCAGCTCGACGTGGCGGATTTC GCAACAACCATCTGGCAGCAGATGGAGGAACTGGGGATGGCAC CCGCGCTGCAGCCCACGCAGGGGGCAATGCCGGCCTTTGCGTC CGCGTTTCAGCGCAGGGCGGGTGGAGTCCTCGTAGCGAGCCAC CTTCAATCATTTTTGGAAGTCTCGTACCGGGTGCTGAGACATCT TGCGCAGCCGTGATAATAGGCTGCCTTCTGCGGGGCTTGCCTTC TGGCCATGCCCTTCTTCTCTCCCTTGCACCTGTACCTCTAGTAGT GCTTTCTACTTTATGTGGTCTTTGAATAAAGCCTGAGTAGGAAG GCGGCCGCTCGAGCATGCATCTAGA |
| 4986 | mRNA sequence: G-CSF miR-142-5p | GGGAAAUAAGAGAGAAAAGAAGAGUAAGAAGAAAUAUAAGA GCCACCAUGGCCGGUCCCGCGACCCAAAGCCCCAUGAAACUU AUGGCCCUGCAGUUGCUGCUUUGGCACUCGGCCCUCUGGACA GUCCAAGAAGCGACUCCUCUCGGACCUGCCUCAUCGUUGCCG CAGUCAUUCCUUUUGAAGUGUCUGGAGCAGGUGCGAAAGAUU CAGGGCGAUGGAGCCGCACUCCAAGAGAAGCUCUGCGCGACA UACAAACUUUGCCAUCCCGAGGAGCUCGUACUGCUCGGGCAC AGCUUGGGGAUUCCCUGGGCUCCUCUCUCGUCCUGUCCGUCG CAGGCUUUGCAGUUGGCAGGGUGCCUUUCCCAGCUCCACUCC GGUUUGUUCUUGUAUCAGGGACUGCUGCAAGCCCUUGAGGGA AUCUCGCCAGAAUUGGGCCCGACGCUGGACACGUUGCAGCUC GACGUGGCGGAUUUCGCAACAACCAUCUGGCAGCAGAUGGAG GAACUGGGGAUGGCACCCGCGCUGCAGCCCACGCAGGGGGCA AUGCCGGCCUUUGCGUCCGCGUUUCAGCGCAGGGCGGGUGGA GUCCUCGUAGCGAGCCACCUUCAAUCAUUUUUGGAAGUCUCG UACCGGGUGCUGAGACAUCUUGCGCAGCCGUGAUAAUAGGCU GCCUUCUGCGGGGCUUGCCUUCUGGCCAUGCCCUUCUUCUCU CCCUUGCACCUGUACCUCUAGUAGUGCUUUCUACUUUAUGUG GUCUUUGAAUAAAGCCUGAGUAGGAAG |
| 4987 | DNA sequence having the T7 polymerase site and restriction sites: G-CSF miR-142-5p-seed | TAATACGACTCACTATA GGGAAATAAGAGAGAAAAGAAGAGTAAGAAGAAATATAAGAG CCACCATGGCCGGTCCCGCGACCCAAAGCCCCATGAAACTTAT GGCCCTGCAGTTGCTGCTTTGGCACTCGGCCCTCTGGACAGTCC AAGAAGCGACTCCTCTCGGACCTGCCTCATCGTTGCCGCAGTCA TTCCTTTTGAAGTGTCTGGAGCAGGTGCGAAAGATTCAGGGCG ATGGAGCCGCACTCCAAGAGAAGCTCTGCGCGACATACAAACT TTGCCATCCCGAGGAGCTCGTACTGCTCGGGCACAGCTTGGGG ATTCCCTGGGCTCCTCTCTCGTCCTGTCCGTCGCAGGCTTTGCA GTTGGCAGGGTGCCTTTCCCAGCTCCACTCCGGTTTGTTCTTGT ATCAGGGACTGCTGCAAGCCCTTGAGGGAATCTCGCCAGAATT GGGCCCGACGCTGGACACGTTGCAGCTCGACGTGGCGGATTTC GCAACAACCATCTGGCAGCAGATGGAGGAACTGGGGATGGCAC CCGCGCTGCAGCCCACGCAGGGGGCAATGCCGGCCTTTGCGTC |

TABLE 27-continued

G-CSF Constructs with miR binding sites

| SEQ ID NO. | Description | SEQ |
|---|---|---|
| | | CGCGTTTCAGCGCAGGGCGGGTGGAGTCCTCGTAGCGAGCCAC<br>CTTCAATCATTTTTGGAAGTCTCGTACCGGGTGCTGAGACATCT<br>TGCGCAGCCGTGATAATAGGCTGCCTTCTGCGGGGCTTGCCTTC<br>TGGCCATGCCCTTCTTCTCTCCCTTGCACCTGTACCTCTACTTTA<br>TTGGTCTTTGAATAAAGCCTGAGTAGGAAGGCGGCCGCTCGA<br>GCATGCATCTAGA |
| 4988 | mRNA sequence: G-CSF miR-142-5p-seed | GGGAAAUAAGAGAGAAAAGAAGAGUAAGAAGAAAUAUAAGA<br>GCCACC<br><u>AUG</u>GCCGGUCCCGCGACCCAAAGCCCCAUGAAACUUAUGGCC<br>CUGCAGUUGCUGCUUUGGCACUCGCCCUCUGGACAGUCCAA<br>GAAGCGACUCCUCUCGGACCUGCCUCAUCGUUGCCGCAGUCA<br>UUCCUUUUGAAGUGUCUGGAGCAGGUGCGAAAGAUUCAGGGC<br>GAUGGAGCCGCACUCCAAGAGAAGCUCUGCGCGACAUACAAA<br>CUUUGCCAUCCCGAGGAGCUCGUACUGCUCGGGCACAGCUUG<br>GGGAUUCCCUGGGCUCCUCUCUCGUCCUGUCCGUCGCAGGCU<br>UUGCAGUUGGCAGGGUGCCUUUCCCAGCUCCACUCCGGUUUG<br>UUCUUUGUAUCAGGGACUGCUGCAAGCCCUUGAGGGAAUCUCG<br>CCAGAAUUGGGCCCGACGCUGGACACGUUGCAGCUCGACGUG<br>GCGGAUUUCGCAACAACCAUCUGGCAGCAGAUGGAGGAACUG<br>GGGAUGGCACCCGCGCUGCAGCCCACGCAGGGGGCAAUGCCG<br>GCCUUUGCGUCCGCGUUUCAGCGCAGGGCGGGUGGAGUCCUC<br>GUAGCGAGCCACCUUCAAUCAUUUUUGGAAGUCUCGUACCGG<br>GUGCUGAGACAUCUUGCGCAGCCG<br>UGAUAAUAGGCUGCCUUCUGCGGGGCUUGCCUUCUGGCCAUG<br>CCCUUCUUCUCUCCCUUGCACCUGUACCUCUACUUUAUUGGU<br>CUUUGAAUAAAGCCUGAGUAGGAAG |
| 4989 | DNA sequence having the T7 polymerase site and restriction sites: G-CSF miR-142-5p-seedless | TAATACGACTCACTATA<br>GGGAAATAAGAGAGAAAAGAAGAGTAAGAAGAAATATAAGAG<br>CCACC<u>ATG</u>GCCGGTCCCGCGACCCAAAGCCCCATGAAACTTAT<br>GGCCCTGCAGTTGCTGCTTTGGCACTCGGCCCTCTGGACAGTCC<br>AAGAAGCGACTCCTCTCGGACCTGCCTCATCGTTGCCGCAGTCA<br>TTCCTTTTGAAGTGTCTGGAGCAGGTGCGAAAGATTCAGGGCG<br>ATGGAGCCGCACTCCAAGAGAAGCTCTGCGCGACATACAAACT<br>TTGCCATCCCGAGGAGCTCGTACTGCTCGGGCACAGCTTGGGG<br>ATTCCCTGGGCTCCTCTCTCGTCCTGTCCGTCGCAGGCTTTGCA<br>GTTGGCAGGGTGCCTTTCCCAGCTCCACTCCGTTTGTTCTTGT<br>ATCAGGGACTGCTGCAAGCCCTTGAGGGAATCTCGCCAGAATT<br>GGGCCCGACGCTGGACACGTTGCAGCTCGACGTGGCGGATTTC<br>GCAACAACCATCTGGCAGCAGATGGAGGAACTGGGGATGGCAC<br>CCGCGCTGCAGCCCACGCAGGGGGCAATGCCGGCCTTTGCGTC<br>CGCGTTTCAGCGCAGGGCGGGTGGAGTCCTCGTAGCGAGCCAC<br>CTTCAATCATTTTTGGAAGTCTCGTACCGGGTGCTGAGACATCT<br>TGCGCAGCCGTGATAATAGGCTGCCTTCTGCGGGGCTTGCCTTC<br>TGGCCATGCCCTTCTTCTCCCTTGCACCTGTACCTCTAGTAGT<br>GCTTTCTGTGGTCTTTGAATAAAGCCTGAGTAGGAAGGCGGCC<br>GCTCGAGCATGCATCTAGA |
| 4990 | mRNA sequence: G-CSF miR-142-5p-seedless | GGGAAAUAAGAGAGAAAAGAAGAGUAAGAAGAAAUAUAAGA<br>GCCACC<br><u>AUG</u>GCCGGUCCCGCGACCCAAAGCCCCAUGAAACUUAUGGCC<br>CUGCAGUUGCUGCUUUGGCACUCGCCCUCUGGACAGUCCAA<br>GAAGCGACUCCUCUCGGACCUGCCUCAUCGUUGCCGCAGUCA<br>UUCCUUUUGAAGUGUCUGGAGCAGGUGCGAAAGAUUCAGGGC<br>GAUGGAGCCGCACUCCAAGAGAAGCUCUGCGCGACAUACAAA<br>CUUUGCCAUCCCGAGGAGCUCGUACUGCUCGGGCACAGCUUG<br>GGGAUUCCCUGGGCUCCUCUCUCGUCCUGUCCGUCGCAGGCU<br>UUGCAGUUGGCAGGGUGCCUUUCCCAGCUCCACUCCGGUUUG<br>UUCUUUGUAUCAGGGACUGCUGCAAGCCCUUGAGGGAAUCUCG<br>CCAGAAUUGGGCCCGACGCUGGACACGUUGCAGCUCGACGUG<br>GCGGAUUUCGCAACAACCAUCUGGCAGCAGAUGGAGGAACUG<br>GGGAUGGCACCCGCGCUGCAGCCCACGCAGGGGGCAAUGCCG<br>GCCUUUGCGUCCGCGUUUCAGCGCAGGGCGGGUGGAGUCCUC<br>GUAGCGAGCCACCUUCAAUCAUUUUUGGAAGUCUCGUACCGG<br>GUGCUGAGACAUCUUGCGCAGCCG<br>UGAUAAUAGGCUGCCUUCUGCGGGGCUUGCCUUCUGGCCAUG<br>CCCUUCUUCUCUCCCUUGCACCUGUACCUCUAGUAGUGCUUU<br>CUGUGGUCUUUGAAUAAAGCCUGAGUAGGAAG |

TABLE 27-continued

G-CSF Constructs with miR binding sites

| SEQ ID NO. | Description | SEQ |
|---|---|---|
| 4991 | DNA sequence having the T7 polymerase site and restriction sites: G-CSF miR-142-3p | TAATACGACTCACTATA GGGAAATAAGAGAGAAAAGAAGAGTAAGAAGAAATATAAGAG CCACCATGGCCGGTCCCGCGACCCAAAGCCCCATGAAACTTAT GGCCCTGCAGTTGCTGCTTTGGCACTCGGCCCTCTGGACAGTCC AAGAAGCGACTCCTCTCGGACCTGCCTCATCGTTGCCGCAGTCA TTCCTTTTGAAGTGTCTGGAGCAGGTGCGAAAGATTCAGGGCG ATGGAGCCGCACTCCAAGAGAAGCTCTGCGCGACATACAAACT TTGCCATCCCGAGGAGCTCGTACTGCTCGGGCACAGCTTGGGG ATTCCCTGGGCTCCTCTCTCGTCCTGTCCGTCGCAGGCTTTGCA GTTGGCAGGGTGCCTTTCCCAGCTCCACTCCGGTTTGTTCTTGT ATCAGGGACTGCTGCAAGCCCTTGAGGGAATCTCGCCAGAATT GGGCCCGACGCTGGACACGTTGCAGCTCGACGTGGCGGATTTC GCAACAACCATCTGGCAGCAGATGGAGGAACTGGGGATGGCAC CCGCGCTGCAGCCCACGCAGGGGGCAATGCCGGCCTTTGCGTC CGCGTTTCAGCGCAGGGCGGGTGGAGTCCTCGTAGCGAGCCAC CTTCAATCATTTTTGGAAGTCTCGTACCGGGTGCTGAGACATCT TGCGCAGCCGTGATAATAGGCTGCCTTCTGCGGGGCTTGCCTTC TGGCCATGCCCTTCTTCTCTCCCTTGCACCTGTACCTCTTCCATA AAGTAGGAAACACTACATGGTCTTTGAATAAAGCCTGAGTAGG AAGGCGGCCGCTCGAGCATGCATCTAGA |
| 4992 | mRNA sequence: G-CSF miR-142-3p | GGGAAAUAAGAGAGAAAAGAAGAGUAAGAAGAAAUAUAAGA GCCACC AUGGCCGGUCCCGCGACCCAAAGCCCCAUGAAACUUAUGGCC CUGCAGUUGCUGCUUUGGCACUCGGCCCUCUGGACAGUCCAA GAAGCGACUCCUCUCGGACCUGCCUCAUCGUUGCCGCAGUCA UUCCUUUUGAAGUGUCUGGAGCAGGUGCGAAAGAUUCAGGGC GAUGGAGCCGCACUCCAAGAGAAGCUCUGCGCGACAUACAAA CUUUGCCAUCCCGAGGAGCUCGUACUGCUCGGGCACAGCUUG GGGAUUCCCUGGGCUCCUCUCUCGUCCUGUCCGUCGCAGGCU UUGCAGUUGGCAGGGUGCCUUUCCCAGCUCCACUCCGGUUUG UUCUUGUAUCAGGGACUGCUGCAAGCCCUUGAGGGAAUCUCG CCAGAAUUGGGCCCGACGCUGGACACGUUGCAGCUCGACGUG GCGGAUUUCGCAACAACCAUCUGGCAGCAGAUGGAGGAACUG GGGAUGGCACCCGCGCUGCAGCCCACGCAGGGGGCAAUGCCG GCCUUUGCGUCCGCGUUUCAGCGCAGGGCGGGUGGAGUCCUC GUAGCGAGCCACCUUCAAUCAUUUUUGGAAGUCUCGUACCGG GUGCUGAGACAUCUUGCGCAGCCG UGAUAAUAGGCUGCCUUCUGCGGGGCUUGCCUUCUGGCCAUG CCCUUCUUCUCUCCCUUGCACCUGUACCUCUUCCAUAAAGUA GGAAACACUACAUGGUCUUUGAAUAAAGCCUGAGUAGGAAG |
| 4993 | DNA sequence having the T7 polymerase site and restriction sites: G-CSF miR-142-3p-seed | TAATACGACTCACTATA GGGAAATAAGAGAGAAAAGAAGAGTAAGAAGAAATATAAGAG CCACCATGGCCGGTCCCGCGACCCAAAGCCCCATGAAACTTAT GGCCCTGCAGTTGCTGCTTTGGCACTCGGCCCTCTGGACAGTCC AAGAAGCGACTCCTCTCGGACCTGCCTCATCGTTGCCGCAGTCA TTCCTTTTGAAGTGTCTGGAGCAGGTGCGAAAGATTCAGGGCG ATGGAGCCGCACTCCAAGAGAAGCTCTGCGCGACATACAAACT TTGCCATCCCGAGGAGCTCGTACTGCTCGGGCACAGCTTGGGG ATTCCCTGGGCTCCTCTCTCGTCCTGTCCGTCGCAGGCTTTGCA GTTGGCAGGGTGCCTTTCCCAGCTCCACTCCGGTTTGTTCTTGT ATCAGGGACTGCTGCAAGCCCTTGAGGGAATCTCGCCAGAATT GGGCCCGACGCTGGACACGTTGCAGCTCGACGTGGCGGATTTC GCAACAACCATCTGGCAGCAGATGGAGGAACTGGGGATGGCAC CCGCGCTGCAGCCCACGCAGGGGGCAATGCCGGCCTTTGCGTC CGCGTTTCAGCGCAGGGCGGGTGGAGTCCTCGTAGCGAGCCAC CTTCAATCATTTTTGGAAGTCTCGTACCGGGTGCTGAGACATCT TGCGCAGCCGTGATAATAGGCTGCCTTCTGCGGGGCTTGCCTTC TGGCCATGCCCTTCTTCTCTCCCTTGCACCTGTACCTCTACACTA CTGGTCTTTGAATAAAGCCTGAGTAGGAAGGCGGCCGCTCGA GCATGCATCTAGA |
| 4994 | mRNA sequence: G-CSF miR-142-3p-seed | GGGAAAUAAGAGAGAAAAGAAGAGUAAGAAGAAAUAUAAGA GCCACC AUGGCCGGUCCCGCGACCCAAAGCCCCAUGAAACUUAUGGCC CUGCAGUUGCUGCUUUGGCACUCGGCCCUCUGGACAGUCCAA GAAGCGACUCCUCUCGGACCUGCCUCAUCGUUGCCGCAGUCA UUCCUUUUGAAGUGUCUGGAGCAGGUGCGAAAGAUUCAGGGC GAUGGAGCCGCACUCCAAGAGAAGCUCUGCGCGACAUACAAA CUUUGCCAUCCCGAGGAGCUCGUACUGCUCGGGCACAGCUUG GGGAUUCCCUGGGCUCCUCUCUCGUCCUGUCCGUCGCAGGCU UUGCAGUUGGCAGGGUGCCUUUCCCAGCUCCACUCCGGUUUG UUCUUGUAUCAGGGACUGCUGCAAGCCCUUGAGGGAAUCUCG |

TABLE 27-continued

G-CSF Constructs with miR binding sites

| SEQ ID NO. | Description | SEQ |
|---|---|---|
| | | CCAGAAUUGGGCCCGACGCUGGACACGUUGCAGCUCGACGUG GCGGAUUUCGCAACAACCAUCUGGCAGCAGAUGGAGGAACUG GGGAUGGCACCCGCGCUGCAGCCCACGCAGGGGGCAAUGCCG GCCUUUGCGUCCGCGUUUCAGCGCAGGGCGGGUGGAGUCCUC GUAGCGAGCCACCUUCAAUCAUUUUUGGAAGUCUCGUACCGG GUGCUGAGACAUCUUGCGCAGCCG UGAUAAUAGGCUGCCUUCUGCGGGGCUUGCCUUCUGGCCAUG CCCUUCUUCUCUCCCUUGCACCUGUACCCUCUACACUACUGGU CUUUGAAUAAAGCCUGAGUAGGAAG |
| 4995 | DNA sequence having the T7 polymerase site and restriction sites: G-CSF miR-142-3p-seedless | TAATACGACTCACTATA GGGAAATAAGAGAGAAAAGAAGAGTAAGAAGAAATATAAGAG CCACC<u>ATG</u>GCCGGTCCCGCGACCCAAAGCCCCATGAAACTTAT GGCCCTGCAGTTGCTGCTTTGGCACTCGGCCCTCTGGACAGTCC AAGAAGCGACTCCTCTCGGACCTGCCTCATCGTTGCCGCAGTCA TTCCTTTTGAAGTGTCTGGAGCAGGTGCGAAAGATTCAGGGCG ATGGAGCCGCACTCCAAGAGAAGCTCTGCGCGACATACAAACT TTGCCATCCCGAGGAGCTCGTACTGCTCGGGCACAGCTTGGGG ATTCCCTGGGCTCCTCTCTCGTCCTGTCCGTCGCAGGCTTTGCA GTTGGCAGGGTGCCTTTCCCAGCTCCACTCCGGTTTGTTCTTGT ATCAGGGACTGCTGCAAGCCCTTGAGGGAATCTCGCCAGAATT GGGCCCGACGCTGGACACGTTGCAGCTCGACGTGGCGGATTTC GCAACAACCATCTGGCAGCAGATGGAGGAACTGGGGATGGCAC CCGCGCTGCAGCCCACGCAGGGGGCAATGCCGGCCTTTGCGTC CGCGTTTCAGCGCAGGGCGGGTGGAGTCCTCGTAGCGAGCCAC CTTCAATCATTTTTGGAAGTCTCGTACCGGGTGCTGAGACATCT TGCGCAGCCGTGATAATAGGCTGCCTTCTGCGGGGCTTGCCTTC TGGCCATGCCCTTCTTCTCTCCCTTGCACCTGTACCTCTTCCATA AAGTAGGAAATGGTCTTTGAATAAAGCCTGAGTAGGAAGGCG GCCGCTCGAGCATGCATCTAGA |
| 4996 | mRNA sequence: G-CSF miR-142-3p-seedless | GGGAAAUAAGAGAGAAAAGAAGAGUAAGAAGAAAUAUAAGA GCCACC<u>AUG</u>GCCGGUCCCGCGACCCAAAGCCCCAUGAAACUU AUGGCCCUGCAGUUGCUGCUUUGGCACUCGGCCCUCUGGACA GUCCAAGAAGCGACUCCUCUCGGACCUGCCUCAUCGUUGCCG CAGUCAUUCCUUUUGAAGUGUCUGGAGCAGGUGCGAAAGAUU CAGGGCGAUGGAGCCGCACUCCAAGAGAAGCUCUGCGCGACA UACAAACUUUGCCAUCCCGAGGAGCUCGUACUGCUCGGGCAC AGCUUGGGGAUUCCCUGGGCUCCUCUCUCGUCCUGUCCGUCG CAGGCUUUGCAGUUGGCAGGGUGCCUUUCCCAGCUCCACUCC GGUUUGUUCUUGUAUCAGGGACUGCUGCAAGCCCUUGAGGGA AUCUCGCCAGAAUUGGGCCCGACGCUGGACACGUUGCAGCUC GACGUGGCGGAUUUCGCAACAACCAUCUGGCAGCAGAUGGAG GAACUGGGGAUGGCACCCGCGCUGCAGCCCACGCAGGGGGCA AUGCCGGCCUUUGCGUCCGCGUUUCAGCGCAGGGCGGGUGGA GUCCUCGUAGCGAGCCACCUUCAAUCAUUUUUGGAAGUCUCG UACCGGGUGCUGAGACAUCUUGCGCAGCCGUGAUAAUAGGCU GCCUUCUGCGGGGCUUGCCUUCUGGCCAUGCCCUUCUUCUCU CCCUUGCACCUGUACCUCUUCCAUAAAGUAGGAAAUGGUCUU UGAAUAAAGCCUGAGUAGGAAG |
| 4997 | DNA sequence having the T7 polymerase site and restriction sites: G-CSF miR-146a | TAATACGACTCACTATA GGGAAATAAGAGAGAAAAGAAGAGTAAGAAGAAATATAAGAG CCACC<u>ATG</u>GCCGGTCCCGCGACCCAAAGCCCCATGAAACTTAT GGCCCTGCAGTTGCTGCTTTGGCACTCGGCCCTCTGGACAGTCC AAGAAGCGACTCCTCTCGGACCTGCCTCATCGTTGCCGCAGTCA TTCCTTTTGAAGTGTCTGGAGCAGGTGCGAAAGATTCAGGGCG ATGGAGCCGCACTCCAAGAGAAGCTCTGCGCGACATACAAACT TTGCCATCCCGAGGAGCTCGTACTGCTCGGGCACAGCTTGGGG ATTCCCTGGGCTCCTCTCTCGTCCTGTCCGTCGCAGGCTTTGCA GTTGGCAGGGTGCCTTTCCCAGCTCCACTCCGGTTTGTTCTTGT ATCAGGGACTGCTGCAAGCCCTTGAGGGAATCTCGCCAGAATT GGGCCCGACGCTGGACACGTTGCAGCTCGACGTGGCGGATTTC GCAACAACCATCTGGCAGCAGATGGAGGAACTGGGGATGGCAC CCGCGCTGCAGCCCACGCAGGGGGCAATGCCGGCCTTTGCGTC CGCGTTTCAGCGCAGGGCGGGTGGAGTCCTCGTAGCGAGCCAC CTTCAATCATTTTTGGAAGTCTCGTACCGGGTGCTGAGACATCT TGCGCAGCCGTGATAATAGGCTGCCTTCTGCGGGGCTTGCCTTC TGGCCATGCCCTTCTTCTCTCCCTTGCACCTGTACCTCTAACCCA TGGAATTCAGTTCTCATGGTCTTTGAATAAAGCCTGAGTAGGAA GGCGGCCGCTCGAGCATGCATCTAGA |

TABLE 27-continued

G-CSF Constructs with miR binding sites

| SEQ ID NO. | Description | SEQ |
|---|---|---|
| 4998 | mRNA sequence: G-CSF miR-146a | GGGAAAUAAGAGAGAAAAGAAGAGUAAGAAGAAAUAUAAGA GCCACCAUGGCCGGUCCCGCGACCCAAAGCCCCAUGAAACUU AUGGCCCUGCAGUUGCUGCUUUGGCACUCGGCCCUCUGGACA GUCCAAGAAGCGACUCCUCUCGGACCUGCCUCAUCGUUGCCG CAGUCAUUCCUUUUGAAGUGUCUGGAGCAGGUGCGAAAGAUU CAGGGCGAUGGAGCCGCACUCCAAGAGAAGCUCUGCGCGACA UACAAACUUUGCCAUCCCGAGGAGCUCGUACUGCUCGGGCAC AGCUUGGGGAUUCCCUGGGCUCCUCUCUCGUCCUGUCCGUCG CAGGCUUUGCAGUUGGCAGGGUGCCUUUCCCAGCUCCACUCC GGUUUGUUCUUGUAUCAGGGACUGCUGCAAGCCCUUGAGGGA AUCUCGCCAGAAUUGGGCCCGACGCUGGACACGUUGCAGCUC GACGUGGCGGAUUUCGCAACAACCAUCUGGCAGCAGAUGGAG GAACUGGGGAUGGCACCCGCGCUGCAGCCCACGCAGGGGGCA AUGCCGGCCUUUGCGUCCGCGUUUCAGCGCAGGGCGGGUGGA GUCCUCGUAGCGAGCCACCUUCAAUCAUUUUUGGAAGUCUCG UACCGGGUGCUGAGACAUCUUGCGCAGCCGUGAUAAUAGGCU GCCUUCUGCGGGGCUUGCCUUCUGGCCAUGCCCUUCUUCUCU CCCUUGCACCUGUACCUCUAACCCAUGGAAUUCAGUUCUCAU GGUCUUUGAAUAAAGCCUGAGUAGGAAG |
| 4999 | DNA sequence having the T7 polymerase site and restriction sites: G-CSF-146a-seed | TAATACGACTCACTATA GGGAAATAAGAGAGAAAAGAAGAGTAAGAAGAAATATAAGAG CCACCATGGCCGGTCCCGCGACCCAAAGCCCCATGAAACTTAT GGCCCTGCAGTTGCTGCTTTGGCACTCGGCCCTCTGGACAGTCC AAGAAGCGACTCCTCTCGGACCTGCCTCATCGTTGCCGCAGTCA TTCCTTTTGAAGTGTCTGGAGCAGGTGCGAAAGATTCAGGGCG ATGGAGCCGCACTCCAAGAGAAGCTCTGCGCGACATACAAACT TTGCCATCCCGAGGAGCTCGTACTGCTCGGGCACAGCTTGGGG ATTCCCTGGGCTCCTCTCTCGTCCTGTCCGTCGCAGGCTTTGCA GTTGGCAGGGTGCCTTTCCCAGCTCCACTCCGGTTTGTTCTTGT ATCAGGGACTGCTGCAAGCCCTTGAGGGAATCTCGCCAGAATT GGGCCCGACGCTGGACACGTTGCAGCTCGACGTGGCGGATTTC GCAACAACCATCTGGCAGCAGATGGAGGAACTGGGGATGGCAC CCGCGCTGCAGCCCACGCAGGGGGCAATGCCGGCCTTTGCGTC CGCGTTTCAGCGCAGGGCGGGTGGAGTCCTCGTAGCGAGCCAC CTTCAATCATTTTTGGAAGTCTCGTACCGGGTGCTGAGACATCT TGCGCAGCCGTGATAATAGGCTGCCTTCTGCGGGGCTTGCCTTC TGGCCATGCCCTTCTTCTCCCTTGCACCTGTACCTCTAGTTCT CTGGTCTTTGAATAAAGCCTGAGTAGGAAGGCGGCCGCTCGA GCATGCATCTAGA |
| 5000 | mRNA sequence: G-CSF-146a-seed | GGGAAAUAAGAGAGAAAAGAAGAGUAAGAAGAAAUAUAAGA GCCACCAUGGCCGGUCCCGCGACCCAAAGCCCCAUGAAACUU AUGGCCCUGCAGUUGCUGCUUUGGCACUCGGCCCUCUGGACA GUCCAAGAAGCGACUCCUCUCGGACCUGCCUCAUCGUUGCCG CAGUCAUUCCUUUUGAAGUGUCUGGAGCAGGUGCGAAAGAUU CAGGGCGAUGGAGCCGCACUCCAAGAGAAGCUCUGCGCGACA UACAAACUUUGCCAUCCCGAGGAGCUCGUACUGCUCGGGCAC AGCUUGGGGAUUCCCUGGGCUCCUCUCUCGUCCUGUCCGUCG CAGGCUUUGCAGUUGGCAGGGUGCCUUUCCCAGCUCCACUCC GGUUUGUUCUUGUAUCAGGGACUGCUGCAAGCCCUUGAGGGA AUCUCGCCAGAAUUGGGCCCGACGCUGGACACGUUGCAGCUC GACGUGGCGGAUUUCGCAACAACCAUCUGGCAGCAGAUGGAG GAACUGGGGAUGGCACCCGCGCUGCAGCCCACGCAGGGGGCA AUGCCGGCCUUUGCGUCCGCGUUUCAGCGCAGGGCGGGUGGA GUCCUCGUAGCGAGCCACCUUCAAUCAUUUUUGGAAGUCUCG UACCGGGUGCUGAGACAUCUUGCGCAGCCGUGAUAAUAGGCU GCCUUCUGCGGGGCUUGCCUUCUGGCCAUGCCCUUCUUCUCU CCCUUGCACCUGUACCUCUAGUUCUCUGGUCUUUGAAUAAAG CCUGAGUAGGAAG |
| 5001 | DNA sequence having the T7 polymerase site and restriction sites: G-CSF-146a-seedless | TAATACGACTCACTATA GGGAAATAAGAGAGAAAAGAAGAGTAAGAAGAAATATAAGAG CCACCATGGCCGGTCCCGCGACCCAAAGCCCCATGAAACTTAT GGCCCTGCAGTTGCTGCTTTGGCACTCGGCCCTCTGGACAGTCC AAGAAGCGACTCCTCTCGGACCTGCCTCATCGTTGCCGCAGTCA TTCCTTTTGAAGTGTCTGGAGCAGGTGCGAAAGATTCAGGGCG ATGGAGCCGCACTCCAAGAGAAGCTCTGCGCGACATACAAACT TTGCCATCCCGAGGAGCTCGTACTGCTCGGGCACAGCTTGGGG ATTCCCTGGGCTCCTCTCTCGTCCTGTCCGTCGCAGGCTTTGCA GTTGGCAGGGTGCCTTTCCCAGCTCCACTCCGGTTTGTTCTTGT ATCAGGGACTGCTGCAAGCCCTTGAGGGAATCTCGCCAGAATT GGGCCCGACGCTGGACACGTTGCAGCTCGACGTGGCGGATTTC GCAACAACCATCTGGCAGCAGATGGAGGAACTGGGGATGGCAC |

TABLE 27-continued

G-CSF Constructs with miR binding sites

| SEQ ID NO. | Description | SEQ |
|---|---|---|
| | | CCGCGCTGCAGCCCACGCAGGGGGCAATGCCGGCCTTTGCGTC CGCGTTTCAGCGCAGGGCGGGTGGAGTCCTCGTAGCGAGCCAC CTTCAATCATTTTTGGAAGTCTCGTACCGGGTGCTGAGACATCT TGCGCAGCCGTGATAATAGGCTGCCTTCTGCGGGGCTTGCCTTC TGGCCATGCCCTTCTTCTCTCCCTTGCACCTGTACCTCTAACCCA TGGAATTCATGGTCTTTGAATAAAGCCTGAGTAGGAAGGCGGC CGCTCGAGCATGCATCTAGA |
| 5002 | mRNA sequence: G-CSF-146a-seedless | GGGAAAUAAGAGAGAAAAGAAGAGUAAGAAGAAAUAUAAGA GCCACC<u>AUG</u>GCCGGUCCCGCGACCCAAAGCCCCAUGAAACUU AUGGCCCUGCAGUUGCUGCUUUGGCACUCGGCCCUCUGGACA GUCCAAGAAGCGACUCCUCUCGGACCUGCCUCAUCGUUGCCG CAGUCAUUCCUUUUGAAGUGUCUGGAGCAGGUGCGAAAGAUU CAGGGCGAUGGAGCCGCACUCCAAGAGAAGCUCUGCGCGACA UACAAACUUUGCCAUCCCGAGGAGCUCGUACUGCUCGGGCAC AGCUUGGGGAUUCCCUGGGCUCCUCUCUCGUCCUGUCCGUCG CAGGCUUUGCAGUUGGCAGGGUGCCUUUCCCAGCUCCACUCC GGUUUGUUCUUGUAUCAGGGACUGCUGCAAGCCCUUGAGGGA AUCUCGCCAGAAUUGGGCCCGACGCUGGACACGUUGCAGCUC GACGUGGCGGAUUUCGCAACAACCAUCUGGCAGCAGAUGGAG GAACUGGGGAUGGCACCCGCGCUGCAGCCCACGCAGGGGGCA AUGCCGGCCUUUGCGUCCGCGUUUCAGCGCAGGGCGGGUGGA GUCCUCGUAGCGAGCCACCUUCAAUCAUUUUUGGAAGUCUCG UACCGGGUGCUGAGACAUCUUGCGCAGCCGUGAUAAUAGGCU GCCUUCUGCGGGGCUUGCCUUCUGGCCAUGCCCUUCUUCUCU CCCUUGCACCUGUACCUCUAACCCAUGGAAUUCAUGGUCUUU GAAUAAAGCCUGAGUAGGAAG |

It is like that the binding site "seed" sequence is sufficient to induce mircoRNA binding, the expression of G-CSF should be down-regulated in cells transfected with miR-142-3p, miR-142-3p-seed, miR-142-5p, miR-142-5p-seed, miR-146a or miR-146a-seed. Whereas, the miR-142-3p-seedless, miR-142-5p-seedless, miR-146a-seedless should not change the expression of G-CSF, as compared with cells transfected with G-CSF mRNA without microRNA binding sites.

Example 25. APCs Specific microRNA Binding Sites to Suppress Modified Nucleic Acid Mediated Immune Stimulation The binding sites for microRNAs are used in the 3'UTR of mRNA therapeutics to selectively degrade mRNA therapeutics in the immune cells to subdue unwanted immunogenic reactions caused by mRNA therapeutics delivery.

A polynucleotide comprising a series of 3'UTR miR binding sites which make the the nucleic acids or mRNA of the present invention more unstable in antigen presenting cells (APCs), such as, but not limited to mir-142-5p, mir-142-3p, mir-146a-5p and mir-146a-3p, encodes an oncology-related polypeptide of the present invention. The addition of miR binding sites in the 3'UTR making a signal sensor polynucleotide unstable would subdue modified mRNA mediated immune stimulation.

Experiments comparing the cytokine expression (e.g. TNF-alpha) induced by the polypeptide with APCs specific microRNA signature vs. without such signature is performed in vitro by methods described herein and/or known in the art.

Example 26. In Vitro Expression of mRNAs with miR Binding Sites

Human embryonic kidney epithelial cells (HEK293A), antigen-presenting cells or cell lines with highly expressed mir-142/146, such as monocyte-derived dendritic cells (MDDC) or PBMC, are seeded at a density of 200,000 per well in 500 ul cell culture medium (InVitro GRO medium from Celsis, Chicago, Ill.). Cultured cells are transfected with G-CSF mRNAs with or without microRNA signature, as described in Example 24. The cells are transfected for five consecutive days. The transfection complexes are removed four hours after each round of transfection.

The culture supernatant is assayed for secreted G-CSF (R&D Systems, catalog #DCS50), tumor necrosis factor-alpha (TNF-alpha) and interferon alpha (IFN-alpha by ELISA every day after transfection following manufacturer's protocols. The cells are analyzed for viability using CELL TITER GLO® (Promega, catalog #G7570) 6 hrs and 18 hrs after the first round of transfection and every alternate day following that. At the same time from the harvested cells, total RNA is isolated and treated with DNASE® using the RNAEASY micro kit (catalog #74004) following the manufacturer's protocol. 100 ng of total RNA is used for cDNA synthesis using the High Capacity cDNA Reverse Transcription kit (Applied Biosystems, cat #4368814) following the manufacturer's protocol. The cDNA is then analyzed for the expression of innate immune response genes by quantitative real time PCR using SybrGreen in a Biorad CFX 384 instrument following the manufacturer's protocol.

Example 27. In Vivo Detection of Innate Immune Response Study

To test the the nucleic acids or mRNA protein expression and in vivo immune response, female BALB/C mice (n=5) are injected intramuscularly with G-CSF mRNA with or without microRNA signatures as described in Example 24. Blood is collected at 8 hours after dosing. The protein levels of G-CSF, TNF-alpha and IFN-alpha is determined by ELISA.

The difference of cytokine production is seen as measured by mouse TNF-alpha and IFN-alpha level in serum. Injection with G-CSF modified mRNA having miR-142 and miR-146a binding site or binding site seed shows a lower level of cytokine response in vivo.

Example 28. Expression of miR-122 in Primary Hepatocytes

Hepatocyte specific miR-122 level in rat and human primary hepatocytes was measured. Hela Cells and primary rat and human hepatocytes were cultured and RNAs were extracted from cell lysates. The miR-122 level in rat and human primary hepatocytes was compared with that in Hela cells. The miR-122 level is about 6 fold increased in primary human hepatocytes and about 12 fold increased in primary rat hepatocytes, respectively, as compared with that in Hela cells.

Example 29. Expression of Modified Nucleic Acid with Mir-122 Binding Site in Hepatocytes Primary rat and human hepatocytes and Hela cells were seeded at a density of 200,000 per well in 500 ul cell culture medium (InVitro GRO medium from Celsis, Chicago, Ill.). G-CSF mRNA having a miR-122 binding site in the 3'UTR (G-CSF miR-122-1X) (mRNA sequence is shown in SEQ ID NO: 4268; polyA tail of approximately 140 nucleotides not shown in sequence; 5'Cap, Cap1) fully modified with 5-methylcytidine and pseudouridine (5mC/pU), or fully modified with pseudouridine (pU) or G-CSF mRNA with four miR-122 binding sites with the seed deleted (G-CSF no seed) (mRNA sequence is shown in SEQ ID NO: 4270; polyA tail of approximately 140 nucleotides not shown in sequence; 5'Cap, Cap1) fully modified with 5-methylcytidine and pseudouridine (5mC/pU) or fully modified with pseudouridine (pU) was tested at a concentration of 250 ng per well in 24 well plates. The 24 hours after transfection, the expression of G-CSF was measured by ELISA, and the results are shown in Table 28.

TABLE 28

| G-CSF mir122 expression | | | |
|---|---|---|---|
| | Hela cells Protein Expression (ng/mL) | Primary human Hepatocytes Protein Expression (ng/mL) | Primary rat Hepatocytes Protein Expression (ng/mL) |
| G-CSF miR-122 1X (5 mC/pU) | 167.34 | 67.60 | 3.40 |
| G-CSF miR-122 1X (pU) | 292.18 | 116.18 | 25.63 |
| G-CSF no seed (5 mC/pU) | 194.78 | 129.77 | 8.39 |

TABLE 28-continued

| G-CSF mir122 expression | | | |
|---|---|---|---|
| | Hela cells Protein Expression (ng/mL) | Primary human Hepatocytes Protein Expression (ng/mL) | Primary rat Hepatocytes Protein Expression (ng/mL) |
| G-CSF no seed (pU) | 335.78 | 462.88 | 84.93 |

Example 30. Expression of Modified Nucleic Acids with Mir-122 Binding Sites in Hepatocytes MicroRNA control gene expression through the translational suppression and/or degradation of target messenger RNA. Mir-122 binding site containing G-CSF mRNA was translationally regulated in hepatocytes.

Primary rat and human hepatocytes and Hela cells were seeded at a density of 200,000 per well in 500 ul cell culture medium (InVitro GRO medium from Celsis, Chicago, Ill.). G-CSF mRNA (G-CSF alpha) (mRNA sequence is shown in SEQ ID NO: 4266; polyA tail of approximately 140 nucleotides not shown in sequence; 5'Cap, Cap1) fully modified with 5-methylcytidine and pseudouridine (5mC/pU), G-CSF mRNA having a miR-122 binding site in the 3'UTR (G-CSF miR-122-1X) (mRNA sequence is shown in SEQ ID NO: 4268; polyA tail of approximately 140 nucleotides not shown in sequence; 5'Cap, Cap 1) fully modified with 5-methylcytidine and pseudouridine (5mc/pU) or G-CSF mRNA with four miR-122 binding sites with the seed deleted (G-CSF no seed) (mRNA sequence is shown in SEQ ID NO: 4270; polyA tail of approximately 140 nucleotides not shown in sequence; 5'Cap, Cap1) fully modified with 5-methylcytidine and pseudouridine (5mC/pU) was tested at a concentration of 250 ng per well in 24 well plates. 24 hours after transfection, the expression of G-CSF was measured by ELISA. The G-CSF drug (mRNA) levels and protein levels are shown in Table 29.

TABLE 29

| G-CSF drug and protein levels | | | | |
|---|---|---|---|---|
| | Human Hepatocytes | | Rat Hepatocytes | |
| | Drug (mRNA) level (unit normalized to HPRT) | Protein expression (ng/ml) | Drug (mRNA) level (unit normalized to HPRT) | Protein expression (ng/ml) |
| G-CSF alpha (5 mC/pU) | 43237.6 | 247.26 | 26615.88 | 784.6 |
| G-CSF miR-122-1X (5 mC/pU) | 46340.9 | 74.07 | 20171.07 | 40.628 |
| G-CSF no seed (5 mC/pU) | 70239.7 | 298.28 | 23170.47 | 894.06 |

Example 31. Modified mRNA Sequences with or without Kozak and/or IRES Sequences Modified mRNA encoding G-CSF with or without a Kozak and/or IRES sequence, and their corresponding cDNA sequences, are shown below in Table 30. In Table 30, the start codon of each sequence is underlined.

TABLE 30

G-CSF Sequences

| | Sequence | SEQ ID NO: |
|---|---|---|
| G-CSF with Kozak sequence and IRES and human alpha-globin 3'UTR | Optimized G-CSF cDNA sequence containing a T7 polymerase site, kozak sequence, IRES and Xba1 restriction site:<br>TAATACGACTCACTATA<br>GGGAAATAAGAGAGAAAAGAAGAGTAAGAAGAAATATAAG<br>AGCCACC<br>TCGTGAGGATCTATTTCCGGTGAATTCCTCGAGACTAGTTCT<br>AGAGCGGCCGCGGATCCCGCCCCTCTCCCTCCCCCCCCCTA<br>ACGTTACTGGCCGAAGCGCTTGGAATAAGGCCGGTGTGCG<br>TTTGTCTATATGTTATTTTCCACCATATTGCCGTCTTTTGGCA<br>ATGTGAGGGCCCGGAAACCTGGCCCTGTCTTCTTGACGAGC<br>ATTCCTAGGGGTCTTTCCCCTCTCGCCAAAGGAATGCAAGGT<br>CTGTTGAATGTCGTGAAGGAAGCAGTTCCTCTGGAAGCTTCT<br>TGAAGACAAACAACGTCTGTAGCGACCCTTTGCAGGCAGCG<br>GAACCCCCCACCTGGCGACAGGTGCCTCTGCGGCCAAAAGC<br>CACGTGTATAAGATACACCTGCAAAGGCGGCACAACCCCAG<br>TGCCACGTTGTGAGTTGGATAGTTGTGGAAAGAGTCAAATG<br>GCTCACCTCAAGCGTATTCAACAAGGGGCTGAAGGATGCCC<br>AGAAGGTACCCCATTGTATGGGATCTGATCTGGGGCCTCGG<br>TGCACATGCTTTACATGTGTTTAGTCGAGGTTAAAAAACGTC<br>TAGGCCCCCCGAACCACGGGGACGTGGTTTTCCTTTGAAAA<br>ACACGATGATAAT<br>ATGGCCGGTCCCGCGACCCAAAGCCCCATGAAACTTATGGC<br>CCTGCAGTTGCTGCTTTGGCACTCGGCCCTCTGGACAGTCCA<br>AGAAGCGACTCCTCTCGGACCTGCCTCATCGTTGCCGCAGTC<br>ATTCCTTTTGAAGTGTCTGGAGCAGGTGCGAAAGATTCAGG<br>GCGATGGAGCCGCACTCCAAGAGAAGCTCTGCGCGACATAC<br>AAACTTTGCCATCCCGAGGAGCTCGTACTGCTCGGGCACAG<br>CTTGGGGATTCCCTGGGCTCCTCTCTCGTCCTGTCCGTCGCA<br>GGCTTTGCAGTTGGCAGGGTGCCTTTCCCAGCTCCACTCCGG<br>TTTGTTCTTGTATCAGGGACTGCTGCAAGCCCTTGAGGGAAT<br>CTCGCCAGAATTGGGCCCGACGCTGGACACGTTGCAGCTCG<br>ACGTGGCGGATTTCGCAACAACCATCTGGCAGCAGATGGAG<br>GAACTGGGGATGGCACCCGCGCTGCAGCCCACGCAGGGGG<br>CAATGCCGGCCTTTGCGTCCGCGTTTCAGCGCAGGGCGGGT<br>GGAGTCCTCGTAGCGAGCCACCTTCAATCATTTTTGGAAGTC<br>TCGTACCGGGTGCTGAGACATCTTGCGCAGCCG<br>TGATAATAG<br>GCTGGAGCCTCGGTGGCCATGCTTCTTGCCCCTTGGGCCTCC<br>CCCCAGCCCCTCCTCCCCTTCCTGCACCCGTACCCCCGTGGT<br>CTTTGAATAAAGTCTGAGTGGGCGGCTCTAGA | 5003 |
| | mRNA sequence (transcribed):<br>GGGAAAUAAGAGAGAAAAGAAGAGUAAGAAGAAAUAUAA<br>GAGCCACC<br>UCGUGAGGAUCUAUUUCCGGUGAAUUCCUCGAGACUAGUU<br>CUAGAGCGGCCGCGGAUCCCGCCCCUCUCCCUCCCCCCCC<br>CUAACGUUACUGGCCGAAGCCGCUUGGAAUAAGGCCGGUG<br>UGCGUUUGUCUAUAUGUUAUUUUCCACCAUAUUGCCGUCU<br>UUUGGCAAUGUGAGGGCCCGGAAACCUGGCCCUGUCUUCU<br>UGACGAGCAUUCCUAGGGGUCUUUCCCCUCUCGCCAAAGG<br>AAUGCAAGGUCUGUUGAAUGUCGUGAAGGAAGCAGUUCC<br>UCUGGAAGCUUCUUGAAGACAAACAACGUCUGUAGCGACC<br>CUUUGCAGGCAGCGGAACCCCCCACCUGGCGACAGGUGCC<br>UCUGCGGCCAAAAGCCACGUGUAUAAGAUACACCUGCAAA<br>GGCGGCACAACCCCAGUGCCACGUUGUGAGUUGGAUAGUU<br>GUGGAAAGAGUCAAAUGGCUCACCUCAAGCGUAUUCAACA<br>AGGGGCUGAAGGAUGCCCAGAAGGUACCCCAUUGUAUGGG<br>AUCUGAUCUGGGGCCUCGGUGCACAUGCUUUACAUGUGUU<br>UAGUCGAGGUUAAAAAACGUCUAGGCCCCCCGAACCACGG<br>GGACGUGGUUUUCCUUUGAAAAACACGAUGAUAAU<br>AUGGCCGGUCCCGCGACCCAAAGCCCCAUGAAACUUAUGG<br>CCCUGCAGUUGCUGCUUUGGCACUCGGCCCUCUGGACAGU<br>CCAAGAAGCGACUCCUCUCGGACCUGCCUCAUCGUUGCCG<br>CAGUCAUUCCUUUUGAAGUGUCUGGAGCAGGUGCGAAAG<br>AUUCAGGGCGAUGGAGCCGCACUCCAAGAGAAGCUCUGCG<br>CGACAUACAAACUUUGCCAUCCCGAGGAGCUCGUACUGCU<br>CGGGCACAGCUUGGGGAUUCCCUGGGCUCCUCUCUCGUCC<br>UGUCCGUCGCAGGCUUUGCAGUUGGCAGGGUGCCUUUCCC<br>AGCUCCACUCCGGUUUGUUCUUGUAUCAGGGACUGCUGCA<br>AGCCCUUGAGGGAAUCUCGCCAGAAUUGGGCCCGACGCUG<br>GACACGUUGCAGCUCGACGUGGCGGAUUUCGCAACAACCA<br>UCUGGCAGCAGAUGGAGGAACUGGGGAUGGCACCCGCGCU<br>GCAGCCCACGCAGGGGGCAAUGCCGGCCUUUGCGUCCGCG<br>UUUCAGCGCAGGGCGGGUGGAGUCCUCGUAGCGAGCCACC<br>UUCAAUCAUUUUUGGAAGUCUCGUACCGGGUGCUGAGACA | 5004 |

TABLE 30-continued

G-CSF Sequences

| | Sequence | SEQ ID NO: |
|---|---|---|
| | UCUUGCGCAGCCG<br>UGAUAAUAG<br>GCUGGAGCCUCGGUGGCCAUGCUUCUUGCCCCUUGGGCCU<br>CCCCCCAGCCCCUCCUCCCCUUCCUGCACCCGUACCCCCGU<br>GGUCUUUGAAUAAAGUCUGAGUGGGCGGC | |
| G-CSF without a Kozak sequence and with an IRES and human alpha-globin 3'UTR | Optimized G-CSF cDNA sequence containing a T7 polymerase site, IRES and XbaI restriction site:<br>TAATACGACTCACTATA<br>GGGAAATAAGAGAGAAAAGAAGAGTAAGAAGAAATATAAGA<br>TCGTGAGGATCTATTTCCGGTGAATTCCTCGAGACTAGTTCT<br>AGAGCGGCCGCGGATCCCGCCCCTCTCCCTCCCCCCCCCTA<br>ACGTTACTGGCCGAAGCCGCTTGGAATAAGGCCGGTGTGCG<br>TTTGTCTATATGTTATTTTCCACCATATTGCCGTCTTTTGGCA<br>ATGTGAGGGCCCGGAAACCTGGCCCTGTCTTCTTGACGAGC<br>ATTCCTAGGGGTCTTTCCCCTCTCGCCAAAGGAATGCAAGGT<br>CTGTTGAATGTCGTGAAGGAAGCAGTTCCTCTGGAAGCTTCT<br>TGAAGACAAACAACGTCTGTAGCGACCCTTTGCAGGCAGCG<br>GAACCCCCCACCTGGCGACAGGTGCCTCTGCGGCCAAAAGC<br>CACGTGTATAAGATACACCTGCAAAGGCGGCACAACCCCAG<br>TGCCACGTTGTGAGTTGGATAGTTGTGGAAAGAGTCAAATG<br>GCTCACCTCAAGCGTATTCAACAAGGGGCTGAAGGATGCCC<br>AGAAGGTACCCCATTGTATGGGATCTGATCTGGGGCCTCGG<br>TGCACATGCTTTACATGTGTTTAGTCGAGGTTAAAAAACGTC<br>TAGGCCCCCCGAACCACGGGACGTGGTTTTCCTTTGAAAA<br>ACACGATGATAAT<br><u>ATG</u>GCCGGTCCCGCGACCCAAAGCCCCATGAAACTTATGGC<br>CCTGCAGTTGCTGCTTTGGCACTCGGCCCTCTGGACAGTCCA<br>AGAAGCGACTCCTCTCGGACCTGCCTCATCGTTGCCGCAGTC<br>ATTCCTTTTGAAGTGTCTGGAGCAGGTGCGAAAGATTCAGG<br>GCGATGGAGCCGCACTCCAAGAGAAGCTCTGCGCGACATAC<br>AAACTTTGCCATCCCGAGGAGCTCGTACTGCTCGGGCACAG<br>CTTGGGGATTTCCTGGGCTCCTCTCTCGTCCTGTCCGTCGCA<br>GGCTTTGCAGTTGGCAGGGTGCCTTTCCCAGCTCCACTCCGG<br>TTTGTTCTTGTATCAGGGACTGCTGCAAGCCCTTGAGGGAAT<br>CTCGCCAGAATTGGGCCCGACGCTGGACACGTTGCAGCTCG<br>ACGTGGCGGATTTCGCAACAACCATCTGGCAGCAGATGGAG<br>GAACTGGGGATGGCACCCGCGCTGCAGCCCACGCAGGGGG<br>CAATGCCGGCCTTTGCGTCCGCGTTTCAGCGCAGGGCGGGT<br>GGAGTCCTCGTAGCGAGCCACCTTCAATCATTTTTGGAAGTC<br>TCGTACCGGGTGCTGAGACATCTTGCGCAGCCG<br>TGATAATAG<br>GCTGGAGCCTCGGTGGCCATGCTTCTTGCCCCTTGGGCCTCC<br>CCCCAGCCCCTCCTCCCCTTCCTGCACCCGTACCCCCGTGGT<br>CTTTGAATAAAGTCTGAGTGGGCGGCTCTAGA | 5005 |
| | mRNA sequence (transcribed):<br>GGGAAAUAAGAGAGAAAAGAAGAGUAAGAAGAAAUAUAA<br>GA<br>UCGUGAGGAUCUAUUUCCGGUGAAUUCCUCGAGACUAGUU<br>CUAGAGCGGCCGCGGAUCCCGCCCCUCUCCCUCCCCCCCCC<br>CUAACGUUACUGGCCGAAGCCGCUUGGAAUAAGGCCGGUG<br>UGCGUUUGUCUAUAUGUUAUUUUCCACCAUAUUGCCGUCU<br>UUUGGCAAUGUGAGGGCCCGGAAACCUGGCCCUGUCUUCU<br>UGACGAGCAUUCCUAGGGGUCUUUCCCCUCUCGCCAAAGG<br>AAUGCAAGGUCUGUUGAAUGUCGUGAAGGAAGCAGUUCC<br>UCUGGAAGCUUCUUGAAGACAAACAACGUCUGUAGCGACC<br>CUUUGCAGGCAGCGGAACCCCCCACCUGGCGACAGGUGCC<br>UCUGCGGCCAAAAGCCACGUGUAUAAGAUACACCUGCAAA<br>GGCGGCACAACCCCAGUGCCACGUUGUGAGUUGGAUAGUU<br>GUGGAAAGAGUCAAAUGGCUCACCUCAAGCGUAUUCAACA<br>AGGGGCUGAAGGAUGCCCAGAAGGUACCCCAUUGUAUGGG<br>AUCUGAUCUGGGGCCUCGGUGCACAUGCUUUACAUGUGUU<br>UAGUCGAGGUUAAAAAACGUCUAGGCCCCCCGAACCACGG<br>GGACGUGGUUUUCCUUUGAAAAACACGAUGAUAAU<br><u>AUG</u>GCCGGUCCCGCGACCCAAAGCCCCAUGAAACUUAUGG<br>CCCUGCAGUUGCUGCUUUGGCACUCGGCCCUCUGGACAGU<br>CCAAGAAGCGACUCCUCUCGGACCUGCCUCAUCGUUGCCG<br>CAGUCAUUCCUUUUGAAGUGUCUGGAGCAGGUGCGAAAG<br>AUUCAGGGCGAUGGAGCCGCACUCCAAGAGAAGCUCUGCG<br>CGACAUACAAACUUUGCCAUCCCGAGGAGCUCGUACUGCU<br>CGGGCACAGCUUGGGGAUUCCCUGGGCUCCUCUCUCGUCC<br>UGUCCGUCGCAGGCUUUGCAGUUGGCAGGGUGCCUUUCCC<br>AGCUCCACUCCGGUUUGUUCUUGUAUCAGGGACUGCUGCA<br>AGCCCUUGAGGGAAUCUCGCCAGAAUUGGGCCCGACGCUG | 5006 |

TABLE 30-continued

G-CSF Sequences

| | Sequence | SEQ ID NO: |
|---|---|---|
| | GACACGUUGCAGCUCGACGUGGCGGAUUUCGCAACAACCA UCUGGCAGCAGAUGGAGGAACUGGGGAUGGCACCCGCGCU GCAGCCCACGCAGGGGGCAAUGCCGGCCUUUGCGUCCGCG UUUCAGCGCAGGGCGGGUGGAGUCCUCGUAGCGAGCCACC UUCAAUCAUUUUUGGAAGUCUCGUACCGGGUGCUGAGACA UCUUGCGCAGCCG UGAUAAUAG GCUGGAGCCUCGGUGGCCAUGCUUCUUGCCCCUUGGGCCU CCCCCCAGCCCCUCCUCCCCUUCCUGCACCCGUACCCCCGU GGUCUUUGAAUAAAGUCUGAGUGGGCGGC | |
| G-CSF without a Kozak sequence and with a human alpha-globin 3'UTR | Optimized G-CSF cDNA sequence containing a T7 polymerase site, a Kozak sequence and Xba1 restriction site: TAATACGACTCACTATA GGGAAATAAGAGAGAAAAGAAGAGTAAGAAGAAATATAAGA ATGGCCGGTCCCGCGACCCAAAGCCCCATGAAACTTATGGC CCTGCAGTTGCTGCTTTGGCACTCGGCCCTCTGGACAGTCCA AGAAGCGACTCCTCTCGGACCTGCCTCATCGTTGCCGCAGTC ATTCCTTTTGAAGTGTCTGGAGCAGGTGCGAAAGATTCAGG GCGATGGAGCCGCACTCCAAGAGAAGCTCTGCGCGACATAC AAACTTTGCCATCCCGAGGAGCTCGTACTGCTCGGCACAG CTTGGGGATTCCCTGGGCTCCTCTCTCGTCCTGTCCGTCGCA GGCTTTGCAGTTGGCAGGGTGCCTTTTCCCAGCTCCACTCCGG TTTGTTCTTGTATCAGGGACTGCTGCAAGCCCTTGAGGGAAT CTCGCCAGAATTGGGCCCGACGCTGGACACGTTGCAGCTCG ACGTGGCGGATTTCGCAACAACCATCTGGCAGCAGATGGAG GAACTGGGGATGGCACCCGCGCTGCAGCCCACGCAGGGGG CAATGCCGGCCTTTGCGTCCGCGTTTCAGCGCAGGGCGGGT GGAGTCCTCGTAGCGAGCCACCTTCAATCATTTTTGGAAGTC TCGTACCGGGTGCTGAGACATCTTGCGCAGCCG TGATAATAG GCTGGAGCCTCGGTGGCCATGCTTCTTGCCCCTTGGGCCTCC CCCCAGCCCCTCCTCCCCTTCCTGCACCCGTACCCCCGTGGT CTTTGAATAAAGTCTGAGTGGGCGGCTCTAGA | 5007 |
| | mRNA sequence (transcribed): GGGAAAUAAGAGAGAAAAGAAGAGUAAGAAGAAAUAUAA GA AUGGCCGGUCCCGCGACCCAAAGCCCCAUGAAACUUAUGG CCCUGCAGUUGCUGCUUUGGCACUCGGCCCUCUGGACAGU CCAAGAAGCGACUCCUCUCGGACCUGCCUCAUCGUUGCCG CAGUCAUUCCUUUUGAAGUGUCUGGAGCAGGUGCGAAAG AUUCAGGGCGAUGGAGCCGCACUCCAAGAGAAGCUCUGCG CGACAUACAAACUUUGCCAUCCCGAGGAGCUCGUACUGCU CGGGCACAGCUUGGGGAUUCCCUGGGCUCCUCUCUCGUCC UGUCCGUCGCAGGCUUUGCAGUUGGCAGGGUGCCUUUCCC AGCUCCACUCCGGUUUGUUCUUGUAUCAGGGACUGCUGCA AGCCCUUGAGGGAAUCUCGCCAGAAUUGGGCCCGACGCUG GACACGUUGCAGCUCGACGUGGCGGAUUUCGCAACAACCA UCUGGCAGCAGAUGGAGGAACUGGGGAUGGCACCCGCGCU GCAGCCCACGCAGGGGGCAAUGCCGGCCUUUGCGUCCGCG UUUCAGCGCAGGGCGGGUGGAGUCCUCGUAGCGAGCCACC UUCAAUCAUUUUUGGAAGUCUCGUACCGGGUGCUGAGACA UCUUGCGCAGCCG UGAUAAUAG GCUGGAGCCUCGGUGGCCAUGCUUCUUGCCCCUUGGGCCU CCCCCCAGCCCCUCCUCCCCUUCCUGCACCCGUACCCCCGU GGUCUUUGAAUAAAGUCUGAGUGGGCGGC | 5008 |
| G-CSF with an IRES, a human alpha-globin 3'UTR and a polyA tail of 80 nucleotides | Optimized G-CSF cDNA sequence containing a T7 polymerase site, IRES, a polyA tail of 80 nucleotides and Asc1 restriction site: TAATACGACTCACTATA GGGAAATAAGAGAGAAAAGAAGAGTAAGAAGAAATATAAG AGCCACC TCGTGAGGATCTATTTCCGGTGAATTCCTCGAGACTAGTTCT AGAGCGGCCGCGGATCCCGCCCCTCTCCCTCCCCCCCCCCTA ACGTTACTGGCCGAAGCCGCTTGGAATAAGGCCGGTGTGCG TTTGTCTATATGTTATTTTCCACCATATTGCCGTCTTTTGGCA ATGTGAGGGCCCGGAAACCTGGCCCTGTCTTCTTGACGAGC ATTCCTAGGGGTCTTTCCCCTCTCGCCAAAGGAATGCAAGGT CTGTTGAATGTCGTGAAGGAAGCAGTTCCTCTGGAAGCTTCT TGAAGACAAACAACGTCTGTAGCGACCCTTTGCAGGCAGCG GAACCCCCCACCTGGCGACAGGTGCCTCTGCGGCCAAAAGC CACGTGTATAAGATACACCTGCAAAGGCGGCACAACCCCAG TGCCACGTTGTGAGTTGGATAGTTGTGGAAAGAGTCAAATG | 5009 |

TABLE 30-continued

G-CSF Sequences

| Sequence | SEQ ID NO: |
|---|---|
| GCTCACCTCAAGCGTATTCAACAAGGGGCTGAAGGATGCCC<br>AGAAGGTACCCCATTGTATGGGATCTGATCTGGGGCCTCGG<br>TGCACATGCTTTACATGTGTTTAGTCGAGGTTAAAAAACGTC<br>TAGGCCCCCCGAACCACGGGGACGTGGTTTTCCTTTGAAAA<br>ACACGATGATAAT<br>ATGGCCGGTCCCGCGACCCAAAGCCCCATGAAACTTATGGC<br>CCTGCAGTTGCTGCTTTGGCACTCGGCCCTCTGGACAGTCCA<br>AGAAGCGACTCCTCTCGGACCTGCCTCATCGTTGCCGCAGTC<br>ATTCCTTTTGAAGTGTCTGGAGCAGGTGCGAAAGATTCAGG<br>GCGATGGAGCCGCACTCCAAGAGAAGCTCTGCGCGACATAC<br>AAACTTTGCCATCCCGAGGAGCTCGTACTGCTCGGGCACAG<br>CTTGGGGATTCCCTGGGCTCCTCTCTCGTCCTGTCCGTCGCA<br>GGCTTTGCAGTTGGCAGGGTGCCTTTCCCAGCTCCACTCCGG<br>TTTGTTCTTGTATCAGGGACTGCTGCAAGCCCTTGAGGGAAT<br>CTCGCCAGAATTGGGCCCGACGCTGGACACGTTGCAGCTCG<br>ACGTGGCGGATTTCGCAACAACCATCTGGCAGCAGATGGAG<br>GAACTGGGGATGGCACCCGCGCTGCAGCCCACGCAGGGGG<br>CAATGCCGGCCTTTGCGTCCGCGTTTCAGCGCAGGGCGGGT<br>GGAGTCCTCGTAGCGAGCCACCTTCAATCATTTTTGGAAGTC<br>TCGTACCGGGTGCTGAGACATCTTGCGCAGCCG<br>TGATAATAG<br>GCTGGAGCCTCGGTGGCCATGCTTCTTGCCCCTTGGGCCTCC<br>CCCCAGCCCCTCCTCCCCTTCCTGCACCCGTACCCCCGTGGT<br>CTTTGAATAAAGTCTGAGTGGGCGGCAAAAAAAAAAAAAAA<br>AAAAAAAAAAAAAAAAAAAAAAAAAAAAAAAAAAAAAA<br>AAAAAAAAAAAAAAAAAAAAAAAAAGGCGCGCC | |
| mRNA sequence (transcribed):<br>GGGAAAUAAGAGAGAAAAGAAGAGUAAGAAGAAAUAUAA<br>GAGCCACC<br>UCGUGAGGAUCUAUUUCCGGUGAAUUCCUCGAGACUAGUU<br>CUAGAGCGGCCGCGGAUCCCGCCCCUCUCCCUCCCCCCCCC<br>CUAACGUUACUGGCCGAAGCCGCUUGGAAUAAGGCCGGUG<br>UGCGUUUGUCUAUAUGUUAUUUUCCACCAUAUUGCCGUCU<br>UUUGGCAAUGUGAGGGCCCGGAAACCUGGCCCUGUCUUCU<br>UGACGAGCAUUCCUAGGGGUCUUUCCCCUCUCGCCAAAGG<br>AAUGCAAGGUCUGUUGAAUGUCGUGAAGGAAGCAGUUCC<br>UCUGGAAGCUUCUUGAAGACAAACAACGUCUGUAGCGACC<br>CUUUGCAGGCAGCGGAACCCCCCACCUGGCGACAGGUGCC<br>UCUGCGGCCAAAAGCCACGUGUAUAAGAUACACCUGCAAA<br>GGCGGCACAACCCCAGUGCCACGUUGUGAGUUGGAUAGUU<br>GUGGAAAGAGUCAAAUGGCUCACCUCAAGCGUAUUCAACA<br>AGGGGCUGAAGGAUGCCCAGAAGGUACCCCAUUGUAUGGG<br>AUCUGAUCUGGGGCCUCGGUGCACAUGCUUUACAUGUGUU<br>UAGUCGAGGUUAAAAAACGUCUAGGCCCCCCGAACCACGG<br>GGACGUGGUUUUCCUUUGAAAAACACGAUGAUAAU<br>AUGGCCGGUCCCGCGACCCAAAGCCCCAUGAAACUUAUGG<br>CCCUGCAGUUGCUGCUUUGGCACUCGGCCCUCUGGACAGU<br>CCAAGAAGCGACUCCUCUCGGACCUGCCUCAUCGUUGCCG<br>CAGUCAUUCCUUUUGAAGUGUCUGGAGCAGGUGCGAAAG<br>AUUCAGGGCGAUGGAGCCGCACUCCAAGAGAAGCUCUGCG<br>CGACAUACAAACUUUGCCAUCCCGAGGAGCUCGUACUGCU<br>CGGGCACAGCUUGGGGAUUCCCUGGGCUCCUCUCUCGUCC<br>UGUCCGUCGCAGGCUUUGCAGUUGGCAGGGUGCCUUUCCC<br>AGCUCCACUCCGGUUUGUUCUUGUAUCAGGGACUGCUGCA<br>AGCCCUUGAGGGAAUCUCGCCAGAAUUGGGCCCGACGCUG<br>GACACGUUGCAGCUCGACGUGGCGGAUUUCGCAACAACCA<br>UCUGGCAGCAGAUGGAGGAACUGGGGAUGGCACCCGCGCU<br>GCAGCCCACGCAGGGGGCAAUGCCGGCCUUUGCGUCCGCG<br>UUUCAGCGCAGGGCGGGUGGAGUCCUCGUAGCGAGCCACC<br>UUCAAUCAUUUUUGGAAGUCUCGUACCGGGUGCUGAGACA<br>UCUUGCGCAGCCG<br>UGAUAAUAG<br>GCUGGAGCCUCGGUGGCCAUGCUUCUUGCCCCUUGGGCCU<br>CCCCCCAGCCCCUCCUCCCCUUCCUGCACCCGUACCCCCGU<br>GGUCUUUGAAUAAAGUCUGAGUGGGCGGC<br>AAAAAAAAAAAAAAAAAAAAAAAAAAAAAAAAAAA<br>AAAAAAAAAAAAAAAAAAAAAAAAAAAAAAAAAA<br>AA | 5010 |

TABLE 30-continued

G-CSF Sequences

| | Sequence | SEQ ID NO: |
|---|---|---|
| G-CSF without a Kozak sequence and with an IRES, a human alpha-globin 3'UTR and a polyA tail of 80 nucleotides | Optimized G-CSF cDNA sequence containing a T7 polymerase site, an IRES sequence, a polyA tail of 80 nucleotides and Asc1 restriction site:<br>TAATACGACTCACTATA<br>GGGAAATAAGAGAGAAAAGAAGAGTAAGAAGAAATATAAGA<br>TCGTGAGGATCTATTTCCGGTGAATTCCTCGAGACTAGTTCT<br>AGAGCGGCCGCGGATCCCGCCCCTCTCCCTCCCCCCCCCTA<br>ACGTTACTGGCCGAAGCCGCTTGGAATAAGGCCGGTGTGCG<br>TTTGTCTATATGTTATTTTCCACCATATTGCCGTCTTTTGGCA<br>ATGTGAGGGCCCGGAAACCTGGCCCTGTCTTCTTGACGAGC<br>ATTCCTAGGGGTCTTTCCCCTCTCGCCAAAGGAATGCAAGGT<br>CTGTTGAATGTCGTGAAGGAAGCAGTTCCTCTGGAAGCTTCT<br>TGAAGACAAACAACGTCTGTAGCGACCCTTTGCAGGCAGCG<br>GAACCCCCCACCTGGCGACAGGTGCCTCTGCGGCCAAAAGC<br>CACGTGTATAAGATACACCTGCAAAGGCGGCACAACCCCAG<br>TGCCACGTTGTGAGTTGGATAGTTGTGGAAAGAGTCAAATG<br>GCTCACCTCAAGCGTATTCAACAAGGGGCTGAAGGATGCCC<br>AGAAGGTACCCCATTGTATGGGATCTGATCTGGGGCCTCGG<br>TGCACATGCTTTACATGTGTTTAGTCGAGGTTAAAAAACGTC<br>TAGGCCCCCCGAACCACGGGGACGTGGTTTTCCTTTGAAAA<br>ACACGATGATAAT<br>ATGGCCGGTCCCGCGACCCAAAGCCCCATGAAACTTATGGC<br>CCTGCAGTTGCTGCTTTGGCACTCGGCCCTCTGGACAGTCCA<br>AGAAGCGACTCCTCTCGGACCTGCCTCATCGTTGCCGCAGTC<br>ATTCCTTTTGAAGTGTCTGGAGCAGGTGCGAAAGATTCAGG<br>GCGATGGAGCCGCACTCCAAGAGAAGCTCTGCGCGACATAC<br>AAACTTTGCCATCCCGAGGAGCTCGTACTGCTCGGGCACAG<br>CTTGGGGATTCCCTGGGCTCCTCTCTCGTCCTGTCCGTCGCA<br>GGCTTTGCAGTTGGCAGGGTGCCTTTCCCAGCTCCACTCCGG<br>TTTGTTCTTGTATCAGGGACTGCTGCAAGCCCTTGAGGGAAT<br>CTCGCCAGAATTGGGCCCGACGCTGGACACGTTGCAGCTCG<br>ACGTGGCGGATTTCGCAACAACCATCTGGCAGCAGATGGAG<br>GAACTGGGGATGGCACCCGCGCTGCAGCCCACGCAGGGGG<br>CAATGCCGGCCTTTGCGTCCGCGTTTCAGCGCAGGGCGGGT<br>GGAGTCCTCGTAGCGAGCCACCTTCAATCATTTTTGGAAGTC<br>TCGTACCGGGTGCTGAGACATCTTGCGCAGCCG<br>TGATAATAG<br>GCTGGAGCCTCGGTGGCCATGCTTCTTGCCCCTTGGGCCTCC<br>CCCCAGCCCCTCCTCCCCTTCCTGCACCCGTACCCCCGTGGT<br>CTTTGAATAAAGTCTGAGTGGGCGGCAAAAAAAAAAAAAA<br>AAAAAAAAAAAAAAAAAAAAAAAAAAAAAAAAAAA<br>AAAAAAAAAAAAAAAAAAAAAAAAAGGCGCGCC | 5011 |
| | mRNA sequence (transcribed):<br>GGGAAAUAAGAGAGAAAAGAAGAGUAAGAAGAAAUAUAA<br>GA<br>UCGUGAGGAUCUAUUUCCGGUGAAUUCCUCGAGACUAGUU<br>CUAGAGCGGCCGCGGAUCCCGCCCCUCUCCCUCCCCCCCC<br>CUAACGUUACUGGCCGAAGCCGCUUGGAAUAAGGCCGGUG<br>UGCGUUUGUCUAUAUGUUAUUUUCCACCAUAUUGCCGUCU<br>UUUGGCAAUGUGAGGGCCCGGAAACCUGGCCCUGUCUUCU<br>UGACGAGCAUUCCUAGGGGUCUUUCCCCUCUCGCCAAAGG<br>AAUGCAAGGUCUGUUGAAUGUCGUGAAGGAAGCAGUUCC<br>UCUGGAAGCUUCUUGAAGACAAACAACGUCUGUAGCGACC<br>CUUUGCAGGCAGCGGAACCCCCCACCUGGCGACAGGUGCC<br>UCUGCGGCCAAAAGCCACGUGUAUAAGAUACACCUGCAAA<br>GGCGGCACAACCCCAGUGCCACGUUGUGAGUUGGAUAGUU<br>GUGGAAAGAGUCAAAUGGCUCACCUCAAGCGUAUUCAACA<br>AGGGGCUGAAGGAUGCCCAGAAGGUACCCCAUUGUAUGGG<br>AUCUGAUCUGGGGCCUCGGUGCACAUGCUUUACAUGUGUU<br>UAGUCGAGGUUAAAAAACGUCUAGGCCCCCCGAACCACGG<br>GGACGUGGUUUUCCUUUGAAAAACACGAUGAUAAU<br>AUGGCCGGUCCCGCGACCCAAAGCCCCAUGAAACUUAUGG<br>CCCUGCAGUUGCUGCUUUGGCACUCGGCCCUCUGGACAGU<br>CCAAGAAGCGACUCCUCUCGGACCUGCCUCAUCGUUGCCG<br>CAGUCAUUCCUUUUGAAGUGUCUGGAGCAGGUGCGAAAG<br>AUUCAGGGCGAUGGAGCCGCACUCCAAGAGAAGCUCUGCG<br>CGACAUACAAACUUUGCCAUCCCGAGGAGCUCGUACUGCU<br>CGGGCACAGCUUGGGGAUUCCCUGGGCUCCUCUCUCGUCC<br>UGUCCGUCGCAGGCUUUGCAGUUGGCAGGGUGCCUUUCCC<br>AGCUCCACUCCGGUUUGUUCUUGUAUCAGGGACUGCUGCA<br>AGCCCUUGAGGGAAUCUCGCCAGAAUUGGGCCCGACGCUG<br>GACACGUUGCAGCUCGACGUGGCGGAUUUCGCAACAACCA<br>UCUGGCAGCAGAUGGAGGAACUGGGGAUGGCACCCGCGCU<br>GCAGCCCACGCAGGGGGCAAUGCCGGCCUUUGCGUCCGCG | 5012 |

TABLE 30-continued

G-CSF Sequences

| | Sequence | SEQ ID NO: |
|---|---|---|
| | UUUCAGCGCAGGGCGGGUGGAGUCCUCGUAGCGAGCCACC<br>UUCAAUCAUUUUUGGAAGUCUCGUACCGGGUGCUGAGACA<br>UCUUGCGCAGCCG<br>UGAUAAUAG<br>GCUGGAGCCUCGGUGGCCAUGCUUCUUGCCCCUUGGGCCU<br>CCCCCCAGCCCCUCCUCCCCUUCCUGCACCCGUACCCCCGU<br>GGUCUUUGAAUAAAGUCUGAGUGGGCGGCAAAAAAAAAA<br>AAAAAAAAAAAAAAAAAAAAAAAAAAAAAAAAAAAAA<br>AAAAAAAAAAAAAAAAAAAAAAAAAAAAA | |
| G-CSF with a human alpha-globin 3'UTR and a polyA tail of 80 nucleotides | Optimized G-CSF cDNA sequence containing a T7 polymerase site, a polyA tail of 80 nucleotides and Asc1 restriction site:<br>TAATACGACTCACTATA<br>GGGAAATAAGAGAGAAAAGAAGAGTAAGAAGAAATATAAG<br>AGCCACC<br>ATGGCCGGTCCCGCGACCCAAAGCCCCATGAAACTTATGGC<br>CCTGCAGTTGCTGCTTTGGCACTCGGCCCTCTGGACAGTCCA<br>AGAAGCGACTCCTCTCGGACCTGCCTCATCGTTGCCGCAGTC<br>ATTCCTTTTGAAGTGTCTGGAGCAGGTGCGAAAGATTCAGG<br>GCGATGGAGCCGCACTCCAAGAGAAGCTCTGCGCGACATAC<br>AAACTTTGCCATCCCGAGGAGCTCGTACTGCTCGGGCACAG<br>CTTGGGGATTCCCTGGGCTCCTCTCTCGTCCTGTCCGTCGCA<br>GGCTTTGCAGTTGGCAGGGTGCCTTTCCCAGCTCCACTCCGG<br>TTTGTTCTTGTATCAGGGACTGCTGCAAGCCCTTGAGGGAAT<br>CTCGCCAGAATTGGGCCCGACGCTGGACACGTTGCAGCTCG<br>ACGTGGCGGATTTCGCAACAACCATCTGGCAGCAGATGGAG<br>GAACTGGGGATGGCACCCGCGCTGCAGCCCACGCAGGGGG<br>CAATGCCGGCCTTTGCGTCCGCGTTTCAGCGCAGGGCGGGT<br>GGAGTCCTCGTAGCGAGCCACCTTCAATCATTTTTGGAAGTC<br>TCGTACCGGGTGCTGAGACATCTTGCGCAGCCG<br>TGATAATAG<br>GCTGGAGCCTCGGTGGCCATGCTTCTTGCCCCTTGGGCCTCC<br>CCCCAGCCCCTCCTCCCCTTCCTGCACCCGTACCCCCGTGGT<br>CTTTGAATAAAGTCTGAGTGGGCGGCAAAAAAAAAAAAAA<br>AAAAAAAAAAAAAAAAAAAAAAAAAAAAAAAAAAAAA<br>AAAAAAAAAAAAAAAAAAAAAAAAAAGGCGCGCC | 5013 |
| | mRNA sequence (transcribed):<br>GGGAAAUAAGAGAGAAAAGAAGAGUAAGAAGAAAUAUAA<br>GAGCCACC<br>AUGGCCGGUCCCGCGACCCAAAGCCCCAUGAAACUUAUGG<br>CCCUGCAGUUGCUGCUUUGGCACUCGGCCCUCUGGACAGU<br>CCAAGAAGCGACUCCUCUCGGACCUGCCUCAUCGUUGCCG<br>CAGUCAUUCCUUUUGAAGUGUCUGGAGCAGGUGCGAAAG<br>AUUCAGGGCGAUGGAGCCGCACUCCAAGAGAAGCUCUGCG<br>CGACAUACAAACUUUGCCAUCCCGAGGAGCUCGUACUGCU<br>CGGGCACAGCUUGGGGAUUCCCUGGGCUCCUCUCUCGUCC<br>UGUCCGUCGCAGGCUUUGCAGUUGGCAGGGUGCCUUUCCC<br>AGCUCCACUCCGGUUUGUUCUUGUAUCAGGGACUGCUGCA<br>AGCCCUUGAGGGAAUCUCGCCAGAAUUGGGCCCGACGCUG<br>GACACGUUGCAGCUCGACGUGGCGGAUUUCGCAACAACCA<br>UCUGGCAGCAGAUGGAGGAACUGGGGAUGGCACCCGCGCU<br>GCAGCCCACGCAGGGGGCAAUGCCGGCCUUUGCGUCCGCG<br>UUUCAGCGCAGGGCGGGUGGAGUCCUCGUAGCGAGCCACC<br>UUCAAUCAUUUUUGGAAGUCUCGUACCGGGUGCUGAGACA<br>UCUUGCGCAGCCG<br>UGAUAAUAG<br>GCUGGAGCCUCGGUGGCCAUGCUUCUUGCCCCUUGGGCCU<br>CCCCCCAGCCCCUCCUCCCCUUCCUGCACCCGUACCCCCGU<br>GGUCUUUGAAUAAAGUCUGAGUGGGCGGCAAAAAAAAAA<br>AAAAAAAAAAAAAAAAAAAAAAAAAAAAAAAAAAAAA<br>AAAAAAAAAAAAAAAAAAAAAAAAAAAAA | 5014 |
| G-CSF without a kozak sequence and with a human alpha-globin | Optimized G-CSF cDNA sequence containing a T7 polymerase site, a polyA tail of 80 nucleotides and Asc1 restriction site:<br>TAATACGACTCACTATA<br>GGGAAATAAGAGAGAAAAGAAGAGTAAGAAGAAATATAAGA<br>ATGGCCGGTCCCGCGACCCAAAGCCCCATGAAACTTATGGC<br>CCTGCAGTTGCTGCTTTGGCACTCGGCCCTCTGGACAGTCCA<br>AGAAGCGACTCCTCTCGGACCTGCCTCATCGTTGCCGCAGTC<br>ATTCCTTTTGAAGTGTCTGGAGCAGGTGCGAAAGATTCAGG | 5015 |

TABLE 30-continued

G-CSF Sequences

| Sequence | | SEQ ID NO: |
|---|---|---|
| 3'UTR and a polyA tail of 80 nucleotides | GCGATGGAGCCGCACTCCAAGAGAAGCTCTGCGCGACATAC<br>AAACTTTGCCATCCCGAGGAGCTCGTACTGCTCGGGCACAG<br>CTTGGGGATTCCCTGGGCTCCTCTCTCGTCCTGTCCGTCGCA<br>GGCTTTGCAGTTGGCAGGGTGCCTTTCCCAGCTCCACTCCGG<br>TTTGTTCTTGTATCAGGGACTGCTGCAAGCCCTTGAGGGAAT<br>CTCGCCAGAATTGGGCCCGACGCTGGACACGTTGCAGCTCG<br>ACGTGGCGGATTTCGCAACAACCATCTGGCAGCAGATGGAG<br>GAACTGGGGATGGCACCCGCGCTGCAGCCCACGCAGGGGG<br>CAATGCCGGCCTTTGCGTCCGCGTTTCAGCGCAGGGCGGGT<br>GGAGTCCTCGTAGCGAGCCACCTTCAATCATTTTTGGAAGTC<br>TCGTACCGGGTGCTGAGACATCTTGCGCAGCCG<br>TGATAATAG<br>GCTGGAGCCTCGGTGGCCATGCTTCTTGCCCCTTGGGCCTCC<br>CCCCAGCCCCTCCTCCCCTTCCTGCACCCGTACCCCCGTGGT<br>CTTTGAATAAAGTCTGAGTGGGCGGCAAAAAAAAAAAAA<br>AAAAAAAAAAAAAAAAAAAAAAAAAAAAAAAAAAA<br>AAAAAAAAAAAAAAAAAAAAAAAAAAAGGCGCGCC<br>mRNA sequence (transcribed):<br>GGGAAAUAAGAGAGAAAAGAAGAGUAAGAAGAAAUAUAA<br>GA<br><u>AUG</u>GCCGGUCCCGCGACCCAAAGCCCCAUGAAACUUAUGG<br>CCCUGCAGUUGCUGCUUUGGCACUCGGCCCUCUGGACAGU<br>CCAAGAAGCGACUCCUCUCGGACCUGCCUCAUCGUUGCCG<br>CAGUCAUUCCUUUUGAAGUGUCUGGAGCAGGUGCGAAAG<br>AUUCAGGGCGAUGGAGCCGCACUCCAAGAGAAGCUCUGCG<br>CGACAUACAAACUUUGCCAUCCCGAGGAGCUCGUACUGCU<br>CGGGCACAGCUUGGGGAUUCCCUGGGCUCCUCUCUCGUCC<br>UGUCCGUCGCAGGCUUUGCAGUUGGCAGGGUGCCUUUCCC<br>AGCUCCACUCCGGUUUGUUCUUGUAUCAGGGACUGCUGCA<br>AGCCCUUGAGGGAAUCUCGCCAGAAUUGGGCCCGACGCUG<br>GACACGUUGCAGCUCGACGUGGCGGAUUUCGCAACAACCA<br>UCUGGCAGCAGAUGGAGGAACUGGGGAUGGCACCCGCGCU<br>GCAGCCCACGCAGGGGGCAAUGCCGGCCUUUGCGUCCGCG<br>UUUCAGCGCAGGGCGGGUGGAGUCCUCGUAGCGAGCCACC<br>UUCAAUCAUUUUUGGAAGUCUCGUACCGGGUGCUGAGACA<br>UCUUGCGCAGCCG<br>UGAUAAUAG<br>GCUGGAGCCUCGGUGGCCAUGCUUCUUGCCCCUUGGGCCU<br>CCCCCCAGCCCCUCCUCCCCUUCCUGCACCCGUACCCCCGU<br>GGUCUUUGAAUAAAGUCUGAGUGGGCGGCAAAAAAAAAA<br>AAAAAAAAAAAAAAAAAAAAAAAAAAAAAAAAAAA<br>AAAAAAAAAAAAAAAAAAAAAAAAAAAAAA | 5016 |

These modified mRNA sequences can include at least one chemical modification described herein. The G-CSF modified mRNA sequence can be formulated, using methods described herein and/or known in the art, prior to transfection and/or administration.

The modified mRNA sequence encoding G-CSF can be transfected in vitro to various cell types such as HEK293, HeLa, PBMC and BJ fibroblast and those described in Table 25 using methods disclosed herein and/or are known in the art. The cells are then analyzed using methods disclosed herein and/or are known in the art to determine the concentration of G-CSF and/or cell viability.

The modified mRNA sequence encoding G-CSF can also be administered to mammals including mat, rats, non-human primates and humans. The serum and surrounding tissue can be collected at pre-determined intervals and analyzed using methods disclosed herein and/or are known in the art to determine the concentration of G-CSF and other pharmacokinetic properties mentioned herein.

Example 32. Modified mRNA Sequences miR-122 Sequences in an Alpha-Globin UTR Modified mRNA encoding G-CSF or Factor IX with a mir-122 sequence in a human or mouse alpha-globin 3'UTR, and their corresponding cDNA sequences, are shown below in Table 31. In Table 31, the start codon of each sequence is underlined.

TABLE 31

G-CSF and FIX Sequences

| Description | Sequence | SEQ ID NO: |
|---|---|---|
| G-CSF with 1 miR-122 sequence in | Optimized G-CSF cDNA sequence containing a T7 polymerase site and Xba1 restriction site:<br>TAATACGACTCACTATA | 5017 |

TABLE 31-continued

G-CSF and FIX Sequences

| Description | Sequence | SEQ ID NO: |
|---|---|---|
| human alpha-globin 3'UTR | GGGAAATAAGAGAGAAAAGAAGAGTAAGAAGAAATATAA<br>GAGCCACC<br>ATGGCCGGTCCCGCGACCCAAAGCCCCATGAAACTTATGGC<br>CCTGCAGTTGCTGCTTTGGCACTCGGCCCTCTGGACAGTCCA<br>AGAAGCGACTCCTCTCGGACCTGCCTCATCGTTGCCGCAGT<br>CATTCCTTTTGAAGTGTCTGGAGCAGGTGCGAAAGATTCAG<br>GGCGATGGAGCCGCACTCCAAGAGAAGCTCTGCGCGACATA<br>CAAACTTTGCCATCCCGAGGAGCTCGTACTGCTCGGGCACA<br>GCTTGGGGATTCCCTGGGCTCCTCTCTCGTCCTGTCCGTCGC<br>AGGCTTTGCAGTTGGCAGGGTGCCTTTCCCAGCTCCACTCCG<br>GTTTGTTCTTGTATCAGGGACTGCTGCAAGCCCTTGAGGGA<br>ATCTCGCCAGAATTGGGCCCGACGCTGGACACGTTGCAGCT<br>CGACGTGGCGGATTTCGCAACAACCATCTGGCAGCAGATGG<br>AGGAACTGGGGATGGCACCCGCGCTGCAGCCCACGCAGGG<br>GGCAATGCCGGCCTTTGCGTCCGCGTTTCAGCGCAGGGCGG<br>GTGGAGTCCTCGTAGCGAGCCACCTTCAATCATTTTTGGAA<br>GTCTCGTACCGGGTGCTGAGACATCTTGCGCAGCCG<br>TGATAATAG<br>GCTGGAGCCTCGGTGGCCATGCTTCTTGCCCCTTGGGCCTCC<br>CCCCAGCCCCTCCTCCCCTTCCTGCACCCGTACCCCCCAAAC<br>ACCATTGTCACACTCCAGTGGTCTTTGAATAAAGTCTGAGTG<br>GGCGGCTCTAGA | |
| | mRNA sequence (transcribed):<br>GGGAAAUAAGAGAGAAAAGAAGAGUAAGAAGAAAUAUAA<br>GAGCCACC<br>AUGGCCGGUCCCGCGACCCAAAGCCCCAUGAAACUUAUGG<br>CCCUGCAGUUGCUGCUUUGGCACUCGGCCCUCUGGACAGU<br>CCAAGAAGCGACUCCUCUCGGACCUGCCUCAUCGUUGCCG<br>CAGUCAUUCCUUUUGAAGUGUCUGGAGCAGGUGCGAAAG<br>AUUCAGGGCGAUGGAGCCGCACUCCAAGAGAAGCUCUGCG<br>CGACAUACAAACUUUGCCAUCCCGAGGAGCUCGUACUGCU<br>CGGGCACAGCUUGGGGAUUCCCUGGGCUCCUCUCUCGUCC<br>UGUCCGUCGCAGGCUUUGCAGUUGGCAGGGUGCCUUUCCC<br>AGCUCCACUCCGGUUUGUUCUUGUAUCAGGGACUGCUGCA<br>AGCCCUUGAGGGAAUCUCGCCAGAAUUGGGCCCGACGCUG<br>GACACGUUGCAGCUCGACGUGGCGGAUUUCGCAACAACCA<br>UCUGGCAGCAGAUGGAGGAACUGGGGAUGGCACCCGCGCU<br>GCAGCCCACGCAGGGGGCAAUGCCGGCCUUUGCGUCCGCG<br>UUUCAGCGCAGGGCGGGUGGAGUCCUCGUAGCGAGCCACC<br>UUCAAUCAUUUUUGGAAGUCUCGUACCGGGUGCUGAGAC<br>AUCUUGCGCAGCCG<br>UGAUAAUAG<br>GCUGGAGCCUCGGUGGCCAUGCUUCUUGCCCCUUGGGCCU<br>CCCCCCAGCCCCUCCUCCCCUUCCUGCACCCGUACCCCCCA<br>AACACCAUUGUCACACUCCAGUGGUCUUUGAAUAAAGUCU<br>GAGUGGGCGGC | 5018 |
| G-CSF with 1 miR-122 seed sequence in human alpha-globin 3'UTR | Optimized G-CSF cDNA sequence containing a T7 polymerase site and Xbal restriction site:<br>TAATACGACTCACTATA<br>GGGAAATAAGAGAGAAAAGAAGAGTAAGAAGAAATATAA<br>GAGCCACC<br>ATGGCCGGTCCCGCGACCCAAAGCCCCATGAAACTTATGGC<br>CCTGCAGTTGCTGCTTTGGCACTCGGCCCTCTGGACAGTCCA<br>AGAAGCGACTCCTCTCGGACCTGCCTCATCGTTGCCGCAGT<br>CATTCCTTTTGAAGTGTCTGGAGCAGGTGCGAAAGATTCAG<br>GGCGATGGAGCCGCACTCCAAGAGAAGCTCTGCGCGACATA<br>CAAACTTTGCCATCCCGAGGAGCTCGTACTGCTCGGGCACA<br>GCTTGGGGATTCCCTGGGCTCCTCTCTCGTCCTGTCCGTCGC<br>AGGCTTTGCAGTTGGCAGGGTGCCTTTCCCAGCTCCACTCCG<br>GTTTGTTCTTGTATCAGGGACTGCTGCAAGCCCTTGAGGGA<br>ATCTCGCCAGAATTGGGCCCGACGCTGGACACGTTGCAGCT<br>CGACGTGGCGGATTTCGCAACAACCATCTGGCAGCAGATGG<br>AGGAACTGGGGATGGCACCCGCGCTGCAGCCCACGCAGGG<br>GGCAATGCCGGCCTTTGCGTCCGCGTTTCAGCGCAGGGCGG<br>GTGGAGTCCTCGTAGCGAGCCACCTTCAATCATTTTTGGAA<br>GTCTCGTACCGGGTGCTGAGACATCTTGCGCAGCCG<br>TGATAATAG<br>GCTGGAGCCTCGGTGGCCATGCTTCTTGCCCCTTGGGCCTCC<br>CCCCAGCCCCTCCTCCCCTTCCTGCACCCGTACCCCCACACT<br>CCGTGGTCTTTGAATAAAGTCTGAGTGGGCGGCTCTAGA | 5019 |

TABLE 31-continued

G-CSF and FIX Sequences

| Description | Sequence | SEQ ID NO: |
|---|---|---|
| | mRNA sequence (transcribed):<br>GGGAAAUAAGAGAGAAAAGAAGAGUAAGAAGAAAUAUAA<br>GAGCCACC<br>AUGGCCGGUCCCGCGACCCAAAGCCCCAUGAAACUUAUGG<br>CCCUGCAGUUGCUGCUUUGGCACUCGGCCCUCUGGACAGU<br>CCAAGAAGCGACUCCUCUCGGACCUGCCUCAUCGUUGCCG<br>CAGUCAUUCCUUUUGAAGUGUCUGGAGCAGGUGCGAAAG<br>AUUCAGGGCGAUGGAGCCGCACUCCAAGAGAAGCUCUGCG<br>CGACAUACAAACUUUGCCAUCCCGAGGAGCUCGUACUGCU<br>CGGGCACAGCUUGGGGAUUCCCUGGGCUCCUCUCUCGUCC<br>UGUCCGUCGCAGGCUUUGCAGUUGGCAGGGUGCCUUUCCC<br>AGCUCCACUCCGGUUUGUUCUUGUAUCAGGGACUGCUGCA<br>AGCCCUUGAGGGAAUCUCGCCAGAAUUGGGCCCGACGCUG<br>GACACGUUGCAGCUCGACGUGGCGGAUUUCGCAACAACCA<br>UCUGGCAGCAGAUGGAGGAACUGGGGAUGGCACCCGCGCU<br>GCAGCCCACGCAGGGGGCAAUGCCGGCCUUUGCGUCCGCG<br>UUUCAGCGCAGGGCGGGUGGAGUCCUCGUAGCGAGCCACC<br>UUCAAUCAUUUUUGGAAGUCUCGUACCGGGUGCUGAGAC<br>AUCUUGCGCAGCCG<br>UGAUAAUAG<br>GCUGGAGCCUCGGUGGCCAUGCUUCUUGCCCCUUGGGCCU<br>CCCCCCAGCCCCUCCUCCCCUUCCUGCACCCGUACCCCCAC<br>ACUCCGUGGUCUUUGAAUAAAGUCUGAGUGGGCGGC | 5020 |
| G-CSF with 1 miR-122 sequence without the seed in human alpha-globin 3'UTR | Optimized G-CSF cDNA sequence containing a T7 polymerase site and Xba1 restriction site:<br>TAATACGACTCACTATA<br>GGGAAATAAGAGAGAAAAGAAGAGTAAGAAGAAATATAA<br>GAGCCACC<br>ATGGCCGGTCCCGCGACCCAAAGCCCCATGAAACTTATGGC<br>CCTGCAGTTGCTGCTTTGGCACTCGGCCCTCTGGACAGTCCA<br>AGAAGCGACTCCTCTCGGACCTGCCTCATCGTTGCCGCAGT<br>CATTCCTTTTGAAGTGTCTGGAGCAGGTGCGAAAGATTCAG<br>GGCGATGGAGCCGCACTCCAAGAGAAGCTCTGCGCGACATA<br>CAAACTTTGCCATCCCGAGGAGCTCGTACTGCTCGGGCACA<br>GCTTGGGGATTCCCTGGGCTCCTCTCGTCCTGTCCGTCGC<br>AGGCTTTGCAGTTGGCAGGGTGCCTTTCCCAGCTCCACTCCG<br>GTTTGTTCTTGTATCAGGGACTGCTGCAAGCCCTTGAGGGA<br>ATCTCGCCAGAATTGGGCCCGACGCTGGACACGTTGCAGCT<br>CGACGTGGCGGATTTCGCAACAACCATCTGGCAGCAGATGG<br>AGGAACTGGGGATGGCACCCGCGCTGCAGCCCACGCAGGG<br>GGCAATGCCGGCCTTTGCGTCCGCGTTTCAGCGCAGGGCGG<br>GTGGAGTCCTCGTAGCGAGCCACCTTCAATCATTTTTGGAA<br>GTCTCGTACCGGGTGCTGAGACATCTTGCGCAGCCG<br>TGATAATAG<br>GCTGGAGCCTCGGTGGCCATGCTTCTTGCCCCTTGGGCCTCC<br>CCCCAGCCCCTCCTCCCCTTCCTGCACCCGTACCCCCCAAAC<br>ACCATTGTCAGTGGTCTTTGAATAAAGTCTGAGTGGGCGGC<br>TCTAGA | 5021 |
| | mRNA sequence (transcribed):<br>GGGAAAUAAGAGAGAAAAGAAGAGUAAGAAGAAAUAUAA<br>GAGCCACC<br>AUGGCCGGUCCCGCGACCCAAAGCCCCAUGAAACUUAUGG<br>CCCUGCAGUUGCUGCUUUGGCACUCGGCCCUCUGGACAGU<br>CCAAGAAGCGACUCCUCUCGGACCUGCCUCAUCGUUGCCG<br>CAGUCAUUCCUUUUGAAGUGUCUGGAGCAGGUGCGAAAG<br>AUUCAGGGCGAUGGAGCCGCACUCCAAGAGAAGCUCUGCG<br>CGACAUACAAACUUUGCCAUCCCGAGGAGCUCGUACUGCU<br>CGGGCACAGCUUGGGGAUUCCCUGGGCUCCUCUCUCGUCC<br>UGUCCGUCGCAGGCUUUGCAGUUGGCAGGGUGCCUUUCCC<br>AGCUCCACUCCGGUUUGUUCUUGUAUCAGGGACUGCUGCA<br>AGCCCUUGAGGGAAUCUCGCCAGAAUUGGGCCCGACGCUG<br>GACACGUUGCAGCUCGACGUGGCGGAUUUCGCAACAACCA<br>UCUGGCAGCAGAUGGAGGAACUGGGGAUGGCACCCGCGCU<br>GCAGCCCACGCAGGGGGCAAUGCCGGCCUUUGCGUCCGCG<br>UUUCAGCGCAGGGCGGGUGGAGUCCUCGUAGCGAGCCACC<br>UUCAAUCAUUUUUGGAAGUCUCGUACCGGGUGCUGAGAC<br>AUCUUGCGCAGCCG<br>UGAUAAUAG<br>GCUGGAGCCUCGGUGGCCAUGCUUCUUGCCCCUUGGGCCU<br>CCCCCCAGCCCCUCCUCCCCUUCCUGCACCCGUACCCCCCA<br>AACACCAUUGUCAGUGGUCUUUGAAUAAAGUCUGAGUGG<br>GCGGC | 5022 |

TABLE 31-continued

G-CSF and FIX Sequences

| Description | Sequence | SEQ ID NO: |
|---|---|---|
| G-CSF with 1 miR-122 sequence in mouse alpha-globin 3'UTR | Optimized G-CSF cDNA sequence containing a T7 polymerase site and XbaI restriction site:<br>TAATACGACTCACTATA<br>GGGAAATAAGAGAGAAAAGAAGAGTAAGAAGAAATATAA<br>GAGCCACC<br>ATGGCCGGTCCCGCGACCCAAAGCCCCATGAAACTTATGGC<br>CCTGCAGTTGCTGCTTTGGCACTCGGCCCTCTGGACAGTCCA<br>AGAAGCGACTCCTCTCGGACCTGCCTCATCGTTGCCGCAGT<br>CATTCCTTTTGAAGTGTCTGGAGCAGGTGCGAAAGATTCAG<br>GGCGATGGAGCCGCACTCCAAGAGAAGCTCTGCGCGACATA<br>CAAACTTTGCCATCCCGAGGAGCTCGTACTGCTCGGGCACA<br>GCTTGGGGATTCCCTGGGCTCCTCTCTCGTCCTGTCCGTCGC<br>AGGCTTTGCAGTTGGCAGGGTGCCTTTCCCAGCTCCACTCCG<br>GTTTGTTCTTGTATCAGGGACTGCTGCAAGCCCTTGAGGGA<br>ATCTCGCCAGAATTGGGCCCGACGCTGGACACGTTGCAGCT<br>CGACGTGGCGGATTTCGCAACAACCATCTGGCAGCAGATGG<br>AGGAACTGGGGATGGCACCCGCGCTGCAGCCCACGCAGGG<br>GGCAATGCCGGCCTTTGCGTCCGCGTTTCAGCGCAGGGCGG<br>GTGGAGTCCTCGTAGCGAGCCACCTTCAATCATTTTTGGAA<br>GTCTCGTACCGGGTGCTGAGACATCTTGCGCAGCCG<br>TGATAATAG<br>GCTGCCTTCTGCGGGCTTGCCTTCTGGCCATGCCCTTCTTC<br>TCTCCCTTGCACCTGTACCTCTCAAACACCATTGTCACACTC<br>CATGGTCTTTGAATAAAGCCTGAGTAGGAAGGCGGCCGCTC<br>GAGCATGCATCTAGA | 5023 |
| | mRNA sequence (transcribed):<br>GGGAAAUAAGAGAGAAAAGAAGAGUAAGAAGAAAUAUAA<br>GAGCCACC<br>AUGGCCGGUCCCGCGACCCAAAGCCCAUGAAACUUAUGG<br>CCCUGCAGUUGCUGCUUUGGCACUCGGCCCUCUGGACAGU<br>CCAAGAAGCGACUCCUCUCGGACCUGCCUCAUCGUUGCCG<br>CAGUCAUUCCUUUUGAAGUGUCUGGAGCAGGUGCGAAAG<br>AUUCAGGGCGAUGGAGCCGCACUCCAAGAGAAGCUCUGCG<br>CGACAUACAAACUUUGCCAUCCCGAGGAGCUCGUACUGCU<br>CGGGCACAGCUUGGGGAUUCCCUGGGCUCCUCUCUCGUCC<br>UGUCCGUCGCAGGCUUUGCAGUUGGCAGGGUGCCUUUCCC<br>AGCUCCACUCCGGUUUGUUCUUGUAUCAGGGACUGCUGCA<br>AGCCCUUGAGGGAAUCUCGCCAGAAUUGGGCCCGACGCUG<br>GACACGUUGCAGCUCGACGUGGCGGAUUUCGCAACAACCA<br>UCUGGCAGCAGAUGGAGGAACUGGGGAUGGCACCCGCGCU<br>GCAGCCCACGCAGGGGGCAAUGCCGGCCUUUGCGUCCGCG<br>UUUCAGCGCAGGGCGGGUGGAGUCCUCGUAGCGAGCCACC<br>UUCAAUCAUUUUUGGAAGUCUCGUACCGGGUGCUGAGAC<br>AUCUUGCGCAGCCG<br>UGAUAAUAG<br>GCUGCCUUCUGCGGGCUUGCCUUCUGGCCAUGCCCUUCU<br>UCUCUCCCUUGCACCUGUACCUCUCAAACACCAUUGUCAC<br>ACUCCAUGGUCUUUGAAUAAAGCCUGAGUAGGAAG | 5024 |
| G-CSF with 1 miR-122 seed sequence in mouse alpha-globin 3'UTR | Optimized G-CSF cDNA sequence containing a T7 polymerase site and XbaI restriction site:<br>TAATACGACTCACTATA<br>GGGAAATAAGAGAGAAAAGAAGAGTAAGAAGAAATATAA<br>GAGCCACC<br>ATGGCCGGTCCCGCGACCCAAAGCCCCATGAAACTTATGGC<br>CCTGCAGTTGCTGCTTTGGCACTCGGCCCTCTGGACAGTCCA<br>AGAAGCGACTCCTCTCGGACCTGCCTCATCGTTGCCGCAGT<br>CATTCCTTTTGAAGTGTCTGGAGCAGGTGCGAAAGATTCAG<br>GGCGATGGAGCCGCACTCCAAGAGAAGCTCTGCGCGACATA<br>CAAACTTTGCCATCCCGAGGAGCTCGTACTGCTCGGGCACA<br>GCTTGGGGATTCCCTGGGCTCCTCTCTCGTCCTGTCCGTCGC<br>AGGCTTTGCAGTTGGCAGGGTGCCTTTCCCAGCTCCACTCCG<br>GTTTGTTCTTGTATCAGGGACTGCTGCAAGCCCTTGAGGGA<br>ATCTCGCCAGAATTGGGCCCGACGCTGGACACGTTGCAGCT<br>CGACGTGGCGGATTTCGCAACAACCATCTGGCAGCAGATGG<br>AGGAACTGGGGATGGCACCCGCGCTGCAGCCCACGCAGGG<br>GGCAATGCCGGCCTTTGCGTCCGCGTTTCAGCGCAGGGCGG<br>GTGGAGTCCTCGTAGCGAGCCACCTTCAATCATTTTTGGAA<br>GTCTCGTACCGGGTGCTGAGACATCTTGCGCAGCCG<br>TGATAATAG<br>GCTGCCTTCTGCGGGCTTGCCTTCTGGCCATGCCCTTCTTC<br>TCTCCCTTGCACCTGTACCTCTACACTCCTGGTCTTTGAATA<br>AAGCCTGAGTAGGAAGGCGGCCGCTCGAGCATGCATCTAGA | 5025 |

TABLE 31-continued

G-CSF and FIX Sequences

| Description | Sequence | SEQ ID NO: |
|---|---|---|
| | mRNA sequence (transcribed):<br>GGGAAAUAAGAGAGAAAAGAAGAGUAAGAAGAAAUAUAA<br>GAGCCACC<br>AUGGCCGGUCCCGCGACCCAAAGCCCCAUGAAACUUAUGG<br>CCCUGCAGUUGCUGCUUUGGCACUCGGCCCUCUGGACAGU<br>CCAAGAAGCGACUCCUCUCGGACCUGCCUCAUCGUUGCCG<br>CAGUCAUUCCUUUUGAAGUGUCUGGAGCAGGUGCGAAAG<br>AUUCAGGGCGAUGGAGCCGCACUCCAAGAGAAGCUCUGCG<br>CGACAUACAAACUUUGCCAUCCCGAGGAGCUCGUACUGCU<br>CGGGCACAGCUUGGGGAUUCCCUGGGCUCCUCUCUCGUCC<br>UGUCCGUCGCAGGCUUUGCAGUUGGCAGGGUGCCUUUCCC<br>AGCUCCACUCCGGUUUGUUCUUGUAUCAGGGACUGCUGCA<br>AGCCCUUGAGGGAAUCUCGCCAGAAUUGGGCCCGACGCUG<br>GACACGUUGCAGCUCGACGUGGCGGAUUUCGCAACAACCA<br>UCUGGCAGCAGAUGGAGGAACUGGGGAUGGCACCCGCGCU<br>GCAGCCCACGCAGGGGGCAAUGCCGGCCUUUGCGUCCGCG<br>UUUCAGCGCAGGGCGGGUGGAGUCCUCGUAGCGAGCCACC<br>UUCAAUCAUUUUUGGAAGUCUCGUACCGGGUGCUGAGAC<br>AUCUUGCGCAGCCG<br>UGAUAAUAG<br>GCUGCCUUCUGCGGGGCUUGCCUUCUGGCCAUGCCCUUCU<br>UCUCUCCCUUGCACCUGUACCUCUACACUCCUGGUCUUUG<br>AAUAAAGCCUGAGUAGGAAG | 5026 |
| G-CSF with 1 miR-122 sequence without the seed in mouse alpha-globin 3'UTR | Optimized G-CSF cDNA sequence containing a T7 polymerase site and Xba1 restriction site:<br>TAATACGACTCACTATA<br>GGGAAATAAGAGAGAAAAGAAGAGTAAGAAGAAATATAA<br>GAGCCACC<br>ATGGCCGGTCCCGCGACCCAAAGCCCCATGAAACTTATGGC<br>CCTGCAGTTGCTGCTTTGGCACTCGGCCCTCTGGACAGTCCA<br>AGAAGCGACTCCTCTCGGACCTGCCTCATCGTTGCCGCAGT<br>CATTCCTTTTGAAGTGTCTGGAGCAGGTGCGAAAGATTCAG<br>GGCGATGGAGCCGCACTCCAAGAGAAGCTCTGCGCGACATA<br>CAAACTTTGCCATCCCGAGGAGCTCGTACTGCTCGGGCACA<br>GCTTGGGGATTCCCTGGGCTCCTCTCGTCCTGTCCGTCGC<br>AGGCTTTGCAGTTGGCAGGGTGCCTTTCCCAGCTCCACTCCG<br>GTTTGTTCTTGTATCAGGGACTGCTGCAAGCCCTTGAGGGA<br>ATCTCGCCAGAATTGGGCCCGACGCTGGACACGTTGCAGCT<br>CGACGTGGCGGATTTCGCAACAACCATCTGGCAGCAGATGG<br>AGGAACTGGGGATGGCACCCGCGCTGCAGCCCACGCAGGG<br>GGCAATGCCGGCCTTTGCGTCCGCGTTTCAGCGCAGGGCGG<br>GTGGAGTCCTCGTAGCGAGCCACCTTCAATCATTTTTGGAA<br>GTCTCGTACCGGGTGCTGAGACATCTTGCGCAGCCG<br>TGATAATAG<br>GCTGCCTTCTGCGGGCTTGCCTTCTGGCCATGCCCTTCTTC<br>TCTCCCTTGCACCTGTACCTCTCAAACACCATTGTCATGGTC<br>TTTGAATAAAGCCTGAGTAGGAAGGCGGCCGCTCGAGCATG<br>CATCTAGA | 5027 |
| | mRNA sequence (transcribed):<br>GGGAAAUAAGAGAGAAAAGAAGAGUAAGAAGAAAUAUAA<br>GAGCCACC<br>AUGGCCGGUCCCGCGACCCAAAGCCCCAUGAAACUUAUGG<br>CCCUGCAGUUGCUGCUUUGGCACUCGGCCCUCUGGACAGU<br>CCAAGAAGCGACUCCUCUCGGACCUGCCUCAUCGUUGCCG<br>CAGUCAUUCCUUUUGAAGUGUCUGGAGCAGGUGCGAAAG<br>AUUCAGGGCGAUGGAGCCGCACUCCAAGAGAAGCUCUGCG<br>CGACAUACAAACUUUGCCAUCCCGAGGAGCUCGUACUGCU<br>CGGGCACAGCUUGGGGAUUCCCUGGGCUCCUCUCUCGUCC<br>UGUCCGUCGCAGGCUUUGCAGUUGGCAGGGUGCCUUUCCC<br>AGCUCCACUCCGGUUUGUUCUUGUAUCAGGGACUGCUGCA<br>AGCCCUUGAGGGAAUCUCGCCAGAAUUGGGCCCGACGCUG<br>GACACGUUGCAGCUCGACGUGGCGGAUUUCGCAACAACCA<br>UCUGGCAGCAGAUGGAGGAACUGGGGAUGGCACCCGCGCU<br>GCAGCCCACGCAGGGGGCAAUGCCGGCCUUUGCGUCCGCG<br>UUUCAGCGCAGGGCGGGUGGAGUCCUCGUAGCGAGCCACC<br>UUCAAUCAUUUUUGGAAGUCUCGUACCGGGUGCUGAGAC<br>AUCUUGCGCAGCCG<br>UGAUAAUAG<br>GCUGCCUUCUGCGGGGCUUGCCUUCUGGCCAUGCCCUUCU<br>UCUCUCCCUUGCACCUGUACCUCUCAAACACCAUUGUCAU<br>GGUCUUUGAAUAAAGCCUGAGUAGGAAG | 5028 |

TABLE 31-continued

G-CSF and FIX Sequences

| Description | Sequence | SEQ ID NO: |
|---|---|---|
| Factor IX with 1 miR-122 sequence in human alpha-globin 3'UTR | Optimized Factor IX cDNA sequence containing a T7 polymerase site and Xba1 restriction site:<br>TAATACGACTCACTATA<br>GGGAAATAAGAGAGAAAAGAAGAGTAAGAAGAAATATAA<br>GAGCCACC<br>ATGCAGCGCGTCAACATGATTATGGCCGAATCGCCGGGACT<br>CATCACAATCTGCCTCTTGGGTTATCTCTTGTCGGCAGAATG<br>TACCGTGTTCTTGGATCACGAAAACGCGAACAAAATTCTTA<br>ATCGCCCGAAGCGGTATAACTCCGGGAAACTTGAGGAGTTT<br>GTGCAGGGCAATCTTGAACAGAGTGCATGGAGGAGAAAT<br>GCTCCTTTGAGGAGGCGAGGGAAGTGTTTGAAAACACAGAG<br>CGAACAACGGAGTTTTGGAAGCAATACGTAGATGGGGACC<br>AGTGTGAGTCGAATCCGTGCCTCAATGGGGGATCATGTAAA<br>GATGACATCAATAGCTATGAATGCTGGTGCCCGTTTGGGTTT<br>GAAGGGAAGAACTGTGAGCTGGATGTGACGTGCAACATCA<br>AAAACGGACGCTGTGAGCAGTTTTGTAAGAACTCGGCTGAC<br>AATAAGGTAGTATGCTCGTGCACAGAGGGATACCGGCTGGC<br>GGAGAACCAAAAATCGTGCGAGCCCGCAGTCCCGTTCCCTT<br>GTGGGAGGGTGAGCGTGTCACAGACTAGCAAGTTGACGAG<br>AGCGGAGACTGTATTCCCCGACGTGGACTACGTCAACAGCA<br>CCGAAGCCGAAACAATCCTCGATAACATCACGCAGAGCACT<br>CAGTCCTTCAATGACTTTACGAGGGTCGTAGGTGGTGAGGA<br>CGCGAAACCCGGTCAGTTCCCCTGGCAGGTGGTATTGAACG<br>GAAAAGTCGATGCCTTTTGTGGAGGTTCCATTGTCAACGAG<br>AAGTGGATTGTCACAGCGGCACACTGCGTAGAAACAGGAGT<br>GAAAATCACGGTAGTGGCGGGAGAGCATAACATTGAAGAG<br>ACAGAGCACACGGAACAAAAGCGAAATGTCATCAGAATCA<br>TTCCACACCATAACTATAACGCGGCAATCAATAAGTACAAT<br>CACGACATCGCACTTTTGGAGCTTGACGAACCTTTGGTGCTT<br>AATTCGTACGTCACCCCTATTTGTATTGCCGACAAAGAGTAT<br>ACAAACATCTTCTTGAAATTCGGCTCCGGGTACGTATCGGG<br>CTGGGGCAGAGTGTTCCATAAGGGTAGATCCGCACTGGTGT<br>TGCAATACCTCAGGGTGCCCCTCGTGGATCGAGCCACTTGT<br>CTGCGGTCCACCAAATTCACAATCTACAACAATATGTTCTGT<br>GCGGGATTCCATGAAGGTGGGAGAGATAGCTGCCAGGGAG<br>ACTCAGGGGGTCCCCACGTGACGGAAGTCGAGGGGACGTC<br>ATTTCTGACGGGAATTATCTCATGGGGAGAGGAATGTGCGA<br>TGAAGGGGAAATATGGCATCTACACTAAAGTGTCACGGTAT<br>GTCAATTGGATCAAGGAAAAGACGAAACTCACG<br>TGATAATAG<br>GCTGGAGCCTCGGTGGCCATGCTTCTTGCCCCTTGGGCCTCC<br>CCCCAGCCCCTCCTCCCCTTCCTGCACCCGTACCCCCCAAAC<br>ACCATTGTCACACTCCAGTGGTCTTTGAATAAAGTCTGAGTG<br>GGCGGCTCTAGA | 5029 |
| | mRNA sequence (transcribed):<br>GGGAAAUAAGAGAGAAAAGAAGAGUAAGAAGAAAUAUAA<br>GAGCCACC<br>AUGCAGCGCGUCAACAUGAUUAUGGCCGAAUCGCCGGGAC<br>UCAUCACAAUCUGCCUCUUGGGUUAUCUCUUGUCGGCAGA<br>AUGUACCGUGUUCUUGGAUCACGAAAACGCGAACAAAAU<br>UCUUAAUCGCCCGAAGCGGUAUAACUCCGGGAAACUUGAG<br>GAGUUUGUGCAGGGCAAUCUUGAACAGAGUGCAUGGAG<br>GAGAAAUGCUCCUUUGAGGAGGCGAGGGAAGUGUUUGAA<br>AACACAGAGCGAACAACGGAGUUUUGGAAGCAAUACGUA<br>GAUGGGGACCAGUGUGAGUCGAAUCCGUGCCUCAAUGGG<br>GGAUCAUGUAAAGAUGACAUCAAUAGCUAUGAAUGCUGG<br>UGCCCGUUUGGGUUUGAAGGGAAGAACUGUGAGCUGGAU<br>GUGACGUGCAACAUCAAAAACGGACGCUGUGAGCAGUUU<br>UGUAAGAACUCGGCUGACAAUAAGGUAGUAUGCUCGUGC<br>ACAGAGGGAUACCGGCUGGCGGAGAACCAAAAAUCGUGCG<br>AGCCCGCAGUCCCGUUCCCUUGUGGGAGGGUGAGCGUGUC<br>ACAGACUAGCAAGUUGACGAGAGCGGAGACUGUAUUCCCC<br>GACGUGGACUACGUCAACAGCACCGAAGCCGAAACAAUCC<br>UCGAUAACAUCACGCAGAGCACUCAGUCCUUCAAUGACUU<br>UACGAGGGUCGUAGGUGGUGAGGACGCGAAACCCGGUCA<br>GUUCCCCUGGCAGGUGGUAUUGAACGGAAAAGUCGAUGCC<br>UUUUGUGGAGGUUCCAUUGUCAACGAGAAGUGGAUUGUC<br>ACAGCGGCACACUGCGUAGAAACAGGAGUGAAAAUCACGG<br>UAGUGGCGGGAGAGCAUAACAUUGAAGAGACAGAGCACA<br>CGGAACAAAAGCGAAAUGUCAUCAGAAUCAUUCCACACCA<br>UAACUAUAACGCGGCAAUCAAUAAGUACAAUCACGACAUC<br>GCACUUUUGGAGCUUGACGAACCUUUGGUGCUUAAUUCG<br>UACGUCACCCCUAUUUGUAUUGCCGACAAAGAGUAUACAA<br>ACAUCUUCUUGAAAUUCGGCUCCGGGUACGUAUCGGGCUG | 5030 |

TABLE 31-continued

G-CSF and FIX Sequences

| Description | Sequence | SEQ ID NO: |
|---|---|---|
| | GGGCAGAGUGUUCCAUAAGGGUAGAUCCGCACUGGUGUU<br>GCAAUACCUCAGGGUGCCCCUCGUGGAUCGAGCCACUUGU<br>CUGCGGUCCACCAAAUUCACAAUCUACAACAAUAUGUUCU<br>GUGCGGGAUUCCAUGAAGGUGGGAGAGAUAGCUGCCAGG<br>GAGACUCAGGGGGUCCCCACGUGACGGAAGUCGAGGGGAC<br>GUCAUUUCUGACGGGAAUUAUCUCAUGGGGAGAGGAAUG<br>UGCGAUGAAGGGGAAAUAUGGCAUCUACACUAAAGUGUC<br>ACGGUAUGUCAAUUGGAUCAAGGAAAAGACGAAACUCACG<br>UGAUAAUAG<br>GCUGGAGCCUCGGUGGCCAUGCUUCUUGCCCCUUGGGCCU<br>CCCCCCAGCCCCUCCUCCCCUUCCUGCACCCGUACCCCCCA<br>AACACCAUUGUCACACUCCAGUGGUCUUUGAAUAAAGUCU<br>GAGUGGGCGGC | |
| Factor IX with 1 miR-122 seed sequence in human alpha-globin 3'UTR | Optimized Factor IX cDNA sequence containing a T7 polymerase site and Xba1 restriction site:<br>TAATACGACTCACTATA<br>GGGAAATAAGAGAGAAAAGAAGAGTAAGAAGAAATATAA<br>GAGCCACC<br>ATGCAGCGCGTCAACATGATTATGGCCGAATCGCCGGGACT<br>CATCACAATCTGCCTCTTGGGTTATCTCTTGTCGGCAGAATG<br>TACCGTGTTCTTGGATCACGAAAACGCGAACAAAATTCTTA<br>ATCGCCCGAAGCGGTATAACTCCGGGAAACTTGAGGAGTTT<br>GTGCAGGGCAATCTTGAACGAGAGTGCATGGAGGAGAAAT<br>GCTCCTTTGAGGAGGCGAGGGAAGTGTTTGAAAACACAGAG<br>CGAACAACGGAGTTTTGGAAGCAATACGTAGATGGGGACC<br>AGTGTGAGTCGAATCCGTGCCTCAATGGGGGATCATGTAAA<br>GATGACATCAATAGCTATGAATGCTGGTGCCCGTTTGGGTTT<br>GAAGGGAAGAACTGTGAGCTGGATGTGACGTGCAACATCA<br>AAAACGGACGCTGTGAGCAGTTTTGTAAGAACTCGGCTGAC<br>AATAAGGTAGTATGCTCGTGCACAGAGGGATACCGGCTGGC<br>GGAGAACCAAAAATCGTGCGAGCCCGCAGTCCCGTTCCCTT<br>GTGGGAGGGTGAGCGTGTCACAGACTAGCAAGTTGACGAG<br>AGCGGAGACTGTATTCCCCGACGTGGACTACGTCAACAGCA<br>CCGAAGCCGAAACAATCCTCGATAACATCACGCAGAGCACT<br>CAGTCCTTCAATGACTTTACGAGGGTCGTAGGTGGTGAGGA<br>CGCGAAACCCGGTCAGTTCCCCTGGCAGGTGGTATTGAACG<br>GAAAAGTCGATGCCTTTTGTGGAGGTTCCATTGTCAACGAG<br>AAGTGGATTGTCACAGCGGCACACTGCGTAGAAACAGGAGT<br>GAAAATCACGGTAGTGGCGGGAGAGCATAACATTGAAGAG<br>ACAGAGCACACGGAACAAAAGCGAAATGTCATCAGAATCA<br>TTCCACACCATAACTATAACGCGGCAATCAATAAGTACAAT<br>CACGACATCGCACTTTTTGGAGCTTGACGAACCTTTGGTGCTT<br>AATTCGTACGTCACCCCTATTTGTATTGCCGACAAAGAGTAT<br>ACAAACATCTTCTTGAAATTCGGCTCCGGGTACGTATCGGG<br>CTGGGGCAGAGTGTTCCATAAGGGTAGATCCGCACTGGTGT<br>TGCAATACCTCAGGGTGCCCCTCGTGGATCGAGCCACTTGT<br>CTGCGGTCCACCAAATTCACAATCTACAACAATATGTTCTGT<br>GCGGGATTCCATGAAGGTGGGAGAGATAGCTGCCAGGGAG<br>ACTCAGGGGGTCCCCACGTGACGGAAGTCGAGGGGACGTC<br>ATTTCTGACGGGAATTATCTCATGGGGAGAGGAATGTGCGA<br>TGAAGGGGAAATATGGCATCTACACTAAAGTGTCACGGTAT<br>GTCAATTGGATCAAGGAAAAGACGAAACTCACG<br>TGATAATAG<br>GCTGGAGCCTCGGTGGCCATGCTTCTTGCCCCTTGGGCCTCC<br>CCCCAGCCCCTCCTCCCCTTCCTGCACCCGTACCCCCACACT<br>CCGTGGTCTTTGAATAAAGTCTGAGTGGGCGGCTCTAGA | 5031 |
| | mRNA sequence (transcribed):<br>GGGAAAUAAGAGAGAAAAGAAGAGUAAGAAGAAAUAUAA<br>GAGCCACC<br>AUGCAGCGCGUCAACAUGAUUAUGGCCGAAUCGCCGGGAC<br>UCAUCACAAUCUGCCUCUUGGGUUAUCUCUUGUCGGCAGA<br>AUGUACCGUGUUCUUGGAUCACGAAAACGCGAACAAAAU<br>UCUUAAUCGCCCGAAGCGGUAUAACUCCGGGAAACUUGAG<br>GAGUUUGUGCAGGGCAAUCUUGAACGAGAGUGCAUGGAG<br>GAGAAAUGCUCCUUUGAGGAGGCGAGGGAAGUGUUUGAA<br>AACACAGAGCGAACAACGGAGUUUUGGAAGCAAUACGUA<br>GAUGGGGACCAGUGUGAGUCGAAUCCGUGCCUCAAUGGG<br>GGAUCAUGUAAAGAUGACAUCAAUAGCUAUGAAUGCUGG<br>UGCCCGUUUGGGUUUGAAGGGAAGAACUGUGAGCUGGAU<br>GUGACGUGCAACAUCAAAAACGGACGCUGUGAGCAGUUU<br>UGUAAGAACUCGGCUGACAAUAAGGUAGUAUGCUCGUGC<br>ACAGAGGGAUACCGGCUGGCGGAGAACCAAAAAUCGUGCG<br>AGCCCGCAGUCCCGUUCCCUUGUGGGAGGGUGAGCGUGUC | 5032 |

TABLE 31-continued

G-CSF and FIX Sequences

| Description | Sequence | SEQ ID NO: |
|---|---|---|
| | ACAGACUAGCAAGUUGACGAGAGCGGAGACUGUAUUCCCC<br>GACGUGGACUACGUCAACAGCACCGAAGCCGAAACAAUCC<br>UCGAUAACAUCACGCAGAGCACUCAGUCCUUCAUGACUU<br>UACGAGGGUCGUAGGUGGUGAGGACGCGAAACCCGGUCA<br>GUUCCCCUGGCAGGUGGUAUUGAACGGAAAAGUCGAUGCC<br>UUUUGUGGAGGUUCCAUUGUCAACGAGAAGUGGAUUGUC<br>ACAGCGGCACACUGCGUAGAAACAGGAGUGAAAAUCACGG<br>UAGUGGCGGGAGAGCAUAACAUUGAAGAGACAGAGCACA<br>CGGAACAAAAGCGAAAUGUCAUCAGAAUCAUUCCACACCA<br>UAACUAUAACGCGGCAAUCAAUAAGUACAAUCACGACAUC<br>GCACUUUUGGAGCUUGACGAACCUUUGGUGCUUAAUUCG<br>UACGUCACCCCUAUUUGUAUUGCCGACAAAGAGUAUACAA<br>ACAUCUUCUUGAAAUUCGGCUCCGGGUACGUAUCGGGCUG<br>GGGCAGAGUGUUCCAUAAGGGUAGAUCCGCACUGGUGUU<br>GCAAUACCUCAGGGUGCCCCUCGUGGAUCGAGCCACUUGU<br>CUGCGGUCCACCAAAUUCACAAUCUACAACAAUAUGUUCU<br>GUGCGGGAUUCCAUGAAGGUGGGAGAGAUAGCUGCCAGG<br>GAGACUCAGGGGGUCCCCACGUGACGGAAGUCGAGGGGAC<br>GUCAUUUCUGACGGGAAUUAUCUCAUGGGGAGAGGAAUG<br>UGCGAUGAAGGGGAAAUAUGGCAUCUACACUAAAGUGUC<br>ACGGUAUGUCAAUUGGAUCAAGGAAAAGACGAAACUCACG<br>UGAUAAUAG<br>GCUGGAGCCUCGGUGGCCAUGCUUCUUGCCCCUUGGGCCU<br>CCCCCCAGCCCCUCCUCCCCUUCCUGCACCCGUACCCCCAC<br>ACUCCGUGGUCUUUGAAUAAAGUCUGAGUGGGCGGC | |
| Factor IX with 1 miR-122 sequence without the seed in human alpha-globin 3'UTR | Optimized Factor IX cDNA sequence containing a T7 polymerase site and XbaI restriction site:<br>TAATACGACTCACTATA<br>GGGAAATAAGAGAGAAAAGAAGAGTAAGAAGAAATATAA<br>GAGCCACC<br>ATGCAGCGCGTCAACATGATTATGGCCGAATCGCCGGGACT<br>CATCACAATCTGCCTCTTGGGTTATCTCTTGTCGGCAGAATG<br>TACCGTGTTCTTGGATCACGAAAACGCGAACAAATTCTTA<br>ATCGCCCGAAGCGGTATAACTCCGGGAAACTTGAGGAGTTT<br>GTGCAGGGCAATCTTGAACGAGAGTGCATGGAGGAGAAAT<br>GCTCCTTTGAGGAGGCGAGGGAAGTGTTTGAAAACACAGAG<br>CGAACAACGGAGTTTTGGAAGCAATACGTAGATGGGGACC<br>AGTGTGAGTCGAATCCGTGCCTCAATGGGGGATCATGTAAA<br>GATGACATCAATAGCTATGAATGCTGGTGCCCGTTTGGGTTT<br>GAAGGGAAGAACTGTGAGCTGGATGTGACGTGCAACATCA<br>AAAACGGACGCTGTGAGCAGTTTTGTAAGAACTCGGCTGAC<br>AATAAGGTAGTATGCTCGTGCACAGAGGGATACCGGCTGGC<br>GGAGAACCAAAAATCGTGCGAGCCCGCAGTCCCGTTCCCTT<br>GTGGGAGGGTGAGCGTGTCACAGACTAGCAAGTTGACGAG<br>AGCGGAGACTGTATTCCCCGACGTGGACTACGTCAACAGCA<br>CCGAAGCCGAAACAATCCTCGATAACATCACGCAGAGCACT<br>CAGTCCTTCAATGACTTTACGAGGGTCGTAGGTGGTGAGGA<br>CGCGAAACCCGGTCAGTTCCCCTGGCAGGTGGTATTGAACG<br>GAAAAGTCGATGCCTTTTGTGGAGGTTCCATTGTCAACGAG<br>AAGTGGATTGTCACAGCGGCACACTGCGTAGAAACAGGAGT<br>GAAAATCACGGTAGTGGCGGGAGAGCATAACATTGAAGAG<br>ACAGAGCACACGGAACAAAAGCGAAATGTCATCAGAATCA<br>TTCCACACCATAACTATAACGCGGCAATCAATAAGTACAAT<br>CACGACATCGCACTTTTGGAGCTTGACGAACCTTTGGTGCTT<br>AATTCGTACGTCACCCCTATTTGTATTGCCGACAAAGAGTAT<br>ACAAACATCTTCTTGAAATTCGGCTCCGGGTACGTATCGGG<br>CTGGGGCAGAGTGTTCCATAAGGGTAGATCCGCACTGGTGT<br>TGCAATACCTCAGGGTGCCCCTCGTGGATCGAGCCACTTGT<br>CTGCGGTCCACCAAATTCACAATCTACAACAATATGTTCTGT<br>GCGGGATTCCATGAAGGTGGGAGAGATAGCTGCCAGGGAG<br>ACTCAGGGGGTCCCCACGTGACGGAAGTCGAGGGGACGTC<br>ATTTCTGACGGGAATTATCTCATGGGGAGAGGAATGTGCGA<br>TGAAGGGGAAATATGGCATCTACACTAAAGTGTCACGGTAT<br>GTCAATTGGATCAAGGAAAAGACGAAACTCACG<br>TGATAATAG<br>GCTGGAGCCTCGGTGGCCATGCTTCTTGCCCCTTGGGCCTCC<br>CCCCAGCCCCTCCTCCCCTTCCTGCACCCGTACCCCCAAAC<br>ACCATTGTCAGTGGTCTTTGAATAAAGTCTGAGTGGGCGGC<br>TCTAGA | 5033 |
| | mRNA sequence (transcribed):<br>GGGAAAUAAGAGAGAAAAGAAGAGUAAGAAGAAAUAUAA<br>GAGCCACC<br>AUGCAGCGCGUCAACAUGAUUAUGGCCGAAUCGCCGGGAC | 5034 |

TABLE 31-continued

G-CSF and FIX Sequences

| Description | Sequence | SEQ ID NO: |
|---|---|---|
| | UCAUCACAAUCUGCCUCUUGGGUUAUCUCUUGUCGGCAGA<br>AUGUACCGUGUUCUUGGAUCACGAAAACGCGAACAAAAU<br>UCUUAAUCGCCCGAAGCGGUAUAACUCCGGGAAACUUGAG<br>GAGUUUGUGCAGGGCAAUCUUGAACGAGAGUGCAUGGAG<br>GAGAAAUGCUCCUUUGAGGAGGCGAGGGAAGUGUUUGAA<br>AACACAGAGCGAACAACGGAGUUUUGGAAGCAAUACGUA<br>GAUGGGGACCAGUGUGAGUCGAAUCCGUGCCUCAAUGGG<br>GGAUCAUGUAAAGAUGACAUCAAUAGCUAUGAAUGCUGG<br>UGCCCGUUUGGGUUUGAAGGGAAGAACUGUGAGCUGGAU<br>GUGACGUGCAACAUCAAAAACGGACGCUGUGAGCAGUUU<br>UGUAAGAACUCGGCUGACAAUAAGGUAGUAUGCUCGUGC<br>ACAGAGGGAUACCGGCUGGCGGAGAACCAAAAAUCGUGCG<br>AGCCCGCAGUCCCGUUCCCUUGUGGGAGGGUGAGCGUGUC<br>ACAGACUAGCAAGUUGACGAGAGCGGAGACUGUAUUCCCC<br>GACGUGGACUACGUCAACAGCACCGAAGCCGAAACAAUCC<br>UCGAUAACAUCACGCAGAGCACUCAGUCCUUCAAUGACUU<br>UACGAGGGUCGUAGGUGGUGAGGACGCGAAACCCGGUCA<br>GUUCCCCUGGCAGGUGGUAUUGAACGGAAAAGUCGAUGCC<br>UUUUGUGGAGGUUCCAUUGUCAACGAGAAGUGGAUUGUC<br>ACAGCGGCACACUGCGUAGAAACAGGAGUGAAAAUCACGG<br>UAGUGGCGGGAGAGCAUAACAUUGAAGAGACAGAGCACA<br>CGGAACAAAAGCGAAAUGUCAUCAGAAUCAUUCCACACCA<br>UAACUAUAACGCGGCAAUCAAUAAGUACAAUCACGACAUC<br>GCACUUUUGGAGCUUGACGAACCUUUGGUGCUUAAUUCG<br>UACGUCACCCCUAUUUGUAUUGCCGACAAAGAGUAUACAA<br>ACAUCUUCUUGAAAUUCGGCUCCGGGUACGUAUCGGGCUG<br>GGGCAGAGUGUUCCAUAAGGGUAGAUCCGCACUGGUGUU<br>GCAAUACCUCAGGGUGCCCCUCGUGGAUCGAGCCACUUGU<br>CUGCGGUCCACCAAAUUCACAAUCUACAACAAUAUGUUCU<br>GUGCGGGAUUCCAUGAAGGUGGGAGAGAUAGCUGCCAGG<br>GAGACUCAGGGGGUCCCCACGUGACGGAAGUCGAGGGGAC<br>GUCAUUUCUGACGGGAAUUAUCUCAUGGGGAGAGGAAUG<br>UGCGAUGAAGGGGAAAUAUGGCAUCUACACUAAAGUGUC<br>ACGGUAUGUCAAUUGGAUCAAGGAAAAGACGAAACUCACG<br>UGAUAAUAG<br>GCUGGAGCCUCGGUGGCCAUGCUUCUUGCCCCUUGGGCCU<br>CCCCCCAGCCCCUCCUCCCCUUCCUGCACCCGUACCCCCCA<br>AACACCAUUGUCAGUGGUCUUUGAAUAAAGUCUGAGUGG<br>GCGGC | |
| Factor IX with 1 miR-122 sequence in mouse alpha-globin 3'UTR | Optimized Factor IX cDNA sequence containing a T7 polymerase site and XbaI restriction site:<br>TAATACGACTCACTATA<br>GGGAAATAAGAGAGAAAAGAAGAGTAAGAAGAAATATAA<br>GAGCCACC<br>ATGCAGCGCGTCAACATGATTATGGCCGAATCGCCGGGACT<br>CATCACAATCTGCCTCTTGGGTTATCTCTTGTCGGCAGAATG<br>TACCGTGTTCTTGGATCACGAAAACGCGAACAAAATTCTTA<br>ATCGCCCGAAGCGGTATAACTCCGGGAAACTTGAGGAGTTT<br>GTGCAGGGCAATCTTGAACGAGAGTGCATGGAGGAGAAAT<br>GCTCCTTTGAGGAGGCGAGGGAAGTGTTTGAAAACACAGAG<br>CGAACAACGGAGTTTTGGAAGCAATACGTAGATGGGGACC<br>AGTGTGAGTCGAATCCGTGCCTCAATGGGGATCATGTAAA<br>GATGACATCAATAGCTATGAATGCTGGTGCCCCGTTTGGGTTT<br>GAAGGGAAGAACTGTGAGCTGGATGTGACGTGCAACATCA<br>AAAACGGACGCTGTGAGCAGTTTTGTAAGAACTCGGCTGAC<br>AATAAGGTAGTATGCTCGTGCACAGAGGGATACCGGCTGGC<br>GGAGAACCAAAAATCGTGCGAGCCCGCAGTCCCGTTCCCTT<br>GTGGGAGGGTGAGCGTGTCACAGACTAGCAAGTTGACGAG<br>AGCGGAGACTGTATTCCCCGACGTGGACTACGTCAACAGCA<br>CCGAAGCCGAAACAATCCTCGATAACATCACGCAGAGCACT<br>CAGTCCTTCAATGACTTTACGAGGGTCGTAGGTGGTGAGGA<br>CGCGAAACCCGGTCAGTTCCCCTGGCAGGTGGTATTGAACG<br>GAAAAGTCGATGCCTTTTGTGGAGGTTCCATTGTCAACGAG<br>AAGTGGATTGTCACAGCGGCACACTGCGTAGAAACAGGAGT<br>GAAAATCACGGTAGTGGCGGGAGAGCATAACATTGAAGAG<br>ACAGAGCACACGGAACAAAAGCGAAATGTCATCAGAATCA<br>TTCCACACCATAACTATAACGCGGCAATCAATAAGTACAAT<br>CACGACATCGCACTTTTGGAGCTTGACGAACCTTTGGTGCTT<br>AATTCGTACGTCACCCCTATTTGTATTGCCGACAAAGAGTAT<br>ACAAACATCTTCTTGAAATTCGGCTCCGGGTACGTATCGGG<br>CTGGGGCAGAGTGTTCCATAAGGGTAGATCCGCACTGGTGT<br>TGCAATACCTCAGGGTGCCCCTCGTGGATCGAGCCACTTGT<br>CTGCGGTCCACCAAATTCACAATCTACAACAATATGTTCTGT | 5035 |

TABLE 31-continued

G-CSF and FIX Sequences

| Description | Sequence | SEQ ID NO: |
|---|---|---|
| | GCGGGATTCCATGAAGGTGGGAGAGATAGCTGCCAGGGAG<br>ACTCAGGGGGTCCCCACGTGACGGAAGTCGAGGGGACGTC<br>ATTTCTGACGGGAATTATCTCATGGGGAGAGGAATGTGCGA<br>TGAAGGGGAAATATGGCATCTACACTAAAGTGTCACGGTAT<br>GTCAATTGGATCAAGGAAAAGACGAAACTCACG<br>TGATAATAG<br>GCTGCCTTCTGCGGGGCTTGCCTTCTGGCCATGCCCTTCTTC<br>TCTCCCTTGCACCTGTACCTCTCAAACACCATTGTCACACTC<br>CATGGTCTTTGAATAAAGCCTGAGTAGGAAGGCGGCCGCTC<br>GAGCATGCATCTAGA | |
| | mRNA sequence (transcribed):<br>GGGAAAUAAGAGAGAAAAGAAGAGUAAGAAGAAAUAUAA<br>GAGCCACC<br>AUGCAGCGCGUCAACAUGAUUAUGGCCGAAUCGCCGGGAC<br>UCAUCACAAUCUGCCUCUUGGGUUAUCUCUUGUCGGCAGA<br>AUGUACCGUGUUCUUGGAUCACGAAAACGCGAACAAAAU<br>UCUUAAUCGCCCGAAGCGGUAUAACUCCGGGAAACUUGAG<br>GAGUUUGUGCAGGGCAAUCUUGAACGAGAGUGCAUGGAG<br>GAGAAAUGCUCCUUUGAGGAGGCGAGGGAAGUGUUUGAA<br>AACACAGAGCGAACAACGGAGUUUUGGAAGCAAUACGUA<br>GAUGGGGACCAGUGUGAGUCGAAUCCGUGCCUCAAUGGG<br>GGAUCAUGUAAAGAUGACAUCAAUAGCUAUGAAUGCUGG<br>UGCCCGUUUGGGUUUGAAGGGAAGAACUGUGAGCUGGAU<br>GUGACGUGCAACAUCAAAAACGGACGCUGUGAGCAGUUU<br>UGUAAGAACUCGGCUGACAAUAAGGUAGUAUGCUCGUGC<br>ACAGAGGGAUACCGGCUGGCGGAGAACCAAAAAUCGUGCG<br>AGCCCGCAGUCCCGUUCCCUUGUGGGAGGGUGAGCGUGUC<br>ACAGACUAGCAAGUUGACGAGAGCGGAGACUGUAUUCCCC<br>GACGUGGACUACGUCAACAGCACCGAAGCCGAAACAAUCC<br>UCGAUAACAUCACGCAGAGCACUCAGUCCUUCAAUGACUU<br>UACGAGGGUCGUAGGUGGUGAGGACGCGAAACCCGGUCA<br>GUUCCCUGGCAGGUGGUAUUGAACGGAAAAGUCGAUGCC<br>UUUUGUGGAGGUUCCAUUGUCAACGAGAAGUGGAUUGUC<br>ACAGCGGCACACUGCGUAGAAACAGGAGUGAAAAUCACGG<br>UAGUGGCGGGAGAGCAUAACAUUGAAGAGACAGAGCACA<br>CGGAACAAAAGCGAAAUGUCAUCAGAAUCAUUCCACACCA<br>UAACUAUAACGCGGCAAUCAAUAAGUACAAUCACGACAUC<br>GCACUUUUGGAGCUUGACGAACCUUUGGUGCUUAAUUCG<br>UACGUCACCCCUAUUUGUAUUGCCGACAAAGAGUAUACAA<br>ACAUCUUCUUGAAAUUCGGCUCCGGGUACGUAUCGGGCUG<br>GGGCAGAGUGUUCCAUAAGGGUAGAUCCGCACUGGUGUU<br>GCAAUACCUCAGGGUGCCCCUCGUGGAUCGAGCCACUUGU<br>CUGCGGUCCACCAAAUUCACAAUCUACAACAAUAUGUUCU<br>GUGCGGGAUUCCAUGAAGGUGGGAGAGAUAGCUGCCAGG<br>GAGACUCAGGGGGUCCCCACGUGACGGAAGUCGAGGGGAC<br>GUCAUUUCUGACGGGAAUUAUCUCAUGGGGAGAGGAAUG<br>UGCGAUGAAGGGGAAAUAUGGCAUCUACACUAAAGUGUC<br>ACGGUAUGUCAAUUGGAUCAAGGAAAAGACGAAACUCACG<br>UGAUAAUAG<br>GCUGCCUUCUGCGGGGCUUGCCUUCUGGCCAUGCCCUUCU<br>UCUCUCCCUUGCACCUGUACCUCUCAAACACCAUUGUCAC<br>ACUCCAUGGUCUUUGAAUAAAGCCUGAGUAGGAAG | 5036 |
| Factor IX with 1 miR-122 seed sequence in mouse alpha-globin 3'UTR | Optimized Factor IX cDNA sequence containing a T7 polymerase site and Xba1 restriction site:<br>TAATACGACTCACTATA<br>GGGAAATAAGAGAGAAAAGAAGAGTAAGAAGAAATATAA<br>GAGCCACC<br>ATGCAGCGCGTCAACATGATTATGGCCGAATCGCCGGGACT<br>CATCACAATCTGCCTCTTGGGTTATCTCTTGTCGGCAGAATG<br>TACCGTGTTCTTGGATCACGAAAACGCGAACAAAATTCTTA<br>ATCGCCCGAAGCGGTATAACTCCGGGAAACTTGAGGAGTTT<br>GTGCAGGGCAATCTTGAACGAGAGTGCATGGAGGAGAAAT<br>GCTCCTTTGAGGAGGCGAGGGAAGTGTTTGAAAACACAGAG<br>CGAACAACGGAGTTTTGGAAGCAATACGTAGATGGGGACC<br>AGTGTGAGTCGAATCCGTGCCTCAATGGGGGATCATGTAAA<br>GATGACATCAATAGCTATGAATGCTGGTGCCCCGTTTGGGTTT<br>GAAGGGAAGAACTGTGAGCTGGATGTGACGTGCAACATCA<br>AAAACGGACGCTGTGAGCAGTTTTGTAAGAACTCGGCTGAC<br>AATAAGGTAGTATGCTCGTGCACAGAGGGATACCGGCTGGC<br>GGAGAACCAAAAATCGTGCGAGCCCGCAGTCCCGTTCCCTT<br>GTGGGAGGGTGAGCGTGTCACAGACTAGCAAGTTGACGAG<br>AGCGGAGACTGTATTCCCCGACGTGGACTACGTCAACAGCA<br>CCGAAGCCGAAACAATCCTCGATAACATCACGCAGAGCACT | 5037 |

TABLE 31-continued

G-CSF and FIX Sequences

| Description | Sequence | SEQ ID NO: |
|---|---|---|
| | CAGTCCTTCAATGACTTTACGAGGGTCGTAGGTGGTGAGGA<br>CGCGAAACCCGGTCAGTTCCCCTGGCAGGTGGTATTGAACG<br>GAAAAGTCGATGCCTTTTGTGGAGGTTCCATTGTCAACGAG<br>AAGTGGATTGTCACAGCGGCACACTGCGTAGAAACAGGAGT<br>GAAAATCACGGTAGTGGCGGGAGAGCATAACATTGAAGAG<br>ACAGAGCACACGGAACAAAAGCGAAATGTCATCAGAATCA<br>TTCCACACCATAACTATAACGCGGCAATCAATAAGTACAAT<br>CACGACATCGCACTTTTGGAGCTTGACGAACCTTTGGTGCTT<br>AATTCGTACGTCACCCCTATTTGTATTGCCGACAAAGAGTAT<br>ACAAACATCTTCTTGAAATTCGGCTCCGGGTACGTATCGGG<br>CTGGGGCAGAGTGTTCCATAAGGGTAGATCCGCACTGGTGT<br>TGCAATACCTCAGGGTGCCCCTCGTGGATCGAGCCACTTGT<br>CTGCGGTCCACCAAATTCACAATCTACAACAATATGTTCTGT<br>GCGGGATTCCATGAAGGTGGGAGAGATAGCTGCCAGGGAG<br>ACTCAGGGGGTCCCCACGTGACGGAAGTCGAGGGGACGTC<br>ATTTCTGACGGGAATTATCTCATGGGGAGAGGAATGTGCGA<br>TGAAGGGGAAATATGGCATCTACACTAAAGTGTCACGGTAT<br>GTCAATTGGATCAAGGAAAAGACGAAACTCACG<br>TGATAATAG<br>GCTGCCTTCTGCGGGGCTTGCCTTCTGGCCATGCCCTTCTTC<br>TCTCCCTTGCACCTGTACCTCTACACTCCTGGTCTTTGAATA<br>AAGCCTGAGTAGGAAGGCGGCCGCTCGAGCATGCATCTAGA | |
| | mRNA sequence (transcribed):<br>GGGAAUAAGAGAGAAAAGAAGAGUAAGAAGAAAUAUAA<br>GAGCCACC<br>AUGCAGCGCGUCAACAUGAUUAUGGCCGAAUCGCCGGGAC<br>UCAUCACAAUCUGCCUCUUGGGUUAUCUCUUGUCGGCAGA<br>AUGUACCGUGUUCUUGGAUCACGAAAACGCGAACAAAAU<br>UCUUAAUCGCCCGAAGCGGUAUAACUCCGGGAAACUUGAG<br>GAGUUUGUGCAGGGCAAUCUUGAACGAGAGUGCAUGGAG<br>GAGAAAUGCUCCUUUGAGGAGGCGAGGGAAGUGUUUGAA<br>AACACAGAGCGAACAACGGAGUUUUGGAAGCAAUACGUA<br>GAUGGGGACCAGUGUGAGUCGAAUCCGUGCCUCAAUGGG<br>GGAUCAUGUAAAGAUGACAUCAAUAGCUAUGAAUGCUGG<br>UGCCCGUUUGGGUUUGAAGGGAAGAACUGUGAGCUGGAU<br>GUGACGUGCAACAUCAAAAACGGACGCUGUGAGCAGUUU<br>UGUAAGAACUCGGCUGACAAUAAGGUAGUAUGCUCUGUGC<br>ACAGAGGGAUACCGGCUGGCGGAGAACCAAAAAUCGUGCG<br>AGCCCGCAGUCCCGUUCCCUUGUGGGAGGGUGAGCGUGUC<br>ACAGACUAGCAAGUUGACGAGAGCGGAGACUGUAUUCCCC<br>GACGUGGACUACGUCAACAGCACCGAAGCCGAAACAAUCC<br>UCGAUAACAUCACGCAGAGCACUCAGUCCUUCAAUGACUU<br>UACGAGGGUCGUAGGUGGUGAGGACGCGAAACCCGGUCA<br>GUUCCCCUGGCAGGUGGUAUUGAACGGAAAAGUCGAUGCC<br>UUUUGUGGAGGUUCCAUUGUCAACGAGAAGUGGAUUGUC<br>ACAGCGGCACACUGCGUAGAAACAGGAGUGAAAAUCACGG<br>UAGUGGCGGGAGAGCAUAACAUUGAAGAGACAGAGCACA<br>CGGAACAAAAGCGAAAUGUCAUCAGAAUCAUUCCACACCA<br>UAACUAUAACGCGGCAAUCAAUAAGUACAAUCACGACAUC<br>GCACUUUUGGAGCUUGACGAACCUUUGGUGCUUAAUUCG<br>UACGUCACCCCUAUUUGUAUUGCCGACAAAGAGUAUACAA<br>ACAUCUUCUUGAAAUUCGGCUCCGGGUACGUAUCGGGCUG<br>GGGCAGAGUGUUCCAUAAGGGUAGAUCCGCACUGGUGUU<br>GCAAUACCUCAGGGUGCCCCUCGUGGAUCGAGCCACUUGU<br>CUGCGGUCCACCAAAUUCACAAUCUACAACAAUAUGUUCU<br>GUGCGGGAUUCCAUGAAGGUGGGAGAGAUAGCUGCCAGG<br>GAGACUCAGGGGGUCCCCACGUGACGGAAGUCGAGGGGAC<br>GUCAUUUCUGACGGGAAUUAUCUCAUGGGGAGAGGAAUG<br>UGCGAUGAAGGGGAAAUAUGGCAUCUACACUAAAGUGUC<br>ACGGUAUGUCAAUUGGAUCAAGGAAAAGACGAAACUCACG<br>UGAUAAUAG<br>GCUGCCUUCUGCGGGGCUUGCCUUCUGGCCAUGCCCUUCU<br>UCUCUCCCUUGCACCUGUACCUCUACACUCCUGGUCUUUG<br>AAUAAAGCCUGAGUAGGAAG | 5038 |
| Factor IX with 1 miR-122 sequence without the seed in mouse alpha-globin 3'UTR | Optimized Factor IX cDNA sequence containing a T7 polymerase site and XbaI restriction site:<br>TAATACGACTCACTATA<br>GGGAAATAAGAGAGAAAAGAAGAGTAAGAAGAAATATAA<br>GAGCCACC<br>ATGCAGCGCGTCAACATGATTATGGCCGAATCGCCGGGACT<br>CATCACAATCTGCCTCTTGGGTTATCTCTTGTCGGCAGAATG<br>TACCGTGTTCTTGGATCACGAAAACGCGAACAAAATTCTTA<br>ATCGCCCGAAGCGGTATAACTCCGGGAAACTTGAGGAGTTT | 5039 |

TABLE 31-continued

G-CSF and FIX Sequences

| Description | Sequence | SEQ ID NO: |
|---|---|---|
| | GTGCAGGGCAATCTTGAACGAGAGTGCATGGAGGAGAAAT<br>GCTCCTTTGAGGAGGCGAGGGAAGTGTTTGAAAACACAGAG<br>CGAACAACGGAGTTTTGGAAGCAATACGTAGATGGGGACC<br>AGTGTGAGTCGAATCCGTGCCTCAATGGGGGATCATGTAAA<br>GATGACATCAATAGCTATGAATGCTGGTGCCCGTTTGGGTTT<br>GAAGGGAAGAACTGTGAGCTGGATGTGACGTGCAACATCA<br>AAAACGGACGCTGTGAGCAGTTTTGTAAGAACTCGGCTGAC<br>AATAAGGTAGTATGCTCGTGCACAGAGGGATACCGGCTGGC<br>GGAGAACCAAAAATCGTGCGAGCCCGCAGTCCCGTTCCCTT<br>GTGGGAGGGTGAGCGTGTCACAGACTAGCAAGTTGACGAG<br>AGCGGAGACTGTATTCCCCGACGTGGACTACGTCAACAGCA<br>CCGAAGCCGAAACAATCCTCGATAACATCACGCAGAGCACT<br>CAGTCCTTCAATGACTTTACGAGGGTCGTAGGTGGTGAGGA<br>CGCGAAACCCGGTCAGTTCCCCTGGCAGGTGGTATTGAACG<br>GAAAAGTCGATGCCTTTTGTGGAGGTTCCATTGTCAACGAG<br>AAGTGGATTGTCACAGCGGCACACTGCGTAGAAACAGGAGT<br>GAAAATCACGGTAGTGGCGGGAGAGCATAACATTGAAGAG<br>ACAGAGCACACGGAACAAAAGCGAAATGTCATCAGAATCA<br>TTCCACACCATAACTATAACGCGGCAATCAATAAGTACAAT<br>CACGACATCGCACTTTTGGAGCTTGACGAACCTTTGGTGCTT<br>AATTCGTACGTCACCCCTATTTGTATTGCCGACAAAGAGTAT<br>ACAAACATCTTCTTGAAATTCGGCTCCGGGTACGTATCGGG<br>CTGGGGCAGAGTGTTCCATAAGGGTAGATCCGCACTGGTGT<br>TGCAATACCTCAGGGTGCCCCTCGTGGATCGAGCCACTTGT<br>CTGCGGTCCACCAAATTCACAATCTACAACAATATGTTCTGT<br>GCGGGATTCCATGAAGGTGGGAGAGATAGCTGCCAGGGAG<br>ACTCAGGGGGTCCCCACGTGACGGAAGTCGAGGGGACGTC<br>ATTTCTGACGGGAATTATCTCATGGGGAGAGGAATGTGCGA<br>TGAAGGGGAAATATGGCATCTACACTAAAGTGTCACGGTAT<br>GTCAATTGGATCAAGGAAAAGACGAAACTCACG<br>TGATAATAG<br>GCTGCCTTCTGCGGGCTTGCCTTCTGGCCATGCCCTTCTTC<br>TCTCCCTTGCACCTGTACCTCT<br>CAAACACCATTGTCATGGTCTTTGAATAAAGCCTGAGTAGG<br>AAGGCGGCCGCTCGAGCATGCATCTAGA | |
| mRNA sequence (transcribed):<br>GGGAAAUAAGAGAGAAAAGAAGAGUAAGAAGAAAUAUAA<br>GAGCCACC<br><u>AUG</u>CAGCGCGUCAACAUGAUUAUGGCCGAAUCGCCGGGAC<br>UCAUCACAAUCUGCCUCUUGGGUUAUCUCUUGUCGGCAGA<br>AUGUACCGUGUUCUUGGAUCACGAAAACGCGAACAAAAU<br>UCUUAAUCGCCCGAAGCGGUAUAACUCCGGGAAACUUGAG<br>GAGUUUGUGCAGGGCAAUCUUGAACGAGAGUGCAUGGAG<br>GAGAAAUGCUCCUUUGAGGAGGCGAGGGAAGUGUUUGAA<br>AACACAGAGCGAACAACGGAGUUUUGGAAGCAAUACGUA<br>GAUGGGGACCAGUGUGAGUCGAAUCCGUGCCUCAAUGGG<br>GGAUCAUGUAAAGAUGACAUCAAUAGCUAUGAAUGCUGG<br>UGCCCGUUUGGGUUUGAAGGGAAGAACUGUGAGCUGGAU<br>GUGACGUGCAACAUCAAAAACGGACGCUGUGAGCAGUUU<br>UGUAAGAACUCGGCUGACAAUAAGGUAGUAUGCUCGUGC<br>ACAGAGGGAUACCGGCUGGCGGAGAACCAAAAAUCGUGCG<br>AGCCCGCAGUCCCGUUCCCUUGUGGGAGGGUGAGCGUGUC<br>ACAGACUAGCAAGUUGACGAGAGCGGAGACUGUAUUCCCC<br>GACGUGGACUACGUCAACAGCACCGAAGCCGAAACAAUCC<br>UCGAUAACAUCACGCAGAGCACUCAGUCCUUCAAUGACUU<br>UACGAGGGUCGUAGGUGGUGAGGACGCGAAACCCGGUCA<br>GUUCCCCUGGCAGGUGGUAUUGAACGGAAAAGUCGAUGCC<br>UUUUGUGGAGGUUCCAUUGUCAACGAGAAGUGGAUUGUC<br>ACAGCGGCACACUGCGUAGAAACAGGAGUGAAAAUCACGG<br>UAGUGGCGGGAGAGCAUAACAUUGAAGAGACAGAGCACA<br>CGGAACAAAAGCGAAAUGUCAUCAGAAUCAUUCCACACCA<br>UAACUAUAACGCGGCAAUCAAUAAGUACAAUCACGACAUC<br>GCACUUUUGGAGCUUGACGAACCUUUGGUGCUUAAUUCG<br>UACGUCACCCCUAUUUGUAUUGCCGACAAAGAGUAUACAA<br>ACAUCUUCUUGAAAUUCGGCUCCGGGUACGUAUCGGGCUG<br>GGGCAGAGUGUUCCAUAAGGGUAGAUCCGCACUGGUGUU<br>GCAAUACCUCAGGGUGCCCCUCGUGGAUCGAGCCACUUGU<br>CUGCGGUCCACCAAAUUCACAAUCUACAACAAUAUGUUCU<br>GUGCGGGAUUCCAUGAAGGUGGGAGAGAUAGCUGCCAGG<br>GAGACUCAGGGGGUCCCCACGUGACGGAAGUCGAGGGGAC<br>GUCAUUUCUGACGGGAAUUAUCUCAUGGGGAGAGGAAUG<br>UGCGAUGAAGGGGAAAUAUGGCAUCUACACUAAAGUGUC<br>ACGGUAUGUCAAUUGGAUCAAGGAAAAGACGAAACUCACG<br>UGAUAAUAG | 5040 |

TABLE 31-continued

G-CSF and FIX Sequences

| Description | Sequence | SEQ ID NO: |
|---|---|---|
| | GCUGCCUUCUGCGGGGCUUGCCUUCUGGCCAUGCCCUUCU UCUCUCCCUUGCACCUGUACCUCU CAAACACCAUUGUCAUGGUCUUUGAAUAAAGCCUGAGUA GGAAG | |

These modified mRNA sequences can include at least one chemical modification described herein. The G-CSF and/or Factor IX modified mRNA sequence can be formulated, using methods described herein and/or known in the art, prior to transfection and/or administration.

The modified mRNA sequence encoding G-CSF or Factor IX can be transfected in vitro to various cell types such as HEK293, HeLa, PBMC and BJ fibroblast and those described in Table 25 using methods disclosed herein and/or are known in the art. The cells are then analyzed using methods disclosed herein and/or are known in the art to determine the concentration of G-CSF or Factor IX and/or cell viability.

The modified mRNA sequence encoding G-CSF or Factor IX can also be administered to mammals including mat, rats, non-human primates and humans. The serum, surrounding tissue and organs can be collected at pre-determined intervals and analyzed using methods disclosed herein and/or are known in the art to determine the concentration of G-CSF or Factor IX and other pharmacokinetic properties mentioned herein.

Example 33. Microphysiological Systems

The polynucleotides, primary constructs and/or mmRNA described herein are formulated using one of the methods described herein such as in buffer, lipid nanoparticles and PLGA. These formulations are then administered to or contacted with microphysiological systems created from organ chips as described in International Publication Nos. WO2013086502, WO2013086486 and WO2013086505, the contents of each of which are herein incorporated by reference in its entirety.

Example 34. Translation Enhancing Elements (TEEs) in Untranslated Regions

The 5' and/or 3' untranslated regions (UTRs) in the polynucleotides, primary constructs and/or mmRNA described herein may include at least one translation enhancing element (TEE). Such TEE which may be included in the 5'UTR and/or 3'UTR include, but are not limited to, those listed in Table 32, including portion and/or fragments thereof. The TEE sequence may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in Table 28 and/or the TEE sequence may include a 5-30 nucleotide fragment, a 5-25 nucleotide fragment, a 5-20 nucleotide fragment, a 5-15 nucleotide fragment, a 5-10 nucleotide fragment of the TEE sequences disclosed in Table 32.

TABLE 32

TEE Sequences

| TEE Identifier | Sequence | SEQ ID NO |
|---|---|---|
| TEE-001 | MSCSGCNGMWA | 5041 |
| TEE-002 | RNSGAGMGRMR | 5042 |
| TEE-003 | RNSGAGMGRMRRR | 5043 |
| TEE-004 | RMSCSGCNGMWR | 5044 |
| TEE-005 | GCGAGAGAA | — |
| TEE-006 | GGGAGCGAA | — |
| TEE-007 | GCGAGAGGA | — |
| TEE-008 | GCGAGCGGA | — |
| TEE-009 | CGGAGCGAA | — |
| TEE-010 | CGGAGCGGA | — |
| TEE-011 | ACGAGAGGA | — |
| TEE-012 | ACGAGCGGA | — |
| TEE-013 | GACGAGAGGA | 5045 |

TABLE 32-continued

TEE Sequences

| TEE Identifier | Sequence | SEQ ID NO |
|---|---|---|
| TEE-014 | GACGAGAGAA | 5046 |
| TEE-015 | AGCGAGCG | — |
| TEE-016 | AGGAGAGGA | — |
| TEE-017 | GCCGAGAGA | — |
| TEE-018 | CGAGAGGCA | — |
| TEE-019 | GAGAGGAGC | — |
| TEE-020 | CGCGGCGGA | — |
| TEE-021 | CGCCGCCGC | — |
| TEE-022 | GCGGCTGAA | — |
| TEE-023 | CCGGCTGAA | — |
| TEE-024 | CGCCGCTGAA | 5047 |
| TEE-025 | CGCCGCGGAA | 5048 |
| TEE-026 | CGCCGCCGAA | 5049 |
| TEE-027 | CCCGCGGAA | — |
| TEE-028 | CCCGCCGAA | — |
| TEE-029 | CCCGCTGAA | — |
| TEE-030 | CCCGGCGGA | — |
| TEE-031 | CGCGGCTGA | — |
| TEE-032 | CGGCTGCTA | — |
| TEE-033 | CCCGGCGGA | — |
| TEE-034 | AGCCGCCGCA | 5050 |
| TEE-035 | ACGCCGCCGA | 5051 |
| TEE-036 | GGCATTCATCGT | 5052 |
| TEE-037 | GCATTAGTATCT | 5053 |
| TEE-038 | TCGGTTATTGTT | 5054 |
| TEE-039 | TCCAATTGGGAA | 5055 |
| TEE-040 | ATCTATTGGCCA | 5056 |
| TEE-041 | TTACTGGGTGTT | 5057 |
| TEE-042 | AGGGTGAAGGTC | 5058 |
| TEE-043 | GGTGGGTGTGTC | 5059 |
| TEE-044 | CGCTTCAATGCT | 5060 |
| TEE-045 | TGCTTCAATGCC | 5061 |
| TEE-046 | TGTGTCTTTGCA | 5062 |
| TEE-047 | CACGGGGACAGC | 5063 |
| TEE-048 | AAGCTGTACATG | 5064 |
| TEE-049 | GATGGGGGCACA | 5065 |
| TEE-050 | ATATGTGCCCTT | 5066 |
| TEE-051 | TCCTTCTGGGTC | 5067 |

TABLE 32-continued

TEE Sequences

| TEE Identifier | Sequence | SEQ ID NO |
|---|---|---|
| TEE-052 | GGTGGGTGTGTC | 5068 |
| TEE-053 | GAATGGATGGGG | 5069 |
| TEE-054 | CAXGTGATATTC | 5070 |
| TEE-055 | AGGAGGGTTTGT | 5071 |
| TEE-056 | TGGGCGAGTGGG | 5072 |
| TEE-057 | CGGCTCACCAGT | 5073 |
| TEE-058 | GGTTTCXATAAC | 5074 |
| TEE-059 | GGTGGGTGTGTC | 5075 |
| TEE-060 | TTACTGGGTGTT | 5076 |
| TEE-061 | AAGTCTTTGGGT | 5077 |
| TEE-062 | CCGGCGGGU | — |
| TEE-063 | CCGGCGGG | — |
| TEE-064 | CCGGCGG | — |
| TEE-065 | CCGGCG | — |
| TEE-066 | CCGGC | — |
| TEE-067 | CGGCGGGU | — |
| TEE-068 | GGGAGACGGCGGCGGTGGCGGCGCGGGCAGAGCAAGGACGCGGCGGATCCCACTCGCACAGCAGCGCACTCGGTGCCCCGCGCAGGGTCG | 5078 |
| TEE-069 | AAAGAAATGGAATCGAAGAGAATGGAAACAAATGGAATGGAATTGAATGGAATGGAATTGAATGGAATGGGAACG | 5079 |
| TEE-070 | AAAGAAATGGAATCGAAGAGAATGGAAACAAATGGAATGGAATTGAATGGAATGGAATTGAATGGAATGGGAACG | 5080 |
| TEE-071 | AGACAGTCAGACAATCACAAAGAAACAAGAATGAAAATGAATGAACAAAACCTTCAAGAAATATGGGATTATGAAGAGGCCAAATGT | 5081 |
| TEE-072 | AAAAGGAAATACAAGACAACAAACACAGAAACACAACCATCGGGCATCATGAAACCTCGTGAAGATAATCATCAGGGT | 5082 |
| TEE-073 | AGACCCTAATATCACAGTTAAACGAACTAGAGAAGGAAGAGCAAACAAATTCAAAAGCTAGCGGAAAGCAAGAAATAACTAAGACCAG | 5083 |
| TEE-074 | AAAGACTTAAACATAAGACCTAAAACCATAAAAACCACAGAAGAAAACATAGGCAATGCCATTCAGGACATAGGCATGGGCAAAGACTTC | 5084 |
| TEE-075 | AGCAATAACCAAACAACCTCATTAAAAAGTAGGCAAAGGACATAAACAGACACTTTTCAAAAGAAGACATACACGTGGCCAACAAACATATG | 5085 |
| TEE-076 | AGAAAGAATCAAGAGGAAATGCAAGAAATCCAAAACACTGTAACAGATATGATGAATAATGAGGTATGCACTCATCAGCAGACTCGACAT | 5086 |
| TEE-077 | GCACTAGTCAGATCAAGACAGAAAGTCAACGAACAAGAACAGACTTAAACTACACTCTAGAACAAATGGACCTA | 5087 |
| TEE-078 | AGCAGCCAACAAGCATATGAAATAATGCTCCACAACACTCATCATCAGAGAAATGCAAATCAAAACCAAAAT | 5088 |

TABLE 32-continued

TEE Sequences

| TEE Identifier | Sequence | SEQ ID NO |
|---|---|---|
| TEE-079 | AATATACGCAAATCAATAAATGTAATCCAGCATATA AACAGTACTAAAGACAAAAACCACATGATTATCTCA ATAGATGCAGAAAAGGCC | 5089 |
| TEE-080 | ATGTACACAAATCAATAAATGCAGTCCAGCATATAA ACAGAACCAAACACAAAAACCACATGATTATCTCAA TAGATGCAGAAAAGGCCTTT | 5090 |
| TEE-081 | TATACCACACAAATGCAAAAGATTATTAGCAACAAT TATCAACAGCAATATGTCAACAAGTTGACAAACCTA GAGGACATGGAT | 5091 |
| TEE-082 | AAACACACAAAGCAACAAAAGAACGAAGCAACAAA AGCATAGATTTATTGAAATGAAAGTACATTCTACAG AGTGGGGGCAGGCT | 5092 |
| TEE-083 | GAAATCATCATCAAACGGAATCGAATGGAATCATTG AATGGAATGGAATGGAATCATCATGGAATGGAAACG | 5093 |
| TEE-084 | AACAGAATGGAATCAAATCGAATGAAATGGAATGG AATAGAAAGGAATGGAATGAAATGGAATGGAAAGG ATTCGAATGGAATGCAATCG | 5094 |
| TEE-085 | TACAAAGAACTCAAACAAATCAGCAAGAACAAAAA CAATCCCAACAAAATGTTGGACAAAGACATGAATAG ACAATTCTCGAAAGAAGATGTACAAATGGCT | 5095 |
| TEE-086 | TGTTGAGAGAAATTAAACAAAGCACAGATAAATGGA AAAACGTGTTCATAGATTGAAAGACTTCATGTTGTAT GGTGTC | 5096 |
| TEE-087 | AAACGATTGGACAGGAATGGAATCACCATCGAATGG AAACGAATGGAATCTTCGAATGGAATTGAATGAAAT TATTGAACGGAATCAAATAGAATCATCATTGAACAG AATCAAATTGGATCAT | 5097 |
| TEE-088 | AACAATAAACAAACTCCAACTAGACACAATAGTCAA ATTGCTGAAAATGAAATATAAAGGAACAATCTCGAT GGTAGCCCAAGGA | 5098 |
| TEE-089 | AAATCAATAAATGTAATTCAGCATATAAACAGAACC AAAGACAAAAACCCACATGATTATCTCAATAGATGCA GAAAAGGCCTTT | 5099 |
| TEE-090 | GCTCAAGGAAATAAAATAGGACACAAAGAAATGGA AAAACATTCCATACTCATGGATAGAAAGAATCAATA TCATGAAATGGCC | 5100 |
| TEE-091 | AACATACGCAAATCAATAAATGTAATCCAGCATATA AACAGAACCAAAGACAAAAACCACATGATTATCTCA ATAGATGCAGAAAAGGCC | 5101 |
| TEE-092 | AACAATCACTAGTCCTTAAGTAAGAGACAACACCTT TTGTCACACACAGTTTGTCCTAACTTTATCTTGGTAA TTGGGGAGACC | 5102 |
| TEE-093 | AGAAAACACACAGACAACAAAAAACACAGAACGAC AATGACAAAATGGCCAAGC | 5103 |
| TEE-094 | ACACAACAACCAAGAAACAACCCCATTAAGAAGTGG GAAAAATACATGAATAAACACATCTCAAAAGAAGAC AAACAAGTGGCTAAC | 5104 |
| TEE-095 | ACAGCAGAAAACGAACATCAGAAAATCACTCTACAT GATGCTTAAATACAGAGGGCAAGCAACCCAAGAGA AAACACCACTTCCTAAT | 5105 |
| TEE-096 | GAATAGAACAGAATGGAATCAAATCGAATGAAATG GAATGGAATAGAAAGGAATGGAATGAAATGGAATG GAAAGGATTCGAATGGAATG | 5106 |
| TEE-097 | TAAGCAGAGAAAATATCAACACGAAAATAATGCAA GGAGAAAAATACAGAACAATCCAAAATGTGGCC | 5107 |

TABLE 32-continued

TEE Sequences

| TEE Identifier | Sequence | SEQ ID NO |
|---|---|---|
| TEE-098 | GAACAATCAATGGAAGCAGAAACAAATAAACCAAG GTGTGCATCAAGGAATACATTCACGCATGATGGCTG TATGAGTAAAATG | 5108 |
| TEE-099 | GATCAATAAATGTAATTCATCATATAAACAGAGAAC TAAAGACAAAAACACATGATTATCGCAATACATGCA GAAAAGGCC | 5109 |
| TEE-100 | GACAAGAGTTCAGAAAGGAAGACTACACAGAAATA CGCATTTTAAAGTCACTGACATGGAGATGACACTTA AAACCATGAACATGGATGGG | 5110 |
| TEE-101 | AAGCAAAGAAAGAATGAAGCAGCAAAGAACGAAA GCAGGAATTTATTGAAAACCAAAGTACACTCCACAG TATGGGAGCGGACCCGAGCA | 5111 |
| TEE-102 | ACCAACATAAGACAAAGAAACATCCAGCAGCTGCCT ATGGCAAAAGATTACAATGTGTCAAACAAGAGGGCA ATG | 5112 |
| TEE-103 | GGACAAATTGCTAGAAATAAACAAATTACCAAAAAT GATTCAAGTAGAGACAGAGAATCAAATAGAACTAC ACATAAGTGGGCCAAG | 5113 |
| TEE-104 | AACATAATCCATCAAATAAACAGAACCAAAGACAAA AACCACATGATTATCTCAATAGATGCAGAAAAGGCC TTC | 5114 |
| TEE-105 | AAAATCAATATGAAAACAAACACAAGCAGACAAAG AAAATTGGGCAAAAGGTTTGAGCAGACACTTCACCA AAGAAGTACAAATGGCAAATCAGCA | 5115 |
| TEE-106 | AACCAAATTAGACAAATTGGAAATCATTACACATAA CAAAAGTAATAAACTGTCAGCCTCAGTAGTATTCATT GTACATAAACTGGCC | 5116 |
| TEE-107 | AAGGAATTTAAGCAAATCAACAAGCAAAACCAAAT AATCCCATTAAAAAGTGGGTAAAGGACATGAATACA CACTTGTCAATAGAGGACATTCAAGTGGCCAAC | 5117 |
| TEE-108 | TAACCTGATTTGCCATAATCCACGATACGCTTACAAC AGTGATATACAAGTTACATGAGAAACACAAACATTT TGCAAGGAAACTGTGGCCAGATG | 5118 |
| TEE-109 | AACTAACACAAGAACAGAAAAACCAAACATCACATGT TCTCACTCATAAGCGGGAGCTGAACAATGAGAACAC ACGGACACAGGGAGAGGAACATG | 5119 |
| TEE-110 | TAAACTGACACAAACACAGACACACAGATACACACA TACATACAGAAATACACATTCACACACAGACCTGGT CTTTGGAGCCAGAGATG | 5120 |
| TEE-111 | ATCAACAGACAACAGAAACAAATCCACAAAGCACTT AGTTATTAGAACTGTCATACAGACTGTACAACAACC ACATTTACCAT | 5121 |
| TEE-112 | AAATAAGCCAACGGTCATAAATTGCAAAGCCTTTTA CAATCCAAACATGATGGAAACGATATGCCATTTTGA AGGTGATTTGAAAAGCACATGGTTT | 5122 |
| TEE-113 | AAACAGTTCAAAAATTATTGCAACAAAATGAGAGAG ATGAGTTTATCTTGCAAACTAATGGATGGTAGCAGT GACAGTGGCAAAACGTGGTTTGATTCT | 5123 |
| TEE-114 | TAAGCAACTTCAGCAAAGTCTCAGGATACAAAATCA ATGTACAAAAATCACAAGCATTCTTATACACCAACA ACAGACAAACAAGAGTGCCAAATCATG | 5124 |
| TEE-115 | AGCAAACAAACAAACAAACAAACAAACTATGACAG GAACAAAACGTCACATATCAACATTAACAAAGAATG TAAACAGCCTAAATGCTTCACTTAAAAGTTATAGAC AGGGGCTGGGCATGGTGGCTCACGCC | 5125 |

TABLE 32-continued

TEE Sequences

| TEE Identifier | Sequence | SEQ ID NO |
|---|---|---|
| TEE-116 | GGAAATAACAGAGAACACAAACAAATGGGAAAACA TTCCATGTTCATGGATAGGAAGAATCAATATTGTGA AAATGGCCATACT | 5126 |
| TEE-117 | AGCAACTTCAGCAAAGTCTCAGGATACAAAATCAAT GTACAAAAATCACAAGCATTCTTATACACCAATAAC AGACAAACAGAGAGCC | 5127 |
| TEE-118 | AGATAAGAATAAGGCAAACATAGTAATAGGGAGTTC ATGAATAACACACGGAAAGAGAACTTACAGGGCTGT GATCAGGAAACG | 5128 |
| TEE-119 | AGGAAATAAAGAAGACACAAACAAATGGAAGAAC ATTCCATGCTTATGGATAGGGAGAATCAGTATCGTG AAAATGGCCATACT | 5129 |
| TEE-120 | AACATACGAAAATCAATAAACGTAATCCAGCATATA AACAGAACCAAAGACAAAAACCACATGATTATCTCA ATAGATGCAGAAAAGGCCTTT | 5130 |
| TEE-121 | AATGGACTCGAATGAAATCATCATCAAACGGAATCG AATGGAATCATTGAATGGAATGGAATGGAATCATCA TGGAATGGAAACG | 5131 |
| TEE-122 | AAGATTTAAACATAAGACCTAAAACGACAAAAATCC TAGGAGAAAACCTAAGCAATACCATTCAGGACATAG GCATGGGCAAAGACTTCATG | 5132 |
| TEE-123 | TAATGAGAAGACACAGACAACACAAAGAATCACAG AAACATGACACAGGTGACAAGAACAGGCAAGGACC TGCAGTGCACAGGAGCC | 5133 |
| TEE-124 | TAAACGTTAGACCTAAAACCATAAAAACCCTAGAAG AAAACCTAGGCATTACCATTCAGGACATAGGCATGG GCAAGGAC | 5134 |
| TEE-125 | GAATTGAATTGAATGGAATGGAATGCAATGGAATCT AATGAAACGGAAAGGAAAGGAATGGAATGGAATGG AATG | 5135 |
| TEE-126 | GTAATGGAATGGAATGGAAAGGAATCGAAACGAAA GGAATGGAGACAGATGGAATGGAATGGAACAGAG | 5136 |
| TEE-127 | AGAGAAATGCAAATCAAAACCACAATGGAATACCAT CTCACGCCAGTCAGAATGGCAATTATTAAAAAATCA CAACAATTAATGATGGCAAGGCTGTGG | 5137 |
| TEE-128 | AACATACACAAATCAATAAACGTAATCCAGCTTATA AACAGAACCAAAGACAAAAACCACATGATTATCTCA ATAGATGCGGAAAAGGCC | 5138 |
| TEE-129 | TAAACAGAACCAAAGACAAAAATCACATGATTATCT CAATAGATGCAGAAAAGGCC | 5139 |
| TEE-130 | AATGGAATGCAATCGAATGGAATGGAATCGAACGGA ATGGAATAAAATGGAAGAAAACTGGCAAGAAATGG AATCG | 5140 |
| TEE-131 | AGATAAAAGAACAGCAGCCAAAATGACAAAAGCA AAAAGCAAATCGTGTTAGAGCCAGGTGTGGTGATG TGTGCT | 5141 |
| TEE-132 | AGGAAAGTTTTCAATATGAGAAAGATACAAACCAAC AGAATAAGCAAACTGGATAAACAGAAAATACAGAG AGAGCCAAGG | 5142 |
| TEE-133 | GCAATCTCAGGATACAAAATCAATGTGCAAAAATCA CAAGCATTCTCATACACCAATAACAGACAAACAGAG CCAAATCATG | 5143 |
| TEE-134 | AGCATTCATATCTTGCAGTGTTGGGAAAGAGTGAGA GGTTGTGATGTCAAGAAGGATAGGTCAGAAGTGGAA GGTATGGGGGATTGTGCCTGCTGTCATGGCT | 5144 |

TABLE 32-continued

TEE Sequences

| TEE Identifier | Sequence | SEQ ID NO |
|---|---|---|
| TEE-135 | AGCAACTTCAGCAAAGTCTCAGGATACAAAATCAAT GTGCAAAAATCACAAGCATTCTTATACACCAATAAC AGACAAACAGAGAGCC | 5145 |
| TEE-136 | AGCAACTTCAGCAAAGTCTCAGGATACAAAATCAAT GTGCAAAAATCACAAGCATTCTTATACACCAACAAC AGACAAACAGAGAGCC | 5146 |
| TEE-137 | TAAGCCGATAAGCAACTTCAGCAAAGTCTCAGGAGA CAAAATCAATGTGCAAAAAATCACAAGCATTCTTAT ACACTAATAACAGACAAACAGAGAGCCAAATCATG | 5147 |
| TEE-138 | AACGTGACATACATACAAAAAGTTTTTAGAGCAAGT GAAATTTTAGCTGCTATATGTTAATTGGTGGTAATCCC | 5148 |
| TEE-139 | TACGCAAATCGATAAATGTAATCCAGCATATAAACA GAACCAAAGACAAAAACCACATGATTATCTCAATAG ATGCAGAAAAGGCC | 5149 |
| TEE-140 | GCAATCGAATGGAATGGAATCGAACGGAATGGAATA AAATGGAAGAAAACTGGCAAGAAATGGAATCG | 5150 |
| TEE-141 | TTGAATCGAATGGAATCGAATGGATTGGAAAGGAAT AGAATGGAATGGAATGGAATTGACTCAAATGGAATG | 5151 |
| TEE-142 | TAAAGAAAAACAAACAAACAGAAATCAATGAAAAT CCCATTCAAAGGTCAGCAACCTCAAAGACTGAAGGT AGATAAGCCCACAAGGATG | 5152 |
| TEE-143 | GTCATATTTGGGATTTATCATCTGTTTCTATTGTTGTT GTTTTAGTACACACAAAGCCACAATAAATATTCTAG GCT | 5153 |
| TEE-144 | AAAAGTACAGAAGACAACAAAAAATGAGAGAGAGA AAGATAACAGACTATAGCAGCATTGGTGATCAGAGC CACCAG | 5154 |
| TEE-145 | AACCCACAAAGACAACAGAAGAAAAGACAACAGTA GACAAGGATGTCAACCACATTTTGGAAGAGACAAGT AATCAAACACATGGCA | 5155 |
| TEE-146 | AAAGACCGAAACAACAACAGAAACAGAAACAAACA ACAATAAGAAAAAATGTTAAGCAAAACAAATGATTG CACAACTTACATGATTACTGAGTGTTCTAATGGT | 5156 |
| TEE-147 | AATCAGTAAACGTAATACAGCATATAAACAGAACCA AAGACAAAAACCACATGATTATCTCAATAGATGCAG AAAAGGCC | 5157 |
| TEE-148 | AAGCAACTTCAGCAAAGTCTCAGGACACAAAATCAA TATGCGAAAATCACAAGCATTCCTATACACCAATAA TAGACAAACAGAGAGCCAAATCATG | 5158 |
| TEE-149 | AGCAACTTCAGCAAAATCTCAGGATACAAAATCAAT GTACAAAAATCACAAGCATTCTTATACACCAACAAC AGACAAACAGAGAGCC | 5159 |
| TEE-150 | TAATGCAAACTAAAACGACAATGAGATATCAATACA TAACTACCAGAAAGGCTAACAAAAAAACAGTCATAA CACACCAAAGGCTGATGAGTGAGGATGTGCAG | 5160 |
| TEE-151 | AGCAACTTCAGCAAAGTCTCAGGATACAAAATCGAT GTGCAAAAATCACAAGCATTCTTATACACCAATAAC AGGCAAACAGAGAGCC | 5161 |
| TEE-152 | GATATATAAACAAGAAAACAACTAATCACAACTCAA TATCAAAGTGCAATGATGGTGCAAAATGCAAGTATG GTGGGGACAGAGAAAGGATGC | 5162 |
| TEE-153 | AAGACAGAACACTGAAACTCAACAGAGAAGTAACA AGAACACCTAAGACAAGGAAGGAGAGGGAAGGCAG GCAG | 5163 |

TABLE 32-continued

TEE Sequences

| TEE Identifier | Sequence | SEQ ID NO |
|---|---|---|
| TEE-154 | TAAGACACATAGAAAACATAAAGCAAAATGGCAGA TGTAAATGCAACCTATCAATCAAAACATTACGAATG GCTT | 5164 |
| TEE-155 | TGAAACAAATGATAATGAAAATACAACATACCAAAC ATACGAGATACAGTAAAAGCAGTACTAAGATGCAAG TATATATTGCTACAAGTGCCTAC | 5165 |
| TEE-156 | AATGTAATCCAGCATATAAACAGAGCCAAAGACAAA AACCACATGATTATCTCAATAGATGCAGAAAAAGCC TTTGACAAAATTCAACAACCCTTCATGCTAAAAACTC TCAATAAATTAGGTATTGATGGGACG | 5166 |
| TEE-157 | ACAAAATTGATAGACCACTAGCAAGACTAATAAAGA AGAAAAGAGAGAAGAATCATTACCATTCAGGACATA GGCATGGGCAAGGAC | 5167 |
| TEE-158 | AAGGATTCGAATGGAATGCAATCGAATGGAATGGAA TCGAACGGAATGGAATAAAATGGAAGAAAACTGGC AAGAAATGGAATCG | 5168 |
| TEE-159 | GATCATCAGAGAAACAGAGAAATGCAAATTAAAACC ACAATGAGATACTATCTCCACACAAGTCAGAATGGC TAT | 5169 |
| TEE-160 | ATCAAAAGAAAAGCAACCTAACAAATACGGGAAGA ATATTTGAATAGACATTTCACAGGAAAAGATATATG AATGGCCAAAAAGCAAATGAAAAG | 5170 |
| TEE-161 | AACAGCAATGACAATGATCAGTAACAACAAGACTTT TAACTTTGAAAAAATCAGGACC | 5171 |
| TEE-162 | AAGAGCCTGAATAGCTAAAGTGATCATAAGCAAAAA GAACAAAGTCGGAAGCATCACATTACCTGACTTCAA ACTATACTCAAAGGCTATG | 5172 |
| TEE-163 | ACTCAGGAAAAATAACGAATCCAACTCACAGGAGAA AGAAGTACAAACCAGAAACCAATTTCAAATTACAAG GACCAGAATACTCATGTTGGCTGGCCAGT | 5173 |
| TEE-164 | TTGACCAGAACACATTACACAATGCTAATCAACTGC AAAGGAGAATATGAACAGAGAGGAGGACATGGATA TTTTGTG | 5174 |
| TEE-165 | AACATATGGAAAAAAACTCAACATCACTGATCATTA GAGAAATGCAAATCAAAACCACAATGAGATACCATC TCACGCCAGTCAGAATGGCG | 5175 |
| TEE-166 | AGCAACTTCAGCAAAGACTCAGGATACAAAATCAAT GTGCAAAAATCACAAGCATTCTTATACACCAATAAC AGACAGAGAGCCAAAT | 5176 |
| TEE-167 | TGGGATATGGGTGAAAGAACAAGTTTGCAGAAAAGA TACAGTGAATTATGGACCATGAGTTCGGGAAAGAAG GGTAGGACTGCG | 5177 |
| TEE-168 | AGCAGTGCAAGAACAACATAACATACAAGTAAACA AACACATGGGGCCAGGTAATAAAAAGTCAGGCTCAA GAGGTCAG | 5178 |
| TEE-169 | AAGGAAAAGTAAAAGGAACTTAACACCTTCAAGAA AAGACAGACAAATAACAAAACAGCAGTTTGATAGA ATGAGATATCAGGGGATGGCA | 5179 |
| TEE-170 | GCTAGTTCAACATATGCAAATCAATAAACGTAATCC ATCACATAAACAGAACCAATGACAAAAACCACGATT ATCTCAATAGATGCAGAAAAGGCC | 5180 |
| TEE-171 | AACATCACTGATCATTAGAAACACACAAATCAAAAC CACAATAAGATACCATCTAACACCAGTCACAATGGC TATT | 5181 |
| TEE-172 | AGAGCATCCACAAGGCCCAATTCAAAGAATCTGAAA TAATGTATTGTTACTGCAACAGTTGTGAGTACCAGTG GCATCAG | 5182 |

TABLE 32-continued

TEE Sequences

| TEE Identifier | Sequence | SEQ ID NO |
|---|---|---|
| TEE-173 | GGAATAACAACAACAACAACCAAAAGACATATAGA<br>AAACAAACAGCACGATGGCAGATGTAAAGCCTACC | 5183 |
| TEE-174 | AAACGCAGAAACAAATCAACGAAAGAACGAAGCAA<br>TGAAAGACAAAGCAACAAAAGAATGGAGTAAGAAA<br>GCACACTCCACAAAGTGGAAGCAGGCTGGGACA | 5184 |
| TEE-175 | AGCAACTTCAGCAAAGTCTCAGGATACAAAATCAAT<br>GTGCAAAAATCACAAGCATTCCTATACACCAACAAC<br>AGACAAACAGAGAGCC | 5185 |
| TEE-176 | AGCAACTTCAGCAAAGTCTCAGGATACAAAATCAAT<br>GGGAAAAAATCACAAGCATTCCTATACATCAATAAC<br>AGACAAACAGAGAGCC | 5186 |
| TEE-177 | ACACATTTCAAGGAAGGAAACAAGAACAGACAGAA<br>ACACAACATACTTCATGAAACCACATTTTAGCATCCT<br>GGCCGAGTATTCATCA | 5187 |
| TEE-178 | AGCAACTTCAGCAAAGTCTCAGGACACAAAATCAAT<br>GTGCAAAAATCACAAGCATTCTTATACACCAATAAC<br>AGACAAACAGAGAGCC | 5188 |
| TEE-179 | TATTTTACCAGATTATTCAAGCAATATATAGACAGCT<br>TAAAGCATACAAGAAGACATGTATAGATTTACATGC<br>AAACACTGCACCACTTTACATAAGGGACTTGAGCAC | 5189 |
| TEE-180 | CCCAACTTCAAATTATACTACAAGGCTACAGTAATC<br>AAAAAAGCATAGTACTATTACAAAAACAGACACACA<br>GGCCAATGGAATACAAT | 5190 |
| TEE-181 | AGAAAGGATTCGAATGGAATGAAAAAGAATTGAAT<br>GGAATAGAACAGAATGGAATCAAATCGAATGAAAT<br>GGAATGGAATAGAAAGGAATGGAATG | 5191 |
| TEE-182 | GTTTACAGTCAAGTGTACAAACAGAATATAAGCAAA<br>CAAAAGAGAACATATACTTACAAACTATGCTAAGTG<br>CCATGAAGGAAAAG | 5192 |
| TEE-183 | AAGAGTATTGAAGTTGACATATCTAGACTGATCAAG<br>AACAAAGACAAAAGGTACAGATTATCAAGAAAATG<br>AGCGGGCAAAGCAAGATGGCC | 5193 |
| TEE-184 | AGTAGAATTGCAATTGCAAATTTCACACATATACTCA<br>CACACAAGTACACACATCCACTTTTACAACTAAAAA<br>AACTAGCACCCAGGACAGGTGCAGTGGCT | 5194 |
| TEE-185 | TGAATGCTATAGAGCAGTAAAAACAAATAAATGAAC<br>TACATTACAGCTACTTACAACCATATGAAAGAATAT<br>AACCATAACAATGATGAGTGGACAAAAGCTAAGTGT<br>GAAAGAATGCATAGTGCTACAGCAGCCAACATTTAC<br>AGC | 5195 |
| TEE-186 | GAATGGAATCAAATAGAATGGAATCGAAACAAATG<br>GAATGGAATGGAATGGGAGCTGAGATTGTGTCACTG<br>CAC | 5196 |
| TEE-187 | TAAAAGTGTGCTCAACATCATTGATCATCAGAGAAA<br>TGCAAATCAAAACTACAATGAGATATCATCTCATCC<br>CAGTCAAAGTGGCT | 5197 |
| TEE-188 | TCAGACCATAGCAGATAACATGCACATTAGCAATAC<br>GATTGCCATGACAGAGTGGTTGGTG | 5198 |
| TEE-189 | ACAAACAATCCAATTCGAAAATGGGCAAGATATTTC<br>ACCAAAGACATGAGCTGATATTTCAC | 5199 |
| TEE-190 | AGGAAAAACAACAACAACAACAGGAAAACAACCTC<br>AGTATGAAGACAAGTACATTGATTTATTCAACATTTA<br>CTGATCACTTTTCAGGTGGTAGGCAG | 5200 |
| TEE-191 | AACAAAACAAAAACCCAACTCAATAACAAGAAGAC<br>AAACAACCCAATTTAAAATGAGCAAAGAACTTGATA<br>AACATGTCTCCAAAGAAGATACGGCCAAAGAGCAC | 5201 |

TABLE 32-continued

TEE Sequences

| TEE Identifier | Sequence | SEQ ID NO |
|---|---|---|
| TEE-192 | ATACAACTAAAGCAAATATAAGCAACTAAAGCAACA GTACAACTAAAGCAAAACAGAACAAGACTGCCAGG GCCTAGAAAAGCCAAGAAC | 5202 |
| TEE-193 | AACAACAACAACAACAGGAAAACAACCTCAGTATG AAGACAAGTACATTGATTTATTCAACATTTACTGATC ACTTTTCAGGTGGTAGGCAGACC | 5203 |
| TEE-194 | AGAGAGTATTCATCATGAGGAGTATTACTGGACAAA TAATTCACAAACGAACAAACCAAAGCGATCATCTTT GTACTGGCTGGCTA | 5204 |
| TEE-195 | AGTAAATCACCATAAAGAAGGTAAGAGTTCATTCAC AAAAACAACAAACTGAAGAATCAGGCCATAGTA | 5205 |
| TEE-196 | AAAATAGAATGAAAGAGAATCAAATGGAATTGAATC GAATGGAATCGAATGGATTGGAAAGGAATAGAATG GAATGGAATGGAATG | 5206 |
| TEE-197 | AAAAGATGCAAAAGTAGCAAATGCAATGTTAAAACA AGCAAAGAAAGAATCAGGTGGACCACATAGTGCAGT GCTTCTC | 5207 |
| TEE-198 | TTCACAGCAGCATTACGCACAATAGCCAGAAGGTGG GAACAGACAAAATGCCTTTTGATGGG | 5208 |
| TEE-199 | CCATAACACAATTAAAAACAACCTAAATGTCTAATA GAAGAACACTGTTCAGACCGGGCATGGTGGCTTATA CC | 5209 |
| TEE-200 | TGGATTTCAGATATTTAACACAAAATAGTCAAAGCA GATAAATACTAGCAACTTATTTTTAATGGGTAACATC ATATGTTCGTGCCTT | 5210 |
| TEE-201 | ATCATTGAATGCAATCACATGGAATCATCACAGAAT GGAATCGTACGGAATCATCATCGAATGGAATTGAAT GGAATCATCAATTGGACTCGAATGGAAACATCAAAT GGAATCGATTGGAAGTGTCGAATGGACTCG | 5211 |
| TEE-202 | AGAAACAGCCAGAAAACAATTATTACCTACAGCATT AAAACTATTCAAATGACAGCATATTTTTCAGCAGAA ATCATGAAGGCCAGAAGGACGTGTCAT | 5212 |
| TEE-203 | AAAATGATCATGAGAAAATTCAGCAACAAAACCATG AAATTGCAAAGATATTACTTTTGGGATGGAACAGAG CTGGAAGGCAAAGAG | 5213 |
| TEE-204 | AACCACTGCTCAAGGAAATAAGAGAGAACACAAAC AAATGAAAAAACATTCCATGCTCATGGATAGGAAGA ATCAG | 5214 |
| TEE-205 | TACTCTCAGAAGGGAAGCAGATATTCAGCATAAATC ATATTGTTTGTACAAAGAGTCTGGGCATGGTGAATG ACACT | 5215 |
| TEE-206 | TATAGTTGAATGAACACACATACACACACACATGCC ACAAAACAAAAACAAAGTTATCCTCACACACAGGAT AGAAACCAAACCAAATCCCAACACATGGCAAGATGAT | 5216 |
| TEE-207 | GCTCAAAGAAATCAGAAATGACACAAGCAAATGGA AAAACATGCCATGTTCATGAATATGAAGAATCAATA TTGTTAAAATGGCCATACTGCTCA | 5217 |
| TEE-208 | GGATACAAAATCAATGTACAAAAATCACAAGCATTC TTATACACCAATAACAGACAAACAGAGAGCC | 5218 |
| TEE-209 | AGCAACTTCAGCAAAGTCTCAGGATACAAAATCAAT GTACAAAAATCACAAGCATTCTTATACACCAACAAC AGACAAACAGAGAGCC | 5219 |
| TEE-210 | AGGAGAATAGCAGTAGAATGACAAAATTAGATTTTC ACATGAAACTTGATGACAGTGTAGGAAATGGACTGA AAGGACAAGAC | 5220 |

TABLE 32-continued

TEE Sequences

| TEE Identifier | Sequence | SEQ ID NO |
|---|---|---|
| TEE-211 | AGCAACTTCAGCAAAGTCTCGGGATACAAAATCAAT GTGCAAAAATCACAAGCATTCCTATACACCAATAAC AGGCAAACAGAGAGCC | 5221 |
| TEE-212 | AAGTTCAAACATCAGTATTAACCTTGAACATCAATG GCCTACATGCATCACTTAAAACATACAGACAGGCAA ATTGGGTTAAGAAAACAAACAAGCAAACAAAACAT GTTCCAAACATTTGTTGGCTAT | 5222 |
| TEE-213 | AAGAAACAATCAAAAGGAAGTGCTAGAAATAAAAC ACACTGTAATAGAAAAGAAGAATGCCTTATGGGCTT ATCAATAGACTAGACATGGCCAGG | 5223 |
| TEE-214 | AAAGAAAGACAGAGAACAAACGTAATTCAAGATGA CTGATTACATATCCAAGAACATTAGATGGTCAAAGA CTTTAAGAAGGAATACATTCAAAGGCAAAAAGTCAC TTACTGATTTTGGTGGAGTTTGCCACATGGAC | 5224 |
| TEE-215 | AGCAACTTCAGCAAAGTTTCAGGATACAAAATCAAT GTGCAAAAATCACAAGCATTCTTATACACCAACAAC AGACAAACAGAGAGCC | 5225 |
| TEE-216 | AGAATCAAATGGAATTGAATCGAATGGAATCGAATG GATTGGAAAGGAATAGAATGGAATGGAATGGAATG | 5226 |
| TEE-217 | AAACAGAACCACAGATATCTGTAAAGGATTACACTA TAGTATTCAACAGAGTATGGAACAGAGTATAGTATT CAACAGAGTATGCAAAGAAACTAAGGCCAGAAAG | 5227 |
| TEE-218 | AAAAAATGTTCAACATCACTAGTCAGCAGAGAAATG CAAATCAAAATCACAATGAGATAACTTCTCACACCA GACAGCATGGC | 5228 |
| TEE-219 | GAATCCATGTTCATAGCACAACAACCAAACAGAAGA AATCACTGTGAAATAAGAAACAAAGCAAAACACAG ATGTCGACACATGGCA | 5229 |
| TEE-220 | AGGATACAAAATCAAGTGCAAAAATCACAAGCATT CTTATACACCAATAACAGACAAACAGAGAGCC | 5230 |
| TEE-221 | AACAGATTTAAACAAACCAACAAGCAAAAAACGAA CAACTCCATTCAAACATGGACAAAAGACACGAACAG ACACTTTTCAAAGAAGACATACATGTGGCC | 5231 |
| TEE-222 | AAAGACAATATACAAATGGCCAATAAGCACATGAAA AGACGCTCAACATCCTTAGTCGTTAAGGCAATGCAA ATCAAAACCACAATG | 5232 |
| TEE-223 | TAAACAACGAGAACACATGAACACAAAGAGGGGAA CAACAGACACCAAGACCTTCTTGAGGGTGGAGGATG GGAGGAGGGAG | 5233 |
| TEE-224 | GGTTCAACTTACAATATTTTGACTTGACAACAGTGCA AAAGCAATACACGATTAGTAGAAACACACTTCCAAT GCCCATAGGACCATTCTGC | 5234 |
| TEE-225 | AGCAACTTCAGCAAAGTCTCAGGATACAAAATCAAT GAGCAAAAATCACAAGCATTCTTACACACCAATAAC AGACAAACAGAGAGCC | 5235 |
| TEE-226 | AATCCAGCATATAAACAGAACCAAAGACAAAAACC ACATGATTATCTCAATAGATGCAGAAAAGGCC | 5236 |
| TEE-227 | TGAAAATACAAATGACCATGCAAGTAATTCCGCAGG GAGAGAGCGGATATGAACAAACAGAAGAAATCAGA TGGGATAGTGCTGGCGGGAAGTCA | 5237 |
| TEE-228 | GCAAATGATTATAAGTGCTGTTATAGAAACATTCAA AGACCAGAAAAGGACCACAATGGCTGACCAC | 5238 |
| TEE-229 | AGTCAATAACAAGAAGACAAACAACCCAATTACAAA ATGGGATATGAATTTAATAGATGTTACTCCAAGGAA GATACACAAATGGCCAAC | 5239 |

TABLE 32-continued

TEE Sequences

| TEE Identifier | Sequence | SEQ ID NO |
|---|---|---|
| TEE-230 | ATGGTTAAAACTCAACAATGAAAACACAAACAGCGC AATTTAAAAATGGGCAAAATGACAGGCCAGACCCAG TGGCTCATGCG | 5240 |
| TEE-231 | TAACTACTCACAGAACTCAACAAAACACTATACATG CATTTACCAGTTTATTATAAAGATACAAGTCAGGAA CAGCCAAATGGAAGAAATGTAAATGGCAAG | 5241 |
| TEE-232 | AACAGACCATAAATAAACACAGAAGACACACGAGT GTAAAGTCAGTGCCCCGCTGCGAATTAAATCGGGGT GATGTGATGGCGAGTGAGTGGGTAGTT | 5242 |
| TEE-233 | GAATAGAATAGAATGGAATCATCGAATGGAATCGAA TGGAATCATCATGATATGGAATTGAGTGGAATC | 5243 |
| TEE-234 | GGAATCTATAATACAGCTGTTTATAGCCAAGCACTA AATCATATGATACAGAAAACAAATGCAGATGGTTTG AAGGGTGGG | 5244 |
| TEE-235 | AAGATAGAGTTGAAACAGTGGACAATTAAAGAGTAA TTTGGAAGAATGGTGAAATTACAGCCATGCTTTGAA TCAGGCGGGTTCACTGGC | 5245 |
| TEE-236 | TGAAAAGAAGAATGACCATAAGCAAGCAGATGAAA AACAAAACAGAATTTTTACAGACGTCTTGGACTGAT ATCTTGGGC | 5246 |
| TEE-237 | AGGAATCTATAATACAGCTGTTTATAGCCAAGCACT AAATCATATGATACAGAAAACAAATGCAGATGGTTT GAAGGGTGGG | 5247 |
| TEE-238 | AGGAAAAGAAAGAAATAGAAAATGCGAAATGGTAA GAAAAAACAGCATAATAAACATTTGTATGGTGTTGA TGGACAATGCATT | 5248 |
| TEE-239 | TAACAGTACCAAAAAACAGTCATAATCTTCAAGAGC TTAAATTTAGCATGAAAGGAAGACATTCATCAAAGA ATCACACAAAGGAATGTAAAATTAAATGGAGATTAG TGCCAGGAAAGAGC | 5249 |
| TEE-240 | GCAAAACACAAACAACGCCATAAAAAACTGGGCAA AGGATATGAACAGACATTTTTCAAAACAAAACATAC TTATGGCCAAC | 5250 |
| TEE-241 | AACAAAATTGAACAACATGCAAAGAAACATAAACG AAGCAATGAAAGTGTGCAGATCCACTGAAATGAAAG TGCTGTCCAGAGTGGGAGCCAGCTCGAGA | 5251 |
| TEE-242 | GAATGGAATCAACATCAAACGGAATCAAACGGAATT ATCGAATGGAATCGAAGAGAATCATCGAATGGCCAC GAATGGAATCATCTAATGGAATGGAATGGAATAATC CATGG | 5252 |
| TEE-243 | TACAAGAAAATCACAGTAACATTTATAAAACACAGA AGTGTGAACACACAGCTATTGACCTTGAAAACAGTG AAAGAGGGTCAGCTGTAGAACTAAGACATAAGCAA AGTTTTTCAATCAAGAATACATGGGTGGCC | 5253 |
| TEE-244 | AAGAATTGGACAAAACACACAAACAAAGCAAGGAA GGAATGAAAGGATTTGTTGAAAATGAAAGTACACTC CACAGTGTGGGAGCAG | 5254 |
| TEE-245 | ACAGTTAACAAAAACCGAACAATCTAATTACGAAAT GAACAAAAGATATGAACAGACATTTCACCCGAGAGT ATACAGGGGCCAGGCATGGT | 5255 |
| TEE-246 | AAACGCACAAACAAAGCAAGGAAAGAATGAAGCAA CAAAAGCAGAGATTTATTGAAAATGAAAAATACACT CCACAGGGTGGG | 5256 |
| TEE-247 | CACCATGAGTCATTAGGTAAATGCAAATCAAAACCA CAATGAAATACTTCACACCCATGAAGATGGCTATAA TAAAAAAACAGACA | 5257 |

TABLE 32-continued

TEE Sequences

| TEE Identifier | Sequence | SEQ ID NO |
|---|---|---|
| TEE-248 | AGCAACTTCAGCAAAGTCTCAGGAGACAAAATCAAT GTACAAAAATCACAAGCATTCTTATACACCAATAAC AGACAAACAGAGAGCC | 5258 |
| TEE-249 | TGACATGCAAGAAATAAGGAAGTGCAAAAACAAAC AAACAAACAACAACAACAACAACAACAACAACAAC AAAAAACAGTCCCAAAAGGATGGGCAG | 5259 |
| TEE-250 | AGACTTGAAAAGCACAGACAACGAAAGCAAAAATG GACAAATGGAATCACATCAAGCTAAAAGGTTTTGCA TGGCAAAGG | 5260 |
| TEE-251 | GCAAAGAAACAATCAGTAGAGTAAACAGACAACT CATAGAATGCAAGAAAATCATCGCAATCTGTACATC CAACAAAGGGCT | 5261 |
| TEE-252 | ACAAAATCAAACTAACCTCGATAAGAATGCAAGTGA ATCAAAATGAGTTTCAAGGGGTTGTGGCTAGTACAC GCTTTCTACAGCTG | 5262 |
| TEE-253 | ACAAACCACTGCTCAAGGAAATAAGGACACAAACA AATGGAACAACATTCCGTGCTCATGGATAGGAAGAA TCAATATCGTGAAAATGGCCATACT | 5263 |
| TEE-254 | GAACGATTTATCACTGAAAATTAATACTCATGCAAG TAGTAAACGAATGTAATGACCATGATAAGGAGACGG ACGGTGGTGATAGT | 5264 |
| TEE-255 | AGCAGAAGAAATAACTGAAATCAGAGTGAAACTGA ATCAAATTGAGATGCAAAAATACATACGAAATGGCC AG | 5265 |
| TEE-256 | TGAATAGACACACAGACCAATGGAACAGAATAGAG AACACAGAATAAATCTGCACACTTATAGCCAGCTGA TTTTTGACAAATTTGCCAAG | 5266 |
| TEE-257 | AGCAACTTCAGCAGTCTCAGTATACAAAAACAATGT GCAAAAATCACAAGCATTCCTATATGCCAATAACAG ACAAACAGAGAGCC | 5267 |
| TEE-258 | ACCAATCAAGAAAACAATGCAACCCACAGAGAATG GACAAAAGCAAGGCAGGACAATGGCT | 5268 |
| TEE-259 | GCCACAATTTTGAAACAACCATAATAATGAGAATAC ACAAGACAACTCCAATAATGTGGGAAGACAAACTTT GCAATTCACATCATGGC | 5269 |
| TEE-260 | GAAAATGAACAATATGAACAAACAAACAAAATTACT ACCCTTACGAAAGTACGTGCATTCTAGTATGGTGAC AAAAAGGAAA | 5270 |
| TEE-261 | TATGCAAATCAATAAACATAATCCATCACATAAACA GAAACAAAGACAAAATGACATGATTATCTCAATAGA TGCAGAAAAGGCC | 5271 |
| TEE-262 | CACCCATCTGTAGGACCAGGAAGCCTGATGTGGGAG AGAACAGCAGGCTAAATCCAGGGTTGGTCTCTACAG CAGAGGGAATCACAAGCCTGTTAGCAAGTGAAGAAC CAACACTGGCAAGAGTGTGAAGGCC | 5272 |
| TEE-263 | AGGATACAAAATCAATGTACAAAAATCACAAACATT CTTATACACCAACAACAGACAAACAGAGAGCCAAAT CATGGGTG | 5273 |
| TEE-264 | AGGAAAATGCAAATCAGAACGACTATAACACACCAT CTCAAACTCGTTAGGATGGCTATTATCAAAAAGTCA AGAGATAACAAATGTGGGCAAGGG | 5274 |
| TEE-265 | GTAACAAAACAGACTCATAGACCAATAGAACAGAAT AGAGAATTCAGAAATAAGACTGCACTTCTATGACCA TGTGATCTTAGACAAACCT | 5275 |
| TEE-266 | AAAGGAAAACTACAAAACACTGCTGAAAGAAATCAT TGACAACACAAACAAATGGAAACACATCCCAAGATC ATGGGTGGGTGGAATCAAT | 5276 |

TABLE 32-continued

TEE Sequences

| TEE Identifier | Sequence | SEQ ID NO |
|---|---|---|
| TEE-267 | ACACACATACCAACAGAACATGACAAAAGAACAAA ACCAGCCGCATGCATACTCGATGGAGACAAAGGTAA CACTGCAGAATGGTGAAGGAAGAACAGTCATTTTAA TGACAGTGTTGGCT | 5277 |
| TEE-268 | AACTAAGACAACAGATTGATTTACACTACTATTTTCA CACAGCCAAAAATATCACTATGGCAATCGTCAAAAG GTCAATTCAAAGATGGGACAGT | 5278 |
| TEE-269 | GATCAGCTTAGAATACAATGGAACAGAACAGATTAG AACAATGTGATTTTATTAGGGGCCACAGCACTGTTG ACTCAAGTACAAGTTCTGACTCATGTAGAACTAACA CTTTT | 5279 |
| TEE-270 | GAATGGAATCAAATCGAATGAAATGGAATGGAATAG AAAGGAATGGAATGAAATGGAATGGAAAGGATTCG AAT | 5280 |
| TEE-271 | AAATGAACAAAACTAGAGGAATGACATTACCTGACT TCAAATTATACTACAGAGCTATAGTAACCAAAACAG CATGGTACAGGCAT | 5281 |
| TEE-272 | GGACAACATACACAAATCAGTCAAGATACATCATTT CAACAGAATGAAAGACAAAAACCATTTGATCACTTC AATCGATGATGAAAAAGCA | 5282 |
| TEE-273 | AACTTCAGCAAATTCTCAGGATACAAAATCAATGTG CAAAAACCACAAGCATTCCTATACACCAATAATAGA CAGTGAGCCAAAT | 5283 |
| TEE-274 | TATGACTTTCACAAATTACAGAAAAAGACACCCATT TGACAAGGGAACTGAAGGTGGTGAAGACATACTGGC AGGCTAC | 5284 |
| TEE-275 | AACAGCAATAGACACAAAGTCAGCACTTACAGTACA AAAACTAATGGCAAAAGCACATGAAGTGGGACAT | 5285 |
| TEE-276 | TGTAACACTGCAAACCATAAAAACCGTAGAAGAAAA CCTAGACAATACTATTCAGGACATAGGCATGGGCAA AGAC | 5286 |
| TEE-277 | GAAGAAGAAAAAACATGGATATACAATGTCAACAG AAATCAAGGAGAAACGGAATTTCACCAATCAATTTA GTGATCTGGGTT | 5287 |
| TEE-278 | AAAACACACAAACATACATGTGGATGCACATATAAA CATGCACATACACACACATAAATGCACAAACACA CTTAACACAAGCACACATGCAAACAAACACATGG | 5288 |
| TEE-279 | TAGAAGGAATTTGATACATGCTCAGAAATACAGGCA AAGGAAGTAGGTGCCTGCCAGTGAACACAGGGGAA CTATGGCTCCTA | 5289 |
| TEE-280 | TGACTAAACAGAGTTGAACAAGAACAAAAAGCAAA TTTGCAGAAATGAAATACATACTAATTGAAAGTCCA TGGACAGGCTCAACAGATGATATAGATACAGCTAAA GAGATAATTAGTGAAATGGATCAG | 5290 |
| TEE-281 | AAGTAATAAGACTGAATTAGTAATACAAAGTGTCTC AACAAAGAAAATTGCGGGACTGTTCATGCTCATGGA CAGGAAGAATCAATATCATGAAAATGGCC | 5291 |
| TEE-282 | ACAGACAGAGATTTAAAACAATAAACAAGCAGTAA GCAAACACAGATAACAAAATGACATGATCCAACAAA TACTCAGAAGGAGACTTAGAAATGAATTGAGGGTC | 5292 |
| TEE-283 | AGAAAAAAACAAACAGCCCATTAAAAGGTAGACAA AGGACATGAACACTTTTCAAAAGAAGACATACATGT GGCCAAACAGCATG | 5293 |
| TEE-284 | AAAAATGACCAGAGCAATAGAATGCATTGACCAGAT AAAGACCTTCACGTATGTTGAACTAAAATGTGTGGT GCAGGTG | 5294 |

TABLE 32-continued

TEE Sequences

| TEE Identifier | Sequence | SEQ ID NO |
|---|---|---|
| TEE-285 | AATCAGTCTAGATCTTAAAGGAACACCAGAGGGAGT ATTTAAATGTGCCCAATAAGCAAGAATTATGGTGAT GTGGAAGTA | 5295 |
| TEE-286 | GAATGGAATGGAAAGGAATCGAAACGAAAGGAATG GAGACAGATGGAATGGAATGGAACAGAGAGCAATGG | 5296 |
| TEE-287 | GGAATGGAATGAACACGAATGTAATGCAACCCAATA GAATGGAATCGAATGGCATGGAATATAAAGAAATGG AATCGAAGAGAATGGAAACAAATGGAATGGAATTG | 5297 |
| TEE-288 | AGGACATGAATAGACAATTCTCAAAAGAAGATACAC AAGTGGCAAACAAACACATGAAAAAAGACTCAACA TTAGTAATGACCATGGAAATGCAAATC | 5298 |
| TEE-289 | TCCAGTCGATCATCATATAGTCAGCACTTATCATACA CCAAGCCGTGTGCAAGGAAAGGGAATACAACCATGA ACATGATAGATGGATGGTT | 5299 |
| TEE-290 | TACAGATAAGAAAATTGAGACTCAAGAGTATTACAT AAATTGTTTCAGCTACCACAGCAAAAAATGGTATGG TTGGGAATCAAGCTCAGGG | 5300 |
| TEE-291 | AGCCTATCAAAAAGTGGGCTAAGAATATGAATACAC AATTCTCAAAAGAAGATATACAAATGGGCAACAAAC ATATGAAAACATACTCAACATCACTAATGATCAGGG AAATG | 5301 |
| TEE-292 | GAAAATGAACAATATGAACAAACAAACAAAATTACT ACCCTTACGAAAGTACGTGCATTCTAGTATGGTGAC AAAAAGGAAAG | 5302 |
| TEE-293 | ACATACGCAAATCAATAAACATAATCCATCACATAA ACAGAACCAAAGACAAAAATCACATGATTATCTCAA TAGATGCAGAAAAGGCCTTCGAC | 5303 |
| TEE-294 | AAGAGTATCAACAGTAAATTACATTAGCAGAAGAAT CAACAAACATGAAAATAGAAATTATGGTAGCCAAAG AACAG | 5304 |
| TEE-295 | AATCGAATGGAATCAACATCAAACGGAAAAAAACG GAATTATCGAATGGAATCGAAGAGAATCATCGAATG GACC | 5305 |
| TEE-296 | GAAAGGAATAGAATGGAATGGATCGTTATGGAAAG ACATCGAATGGGATGGAATTGACTCGAATGGATTGG ACTGGAATGGAACGGACTCGAATGGAATGGACTGGA ATG | 5306 |
| TEE-297 | TAAGCAATTTCAGCAGTCTCAGGATACAAAATCAAT GTGCAAAAATCACAAGCATTCTTATACACCAACAAC AGACAAACAGAGAGCCAAATCG | 5307 |
| TEE-298 | AACGGAATCAAACGGAATTATCGAATGGAATCGAAG AGAATCATCGAATGGCCACGAATGGAATCATCTAAT GGAATGGAATGGAATAATCCATGGACCCGAATG | 5308 |
| TEE-299 | ACATCAAACGGAATCAAACGGAATTATCGAATGGAA TCGAAAAGAATCATCGAACGGACTCGAATGGAATCA TCTAATGGAATGGAATGGAAG | 5309 |
| TEE-300 | ATCGAATGGAATCAACATCAAACGGAAAAAAACGG AATTATCAAATGGAATCGAAGAGAATCATCGAATGG ACC | 5310 |
| TEE-301 | GAATAATCATTGAACGGAATCGAATGGAAACATCAT CGAATGGAAACGAATGGAATCATCATCGAATGGAAA TGAAAGGAGTCATC | 5311 |
| TEE-302 | CATCAAACGGAATCAAACGGAATTATCGAATGGAAT CGAAAAGAATCATCGAACGGACTCGAATGGAATCAT CTAATGGAATGGAATGGAAGAATCCATGGACTCGAA TG | 5312 |

TABLE 32-continued

TEE Sequences

| TEE Identifier | Sequence | SEQ ID NO |
|---|---|---|
| TEE-303 | AAACGGAATCAAACGGAATTATCGAATGGAATCGAA GAGAATCATCGAATGGACTCGAATGGAATCATCTAA TGGAATGGAATGGAAGAATCCATGG | 5313 |
| TEE-304 | ATACACAAATCAATAAATGTAATCCAGCATATAAAC AGAACCAAAGACAAAAACCATATGATTATCTCAATG GATGCAGAAAAGGCC | 5314 |
| TEE-305 | AATCGAATAGAATCATCGAATGGACTCGAATGGAAT CATCGAATGTAATGATGGAACAGTC | 5315 |
| TEE-306 | TGGAATGGAATCATCGCATAGAATCGAATGGAATTA CCATCGAATGGGATCGAATGGTATCAACATCAAACG CAAAAAAACGGAATTATCGAATGGAATCGAAGAGA ATCTTCGAACGGACCCG | 5316 |
| TEE-307 | ATGGAATGGAATGGAATGGAATTAAATGGAATGGAA AGGAATGGAATCGAATGGAAAGGAATC | 5317 |
| TEE-308 | GTCGAAATGAATAGAATGCAATCATCATCAAATGGA ATCCAATGGAATCATCATCAAATAGAATCGAATGGA ATCATCAAATGGAATCGAATGGAGTCATTG | 5318 |
| TEE-309 | TGGAATTATCGAAAGCAAACGAATAGAATCATCGAA TGGACTCGAATGGAATCATCGAATGGAATGGAATGG AACAG | 5319 |
| TEE-310 | AAAGGAATGGAATGCAATGGAATGCAATGGAATGC ACAGGAATGGAATGGAATGGAATGGAAAGGAATG | 5320 |
| TEE-311 | AATCTAATGGAATCAACATCAAACGGAAAAAAACGG AATTATCGAATGGAATCGAAGAGAATCATCGAATGG ACC | 5321 |
| TEE-312 | TACACAACAAAAGAAATACTCAACACAGTAAACAGA CAACCTTCAGAACAGGAGAAAATATTTGCAAATACA TCTAACAAAGGGCTAATATCCAGAATCT | 5322 |
| TEE-313 | TGCAATCCTAGTCTCAGATAAAACAGACATTAAACC AACAAAGATCAAAAGAGACAAAGAAGGCCATTAC | 5323 |
| TEE-314 | GAATCGAATGGAATCAACATCAAACGGAAAAAAAC GGAATTATCGAATGGAATCGAAAAGAATCATCGAAT GGACC | 5324 |
| TEE-315 | AATGGAATCGAATGGAATGCAATCCAATGGAATGGA ATGCAATGCAATGGAATGGAATCGAACGGAATGCAG TGGAAGGGAATGG | 5325 |
| TEE-316 | GAACACAGAAAAATTTCAAAGGAATAATCAACAGG GATTGATAACTAACTGGATTTAGAGAGCCAAGGCAA AGAGAATCAAAGCACAGGGCCTGAGTCGGAG | 5326 |
| TEE-317 | AGTTGAATAGAACCAATCCGAATGAAATGGAATGGA ATGGAACGGAATGGAATTGAATGGAATGGAATGGA ATGCAATGGA | 5327 |
| TEE-318 | AACTCGATTGCAATGGAATGTAATGTAATGGAATGG AATGGAATTAACGCGAATAGAATGGAATGGAATGTA ATGGAACGGAATGGAATG | 5328 |
| TEE-319 | AAGCGGAATAGAATTGAATCATCATTGAATGGAATC GAGTAGAATCATTGAAATCGAATGGAATCATAGAAT GGAATCCAAT | 5329 |
| TEE-320 | AATGGAATCGAAAGGAATAGAATGGAATGGATCGTT ATGGAAAGATATCGAATGGAATGGAATTGACTCGAA TGGAATGGACTGGAATGGAACG | 5330 |
| TEE-321 | TAACGGAATAATCATCGAACAGAATCAAATGGAATC ATCATTGAATGGAATTGAATGGAATCTTCGAATAGA CATGAATGGACCATCATCG | 5331 |

TABLE 32-continued

TEE Sequences

| TEE Identifier | Sequence | SEQ ID NO |
|---|---|---|
| TEE-322 | AACGGAATCAAACGGAATTATCGAATGGAATCGAAT AGAATCATCGAACGGACTCGAATGGAATCATCTAAT GGAATGGAATGGAAG | 5332 |
| TEE-323 | ATTGGAATGGAACGGAACAGAACGGAATGGAATGG AATAGAATGGAATGGAATGGAATGGTATGGAATGGA ATGGAATGGTACG | 5333 |
| TEE-324 | AATCCACAAAGACAACAGAAGAAAAGACAACAGTA GACAAGGATGTCAACCACATTTTGGAAGAGACAAGT AATCAAACACATGGCA | 5334 |
| TEE-325 | GAATCGAATGGAATCAACATCAAACGGAAAAAAAC GGAATTATCGAATGGAATCGAAAAGAATCATCGAAC GGACTCGAATGGAATCATCTAATGGAATGGAATGGA AGAATCCATGG | 5335 |
| TEE-326 | AATGGAATCGAATGGAATCATCATCAAATGGAATCT AATGGAATCATTGAACGGAATTGGATGGAATCGTCAT | 5336 |
| TEE-327 | CAACATCAAACGGAAAAAAACGGAATTATCGAATGG AATCGAAGAGAATCATCGAATGGACC | 5337 |
| TEE-328 | CACAACCAAAGCAATGAAAGAAAAGCACAGACTTAT TGAAATGAAAGTACACACCACAGAATGGGAGCAGG CTCAAGCAAGC | 5338 |
| TEE-329 | ATCAAAGGGAATCAAGCGGAATTATCGAATGGAATC GAAGAATCATCGAATGGACTCGAATGGAATCATG TGATGGAATGGAATGGAATAATCCACGGACT | 5339 |
| TEE-330 | GGAATCGAATGGAATCAATATCAAACGGAGAAAAA CGGAATTATCGAATGGAATCGAAGAGAATCATCGAA TGGACC | 5340 |
| TEE-331 | AGGAATGGACACGAACGGAATGCAATCGAATGGAA TGGAATCTAATAGAAAGGAATTGAATGAAATGGACT GG | 5341 |
| TEE-332 | GGAAGGGAATCAAATGCAACAGAATGTAATGGAAT GGAATGCAATGGAATGCAATGGAATGGAATGGAATG CAATGGAATGG | 5342 |
| TEE-333 | AAATTGGATTGAATCGAATCGAATGGAAAAAATGAA ATCAAATGAAATTGAATGGAATCGAAATGAATGTAA ACAATGGAATCCAATGGAATCCAATGGAATCGAATC AAATGGTTTTGAGTGGCGTAAAATG | 5343 |
| TEE-334 | AATGGAAGGGAATGGAATGGAATCGAATCGAATGG AACAGAATTCAATGGAATGGAATGGAATGGAATGGA ATCGAATGGAATGG | 5344 |
| TEE-335 | GAAAAATCATTGAACGGAATCGAATGGAATCATCAT CGGATGGAAACGAATGGAATCATCATCGAATGGAAA TGAAAGGAGTCATC | 5345 |
| TEE-336 | GGAATCGAATGGAATCAACATCAAACGGAGAAAAA CGGAATTATCGAATGGAATCGAAGAGAATCATCGAA TGGACC | 5346 |
| TEE-337 | AAAGAAATGTCACTGCGTATACACACACACGCACAT ACACACACCATGGAATACTACTCAGCTATACAAAGG AATGAAATAATCCACAGCCAC | 5347 |
| TEE-338 | GGAATCGAATGGAATCAATATCAAACGGAAAAAAA CGGAATTATCGAATGGAATCGAAGAGAATCATCGAA TGGACC | 5348 |
| TEE-339 | TGAACGGAATCGAATGGAATCATCATCGGATGGAAA CGAATGGAATCATCATCGAATGGAAATGAAAGGAGT CATC | 5349 |
| TEE-340 | GAATAGAACGAAATGGAATGGAATGGAATGGAATG GAAGGAATGGAATGGAATGGAATGGAACG | 5350 |

TABLE 32-continued

TEE Sequences

| TEE Identifier | Sequence | SEQ ID NO |
|---|---|---|
| TEE-341 | TGGAATTATCGTCGAATAGAATCGAATGGTATCAAC ATCAAACGGAAAAAAACGGAATTATCGAATGGAATC GAAGAGAATCATCGAACGGACTCGAATGGAATCATC TAATGGAATGGAATGGAATAATCCATGG | 5351 |
| TEE-342 | GACAAAAAGAATCATCATCGAATAGAATCAAATGGA ATCTTTGAATGGACTCAAAAGGAATATCGTCAAATG GAATCAAAAGCCATCATCGAATGGACTGAAATGGAA TTATCAAATGGACTCG | 5352 |
| TEE-343 | AACCAAACCAAGCAAACAAACAAACAGTAAAAACT CAATAACAACCAACAAACAGGAAATACCAGGTAATT CAGATTATCTAGTTATGTGCCATAGT | 5353 |
| TEE-344 | GAATGAATTGAATGCAAACATCGAATGGTCTCGAAT GGAATCATCTTCAAATGGAATGGAATGAATCATCG CATAGAATCGAATGGAATTATCAACGAATGGAATCG AATGGAATCATCATCAGATGGAAATGAATGGAATCG TCAT | 5354 |
| TEE-345 | TGGAATGGAATCAAATCGCATGGAATCGAATGGAAT AGAAAAGAATCAAACAGAGTGGAATGGAATGGAAT GGAATGGAATCATGCCGAATGGAATG | 5355 |
| TEE-346 | AAATGGAATAATGAAATGGAATCGAACGGAATCATC ATCAAAAGGAACCGAATGAAGTCATTGAATGGAATC AAAGGCAATCATGGTCGAATGGAATCAAATGGAAAC AGCATTGAATAGAATTGAATGGAGTCATCACATGGA ATCG | 5356 |
| TEE-347 | GAATTAACCCGAATAGAATGGAATGGAATGGAATGG AACAGAACGGAACGGAATGGAATGGAATGGAATGG AATGGAATG | 5357 |
| TEE-348 | AAGATATACAAGCAGCCAACAAACATACGAAAGAA TGCTCAACATCACTAATCCTCAGAGAAATTTAAATCA AAACCACAATGAGTTACAATCTCATACCAGTCAGAAT | 5358 |
| TEE-349 | AGATAAGTGGATGAACAGATGGACAGATGGATGGAT GGATGGATGGATGGATGGATGCCTGGAAGAAAGAA GAATGGATAGTAAGCTGGGTATA | 5359 |
| TEE-350 | AGAATTACAAACCACTGCTCAACAAAATAAAAGAGT ACACAAACAAATGGAAGAATATTCCATGCTTATGGA TAGGAAGAATCAATATTGTGAAAATGGCCATACT | 5360 |
| TEE-351 | CATCGAATGGACTCGAATGGAATAATCATTGAACGG AATCGAAGGGAATCATCATCGGATGGAAACGAATGG AATCATCATCGAATGGAAATG | 5361 |
| TEE-352 | AAAGGAATCAAACGGAATTATCGAATGGAATCGAAA AGAATCATCGAACGGACTCGAATGGAATCATCTAAT GGAATGGAATGGAAGAATCCATGGACTCGAATG | 5362 |
| TEE-353 | GGATATAAACAAGAAAACAACTAATCACAACTCAAT ATCAAAGTGCAATGATGGTGCAAAATGCAAGTATGG TGGGGACAGAGAAAGGATGC | 5363 |
| TEE-354 | AACATCAAACGGAAAAAAACGGAAATATCGAATGG AATCGAAGAGAATCATCGAATGGACC | 5364 |
| TEE-355 | TAAAATGGAATCGAATGGAATCAACATCAAATGGAA TCAAATGGAATCATTGAACGGAATTGAATGGAATCG TCAT | 5365 |
| TEE-356 | AATCATCATCGAATGGAATCGAATGGTATCATTGAA TGGAATCGAATGGAATCATCATCAGATGGAAATGAA TGGAATCGTCAT | 5366 |
| TEE-357 | CAATGCGTCAAGCTCAGACGTGCCTCACTACGGCAA TGCGTCAAGCTCAGGCGTGCCTCACTAT | 5367 |
| TEE-358 | TAAGCTGATAAGCAACTTTAGCAAAGTCTCAGGATA CAAAATCAATGTACAAAAATCACAAGCATTCTTATA CACCAACAACAGACAGACGGAGAGCCAAA | 5368 |

TABLE 32-continued

TEE Sequences

| TEE Identifier | Sequence | SEQ ID NO |
|---|---|---|
| TEE-359 | AATCAAAGAATTGAATCGAATGGAATCATCTAATGT ACTCGAATGGAATCACCAT | 5369 |
| TEE-360 | ATGAACACGAATGTAATGCAATCCAATAGAATGGAA TCGAATGGCATGGAATATAAAGAAATGGAATCGAAG AGAATGGAAACAAATGGAATGGAATTGAATGGAAT GGAATTG | 5370 |
| TEE-361 | ATCAAACGGAATCAAACGGAATTATCGAATGGAATC GAAGAGAATCATCGAACGGACTCGAATGGAATCATC TAATGGAATGGGATGG | 5371 |
| TEE-362 | AATGGAAAGGAATCAAATGGAATATAATGGAATGCA ATGGACTCGAATGGAATGGAATGGAATGGACCCAAA TGGAATGGAATGGAATGGAATG | 5372 |
| TEE-363 | GGAATACAACGGAATGGAATCGAAAAAAATGGAAA GGAATGAAATGAATGGAATGGAATGGAATGGAATG GATGGGAATGGAATGGAATGG | 5373 |
| TEE-364 | GAATCAAGCGGAATTATCGAATGGAATCGAAGAGAA TCATCGAAAGGACTCGAATGGAATCATCTAATGGAA TGGAATGGAATAATACACGGACC | 5374 |
| TEE-365 | AAGATAACCTGTGCCCAGGAGAAAAACAATCAATGG CAACAAAAGCAGAAACAACACAAATGATACAATTA GCAGACAGAAACATTGAGATTGCTATT | 5375 |
| TEE-366 | AATGGACTCCAATGGAATAATCATTGAACGGAATCT AATGGAATCATCATCGGATGGAAATGAGTGGAATCA TCATCGAATGGAATCG | 5376 |
| TEE-367 | AATCTATAAACGTAATCCATCACATAAACAGGACCA AAGAGAAAAACCGCATGATTATCTCAAGAATGCAGA AAAGGCC | 5377 |
| TEE-368 | TAATTGATTCGAAATTAATGGAATTGAATGGAATGC AATCAAATGGAATGGAATGTAATGCAATGGAATGTA ATAGAATGGAAAGCAATGGAATG | 5378 |
| TEE-369 | AAAGGAATGGACTTGAACAAAATGAAATCGAACGAT AGGAATCGTACAGAACGGAAAGAAATGGAACGGAA TGGAATG | 5379 |
| TEE-370 | TGAGCAGGGAACAATGCGGATAAATTTCACAAATAC AATGTTGAGCAAAAGAAAGACACAAAAGAATACAC ACATACACACCATATGGGCTAGG | 5380 |
| TEE-371 | AATGGAATCGAACGGAATCATCATCAAACGGAACCG AATGGAATCATTGAATGGAATCAAAGGCAATCATGG TCGAATG | 5381 |
| TEE-372 | AATGGAATGGAATGTACAAGAAAGGAATGGAATGA AACCGAATGGAATGGAATGGACGCAAAATGAATGG AATGGAAGTCAATGG | 5382 |
| TEE-373 | AACGGAAAAAACGGAATTATCGAATGGAATCGAA GAGAATCATCGAATGGACC | 5383 |
| TEE-374 | GGAATAATCATTGAACGGAATCGAATGGAATCATCA TCGGATGGAAACGAATGGAATCATCATCGAATGGAA ATGAAAGGAGTCATC | 5384 |
| TEE-375 | GGAACGAAATCGAATGGAACGGAATAGAATAGACT CGAATGTAATGGATTGCTATGTAATTGATTCGAATGG AATGGAATCG | 5385 |
| TEE-376 | TGAAAGGAATAGACTGGAACAAAATGAAATCGAAT GGTAGGAATCATACAGAACAGAAAGAAATGGAACG GAATGGAATG | 5386 |
| TEE-377 | AACCCGAATAGAATGGAATGGAATGGAATGGAACG GAACGGAATGGAATGGAATGGATTGGAATGGAATG GAATG | 5387 |

TABLE 32-continued

TEE Sequences

| TEE Identifier | Sequence | SEQ ID NO |
|---|---|---|
| TEE-378 | AAAGAGAATCAAATGGAATTGAATCGAATGGAATCG<br>AATGGATTGGAAAGGAATAGAATGGAATGGAATGG<br>AATGGAATGGAATGGAATG | 5388 |
| TEE-379 | AATGGAATCATCAGTAATGGAATGGAAAGGAATGGA<br>AAGGACTGGAATGGAATGGAATGGAATGGAATGG | 5389 |
| TEE-380 | GGAACAAAATGAAATCGAACGGTAGGAATCGTACA<br>GAACGGAAAGAAATGGAACGGAATGGAATGCACTC<br>AAATGGAAAGGAGTCCAATGGAATCGAAAGGAATA<br>GAATGGAATGG | 5390 |
| TEE-381 | AGAATGAGATCAAGCAGTATAATAAAGGAAGAAGT<br>AGCAAAATTACAACAGAGCAGTGAAATGGATATGCT<br>TTCTGGCAATAATTGTGAAAGGTCTGGTAATGAGAA<br>AGTAGCAACAGCTAGTGGCTGCCAC | 5391 |
| TEE-382 | AACAAATGGAATCAACATCGAATGGAATCGAATGGA<br>AACACCATCGAATTGAAACGAATGGAATTATCATGA<br>AATTGAAATGGATGGACTCATCATCG | 5392 |
| TEE-383 | TAACATGCAGCATGCACACACGAATACACAACACAC<br>AAACATGTATGCACGCACACGTGAATACACAACACA<br>CACAAACATGCATGCATGCATACATGAATACACAGC<br>ACACAAATATCCAGCAT | 5393 |
| TEE-384 | GAATGGAATCAACATCAAACGGAAAAAAAACGGAA<br>TTATCGAATGGAATCGAATAGAATCATCGAATGGACC | 5394 |
| TEE-385 | AATCGAATGAAATGGAGTCAAAAGGAATGGAATCG<br>AATGGCAAGAAATCGAATGTAATGGAATCGCAAGGA<br>ATTGATGTGAACGGAACGGAATGGAAT | 5395 |
| TEE-386 | AATGGAATTGAACGGAAACATCAGCGAATGGAATCG<br>AAAGGAATCATCATGGAATAGATTCGAATGGAATGG<br>AAAGGAATGGAATGGAATG | 5396 |
| TEE-387 | ATGGAATCAACATCAAACAGAATCAAACGGAATTAT<br>CGAATGGAATCGAAGACAATCATCGAATGGACTCGA<br>ATGGAATCATCTAATGGAATGGAATGGAAGAATCCA<br>TGGTCTCGAATGCAATCATCATCG | 5397 |
| TEE-388 | GAATAATCATTGAACGGAATCGAATGGAATCATCTT<br>CGGATGGAAACGAATGGAATCATCATCGAATGGAAA<br>TGAAAGGAGTCATC | 5398 |
| TEE-389 | AATGGACTCGAATGGAATAATCATTGAACGGAATCG<br>AATGGAATCATCATCGGATGGAAATGAGTGGAATCA<br>TCATCGAATGGAATCG | 5399 |
| TEE-390 | AAATGAAATCGAACGGTAGGAATCGTACAGAACGG<br>AAAGAAATGGAACGGAATGGAATGCAATCGAATGG<br>AAAGGAGTCCAATGGAAGGGAATCGAAT | 5400 |
| TEE-391 | TACCAAACATTTAAAGAACAAATATCAATCCTACGC<br>AAACCATTCTGAAACACAGAGATGGAGGATATACAG<br>CGAAACTCATTCTACATGGCC | 5401 |
| TEE-392 | TATTGGAATGGAATGGAATGGAGTCGAATGGAACGG<br>AATGCACTCGAATGGAAGGCAATGCAATGGAATGCA<br>CTCAACAGGAATAGAATGGAATGGAATGGAATGG | 5402 |
| TEE-393 | GGAATTTAATAGAATGTACCCGAATGGAACGGAATG<br>GAATGGAATTGTATGGCATGGAATGGAA | 5403 |
| TEE-394 | GCAATCCAATAGAATGGAATCGAATGGCATGGAATA<br>TAAAGAAATGGAATCGAAGAGAATGGAGACAAATG<br>GAATGGAATTGAATGGAATGGAATTG | 5404 |
| TEE-395 | AATGGAATCGAATGGAATCATCATCAAATGGAATCT<br>AATGGAATCATTGAACGGAATTAAATGGAATCGTCA<br>TCGAATGAATTCAATGCAATCAACGAATGGTCTCGA<br>ATGGAACCAC | 5405 |

TABLE 32-continued

TEE Sequences

| TEE Identifier | Sequence | SEQ ID NO |
|---|---|---|
| TEE-396 | AATTGCAAAAGAAACACACATATACACATATAAAAC TCAAGAAAGACAAAACTAACCTATGGTGATAGAAAT CAGAAAAGTACAGTACATTGGTTGTCTTGGTGGG | 5406 |
| TEE-397 | TGACATCATTATTATCAAGAAACATTCTTACCACTGT TACCAACTTCCCAACACAGACTATGGAGAGAGAGAT AAGACAGAATAGCATT | 5407 |
| TEE-398 | AAAGAATTGAATTGAATAGAATCACCAATGAATTGA ATCGAATGGAATCGTCATCGAATGGAATCGAAGGGA ATCATTGGATGGGCTCA | 5408 |
| TEE-399 | ATCATCGAATGGAATCGAATGGAATCAATATCAAAC GGAAAAAAACGGAATTATCGAATGGAATCGAATAG AATCATCGAATGGACC | 5409 |
| TEE-400 | GAATGAAATCGTATAGAATCATCGAATGCAACTGAA TGGAATCATTAAATGGACTTGAAAGGAATTATTATG GAATGGAATTG | 5410 |
| TEE-401 | TAAGCAACTTCAGCAAAGTCTCAGGATACAAAATCA ATGTGCAAAAATCTCAAGCATTCTTATACACGAACA ACAGACAAACAGAGAGCT | 5411 |
| TEE-402 | ACTCAAAAGGAATTGATTCGAATGGAATAGAATGGC AAGGAATAGTATTGAATTGAATGGAATGGAATGGAC CCAAATG | 5412 |
| TEE-403 | GAATGGAATTTAAAGGAATAGAATGGAAGGAATCG GATGGAATGGAATGGAATAGAATGGAGTCGAATGG AATAGAATCGAATGGAATGGCATTG | 5413 |
| TEE-404 | TGAGAAAATGATGGAAAAGAGGAATAAAACGAAAC AAAACCACAGGAACACAGGTGCATGTGAATGTGCAC AGACAAAGATACAGGGCGGACTGGGAAGGAAGTTT CTGCACCAGAATTTGGGG | 5414 |
| TEE-405 | AACAAAAAATGAGTCAAGCCTTAAATAAAATCAGAG CCAAAAAAGAAGACATTACATCTGATAAGACAAAAA TTCAAAGGACCATC | 5415 |
| TEE-406 | AACCCAGTGGAATTGAATTGAATGGAATTGAATGGA ATGGAAAGAATCAATCCGAGTCGAATGGAATGGTAT GGAATGGAATGGCATGGAATCAAC | 5416 |
| TEE-407 | ATCAACATCAAACGGAAAAAAAACGGAATTATCGAA TGGAATCGAAGAGAATCATCGAATGGACC | 5417 |
| TEE-408 | AAGGAATGGAATGGTACGGAATAGAATGGAATGGA ACGAATTGTAATGGAATGGAATTTAATGGAACGGAA TGGAATGGAATGGAATCAACG | 5418 |
| TEE-409 | AACGGAATGGAAAGCAATTTAATCAAATGCAATACA GTGGAATTGAAGGGAATGGAATGGAATGGC | 5419 |
| TEE-410 | AATCGAATGGAACGGAATAGAATAGACTCGAATGTA ATGGATTGCTATGTAATTGATTCGAATGGAATGGAA TCGAATGGAATGCAATCCAATGGAATGGAATGCAAT GCAATGGAATGGAATCGAACGGAATGCAGTGGAAG GGAATGG | 5420 |
| TEE-411 | TAGCAACATTTTAGTAACATGATAGAAACAAAACAG CAACATAGCAATGCAATAGTAACACAACAGCAACAT CATAACATGGCAGCA | 5421 |
| TEE-412 | AATGGAATCGAAGAGAATGGAAACAAATGGAATGG AATTGAATGGAATGGAATTGAATGGAATGGGAAGGA ATGGAGTG | 5422 |
| TEE-413 | AGCAAACAAGTGAATAAACAAGCAAACAAGTGAAC AAGCAAACAAGTGAATAAACAAGCAAACAAGTGAA CAAGCAAACAAGTGAATAAACAAGCAAACAAGTGA ACAAGGAAACAAGTGAATAAACAAAGGCTCT | 5423 |

TABLE 32-continued

TEE Sequences

| TEE Identifier | Sequence | SEQ ID NO |
|---|---|---|
| TEE-414 | AATGGAATCAACACGAGTGCAATTGAATGGAATCGA ATGGAATGGAATGGAATGGAATGAATTCAACCCGAA TGGAATGGAAAGGAATGGAATC | 5424 |
| TEE-415 | GAATCGAATGGAATCAACATCAAACGGAAAAAAAC GGAATTATCGAATGGAATCGAAGAGAATCATCGAAT GGACC | 5425 |
| TEE-416 | AACACGAATGTAATGCAATCCAATAGAATGGAATCG AATGGCATGGAATATAAAGAAATGGAATCGAAGAG AATGGAAACAAACGGAATGGAATTGAATGGAATGG AATTGAATGGAATGGGAACGAATGGAGTGAAATTG | 5426 |
| TEE-417 | GAATGGAACGGAATAGAACAGACTCGAATGTAATGG ATTGCTATGTAATTGATTCGAATGGAATGGAATCGA ATGGAATGCAATCCAATGGAATGGAATGCAATGCAA TGGAATGGAATCGAATGGAATGCAGTGGAAGGGAAT GG | 5427 |
| TEE-418 | GAATCGAATGGAATCAATATCAAACGGAAAAAAAC GGAATTATCGAATGGAATCGAAGAGAATCATCGAAT GGACC | 5428 |
| TEE-419 | ATAAACATCAAACGGAATCAAACGGAATTATCGAAT GGAATCGAAGAGAATAATCGAATGGACTCAAATGGA GTCATCTAATGGAATGGTATGGAAGAATCCATGGAC TCCAACGCAATCATCAGCGAATGGAATC | 5429 |
| TEE-420 | AAAAGAAAAGACAAAAGACACCAATTGCCAATACT GAAATGAAAAACAGGTAATAACTATTGATCCCATG GACATTAAAATGATGTTGAAGGAACACCAC | 5430 |
| TEE-421 | AATGTCAAGTGGAATCGAGTGGAATCATCGAAAGAA ATCGAATGGAATCGAAGGGAATCATTGGATGGGCTC AAAT | 5431 |
| TEE-422 | ATCATCGAATGGAATAGAATGGTATCAACATCAAAC GGAGAAAAACGGAATTATCGAATGGAATCGAAGAG AATCTTCGAACGGACC | 5432 |
| TEE-423 | GAATGGAATCATCGCATAGAATCGGATGGAATTATC ATCGAATGGAATCGAATGGTATCAACATCAAACGGA AAAAAACGGAATTATCGAATGGAATCGAATTGAATC ATCGAACGGACCCG | 5433 |
| TEE-424 | AATGGACTCGAATGGAATAATCATTGAACGGAATCG AATGGAATCATCATCGGATGGAAATGAATGGAATAA TCCATGGACTCGAATGCAATCATCATCGAATGGAAT CGAATGGAATCATCGAATGGACTCG | 5434 |
| TEE-425 | AATGCAATCATCAACTGGCTTCGAATGGAATCATCA AGAATGGAATCGAATGGAATCATCGAATGGACTC | 5435 |
| TEE-426 | AAGAGACCAATAAGGAATAAGTAAGCAACAAGAGG AAGGAGAAAAGGGCAAGAGAGATGACCAGAGTT | 5436 |
| TEE-427 | TGGAATCATCATAAAATGGAATCGAATGGAATCAAC ATCAAATGGAATCAAATGGAATCATTGAACGGAATT GAATGGAATCGTCAT | 5437 |
| TEE-428 | GGAATCATCGCATAGAATCGAATGGAATTATCATCG AATGGAATCGAATGGAATCAACATCAAACGAAAAA AAACCGGAATTATCGAATGGAATCGAAGAGAATCAT CGAACGGACC | 5438 |
| TEE-429 | AAATCATCATCGAATGGGATCGAATGGTATCCTTGA ATGGAATCGAATGGAATCATCATCAGATGGAAATGA ATGGAATCGTCAT | 5439 |
| TEE-430 | GGAATGTAATAGAACGGAAAGCAATGGAATGGAAC GCACTGGATTCGAGTGCAATGGAATCTATTGGAATG GAATCGAATGGAATGGTTTGGCATGGAATGGAC | 5440 |

TABLE 32-continued

TEE Sequences

| TEE Identifier | Sequence | SEQ ID NO |
|---|---|---|
| TEE-431 | AAACAATGGAAGATAATGGAAAGATATCGAATGGA ATAGAATGGAATGGAATGGACTCAAATGGAATGGAC TTTAATGGAATGG | 5441 |
| TEE-432 | GGAACGAAATCGAATGGAACGGAATAGAATAGACT CGAATGTAATGGATTGCTATGTAATTGATTCGAATGG AATGGAATCGAATGGAATGCAATCCAATGGAATGGA ATGCAATGCAATGAATGGAATGGAATGGAATGGAAT GGAA | 5442 |
| TEE-433 | AAACCGAATGGAATGGAATGGACGCAAAATGAATG GAATGGAAGTCAATGGACTCGAAATGAATGGAATGG AATGGAATGGAATG | 5443 |
| TEE-434 | GGAATCGAATGGAATCAACATCAAACGGAAAAAAA CAGAATTATCGTATGGAATCGAATAGAATCATCGAA TGGACC | 5444 |
| TEE-435 | CAACCCGAGTGGAATAAAATGGAATGGAATGGAATG AAATGGAATGGATCGGAATGGAATCCAATGGAATCA ACTGGAATGGAATGGAATGGAATG | 5445 |
| TEE-436 | TATCATCGAATGGAATCGAATGGAATCAACATCAAA CGGAAAAAAACGGAATTATCGAATGGAATCGAAGA GAATCATCGAATGGACC | 5446 |
| TEE-437 | CGGAATAATCATTGAACGGAATCGAATGGAATCATC ATCGGATGGAAACGAATGGAATCATCATCGAATGGA AATGAAAGGAGTCATC | 5447 |
| TEE-438 | CAACACACAGAGATTAAAACAAACAAACAAACAAT CCAGCCCTGACATTTATGAGTTTACAGACTGGTGGA GAGGCAGAGAAG | 5448 |
| TEE-439 | CACTACAAACCACGCTCAAGGCAATAAAAGAACACA AACAAATGGAAAAACATTCCATGCTCATGGATGGG | 5449 |
| TEE-440 | AATCGAATGGAATTAACATCAAACGGAAAAAAACG GAATTATCGAATGGAATCGAAGAGAATCATCGAATG GACC | 5450 |
| TEE-441 | TGGAAAAGAATCAAATTGAATGGCATCGAACGGAAT GGGATGGAATGGAATAGACCCAGATGTAATGGACTC GAATGGAATG | 5451 |
| TEE-442 | GACTAATATTCAGAATATACAAGGAACTCAAACAAC TCAACAGTAGAAAAAAAAACCTGAATAGACATTTCT CAAAAGAAGACATACAAATGGCC | 5452 |
| TEE-443 | GGTCCATTCGATGATTCTCTTCGATTCCATTCGATAA TTCCGTTTTTTCCCGTTTGATGTTGATTCC | 5453 |
| TEE-444 | GGAACGAAATCGAATGGAACGGAATAGAATAGACT CGAATGTAATGGATTGCTATGTAATTGATTCGAATGG AATGGAATCGAATGGAATGCAATCCAATGGAATGGA ATGCAATGCAATGAATGGAATGGAATGGAATGGAAT GGA | 5454 |
| TEE-445 | AGCAACTTCAGTAAAGTGTCAGGATACAAAATCAAT GTGCAAAAATCACAAGCATTCTTATACATCAATAAC AGACAAACAGAGAGCCAAA | 5455 |
| TEE-446 | GAATAATCATTGAACGGAATCGAATGGAATCATCAT CGGATGGAAACGAATGGAATCATCATCGAATGGAAA TGAAAGGAGTCATC | 5456 |
| TEE-447 | TAATCATCTTCGAATTGAAAACAAAGCAATCATTAA ATGTACTCTAACGGAATCATCGAATGGACC | 5457 |
| TEE-448 | GGAATCGAATGGAATCAACATCAAACGGAAAAAAA CGGAATTATCGAATGGAATCGAAGAGAATCATCGAA TGGACC | 5458 |

TABLE 32-continued

TEE Sequences

| TEE Identifier | Sequence | SEQ ID NO |
|---|---|---|
| TEE-449 | AGAGAAAAGATGATCATGTAACCATTGAAAAGACAA TGTACAAAACTAATACTAATCACACAGGACCAGAAA GCAATTTAGACCAT | 5459 |
| TEE-450 | AATGGAATCGAATGGAATCAACATCAAACGGAAAA AACGGAATTATCGAATGGAATCAAAGAGAATCATCG AATGGACC | 5460 |
| TEE-451 | AATGGAATTATCATCGAATGGAATCGAATGGAATCA ACATCAAACGGAAAAAAACGGAATTATCGAATGGA ATCGAAGAGAATCATCGAATGGACC | 5461 |
| TEE-452 | GTCAACACAGGACCAACATAGGACCAACACAGGGTC AACACAGGACCAACATAGGACCAACACAGGGTCAA CACAAGACCAACATGGGACCAACACAGGGTCAACAT AGGACCAACATGGGACCAACACAGGGTCAACACAG GACCAAC | 5462 |
| TEE-453 | GAATCAACTCGATTGCAATCGAATGGAATGGAATGG TATTAACAGAATAGAATGGAATGGAATGGAATGGAA CGGAACG | 5463 |
| TEE-454 | ACTCGAATGCAATCAACATCAAACGGAATCAAACGG AATTATCGAATGGAATCGAAGAGAATCATCGAACGG ACTCGAATGGAATCATCTAATGGAATGGAATGG | 5464 |
| TEE-455 | AATGGAATGGAATAATCGACGGACCCGAATGCAATC ATCATCGTACAGAATCGAATGGAATCATCGAATGGA CTGGAATGGAATGG | 5465 |
| TEE-456 | AATACAAACCACTGCTCAACGAAATAAAAGAGGATA CAAACAAATGGAAGAACATTCTATGCTCATGGGTAG GATGAATTCATATCGTGAAAATGGCCATACTGCC | 5466 |
| TEE-457 | AAACACGCAAACACACACACAAGCACACTACCACAC AAGCGGACACACATGCAAACACGCGAACACACACA CATATACACACAAGCACATTACAAAACACAAGCAAA CACCAGCAGACACACAAACACACAAACATACATGG | 5467 |
| TEE-458 | AATCGAACGGAATCAACATCAAACGGAAAAAAAAC GGAATTATCGAATGGAATCGAAGAGAATCATCGAAT GGACC | 5468 |
| TEE-459 | TAATTGATTCGAATGGAATGGAATAGAATGGAATTG AATGGAATGGACCATAATGGATTGGACTTTAATAGA AAGGGCATG | 5469 |
| TEE-460 | AGCAACTTCAGCAAAGTCTCAGGATACAAAATCAAT GTACAAAAGTCACAAGCATTCTTATACACCAACAAA AGACAAACAGAGAGCC | 5470 |
| TEE-461 | ACATCAAACGGAAAAAAAAAACAAACGGAATTAT CGAATGGAATCGAAGAGAATCATCGAATGGACC | 5471 |
| TEE-462 | GAAATTCCAATTAAAATGAAATCGACTTATCTTAAC AAATATAGCAATGCTGACAACACTTCTCCGGATATG GGTACTGCT | 5472 |
| TEE-463 | ACATCTCACTTTTAGTAATGAACAGATCATTCAGACA GAAAATTAGCAAAGAAACATCAGAGTTAAACTACAC TCTAAACCAAATGGACCTA | 5473 |
| TEE-464 | GAAGAAAGCATTCATTCAAGACATCTAACTCGTTGA TATAATGCATACAGTTCAAAATGATTACACTATCATT ACATCTAGGGCTTTC | 5474 |
| TEE-465 | ACACACACATTCAAAGCAGCAATATTTACAACAGCC AAAAGGTGGAAACAATTGAGCAATTG | 5475 |
| TEE-466 | ATCATCGAATAGAATCGAATGGTATCAACACCAAAC GGAAAAAAACGGAATTATCGAATGGAATCGAAGAG AATCTTCGAACGGACC | 5476 |
| TEE-467 | ATCAACATCAAACGGAAAAAACGGAATTATCGAATG GAATCGAAGAGAATCATCGAACGGACC | 5477 |

TABLE 32-continued

TEE Sequences

| TEE Identifier | Sequence | SEQ ID NO |
|---|---|---|
| TEE-468 | AATCGAAAGGAATGTCATCGAATGGAATGGACTCAA ATGGAATAGAATCGGATGGAATGGCATCGAATGGAA TGGAATGGAATTGGATGGAC | 5478 |
| TEE-469 | AACATGAACAGTGGAACAATCAGTGAACCAATACAA GGGTTAAATAAGCTAGCAATTAAAAGCTGTATCACT GGTCTAAAGATAGAAGATCAAGTAGAAAATCAGCGC AAGAGGAAAGATATACGAAAACTAATGGCC | 5479 |
| TEE-470 | CGAATGGAATCATTATGGAATGGAATGAAATGGAAT AATCAAATGGAATTGAATGGAATCATCGAATGGAAT CGAACAAAATCCTCTTTGAATGGAATAAGATGGAAT CACCAAATGGAATTG | 5480 |
| TEE-471 | AAGGGAATTGAATAGAATGAATCCGAATGGAATGGA ATGGAATGGAATGGAATGGAATGGAATGGAATGGA ATGGAATG | 5481 |
| TEE-472 | GAATGGAATCGAATCAAATTAAATCAAATGGAATGC AATAGAAGGGAATACAATGGAATAGAATGGAATGG AATGGAATGGACT | 5482 |
| TEE-473 | AAACGGAATCAAACGGAATTATCGAATGGAATCGAA GAGAATCATCGAACGGACTCGAATGGAATCATCTAA TGGAATGGAATGGAAGAATCCATGGACT | 5483 |
| TEE-474 | ATGGAATCAACATCAAACGGAAAAAAAAACGGAAT TATCGAATGGAATCGAAGAGAATCATCGAATGGACC AGAATGGAATCATCTAATGGAATGGAATGG | 5484 |
| TEE-475 | AATGGAATCATCATCGAATGGAATCGAATGGAATCA TGGAATGGAATCAAATGGAATCAAATGGAATCGAAT GGAATGGAATGGAATG | 5485 |
| TEE-476 | AACGGAATCAAACGGAATTACCGAATGGAATCGAAT AGAATCATCGAACGGACTCGAATGGAATCATCTAAT GGAATGGAATGGAAG | 5486 |
| TEE-477 | AAACGGAATCAAACGGAATTATCGAATGGAATCGAA AAGAATCATCGAACGGACTCGAATGGAATCATCTAA TGGAATGGAATGGAAGAATCCATGG | 5487 |
| TEE-478 | GAATGATACGGAATACAATGGAATGGAACGAAATG AAATGGAATGGAATGGAATGGAATGGAATGGAATGG | 5488 |
| TEE-479 | ACAGCAAGAGAGAAATAAAACGACAAGAAAACTAC AAAATGCCTATCAATAGTTACTTTAAATATCAGTGGA CCAAATCAGTGAAACAAAAGACACAGAGTGGC | 5489 |
| TEE-480 | AATGGACTCGAATGGATTAATCATTGAACGGAATCG AATGGAATCATCATCGGATGGTAATGAATGGAATCA TCATCGAATGGAATCGG | 5490 |
| TEE-481 | GAATGGAATCGAAAGGAATGTCATCGAATGGAATGG AATGGAACGGAATGGAATCGAATGGAATGGACTCGA ATGGAATAGAATCGAATGCAATGGCATCG | 5491 |
| TEE-482 | ATCGAATGGAATCAACATCAGACGGAAAAAAACGG AATTATCAAATGGAATCGAAGAGAATCATCGAATGG ACC | 5492 |
| TEE-483 | AGCAACTTCAGCAAAGTCTCAGGATACAAAATCAAT GTGCAAAAATCAAAAGCATTCTTATGCACCAATAAC AGACACAGAGCCAAAT | 5493 |
| TEE-484 | AATGGAATGGAACGCAATTGAATGGAATGGAATGGA ACGGAATCAACCTGAGTCAAATGGAATGGAATGGAA TGGAATG | 5494 |
| TEE-485 | GGAACGAAATCGAATGGAACGGAATAGAATAGACT CGAATGTCATGGATTGCTATGTAATTGATTGGAATGG AATGGAATCG | 5495 |

TABLE 32-continued

TEE Sequences

| TEE Identifier | Sequence | SEQ ID NO |
|---|---|---|
| TEE-486 | TAGCAGGAAACAGCAAACTCAAATTAAGTAATTTCA AGAGCGTATCATCAATGAACTATTTTCAAAGATGTG GGCAAGAT | 5496 |
| TEE-487 | GAATTGAAAGGAATGTATTGGAATAAAATGGAATCG AATAGGTTGAAATACCATAGGTTCGAATTGAATGGA ATGGGAGGGACACCAATGGAATTG | 5497 |
| TEE-488 | AAGCAACTTCAGCAAAGTCTCGGGATACAAAATCAA TGTGCAAAAATCACAAGCATTCTTATACACCACTAA CAGACAAATGGAGAGTC | 5498 |
| TEE-489 | GAATGGAATCAACATCAAACGGAAAAAAACGGAAT TATCGAATGGAATCGAAGAGAATCATCGAATGGACC AGAATGGAATCATCTAATGGAATGGAATGGAATAAT CCATGG | 5499 |
| TEE-490 | AAAAGCAATTGGACTGATTTTAAATATACGTGGCAA CAAGGATAAACTGCTAATGATGGGTTTGCAAATACA GATCG | 5500 |
| TEE-491 | AATGGAATCAACATCGAACGGAAAAAAACGGAATT ATCGAATGGAATCGAAGAGAATCATCGAATGGACC | 5501 |
| TEE-492 | AAACGGAATTATCAAATGGAATCGAAGAGAATCATC GAACGGACTCGAATGGAATCATCTAATGGAATGGAA TGGAAG | 5502 |
| TEE-493 | TGCAAGATAACACATTTTAGTTGACACCATTGAAAA CAGTTTTAACCAAGAATATTAGAACCAATGAAGCAG AGAAATCAAAAGGGTGGATGGAACTGCCAAAGGATG | 5503 |
| TEE-494 | TAGAACAGAATTGAATGGAATGGCATCAAATGGAAT GGAAACGAAAGGAATGGAATTGAATGGACTCAAAT GTTATGGAATCAAAGGGAATGGACTC | 5504 |
| TEE-495 | AAGAGAATCATCGAATGGAATCGAATGGAATCAACA TCAAACGGAAAAAAACGGAATTATCGAATGGAATCG AAGAGAATCATCGAATGGACC | 5505 |
| TEE-496 | ATCAACATCAAACGGAAAAAAACGGAATTATCGAAT GGAATCGAAGAGAATCATCGAATGGACC | 5506 |
| TEE-497 | GAATCAACATCAAACGGAAAAAAACCGAATTATCGA ATGGAATCGAAGAGAATCATCGAATGGACC | 5507 |
| TEE-498 | ATCAACATCAAACGGAATCAAACGGAATTATCGAAT GGAATCGAAGAGAATCATCAAATGGACTCGAATGGA ATCATCTAATGGAATGGAATGGAAGAATCCATGG | 5508 |
| TEE-499 | ATCGAATGGAATCATTGAATGGAAAGGAATGGAATC ATCATGGAATGGAAACGAATGGAATCACTGAATGGA CTCGAATGGGATCATCA | 5509 |
| TEE-500 | ATTCAGCCTTTAAAAAAGAAGACAGTCCTGTCATTT GTGACAATATGAATGAAACAGACATCACATTAAATG AAATGAGCCAGGCGCAG | 5510 |
| TEE-501 | GAATGAAATGAAATCAAATGGAATGTACATGAATGG AATAGAAAGAATGCATCTTTCTCGAACGGAAGTGC ATTGAATGGAAAGGAATCTACTGGAATGGATTCGAA TGGAATGGAATGGGATGAATGGTATGG | 5511 |
| TEE-502 | AACATCAAACGGAATCAAACGGAATTATCGAATGGA ATCGAAGAGAATCATCGAACGGACTCGAATGGAATC ATCTAATGGAATGGAAGAATCCATGGACTCG AATGCAATCATCATCGAATGAAATCGAATGGAATCA TCGAATGGACTCG | 5512 |
| TEE-503 | ATGGAATTCAATGGAATGGACATGAATGGAATGGAC TTCAATGGAATGGTATCAAATGGAATGGAATTCAGT | 5513 |
| TEE-504 | AATGGAAAGGAATCGAATGGAAGGGAATGAAATTG AATCAACAGGAATGGAAGGGAATAGAATAGACGGC AATGGAATGGACTCG | 5514 |

TABLE 32-continued

TEE Sequences

| TEE Identifier | Sequence | SEQ ID NO |
|---|---|---|
| TEE-505 | AGCAACTTCAGCAAAGTATCAGGATACAAAATCAAT GTACAAAAATCCCAAGCATTCTTATACACCAACAAC AGACAAACAGAGAGCC | 5515 |
| TEE-506 | AGCAACTTCAGCAAAGTCTCAGGATACAAAATCGAT GTGCAAAAATCACAAGCATTCTTATACACCAACAAC AGATAAACAGAGAGCC | 5516 |
| TEE-507 | AACGGAAAAAAACGGAATTATCGAATGGAATCGA AGAGAATCATCGAATGGACCAGAATGGAATCATCTA ATGGAATGGAATGGAATAATCCATGGACTCGAATG | 5517 |
| TEE-508 | GGAATCAAACGGAATTATCGAATGGAATCGAAGAGA ATCATAGAACGGACTCAAATGGAATCATCTAATGGA ATGGAATGGGAGAATCCATGGACTCGAATG | 5518 |
| TEE-509 | AATGGAATCAATATCAAACGGAAAAAAACGGAATTA TCGAATGGAATCGAAGAGAATCATCGAATGGACC | 5519 |
| TEE-510 | AACGGAATCAAACGGAATTATCGAATGGAATCGAAA AGAATCATCGAACGGACTCGAATGGAATCATCTAAT GGAATGGAATGGAAGAATCCATGG | 5520 |
| TEE-511 | AAACGGAATTATCGAATGGAATCAAAGAGAATCATC GAATGGCCACGAATGGAATCATATAATGGAATGGAA TGGAATAATCCATGGACC | 5521 |
| TEE-512 | AATGGAATCGAATGGATTGATATCAAATGGAATGGA ATGGAAGGGAATGGAATGGAATGGAATTGAACCAA ATGTAATGGATTTG | 5522 |
| TEE-513 | TAAAAGACGGAACAGATAGAAAGCAGAAAGGAAAG GTGAATTGCATTACCACTATTCATACTGCCACACACA TGACATTAGGCCAAGTC | 5523 |
| TEE-514 | AATGGAATCGAATGGAACAATCAAATGGACTCCAAT GGAGTCATCTAATGGAATCGAGTGGAATCATCGAAT GGACTCG | 5524 |
| TEE-515 | TAACACATAAACAAACACAGAGACAAAATCTCCGAG ATGTTAATCTGCTCCAGCAATACAGAACAATTTCTAT TACCAACAGAATGCTTAATTTTTCTGCCT | 5525 |
| TEE-516 | GGAATCGAATGGAATCAACATCAAACGGAAAAAAA CGGAATTATCGAATGGAATCAAAGAGAATCATCGAA TGGACC | 5526 |
| TEE-517 | AGAATGGAAAGGAATCGAAACGAAAGGAATGGAGA CAGATGGAATGGAATG | 5527 |
| TEE-518 | GAATCATCATAAAATGGAATCGAATGGAATCAACAT CAAATGGAATCAAATGGTCTCGAATGGAATCATCTT CAAATGGAATGGAATGG | 5528 |
| TEE-519 | AACAACAATGACAAACAAACAACAACGACAAAGAC ATTTATTTGGTTCACAAATCTCCAGGGTGTACAAGAA GCATGGTGCCAGCATCTGCTCAGCTTCTGATGAGGG CTCTGGGAAGCTTTTACTC | 5529 |
| TEE-520 | AACGGACTCGAACGGAATATAATGGAATGGAATGGA TTCGAAAGGAATGGAATGGAATGGACAGGAAAAGA ATTGAATGGGATTGGAATGGAATCG | 5530 |
| TEE-521 | AACATCAAACGAAATCAAACGGAATTATCAAATTGA ATCGAAGAGAATCATCGAATTGCCACGAATGCAATC ATCTAATGGTATGGAATGGAATAATCCATGGACCCA GATG | 5531 |
| TEE-522 | AGAAATTAACAGCAAAAGAAGGATGCAGTGCAACTC AGGACAACACATACAATTCAAGCAACAAATGTATAG TGGCTGGGCACCAAGGATACAG | 5532 |
| TEE-523 | GCAATAAAATCGACTCAGATAGAGAAGAATGCAATG GAATGGAATGGAATGGAATGGAATGGGATGGAATG GTATGGAATGG | 5533 |

TABLE 32-continued

TEE Sequences

| TEE Identifier | Sequence | SEQ ID NO |
|---|---|---|
| TEE-524 | AATGGACTCGAATGAAATCATCATCAAACGGAATCG<br>AATGGAATCATTGAATGGAAAGGATGGGATCATCAT<br>GGAATGGAAACGAATGGAATCACTG | 5534 |
| TEE-525 | CCACATAAAACAAAACTACAAGACAATGATAAAGTT<br>CACAACATTAACACAATCAGTAATGGAAAAGCCTAG<br>TCAATGGCAG | 5535 |
| TEE-526 | TGGAATGGAATGGAATGGAATCAAATCGCATGGTAA<br>TGAATCAAATGGAATCAAATCGAATGGAAATAATGG<br>AATCGAAGGGAAACGAATGGAATCGAATTGCACTGA<br>TTCTACTGACTTCGAGGAAAATGAAATGAAATGCGG<br>TGAAGTGGAATGG | 5536 |
| TEE-527 | GAATGTTATGAAATCAACTCGAACGGAATGCAATAG<br>AATGGAATGGAATGGAATGGAATGGAATGGAATGG | 5537 |
| TEE-528 | AATGGAATCATTGAATGGAATGGAATGGAATCATCA<br>AAGAAAGGAATCGAAGGGAATCATCGAATGGAATC<br>AAACGGAATCATCGAATGGAATGGAATGGAATG | 5538 |
| TEE-529 | GGAATCAACATCAAACGGAAAAAAAACGGAATTATC<br>GAATGGAATCGAAGAGAATCATCGAATGGACC | 5539 |
| TEE-530 | GGAATAATCATCATCAAACAGAACCAAATGGAATCA<br>TTGAATGGAATCAAAGGCAATCATGGTCGAATG | 5540 |
| TEE-531 | GCATAGAATCGAATGGAATTATCATTGAATGGAATC<br>GAATGGAATCAACATCAAACGGAAAAAAACGGAAT<br>TATCGAATGGAATCGAAGAGAATCATCGAATGGACCC | 5541 |
| TEE-532 | AATGGAATCGAAGAGAATCATCGAACGGACTCGAAT<br>GGAATCATCTAATGGAATGGAATGGAATAATCCATG<br>GACCCGAATG | 5542 |
| TEE-533 | AAATGAATCGAATGGAATTGAATGGAATCAAATAGA<br>ACAAATGGAATCGAAATGAATCAAATGGAATCGAAT<br>CGAATGGAATTGAATGGCATGGAATTG | 5543 |
| TEE-534 | AGTTAATCCGAATAGAATGGAATGGAATGCAATGGA<br>ACGGAATGGAACGGAATGGAATGGAATGGAATGGA<br>ATGGAATG | 5544 |
| TEE-535 | ATCACAATCACACAACACATTGCACATGCATAACAT<br>GCACTCACAATACACACAACACATACACAACACA<br>CATGCAATACAACACAAAACGCAACACAACATATAC<br>ACAACACACAGCACACACATGCC | 5545 |
| TEE-536 | AAAGACTTAAACGTTAGACCTAAAACCATAAAAACC<br>CTAGAGGAAAACCTAGGCATTACCATTCAGGACTTA<br>GGCATGGGCAAGGAC | 5546 |
| TEE-537 | AAAGTCCAAAGATGAACAAAATATCCAGAAGGAAA<br>ACAAATGCACTTGGGGAGTGGGAAAGAAAACCAAG<br>ACTGAGCAATGCGTCAAGCTCAGACGTGCCTCACTA<br>CG | 5547 |
| TEE-538 | AAACGGAATCAAACGGAATTATCGAATGGAGTCGAA<br>AAGAATCATCGAACGGACTCGAATGGAATCATCTAA<br>TGGAATGGAATGGAAGAATCCATGG | 5548 |
| TEE-539 | AATTGATTCGAAATTAATGGAATTGAATGGAATGCA<br>ATCAAATGGAATGGAATGTAATGCAATGGAATGTAA<br>TAGAATGGAAAGCAATGGAATG | 5549 |
| TEE-540 | TACAGAACACATGACTCAACAACAGCAGAAAGCATA<br>TTCTTTTCAAATGCACATGAAACATTATCATGATGGA<br>CCAAAT | 5550 |
| TEE-541 | GGAACAAAATGAAATCGAACGGTAGGAATCATACA<br>GAACAGAAAGAAATGGAACGGAATGGAATG | 5551 |
| TEE-542 | AACGGAAAAAACGGAATTATCGAATGGAATCGAAG<br>AGAATCATCGAATGGAATCGAATGGAGTCATCG | 5552 |

TABLE 32-continued

TEE Sequences

| TEE Identifier | Sequence | SEQ ID NO |
|---|---|---|
| TEE-543 | AATCGAACGGAATCAACATCAAACGGAAAAAAACG GAATTATCGAATGGAATCGAAGAGAATCATCGAATG GACC | 5553 |
| TEE-544 | AGAATGGAATGCAATAGAATGGAATGCAATGGAATG GAGTCATCCGTAATGGAATGGAAAGGAATGCAATGG AATGGAATGGAATGG | 5554 |
| TEE-545 | ATGGAATCAACATCAAACGGAATCAAACGGAATTAT CGAATGGAATCGAAGAGAATCATCGAACGGATTCGA ATGGAATCATCTAATGGAATGGAATGGAAGAATCCA TGGACTCGAATGCAATCATCAGCGAATGGAATCGAA TGGAATCATCGAATGGACTCG | 5555 |
| TEE-546 | GGAATAAAACGGACTCAATAGTAATGGATTGCAATG TAATTGATTCGATTTCGAATGGAATCGCATGGAATGT AATGGAATGGAATGGAATGGAAGGC | 5556 |
| TEE-547 | AATGGAATCAACATCAAACGGAAAAAAACGGAATT ATCGTATGGAATCGAAAAGAATTATCGAATGGACC | 5557 |
| TEE-548 | TCAAACGGAAAAAAACGGAATTATCGAATGGAATCG AAGAGAATCATCGAATGGACC | 5558 |
| TEE-549 | ACATCAAACGGAATCAAACGGAATTATCGAATGGAA TCGAAAAGAATCATCGAACGGACTCGAATGGAATCA TCTAATGGAATGGAATGGAAGAATCCATGGACTCGA ATG | 5559 |
| TEE-550 | TGGAATCGAATGGAATCAACATCAAACGGAAAAAA ACGGAATTATCGAATGGAATCGAAGAGAATCATCGA ATGGACC | 5560 |
| TEE-551 | AATGGAATCGAATGCAATCATCGAACGGAATCGAAT GGCATCACCGAATGGAATGGAATGGAATGGAATGGA ATGG | 5561 |
| TEE-552 | AGAATTGATTGAATCCAAGTGGAATTGAATGGAATG GAATGGATTAGAAAGGAATGGAATGGATTGGAATGG ATTGGAATGGAAAGG | 5562 |
| TEE-553 | AACTGCATCAACTAACAGGCAAAATAACCAGCTAAT ATCATAATGACAGGATTAAATTCACAAATGACAATA TTAACCGTAAATGTAAATGGGCTA | 5563 |
| TEE-554 | GTAAACAAACAATCAAGCAAGTAAGAACAGAAATA ACAGCATTTGGCTTTTGAGTTAATGACAAGAACACTC GGCATGGGAGCCTGGGTGAGCAAATCACAGATCTTC | 5564 |
| TEE-555 | AAAGGAATGGACTGGAACAAAATGAAATCGAACGG TAGGAATCGTACAGAACGGACAGAAATGGAACGGC ATGGAATGCACTCG | 5565 |
| TEE-556 | GAATCAACCCGAGCGGAAAGGAATGGAATGGAATG GAATCAACACGAATGGAATGGAACGGAATGGAATG GGATGGGATGAAATGGAATGG | 5566 |
| TEE-557 | AAGAAATGGAATCGAAGAGAATGGAAACAAACGGA ATGGAATTGAATGGAATGGAATTGAATGGAATGGGA | 5567 |
| TEE-558 | GACATGCAAACACAACACACAGCACACATGGAACAT GCATCAGACATGCAAACACAACACACATACCACACA TGGCATATGCATCAGACGTGCCTCACTAC | 5568 |
| TEE-559 | AAAGGAATGCACTCGAATGGAATGGACTTGAATGGA ATGTCTCCGAATGGAACAGACTCGTATGAAATGGAA TCGAATGGAATGGAATCAAATGGAATTGATTTGAGT GAAATGGAATCAAATGGAATGGCAACG | 5569 |
| TEE-560 | GGAACAAAATGAAATCGAACGGTAGGAATCGTACA GAACGGAAAGAAATGGAACGGAATGGAATGCACTC GAATGGAAAGGAGTCCAAT | 5570 |

TABLE 32-continued

TEE Sequences

| TEE Identifier | Sequence | SEQ ID NO |
|---|---|---|
| TEE-561 | AAATTGATTGAAATCATCATAAAATGGAATCGAAGG GAATCAACATCAAATGGAATCAAATGGAATCATTGA ACGGAATTGAATGGAATCGTCAT | 5571 |
| TEE-562 | AGAATGGAAAGCAATAGAATGGAACGCACTGGATTC GAGTGCAATGGAATCAATTGGAATGGAATCGAATGG AATGGATTGGCA | 5572 |
| TEE-563 | AACACCAAACGGAAAAAAACGGAATTATCGAATGG AATCGAAGAGAATCTTCGAACGGACCCGAATGGGAT CATCTAATGGAATGGAATGGAATAATCCATGG | 5573 |
| TEE-564 | AATGGAGACTAATGTAATAGAATCAAATGGAATGGC ATCGAATGGAATGGACTGGAATGGAATGTGCATGAA TGGAATGGAATCGAATGGATTG | 5574 |
| TEE-565 | AAATCGAATGGAACGCAATAGAATAGACTCGAATGT AATGGATTGCTATGTAATTGATTCGAATGGAATGGA ATCGACTGGAATGCAATCCAATGGAATGGAATGCAA TGCAATGGAATGGAATCGAACGGAATGCAGTGGAAG GGAATGG | 5575 |
| TEE-566 | AATCAACAAGGAACTGAAACAAGTAAACAAGAAAA CAAATAACACCATAAAACATGGGCAAAGGACATAA ACAGACATTTTTCAAAAAGACATACAAATGGCCGAG | 5576 |
| TEE-567 | AATGGAATCAACATCAAACGGAAAAAAACGGAATT ATCGAATGGAATCGAAGAGAATCATCGAATGGACCC AGGCTGGTCTTGAACTCC | 5577 |
| TEE-568 | ATTGAATGGGCTAGAATGGAATCATCTTTGAACGGA ATCAAAGGGAATCATCATCGAATGGAATCGAATGGA AATGTCAACG | 5578 |
| TEE-569 | AATGGACTCGAATGGAATCAACATCAAATGGAATCA AGCGGAATTATCGAATGAAATCGAAGAGAATCATCG AATGGACTCGAAAGGAATCATCTAATGGAATGGAAT GGAATAATCCATGGACTCGAATGCAATCATCATCG | 5579 |
| TEE-570 | AAACGGAAAAAAACGGAATTATTGAATGGAATCGA AGAGAATCTTCGAACGGACCCGAATGGAATCATCTA ATGGAATGGAATGGAATAATCCATGG | 5580 |
| TEE-571 | ACTCGAGTGGAATTGACTGTAACAAAATGGAAAGTA ACGGATTGGAATCGAATGGAACGGAATGGAATGGA ATGGACAT | 5581 |
| TEE-572 | TACAAACTTTAAAAAATGATCAACAGATACACAGTT AGCAAGAAAGAATTGAGGGCAAAGAATATGCCAGA CAAACTCAAGAGGAAGATGATGGTAGAGATAGGTCA CATTGGAGTGTCA | 5582 |
| TEE-573 | AAATCAACAACAAACGGAAAAAAAAGGAATTATCG AATGGAATCAAAGAGAATCATCGAATGGACC | 5583 |
| TEE-574 | AACGGAATCAAACGGAATTATCGAATGGAATCGAAA AGAATCATCGAACGGACTCGAATGGAATCATCTAAT GTAATGGAATGGAAGAATCCATGGACTCGAATG | 5584 |
| TEE-575 | AACGGAAAAAAACGGAATTATCGAATGGAATCGAA GAGAATCATCGAATGGACCAGAATGGAATCATCTAA TGGAATGGAATGGAATAATCCATGGACTCGAATG | 5585 |
| TEE-576 | CAACATCAAACGGAAAAAAACGGAATTATGGAATG GAATCGAAGAGAATCATCGAATGGACCCGAATGGAA TCATCTGAAATATAATAGACTCGAAAGGAATG | 5586 |
| TEE-577 | ATGGAATCGAATGGAATGGACTGGAATGGAATGGAT TCGAATGGAATCGAATGGAACAATATGGAATGGTAC CAAATG | 5587 |
| TEE-578 | GAATGGAATCAACATCAAACGGAAAAAAACGGAAT TATCGAATGGAATCGAAGAGAATCATCGAATGGACC | 5588 |

TABLE 32-continued

TEE Sequences

| TEE Identifier | Sequence | SEQ ID NO |
|---|---|---|
| TEE-579 | AAATGGACTCGAATGGAATCATCATAGAATGGAATC<br>GAATGCAATGGAATGGAATCTTCCGGAATGGAATGG<br>AATGGAATGGAATGGAG | 5589 |
| TEE-580 | GAATCATCATAAAATGGAATCGAATGGAATCAACAT<br>CAAATGGAATCAAATGGAATCATTGAACGGAATTGA<br>ATGGAATCGTCAT | 5590 |
| TEE-581 | ATCGAATGGAATCAACATCAAACGGAAAAAAACGG<br>AATTATCGAATGGAATCGAAGAGAATCATCGAATGG<br>ACC | 5591 |
| TEE-582 | AGCAACTTCAGCAAAGTCTCAGGATACAAAATCAAT<br>GTACAAAAATCACAAGCATTCTTATACACCAATAAC<br>AGACAAACAGAGAGCCAAAA | 5592 |
| TEE-583 | AGAAACAGAAAACAGTCAAACCAATGGGCAATCCAT<br>ATCAGATGCAGTATTATGAACAGAAGTGTAAAGAAT<br>GCACCAGGCACAATGGC | 5593 |
| TEE-584 | GATTGGAACGAAATCGAATGGAACGGAATAGAATA<br>GACTCGAATGTAATGGATTGCTATGTAATTGATTCGA<br>ATGGAATGGAATCGAATGGAATGCAATCCAATGGAA<br>TGGAATGCAATGCAATGGAATGG | 5594 |
| TEE-585 | ATGGAATGGAATAATCAACGTACTCGAATGCAATCA<br>TCATCGTATAGAATCGAATGGAATCATCGAATGGAC<br>TCGAATGGAATAATCATTGAACGGAGTCGAATGGAA<br>TCATCATCGGATGGAAAC | 5595 |
| TEE-586 | AAAGAAATCGAATGGAATCAGTGTCGAATGGAATGG<br>AATGGAATCGAAGAATTGAATTGAGTAGAATCGAAG<br>GGAATCATTGGATGGGCTCAAAT | 5596 |
| TEE-587 | AGAAAAGATAACTCGATTAACAAATGAACAAACACC<br>TGAATACACAAGTCTCAAAAGAAGACATAAAAATGG<br>CCAAC | 5597 |
| TEE-588 | ATGGAATCAACATCAAACGGAATCACACGGAATTAT<br>CGAATGGAATCGAAAAGAATCATCGAACGGACTCGA<br>ATGGAATCATCTAATGGAATGGAATGGAAG | 5598 |
| TEE-589 | AATGGAATCAACATCAAACGGAATCAAGCGAAATTA<br>TCGAATGGAATCGAAGAGAATCATCGAATGGACTCG<br>AATGGAATCATCTAATGGAATGGAATGGGAT | 5599 |
| TEE-590 | AAACACAGTACAAATACTAATTCAAATCAAACTTAC<br>TCAAAGTCATAATCAAACATGCCAGACGGGCTGAGG<br>GGCAGCATTA | 5600 |
| TEE-591 | GGAATCGAGTGGAATCATCGAAAGAAATCGAATGGA<br>ATCATTGTCGAATGGAATGGAATGGAATCAAAGAAT<br>GGAATCGAAGGGAATCATTGGATGGGCT | 5601 |
| TEE-592 | AAAGAAAGACAGAGAACAAACGTAATTCAAGATGA<br>CTGTTTACATATCCAAGAACATTAGATGGTCAAAGA<br>CTTTAAGAAGGAATACATTCAAAGGCAAAAAGTCAC<br>TTACTGATTTTGGTGGAGTTTGCCACATGGAC | 5602 |
| TEE-593 | GAAAGGAATCATCATTGAATGCAATCACATGGAATC<br>ATCACAGAATGGAATCGTACGGAATCATCATCGAAT<br>GGAATTGAATGGAATCATCAATTGGACTCGAATGGA<br>ATCATCAAATGGAATCGATTGGAAGTGTCAAATGGA<br>CTCG | 5603 |
| TEE-594 | CAATCAGAGCGGACACAAACAAATTGCATGGGAAG<br>AATCAATATCGTGAAAATGGCC | 5604 |
| TEE-595 | CAGCGCACCACAGCACACACAGTATACACATGACCC<br>ACAATACACACAACACACAACACATTCACACACCAC | 5605 |
| TEE-596 | GCAAACAGAATTCAACACTACATTAGAACGATCATT<br>CATCACGACCTAGTAGGATGTTTTTCCTGGGATGCAA<br>GGATGGTTCAACAT | 5606 |

TABLE 32-continued

TEE Sequences

| TEE Identifier | Sequence | SEQ ID NO |
|---|---|---|
| TEE-597 | CAATCAAAACAGCAATGAGATACCATTTTACACCAA<br>TCAAAATGGCTACTAAAAAGTCAAAAGCAAATGCC | 5607 |
| TEE-598 | TGGAATAGAATGGAATCAATGTTAAGTGGAATCGAG<br>TGGAATCATCGAAAGAAATCGAATGGAATCATTGTC<br>GAATGGTATGGAATGGAATCA | 5608 |
| TEE-599 | AATGGAATGGAATCATCGCATAGAATGGAATGGAAT<br>TATCATCGAATTGAATCGAATGGTATCAACATCAAA<br>CGGAAAAAAACGGAAATATCGAATGGAATCGAAGA<br>GAATCATCGAACGGACC | 5609 |
| TEE-600 | GAAAAACAAACAAACAAACAAACAAACAATCAA<br>AAAAGTGGTAGCAGAAACCAGAAAGTCCATGTATAT<br>AGCTAATTGGCCTGGTTGT | 5610 |
| TEE-601 | AGACCTTTCTCAGAAGACACACAAATTGCCAACAGG<br>TATATGAAAAATGTTCAATATCACTAATCATCAGG<br>GCGATGCC | 5611 |
| TEE-602 | CATGGAATCGAATGGAATTATCATCGAATGGAATCG<br>AATGGTACCAACACCAAACGGAAAAAAACGGAATT<br>ATCGAATGGAATCGAAGAGAATCTTCGAACGGACC | 5612 |
| TEE-603 | AGAGCAGAAACAAATGGAATTGAAATGAAGACAAC<br>AATCAAAAGCATCAATGAAATGAAAAGTTGGGTTTT<br>GGAAGAGAGAAACAAT | 5613 |
| TEE-604 | ACACAAACACACACACACACACACACACACACACAC<br>ACACACACACACACACACACACACACACATAC | 5614 |
| TEE-605 | AACAAACAAATGAGATGATTTCAGATAGTGATAAAC<br>ACTATAACATAATTAATTCGTGCCAATCAGAGCATA<br>ACAGTGGTGTGGCTGTGGAACAGATAGCAGAC | 5615 |
| TEE-606 | AATGGAATCGAGTGGAATGGAAGGCAATGGAATAG<br>AATGGAATGGAATCGAAAGGAACGGAATGGAATGG<br>AATGGAATG | 5616 |
| TEE-607 | AGAAATGGAATCGGAGAGAATGGAAACAAATGGAA<br>TGGAATTGAATGGAATGGAATTGAATGGAATGGGAA<br>CG | 5617 |
| TEE-608 | AAGAGAACTGCAAAACACTGCTCAAAGAAATCAGA<br>GATGACAAAAACACATGGAAAAACGTTTCATGCTCA<br>TGGATTGGAAGACTTA | 5618 |
| TEE-609 | AATCAACACGAATAGAATGGAACGGAATGGAATGG<br>AATGGAATGGAATGGAATGGAGTGGAATGGAACAG<br>AATGGAGTGGAAT | 5619 |
| TEE-610 | AACATCAAACGAAATCAAACGGAATTATCAAATTGA<br>ATCGAAGAGAATCATCGAATTGCCACGAATGCAACC<br>ATCTAATGGTATGGAATGGAATAATCCATGGACCCA<br>GATG | 5620 |
| TEE-611 | CGGAATTATCATCGAATGTAATCGAATGGAATCAAC<br>ATCAAACGGAAAAAAACGGAATTATCGAATGGAATC<br>GAAGAGAATCATCGAATGGACC | 5621 |
| TEE-612 | TGGACACACACGAACACACACCTACACACACGTGGA<br>CACACACGGACACATGGACACACACGAACACATGGA<br>CACACACACGGGGACACACACAGACACACACAGAG<br>ACACACACGGACACATGG | 5622 |
| TEE-613 | ATCAAACGGAATCAAACGGAATTATCGAATGGAATC<br>GAAGAGAATCATCGAATGGACTCGAATGGAATCATC<br>TAATGGAATGGAATGGAAGAATCCATGG | 5623 |
| TEE-614 | AAATGGAATGGAATGCACTTGAAAGGAATAGACTGG<br>AACAAATGAAATCGAACGGTAGGAATCATACAGA<br>ACAGAAAGAAATGGAACGGAATGGAATG | 5624 |
| TEE-615 | ACCACACACAAAATACACCACACACCACACACACAC<br>CACACACTATACACACACCACACACCACACAC | 5625 |

TABLE 32-continued

TEE Sequences

| TEE Identifier | Sequence | SEQ ID NO |
|---|---|---|
| TEE-616 | AAAGAAATAGAAGGGAGTTGAACAGAATCGAATGG AATCGAATCAAATGGAATCGAATGGCATCAAATGGA ATCGAATGGAATGTGGTGAAGTGGATTGG | 5626 |
| TEE-617 | GGAATCATCATAAAATGGAATCGAATGGAATCATCA TCAAATGGAATCAAATGGAATCATTGAACGGAATTG AATGGAATCGTCAT | 5627 |
| TEE-618 | AAAGATCAATGTACAAAAATCAGCAGCATTTCTATA AACCAACAATGTCCAGGCTGAGAGAGAAATCAAGA AAACAATTC | 5628 |
| TEE-619 | TGGAATGGAATGGAATGAAATAAACACGAATAGAAT GGAACGGAATGGAACGGAATGGAATGGAATGGAAT GGAAAG | 5629 |
| TEE-620 | TAATCAGCACAATCAACTGTAGTCACAAAACAAATA GTAACGCAATGATAAAGAAACAGAGAACTAGTTCAA ATAAACATGATAAGATGGGG | 5630 |
| TEE-621 | AAGCGGAATTATCAAATGGAATCGAAGAGAATGGA AACAAATGGAATGGAATTGAATGGAATGGAATTGAA TGGAATG | 5631 |
| TEE-622 | AATGGAATCAACATCAAACGGAAAAAAACGGAATT ATCGAATGGAATCGAAGAGAATCATCGAATGGACC | 5632 |
| TEE-623 | ACTTGAATCGAATGGAAAGGAATTTAATGAACTTAA ATCGAATGGAATATAATGGTATGGAATGGACTCATG GAATGGAATGGAAAGGAATC | 5633 |
| TEE-624 | TGGAATCATCATCGAAAGCAAGCGAATGGAATCATC AAATGGAAACGAATGGAATCATCGAATGGACTCGGA TGGAATTGTTGAATGGACT | 5634 |
| TEE-625 | TGGAATCAACATCAAACGGAAAAAAACGGAATTATC GAATGGAATCGAAGAGAATCATCGAATGGACC | 5635 |
| TEE-626 | TAAGTGAATTGAATAGAATCAATCTGAATGTAATGA ATGGAATGGAACGGAATGGAATGGAATGGAATGG AATGGAATGGAATGG | 5636 |
| TEE-627 | AGGAAAATTTAATCAGCAGGAATAGAAACACACTTG AGAAATCCATGTGGAATGAAAAGAGAATGGCTGAGC AGCAACAGATTGTCAAAAAGGAAATC | 5637 |
| TEE-628 | AACATCAAACGGAAAAAAAACGGAATTATCGAATG GAATCGAAGAGAATCATCGAATGGACC | 5638 |
| TEE-629 | TAATTGAGAATAAGCATTCCAGTGGAAAAAAAACTA AACAAATTTGTTGTAAAACATCCTTAAAAGCATCAGA AAGTTAATACAGCAATGAAGAATTACAGGACCAAAT TAAGAATGGTATGGAAGCCTGTTA | 5639 |
| TEE-630 | TATCATCGAATGGAATCGAATGGAATCAACATCAAA CGGAAAAAAACGGAATTATCGAATTGAATCGAAGAG AATCATCGAATGGACC | 5640 |
| TEE-631 | AGCAAAACAAACACAATCTGTCGTTCATGGTACTAC GACATACTGGGAGAGATATTCAAATGATCACACAAA ACAACATG | 5641 |
| TEE-632 | AAGGATTCGAATGGAATGAAAAGAATTGAATGGA ATAGAACAGAATGGAATCAAATCGAATGAAATGGA GTGGAATAGAAAGGAATGGAATG | 5642 |
| TEE-633 | AACGGAATCAAACGGAATTATCGAATGGAATCGAAG AGAATCATCGAACGGACTCGAATGGAATCATCTAAT GGAATGGAATGGAAGAATCCATGGACTCGAATGCAA TCATCATCGAATGGAATCGAACGGAATCATCGAATG GCC | 5643 |
| TEE-634 | AATCAACTAGATGTCAATGGAATGCAATGGAATAGA ATGGAATGGAATTAACACGAATAGAATGGAATGGAA TGGAATGGAATGG | 5644 |

TABLE 32-continued

TEE Sequences

| TEE Identifier | Sequence | SEQ ID NO |
|---|---|---|
| TEE-635 | AATGGACTCGAATGGAATAATCATTGAACGGAATCG AATGGAATCATCATCGGATGGAAATGAATGGAATCA TCATCGCATGGAATCG | 5645 |
| TEE-636 | GAATGGAATGATACGGAATAGAATGGAATGGAACG AAATGGAATTGAAAGGAAAGGAATGGAATGGAATG GAATGG | 5646 |
| TEE-637 | AATCATCATCGAATGGAATCGAATGGTATCATTGAG TGGAATCGAATGGAATCATCATCAGATGGAAATGAA TGGAATCGTCAT | 5647 |
| TEE-638 | GAATCAAATCAATGGAATCAAATCAAATGGAATGGA ATGGAATTGTATGGAATGGAATGGCATGG | 5648 |
| TEE-639 | TAATGCAGTCCAATAGAATGGAATCGAATGGCATGG AATATAAAGAAATGGAATCGAAGAGAATGGGAACA AATGGAATGGAATTGAGTGGAATGGAATTGAATGGA ATGGGAACGAATGGAGTG | 5649 |
| TEE-640 | AACATCAAACGGAAAAAAACGGAATTATCGAATGG AATCGAAGAGAATCATCGAATGGACC | 5650 |
| TEE-641 | ATCAAAAGGAACGGAATGGAATGGAATGGAATGGA ATGGAATGGAATGGAATGGAATGAAATCAACCCGAA TGGAATGGATTGGCATAGAGTGGAATGG | 5651 |
| TEE-642 | GCCAACAATCATATGAGAAAAAGCTCAACATCACTG ATCATTTCAGGAATGCAAATCAAAACCACAATGAGA TACTATCA | 5652 |
| TEE-643 | AATCAAATGGAATGAAATCGAATGGAATTGAATCGA ATGGAATGCAATAGAATGTCTTCAAATGGAATCGAA TGGAAATTGGTGAAGTGGACGGGAGTG | 5653 |
| TEE-644 | TAATGGAATCAACATCAAACGGAAAAAAACGGAATT ATCGAATGCAATCGAAGAGAATCATCGAATGGACC | 5654 |
| TEE-645 | AGCAACTTCAGCAAAGTCTCAGCATACAAAATCAAT GTGCAAAAATCACACGCATTCCTATACACCAATAAC AGACAAACAGAGAGCC | 5655 |
| TEE-646 | GAATCAAATGGAATGGACTGTAATGGAATGGATTCG AATGGAATCGAATGGAGTGGACTCAAATGGAATG | 5656 |
| TEE-647 | AACAAGTGGACGAAGGATATGAACAGACACTTCTCA AGACATTTATGCAGCCAACAGACACACGAAAAAATG CTCATCATCACTGGCCATCAG | 5657 |
| TEE-648 | AAACGGAAAAAAACGGAATTATCGAATGGAATCGA ATAGAATCATCGAATGGACC | 5658 |
| TEE-649 | TGGAACCGAACAAAGTCATCACCGAATGGAATTGAA ATGAATCATAATCGAATGGAATCAAATGGCATCTTC GAATTGACTCGAATGCAATCATCCACTGGGCTT | 5659 |
| TEE-650 | AACGGAATCACGCGGAATTATCGAATGGAATCGAAG AGAATCATCGAATGGACTCGAATGGAATCATCTAAT GGAATGGAATGG | 5660 |
| TEE-651 | GGAATCAACTCGATTGCAATGGAATGCAATGGAAAG GAATGGAATGCAATTAAAGCGAATAGAATGGAATGG AATGGAATGGAACGGAATGGAATG | 5661 |
| TEE-652 | AAAACAAACAACAACGACAAATCATGAGACCAGAG TTAAGAAACAATGAGACCAGGCTGGGTGTGGTG | 5662 |
| TEE-653 | AATCGAAAGGAATGCAATATTATTGAACAGAATCGA AAAGAATGGAATCAAATGGAATGGAACAGAGTGGA ATGGACTGC | 5663 |
| TEE-654 | AAGGAATCGAATGGAAGTGAATGAAATTGAATCAAC AGGAATGGAAGGGAATAGAATAGACTGTAATGGAA TGGACTCG | 5664 |

TABLE 32-continued

TEE Sequences

| TEE Identifier | Sequence | SEQ ID NO |
|---|---|---|
| TEE-655 | AACCCGAGTGCAATAGAATGGAATCGAATGGAATGG AATGGAATGGAATGGAATGGAATGGAGTC | 5665 |
| TEE-656 | GAATGGAATTGAAAGGAATGGAATGCAATGGAATG GAATGGGATGGAATGGAATGCAATGGAATCAACTCG ATTGCAATG | 5666 |
| TEE-657 | GAAAAAAACGGAATTATCGAATTGAATCAAATAGAA TCATCGAACGGACCAAAATGGAATCATCTAATGGAA TGGAATGGAATAATCCATGGACTCTAATG | 5667 |
| TEE-658 | TGGAATCATCTAATGGAATGGAATGGAATAATCCAT GGACTCGAATGCAATCATCATAAAATGGAATCGAAT GGAATCAACATCAAATGGAATCAAATGGGATCATTG AACGGAATTGAATGGAATCGTCAT | 5668 |
| TEE-659 | GAAAAAAACGGAATTATCGAATTGAATCGAATAGAA TCATCGAACGGACCAGAATGGAATCATCTAATGGAA TGGAATGGAATAATCCATGGACTCGAATG | 5669 |
| TEE-660 | AACCACTGCTTAAGGAAATAAGAGAGAACACAAAC AAATGGAAAAACGTTCCATGCTCATGGATAGGAGAA TCAATATCGTGAAAATGGCC | 5670 |
| TEE-661 | TATCGAATGGAATGGAAAGGAGTGGAGTAGACTCGA ATAGAATGGACTGGAATGAAATAGATTCGAATGGAA TGGAATGGAATGAAGTGGACTCG | 5671 |
| TEE-662 | GTATCAACATCAAACGGAAAAAAACGGAATTATCGA ATGGAATCATCTAATGGAATGGAATGGAATAATCCA TGGACTCGAATG | 5672 |
| TEE-663 | TAAATGGAGACATCATTGAATACAATTGAATGGAAT CATCACATGGAATCGAATGGAATCATCGTAAATGCA ATCAAGTGGAATCAT | 5673 |
| TEE-664 | GAATGGAATTGAAAGGTATCAACACCAAACGGAAA AAAAACGGAATTATCGAATGGAATCGAAGAGAATC ATCGAACGGACC | 5674 |
| TEE-665 | AGCAATTTCAGCAAAGTCTCAGGATACAAAATCAAT GTACAAATTCACAAGCATTCTTATGGACCAACAACAG | 5675 |
| TEE-666 | GGAATCGAATGGCATCAACATCAAACGGAAAAAAA CGGAATTATCGAATGGAATCGAATGGAATCATC | 5676 |
| TEE-667 | AAACAAAACACAGAAATGCAAAGACAAAACATAAA ACGCAGCCATAAAGGACATATTTTAGATAACTGGGG AAATTTGTATGGGCTGTGT | 5677 |
| TEE-668 | AATGGAATCAACATCAAACGGAATCAAACGGAATTA TCGAATGGAATCGAAGAGAATCATCGAACGGACTCG AATGGAATCATCTAATGGAATGGAATGGAAG | 5678 |
| TEE-669 | AATCGAATGGAATCAGCATCAAACGGAAAAAAACG GAATTATCGAATGGAATCGAAGAGAATCATCGAATG GACC | 5679 |
| TEE-670 | AAACGGAATTATAGAATGGACTGGAAGAGAATCATC GAACGGACTAGAATGGAATCATCTAATCGAATGGAA TGGAACAATCCATGGTCTAGCA | 5680 |
| TEE-671 | TGAACAGAGAATTGGACAAAACGCACAAAGTAAAG AAAAGAATGAAGCAACAAAAGCAGAGATTTATTG AAAACAAAAGTACACACCACACAGGGTGGGAGTGG | 5681 |
| TEE-672 | ATCATAACGACAAGAACAAATTCACACACAACAATA TTAACTTCAAATCCAAATGGGTTAAATGCTCCAATTA AAGGATGCAGACGGGCAAATTGGATA | 5682 |
| TEE-673 | ATCATAACGACAAGAACAAATTCACACACAACAATA TTCACTTCAAATCCAAATGGGTTAAATGCTCCAATTA AAGGATGCAGACGGGCAAATTGGATA | 5683 |

TABLE 32-continued

TEE Sequences

| TEE Identifier | Sequence | SEQ ID NO |
|---|---|---|
| TEE-674 | GAATGGAATCGAATGGATTGATATCAACTGGAATGG AATGGAAGGGAATGGAATGGAATGGAATTGAACCA AATGTAATGACTTGAATGGAATG | 5684 |
| TEE-675 | GAATCAACATCAAACGGAAAAAAACGGAATTATCGA ATGGAATCGAAGAGAATCATCGAATGGACC | 5685 |
| TEE-676 | GGAATCAACATCAAACGGAAAAAAACGGAATTATCG AATGGAATCGAAGAGAATCATCGAATGGACC | 5686 |
| TEE-677 | ATGGAATCAACATCAAACGGAATCAAACGGAATTAT CGAATGGAATCAAAGAGAATCATCGAACGGACTCGA ATGGAATCATCTAATGGAATGGAATGGAAGAATCCA TGGACTCGAATGCAATCATCATCGAAT | 5687 |
| TEE-678 | GGAATGGAATGGAATGGAGCCGAATGGAATGGAAT GTACTCAAATGGAATGC | 5688 |
| TEE-679 | AAAACACCTAGGAATACAGATAACAAGGGACATTAA CTACCTCTTAAAGAGAACTACAAACCACTGCTCAAG GAAATGAGAGAGGACACAAACACATGGAAAAACAT TCCATCCTCATGGATAGGAAGAATCAATATTGTGAA AATGGCC | 5689 |
| TEE-680 | AACACGACTTTGAGAAGAGTAAGTGATTGTTAATTA AAGCAAGAGAATTATTGATGTATCACAGTCATGAGA AATATTGGAAGGAATATGGTCCATAC | 5690 |
| TEE-681 | ACACATATCAAACAAACAAAAGCAATTGACTATCTA GAAATGTCTGGGAAATGGCAAGATATTACA | 5691 |
| TEE-682 | GGAATCATCATATAATGGAATCGAATGGAATCAACA TCAAATGGAATCAAATGGAATCATTGAACGGAATTG AATGGAATCGTCAT | 5692 |
| TEE-683 | AATGGAATCAACATCAAACGGAATCAAATGGAATTA TCGAATGGAATCGAAGAGAATCATCGAATTGTCACG AATGGAATCATCTAATGGAATGGAATGGAATAATCC ATGGCCCCTATGCAATGGACTCGAATGAAATCATCA TCAAACAGAATCGAATGGAATCATCTAATGGAATGG AATGGCATAATCCATGGACTCGAATG | 5693 |
| TEE-684 | TAAAATGAAACAAATATACAACACGAAGGTTATCAC CAGAAATATGCCAAAACTTAAATATGAGAATAAGAC AGTCTCAGGGGCCACAGAG | 5694 |
| TEE-685 | AAAATACAGCGTTATGAAAAGAATGAACACACACAC ACACACACACACAGAAAATGT | 5695 |
| TEE-686 | CAAACAAATAGGTACCAAACAAATAACAACATAAAC CTGACAACACACTTATTTACAAGAGACATCCCTTATA TGAAAGGGTACAGAAAAGTCGATGGTAAGATGATGG GGAAAGGTATACCAACCACTAGCAGAAGG | 5696 |
| TEE-687 | TGGAATCGAATGGAATCAATATCAAACGGAAAAAAA CGGAATTATCGAATGGAATCGAAAAGAATCATCGAA TGGGCCCGAATGGAATCATCT | 5697 |
| TEE-688 | ACAAATGGAATCAACAACGAATGGAATCGAATGGA AACGCCATCGAAAGGAAACGAATGGAATTATCATGA AATTGAAATGGATG | 5698 |
| TEE-689 | AATCAATAAATGTAAACCAGCATATAAACAGAACCA ACGACAAAAACCACATGATTATCTCAATAGATGCAG AAAAGGCC | 5699 |
| TEE-690 | AAAATAAACGCAAATTAAAATCACAAGATACCAACA CATTCCCACGGCTAAGTACGAAGAACAAGGGCGAAT GGTCAGAATTAAGCTCAAACCT | 5700 |
| TEE-691 | CAACATCAAACGGAATCAAACGGAATTATCGAATGG AATCGAAGAGAATCATCGAATGGACTCGAATGGAAT CATCTAATGGAATGGAATGGAAG | 5701 |

TABLE 32-continued

TEE Sequences

| TEE Identifier | Sequence | SEQ ID NO |
|---|---|---|
| TEE-692 | ACATCAAACGGAAAAAAACGGAATTATCGAATGGA ATCGAAGAGAATCATCGAATGGACC | 5702 |
| TEE-693 | AATGGACTCGAATAGAATTGACTGGAATGGAATGGA CTCGAATGGAATGGAATGGAATGGAAGGGACTCG | 5703 |
| TEE-694 | AAGAAAGACAGAGAACAAACGTAATTCAAGATGAC TGATTACATATCCAAGAACATTAGATGGTCAAAGAC TTTAAGAAGGAATACATTCAAAGGCAAAACGTCACT TACTGATTTTGGTGGAGTTTGCCACATGGAC | 5704 |
| TEE-695 | GAATGGAATCGAATGGAATGAACATCAAACGGAAA AAAACGGAATTATCGAATGGAATCAAAGAGAATCAT CGAATGGACCCG | 5705 |
| TEE-696 | ATGGACTCGAATGTAATAATCATTGAACGGAATCGA ATGGAATCATCATCGGATGGAAACGAATGGAATCAT CATCGAATGGAATCGAATGGGATC | 5706 |
| TEE-697 | GAAATGGAATGGAAAGGAATAAAATCAAGTGAAAT TGGATGGAATGGATTGGAATGGATTGGAATG | 5707 |
| TEE-698 | AAACGGAAAAAAACGGAATTATCGAATGGAATCG AAGAGAATCATCGAACGAACCAGAATGGAATCATCT AATGGAATGGAATGGAATAATCCATGG | 5708 |
| TEE-699 | ATTAACCCGAATAGAATGGAATGGAATGGAATGGAA CGGAACGGAATGGAATGGAATGGAATGGAATGGAA TGGATCG | 5709 |
| TEE-700 | AACATCAAACGGAAAAAAACGGAATTATCGTATGGA ATCGAAGAGAATCATCGAATGGACC | 5710 |
| TEE-701 | GAATAGAATTGAATCATCATTGAATGGAATCGAGTA GAATCATTGAAATCGAATGGAATCATCATCGAATGG AATTGGGTGGAATC | 5711 |
| TEE-702 | CACCGAATAGAATCGAATGGAACAATCATCGAATGG ACTCAAATGGAATTATCCTCAAATGGAATCGAATGG AATTATCG | 5712 |
| TEE-703 | AATGCAATCGAATAGAATCATCGAATAGACTCGAAT GGAATCATCGAATGGAATGGAATGGAACAGTC | 5713 |
| TEE-704 | AAATCATCATCGAATGGAATCGAATGGTATCATTGA ATGGAATCGAATGGAATCATCATCAGATGGAAATGA ATGGAATCGTCAT | 5714 |
| TEE-705 | GAATGGAATCGAAAGGAATAGAATGGAATGGATCGT TATGGAAAGACATCGAATGGAATGGAATTGACTCGA ATGGAATGGACTGGAATGGAACG | 5715 |

Example 35. In Vitro Expression of Modified Nucleic Acids with miR-122

MicroRNA controls gene expression through the translational suppression and/or degradation of target messenger RNA. The expression of G-CSF mRNA and Factor IX mRNA with human or mouse alpha-globin 3' untranslated regions (UTRs) were down regulated in human primary hepatocytes using miR-122 sequences in the 3'UTR.

Primary human hepatocytes were seeded at a density of 350000 per well in 500 ul cell culture medium (InVitro GRO medium from Celsis, Chicago, Ill.).

G-CSF mRNA having a human alpha-globin 3'UTR (G-CSF Hs3'UTR; mRNA sequence shown in SEQ ID NO: 5716; polyA tail of approximately 140 nucleotides not shown in sequence; 5'cap, Cap1) or a mouse alpha-globin 3'UTR (G-CSF Mm3'UTR; mRNA sequence shown in SEQ ID NO: 5717; polyA tail of approximately 140 nucleotides not shown in sequence; 5'cap, Cap1) were fully modified with 5-methylcytidine and 1-methylpseudouridine. G-CSF mRNA containing a human 3'UTR having a miR-122 sequence in the 3'UTR (G-CSF Hs3'UTR miR-122; mRNA sequence shown in SEQ ID NO: 5018; polyA tail of approximately 140 nucleotides not shown in sequence; 5'cap, Cap1), or a miR-122 seed sequence in the 3'UTR (G-CSF Hs3'UTR miR-122 seed; mRNA sequence shown in SEQ ID NO: 5020; polyA tail of approximately 140 nucleotides not shown in sequence; 5'cap, Cap1) or a miR-122 sequence without the seed sequence in the 3'UTR (G-CSF Hs3'UTR miR-122 seedless; mRNA sequence shown in SEQ ID NO: 5022; polyA tail of approximately 140 nucleotides not shown in sequence; 5'cap, Cap1) were fully modified with 5-methylcytidine and 1-methylpseudouridine. G-CSF mRNA containing a mouse 3'UTR having a miR-122 sequence in the 3'UTR (G-CSF Mm3'UTR miR-122; mRNA sequence shown in SEQ ID NO: 5024; polyA tail of approximately 140 nucleotides not shown in sequence; 5'cap, Cap1), or a miR-122 seed sequence in the 3'UTR (G-CSF Mm3'UTR miR-122 seed; mRNA sequence shown in SEQ ID NO: 5026; polyA tail of approximately 140 nucleotides not shown in sequence; 5'cap, Cap1) or a miR-122 sequence without the seed sequence in the 3'UTR (G-CSF Mm3'UTR miR-122 seedless; mRNA sequence shown in SEQ ID NO: 5028; polyA tail of approximately 140 nucleotides not shown in sequence; 5'cap, Cap1) were fully modified with 5-methylcytidine and 1-methylpseudouridine.

Factor IX mRNA having a human alpha-globin 3'UTR (Factor IX Hs3'UTR; mRNA sequence shown in SEQ ID NO: 5718; polyA tail of approximately 140 nucleotides not shown in sequence; 5'cap, Cap1) or a mouse alpha-globin 3'UTR (Factor IX Mm3'UTR; mRNA sequence shown in SEQ ID NO: 5719; polyA tail of approximately 140 nucleotides not shown in sequence; 5'cap, Cap1) were fully modified with 5-methylcytidine and 1-methylpseudouridine. Factor IX mRNA containing a human 3'UTR having a miR-122 sequence in the 3'UTR (Factor IX Hs3'UTR miR-122; mRNA sequence shown in SEQ ID NO: 5030; polyA tail of approximately 140 nucleotides not shown in sequence; 5'cap, Cap1), or a miR-122 seed sequence in the 3'UTR (Factor IX Hs3'UTR miR-122 seed; mRNA sequence shown in SEQ ID NO: 5032; polyA tail of approximately 140 nucleotides not shown in sequence; 5'cap, Cap1) or a miR-122 sequence without the seed sequence in the 3'UTR (Factor IX Hs3'UTR miR-122 seedless; mRNA sequence shown in SEQ ID NO: 5034; polyA tail of approximately 140 nucleotides not shown in sequence; 5'cap, Cap1) were fully modified with 5-methylcytidine and 1-methylpseudouridine. Factor IX mRNA containing a mouse 3'UTR having a miR-122 sequence in the 3'UTR (Factor IX Mm3'UTR miR-122; mRNA sequence shown in SEQ ID NO: 5036; polyA tail of approximately 140 nucleotides not shown in sequence; 5'cap, Cap1), or a miR-122 seed sequence in the 3'UTR (Factor IX Mm3'UTR miR-122 seed; mRNA sequence shown in SEQ ID NO: 5038; polyA tail of approximately 140 nucleotides not shown in sequence; 5'cap, Cap1) or a miR-122 sequence without the seed sequence in the 3'UTR (Factor IX Mm3'UTR miR-122 seedless; mRNA sequence shown in SEQ ID NO: 5040; polyA tail of approximately 140 nucleotides not shown in sequence; 5'cap, Cap1) were fully modified with 5-methylcytidine and 1-methylpseudouridine.

Each G-CSF or Factor IX mRNA sequence was tested at a concentration of 500 ng per well in 24 well plates. 24, 48 and 72 hours after transfection, the expression of protein was measured by ELISA. The protein levels for G-CSF are shown in Table 33 and the protein levels for Factor IX are shown in Table 34.

TABLE 33

G-CSF Protein Expression

| Description | Protein Expression (ng/ml) | | |
| --- | --- | --- | --- |
| | 24 Hours | 48 Hours | 72 Hours |
| G-CSF Hs3'UTR | 43.9 | 18.8 | 5.7 |
| G-CSF Hs3'UTR miR-122 | 6.9 | 0.7 | 0.12 |
| G-CSF Hs3'UTR miR-122 seed | 48.5 | 25.6 | 8.2 |
| G-CSF Hs3'UTR miR-122 seedless | 31.7 | 11.7 | 3.4 |
| G-CSF Mm3'UTR | 84.9 | 100.4 | 21.3 |
| G-CSF Mm3'UTR miR-122 | 24.0 | 3.03 | 0.8 |
| G-CSF Mm3'UTR miR-122 seed | 115.8 | 96.4 | 19.2 |
| G-CSF Mm3'UTR miR-122 seedless | 113.1 | 92.9 | 18.9 |

TABLE 34

Factor IX Protein Expression

| Description | Protein Expression (ng/ml) | | |
| --- | --- | --- | --- |
| | 24 Hours | 48 Hours | 72 Hours |
| Factor IX Hs3'UTR | 63.2 | 124.8 | 44.3 |
| Factor IX Hs3'UTR miR-122 | 15.9 | 4.4 | 0.4 |
| Factor IX Hs3'UTR miR-122 seed | 60.2 | 63.0 | 20.1 |
| Factor IX Hs3'UTR miR-122 seedless | 53.7 | 75.0 | 24.5 |
| Factor IX Mm3'UTR | 90.8 | 159.6 | 70.5 |
| Factor IX Mm3'UTR miR-122 | 11.8 | 5.0 | 1.0 |
| Factor IX Mm3'UTR miR-122 seed | 77.2 | 115.0 | 41.7 |
| Factor IX Mm3'UTR miR-122 seedless | 69.3 | 123.8 | 49 |

Example 36. In Vitro Expression of Modified Nucleic Acid with Mir-142 or miR-146 Binding Sites HeLa and RAW264 cells were seeded at a density of 17000 and 80000 per well respectively, in 100 ul cell culture medium (DMEM+10% FBS).

G-CSF mRNA (G-CSF; mRNA sequence shown in SEQ ID NO: 4258; polyA tail of approximately 140 nucleotides not shown in sequence; 5'cap, Cap1) was fully modified with 5-methylcytidine and 1-methylpseudouridine.

G-CSF mRNA having a miR-142-3p sequence in the 3'UTR (G-CSF miR-142-3p; mRNA sequence shown in SEQ ID NO: 4992; polyA tail of approximately 140 nucleotides not shown in sequence; 5'cap, Cap1), or a miR-142-3p seed sequence in the 3'UTR (G-CSF miR-142-3p seed; mRNA sequence shown in SEQ ID NO: 4994; polyA tail of approximately 140 nucleotides not shown in sequence; 5'cap, Cap1) or a miR-142-3p sequence without the seed sequence in the 3'UTR (G-CSF miR-142-3p seedless; mRNA sequence shown in SEQ ID NO: 4996; polyA tail of approximately 140 nucleotides not shown in sequence; 5'cap, Cap1) were fully modified with 5-methylcytidine and 1-methylpseudouridine.

G-CSF mRNA having a miR-142-5p sequence in the 3'UTR (G-CSF miR-142-5p; mRNA sequence shown in SEQ ID NO: 4986; polyA tail of approximately 140 nucleotides not shown in sequence; 5'cap, Cap1), or a miR-142-5p seed sequence in the 3'UTR (G-CSF miR-142-5p seed; mRNA sequence shown in SEQ ID NO: 4988; polyA tail of approximately 140 nucleotides not shown in sequence; 5'cap, Cap1) or a miR-142-5p sequence without the seed sequence in the 3'UTR (G-CSF miR-142-5p seedless; mRNA sequence shown in SEQ ID NO: 4990; polyA tail of approximately 140 nucleotides not shown in sequence; 5'cap, Cap1) were fully modified with 5-methylcytidine and 1-methylpseudouridine.

G-CSF mRNA having a miR-146a sequence in the 3'UTR (G-CSF miR-146a; mRNA sequence shown in SEQ ID NO: 4998; polyA tail of approximately 140 nucleotides not shown in sequence; 5'cap, Cap1), or a miR-146a seed sequence in the 3'UTR (G-CSF miR-146a seed; mRNA sequence shown in SEQ ID NO: 5000; polyA tail of approximately 140 nucleotides not shown in sequence; 5'cap, Cap1) or a miR-146a sequence without the seed sequence in the 3'UTR (G-CSF miR-146a seedless; mRNA sequence shown in SEQ ID NO: 5002; polyA tail of approximately 140 nucleotides not shown in sequence; 5'cap, Cap1) were fully modified with 5-methylcytidine and 1-methylpseudouridine.

Each G-CSF mRNA sequence was tested at a concentration of 500 ng per well in 24 well plates for each cell type. 24 hours after transfection, the expression of protein was measured by ELISA and the protein levels are shown in Table 35. The G-CSF sequences with a miR-142-3p sequence in the 3'UTR down regulated G-CSF expression in RAW264 cells whereas the G-CSF sequences with a miR-142-5p or miR-146a sequence in the 3'UTR did not down regulate G-CSF expression.

TABLE 35

G-CSF Expression

| Description | HeLa Cells Protein Expression (ng/ml) | RAW264 Cells Protein Expression (ng/ml) |
| --- | --- | --- |
| G-CSF | 243.5 | 173.7 |
| G-CSF miR-142-3p | 309.1 | 67.6 |
| G-CSF miR-142-3p seed | 259.8 | 178.1 |
| G-CSF miR-142-3p seedless | 321.7 | 220.2 |
| G-CSF miR-142-5p | 291.8 | 223.3 |
| G-CSF miR-142-5p seed | 261.3 | 233.1 |
| G-CSF miR-142-5p seedless | 330.2 | 255.1 |
| G-CSF miR-146a | 272.6 | 125.2 |
| G-CSF miR-146a seed | 219.4 | 138.3 |
| G-CSF miR-146a seedless | 217.7 | 132.8 |

Example 37. Effect of Kozak Sequence on Expression of Modified Nucleic Acids

HeLa cells were seeded at a density of 17000 per well in 100 ul cell culture medium (DMEM+10% FBS). G-CSF mRNA having an IRES sequence and Kozak sequence (G-CSF IRES Kozak; mRNA sequence shown in SEQ ID NO: 5004; polyA tail of approximately 140 nucleotides not shown in sequence; 5'cap, Cap1), G-CSF mRNA having an IRES sequence but not a Kozak sequence (G-CSF IRES; mRNA sequence shown in SEQ ID NO: 5006; polyA tail of approximately 140 nucleotides not shown in sequence; 5'cap, Cap1), G-CSF mRNA without an IRES or Kozak sequence (GCSF no Kozak; mRNA sequence shown in SEQ ID NO: 5008; polyA tail of approximately 140 nucleotides not shown in sequence; 5'cap, Cap1) or a G-CSF sequence having a Kozak sequence (G-CSF Kozak; mRNA sequence shown in SEQ ID NO: 5720; polyA tail of approximately 140 nucleotides not shown in sequence; 5'cap, Cap1) were fully modified with fully modified with 5-methylcytidine and 1-methylpseudouridine and tested at a concentration of 75 ng per well in 24 well plates. 24 hours after transfection, the expression of G-CSF was measured by ELISA, and the results are shown in Table 36.

TABLE 36

G-CSF expression

| Description | Protein Expression (ng/ml) |
| --- | --- |
| G-CSF IRES Kozak | 2.01 |
| G-CSF IRES | 1.64 |
| G-CSF no Kozak | 795.53 |
| G-CSF Kozak | 606.28 |

Example 38. MALAT1 Constructs

Modified mRNA encoding G-CSF or mCherry with a human or mouse MALAT1 sequence and their corresponding cDNA sequences are shown below in Table 37. In Table 37, the start codon of each sequence is underlined and the MALAT1 sequences are bolded.

TABLE 37

MALAT1 Constructs

| | Sequence | SEQ ID NO: |
| --- | --- | --- |
| G-CSF with Mouse MALAT1 sequence | Optimized G-CSF cDNA sequence containing a T7 polymerase site, kozak sequence, and a Mouse MALAT1 sequence (bold): TAATACGACTCACTATA GGGAAATAAGAGAGAAAAGAAGAGTAAGAAGAAATA TAAGAGCCACC ATGGCCGGTCCCGCGACCCAAAGCCCCATGAAACTTA TGGCCCTGCAGTTGCTGCTTTGGCACTCGGCCCTCTGG ACAGTCCAAGAAGCGACTCCTCTCGGACCTGCCTCAT CGTTGCCGCAGTCATTCCTTTTGAAGTGTCTGGAGCAG GTGCGAAAGATTCAGGGCGATGGAGCCGCACTCCAAG AGAAGCTCTGCGCGACATACAAACTTTGCCATCCCGA GGAGCTCGTACTGCTCGGGCACAGCTTGGGGATTCCC TGGGCTCCTCTCTCGTCCTGTCCGTCGCAGGCTTTGCA GTTGGCAGGGTGCCTTTCCCAGCTCCACTCCGGTTTGT TCTTGTATCAGGGACTGCTGCAAGCCCTTGAGGGAAT CTCGCCAGAATTGGGCCCGACGCTGGACACGTTGCAG CTCGACGTGGCGGATTTCGCAACAACCATCTGGCAGC AGATGGAGGAACTGGGGATGGCACCCGCGCTGCAGCC CACGCAGGGGGCAATGCCGGCCTTTGCGTCCGCGTTT CAGCGCAGGGCGGGTGGAGTCCTCGTAGCGAGCCACC TTCAATCATTTTTGGAAGTCTCGTACCGGGTGCTGAGA CATCTTGCGCAGCCG TGATAATAG GATTCGTCAGTAGGGTTGTAAAGGTTTTTCTTTTCC TGAGAAAACAACCTTTTGTTTTCTCAGGTTTTGCTT TTTGGCCTTTCCCTAGCTTTAAAAAAAAAAAAGCAA AAGTGGTCTTTGAATAAAGTCTGAGTGGGCGGCTCTA GA | 5721 |

TABLE 37-continued

MALAT1 Constructs

| Sequence | SEQ ID NO: |
|---|---|
| mRNA sequence (transcribed):<br>GGGAAAUAAGAGAGAAAAGAAGAGUAAGAAGAAAU<br>AUAAGAGCCACC<br>AUGGCCGGUCCCGCGACCCAAAGCCCCAUGAAACUU<br>AUGGCCCUGCAGUUGCUGCUUUGGCACUCGGCCCUC<br>UGGACAGUCCAAGAAGCGACUCCUCUCGGACCUGCC<br>UCAUCGUUGCCGCAGUCAUUCCUUUUGAAGUGUCUG<br>GAGCAGGUGCGAAAGAUUCAGGGCGAUGGAGCCGCA<br>CUCCAAGAGAAGCUCUGCGCGACAUACAAACUUUGC<br>CAUCCCGAGGAGCUCUACUGCUCGGGCACAGCUUG<br>GGGAUUCCCUGGGCUCCUCUCUCGUCCUGUCCGUCG<br>CAGGCUUUGCAGUUGGCAGGGUGCCUUUCCCAGCUC<br>CACUCCGGUUUGUUCUUGUAUCAGGGACUGCUGCAA<br>GCCCUUGAGGGAAUCUCGCCAGAAUUGGGCCCGACG<br>CUGGACACGUUGCAGCUCGACGUGGCGGAUUUCGCA<br>ACAACCAUCUGGCAGCAGAUGGAGGAACUGGGGAUG<br>GCACCCGCGCUGCAGCCCACGCAGGGGGCAAUGCCG<br>GCCUUUGCGUCCGCGUUUCAGCGCAGGGCGGGUGGA<br>GUCCUCGUAGCGAGCCACCUUCAAUCAUUUUUGGAA<br>GUCUCGUACCGGGUGCUGAGACAUCUUGCGCAGCCG<br>UGAUAAUAG<br>GAUUCGUCAGUAGGGUUGUAAAGGUUUUUCUUUU<br>CCUGAGAAAACAACCUUUUGUUUUCUCAGGUUUUG<br>CUUUUUGGCCUUUCCCUAGCUUUAAAAAAAAAAAA<br>GCAAAAGUGGUCUUUGAAUAAAGUCUGAGUGGGCG<br>GC | 5722 |
| mCherry with Mouse MALAT1 sequence — Optimized mCherry cDNA sequence containing a T7 polymerase site, kozak sequence, and a Mouse MALAT1 sequence (bold):<br>TAATACGACTCACTATA<br>GGGAAATAAGAGAGAAAAGAAGAGTAAGAAGAAATA<br>TAAGAGCCACC<br>ATGGTATCCAAGGGGAGGAGGACAACATGGCGATC<br>ATCAAGGAGTTCATGCGATTCAAGGTGCACATGGAAG<br>GTTCGGTCAACGGACACGAATTTGAAATCGAAGGAGA<br>GGGTGAAGGAAGGCCCTATGAAGGGACACAGACCGC<br>GAAACTCAAGGTCACGAAAGGGGGACCACTTCCTTTC<br>GCCTGGGACATTCTTTCGCCCCAGTTTATGTACGGGTC<br>CAAAGCATATGTGAAGCATCCCGCCGATATTCCTGAC<br>TATCTGAAACTCAGCTTTCCCGAGGGATTCAAGTGGG<br>AGCGGGTCATGAACTTTGAGGACGGGGGTGTAGTCAC<br>CGTAACCCAAGACTCAAGCCTCCAAGACGGCGAGTTC<br>ATCTACAAGGTCAAACTGCGGGGACTAACTTTCCGT<br>CGGATGGGCCGGTGATGCAGAAGAAAACGATGGGAT<br>GGGAAGCGTCATCGGAGAGGATGTACCCAGAAGATG<br>GTGCATTGAAGGGGAGATCAAGCAGAGACTGAAGTT<br>GAAAGATGGGGACATTATGATGCCGAGGTGAAAAC<br>GACATACAAAGCGAAAAAGCCGGTGCAGCTTCCCGGA<br>GCGTATAATGTGAATATCAAGTTGGATATTACTTCACA<br>CAATGAGGACTACACAATTGTCGAACAGTACGAACGC<br>GCTGAGGGTAGACACTCGACGGGAGGCATGGACGAG<br>TTGTACAAA<br>TGATAATAG<br>GATTCGTCAGTAGGGTTGTAAAGGTTTTTCTTTTCC<br>TGAGAAAACAACCTTTTGTTTTCTCAGGTTTTGCTT<br>TTTGGCCTTTCCCTAGCTTTAAAAAAAAAAAAGCAA<br>AAGTGGTCTTTGAATAAAGTCTGAGTGGGCGGCTCTA<br>GA | 5723 |
| mRNA sequence (transcribed):<br>GGGAAAUAAGAGAGAAAAGAAGAGUAAGAAGAAAU<br>AUAAGAGCCACC<br>AUGGUAUCCAAGGGGAGGAGGACAACAUGGCGAUC<br>AUCAAGGAGUUCAUGCGAUUCAAGGUGCACAUGGAA<br>GGUUCGGUCAACGGACACGAAUUUGAAAUCGAAGGA<br>GAGGGUGAAGGAAGGCCCUAUGAAGGGACACAGACC<br>GCGAAACUCAAGGUCACGAAAGGGGGACCACUUCCU<br>UUCGCCUGGGACAUUCUUUCGCCCCAGUUUAUGUAC<br>GGGUCCAAAGCAUAUGUGAAGCAUCCCGCCGAUAUU<br>CCUGACUAUCUGAAACUCAGCUUUCCCGAGGGAUUC<br>AAGUGGGAGCGGGUCAUGAACUUUGAGGACGGGGG<br>UGUAGUCACCGUAACCCAAGACUCAAGCCUCCAAGA<br>CGGCGAGUUCAUCUACAAGGUCAAACUGCGGGGGAC<br>UAACUUUCCGUCGGAUGGGCCGGUGAUGCAGAAGAA<br>AACGAUGGGAUGGGAAGCGUCAUCGGAGAGGAUGU | 5724 |

TABLE 37-continued

| MALAT1 Constructs | | |
|---|---|---|
| | Sequence | SEQ ID NO: |
| | ACCCAGAAGAUGGUGCAUUGAAGGGGGAGAUCAAGC<br>AGAGACUGAAGUUGAAAGAUGGGGGACAUUAUGAU<br>GCCGAGGUGAAAACGACAUACAAAGCGAAAAAGCCG<br>GUGCAGCUUCCCGGAGCGUAUAAUGUGAAUAUCAAG<br>UUGGAUAUUACUUCACACAAUGAGGACUACACAAUU<br>GUCGAACAGUACGAACGCGCUGAGGGUAGACACUCG<br>ACGGGAGGCAUGGACGAGUUGUACAAA<br>UGAUAAUAG<br>GAUUCGUCAGUAGGGUUGUAAAGGUUUUUCUUUU<br>CCUGAGAAAACAACCUUUUGUUUUCUCAGGUUUUG<br>CUUUUUGGCCUUUCCCUAGCUUUAAAAAAAAAAA<br>GCAAAAGUGGUCUUUGAAUAAAGUCUGAGUGGGCG<br>GC | |
| G-CSF with Human MALAT1 sequence | Optimized G-CSF cDNA sequence containing a T7 polymerase site, kozak sequence, and a Human MALAT1 sequence (bold):<br>TAATACGACTCACTATA<br>GGGAAATAAGAGAGAAAAGAAGAGTAAGAAGAAATA<br>TAAGAGCCACC<br>ATGGCCGGTCCCGCGACCCAAAGCCCCATGAAACTTA<br>TGGCCCTGCAGTTGCTGCTTTGGCACTCGGCCCTCTGG<br>ACAGTCCAAGAAGCGACTCCTCTCGGACCTGCCTCAT<br>CGTTGCCGCAGTCATTCCTTTTGAAGTGTCTGGAGCAG<br>GTGCGAAAGATTCAGGGCGATGGAGCCGCACTCCAAG<br>AGAAGCTCTGCGCGACATACAAACTTTGCCATCCCGA<br>GGGAGCTCGTACTGCTCGGGCACAGCTTGGGGATTCCC<br>TGGGCTCCTCTCTCGTCCTGTCCGTCGCAGGCTTTGCA<br>GTTGGCAGGGTGCCTTTCCCAGCTCCACTCCGGTTTGT<br>TCTTGTATCAGGGACTGCTGCAAGCCCTTGAGGGAAT<br>CTCGCCAGAATTGGGCCCGACGCTGGACACGTTGCAG<br>CTCGACGTGGCGGATTTCGCAACAACCATCTGGCAGC<br>AGATGGAGGAACTGGGGATGGCACCCGCGCTGCAGCC<br>CACGCAGGGGGCAATGCCGGCCTTTGCGTCCGCGTTT<br>CAGCGCAGGGCGGGTGGAGTCCTCGTAGCGAGCCACC<br>TTCAATCATTTTTGGAAGTCTCGTACCGGGTGCTGAGA<br>CATCTTGCGCAGCCG<br>TGATAATAG<br>TGCTCTTCAGTAGGGTCATGAAGGTTTTTCTTTTCC<br>TGAGAAAACAACACGTATTGTTTTCTCAGGTTTTGC<br>TTTTTGGCCTTTTTCTAGCTTAAAAAAAAAAAAAGC<br>AAAAGTGGTCTTTGAATAAAGTCTGAGTGGGCGGCTC<br>TAGA | 5725 |
| | mRNA sequence (transcribed):<br>GGGAAAUAAGAGAGAAAAGAAGAGUAAGAAGAAAU<br>AUAAGAGCCACC<br>AUGGCCGGUCCCGCGACCCAAAGCCCCAUGAAACUU<br>AUGGCCCUGCAGUUGCUGCUUUGGCACUCGGCCCUC<br>UGGACAGUCCAAGAAGCGACUCCUCUCGGACCUGCC<br>UCAUCGUUGCCGCAGUCAUUCCUUUUGAAGUGUCUG<br>GAGCAGGUGCGAAAGAUUCAGGGCGAUGGAGCCGCA<br>CUCCAAGAGAAGCUCUGCGCGACAUACAAACUUUGC<br>CAUCCCGAGGAGCUCGUACUGCUCGGGCACAGCUUG<br>GGGAUUCCCUGGGCUCCUCUCUCGUCCUGUCCGUCG<br>CAGGCUUUGCAGUUGGCAGGGUGCCUUUCCCAGCUC<br>CACUCCGGUUUGUUCUUGUAUCAGGGACUGCUGCAA<br>GCCCUUGAGGGAAUCUCGCCAGAAUUGGGCCCGACG<br>CUGGACACGUUGCAGCUCGACGUGGCGGAUUUCGCA<br>ACAACCAUCUGGCAGCAGAUGGAGGAACUGGGGAUG<br>GCACCCGCGCUGCAGCCCACGCAGGGGGCAAUGCCG<br>GCCUUUGCGUCCGCGUUUCAGCGCAGGGCGGGUGGA<br>GUCCUCGUAGCGAGCCACCUUCAAUCAUUUUUGGAA<br>GUCUCGUACCGGGUGCUGAGACAUCUUGCGCAGCCG<br>UGAUAAUAG<br>UGCUCUUCAGUAGGGUCAUGAAGGUUUUUCUUUUC<br>CUGAGAAAACAACACGUAUUGUUUUCUCAGGUUUU<br>GCUUUUUGGCCUUUUUCUAGCUUAAAAAAAAAAAA<br>AGCAAAAGUGGUCUUUGAAUAAAGUCUGAGUGGGC<br>GGC | 5726 |

TABLE 37-continued

MALAT1 Constructs

| | Sequence | SEQ ID NO: |
|---|---|---|
| mCherry with Human MALAT1 sequence | Optimized mCherry cDNA sequence containing a T7 polymerase site, kozak sequence, and a Human MALAT1 sequence (bold): TAATACGACTCACTATA GGGAAATAAGAGAGAAAAGAAGAGTAAGAAGAAATA TAAGAGCCACC ATGGTATCCAAGGGGGAGGAGGACAACATGGCGATC ATCAAGGAGTTCATGCGATTCAAGGTGCACATGGAAG GTTCGGTCAACGGACACGAATTTGAAATCGAAGGAGA GGGTGAAGGAAGGCCCTATGAAGGGACACAGACCGC GAAACTCAAGGTCACGAAAGGGGGACCACTTCCTTTC GCCTGGGACATTCTTTCGCCCCAGTTTATGTACGGGTC CAAAGCATATGTGAAGCATCCCGCCGATATTCCTGAC TATCTGAAACTCAGCTTTCCCGAGGGATTCAAGTGGG AGCGGGTCATGAACTTTGAGGACGGGGGTGTAGTCAC CGTAACCCAAGACTCAAGCCTCCAAGACGGCGAGTTC ATCTACAAGGTCAAACTGCGGGGGACTAACTTTCCGT CGGATGGGCCGGTGATGCAGAAGAAAACGATGGGAT GGGAAGCGTCATCGGAGAGGATGTACCCAGAAGATG GTGCATTGAAGGGGGAGATCAAGCAGAGACTGAAGTT GAAAGATGGGGGACATTATGATGCCGAGGTGAAAAC GACATACAAAGCGAAAAAGCCGGTGCAGCTTCCCGGA GCGTATAATGTGAATATCAAGTTGGATATTACTTCACA CAATGAGGACTACACAATTGTCGAACAGTACGAACGC GCTGAGGGTAGACACTCGACGGGAGGCATGGACGAG TTGTACAAA TGATAATAG TGCTCTTCAGTAGGGTCATGAAGGTTTTTCTTTTCC TGAGAAAACAACACGTATTGTTTTCTCAGGTTTTGC TTTTTGGCCTTTTTCTAGCTTAAAAAAAAAAAAAGC AAAAGTGGTCTTTGAATAAAGTCTGAGTGGGCGGCTC TAGA | 5727 |
| | mRNA sequence (transcribed): GGGAAAUAAGAGAGAAAAGAAGAGUAAGAAGAAAU AUAAGAGCCACC AUGGUAUCCAAGGGGGAGGAGGACAACAUGGCGAUC AUCAAGGAGUUCAUGCGAUUCAAGGUGCACAUGGAA GGUUCGGUCAACGGACACGAAUUUGAAAUCGAAGGA GAGGGUGAAGGAAGGCCCUAUGAAGGGACACAGACC GCGAAACUCAAGGUCACGAAAGGGGGACCACUUCCU UUCGCCUGGGACAUUCUUUCGCCCCAGUUUAUGUAC GGGUCCAAAGCAUAUGUGAAGCAUCCCGCCGAUAUU CCUGACUAUCUGAAACUCAGCUUUCCCGAGGGAUUC AAGUGGGAGCGGGUCAUGAACUUUGAGGACGGGGG UGUAGUCACCGUAACCCAAGACUCAAGCCUCCAAGA CGGCGAGUUCAUCUACAAGGUCAAACUGCGGGGGAC UAACUUUCCGUCGGAUGGGCCGGUGAUGCAGAAGAA AACGAUGGGAUGGGAAGCGUCAUCGGAGAGGAUGU ACCCAGAAGAUGGUGCAUUGAAGGGGGAGAUCAAGC AGAGACUGAAGUUGAAAGAUGGGGGACAUUAUGAU GCCGAGGUGAAAACGACAUACAAAGCGAAAAAGCCG GUGCAGCUUCCCGGAGCGUAUAAUGUGAAUAUCAAG UUGGAUAUUACUUCACACAAUGAGGACUACACAAUU GUCGAACAGUACGAACGCGCUGAGGGUAGACACUCG ACGGGAGGCAUGGACGAGUUGUACAAA UGAUAAUAG UGCUCUUCAGUAGGGUCAUGAAGGUUUUUCUUUUC CUGAGAAAACAACACGUAUUGUUUUCUCAGGUUUU GCUUUUUGGCCUUUUUCUAGCUUAAAAAAAAAAAAA AGCAAAAGUGGUCUUUGAAUAAAGUCUGAGUGGGC GGC | 5728 |

These modified mRNA sequences can include at least one chemical modification described herein. The G-CSF or mCherry modified mRNA sequence can be formulated, using methods described herein and/or known in the art, prior to transfection and/or administration.

The modified mRNA sequence encoding G-CSF or mCherry can be transfected in vitro to various cell types such as HEK293, HeLa, PBMC and BJ fibroblast and those described in Table 25 using methods disclosed herein and/or are known in the art. The cells are then analyzed using methods disclosed herein and/or are known in the art to determine the concentration of G-CSF or mCherry and/or the cell viability.

Example 39. Utilization of Heterologous 5'UTRs

A 5' UTR may be provided as a flanking region to the nucleic acids, modified nucleic acids or mmRNA of the invention. 5'UTR may be homologous or heterologous to the coding region found in the nucleic acids, modified nucleic acids or mmRNA of the invention. Multiple 5' UTRs may be included in the flanking region and may be the same or of different sequences. Any portion of the flanking regions, including none, may be codon optimized and any may independently contain one or more different structural or chemical modifications, before and/or after codon optimization.

Shown in Lengthy Table 21 in U.S. Provisional Application No. 61/775,509, filed Mar. 9, 2013, entitled Heterologous Untranslated Regions for mRNA and in Lengthy Table 21 in U.S. Provisional Application No. 61/829,372, filed May 31, 2013, entitled Heterologous Untranslated Regions for mRNA is a listing of the start and stop site of the polynucleotides, primary constructs or mmRNAs of the invention. Each 5'UTR (5'UTR-005 to 5'UTR 68511) is identified by its start and stop site relative to its native or wild type (homologous) transcript (ENST; the identifier used in the ENSEMBL database).

To alter one or more properties of the nucleic acids, modified nucleic acids or mmRNA of the invention, 5'UTRs which are heterologous to the coding region of the nucleic acids, modified nucleic acids or mmRNA of the invention are engineered into compounds of the invention. The nucleic acids, modified nucleic acids or mmRNA are then administered to cells, tissue or organisms and outcomes such as protein level, localization and/or half life are measured to evaluate the beneficial effects the heterologous 5'UTR may have on the nucleic acids, modified nucleic acids or mmRNA of the invention. Variants of the 5' UTRs may be utilized wherein one or more nucleotides are added or removed to the termini, including A, T, C or G. 5'UTRs may also be codon-optimized or modified in any manner described herein.

Example 40. Further Utilization of 5' Untranslated Regions

A 5' UTR may be provided as a flanking region to the nucleic acids, modified nucleic acids or mmRNA of the invention. 5'UTR may be homologous or heterologous to the coding region found in the nucleic acids, modified nucleic acids or mmRNA of the invention. Multiple 5' UTRs may be included in the flanking region and may be the same or of different sequences. Any portion of the flanking regions, including none, may be codon optimized and any may independently contain one or more different structural or chemical modifications, before and/or after codon optimization.

Shown in Table 38 is a listing of 5'-untranslated regions which may be used with the nucleic acids, modified nucleic acids or mmRNA of the present invention.

To alter one or more properties of the nucleic acids, modified nucleic acids or mmRNA of the invention, 5'UTRs which are heterologous to the coding region of the nucleic acids, modified nucleic acids or mmRNA of the invention are engineered into compounds of the invention. The nucleic acids, modified nucleic acids or mmRNA are then administered to cells, tissue or organisms and outcomes such as protein level, localization and/or half life are measured to evaluate the beneficial effects the heterologous 5'UTR may have on the nucleic acids, modified nucleic acids or mmRNA of the invention. Variants of the 5' UTRs may be utilized wherein one or more nucleotides are added or removed to the termini, including A, T, C or G. 5'UTRs may also be codon-optimized or modified in any manner described herein.

TABLE 38

5'-Untranslated Regions

| 5' UTR Identifier | Name/ Description | Sequence | SEQ ID NO. |
|---|---|---|---|
| 5UTR-68512 | Upstream UTR | GGGAGATCAGAGAGAAAAGAAGAGTAAGAAGAAATA TAAGAGCCACC | 5729 |
| 5UTR-68513 | Upstream UTR | GGAATAAAAGTCTCAACACAACATATACAAAACAAAC GAATCTCAAGCAATCAAGCATTCTACTTCTATTGCAGC AATTTAAATCATTTCTTTTAAAGCAAAAGCAATTTTCT GAAAATTTTCACCATTTACGAACGATAGCAAC | 5730 |
| 5UTR-68514 | Upstream UTR | GGGAGACAAGCUUGGCAUUCCGGUACUGUUGGUAAA GCCACC | 5731 |
| 5UTR-68515 | Upstream UTR | GGGAATTAACAGAGAAAAGAAGAGTAAGAAGAAATA TAAGAGCCACC | 5732 |
| 5UTR-68516 | Upstream UTR | GGGAAATTAGACAGAAAAGAAGAGTAAGAAGAAATA TAAGAGCCACC | 5733 |
| 5UTR-68517 | Upstream UTR | GGGAAATAAGAGAGTAAAGAACAGTAAGAAGAAATA TAAGAGCCACC | 5734 |
| 5UTR-68518 | Upstream UTR | GGGAAAAAAGAGAGAAAAGAAGACTAAGAAGAAATA TAAGAGCCACC | 5735 |
| 5UTR-68519 | Upstream UTR | GGGAAATAAGAGAGAAAAGAAGAGTAAGAAGATATA TAAGAGCCACC | 5736 |
| 5UTR-68520 | Upstream UTR | GGGAAATAAGAGACAAAACAAGAGTAAGAAGAAATA TAAGAGCCACC | 5737 |
| 5UTR-68521 | Upstream UTR | GGGAAATTAGAGAGTAAAGAACAGTAAGTAGAATTAA AAGAGCCACC | 5738 |

TABLE 38-continued

5'-Untranslated Regions

| 5' UTR Identifier | Name/ Description | Sequence | SEQ ID NO. |
|---|---|---|---|
| 5UTR-68522 | Upstream UTR | GGGAAATAAGAGAGAATAGAAGAGTAAGAAGAAATA TAAGAGCCACC | 5739 |
| 5UTR-68523 | Upstream UTR | GGGAAATAAGAGAGAAAAGAAGAGTAAGAAGAAAAT TAAGAGCCACC | 5740 |
| 5UTR-68524 | Upstream UTR | GGGAAATAAGAGAGAAAAGAAGAGTAAGAAGAAATT TAAGAGCCACC | 5741 |

Example 41. Protein Production Using Heterologous 5'UTRs

The day before transfection, 20,000 HeLa cells (ATCC no. CCL-2; Manassas, Va.) were harvested by treatment with Trypsin-EDTA solution (LifeTechnologies, Grand Island, N.Y.) and seeded in a total volume of 100 ul EMEM medium (supplemented with 10% FCS and 1× Glutamax) per well in a 96-well cell culture plate (Corning, Manassas, Va.). The cells were grown at 37° C. in 5% $CO_2$ atmosphere overnight. The next day, 37.5 ng, 75 ng or 150 of G-CSF modified RNA comprising a nucleic acid sequence for 5UTR-001 (mRNA sequence shown in SEQ ID NO: 5; polyA tail of approximately 140 nucleotides not shown in sequence; 5'cap, Cap1; fully modified with 5-methylcytidine and 1-methylpseudouridine), G-CSF modified RNA comprising a nucleic acid sequence for 5UTR-68515 (mRNA sequence shown in SEQ ID NO: 5732; polyA tail of approximately 140 nucleotides not shown in sequence; 5'cap, Cap1; fully modified with 5-methylcytidine and 1-methylpseudouridine), G-CSF modified RNA comprising a nucleic acid sequence for 5UTR-68516 (mRNA sequence shown in SEQ ID NO: 5733; polyA tail of approximately 140 nucleotides not shown in sequence; 5'cap, Cap1; fully modified with 5-methylcytidine and 1-methylpseudouridine), G-CSF modified RNA comprising a nucleic acid sequence for 5UTR-68521 (mRNA sequence shown in SEQ ID NO: 5738; polyA tail of approximately 140 nucleotides not shown in sequence; 5'cap, Cap1; fully modified with 5-methylcytidine and 1-methylpseudouridine) or G-CSF modified RNA comprising a nucleic acid sequence for 5UTR-68522 (mRNA sequence shown in SEQ ID NO: 5739; polyA tail of approximately 140 nucleotides not shown in sequence; 5'cap, Cap1; fully modified with 5-methylcytidine and 1-methylpseudouridine) were diluted in 10 ul final volume of OPTI-MEM (LifeTechnologies, Grand Island, N.Y.). Lipofectamine 2000 (LifeTechnologies, Grand Island, N.Y.) was used as transfection reagent and 0.2 ul were diluted in 10 ul final volume of OPTI-MEM. After 5 minutes of incubation at room temperature, both solutions were combined and incubated an additional 15 minute at room temperature. Then the 20 ul combined solution was added to the 100 ul cell culture medium containing the HeLa cells and incubated at room temperature.

After an incubation of 24 hours cells expressing G-CSF were lysed with 100 ul of Passive Lysis Buffer (Promega, Madison, Wis.) according to manufacturer instructions. G-CSF protein production was determined by ELISA.

These results, shown in Table 39, demonstrate that G-CSF mRNA comprising the 5UTR-68515 or 5UTR-68521 produced the most protein whereas G-CSF mRNA comprising 5UTR-68522 produced the least amount of protein.

TABLE 39

G-CSF Protein Production from Heterologous 5'UTRs

| | G-CSF Protein (ng/ml) | | |
|---|---|---|---|
| 5'UTR | 37.5 ng | 75 ng | 150 ng |
| 5UTR-001 | 131.3 | 191.1 | 696.1 |
| 5UTR-68515 | 245.6 | 394.3 | 850.3 |
| 5UTR-68516 | 188.6 | 397.4 | 719.6 |
| 5UTR-68521 | 191.4 | 449.1 | 892.1 |
| 5UTR-68522 | 135.9 | 331.3 | 595.6 |

Example 42. Effect of the Kozak Sequence in Modified Nucleic Acids

HeLa cells were seeded at a density of 15,000 per well in 100 ul cell culture medium DMEM+FBS 10%. G-CSF mRNA having a Kozak sequence (G-CSF Kozak; mRNA sequence shown in SEQ ID NO: 5004; polyA tail of approximately 140 nucleotides not shown in sequence; 5'cap, Cap1; fully modified with 5-methylcytidine and 1-methylpseudouridine) or G-CSF mRNA not having a Kozak sequence (G-CSF no Kozak; mRNA sequence shown in SEQ ID NO: 5008; polyA tail of approximately 140 nucleotides not shown in sequence; 5'cap, Cap1; fully modified with 5-methylcytidine and 1-methylpseudouridine) and transfected in triplicate at a concentration of 75 ng per well in 96 well plates. 24 hours, 48 hours and 72 hours after transfection, the supernatant was collected and expression of G-CSF was measured by ELISA, and the results are shown in Table 40.

TABLE 40

G-CSF Expression

| Time point | G-CSF Kozak Protein Expression (ng/ml) | G-CSF No Kozak Protein Expression (ng/ml) |
|---|---|---|
| 24 hours | 223.93 | 408.23 |
| 48 hours | 604.76 | 1217.29 |
| 72 hours | 365.48 | 703.93 |

Example 43. Effect of the Altering the 5'UTR in Modified Nucleic Acids mRNA encoding a polypeptide of interest and having a polyA sequence and a cap, is fully modified with at least one chemistry described herein and/or in co-pending International Publication No WO2013052523, the contents of which are herein incorporated by reference in its entirety and the mRNA comprises a 5'UTR from Table 41. HeLa cells are seeded in cell culture medium and are transfected with the mRNA at a pre-determined concentration (ng per well) in well plates. At pre-determined intervals (e.g., 2 hours, 4 hours, 6 hours, 8 hours, 10 hours, 12 hours, 14 hours, 16 hours, 18 hours, 20 hours, 22 hours, 24 hours, 36 hours, 48 hours, 60 hours and/or 72 hours) after transfection, the supernatant is collected and expression of protein is measured by ELISA.

TABLE 41

5' UTR

| 5' UTR Identifier | Name/ Description | Sequence | SEQ ID NO. |
|---|---|---|---|
| 5UTR-001 | Synthetic UTR | GGGAAATAAGAGAGAAAAGAAGAGTAAGAAG AAATATAAGAGCCACC | 5 |
| 5UTR-68525 | Synthetic UTR | GGGAAATAAGAGAGAAAAGAAGAGTAAGAAG AAATATAAGAGCCTCC | 5742 |
| 5UTR-68526 | Synthetic UTR | GGGAAATAAGAGAGAAAAGAAGAGTAAGAAG AAATATATGA | 5743 |
| 5UTR-68527 | Synthetic UTR | GGGAAATAAGAGAGAAAAGAAGAGTAAGAAG AAATATA | 5744 |

Example 44. Effect of the PolyA Tail Length in Modified Nucleic Acids

A. Bioanalyzer

Modified G-CSF mRNA (mRNA sequence shown in SEQ ID NO: 5745; 5'cap, Cap 1 fully modified with 5-methylcytidine and 1-methylpseudouridine (5mc/1mpU) or fully modified with 1-methylpseudouridine (1mpU)), modified Factor IX (FIX) mRNA (mRNA sequence shown in SEQ ID NO: 5746; 5'cap, Cap 1 fully modified with 5-methylcytidine and 1-methylpseudouridine (5mc/1mpU) or fully modified with 1-methylpseudouridine (1mpU)), modified erythropoietin (EPO) mRNA (mRNA sequence shown in SEQ ID NO: 5747; 5'cap, Cap 1 fully modified with 5-methylcytidine and 1-methylpseudouridine (5mc/1mpU) or fully modified with 1-methylpseudouridine (1mpU)) or modified mCherry mRNA (mRNA sequence shown in SEQ ID NO: 5748; 5'cap, Cap 1 fully modified with 5-methylcytidine and 1-methylpseudouridine (5mc/1mpU) or fully modified with 1-methylpseudouridine (1mpU)) having a polyA tail of 20, 40, 80, 100, 120, 140 or 160 nucleotides in length or no polyA tail were analyzed by bioanalyzer (Agilent 2100 bioanalyzer). All samples, maintained integrity of the mRNA as determined by bioanalyzer.

B. BJ Fibroblasts

Human primary foreskin fibroblasts (BJ fibroblasts) are obtained from American Type Culture Collection (ATCC) (catalog #CRL-2522) and grown in Eagle's Minimum Essential Medium (ATCC, cat #11095-114) supplemented with 10% fetal bovine serum at 37° C., under 5% CO2. BJ fibroblasts are seeded on a 24-well plate at a density of 100,000 cells per well in 0.5 ml of culture medium. 250 ng of modified G-CSF mRNA (mRNA sequence shown in SEQ ID NO: 5745; 5'cap, Cap 1 fully modified with 5-methylcytidine and 1-methylpseudouridine (5mc/1mpU) or fully modified with 1-methylpseudouridine (1mpU)), modified Factor IX (FIX) mRNA (mRNA sequence shown in SEQ ID NO: 5746; 5'cap, Cap 1 fully modified with 5-methylcytidine and 1-methylpseudouridine (5mc/1mpU) or fully modified with 1-methylpseudouridine (1mpU)), modified erythropoietin (EPO) mRNA (mRNA sequence shown in SEQ ID NO: 5747; 5'cap, Cap 1 fully modified with 5-methylcytidine and 1-methylpseudouridine (5mc/1mpU) or fully modified with 1-methylpseudouridine (1mpU)) or modified mCherry mRNA (mRNA sequence shown in SEQ ID NO: 5748; 5'cap, Cap 1 fully modified with 5-methylcytidine and 1-methylpseudouridine (5mc/1mpU) or fully modified with 1-methylpseudouridine (1mpU)) having a polyA tail of 20, 40, 80, 100, 120, 140 or 160 nucleotides in length or no polyA tail were transfected using Lipofectamine 2000, following manufacturer's protocol. FIX, G-CSF and EPO were transfected in triplicate.

The supernatant was collected at 24 hours, 48 hours and 72 hours for FIX, G-CSF and EPO and at 24 hours for mCherry. The protein expression was analyzed by ELISA for FIX, G-CSF and EPO and fluorescence-activated cell sorting (FACS) for mCherry. The results for G-CSF are shown in Table 42, the results for EPO are shown in Table 43, the results for FIX are shown in Table 44 and the results for mCherry are shown in Table 45.

TABLE 42

G-CSF Protein Expression

| Description | PolyA Tail Length | Time Point | Protein (ng/ml) |
|---|---|---|---|
| G-CSF 5 mC/1 mpU | 0 | 24 | 1.13 |
| | | 48 | 0.39 |
| | | 72 | 0.2 |
| G-CSF 1 mpU | 0 | 24 | 2 |
| | | 48 | 0.3 |
| | | 72 | 0.16 |
| G-CSF 5 mC/1 mpU | 20 | 24 | 41.85 |
| | | 48 | 32.75 |
| | | 72 | 13.38 |
| G-CSF 1 mpU | 20 | 24 | 204.43 |
| | | 48 | 138.71 |
| | | 72 | 96.36 |
| G-CSF 5 mC/1 mpU | 40 | 24 | 102.75 |
| | | 48 | 101.96 |
| | | 72 | 48.97 |
| G-CSF 1 mpU | 40 | 24 | 451.71 |
| | | 48 | 373.75 |
| | | 72 | 217.62 |
| G-CSF 5 mC/1 mpU | 80 | 24 | 135.85 |
| | | 48 | 167.21 |
| | | 72 | 96.66 |
| G-CSF 1 mpU | 80 | 24 | 534.89 |
| | | 48 | 352.39 |
| | | 72 | 203.89 |

TABLE 42-continued

G-CSF Protein Expression

| Description | PolyA Tail Length | Time Point | Protein (ng/ml) |
|---|---|---|---|
| G-CSF 5 mC/1 mpU | 100 | 24 | 168.31 |
|  |  | 48 | 195.16 |
|  |  | 72 | 127.8 |
| G-CSF 1 mpU | 100 | 24 | 561 |
|  |  | 48 | 406.8 |
|  |  | 72 | 265.64 |
| G-CSF 5 mC/1 mpU | 120 | 24 | 152.54 |
|  |  | 48 | 187.06 |
|  |  | 72 | 100.41 |
| G-CSF 1 mpU | 120 | 24 | 656.23 |
|  |  | 48 | 511.01 |
|  |  | 72 | 239.95 |
| G-CSF 5 mC/1 mpU | 140 | 24 | 146.24 |
|  |  | 48 | 202.05 |
|  |  | 72 | 121.89 |
| G-CSF 1 mpU | 140 | 24 | 724.58 |
|  |  | 48 | 627.6 |
|  |  | 72 | 341.61 |
| G-CSF 5 mC/1 mpU | 160 | 24 | 59.83 |
|  |  | 48 | 101.30 |
|  |  | 72 | 64.69 |
| G-CSF 1 mpU | 160 | 24 | 814.54 |
|  |  | 48 | 579.65 |
|  |  | 72 | 274.7 |

TABLE 43

EPO Protein Expression

| Description | PolyA Tail Length | Time Point | Protein (ng/ml) |
|---|---|---|---|
| EPO 5 mC/1 mpU | 0 | 24 | 3.12 |
|  |  | 48 | 0.13 |
|  |  | 72 | 0 |
| EPO 1 mpU | 0 | 24 | 0.77 |
|  |  | 48 | 0.07 |
|  |  | 72 | 0.007 |
| EPO 5 mC/1 mpU | 20 | 24 | 48.93 |
|  |  | 48 | 21.72 |
|  |  | 72 | 5.88 |
| EPO 1 mpU | 20 | 24 | 199.24 |
|  |  | 48 | 42.9 |
|  |  | 72 | 20.29 |
| EPO 5 mC/1 mpU | 40 | 24 | 400.66 |
|  |  | 48 | 165.38 |
|  |  | 72 | 63.36 |
| EPO 1 mpU | 40 | 24 | 210 |
|  |  | 48 | 182.56 |
|  |  | 72 | 54.31 |
| EPO 5 mC/1 mpU | 80 | 24 | 368.09 |
|  |  | 48 | 303.05 |
|  |  | 72 | 117.98 |
| EPO 1 mpU | 80 | 24 | 422.95 |
|  |  | 48 | 229.53 |
|  |  | 72 | 131.05 |
| EPO 5 mC/1 mpU | 100 | 24 | 619.59 |
|  |  | 48 | 366.19 |
|  |  | 72 | 199.63 |
| EPO 1 mpU | 100 | 24 | 374.88 |
|  |  | 48 | 240.21 |
|  |  | 72 | 128.08 |
| EPO 5 mC/1 mpU | 120 | 24 | 430.64 |
|  |  | 48 | 354.6 |
|  |  | 72 | 165.72 |
| EPO 1 mpU | 120 | 24 | 358.02 |
|  |  | 48 | 193.77 |
|  |  | 72 | 104.89 |
| EPO 5 mC/1 mpU | 140 | 24 | 531 |
|  |  | 48 | 426.96 |
|  |  | 72 | 164.3 |

TABLE 43-continued

EPO Protein Expression

| Description | PolyA Tail Length | Time Point | Protein (ng/ml) |
|---|---|---|---|
| EPO 1 mpU | 140 | 24 | 355.96 |
|  |  | 48 | 202.27 |
|  |  | 72 | 99.88 |
| EPO 5 mC/1 mpU | 160 | 24 | 608.66 |
|  |  | 48 | 324.31 |
|  |  | 72 | 181.94 |
| EPO 1 mpU | 160 | 24 | 351.01 |
|  |  | 48 | 197.76 |
|  |  | 72 | 109.64 |

TABLE 44

FIX Protein Expression

| Description | PolyA Tail Length | Time Point | Protein (ng/ml) |
|---|---|---|---|
| FIX 5 mC/1 mpU | 0 | 24 | 0.51 |
|  |  | 48 | 1.14 |
|  |  | 72 | 0.47 |
| FIX 1 mpU | 0 | 24 | 0.61 |
|  |  | 48 | 0.39 |
|  |  | 72 | 0.36 |
| FIX 5 mC/1 mpU | 20 | 24 | 0.92 |
|  |  | 48 | 0.46 |
|  |  | 72 | 0.49 |
| FIX 1 mpU | 20 | 24 | 5.97 |
|  |  | 48 | 14.99 |
|  |  | 72 | 7.47 |
| FIX 5 mC/1 mpU | 40 | 24 | 2.27 |
|  |  | 48 | 1.62 |
|  |  | 72 | 0.5 |
| FIX 1 mpU | 40 | 24 | 15.32 |
|  |  | 48 | 41.92 |
|  |  | 72 | 21.05 |
| FIX 5 mC/1 mpU | 80 | 24 | 7.12 |
|  |  | 48 | 10.14 |
|  |  | 72 | 3.66 |
| FIX 1 mpU | 80 | 24 | 35.32 |
|  |  | 48 | 74.18 |
|  |  | 72 | 38.47 |
| FIX 5 mC/1 mpU | 100 | 24 | 8.47 |
|  |  | 48 | 13.33 |
|  |  | 72 | 6.73 |
| FIX 1 mpU | 100 | 24 | 40.5 |
|  |  | 48 | 90.56 |
|  |  | 72 | 54.85 |
| FIX 5 mC/1 mpU | 120 | 24 | 10.06 |
|  |  | 48 | 15.89 |
|  |  | 72 | 6.2 |
| FIX 1 mpU | 120 | 24 | 47.5 |
|  |  | 48 | 106.55 |
|  |  | 72 | 59.35 |
| FIX 5 mC/1 mpU | 140 | 24 | 11.16 |
|  |  | 48 | 20.13 |
|  |  | 72 | 8.85 |
| FIX 1 mpU | 140 | 24 | 46.44 |
|  |  | 48 | 109.03 |
|  |  | 72 | 60.17 |
| FIX 5 mC/1 mpU | 160 | 24 | 13.06 |
|  |  | 48 | 22.31 |
|  |  | 72 | 10.19 |
| FIX 1 mpU | 160 | 24 | 45.35 |
|  |  | 48 | 99.47 |
|  |  | 72 | 60.48 |

TABLE 45 mCherry Expression

| Description | PolyA Tail Length | Time Point | Expression index |
|---|---|---|---|
| mCherry 5 mC/1 mpU | 0 | 24 | 445946.66 |
| mCherry 1 mpU | 0 | 24 | 509423.33 |
| mCherry 5 mC/1 mpU | 20 | 24 | 510846.66 |
| mCherry 1 mpU | 20 | 24 | 1688910 |
| mCherry 5 mC/1 mpU | 40 | 24 | 1443583.33 |
| mCherry 1 mpU | 40 | 24 | 3398540 |
| mCherry 5 mC/1 mpU | 80 | 24 | 1949826.66 |
| mCherry 1 mpU | 80 | 24 | 5783383.33 |
| mCherry 5 mC/1 mpU | 100 | 24 | 4963426.66 |
| mCherry 1 mpU | 100 | 24 | 4639580 |
| mCherry 5 mC/1 mpU | 120 | 24 | 5372706.66 |
| mCherry 1 mpU | 120 | 24 | 9184466.66 |
| mCherry 5 mC/1 mpU | 140 | 24 | 5127563.33 |
| mCherry 1 mpU | 140 | 24 | 5273213.33 |
| mCherry 5 mC/1 mpU | 160 | 24 | 5627163.33 |
| mCherry 1 mpU | 160 | 24 | 4876160 |

Example 45. Modified Nucleic Acids with a Mir-122 Sequence

A. HeLa Cells

HeLa cells were seeded at a density of 15,000 per well in 100 ul cell culture medium (DMEM+10% FBS). G-CSF mRNA having a miR-122 sequence in the 3'UTR (G-CSF miR122; mRNA sequence shown in SEQ ID NO: 5024; polyA tail of approximately 140 nucleotides not shown in sequence; 5'cap,Cap 1; fully modified with 5-methylcytidine and 1-methylpseudouridine) or G-CSF mRNA having a miR-122 sequence without the seed sequence in the 3'UTR (G-CSF seedless; mRNA sequence shown in SEQ ID NO: 5028; polyA tail of approximately 140 nucleotides not shown in sequence; 5'cap, Cap1; fully modified with 5-methylcytidine and 1-methylpseudouridine) were transfected with 0.3 ul per well of Lipofectamine 2000 at a concentration of 75 ng of mRNA per well in 96 well plates. The supernatant was collected between 16-18 hours after transfection and expression of G-CSF was measured by ELISA, and the results are shown in Table 46.

TABLE 46

G-CSF Expression in HeLa

| Description | Protein Expression (ng/ml) |
|---|---|
| G-CSF miR122 | 292.1 |
| G-CSF seedless | 335.7 |

B. Primary Human and Rat Hepatocytes

Primary human or rat hepatocytes cells were seeded at a density of 350,000 cells per well in 500 ul cell culture medium (InvitroGRO CP and InVitroGRO HI Medium+ 2.2% Torpedo Antibiotic Mix). G-CSF mRNA having a miR-122 sequence in the 3'UTR (G-CSF miR122; mRNA sequence shown in SEQ ID NO: 5024; polyA tail of approximately 140 nucleotides not shown in sequence; 5'cap, Cap1; fully modified with 5-methylcytidine and 1-methylpseudouridine) or G-CSF mRNA having a miR-122 sequence without the seed sequence in the 3'UTR (G-CSF seedless; mRNA sequence shown in SEQ ID NO: 5028; polyA tail of approximately 140 nucleotides not shown in sequence; 5'cap, Cap1; fully modified with 5-methylcytidine and 1-methylpseudouridine) were transfected with 1 ul per well of Lipofectamine 2000 at a concentration of 500 ng of mRNA per well in 24 well plates for the primary human hepatocytes and the primary rat hepatocytes. The supernatant was collected between 16-18 hours after transfection and expression of G-CSF was measured by ELISA, and the results are shown in Table 47. The mir-122 binding site sequence in the mRNA dampened the G-CSF protein expression in the primary hepatocytes.

TABLE 47

G-CSF Expression in Hepatocytes

| Description | Primary Human Hepatocytes Protein Expression (ng/ml) | Primary Rat Hepatocytes Protein Expression (ng/ml) |
|---|---|---|
| G-CSF miR122 | 116 | 26 |
| G-CSF seedless | 463 | 85 |

Example 46. Time Course of Modified Nucleic Acids with a Mir-122 Sequence

A. HeLa Cells

HeLa cells were seeded at a density of 17,000 per well in 100 ul cell culture medium (DMEM+10% FBS). G-CSF mRNA without a miR-122 sequence in the 3'UTR (G-CSF; mouse 3' UTR mRNA sequence shown in SEQ ID NO: 5717; polyA tail of approximately 140 nucleotides not shown in sequence; 5'cap, Cap1; fully modified with 5-methylcytidine and 1-methylpseudouridine; human 3'UTR mRNA sequence shown in SEQ ID NO: 5716; polyA tail of approximately 140 nucleotides not shown in sequence; 5'cap, Cap1; fully modified with 5-methylcytidine and 1-methylpseudouridine), G-CSF mRNA having a miR-122 sequence in the 3'UTR (G-CSF miR122; mouse 3' UTR mRNA sequence shown in SEQ ID NO: 5024; polyA tail of approximately 140 nucleotides not shown in sequence; 5'cap, Cap1; fully modified with 5-methylcytidine and 1-methylpseudouridine; human 3'UTR mRNA sequence shown in SEQ ID NO: 5018; polyA tail of approximately 140 nucleotides not shown in sequence; 5'cap, Cap1; fully modified with 5-methylcytidine and 1-methylpseudouridine), G-CSF mRNA having a miR-122 seed sequence in the 3'UTR (G-CSF seed; mouse 3' UTR mRNA sequence shown in SEQ ID NO: 5026; polyA tail of approximately 140 nucleotides not shown in sequence; 5'cap, Cap1; fully modified with 5-methylcytidine and 1-methylpseudouridine; human 3'UTR mRNA sequence shown in SEQ ID NO: 5020; polyA tail of approximately 140 nucleotides not shown in sequence; 5'cap, Cap1; fully modified with 5-methylcytidine and 1-methylpseudouridine), G-CSF mRNA having a miR-122 sequence without the seed sequence in the 3'UTR (G-CSF seedless; mouse 3' UTR mRNA sequence shown in SEQ ID NO: 5028; polyA tail of approximately 140 nucleotides not shown in sequence; 5'cap, Cap1; fully modified with 5-methylcytidine and 1-methylpseudouridine; human 3'UTR mRNA sequence shown in SEQ ID NO: 5022; polyA tail of approximately 140 nucleotides not shown in sequence; 5'cap, Cap1; fully modified with 5-methylcytidine and 1-methylpseudouridine), Factor IX mRNA without a miR-122 sequence in the 3'UTR (FIX; mouse 3' UTR mRNA sequence shown in SEQ ID NO: 5719; polyA tail of approximately 140 nucleotides not shown in sequence; 5'cap, Cap1; fully modified with 5-methylcytidine and 1-methylpseudouridine; human 3'UTR mRNA sequence shown in SEQ ID NO: 5718; polyA tail of approximately 140 nucleotides not shown in sequence; 5'cap, Cap1; fully modified with 5-methylcytidine and 1-methylpseudouridine), Factor IX mRNA having a miR-122 sequence in the 3'UTR (FIX miR122; mouse 3' UTR mRNA sequence shown in SEQ ID NO: 5036; polyA tail of approximately 140 nucleotides not shown in sequence; 5'cap, Cap1; fully modified with 5-methylcytidine and 1-methylpseudouridine; human 3'UTR mRNA sequence shown in SEQ ID NO: 5030; polyA tail of approximately 140 nucleotides not shown in sequence; 5'cap, Cap1; fully modified with 5-methylcytidine and 1-methylpseudouridine), Factor IX mRNA having a miR-122 seed sequence in the 3'UTR (FIX seed; mouse 3' UTR mRNA sequence shown in SEQ ID NO: 5038; polyA tail of approximately 140 nucleotides not shown in sequence; 5'cap, Cap1; fully modified with 5-methylcytidine and 1-methylpseudouridine; human 3'UTR mRNA sequence shown in SEQ ID NO: 5032; polyA tail of approximately 140 nucleotides not shown in sequence; 5'cap, Cap1; fully modified with 5-methylcytidine and 1-methylpseudouridine) or Factor IX mRNA having a miR-122 sequence without the seed sequence in the 3'UTR (FIX seedless; mouse 3' UTR mRNA sequence shown in SEQ ID NO: 5040; polyA tail of approximately 140 nucleotides not shown in sequence; 5'cap, Cap1; fully modified with 5-methylcytidine and 1-methylpseudouridine; human 3'UTR mRNA sequence shown in SEQ ID NO: 5034; polyA tail of approximately 140 nucleotides not shown in sequence; 5'cap, Cap1; fully modified with 5-methylcytidine and 1-methylpseudouridine) were transfected with 0.3 ul per well of Lipofectamine 2000 at a concentration of 75 ng of mRNA per well in 96 well plates. The supernatant was collected between 16-18 hours after transfection, expression of G-CSF or Factor IX was measured by ELISA, and the results are shown in Table 48.

TABLE 48

Expression in HeLa

| Description | Protein Expression Mm 3'UTR (ng/ml) | Protein Expression Hs 3'UTR (ng/ml) |
| --- | --- | --- |
| G-CSF | 271.72 | 69.4 |
| G-CSF miR122 | 305.36 | 68.8 |
| G-CSF seed | 209.5 | 98.0 |
| G-CSF seedless | 243.2 | 80.9 |
| FIX | 249.8 | 131.6 |
| FIX mir122 | 204.6 | 55.4 |
| FIX seed | 290.05 | 127.6 |
| FIX seedless | 180.9 | 31.6 |

B. Primary Human and Rat Hepatocytes

Primary human or rat hepatocytes cells were seeded at a density of 350,000 cells per well in 500 ul cell culture medium (InvitroGRO CP and InVitroGRO HI Medium+ 2.2% Torpedo Antibiotic). G-CSF mRNA without a miR-122 sequence in the 3'UTR (G-CSF; mouse 3' UTR mRNA sequence shown in SEQ ID NO: 5717; polyA tail of approximately 140 nucleotides not shown in sequence; 5'cap, Cap1; fully modified with 5-methylcytidine and 1-methylpseudouridine; human 3'UTR mRNA sequence shown in SEQ ID NO: 5716; polyA tail of approximately 140 nucleotides not shown in sequence; 5'cap, Cap1; fully modified with 5-methylcytidine and 1-methylpseudouridine), G-CSF mRNA having a miR-122 sequence in the 3'UTR (G-CSF miR122; mouse 3' UTR mRNA sequence shown in SEQ ID NO: 5024; polyA tail of approximately 140 nucleotides not shown in sequence; 5'cap, Cap1; fully modified with 5-methylcytidine and 1-methylpseudouridine; human 3'UTR mRNA sequence shown in SEQ ID NO: 5018; polyA tail of approximately 140 nucleotides not shown in sequence; 5'cap, Cap1; fully modified with 5-methylcytidine and 1-methylpseudouridine), G-CSF mRNA having a miR-122 seed sequence in the 3'UTR (G-CSF seed; mouse 3' UTR mRNA sequence shown in SEQ ID NO: 5026; polyA tail of approximately 140 nucleotides not shown in sequence; 5'cap, Cap1; fully modified with 5-methylcytidine and 1-methylpseudouridine; human 3'UTR mRNA sequence shown in SEQ ID NO: 5020; polyA tail of approximately 140 nucleotides not shown in sequence; 5'cap, Cap1; fully modified with 5-methylcytidine and 1-methylpseudouridine), G-CSF mRNA having a miR-122 sequence without the seed sequence in the 3'UTR (G-CSF seedless; mouse 3' UTR mRNA sequence shown in SEQ ID NO: 5028; polyA tail of approximately 140 nucleotides not shown in sequence; 5'cap, Cap1; fully modified with 5-methylcytidine and 1-methylpseudouridine; human 3'UTR mRNA sequence shown in SEQ ID NO: 5022; polyA tail of approximately 140 nucleotides not shown in sequence; 5'cap, Cap1; fully modified with 5-methylcytidine and 1-methylpseudouridine), Factor IX mRNA without a miR-122 sequence in the 3'UTR (FIX; mouse 3' UTR mRNA sequence shown in SEQ ID NO: 5719; polyA tail of approximately 140 nucleotides not shown in sequence; 5'cap, Cap1; fully modified with 5-methylcytidine and 1-methylpseudouridine; human 3'UTR mRNA sequence shown in SEQ ID NO: 5718; polyA tail of approximately 140 nucleotides not shown in sequence; 5'cap, Cap1; fully modified with 5-methylcytidine and 1-methylpseudouridine), Factor IX mRNA having a miR-122 sequence in the 3'UTR (FIX miR122; mouse 3' UTR mRNA sequence shown in SEQ ID NO: 5036; polyA tail of approximately 140 nucleotides not shown in sequence; 5'cap, Cap1; fully modified with 5-methylcytidine and 1-methylpseudouridine; human 3'UTR mRNA sequence shown in SEQ ID NO: 5030; polyA tail of approximately 140 nucleotides not shown in sequence; 5'cap, Cap1; fully modified with 5-methylcytidine and 1-methylpseudouridine), Factor IX mRNA having a miR-122 seed sequence in the 3'UTR (FIX seed; mouse 3' UTR mRNA sequence shown in SEQ ID NO: 5038; polyA tail of approximately 140 nucleotides not shown in sequence; 5'cap, Cap1; fully modified with 5-methylcytidine and 1-methylpseudouridine; human 3'UTR mRNA sequence shown in SEQ ID NO: 5032; polyA tail of approximately 140 nucleotides not shown in sequence; 5'cap, Cap1; fully modified with 5-methylcytidine and 1-methylpseudouridine) or Factor IX mRNA having a miR-122 sequence without the seed sequence in the 3'UTR (FIX seedless; mouse 3' UTR mRNA sequence shown in SEQ ID NO: 5040; polyA tail of approximately 140 nucleotides not shown in sequence; 5'cap, Cap1; fully modified with 5-methylcytidine and 1-methylpseudouridine; human 3'UTR mRNA sequence shown in SEQ ID NO: 5034; polyA tail of approximately 140 nucleotides not shown in sequence; 5'cap, Cap1; fully modified with 5-methylcytidine and 1-methylpseudouridine) were transfected with 1 ul per well of Lipofectamine 2000 at a concentration of 500 ng per well in 24 well plates for the primary human hepatocytes and the primary rat hepatocytes. The supernatant was collected at 24 hours, 48 hours and 72 hours after transfection, expression of G-CSF and Factor IX was measured by ELISA, and the results are shown in Table 49. The mir-122 binding site sequence in the mRNA dampened the G-CSF and Factor IX protein expression in the primary hepatocytes.

TABLE 49

G-CSF Expression in Hepatocytes

| Description | Time Point | Primary Human Hepatocytes Protein Expression (ng/ml) Mm 3'UTR | Primary Human Hepatocytes Protein Expression (ng/ml) Hs 3'UTR |
|---|---|---|---|
| G-CSF | 24 hours | 43.9 | 84.9 |
|  | 48 hours | 18.8 | 100.4 |
|  | 72 hours | 5.7 | 21.3 |
| G-CSF miR122 | 24 hours | 6.9 | 24.0 |
|  | 48 hours | .7 | 3.03 |
|  | 72 hours | .12 | .88 |
| G-CSF seed | 24 hours | 48.5 | 115.8 |
|  | 48 hours | 25.6 | 96.4 |
|  | 72 hours | 8.2 | 19.2 |
| G-CSF seedless | 24 hours | 31.7 | 113.1 |
|  | 48 hours | 11.7 | 92.9 |
|  | 72 hours | 3.4 | 18.9 |
| FIX | 24 hours | 90.8 | 63.2 |
|  | 48 hours | 159.6 | 124.8 |
|  | 72 hours | 70.5 | 44.3 |
| FIX mir122 | 24 hours | 11.8 | 15.9 |
|  | 48 hours | 5.0 | 4.4 |
|  | 72 hours | 1.0 | .4 |
| FIX seed | 24 hours | 77.2 | 60.2 |
|  | 48 hours | 115.0 | 63.0 |
|  | 72 hours | 41.7 | 20.1 |
| FIX seedless | 24 hours | 69.3 | 53.7 |
|  | 48 hours | 123.8 | 75.0 |
|  | 72 hours | 49.0 | 24.5 |

Example 47. Time Course of Modified Nucleic Acids with a Mir-122 Sequence in Cancer Cells A. Base Level of miR-122

The base level of mir-122 in Human hepatocytes, rat hepatocytes, human hepatocellular carcinoma cells (Hep3B) and HeLa cells were determined by TAQMAN® analysis using the manufacturers protocol. The levels were normalized to U6 and the results are shown in Table 50.

TABLE 50 miR-122 Levels in Various Cell Types

| Cell Type | miR-122 level (normalized to U6) |
|---|---|
| Human Hepatocytes | 16.8 |
| Rat Hepatocytes | 10.9 |
| Hep3B | 0 |
| HeLa | 0 |

B. Primary Human Hepatocytes and Hep3B Cells

Primary human hepatocytes were seeded at a density of 50,000 cells per well in 100 ul cell culture medium (InvitroGRO CP and InVitroGRO HI Medium+2.2% Torpedo Antibiotic Mix) and Hep3B cells were seeded at a density of 20,000 cells per well in 100 ul cell culture medium MEM+ 10% FBS. G-CSF mRNA without a miR-122 sequence in the 3'UTR (G-CSF; mRNA sequence shown in SEQ ID NO: 5745; polyA tail of approximately 140 nucleotides not shown in sequence; 5'cap, cap1; fully modified with 5-methylcytidine and 1-methylpseudouridine), G-CSF mRNA having a miR-122 sequence in the 3'UTR (G-CSF miR122; mRNA sequence shown in SEQ ID NO: 5018; polyA tail of approximately 140 nucleotides not shown in sequence; 5'cap, cap1; fully modified with 5-methylcytidine and 1-methylpseudouridine), G-CSF mRNA having a miR-122 seed sequence in the 3'UTR (G-CSF seed; mRNA sequence shown in SEQ ID NO: 5020; polyA tail of approximately 140 nucleotides not shown in sequence; 5'cap, cap 1; fully modified with 5-methylcytidine and 1-methylpseudouridine) or G-CSF mRNA having a miR-122 sequence without the seed sequence in the 3'UTR (G-CSF seedless; mRNA sequence shown in SEQ ID NO: 5022; polyA tail of approximately 140 nucleotides not shown in sequence; 5'cap, Cap1; fully modified with 5-methylcytidine and 1-methylpseudouridine) were transfected with 0.3 ul per well of Lipofectamine 2000 at a concentration of 75 ng of mRNA per well in 96 well plates for the primary human hepatocytes and the Hep3B cells. The supernatant was collected at 24 hours, 48 hours and 72 hours after transfection, expression of G-CSF was measured by ELISA, and the results are shown in Table 51. The mir-122 binding site sequence in the mRNA dampened the G-CSF protein expression in the primary human hepatocytes but not in the Hep3B cells.

TABLE 51

G-CSF Expression

| Description | Time Point | Primary Human Hepatocytes Protein Expression (ng/ml) Hs 3'UTR | Hep3B Protein Expression (ng/ml) Hs 3'UTR |
|---|---|---|---|
| G-CSF | 24 hours | 76 | 55 |
|  | 48 hours | 12 | 33 |
|  | 72 hours | 6 | 10 |
| G-CSF miR122 | 24 hours | 32 | 37 |
|  | 48 hours | 1 | 27 |
|  | 72 hours | 0 | 6 |
| G-CSF seed | 24 hours | 75 | 39 |
|  | 48 hours | 11 | 28 |
|  | 72 hours | 4 | 6 |
| G-CSF seedless | 24 hours | 79 | 49 |
|  | 48 hours | 15 | 35 |
|  | 72 hours | 6 | 9 |

Example 48. Time Course of Modified Nucleic Acids with a Mir-142 3p Sequence A. Base Level of miR-143 3p The base level of miR-142 3p in RAW264.7 cells and HeLa cells were determined by TAQMAN® analysis using the manufacturer's protocol. The levels were normalized to U6 and the results are shown in Table 52.

TABLE 52 miR-142 3p Levels in Various Cell Types

| Cell Type | miR-122 level (normalized to U6) |
|---|---|
| Human Hepatocytes | 16.8 |
| Rat Hepatocytes | 10.9 |
| Hep3B | 0 |
| HeLa | 0 |

B. HeLa and RAW264.7 Cells

HeLa cells were seeded at a density of 17,000 per well in 100 ul cell culture medium DMEM+10% FBS and RAW264.7 cells were seeded at a density of 200,000 per well in 100 ul cell culture medium DMEM+10% FBS. G-CSF mRNA without a miR-142 3p sequence in the 3'UTR (G-CSF; mRNA sequence shown in SEQ ID NO: 5749;

polyA tail of approximately 140 nucleotides not shown in sequence; 5'cap, Cap1; fully modified with 5-methylcytidine and 1-methylpseudouridine), G-CSF mRNA having a miR-142 3p sequence in the 3'UTR (G-CSF miR142 3p; mRNA sequence shown in SEQ ID NO: 5750; polyA tail of approximately 140 nucleotides not shown in sequence; 5'cap, Cap1; fully modified with 5-methylcytidine and 1-methylpseudouridine), G-CSF mRNA having a miR-142 3p seed sequence in the 3'UTR (G-CSF seed; mRNA sequence shown in SEQ ID NO: 5751; polyA tail of approximately 140 nucleotides not shown in sequence; 5'cap, cap 1; fully modified with 5-methylcytidine and 1-methylpseudouridine) or G-CSF mRNA having a miR-142 3p sequence without the seed sequence in the 3'UTR (G-CSF seedless; mRNA sequence shown in SEQ ID NO: 5752; polyA tail of approximately 140 nucleotides not shown in sequence; 5'cap, Cap1; fully modified with 5-methylcytidine and 1-methylpseudouridine) were transfected with 0.3 ul per well of Lipofectamine 2000 at a concentration of 75 ng of mRNA per well in 96 well plates for HeLa or with 1 ul per well of Lipofectamine 2000 at a concentration of 250 ng of mRNA per well in 24 well plates for RAW264.7 cells. The supernatant was collected 16-18 hours after transfection, expression of G-CSF was measured by ELISA, and the results are shown in Table 53. miR-142 3p sites in G-CSF were shown to downregulate G-CSF expression in RAW264.7 cells.

TABLE 53

| | Expression | |
|---|---|---|
| Description | HeLa Protein Expression (ng/ml) | RAW264.7 Protein Expression (ng/ml) |
| G-CSF | 243.5 | 124.8 |
| G-CSF miR142 3p | 309.1 | 42.8 |
| G-CSF seed | 259.8 | 148.1 |
| G-CSF seedless | 321.7 | 185.2 |

C. Time Course in RAW264.7 Cells

RAW264.7 cells were seeded at a density of 60,000 cells per well in 100 ul cell culture medium (DMEM+10% FBS). G-CSF mRNA without a miR-142 3p sequence in the 3'UTR (G-CSF; mRNA sequence shown in SEQ ID NO: 5749; polyA tail of approximately 140 nucleotides not shown in sequence; 5'cap, cap 1; fully modified with 5-methylcytidine and 1-methylpseudouridine), G-CSF mRNA having a miR-142 3p sequence in the 3'UTR (G-CSF miR142 3p; mRNA sequence shown in SEQ ID NO: 5750; polyA tail of approximately 140 nucleotides not shown in sequence; 5'cap, Cap1; fully modified with 5-methylcytidine and 1-methylpseudouridine), G-CSF mRNA having a miR-142 3p seed sequence in the 3'UTR (G-CSF seed; mRNA sequence shown in SEQ ID NO: 5751; polyA tail of approximately 140 nucleotides not shown in sequence; 5'cap, cap 1; fully modified with 5-methylcytidine and 1-methylpseudouridine) or G-CSF mRNA having a miR-142 3p sequence without the seed sequence in the 3'UTR (G-CSF seedless; mRNA sequence shown in SEQ ID NO: 5752; polyA tail of approximately 140 nucleotides not shown in sequence; 5'cap, cap1; fully modified with 5-methylcytidine and 1-methylpseudouridine) were transfected with 0.3 ul per well of Lipofectamine 2000 at a concentration of 75 ng of mRNA per well in 96 well plates. The supernatant was collected at 24 hours, 48 hours and 72 hours after transfection, expression of G-CSF was measured by ELISA, and the results are shown in Table 54. The mir-142 3p binding site sequence in the mRNA showed a strong suppression of G-CSF expression in RAW264.7 cells over time.

TABLE 54

| | G-CSF Expression | |
|---|---|---|
| Description | Time Point | RAW264.7 Cells Protein Expression (ng/ml) |
| G-CSF | 24 hours | 133.5 |
| | 48 hours | 69.7 |
| | 72 hours | 2.1 |
| G-CSF miR142 3p | 24 hours | 60.1 |
| | 48 hours | 9.2 |
| | 72 hours | .3 |
| G-CSF seed | 24 hours | 244.9 |
| | 48 hours | 68.9 |
| | 72 hours | 2.3 |
| G-CSF seedless | 24 hours | 250.2 |
| | 48 hours | 95.9 |
| | 72 hours | 3.0 |

D. miR-142 3p in PBMC

Peripheral blood mononuclear cells (PBMCs) were seeded at a density of 150,000 cells per well in 100 ul cell culture medium (Opti-MEM and after transfection add 10% FBS). G-CSF mRNA having a miR-142 3p sequence in the 3'UTR (G-CSF miR142 3p; mRNA sequence shown in SEQ ID NO: 5750; polyA tail of approximately 140 nucleotides not shown in sequence; 5'cap, Cap1; fully modified with 5-methylcytidine and 1-methylpseudouridine), G-CSF mRNA having a miR-142 3p seed sequence in the 3'UTR (G-CSF seed; mRNA sequence shown in SEQ ID NO: 5751; polyA tail of approximately 140 nucleotides not shown in sequence; 5'cap, cap1; fully modified with 5-methylcytidine and 1-methylpseudouridine) or G-CSF mRNA having a miR-142 3p sequence without the seed sequence in the 3'UTR (G-CSF seedless; mRNA sequence shown in SEQ ID NO: 5752; polyA tail of approximately 140 nucleotides not shown in sequence; 5'cap, cap1; fully modified with 5-methylcytidine and 1-methylpseudouridine) were transfected in triplicate with 0.4 ul per well of Lipofectamine 2000 at a concentration of 500 ng of mRNA per well in 96 well plates for 2 or 3 donors. The supernatant was collected at 24 hours after transfection and the expression of G-CSF was measured by ELISA. The results for the 2 donors are shown in Table 55 and the results for the 3 donors are shown in Table 56. The mir-142 3p binding site sequence in the mRNA was shown to down regulate G-CSF expression in human PBMC.

TABLE 55

| Expression PBMC (2 donors) | |
|---|---|
| Description | Protein Expression (ng/ml) |
| G-CSF miR142 3p | 5.09 |
| G-CSF seed | 10.06 |
| G-CSF seedless | 9.38 |

TABLE 56

Expression PBMC (3 donors)

| Description | Protein Expression (ng/ml) |
|---|---|
| G-CSF miR142 3p | 7.48 |
| G-CSF seed | 13.40 |
| G-CSF seedless | 13.98 |

Example 49. In Vivo Expression of Modified mRNA

A. BALB/C Nude Mice

BALB/c nude mice were injected intravenously with 0.1 mg/kg luciferase modified mRNA without a miR-122 binding site ("non-targeted mRNA"; mRNA sequence shown in SEQ ID NO: 5753; polyA tail of approximately 140 nucleotides not shown in sequence; 5' cap, Cap1; fully modified with 5-methylcytidine and 1-methylpeudouridine) formulated in a lipid nanoparticle described in Table 57 or luciferase modified mRNA with a miR-122 binding site in the 3'UTR ("miR-122 targeted mRNA"; mRNA sequence shown in SEQ ID NO: 5754; polyA tail of approximately 140 nucleotides not shown in sequence; 5' cap, Cap1; fully modified with 5-methylcytidine and 1-methylpeudouridine) formulated in a lipid nanoparticle described in Table 58.

TABLE 57

Lipid Nanoparticle for Non-targeted mRNA

| LNP | Luciferase: non-targeted mRNA |
|---|---|
| Lipid | DLin-KC2-DMA |
| Lipid/RNA wt/wt | 20 |
| Mean size | 73.3 nm PDI: 0.06 |

TABLE 58

Lipid Nanoparticle for Targeted mRNA

| LNP | Luciferase: targeted mRNA |
|---|---|
| Lipid | DLin-KC2-DMA |
| Lipid/RNA wt/wt | 20 |
| Mean size | 70.6 nm PDI: 0.08 |

24 hours post-treatment, animals were anesthetized, injected with the luciferase substrate D-luciferin and the bioluminescence imaging (BLI) from living animals was evaluated in an IVIS imager 15 minutes later. Signals were obtained from animals injected with non-targeted mRNA and from miR-122 targeted mRNA, and presented in Table 59. The total light signal produced from livers of animals treated with miR 122 targeted mRNA is 29× lower than non-targeted mRNA, showing that the engineered element in the 3'UTR may inhibit protein expression in normal tissue.

TABLE 59

In vivo expression of modified mRNA modulated by an engineered miR122 binding site

| Description | Luciferase signal from liver (photons/sec) |
|---|---|
| Non-targeted mRNA | $7.9 \times 10^7$ |
| miR-122 targted mRNA | $2.7 \times 10^6$ |

B. BALB/c Nude Mice with Hepatocellular Carcinoma Hep3B Cells

BALB/c nude mice were intrahepatically implanted with $2 \times 10^6$ hepatocellular carcinoma Hep3B cells and resulting orthotopic tumors allowed to grow for 24 days. Tumor-bearing mice were then intravenously injected with 0.1 mg/kg luciferase modified mRNA without a miR-122 binding site ("non-targeted mRNA"; mRNA sequence shown in SEQ ID NO: 5753; polyA tail of approximately 140 nucleotides not shown in sequence; 5' cap, Cap1; fully modified with 5-methylcytidine and 1-methylpeudouridine) or luciferase modified mRNA with a miR-122 binding site in the 3'UTR ("miR-122 targeted mRNA"; mRNA sequence shown in SEQ ID NO: 5754; polyA tail of approximately 140 nucleotides not shown in sequence; 5' cap, Cap1; fully modified with 5-methylcytidine and 1-methylpeudouridine) formulated in a lipid nanoparticle described in Table 57 and 58 (above). 24 hr post-treatment animals were anesthetized, injected with the luciferase substrate D-luciferin and bioluminescence imaging (BLI) from living animals was evaluated in an IVIS imager 20 minutes later. Signal from orthotopic tumors compared to adjacent normal liver was quantified, and miR-122-targeted mRNA systemically delivered via lipid nanoparticles achieved over 2-fold enrichment in tumor compared to normal liver.

Example 50. Effect of the Kozak Sequence in Modified Nucleic Acids

HeLa cells were seeded at a density of 15,000 per well in 100 ul cell culture medium DMEM+FBS 10%. G-CSF mRNA having a Kozak sequence (G-CSF Kozak; mRNA sequence shown in SEQ ID NO: 5716; polyA tail of approximately 140 nucleotides not shown in sequence; 5'cap, Cap1; fully modified with 5-methylcytidine and 1-methylpseudouridine), G-CSF mRNA not having a Kozak sequence (G-CSF no Kozak; mRNA sequence shown in SEQ ID NO: 5008; polyA tail of approximately 140 nucleotides not shown in sequence; 5'cap, Cap1; fully modified with 5-methylcytidine and 1-methylpseudouridine), G-CSF mRNA where the −3 position A, upstream of the start codon, was converted to a T, (G-CSF 3t5'; mRNA sequence shown in SEQ ID NO: 5755 (Table 60); polyA tail of approximately 140 nucleotides not shown in sequence; 5'cap, Cap1; fully modified with 5-methylcytidine and 1-methylpseudouridine), G-CSF mRNA where the −9 position A, upstream of the start codon, was converted to a T, (G-CSF 9t5'; mRNA sequence shown in SEQ ID NO: 5756 (Table 60); polyA tail of approximately 140 nucleotides not shown in sequence; 5'cap, Cap1; fully modified with 5-methylcytidine and 1-methylpseudouridine) or G-CSF mRNA where 9 nucleotides upstream of the start codon (AGAGCCACC) were deleted (G-CSF 9del5'; mRNA sequence shown in SEQ ID NO: 5757 (Table 60); polyA tail of approximately 140 nucleotides not shown in sequence; 5'cap, Cap1; fully modified with 5-methylcytidine and 1-methylpseudouridine) and transfected in triplicate at a concentration of 37.5 ng per well in 96 well plates. 24 hours, 48 hours and 72 hours after transfection, the supernatant was collected and expression of G-CSF was measured by ELISA, and the results are shown in Table 61. In Table 61, the start codon in each sequence is underlined. In Table 60, for G-CSF 3t5' the −3 position A, upstream of the start codon is in bold and underlined and for G-CSF 9t5' the −9 position A upstream of the start codon is in bold and underlined.

TABLE 60

G-CSF Sequences

| De-scription | Sequence | SEQ ID NO |
|---|---|---|
| G-CSF 3t5' | GGGAAAUAAGAGAGAAAAGAAGAGUAAGAAGAAA UAUAAGAGCCUCCAUGGCCGGUCCCGCGACCCAAA GCCCCAUGAAACUUAUGGCCCUGCAGUUGCUGCU UUGGCACUCGGCCCUCUGGACAGUCCAAGAAGCG ACUCCUCUCGGACCUGCCUCAUCGUUGCCGCAGUC AUUCCUUUUGAAGUGUCUGGAGCAGGUGCGAAAG AUUCAGGGCGAUGGAGCCGCACUCCAAGAGAAGC UCUGCGCGACAUACAAACUUUGCCAUCCCGAGGA GCUCGUACUGCUCGGGCACAGCUUGGGGAUUCCC UGGGCUCCUCUCUCGUCCUGUCCGUCGCAGGCUUU GCAGUUGGCAGGGUGCCUUUCCCAGCUCCACUCCG GUUUGUUCUUGUAUCAGGGACUGCUGCAAGCCCU UGAGGGAAUCUCGCCAGAAUUGGGCCCGACGCUG GACACGUUGCAGCUCGACGUGGCGGAUUUCGCAA CAACCAUCUGGCAGCAGAUGGAGGAACUGGGGAU GGCACCCGCGCUGCAGCCCACGCAGGGGGCAAUGC CGGCCUUUGCGUCCGCGUUUCAGCGCAGGGCGGG UGGAGUCCUCGUAGCGAGCCACCUUCAAUCAUUU UUGGAAGUCUCGUACCGGGUGCUGAGACAUCUUG CGCAGCCGUGAUAAUAGGCUGGAGCCUCGGUGGC CAUGCUUCUUGCCCCUUGGGCCUCCCCCCAGCCCC UCCUCCCCUUCCUGCACCCGUACCCCCGUGGUCUU UGAAUAAAGUCUGAGUGGGCGGC | 5755 |
| G-CSF 9t5' | GGGAAAUAAGAGAGAAAAGAAGAGUAAGAAGAAA UAUAUGAGCCACCAUGGCCGGUCCCGCGACCCAAA GCCCCAUGAAACUUAUGGCCCUGCAGUUGCUGCU UUGGCACUCGGCCCUCUGGACAGUCCAAGAAGCG ACUCCUCUCGGACCUGCCUCAUCGUUGCCGCAGUC AUUCCUUUUGAAGUGUCUGGAGCAGGUGCGAAAG AUUCAGGGCGAUGGAGCCGCACUCCAAGAGAAGC UCUGCGCGACAUACAAACUUUGCCAUCCCGAGGA GCUCGUACUGCUCGGGCACAGCUUGGGGAUUCCC UGGGCUCCUCUCUCGUCCUGUCCGUCGCAGGCUUU GCAGUUGGCAGGGUGCCUUUCCCAGCUCCACUCCG GUUUGUUCUUGUAUCAGGGACUGCUGCAAGCCCU UGAGGGAAUCUCGCCAGAAUUGGGCCCGACGCUG GACACGUUGCAGCUCGACGUGGCGGAUUUCGCAA CAACCAUCUGGCAGCAGAUGGAGGAACUGGGGAU GGCACCCGCGCUGCAGCCCACGCAGGGGGCAAUGC CGGCCUUUGCGUCCGCGUUUCAGCGCAGGGCGGG UGGAGUCCUCGUAGCGAGCCACCUUCAAUCAUUU UUGGAAGUCUCGUACCGGGUGCUGAGACAUCUUG CGCAGCCGUGAUAAUAGGCUGGAGCCUCGGUGGC CAUGCUUCUUGCCCCUUGGGCCUCCCCCCAGCCCC UCCUCCCCUUCCUGCACCCGUACCCCCGUGGUCUU UGAAUAAAGUCUGAGUGGGCGGC | 5756 |
| G-CSF 9del5' | GGGAAAUAAGAGAGAAAAGAAGAGUAAGAAGAAA UAUAAUGGCCGGUCCCGCGACCCAAAGCCCCAUGA AACUUAUGGCCCUGCAGUUGCUGCUUUGGCACUC GGCCCUCUGGACAGUCCAAGAAGCGACUCCUCUCG GACCUGCCUCAUCGUUGCCGCAGUCAUUCCUUUU GAAGUGUCUGGAGCAGGUGCGAAAGAUUCAGGGC GAUGGAGCCGCACUCCAAGAGAAGCUCUGCGCGA CAUACAAACUUUGCCAUCCCGAGGAGCUCGUACU GCUCGGGCACAGCUUGGGGAUUCCCUGGGCUCCU CUCUCGUCCUGUCCGUCGCAGGCUUUGCAGUUGG CAGGGUGCCUUUCCCAGCUCCACUCCGGUUUGUUC UUGUAUCAGGGACUGCUGCAAGCCCUUGAGGGAA UCUCGCCAGAAUUGGGCCCGACGCUGGACACGUU GCAGCUCGACGUGGCGGAUUUCGCAACAACCAUC UGGCAGCAGAUGGAGGAACUGGGGAUGGCACCCG | 5757 |

TABLE 60-continued

G-CSF Sequences

| De-scription | Sequence | SEQ ID NO |
|---|---|---|
| | CGCUGCAGCCCACGCAGGGGGCAAUGCCGGCCUUU GCGUCCGCGUUUCAGCGCAGGGCGGGUGGAGUCC UCGUAGCGAGCCACCUUCAAUCAUUUUUGGAAGU CUCGUACCGGGUGCUGAGACAUCUUGCGCAGCCG UGAUAAUAGGCUGGAGCCUCGGUGGCCAUGCUUC UUGCCCCUUGGGCCUCCCCCCAGCCCCUCCUCCCC UUCCUGCACCCGUACCCCCGUGGUCUUUGAAUAA AGUCUGAGUGGGCGGC | |

TABLE 61

G-CSF Expression

| | 24 hours Protein Expression (ng/ml) | 48 hours Protein Expression (ng/ml) | 72 hours Protein Expression (ng/ml) |
|---|---|---|---|
| G-CSF Kozak | 239.08 | 339.89 | 283.43 |
| G-CSF No Kozak | 399.83 | 544.08 | 437.23 |
| G-CSF 3t5' | 157.39 | 239.67 | 195.20 |
| G-CSF 9t5' | 171.84 | 263.11 | 195.22 |
| G-CSF 9del5' | 308.16 | 563.64 | 397.20 |

Example 51. Effect of Modification of 5'UTR in Modified Nucleic Acids

BJ Fibroblast cells were seeded at a density of 100,000 per well in 500 ul cell culture medium EMEM+FBS 10%. G-CSF mRNA having a synthetic 5'UTR (G-CSF; mRNA sequence shown in SEQ ID NO: 5716; polyA tail of approximately 140 nucleotides not shown in sequence; 5'cap, Cap1; fully modified with 5-methylcytidine and 1-methylpseudouridine) or G-CSF mRNA containing a 5'UTR with five tandem repeats of an 18 nucleotide sequence from the IRES of the GTX gene (GTX G-CSF; mRNA sequence shown in SEQ ID NO: 5758 (Table 62); polyA tail of approximately 140 nucleotides not shown in sequence; 5'cap, Cap1; fully modified with 5-methylcytidine and 1-methylpseudouridine) and transfected in triplicate at a concentration of 250 ng per well in 24 well plates. 24 hours, 48 hours and 72 hours after transfection, the supernatant was collected and expression of G-CSF was measured by ELISA, and the results are shown in Table 63. In Table 62, the start codon is underlined and the five tandem repeats of an 18 nucleotide sequence from the IRES of the GTX gene is bolded and the first, third and fifth tandem repeat of the 18 nucleotide sequence is also underlined.

TABLE 62

GTX G-CSF Sequence

| De-scription | Sequence | SEQ ID NO |
|---|---|---|
| GTX G-CSF | GGGAAAUUCUGACAUCCGGCGGAAUUCUGACAU CCGGCGGAAUUCUGACAUCCGGCGGAAUUCUGA CAUCCGGCGGAAUUCUGACAUCCGGCGGAAGAC UCACAACCCCAGAAACAGACAUUAAGAGAGAAAA GAAGAGUAAGAAGAAAUAUAAGAGCCACCAUGGC CGGUCCCGCGACCCAAAGCCCCAUGAAACUUAUGG CCCUGCAGUUGCUGCUUUGGCACUCGGCCCUCUGG ACAGUCCAAGAAGCGACUCCUCUCGGACCUGCCUC | 5758 |

TABLE 62-continued

GTX G-CSF Sequence

| Description | Sequence | SEQ ID NO |
|---|---|---|
| | AUCGUUGCCGCAGUCAUUCCUUUUGAAGUGUCUG | |
| | GAGCAGGUGCGAAAGAUUCAGGGCGAUGGAGCCG | |
| | CACUCCAAGAGAAGCUCUGCGCGACAUACAAACU | |
| | UUGCCAUCCCGAGGAGCUCGUACUGCUCGGGCAC | |
| | AGCUUGGGGAUUCCCUGGGCUCCUCUCUCGUCCU | |
| | GUCCGUCGCAGGCUUUGCAGUUGGCAGGGUGCCU | |
| | UUCCCAGCUCCACUCCGGUUUGUUCUUGUAUCAG | |
| | GGACUGCUGCAAGCCCUUGAGGGAAUCUCGCCAG | |
| | AAUUGGGCCCGACGCUGGACACGUUGCAGCUCGA | |
| | CGUGGCGGAUUUCGCAACAACCAUCUGGCAGCAG | |
| | AUGGAGGAACUGGGGAUGGCACCCGCGCUGCAGC | |
| | CCACGCAGGGGCAAUGCCGGCCUUUGCGUCCGCG | |
| | UUUCAGCGCAGGGCGGGUGGAGUCCUCGUAGCGA | |
| | GCCACCUUCAAUCAUUUUUGGAAGUCUCGUACCG | |
| | GGUGCUGAGACAUCUUGCGCAGCCGUGAUAAUAG | |
| | GCUGGAGCCUCGGUGGCCAUGCUUCUUGCCCCUU | |
| | GGGCCUCCCCCCAGCCCCUCCUCCCCUUCCUGCAC | |
| | CCGUACCCCGUGGUCUUUGAAUAAAGUCUGAGU | |
| | GGGCGGC | |

TABLE 63

5' UTR

| Time point | G-CSF Protein Expression (ng/ml) | Gtx G-CSF Protein Expression (ng/ml) |
|---|---|---|
| 24 hours | 26.13 | 79.65 |
| 48 hours | 138.75 | 444.81 |
| 72 hours | 55.37 | 198.14 |

Example 53. Effect of Modification of 5'UTR in Modified Nucleic Acids

BJ Fibroblast cells were seeded at a density of 100,000 per well in 500 ul cell culture medium EMEM+FBS 10%. G-CSF mRNA having a synthetic 5'UTR (G-CSF; mRNA sequence shown in SEQ ID NO: 5716; polyA tail of approximately 140 nucleotides not shown in sequence; 5'cap, Cap1; fully modified with 1-methylpseudouridine) or G-CSF mRNA containing a 5'UTR with five tandem repeats of an 18 nucleotide sequence from the IRES of Gtx gene (Gtx G-CSF; mRNA sequence shown in SEQ ID NO: 5758 (Table 62); polyA tail of approximately 140 nucleotides not shown in sequence; 5'cap, Cap1; fully modified with 1-methylpseudouridine) and transfected in triplicate at a concentration of 250 ng per well in 24 well plates. 24 hours, 48 hours and 72 hours after transfection, the supernatant was collected and expression of G-CSF was measured by ELISA, and the results are shown in Table 64.

TABLE 64

5' UTR

| Time point | G-CSF Protein Expression (ng/ml) | Gtx G-CSF Protein Expression (ng/ml) |
|---|---|---|
| 24 hours | 129.10 | 178.68 |
| 48 hours | 569.97 | 1067.62 |
| 72 hours | 325.16 | 738.30 |

Example 54. In Vivo Effect of the Modification of 5'UTR in Nucleic Acids Modified with 5-Methylcytidine and 1-Methylpseudouridine To study the effect of the modification of the 5'UTR in modified nucleic acids female Balb/c mice (n=3; 12 weeks old; Harlan Laboratories (South Easton, Mass.)) were treated with lipoplexed mRNA.

8 ug of G-CSF mRNA having a synthetic 5'UTR (G-CSF; mRNA sequence shown in SEQ ID NO: 5716; polyA tail of approximately 140 nucleotides not shown in sequence; 5'cap, Cap1; fully modified with 5-methylcytidine and 1-methylpseudouridine) or G-CSF mRNA where 9 nucleotides upstream of the start codon were deleted (G-CSF 9del5'; mRNA sequence shown in SEQ ID NO: 5757 (Table 60); polyA tail of approximately 140 nucleotides not shown in sequence; 5'cap, Cap1; fully modified with 5-methylcytidine and 1-methylpseudouridine) for treatment of 3 mice is diluted with sterile and serum-free DMEM (Life Technologies) to obtain a total volume of 200 ul. A total of 8 ul of Lipofectamine2000 (LifeTechnologies, 11668019) for the treatment of 3 mice was diluted with sterile and serum-free DMEM (LifeTechnologies, Grand Island, N.Y.; 11965-118) to obtain a total volume of 200 ul. After 5 minutes of incubation, the two solutions were combined and carefully mixed with a pipette. After 20 minutes the formation of mRNA-Lipofectamine2000 lipoplexes was completed. The lipoplex solution was transferred to a sterile 1 ml syringe (BD Falcon) carrying a 27 gauge injection needle (0.3 mL BD SafetyGlide insulin syringe with 29 G×½ in BD permanently attached needle (Catalog #305935)). The Balb/C mice were placed under a heat lamp for 5 minutes prior to the 100 ul intravenous tail vein injection containing 2 ug of lipoplexed mRNA. 6 hours after injection the mice were anesthesized and bleed for serum collection by cardiac puncture. The serum samples were then run on a G-CSF ELISA (R&D systems catalog #SCS50) and the results are shown in Table 65. The G-CSF mRNA having the 9 nucleotides upstream of the start codon deleted had a higher G-CSF expression level at 6 hours as compared to the G-CSF having a synthetic UTR.

TABLE 65

G-CSF Kozak Expression In Vivo

| Time Point | G-CSF Expression (ng/ml) | G-CSF 9del5' Expression (ng/ml) |
|---|---|---|
| 6 hours | 256.2 | 752.4 |

Example 55. In Vivo Effect of the GTX Modification of 5'UTR in G-CSF Nucleic Acids Modified with 5-Methylcytidine and 1-Methylpseudouridine To study the effect of the modification of the 5'UTR in modified nucleic acids female Balb/c mice (n=3; 12 weeks old; Harlan Laboratories (South Easton, Mass.)) were treated with lipoplexed mRNA.

8 ug of G-CSF mRNA having a synthetic 5'UTR (G-CSF; mRNA sequence shown in SEQ ID NO: 5716; polyA tail of approximately 140 nucleotides not shown in sequence; 5'cap, Cap1; fully modified with 5-methylcytidine and 1-methylpseudouridine) or G-CSF mRNA containing a 5'UTR with five tandem repeats of an 18 nucleotide sequence from the IRES of GTX gene (GTX G-CSF; mRNA sequence shown in SEQ ID NO: 5758 (Table 62); polyA tail of approximately 140 nucleotides not shown in sequence; 5'cap, Cap1; fully modified with 5-methylcytidine and 1-methylpseudouridine) for treatment of 3 mice is diluted with sterile and serum-free DMEM (Life Technologies) to obtain a total volume of 200 ul. A total of 8 ul of Lipofectamine2000 (LifeTechnologies, 11668019) for the treatment of 3 mice was diluted with sterile and serum-free DMEM (LifeTechnologies, Grand Island, N.Y.; 11965-118) to obtain a total volume of 200 ul. After 5 minutes of incubation, the two solutions were combined and carefully mixed with a pipette. After 20 minutes the formation of mRNA-Lipofectamine2000 lipoplexes was completed. The lipoplex solution was transferred to a sterile 1 ml syringe (BD Falcon) carrying a 27 gauge injection needle (0.3 mL BD SafetyGlide insulin syringe with 29 G×½ in BD permanently attached needle (Catalog #305935)). The Balb/C mice were placed under a heat lamp for 5 minutes prior to the 100 ul intravenous tail vein injection containing 2 ug of lipoplexed mRNA. 6 hours after injection the mice were anesthesized and bleed for serum collection by cardiac puncture. The serum samples were then run on a G-CSF ELISA (R&D systems catalog #SCS50) and the results are shown in Table 66. The G-CSF mRNA having five tandem repeats of an 18 nucleotide sequence from the IRES of GTX gene had a higher G-CSF expression level at 6 hours as compared to the G-CSF having a synthetic UTR.

TABLE 66

GTX G-CSF Expression In Vivo

| Time Point | G-CSF Expression (ng/ml) | GTX G-CSF Expression (ng/ml) |
|---|---|---|
| 6 hours | 266.4 | 1284.4 |

Example 56. In Vivo Effect of the GTX Modification of 5'UTR in G-CSF Nucleic Acids Modified with 1-Methylpseudouridine To study the effect of the modification of the 5'UTR in modified nucleic acids female Balb/c mice (n=3; 12 weeks old; Harlan Laboratories (South Easton, Mass.)) were treated with lipoplexed mRNA.

8 ug of G-CSF mRNA having a synthetic 5'UTR (G-CSF; mRNA sequence shown in SEQ ID NO: 5716; polyA tail of approximately 140 nucleotides not shown in sequence; 5'cap, Cap1; fully modified with 1-methylpseudouridine) or G-CSF mRNA containing a 5'UTR with five tandem repeats of an 18 nucleotide sequence from the IRES of GTX gene (GTX G-CSF; mRNA sequence shown in SEQ ID NO: 5758 (Table 62); polyA tail of approximately 140 nucleotides not shown in sequence; 5'cap, Cap1; fully modified with 1-methylpseudouridine) for treatment of 3 mice is diluted with sterile and serum-free DMEM (Life Technologies) to obtain a total volume of 200 ul. A total of 8 ul of Lipofectamine2000 (LifeTechnologies, 11668019) for the treatment of 3 mice was diluted with sterile and serum-free DMEM (LifeTechnologies, Grand Island, N.Y.; 11965-118) to obtain a total volume of 200 ul. After 5 minutes of incubation, the two solutions were combined and carefully mixed with a pipette. After 20 minutes the formation of mRNA-Lipofectamine2000 lipoplexes was completed. The lipoplex solution was transferred to a sterile 1 ml syringe (BD Falcon) carrying a 27 gauge injection needle (0.3 mL BD SafetyGlide insulin syringe with 29 G×½ in BD permanently attached needle (Catalog #305935)). The Balb/C mice were placed under a heat lamp for 5 minutes prior to the 100 ul intravenous tail vein injection containing 2 ug of lipoplexed mRNA. 6 hours after injection the mice were anesthesized and bleed for serum collection by cardiac puncture. The serum samples were then run on a G-CSF ELISA (R&D systems catalog #SCS50) and the results are shown in Table 67. The G-CSF mRNA having five tandem repeats of an 18 nucleotide sequence from the IRES of GTX gene had a higher G-CSF expression level at 6 hours as compared to the G-CSF having a synthetic UTR.

TABLE 67

GTX G-CSF Expression In Vivo

| Time Point | G-CSF Expression (ng/ml) | GTX G-CSF Expression (ng/ml) |
|---|---|---|
| 6 hours | 5638.2 | 6281.1 |

OTHER EMBODIMENTS

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, databases, database entries, other references and art mentioned herein are incorporated by reference in their entirety, even if not expressly stated in the citation. In case of conflict, the present specification, including definitions, will control. In addition, section headings, the materials, methods, and examples are illustrative only and not intended to be limiting.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10925935B2). An electronic copy of the "Sequence Listing" will also be available from the USPTO upon request and payment of the fee set forth in 37 CFR 1.19(b)(3).

The invention claimed is:

1. A lipid nanoparticle comprising an mRNA, wherein the mRNA comprises
   (a) a 5' untranslated region (5'UTR);
   (b) a region of linked nucleosides encoding a polypeptide of interest;
   (c) a 3' untranslated region (3'UTR) comprising at least one microRNA binding site; and
   (d) a 3' tailing region of linked nucleosides;
   and wherein each uridine in the mRNA is a modified uridine nucleoside.

2. The lipid nanoparticle of claim 1, wherein each uridine in the mRNA is a pseudouridine analog.

3. The lipid nanoparticle of claim 2, wherein the pseudouridine analog is 1-methyl pseudouridine.

4. The lipid nanoparticle of claim 3, wherein each cytidine in the mRNA is a 5-methyl cytidine.

5. The lipid nanoparticle of claim 3, wherein the microRNA binding site is for an immune cell specific microRNA.

6. The lipid nanoparticle of claim 5, wherein the microRNA binding site is for a microRNA selected from miR-142-3p, miR-142-5p, miR-146a and miR-146b.

7. The lipid nanoparticle of claim 6, wherein the microRNA binding site is miR-142-3p.

8. The lipid nanoparticle of claim 7, comprising a cationic or ionizable lipid.

9. The lipid nanoparticle of claim 8, wherein the cationic lipid is DLin-MC3-DMA, DLin-DMA, C12-200, or DLin-KC2-DMA.

10. The lipid nanoparticle of claim 8, comprising a PEG lipid.

11. The lipid nanoparticle of claim 10, comprising 1-5% PEG lipid.

12. The lipid nanoparticle of claim 1, wherein the polypeptide of interest is a therapeutic protein, cytokine, growth factor, antibody or a fusion protein.

13. The lipid nanoparticle of claim 12, wherein the region encoding the polypeptide of interest is codon optimized.

14. The lipid nanoparticle of claim 1, wherein the mRNA further comprises a 5' cap structure.

15. The lipid nanoparticle of claim 14, wherein the 5' cap structure is Cap 1.

16. The lipid nanoparticle of claim 1, wherein the 5' UTR comprises a translation initiation sequence selected from a group consisting of a Kozak sequence and an internal ribosome entry site (IRES).

17. The lipid nanoparticle of claim 1, wherein the 3' tailing region comprises a poly A tail of at least 100 nucleosides.

18. The lipid nanoparticle of claim 1, wherein the microRNA binding site is for a microRNA selected from miR-122, miR-133, miR-206, miR-208, miR-17-92, miR-126, miR-142-3p, miR-142-5p, miR-16, miR-21, miR-223, miR-24, miR-27, let-7, miR-30c, miR-1d, miR-149, miR-192, miR-194, and miR-204.

19. The lipid nanoparticle of claim 3, wherein the microRNA binding site is for a microRNA selected from miR-122, miR-133, miR-206, miR-208, miR-17-92, miR-126, miR-142-3p, miR-142-5p, miR-16, miR-21, miR-223, miR-24, miR-27, let-7, miR-30c, miR-1d, miR-149, miR-192, miR-194, and miR-204.

20. The lipid nanoparticle of claim 1, wherein the microRNA binding site is for miR-142-3p.

21. A lipid nanoparticle comprising an mRNA, wherein the mRNA comprises
   (a) a 5' untranslated region (5'UTR);
   (b) a region of linked nucleosides encoding a polypeptide of interest;
   (c) a 3' untranslated region (3'UTR) comprising at least one miR-142-3p binding site; and
   (d) a 3' tailing region of linked nucleosides;
   and wherein each uridine in the mRNA is a modified uridine nucleoside.

22. The lipid nanoparticle of claim 21, comprising a cationic or ionizable lipid.

23. The lipid nanoparticle of claim 22, comprising a PEG lipid.

24. The lipid nanoparticle of claim 23, comprising 1-5% PEG lipid.

25. The lipid nanoparticle of claim 21, wherein the polypeptide of interest is a therapeutic protein, cytokine, growth factor, antibody or a fusion protein.

26. A lipid nanoparticle comprising an mRNA, wherein the mRNA comprises
   (a) a 5' untranslated region (5'UTR);
   (b) a region of linked nucleosides encoding a polypeptide of interest;
   (c) a 3' untranslated region (3'UTR) comprising at least one miR-126-3p binding site; and
   (d) a 3' tailing region of linked nucleosides;
   and wherein each uridine in the mRNA is a modified uridine nucleoside.

27. The lipid nanoparticle of claim 26, comprising a cationic or ionizable lipid.

28. The lipid nanoparticle of claim 27, comprising a PEG lipid.

29. The lipid nanoparticle of claim 28, comprising 1-5% PEG lipid.

30. The lipid nanoparticle of claim 26, wherein the polypeptide of interest is a therapeutic protein, cytokine, growth factor, antibody or a fusion protein.

31. A lipid nanoparticle comprising an mRNA, wherein the mRNA comprises
   (a) a 5' untranslated region (5'UTR);
   (b) a region of linked nucleosides encoding a polypeptide of interest;
   (c) a 3' untranslated region (3'UTR) comprising at least one miR-122 binding site; and
   (d) a 3' tailing region of linked nucleosides;
   and wherein each uridine in the mRNA is a modified uridine nucleoside.

32. The lipid nanoparticle of claim 31, comprising a cationic or ionizable lipid.

33. The lipid nanoparticle of claim 32, comprising a PEG lipid.

34. The lipid nanoparticle of claim 33, comprising 1-5% PEG lipid.

35. The lipid nanoparticle of claim 31, wherein the polypeptide of interest is a therapeutic protein, cytokine, growth factor, antibody or a fusion protein.

36. The lipid nanoparticle of claim 31, wherein the miR-122 binding site is a miR-122-3p binding site.

37. The lipid nanoparticle of claim 31, wherein the miR-122 binding site is a miR-122-5p binding site.

* * * * *